(12) United States Patent
Brenneman et al.

(10) Patent No.: US 9,353,090 B2
(45) Date of Patent: May 31, 2016

(54) HETEROCYCLIC CARBOXYLIC ACIDS AS ACTIVATORS OF SOLUBLE GUANYLATE CYCLASE

(71) Applicant: Boehringer Ingelheim International GmbH, Ingelheim am Rhein (DE)

(72) Inventors: Jehrod Burnett Brenneman, Southbury, CT (US); John David Ginn, New Milford, CT (US); Tamara Denise Hopkins, Danbury, CT (US); Michael D. Lowe, White Plains, NY (US); Christopher Ronald Sarko, New Milford, CT (US); John A. Westbrook, Woodbridge, CT (US); Maolin Yu, Brookfield, CT (US); Zhonghua Zhang, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/804,363

(22) Filed: Jul. 21, 2015

(65) Prior Publication Data

US 2016/0024059 A1 Jan. 28, 2016

Related U.S. Application Data

(60) Provisional application No. 62/027,376, filed on Jul. 22, 2014.

(51) Int. Cl.
C07D 405/14 (2006.01)
C07D 417/14 (2006.01)
A61K 31/44 (2006.01)

(52) U.S. Cl.
CPC .......... *C07D 405/14* (2013.01); *C07D 417/14* (2013.01)

(58) Field of Classification Search
None
See application file for complete search history.

(56) References Cited

U.S. PATENT DOCUMENTS

| 8,569,339 B2 | 10/2013 | Brenneman et al. |
| 8,815,857 B2 | 8/2014 | Zhang |
| 8,906,904 B2 | 12/2014 | Brenneman |
| 2009/0209556 A1 | 8/2009 | Bittner et al. |
| 2010/0016305 A1 | 1/2010 | Krahn et al. |
| 2010/0216764 A1 | 8/2010 | Kim et al. |
| 2013/0065918 A1 | 3/2013 | Brenneman et al. |
| 2013/0158028 A1 | 6/2013 | Stasch et al. |
| 2013/0203729 A1 | 8/2013 | Bosanac et al. |

FOREIGN PATENT DOCUMENTS

| CA | 2720343 A1 | 10/2009 |
| EP | 2594270 A2 | 5/2013 |
| WO | 2002026712 A2 | 4/2002 |
| WO | 2008021339 A2 | 2/2008 |
| WO | 2008138483 A1 | 11/2008 |
| WO | 2009032249 A1 | 3/2009 |
| WO | 2009068652 A1 | 6/2009 |
| WO | 2009071504 A1 | 6/2009 |
| WO | 2010015652 A2 | 2/2010 |
| WO | 2010015653 A1 | 2/2010 |
| WO | 2010065275 A1 | 6/2010 |
| WO | 2010099054 A2 | 9/2010 |
| WO | 2011095534 A1 | 8/2011 |
| WO | 2011095553 A1 | 8/2011 |
| WO | 2011147810 A1 | 12/2011 |
| WO | 2011161099 A1 | 12/2011 |
| WO | 2012058132 A1 | 5/2012 |
| WO | 2012122340 A1 | 9/2012 |
| WO | 2013025425 A1 | 2/2013 |

OTHER PUBLICATIONS

International Search Report and Written Opinion for PCT/US2015041245, PCT/ISA220, mailed Oct. 7, 2015.
U.S. Appl. No. 61/697,899, filed Sep. 7, 2012.
Schindler, Ursula., "Biochemistry and Pharmacology of Novel Anthranilic Acid Derivates Activating Heme-Oxidized Soluble Guanylyl Cyclase" Molecular Pharmacology (2006) vol. 69', No. 4 pp. 1260-1268.
Stasch, Johannes-Peter, et al., "NO- and HAEM-Independent Activation of Soluble Guanylyl Cyclase: Molecular Basis and Cardiovascular Implications of a New Pharmacological Principle" British Journal of Pharmacology (2002) vol. 136 pp. 773-783.
Evgenov, Oleg, V. et al., "NO-Independent Stimulators and Activators of Soluble Guanylate Cyclase: Discovery and Therapeutic Potential" Nature Reviews / Drug Discovery (2006) vol. 5 pp. 755-768.
International Search Report and Written Opinion for PCT/US2012/028205 mailed Jul. 4, 2012.
International Search Report for PCT/US2012/050052 mailed Oct. 22, 2012.
Notice of Allowance mailed May 23, 2014 for U.S. Appl. No. 13/570,432, filed Aug. 9, 2012, Inventor: Todd Bosanac.
Issue Fee Payment for U.S. Appl. No. 13/570,432, filed Jun. 6, 2014, Inventor: Todd Bosanac.

*Primary Examiner* — Zinna Northington Davis
(74) *Attorney, Agent, or Firm* — Michael P. Morris; Edward S. Lazer

(57) ABSTRACT

The present invention relates to compounds of formula I:

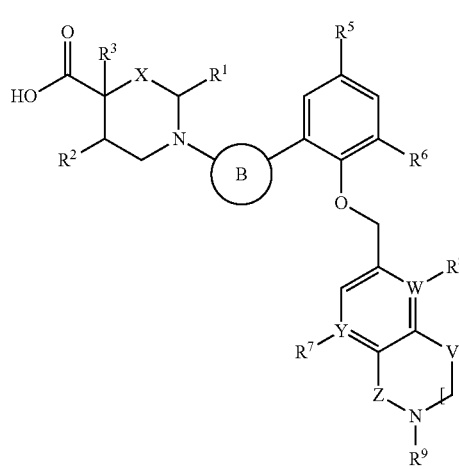

and pharmaceutically acceptable salts thereof, wherein $R^1$, $R^2$, $R^3$, $R^5$, $R^6$, $R^7$, $R^8$, $R^9$, B, V, W, X, Y, Z and m are as defined herein. The invention also relates to pharmaceutical compositions comprising these compounds, methods of using these compounds in the treatment of various diseases and disorders, processes for preparing these compounds and intermediates useful in these processes.

45 Claims, No Drawings

HETEROCYCLIC CARBOXYLIC ACIDS AS ACTIVATORS OF SOLUBLE GUANYLATE CYCLASE

CONTINUING DATA

This application claims benefit of 62/027,376 filed Jul. 22, 2014.

BRIEF SUMMARY OF THE INVENTION

The present invention provides novel compounds which activate or potentiate soluble guanylate cyclase (sGC) and are thus useful for treating a variety of diseases and disorders that are mediated or sustained by decreased or diminished soluble guanylate cyclase activity, including cardiovascular diseases, renal disease, diabetes, fibrotic disorders, urologic disorders, neurological disorders and inflammatory disorders. This invention also relates to pharmaceutical compositions comprising these compounds, methods of using these compounds in the treatment of various diseases and disorders, processes for preparing these compounds and intermediates useful in these processes.

BACKGROUND

Soluble guanylate cyclase (sGC) is a receptor for nitric oxide (NO) which is found in the cytoplasm of many cell types. In humans, functional sGC is a heterodimer composed of either an alpha 1 or alpha 2 subunit combined with the beta 1 subunit which has a heme prosthetic group. Under non-pathophysiological conditions, NO binding to the heme of sGC activates the enzyme to catalyze the conversion of guanosine-5'-triphosphate (GTP) to cyclic guanosine monophosphate (cGMP). cGMP is a second messenger which exerts effects by modulating cGMP dependent protein kinase (PKG) isoforms, phosphodiesterases, and cGMP gated ion channels. In doing so, sGC has been demonstrated to modulate numerous pathways associated with diseases including arterial hypertension, pulmonary hypertension, atherosclerosis, heart failure, liver cirrhosis, renal fibrosis, and erectile dysfunction (O. Evgenov et al., Nature Reviews, 2006, 5, 755-768 and Y. Wang-Rosenke et al., Curr. Med. Chem., 2008, 15, 1396-1406).

Under normal conditions, the iron in sGC exists in the ferrous state which is capable of binding to NO and carbon monoxide (CO). However, under conditions of oxidative stress which can occur in various diseases, published reports indicate that the heme iron becomes oxidized to the ferric state which is incapable of being activated by NO or CO. The inability of NO to signal through sGC with an oxidized heme iron has been hypothesized to contribute to disease processes. Recently, two novel classes of compounds have been described which potentiate sGC activity in a heme dependent (sGC stimulators) and heme independent (sGC activators) manner. The activity of sGC stimulators synergizes with NO to increase cGMP production while sGC activators are only additive with NO to augment cGMP levels (O. Evgenov et al., Nature Reviews, 2006, 5, 755-768). Both stimulators and activators of sGC have demonstrated benefit in animal models of disease. Activators of sGC provide the advantage of being able to preferentially target the diseased, non-functional form of the enzyme. sGC activators include BAY 58-2667 (cinaciguat) (J-P Stasch et al., Brit J. Pharmacol., 2002, 136, 773-783) and HMR-1766 (ataciguat) (U. Schindler et al., 2006, Mol. Pharmacol., 69, 1260-1268).

NO has an important role in maintaining normal cellular and tissue function. However, adequate signaling in the NO pathway can be disrupted at a number of steps. NO signaling can be impaired by reduced levels of nitric oxide synthase (NOS) enzymes, NOS activity, NO bioavailability, sGC levels, and sGC activity. sGC activators have the potential to bypass the functional impediment produced by all of these impairments. Since sGC activation occurs downstream of NO synthesis or NO availability, these deficiencies will not impact the activity of sGC activators. As described above, the activity of sGC in which function is disrupted by heme iron oxidation will be corrected by sGC activators. Thus, sGC activators have the potential to provide benefit in many diseases caused by defective signaling in the NO pathway.

Activation of sGC has the potential to provide therapeutic benefit for atherosclerosis and arteriosclerosis. Cinaciguat treatment has been demonstrated to prevent neointimal hyperplasia after endothelial denudation by wire injury of the carotid artery in rats (K. Hirschberg et al., Cardiovasc. Res., 2010, 87, Suppl. 1, S100, Abstract 343). Ataciguat inhibited atherosclerotic plaque formation in ApoE−/− mice feed a high fat diet (M. van Eickels, BMC Pharmacology, 2007, 7, Suppl. 1, S4). Decreased NO production in endothelial nitric oxide synthase (eNOS) deficient mice increased vascular inflammation and insulin resistance in response to nutrient excess. In the same study, the phosphodiesterase 5 (PDE5) inhibitor sildenafil reduced vascular inflammation and insulin resistance in mice fed a high-fat diet (N. Rizzo et al., Arterioscler. Thromb. Vasc. Biol., 2010, 30, 758-765). In a cerebral ischemia and reperfusion model, mice deficient for the alpha1 subunit had a larger infarct volume and greater neurological deficits that wild-type mice (D. Atochin et al., Stroke 2010, 41, 1815-1819). Lastly, after balloon-injury of rat carotid arteries in vivo, a sGC stimulator (YC-1) inhibited neotima formation (C. Wu, J. Pharmacol. Sci., 2004, 94, 252-260).

The complications of diabetes may be reduced by sGC activation. Glucose induced suppression of glucagon release is lost in pancreatic islets that lack PKG, thus suggesting a role of sGC mediated cGMP production in glucose regulation (V. Leiss et al., BMC Pharmacology, 2009, 9, Suppl. 1, P40).

It is well established clinically that elevation of cGMP by treatment with PDE5 inhibitors is efficacious for the treatment of erectile dysfunction (ED). However, 30% of ED patients are resistant to PDE5 inhibitor treatment (S. Gur et al., Curr. Pharm. Des., 2010, 16, 1619-1633). The sGC stimulator BAY-41-2272 is able to relax corpus cavernosum muscle in a sGC dependent manner, thus suggesting that increased sGC activity could provide benefit in ED patients (C. Teixeira et al., J. Pharmacol. & Exp. Ther., 2007, 322, 1093-1102). Furthermore, sGC stimulators and sGC activators used individually or either in combination with PDE5 inhibitor was able to treat ED in animal models (WO 10/081647).

There is evidence that sGC activation may be useful in preventing tissue fibrosis, including that of the lung, liver, skin and kidney. The processes of epithelial to mesenchyal transition (EMT) and fibroblast to myofibroblast conversion are believed to contribute to tissue fibrosis. When either cinaciguat or BAY 41-2272 was combined with sildenafil, lung fibroblast to myofibroblast conversion was inhibited (T. Dunkern et al., Eur. J. Pharm., 2007, 572, 12-22). NO is capable of inhibiting EMT of alveolar epithelial cells (S. Vyas-Read et al., Am. J. Physiol. Lung Cell Mol. Physiol., 2007, 293, 1212-1221), suggesting that sGC activation is involved in this process. NO has also been shown to inhibit glomerular TGF beta signaling (E. Dreieicher et al., J. Am. Soc. Nephroi., 2009, 20, 1963-1974) which indicates that sGC activation may be able to inhibit glomerular sclerosis. In a pig serum model and carbon tetrachloride model of liver fibrosis, an sGC activator (BAY 60-2260) was effective at inhibiting fibrosis (A. Knorr et al., Arzneimittel-Forschung, 2008, 58, 71-80) which suggests that increasing sGC activity may be used to treat nonalcoholic steatohepatitis (NASH). In the bleomycin-induced dermal fibrosis and the Tsk-1 mouse skin fibrosis models the sGC stimulator BAY 41-2272 was able to inhibit dermal thickening and myofibroblast differentiation (C. Beyer et al., Ann. Rheum. Dis., 2012, 71, 1019-1026) thus indicating that activating sGC may be useful for the treatment of systemic sclerosis.

Clinical studies have demonstrated efficacy using the sGC activator cinaciguat for the treatment of acute decompensated heart failure (H. Lapp et al., Circulation, 2009, 119, 2781-2788). This is consistent with results from a canine tachypacing-induced heart failure model in which acute intrevenous infusion of cinaciguat was able to produce cardiac unloading (G. Boerrigter et al., Hypertension, 2007, 49, 1128-1133). In a rat myocardial infarction induced chronic heart failure model, HMR 1766 improved cardiac function and reduced cardiac fibrosis which was further potentiated by ramipril (F. Daniela, Circulation, 2009, 120, Suppl. 2, S852-S853).

Activators of sGC can be used to treat hypertension. This has been clearly demonstrated in clinical studies in which the dose of cinaciguat is titrated based on the magnitude of blood pressure reduction achieved (H. Lapp et al., Circulation, 2009, 119, 2781-2788). Preclinical studies using cinaciguat had previously shown the ability of sGC activation to reduce blood pressure (J.-P. Stasch et al., 2006, J. Clin. Invest., 116, 2552-2561). Similar findings have been reported using the sGC activator HMR 1766 as well (U. Schindler et al., 2006, Mol. Pharmacol., 69, 1260-1268).

The activation of sGC has the potential to reduce inflammation by effects on the endothelium. BAY 41-2272 and a NO donor inhibited leukocyte rolling and adhesion in eNOS deficient mice. This was demonstrated to be mediated by down-regulation of expression of the adhesion molecule P-selectin (A. Ahluwalla et al., Proc. Natl. Acad. Sci. USA, 2004, 101, 1386-1391). Inhibitors of NOS and sGC were shown to increase endotoxin (LPS) induced ICAM expression on mesenteric microcirculation vessels. This was reduced by an NO donor in a cGMP dependent manner. Treatment of mice with NOS or sGC inhibitors increased neutrophil migration, rolling, and adhesion induced by LPS or carrageenen (D. Dal Secco, Nitric Oxide, 2006, 15, 77-86).

Activation of sGC has been shown to produce protection from ischemia-reperfusion injury using BAY 58-2667 in both in vivo and in an isolated heart model (T. Krieg et al., Eur. Heart J., 2009, 30, 1607-6013). Similar results were obtained using the same compound in a canine model of cardioplegic arrest and extracorporeal circulation (T. Radovits et al., Eur J. Cardiothorac. Surg., 2010).

The ability of sGC activation to inhibit intestinal smooth muscle cell growth in vitro (A.-M. Pelletier et al., Am. J. Physiol. Gastrointest. Liver Physiol. 2010, 298, G896-G907) is consistent with a role in inflammatory bowel diseases including ulcerative colitis and Crohn's disease.

Some studies have indicated the potential of sGC activation to have antinociceptive effects. In streptozotocin-induced diabetes models of nociception in mice (writhing assay) and rats (paw hyperalgesia), elevation of cGMP levels by administration of sildenafil blocked the pain response, which in turn was abrogated by a NOS or sGC inhibitor (C. Patil et al., Pharm., 2004, 72, 190-195). The sGC inhibitor 1H-1,2,4.-oxadiazolo4,2-a.quinoxalin-1-one (ODQ) has been demonstrated to block the antinociceptive effects of various agents including meloxicam and diphenyl diselenide in a formalin induced pain model (P. Aguirre-Banuelos et al., Eur. J. Pharmacol., 2000, 395, 9-13 and L. Savegnago et al., J. Pharmacy Pharmacol., 2008, 60, 1679-1686) and xylazine in a paw pressure model (T. Romero et al., Eur. J. Pharmacol., 2009, 613, 64-67). Furthermore, ataciguat was antinociceptive in the carrageenan model of inflammatory triggered thermal hyperalgesia and the spared nerve injury model of neuropathic pain in mice (WO 09/043495).

Inhibiton of PDE9, a phosphodiesterase specific for cGMP expressed in the brain, has been shown to improve long-term potentiation (F. van der Staay et al., Neuropharmacol. 2008, 55, 908-918). In the central nervous system, sGC is the primary enzyme which catalyzes the formation of cGMP (K. Domek-Lopacinska et al., Mol. Neurobiol., 2010, 41, 129-137). Thus, sGC activation may be beneficial in treating Alzheimer's and Parkinson's disease. In a phase II clinical study, the sGC stimulator riociguat, was efficacious in treating chronic thromboembolic pulmonary hypertension and pulmonary arterial hypertension (H. Ghofrani et al., Eur. Respir. J., 2010, 36, 792-799), These findings extend the preclinical studies in which BAY 41-2272 and cinaciguat reduced pulmonary hypertension in mouse (R. Dumitrascu et al., Circulation, 2006, 113, 286-295) and lamb (O. Evgenov et al 2007, Am. J. Respir. Crit. Care Med., 176, 11384145) models. Similar results were obtained using HMR 1766 in a mouse model of pulmonary hypertension (N. Weissmann et al., 2009, Am. J. Physiol. Lung Cell. Mol. Physiol., 297, L658-665).

Activation of sGC has the potential to treat chronic kidney disease. Both BAY 58-2667 and HMR 1766 improved renal function and structure in a rat subtotal nephrectomy model of kidney disease (P. Kalk et al., 2006, Brit. J. Pharmacol., 148, 853-859 and K. Benz et al., 2007, Kidney Blood Press. Res., 30, 224-233). Improved kidney function and survival was provided by BAY 58-2667 treatment in hypertensive renin transgenic rats (TG(mRen2)27 rats) treated with a NOS inhibitor (J.-P. Stasch et al., 2006, J. Clin. Invest., 116, 2552-2561). BAY 41-2272 treatment preserved kidney function and structure in a chronic model of kidney disease in rats induced by uninephrectomy and anti-thy1 antibody treatment (Y. Wang et al., 2005, Kidney Intl., 68, 47-61), suggesting sGC activators may be useful in chronic and progressive kidney disorders including diabetic nephropathy and hypertensive nephropathy. Support for the use of sGC activators in diabetic nephropathy may also be found in a study in diabetic eNOS knockout mice (I. M. Ott et al., 2012, PLoS ONE, 7, e42623). In this model the sGC stimulator riociguat significantly reduced urinary albumin secretion, an early biomarker of diabetic nephropathy, when administered on top of treatment with an angiotensin II receptor blocker.

Diseases caused by excessive blood clotting may be treated with sGC activators. Activation of sGC using BAY 58-2667 was capable of inhibiting platelet aggregation induced by various stimuli ex vivo. Additionally, this compound inhibited thrombus formation in vivo in mice and prolonged bleeding time (J.-P. Stasch et al., 2002, Brit. J. Pharmacol., 136, 773-783). In another study using HMR 1766, in vivo platelet activation was inhibited in streptozotocin treated rats (A. Schafer et al., 2006, Arterioscler. Thromb. Vasc. Biol., 2006, 26, 2813-2818).

sGC activation may also be beneficial in the treatment of urologic disorders (WO/08138483). This is supported by clinical studies using the PDE5 inhibitor vardenafil (C. Stief et al., 2008, Eur. Urol., 53, 1236-1244). The soluble guanylate cyclase stimulator BAY 41-8543 was able to inhibit prostatic, urethra, and bladder smooth muscle cell proliferation using patient samples (B. Fibbi et al., 2010, J. Sex. Med., 7, 59-69), thus providing further evidence supporting the utility of treating urologic disorders with sGC activators.

Glaucoma affects millions of people worldwide and is a major cause of blindness. Increase in intraocular pressure (TOP) is considered to be causally related to the pathological development of the disease. Aqueous humor, a fluid located in the front of the eye is normally secreted by the trabecular meshwork (TM) and Schlemm's canal, lowering IOP. When the TM is pathologically compromised, fluid builds up, IOP increases and this may result in glaucoma. There is a correlation between changes in TM and Schlemm cell volume and rates of aqueous humor outflow. Activators of sGC been demonstrated to increase the rate of secretion of aqueous humor from the eye in a time course that correlates with sGC-induced decreases in TM and Schlemm cell volume (D. Z Ellis, 2011, Cell. Physiol. Biochem., 28, 1145-1154). Activators of sGC were also shown to reduce IOP upon once or twice daily topical ocular administration in a laser-induced hypertensive eye model in cynomolgus monkeys (C. Adams et al., WO 2015/095515). These studies provide evidence that activators of sGC would be useful in treating IOP and treating or preventing glaucoma.

Obesity can adversely affect one's health by increasing the risk of diseases such as diabetes, hypertension, heart disease, stroke, arthritis and some cancers. Obesity is characterized by expansion of white adipose tissue. An sGC activator was shown to enhance lipid uptake into brown adipose tissue which combusts energy to produce heat and was also shown to induce weight loss in a model of established obesity in mice (L. S. Hoffmann, et al., 2015, Nature Communications, 6, Article number 7235). This study suggests that sGC activators would be useful in treatment of obesity.

In a mouse model of estrogen deficiency-induced osteoporosis, a sGC activator significantly improved trabecular bone microarchitecture with an effect size similar to estrogen replacement therapy (J. Joshua et al., 2014, Endocrinology, 155, 4720-4730). The study also found that the sGC activator increased osteoblast number and activity with little effect on osteoclast numbers. These results suggest that sGC activators would be useful in treating osteoporosis.

The above studies provide evidence for the use of sGC activators to treat cardiovascular diseases including hypertension, atherosclerosis, peripheral artery disease, restenosis, myocardial infarction, stroke, heart failure, coronary vasospasm, cerebral vasospasm, ischemia/reperfusion injury, thromboembolic pulmonary hypertension, pulmonary arterial hypertension, stable and unstable angina, thromboembolic disorders. Additionally, sGC activators have the potential to treat renal disease, diabetes, glaucoma, obesity, osteoporosis, fibrotic disorders including those of the skin, liver, kidney and lungs, urologic disorders including overactive bladder, benign prostatic hyperplasia, and erectile dysfunction, and neurological disorders including Alzheimer's disease, Parkinson's disease, as well as neuropathic pain. Treatment with sGC activators may also provide benefits in inflammatory disorders such as psoriasis, multiple sclerosis, arthritis, asthma, ulcerative colitis, Crohn's disease and chronic obstructive pulmonary disease.

BRIEF SUMMARY OF THE INVENTION

The present invention provides novel compounds which activate or potentiate sGC and are thus useful for treating a variety of diseases and disorders that can be alleviated by sGC activation or potentiation including cardiovascular, inflammatory and renal diseases.

Accordingly, the invention provides novel compounds for use as medicaments, more specifically for use in the treatment of a disease or disorder that can be alleviated by sGC activation or potentiation. Furthermore, the invention provides the use of the novel compounds for the manufacture of a medicament for the treatment of a disease or disorder that can be alleviated by sGC activation or potentiation.

This invention also relates to pharmaceutical compositions comprising these compounds, methods of using these compounds in the treatment of various diseases and disorders, processes for preparing these compounds and intermediates useful in these processes.

In a further aspect, the present invention provides activators of soluble guanylate cyclase having solubility properties consistent with acceptable pharmacokinetic properties. As is known in the art, poorly soluble compounds may suffer from poor human exposure. The compounds of the present invention would be expected to have exposure properties consistent with being a suitable drug.

In a further aspect, the present invention provides compounds with metabolic stability properties consistent with acceptable pharmacokinetic properties. As is known in the art, compounds having poor metabolic stability may not readily achieve desirable therapeutic levels. The compounds of the present invention would be expected to have metabolic stability properties consistent with being a suitable drug.

DETAILED DESCRIPTION OF THE INVENTION

In an embodiment, there are provided compounds of the formula I

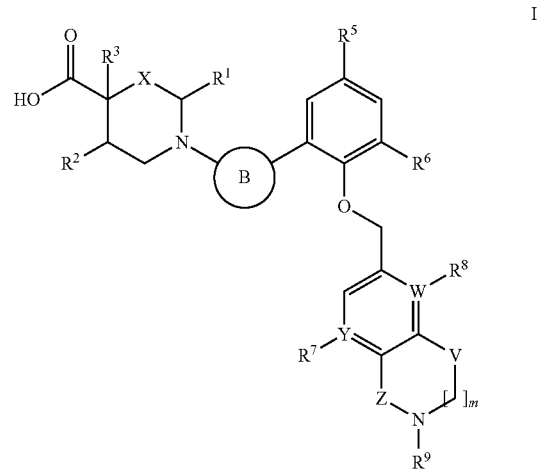

wherein:

X is $CHR^4$ or a bond;

Y is C or N;

W is C or N, provided that Y and W are not both N;

V is $-C(R^{11})(R^{12})-$ or $-OCH_2-$, provided that if V is $-OCH_2$, then Z is $-CH_2-$ and Y and W are both C;

Z is $-CH_2-$, $-C(R^{10})_2CH_2-$ or $-C(O)-$;

$R^1$ is H, Me, or $-CH_2OC_{1-2}$alkyl;

$R^2$ is H, -OMe or -OEt;

$R^3$ is H or $R^2$ and $R^3$ together with the carbons they are bonded to form a fused 3-membered ring;

$R^4$ is H or $R^2$ and $R^4$ form a 2-carbon alkylidene bridge or $R_1$ and $R_4$ together with the piperidine ring they are bonded to may form an octahydropyrano[3,2-b]pyridine ring;

B is

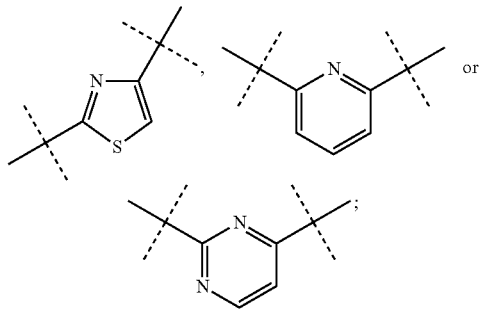

$R^5$ and $R^6$ are independently selected from H, Me, F, Cl and $CF_3$;

$R^7$ is H, Me, Et, -OMe, CN, F, or —$CH_2$OMe or is not present when Y is N;

$R^8$ is H, Me or F or is not present when W is N;

$R^9$ is H or $C_{4-6}$cycloalkyl, optionally substituted with one to two F or $R^9$ is —$(CH_2)_n$ heterocyclyl, wherein the heterocyclyl is selected from tetrahydropyranyl, tetrahydrofuranyl, oxetanyl and [1,4]-dioxanyl or —$CH(R^{10})$heteroaryl, wherein the heteroaryl is selected from the group consisting of pyrazine, imidazole, pyridyl and isoxazolyl and wherein the heteroaryl is optionally substituted with a methyl group;

each $R^{10}$ is independently H or Me;

$R^{11}$ is H or Me;

$R^{12}$ is H or Me;

m is 0 or 1, provided that if m is 0, Z is —$CH_2$—, V is —$C(R^{11})(R^{12})$— and $R^{11}$ and $R^{12}$ are both H; and n is 0 or 1;

or a salt thereof.

In a second embodiment, there are provided compounds as described in the embodiment above wherein:

X is $CHR^4$ or a bond;

Y is C or N;

W is C;

V is —$C(R^{11})(R^{12})$;

Z is —$CH_2$—, —$C(R^{10})_2CH_2$— or —C(O)—;

$R^1$ is H, Me, or —$CH_2$OMe;

$R^2$ is H, -OMe or -OEt;

$R^3$ is H or $R^2$ and $R^3$ together with the carbons they are bonded to form a fused 3-membered ring;

$R^4$ is H or $R^2$ and $R^4$ form a 2-carbon alkylidene bridge;

B is

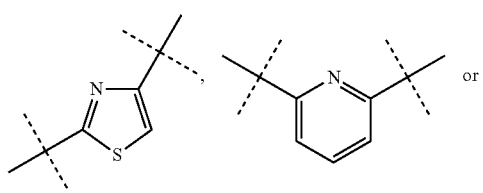

-continued

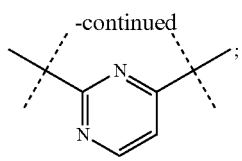

$R^5$ and $R^6$ are independently selected from H, Me, F and Cl;

$R^7$ is H, Me, Et, -OMe, CN, or F or is not present when Y is N;

$R^8$ is H, Me or F;

$R^9$ is $C_{4-6}$cycloalkyl, optionally substituted with one to two F or $R^9$ is —$(CH_2)_n$ heterocyclyl, wherein the heterocyclyl is selected from tetrahydropyranyl, tetrahydrofuranyl, oxetanyl and [1,4]-dioxanyl;

each $R^{10}$ is independently H or Me;

$R^{11}$ is H or Me;

$R^{12}$ is H or Me;

m is 1; and n is 0 or 1;

or a salt thereof.

In another embodiment, there are provided compounds as described in any of the embodiments above wherein:

Y is C;

W is C;

V is —$C(R^{11})(R^{12})$;

Z is —$CH_2$— or —$C(R^{10})_2CH_2$—; and $R^9$ is —$(CH_2)_n$ heterocyclyl, wherein the heterocyclyl is selected from tetrahydropyranyl, tetrahydrofuranyl, oxetanyl and [1,4]-dioxanyl;

or a salt thereof.

In another embodiment, there are provided compounds as described in any of the embodiments above, wherein:

X is $CHR^4$;

$R^1$ is H;

$R^2$ and $R^3$ together with the carbons they are bonded to form a fused 3-membered ring; and $R^4$ is H;

or a salt thereof.

In another embodiment, there are provided compounds as described in any of the embodiments above, wherein:

X is $CHR^4$;

$R^1$ is H;

$R^2$ is -OMe;

$R^3$ is H; and $R^4$ is H;

or a salt thereof.

In another embodiment, there are provided compounds as described in any of the embodiments above, wherein:

X is a bond;

$R^1$ is H, Me, or —$CH_2$OMe; and $R^2$ and $R^3$ together with the carbons they are bonded to form a fused 3-membered ring;

or a salt thereof.

In another embodiment, there are provided compounds as described in any of the embodiments above wherein:

Z is —$CH_2$—;

or a salt thereof.

In another embodiment, there are provided compounds as described in any of the embodiments above wherein:

Z is —$C(R^{10})_2CH_2$—; and $R^{10}$ is H or a salt thereof.

In another embodiment, there are provided compounds as described in any of the embodiments above, wherein:
B is

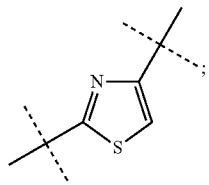

or a salt thereof.

In another embodiment, there are provided compounds as described in any of the embodiments above, wherein:
B is

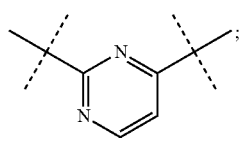

or a salt thereof.

In another embodiment, there are provided compounds as described in any of the embodiments above, wherein:
B is

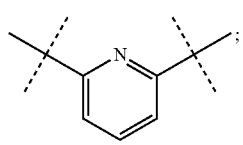

or a salt thereof.

In another embodiment, there are provided compounds as described in any of the embodiments above, wherein:
$R^9$ is selected from —(CH$_2$)$_n$ heterocyclyl, wherein the heterocyclyl is selected from tetrahydropyranyl, tetrahydrofuranyl, oxetanyl and [1,4]-dioxanyl;
or a salt thereof.

In another embodiment, there are provided compounds as described in any of the embodiments above, wherein:
X is CHR$^4$;
Y is C;
W is C;
V is —C(R$^{11}$)(R$^{12}$);
Z is —CH$_2$— or —C(R$^{10}$)$_2$CH$_2$;
$R^1$ is H;
$R^2$ is -OMe;
$R^3$ is H;
$R^4$ is H;
B is

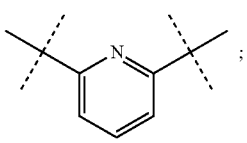

$R^7$ is H, Me, Et, -OMe, CN, F, or —CH$_2$OMe;
$R^8$ is H, Me or F;
$R^9$ is —(CH$_2$)$_n$ heterocyclyl, wherein the heterocyclyl is selected from tetrahydropyranyl, tetrahydrofuranyl, oxetanyl and [1,4]-dioxanyl;
$R^{11}$ is H;
$R^{12}$ is H;
n is 0; and
m is 1;
or a salt thereof.

In another embodiment, there are provided compounds as described in any of the embodiments above, wherein:
X is a bond;
Y is C;
V is —C(R$^{11}$)(R$^{12}$)—;
V is C;
Z is —CH$_2$— or —C(R$^{10}$)$_2$CH$_2$;
$R^1$ is H, Me or —CH$_2$OMe;
$R^2$ and $R^3$ together with the carbons they are bonded to form a fused 3-membered ring;
B is

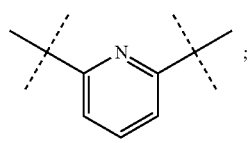

$R^7$ is H, Me, Et, -OMe, CN, F, or —CH$_2$OMe;
$R^8$ is H, Me or F;
$R^9$ is —(CH$_2$)$_n$ heterocyclyl, wherein the heterocyclyl is selected from tetrahydropyranyl, tetrahydrofuranyl, oxetanyl and [1,4]-dioxanyl;
$R^{11}$ is H;
$R^{12}$ is H;
n is 0; and
m is 1;
or a salt thereof.

In another embodiment, there are provided compounds as described in any of the embodiments above, wherein:
$R^9$ is selected from

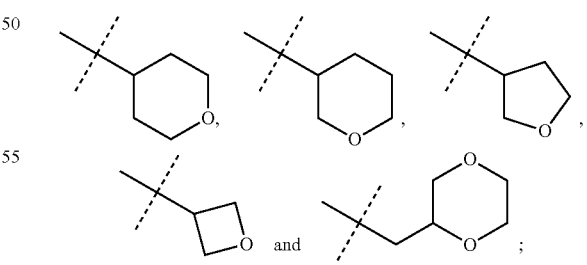

or a salt thereof.

In another embodiment, there are provided compounds as described in any of the embodiments above, wherein:
$R^2$ is H or -OMe; and
$R^5$ and $R^6$ are independently selected from H and Me;
or a salt thereof.

In another embodiment, there are provided compounds as described in any of the embodiments above, wherein:
R$^{10}$ is H;
R$^{11}$ is H; and
R$^{12}$ is H;
or a salt thereof.

In another aspect of the invention, there is provided a compound of the general formula I according to any of the embodiments above, or a pharmaceutically acceptable salt thereof for use in a therapeutic method as described hereinbefore and hereinafter The following are representative compounds of the invention which can be made by the general synthetic schemes, the examples, and known methods in the art.

TABLE 1

| Cpd No | Structure |
|---|---|
| 1 | 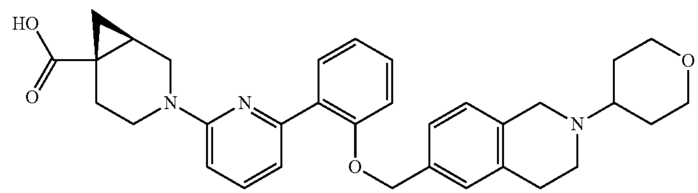 [SMILES: O=C(O)[C@@]12CCN(c3cccc(-c4ccccc4OCc4ccc5c(c4)CCN(C4CCOCC4)C5)n3)C[C@@H]1C2] |
| 2 | 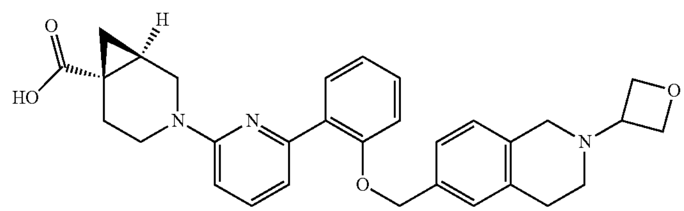 [SMILES: O=C(O)[C@@]12CCN(c3cccc(-c4ccccc4OCc4ccc5c(c4)CCN(C4COC4)C5)n3)C[C@@H]1C2] |
| 3 | 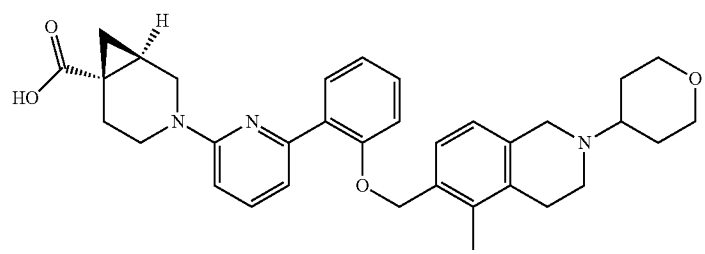 [SMILES: Cc1c(COc2ccccc2-c2cccc(N3CC[C@@]4(C(=O)O)C[C@H]4C3)n2)ccc2c1CCN(C1CCOCC1)C2] |
| 4 | 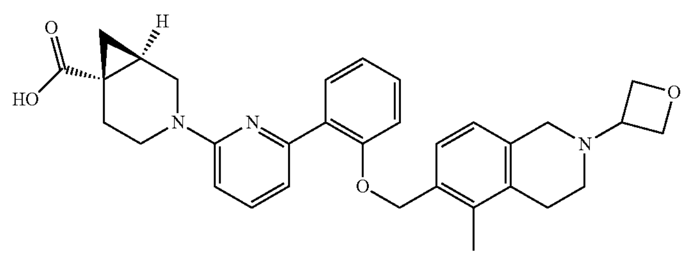 [SMILES: Cc1c(COc2ccccc2-c2cccc(N3CC[C@@]4(C(=O)O)C[C@H]4C3)n2)ccc2c1CCN(C1COC1)C2] |
| 5 | 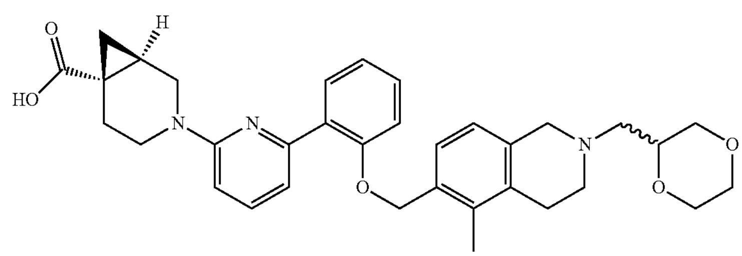 [SMILES: Cc1c(COc2ccccc2-c2cccc(N3CC[C@@]4(C(=O)O)C[C@H]4C3)n2)ccc2c1CCN(CC1COCCO1)C2] |

TABLE 1-continued
| Cpd No | Structure |
|---|---|
| 6 | 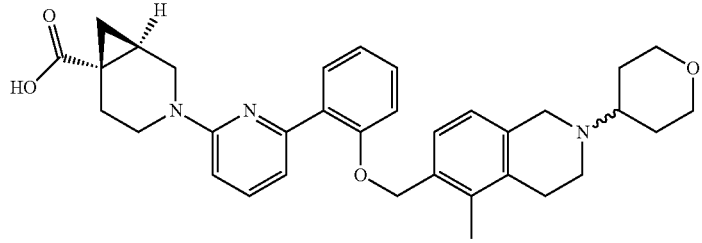 [SMILES: Cc1c(COc2ccccc2-c2cccc(N3CC[C@@]4(C(=O)O)C[C@H]4C3)n2)ccc2c1CCN(C1CCOCC1)C2] |
| 7 | 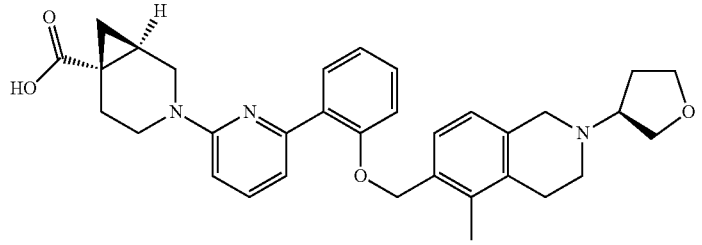 [SMILES: Cc1c(COc2ccccc2-c2cccc(N3CC[C@@]4(C(=O)O)C[C@H]4C3)n2)ccc2c1CCN([C@H]1CCOC1)C2] |
| 8 | 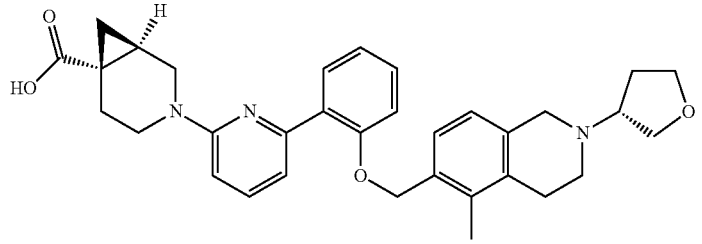 [SMILES: Cc1c(COc2ccccc2-c2cccc(N3CC[C@@]4(C(=O)O)C[C@H]4C3)n2)ccc2c1CCN([C@@H]1CCOC1)C2] |
| 9 | 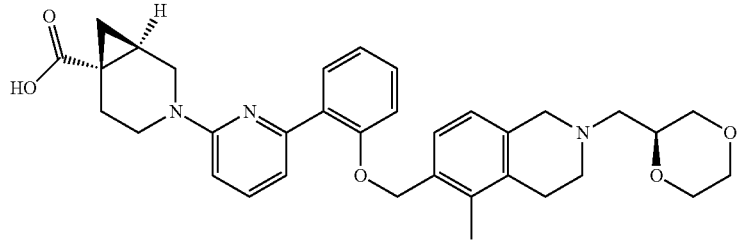 [SMILES: Cc1c(COc2ccccc2-c2cccc(N3CC[C@@]4(C(=O)O)C[C@H]4C3)n2)ccc2c1CCN(C[C@H]1COCCO1)C2] |
| 10 | 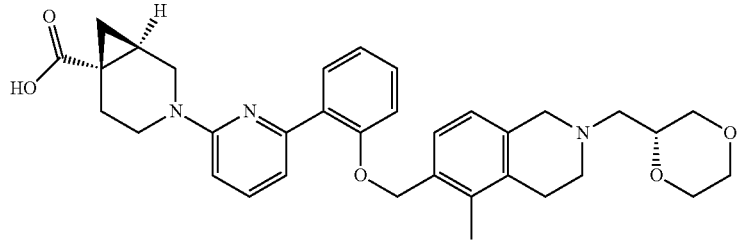 [SMILES: Cc1c(COc2ccccc2-c2cccc(N3CC[C@@]4(C(=O)O)C[C@H]4C3)n2)ccc2c1CCN(C[C@@H]1COCCO1)C2] |
| 11 | 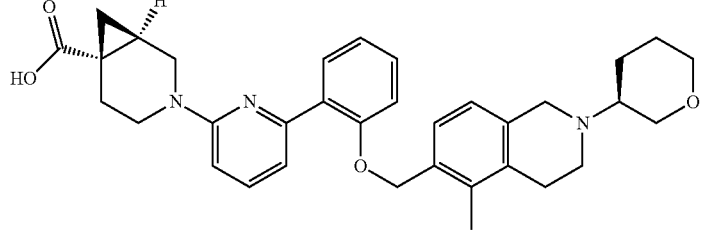 |

TABLE 1-continued

| Cpd No | Structure |
|---|---|
| 12 | (structure) |
| 13 | (structure) |
| 14 | (structure) |
| 15 | (structure) |
| 16 | (structure) |
| 17 | (structure) |
| 18 | (structure) |

TABLE 1-continued
| Cpd No | Structure |
|---|---|
| 19 | 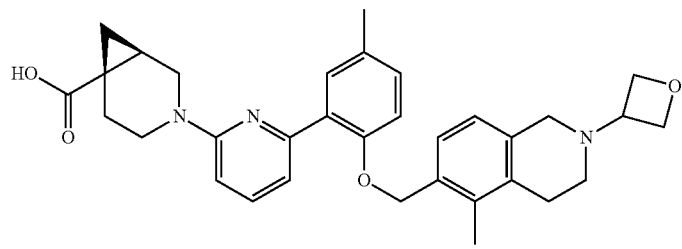 [SMILES: Cc1ccc(OCc2ccc3c(c2C)CCN(C2COC2)C3)c(-c2cccc(N3CC[C@@]4(C(=O)O)C[C@H]4C3)n2)c1] |
| 20 | 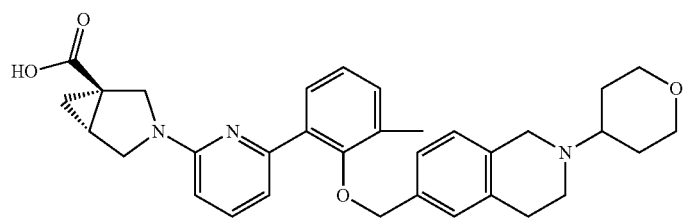 |
| 21 | 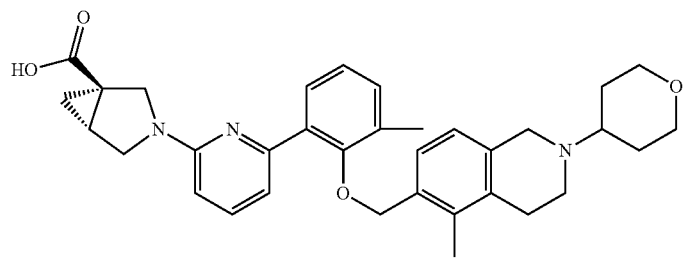 [SMILES: Cc1cccc(-c2cccc(N3C[C@@H]4C[C@]4(C(=O)O)C3)n2)c1OCc1ccc2c(c1C)CCN(C1CCOCC1)C2] |
| 22 | 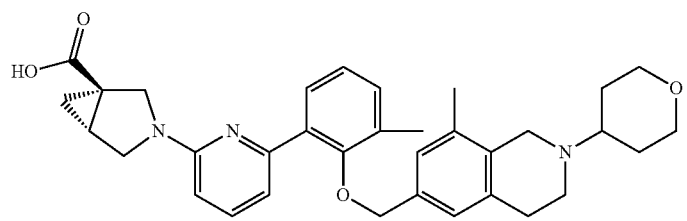 [SMILES: Cc1cc(COc2c(C)cccc2-c2cccc(N3C[C@@H]4C[C@]4(C(=O)O)C3)n2)cc2c1CN(C1CCOCC1)CC2] |
| 23 | 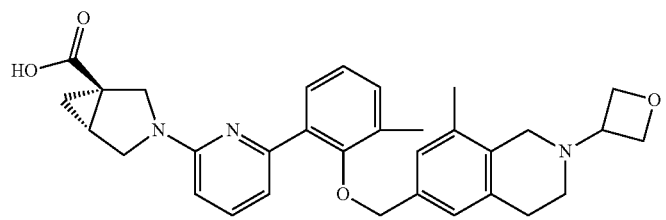 [SMILES: Cc1cc(COc2c(C)cccc2-c2cccc(N3C[C@@H]4C[C@]4(C(=O)O)C3)n2)cc2c1CN(C1COC1)CC2] |
| 24 | 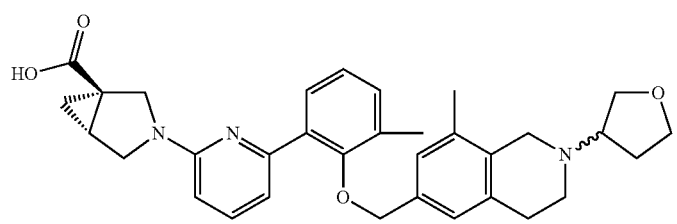 [SMILES: Cc1cc(COc2c(C)cccc2-c2cccc(N3C[C@@H]4C[C@]4(C(=O)O)C3)n2)cc2c1CN(C1CCOC1)CC2] |

TABLE 1-continued

| Cpd No | Structure |
|---|---|
| 25 | (structure) |
| 26 | (structure) |
| 27 | (structure) |
| 28 | (structure) |
| 29 | (structure) |
| 30 | (structure) |
| 31 | (structure) |

TABLE 1-continued
| Cpd No | Structure |
|---|---|
| 32 | 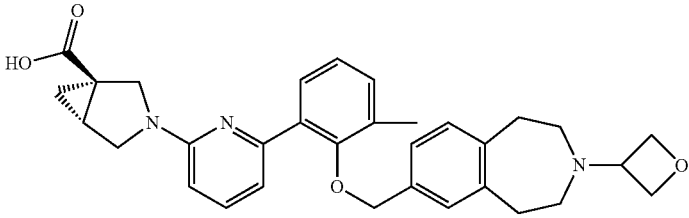 [SMILES: Cc1cccc(-c2cccc(N3C[C@@H]4C[C@]4(C(=O)O)C3)n2)c1OCc1ccc2c(c1)CCN(C1COC1)CC2] |
| 33 | 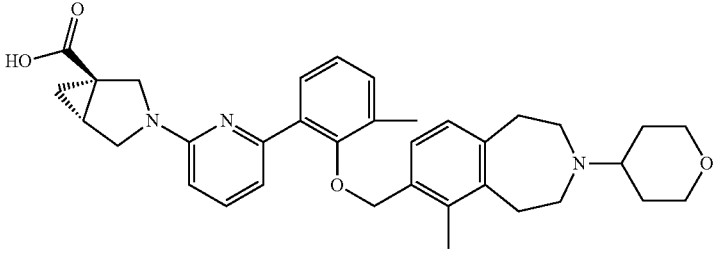 [SMILES: Cc1cccc(-c2cccc(N3C[C@@H]4C[C@]4(C(=O)O)C3)n2)c1OCc1ccc2c(c1C)CCN(C1CCOCC1)CC2] |
| 34 | 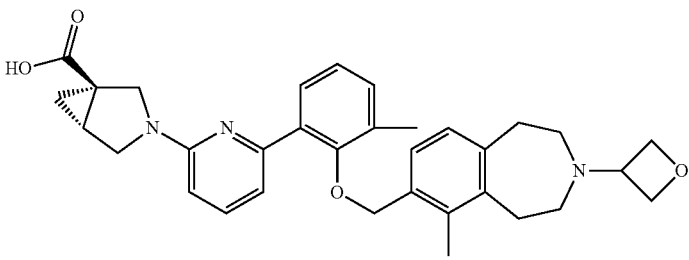 [SMILES: Cc1cccc(-c2cccc(N3C[C@@H]4C[C@]4(C(=O)O)C3)n2)c1OCc1ccc2c(c1C)CCN(C1COC1)CC2] |
| 35 | 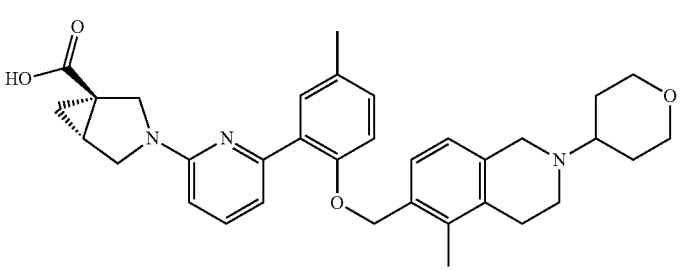 [SMILES: Cc1ccc(OCc2ccc3c(c2C)CCN(C2CCOCC2)C3)c(-c2cccc(N3C[C@@H]4C[C@]4(C(=O)O)C3)n2)c1] |
| 36 | 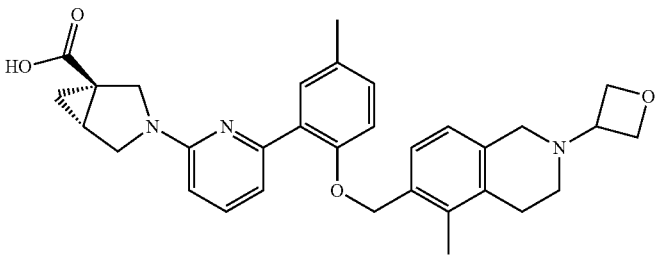 [SMILES: Cc1ccc(OCc2ccc3c(c2C)CCN(C2COC2)C3)c(-c2cccc(N3C[C@@H]4C[C@]4(C(=O)O)C3)n2)c1] |
| 37 | 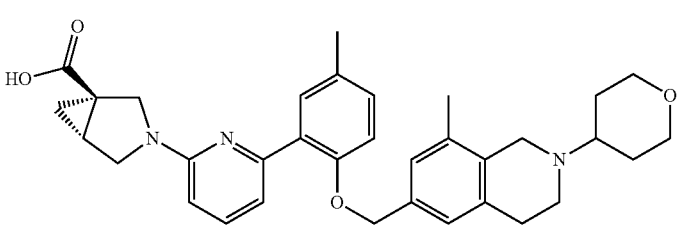 [SMILES: Cc1ccc(OCc2cc(C)c3c(c2)CCN(C2CCOCC2)C3)c(-c2cccc(N3C[C@@H]4C[C@]4(C(=O)O)C3)n2)c1] |

TABLE 1-continued

| Cpd No | Structure |
|---|---|
| 38 | *(structure image)* |
| 39 | *(structure image)* |
| 40 | *(structure image)* |
| 41 | *(structure image)* |
| 42 | *(structure image)* |
| 43 | *(structure image)* |

TABLE 1-continued
| Cpd No | Structure |
|---|---|
| 44 | 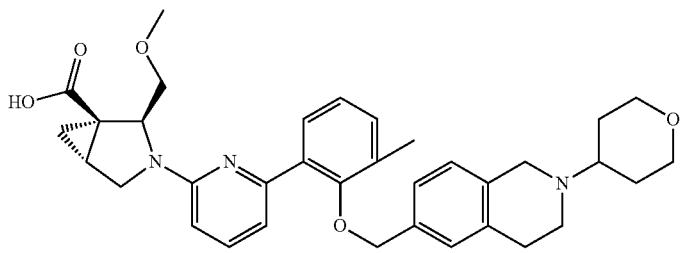 |
| 45 | 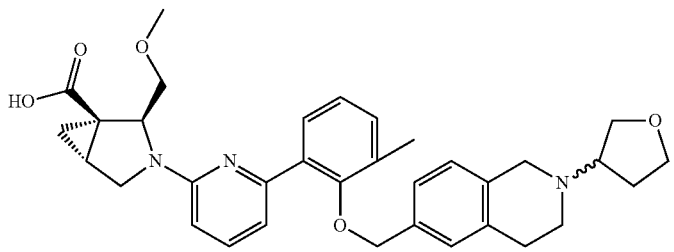 [SMILES: COC[C@H]1N(c2cccc(-c3cccc(C)c3OCc3ccc4c(c3)CCN(C3CCOC3)C4)n2)C[C@@H]2C[C@@]21C(=O)O] |
| 46 | 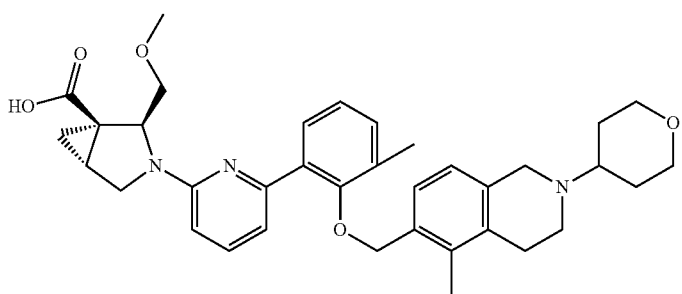 [SMILES: COC[C@H]1N(c2cccc(-c3cccc(C)c3OCc3ccc4c(c3C)CCN(C3CCOCC3)C4)n2)C[C@@H]2C[C@@]21C(=O)O] |
| 47 | 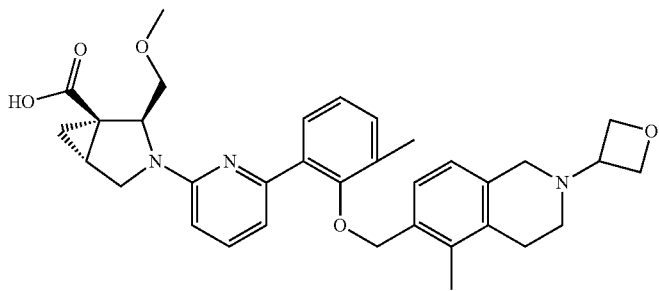 [SMILES: COC[C@H]1N(c2cccc(-c3cccc(C)c3OCc3ccc4c(c3C)CCN(C3COC3)C4)n2)C[C@@H]2C[C@@]21C(=O)O] |
| 48 | 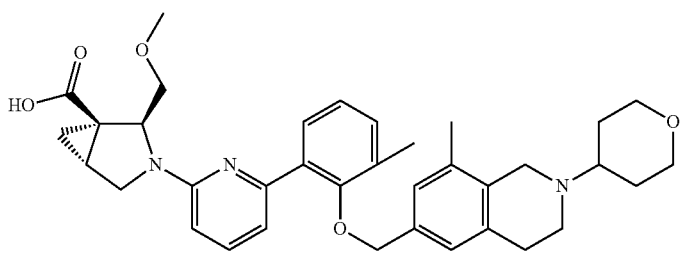 [SMILES: COC[C@H]1N(c2cccc(-c3cccc(C)c3OCc3cc(C)c4c(c3)CCN(C3CCOCC3)C4)n2)C[C@@H]2C[C@@]21C(=O)O] |

TABLE 1-continued

| Cpd No | Structure |
|---|---|
| 49 | 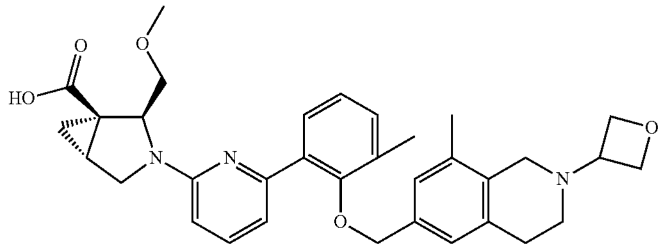 [SMILES: COC[C@H]1N(c2cccc(-c3cccc(C)c3OCc3cc(C)c4c(c3)CCN(C3COC3)C4)n2)C[C@@H]2C[C@@]21C(=O)O] |
| 50 | 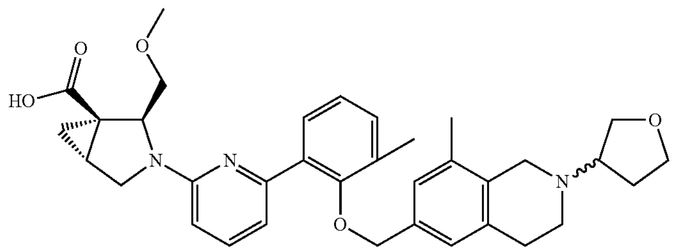 [SMILES: COC[C@H]1N(c2cccc(-c3cccc(C)c3OCc3cc(C)c4c(c3)CCN(C3CCOC3)C4)n2)C[C@@H]2C[C@@]21C(=O)O] |
| 51 | 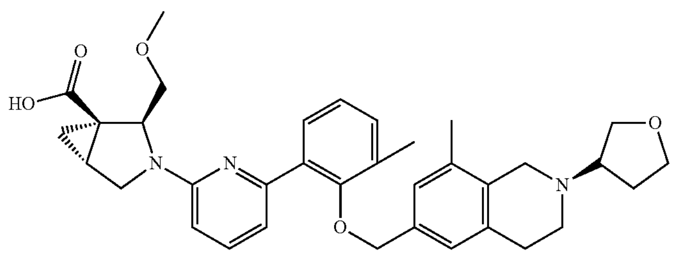 |
| 52 | 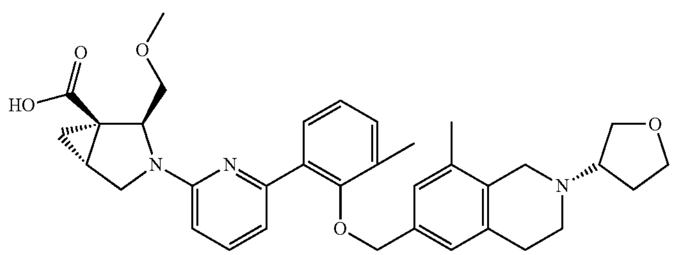 |
| 53 | 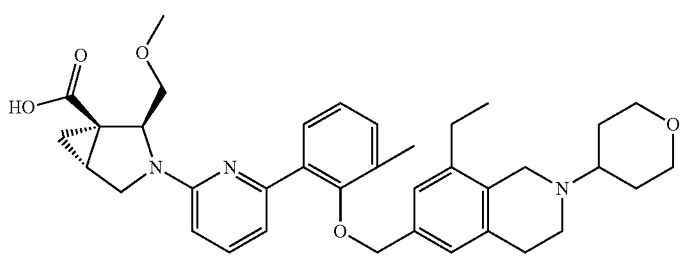 [SMILES: CCc1cc(COc2c(C)cccc2-c2cccc(N3C[C@@H]4C[C@]4(C(=O)O)[C@H]3COC)n2)cc2c1CN(C1CCOCC1)CC2] |
| 54 | 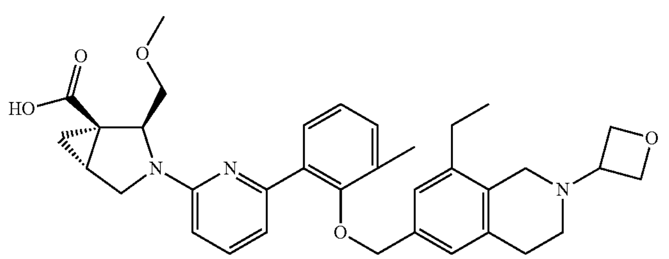 |

TABLE 1-continued

| Cpd No | Structure |
|---|---|
| 55 | 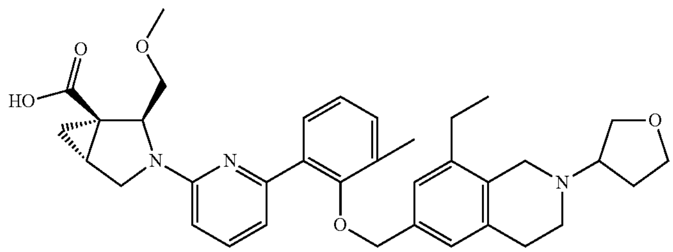 [SMILES: CCc1cc(COc2c(C)cccc2-c2cccc(N3C[C@@H]4C[C@]4(C(=O)O)[C@H]3COC)n2)cc2c1CN(C1CCOC1)CC2] |
| 56 | 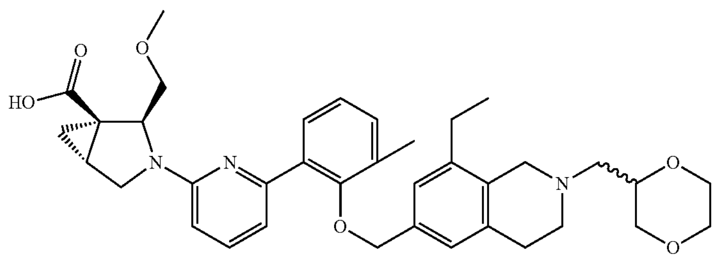 [SMILES: CCc1cc(COc2c(C)cccc2-c2cccc(N3C[C@@H]4C[C@]4(C(=O)O)[C@H]3COC)n2)cc2c1CN(CC1COCCO1)CC2] |
| 57 | 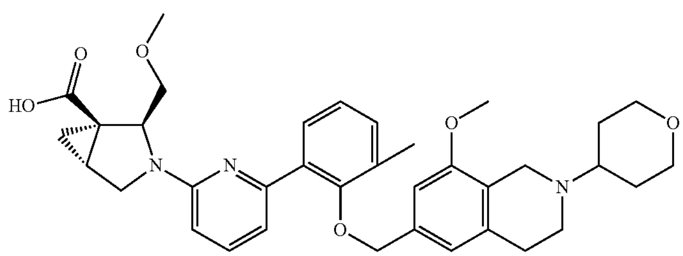 |
| 58 | 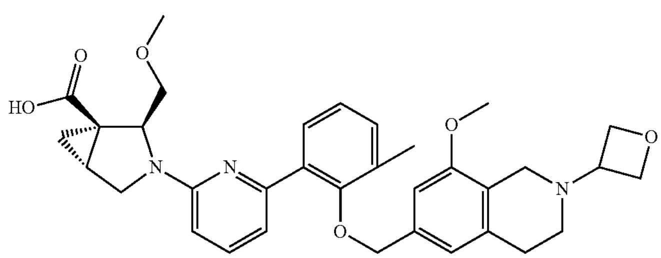 |
| 59 | 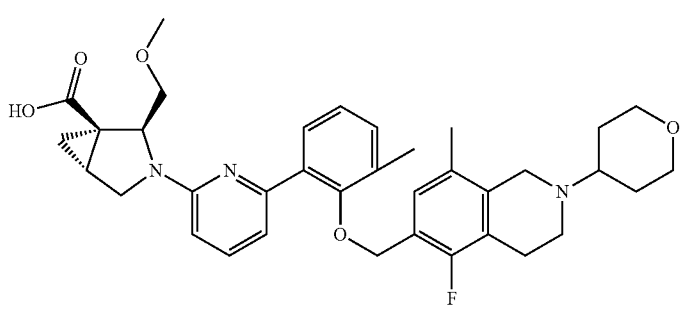 [SMILES: COC[C@H]1N(c2cccc(-c3cccc(C)c3OCc3cc(C)c4c(c3F)CCN(C3CCOCC3)C4)n2)C[C@@H]2C[C@@]21C(=O)O] |

TABLE 1-continued
| Cpd No | Structure |
|---|---|
| 60 | 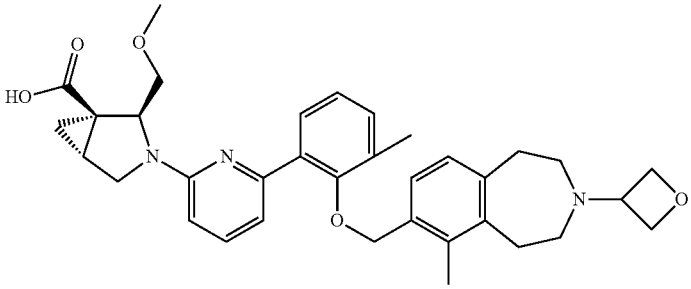 [SMILES: COC[C@H]1N(c2cccc(-c3cccc(C)c3OCc3ccc4c(c3C)CCN(C3COC3)CC4)n2)C[C@@H]2C[C@@]21C(=O)O] |
| 61 | 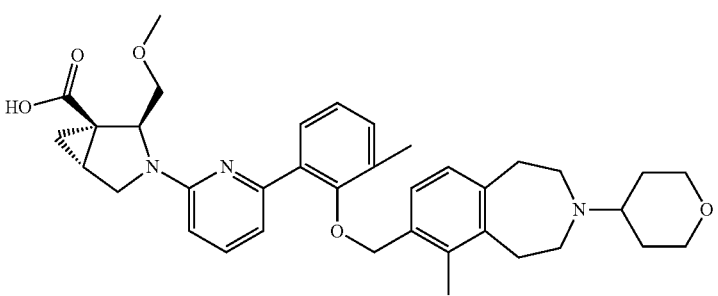 [SMILES: COC[C@H]1N(c2cccc(-c3cccc(C)c3OCc3ccc4c(c3C)CCN(C3CCOCC3)CC4)n2)C[C@@H]2C[C@@]21C(=O)O] |
| 62 | 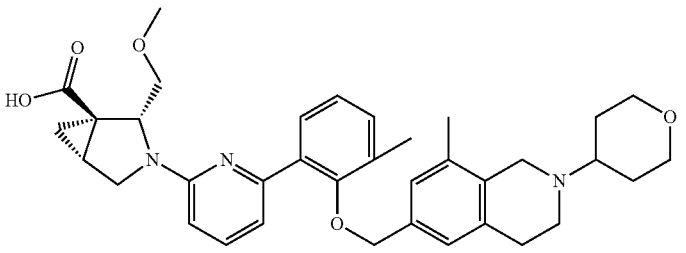 [SMILES: COC[C@@H]1N(c2cccc(-c3cccc(C)c3OCc3cc(C)c4c(c3)CCN(C3CCOCC3)C4)n2)C[C@@H]2C[C@@]21C(=O)O] |
| 63 | 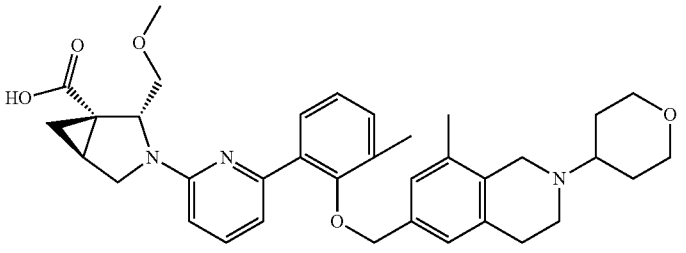 [SMILES: COC[C@@H]1N(c2cccc(-c3cccc(C)c3OCc3cc(C)c4c(c3)CCN(C3CCOCC3)C4)n2)C[C@H]2C[C@]21C(=O)O] |
| 64 | 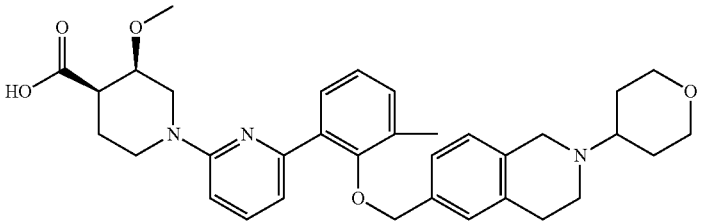 |

TABLE 1-continued
| Cpd No | Structure |
|---|---|
| 65 | 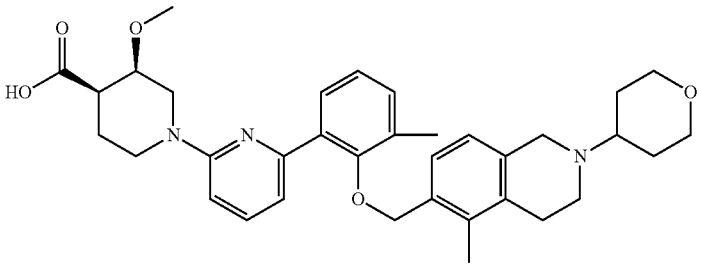 [SMILES: CO[C@H]1CN(c2cccc(-c3cccc(C)c3OCc3ccc4c(c3C)CCN(C3CCOCC3)C4)n2)CC[C@H]1C(=O)O] |
| 66 | 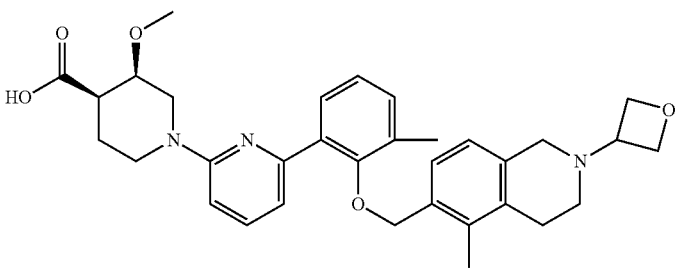 [SMILES: CO[C@H]1CN(c2cccc(-c3cccc(C)c3OCc3ccc4c(c3C)CCN(C3COC3)C4)n2)CC[C@H]1C(=O)O] |
| 67 | 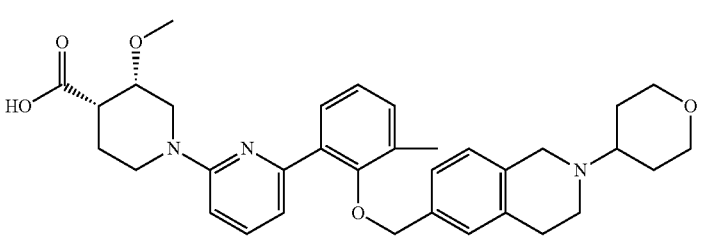 [SMILES: CO[C@@H]1CN(c2cccc(-c3cccc(C)c3OCc3ccc4c(c3)CCN(C3CCOCC3)C4)n2)CC[C@@H]1C(=O)O] |
| 68 | 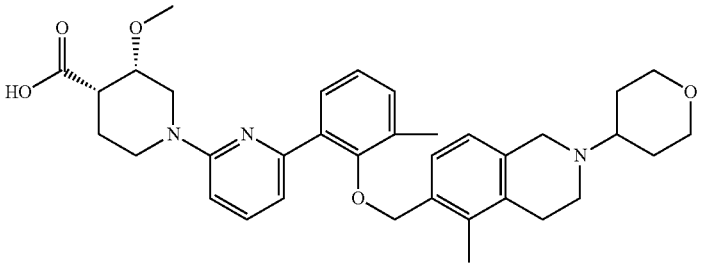 [SMILES: CO[C@@H]1CN(c2cccc(-c3cccc(C)c3OCc3ccc4c(c3C)CCN(C3CCOCC3)C4)n2)CC[C@@H]1C(=O)O] |
| 69 | 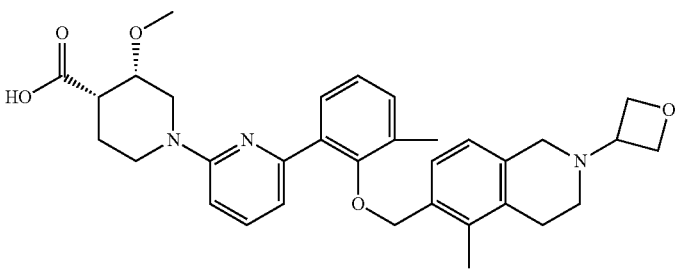 [SMILES: CO[C@@H]1CN(c2cccc(-c3cccc(C)c3OCc3ccc4c(c3C)CCN(C3COC3)C4)n2)CC[C@@H]1C(=O)O] |
| 70 | 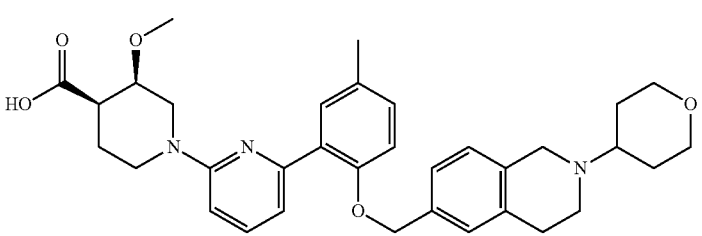 [SMILES: CO[C@H]1CN(c2cccc(-c3cc(C)ccc3OCc3ccc4c(c3)CCN(C3CCOCC3)C4)n2)CC[C@H]1C(=O)O] |

TABLE 1-continued

| Cpd No | Structure |
|---|---|
| 71 | (structure) |
| 72 | (structure) |
| 73 | (structure) |
| 74 | (structure) |
| 75 | (structure) |
| 76 | (structure) |

TABLE 1-continued
| Cpd No | Structure |
|---|---|
| 77 | 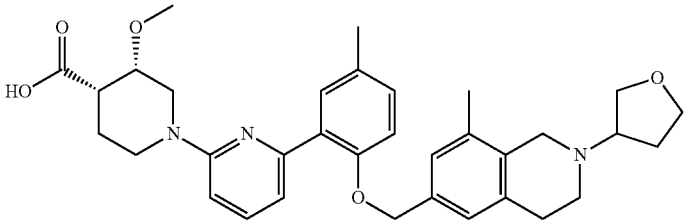 [SMILES: CO[C@@H]1CN(c2cccc(-c3cc(C)ccc3OCc3cc(C)c4c(c3)CCN(C3CCOC3)C4)n2)CC[C@@H]1C(=O)O] |
| 78 | 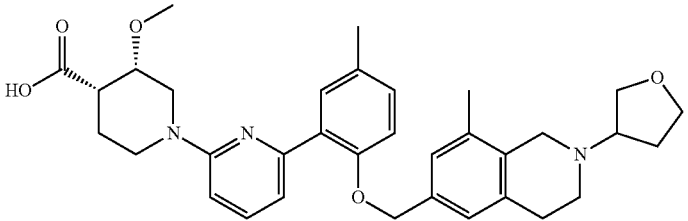 [SMILES: CO[C@@H]1CN(c2cccc(-c3cc(C)ccc3OCc3cc(C)c4c(c3)CCN(C3CCOC3)C4)n2)CC[C@@H]1C(=O)O] |
| 79 | 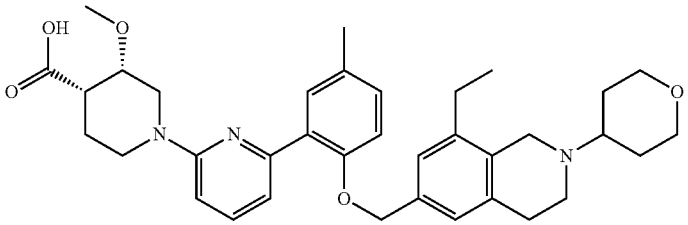 [SMILES: CCc1cc(COc2ccc(C)cc2-c2cccc(N3CC[C@H](C(=O)O)[C@H](OC)C3)n2)cc2c1CN(C1CCOCC1)CC2] |
| 80 | 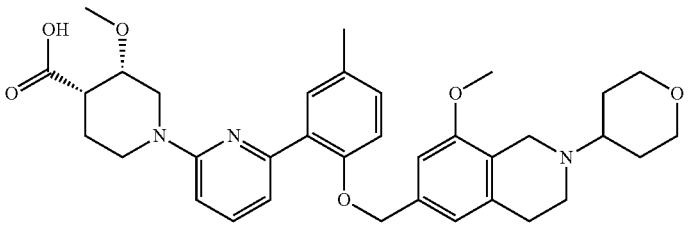 [SMILES: COc1cc(COc2ccc(C)cc2-c2cccc(N3CC[C@H](C(=O)O)[C@H](OC)C3)n2)cc2c1CN(C1CCOCC1)CC2] |
| 81 | 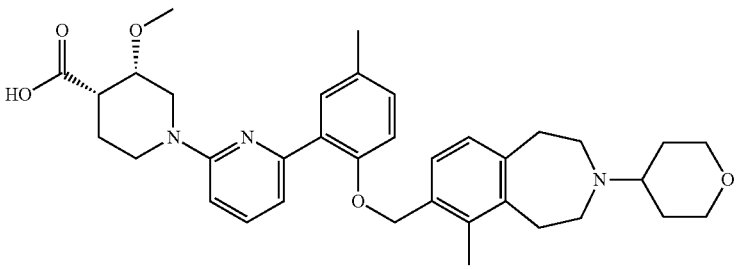 |
| 82 | 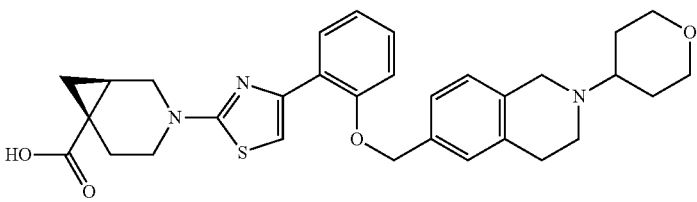 |

TABLE 1-continued

| Cpd No | Structure |
|---|---|
| 83 | 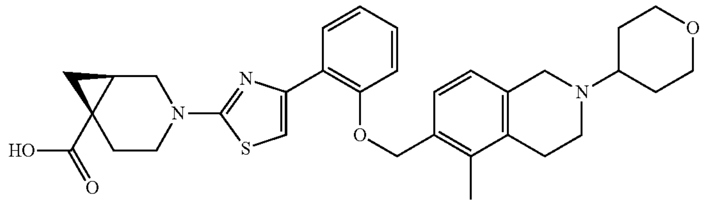 [SMILES: Cc1c(COc2ccccc2-c2csc(N3CC[C@@]4(C(=O)O)C[C@H]4C3)n2)ccc2c1CCN(C1CCOCC1)C2] |
| 84 | 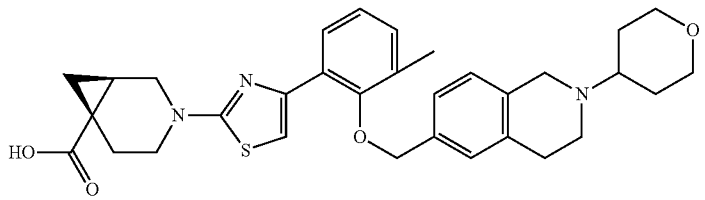 [SMILES: Cc1cccc(-c2csc(N3CC[C@@]4(C(=O)O)C[C@H]4C3)n2)c1OCc1ccc2c(c1)CCN(C1CCOCC1)C2] |
| 85 | 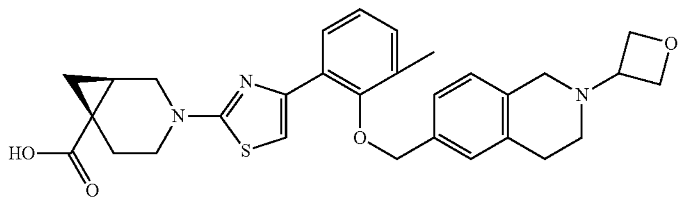 |
| 86 | 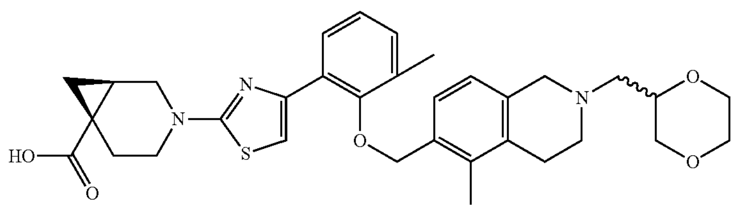 [SMILES: Cc1cccc(-c2csc(N3CC[C@@]4(C(=O)O)C[C@H]4C3)n2)c1OCc1ccc2c(c1C)CCN(CC1COCCO1)C2] |
| 87 | 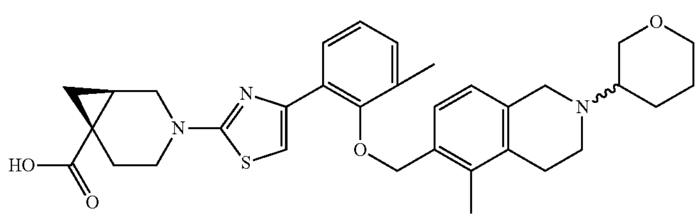 [SMILES: Cc1cccc(-c2csc(N3CC[C@@]4(C(=O)O)C[C@H]4C3)n2)c1OCc1ccc2c(c1C)CCN(C1CCCOC1)C2] |
| 88 | 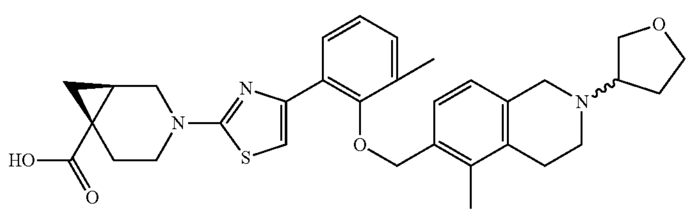 [SMILES: Cc1cccc(-c2csc(N3CC[C@@]4(C(=O)O)C[C@H]4C3)n2)c1OCc1ccc2c(c1C)CCN(C1CCOC1)C2] |
| 89 | 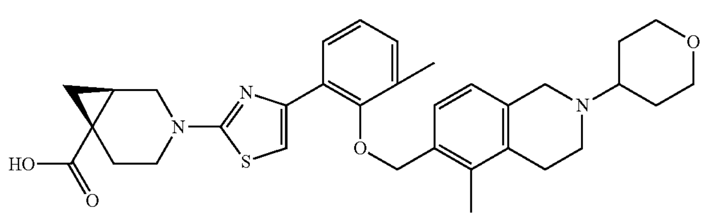 |

TABLE 1-continued

| Cpd No | Structure |
|---|---|
| 90 | 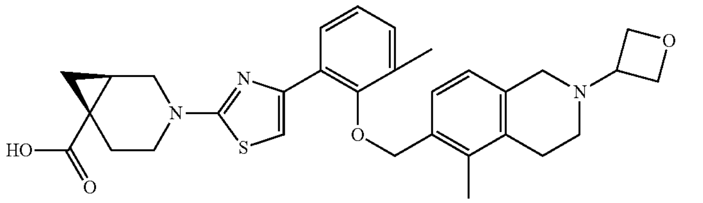 [SMILES: Cc1cccc(-c2csc(N3CC[C@@]4(C(=O)O)C[C@H]4C3)n2)c1OCc1ccc2c(c1C)CCN(C1COC1)C2] |
| 91 | 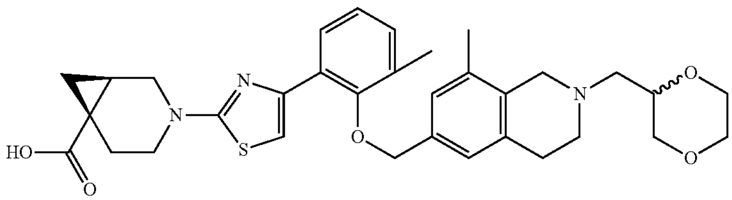 [SMILES: Cc1cc(COc2c(C)cccc2-c2csc(N3CC[C@@]4(C(=O)O)C[C@H]4C3)n2)cc2c1CN(CC1COCCO1)CC2] |
| 92 | 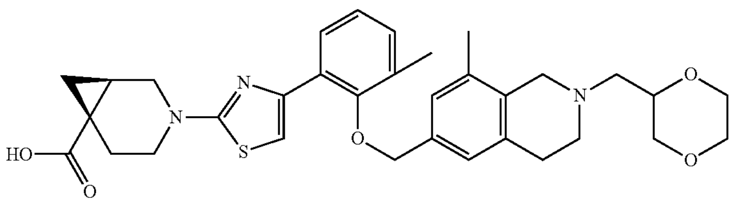 [SMILES: Cc1cc(COc2c(C)cccc2-c2csc(N3CC[C@@]4(C(=O)O)C[C@H]4C3)n2)cc2c1CN(CC1COCCO1)CC2] |
| 93 | 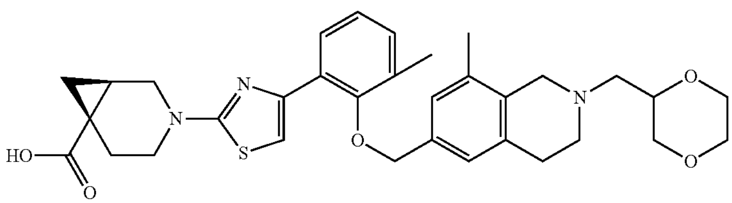 [SMILES: Cc1cc(COc2c(C)cccc2-c2csc(N3CC[C@@]4(C(=O)O)C[C@H]4C3)n2)cc2c1CN(CC1COCCO1)CC2] |
| 94 | 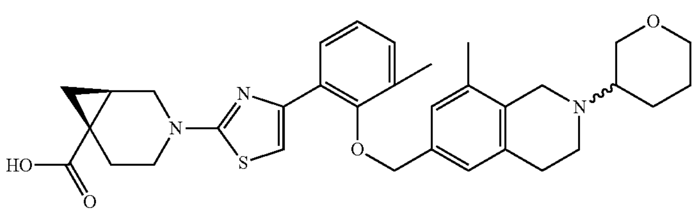 [SMILES: Cc1cc(COc2c(C)cccc2-c2csc(N3CC[C@@]4(C(=O)O)C[C@H]4C3)n2)cc2c1CN(C1CCCOC1)CC2] |
| 95 | 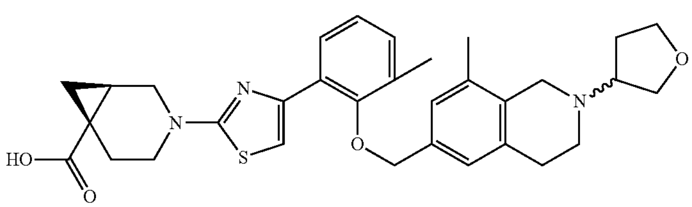 [SMILES: Cc1cc(COc2c(C)cccc2-c2csc(N3CC[C@@]4(C(=O)O)C[C@H]4C3)n2)cc2c1CN(C1CCOC1)CC2] |
| 96 | 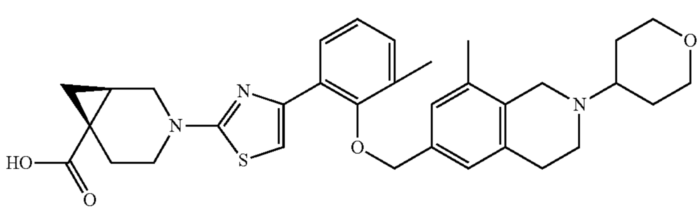 [SMILES: Cc1cc(COc2c(C)cccc2-c2csc(N3CC[C@@]4(C(=O)O)C[C@H]4C3)n2)cc2c1CN(C1CCOCC1)CC2] |

TABLE 1-continued

| Cpd No | Structure |
|---|---|
| 97 | 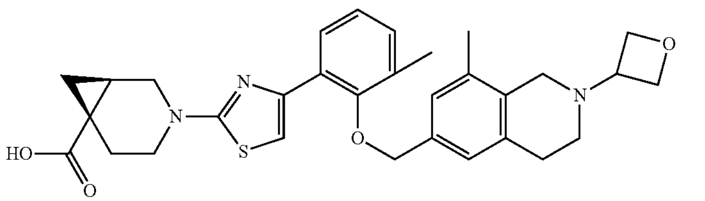 [SMILES: Cc1cc(COc2c(C)cccc2-c2csc(N3CC[C@@]4(C(=O)O)C[C@H]4C3)n2)cc2c1CN(C1COC1)CC2] |
| 98 | 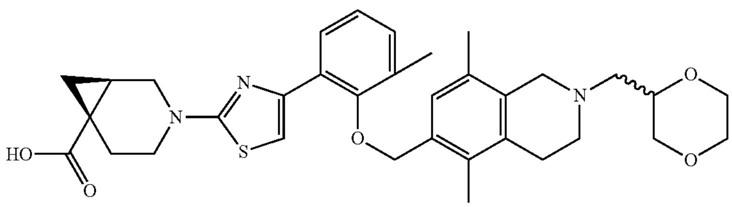 |
| 99 | 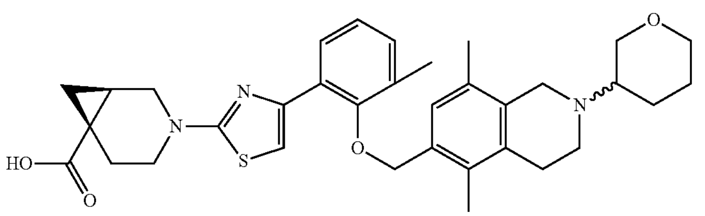 [SMILES: Cc1cc(COc2c(C)cccc2-c2csc(N3CC[C@@]4(C(=O)O)C[C@H]4C3)n2)c(C)c2c1CN(C1CCCOC1)CC2] |
| 100 | 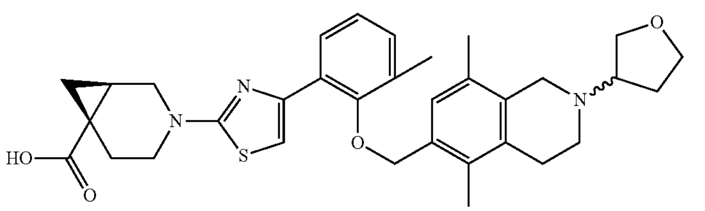 [SMILES: Cc1cc(COc2c(C)cccc2-c2csc(N3CC[C@@]4(C(=O)O)C[C@H]4C3)n2)c(C)c2c1CN(C1CCOC1)CC2] |
| 101 | 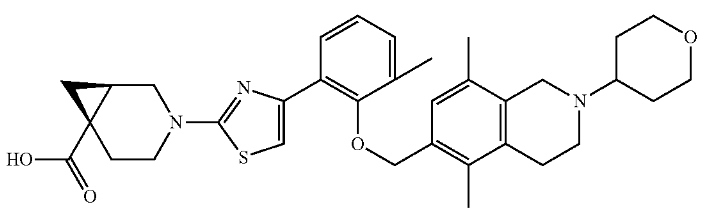 |
| 102 | 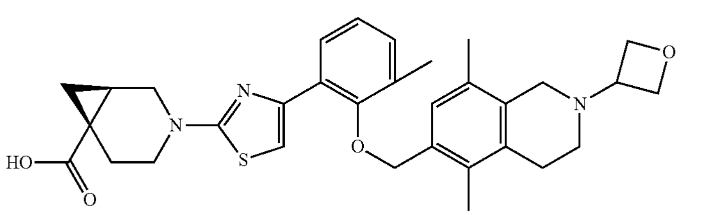 [SMILES: Cc1cc(COc2c(C)cccc2-c2csc(N3CC[C@@]4(C(=O)O)C[C@H]4C3)n2)c(C)c2c1CN(C1COC1)CC2] |
| 103 | 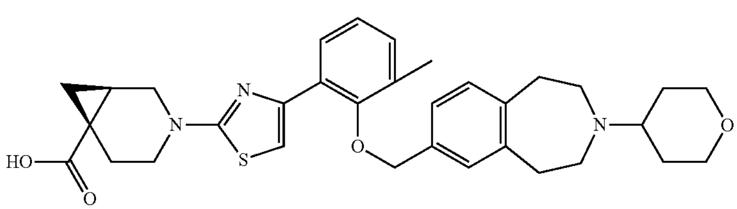 [SMILES: Cc1cccc(-c2csc(N3CC[C@@]4(C(=O)O)C[C@H]4C3)n2)c1OCc1ccc2c(c1)CCN(C1CCOCC1)CC2] |

TABLE 1-continued
| Cpd No | Structure |
|---|---|
| 104 | 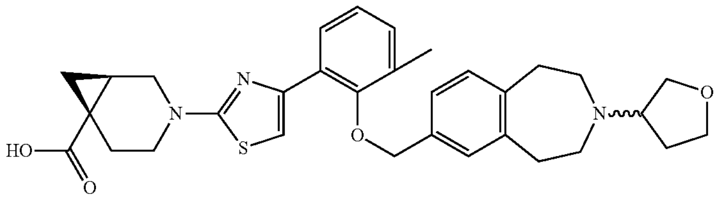 [SMILES: Cc1cccc(-c2csc(N3CC[C@@]4(C(=O)O)C[C@H]4C3)n2)c1OCc1ccc2c(c1)CCN(C1CCOC1)CC2] |
| 105 | 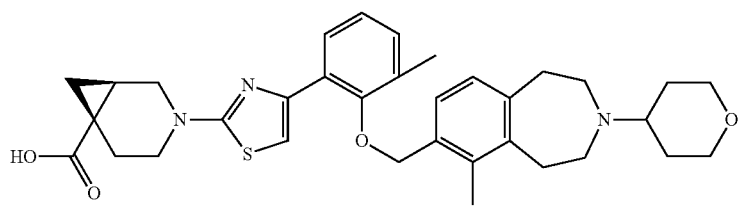 [SMILES: Cc1cccc(-c2csc(N3CC[C@@]4(C(=O)O)C[C@H]4C3)n2)c1OCc1ccc2c(c1C)CCN(C1CCOCC1)CC2] |
| 106 | 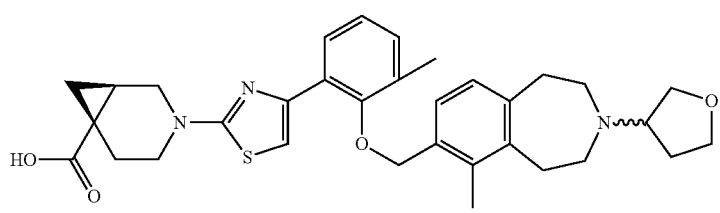 [SMILES: Cc1cccc(-c2csc(N3CC[C@@]4(C(=O)O)C[C@H]4C3)n2)c1OCc1ccc2c(c1C)CCN(C1CCOC1)CC2] |
| 107 | 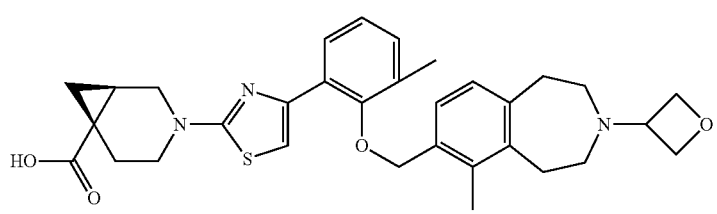 [SMILES: Cc1cccc(-c2csc(N3CC[C@@]4(C(=O)O)C[C@H]4C3)n2)c1OCc1ccc2c(c1C)CCN(C1COC1)CC2] |
| 108 | 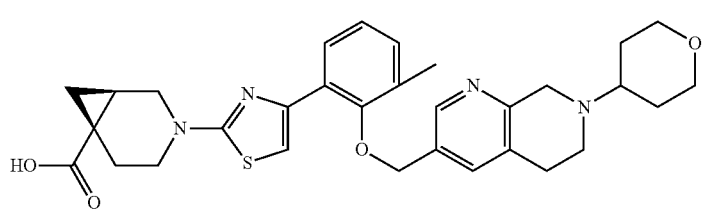 [SMILES: Cc1cccc(-c2csc(N3CC[C@@]4(C(=O)O)C[C@H]4C3)n2)c1OCc1cnc2c(c1)CCN(C1CCOCC1)C2] |
| 109 | 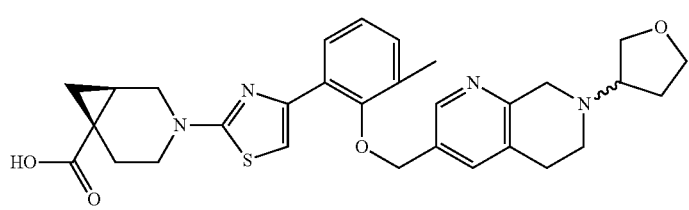 [SMILES: Cc1cccc(-c2csc(N3CC[C@@]4(C(=O)O)C[C@H]4C3)n2)c1OCc1cnc2c(c1)CCN(C1CCOC1)C2] |
| 110 | 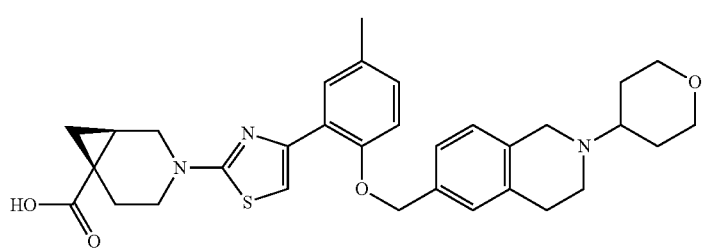 [SMILES: Cc1ccc(OCc2ccc3c(c2)CCN(C2CCOCC2)C3)c(-c2csc(N3CC[C@@]4(C(=O)O)C[C@H]4C3)n2)c1] |

TABLE 1-continued
| Cpd No | Structure |
|---|---|
| 111 | 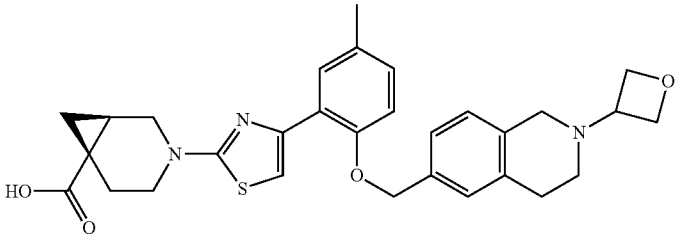 [SMILES: Cc1ccc(OCc2ccc3c(c2)CCN(C2COC2)C3)c(-c2csc(N3CC[C@@]4(C(=O)O)C[C@H]4C3)n2)c1] |
| 112 | 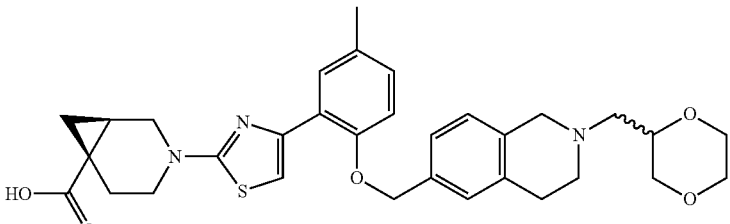 |
| 113 | 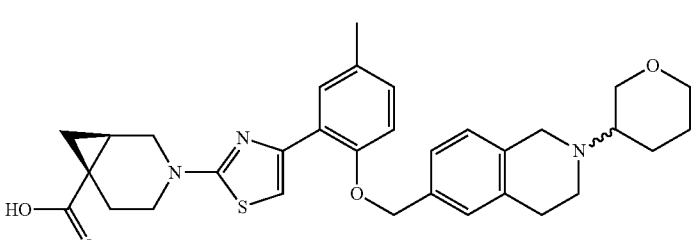 |
| 114 | 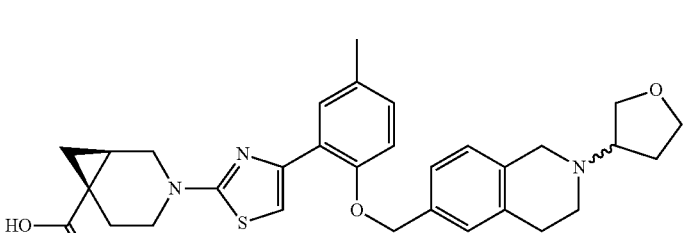 |
| 115 | 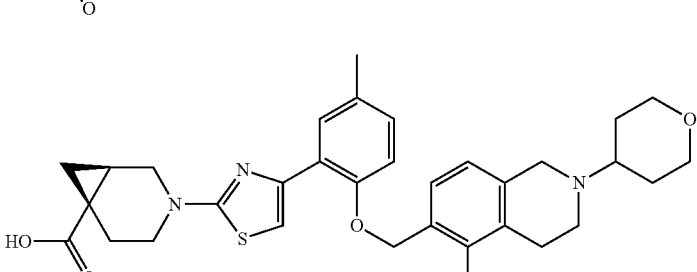 |
| 116 | 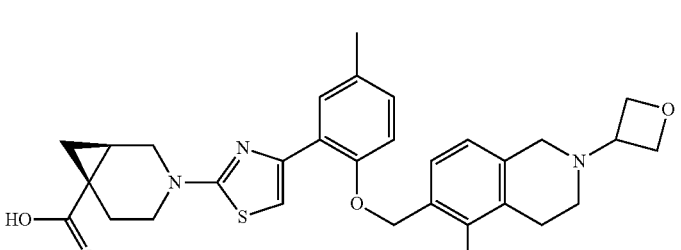 |

TABLE 1-continued
| Cpd No | Structure |
|---|---|
| 117 | 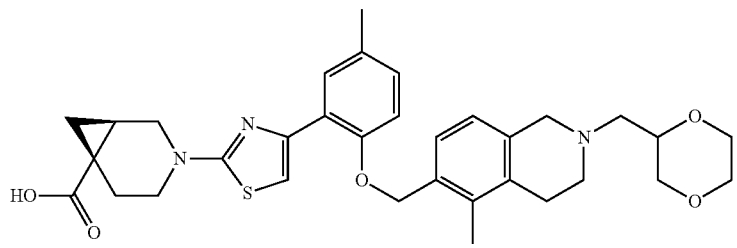 [SMILES: Cc1ccc(OCc2ccc3c(c2C)CCN(CC2COCCO2)C3)c(-c2csc(N3CC[C@@]4(C(=O)O)C[C@H]4C3)n2)c1] |
| 118 | 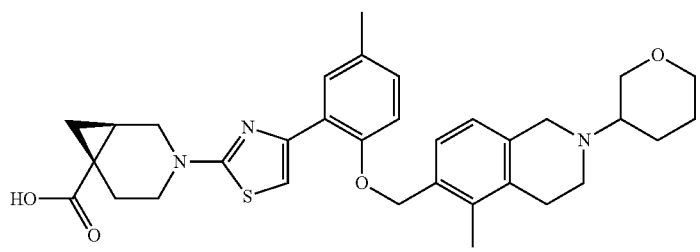 [SMILES: Cc1ccc(OCc2ccc3c(c2C)CCN(C2CCCOC2)C3)c(-c2csc(N3CC[C@@]4(C(=O)O)C[C@H]4C3)n2)c1] |
| 119 | 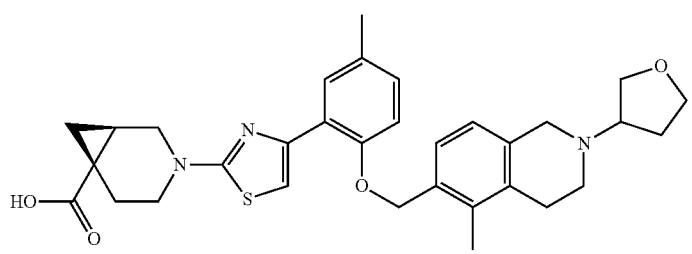 [SMILES: Cc1ccc(OCc2ccc3c(c2C)CCN(C2CCOC2)C3)c(-c2csc(N3CC[C@@]4(C(=O)O)C[C@H]4C3)n2)c1] |
| 120 | 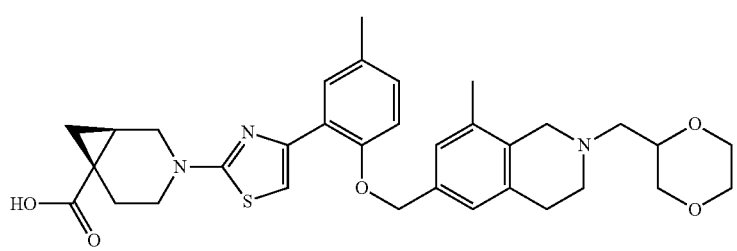 [SMILES: Cc1ccc(OCc2cc(C)c3c(c2)CCN(CC2COCCO2)C3)c(-c2csc(N3CC[C@@]4(C(=O)O)C[C@H]4C3)n2)c1] |
| 121 | 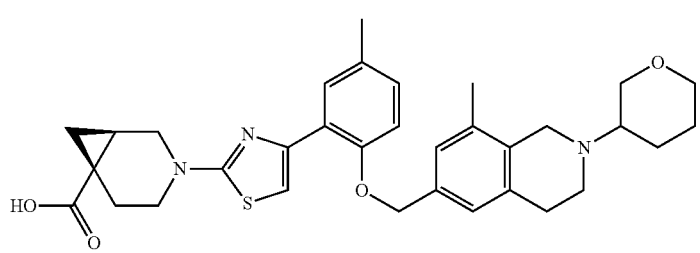 [SMILES: Cc1ccc(OCc2cc(C)c3c(c2)CCN(C2CCCOC2)C3)c(-c2csc(N3CC[C@@]4(C(=O)O)C[C@H]4C3)n2)c1] |
| 122 | 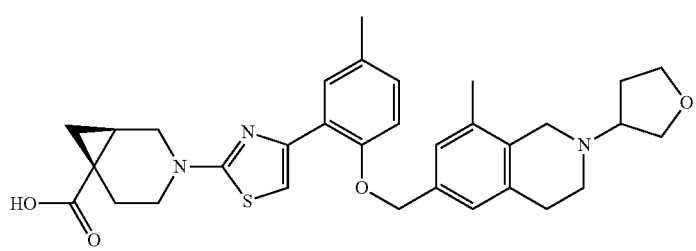 [SMILES: Cc1ccc(OCc2cc(C)c3c(c2)CCN(C2CCOC2)C3)c(-c2csc(N3CC[C@@]4(C(=O)O)C[C@H]4C3)n2)c1] |

US 9,353,090 B2
TABLE 1-continued
| Cpd No | Structure |
|---|---|
| 123 | 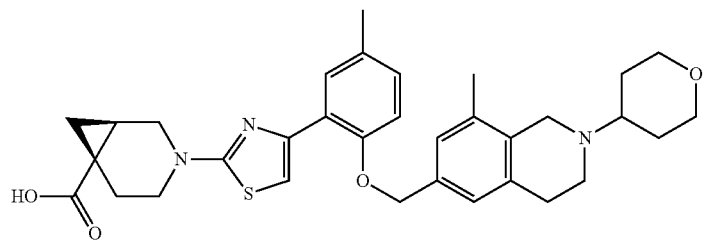 [SMILES: Cc1ccc(OCc2cc(C)c3c(c2)CCN(C2CCOCC2)C3)c(-c2csc(N3CC[C@@]4(C(=O)O)C[C@H]4C3)n2)c1] |
| 124 | 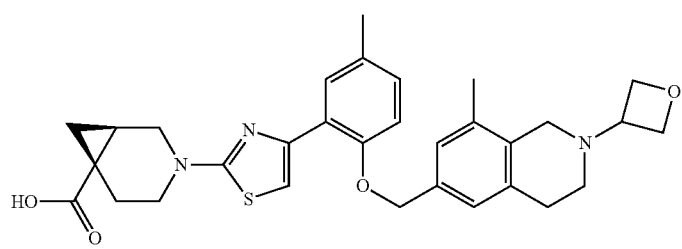 [SMILES: Cc1ccc(OCc2cc(C)c3c(c2)CCN(C2COC2)C3)c(-c2csc(N3CC[C@@]4(C(=O)O)C[C@H]4C3)n2)c1] |
| 125 | 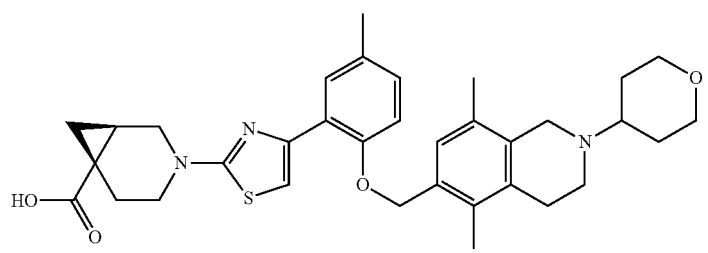 [SMILES: Cc1ccc(OCc2cc(C)c3c(c2C)CCN(C2CCOCC2)C3)c(-c2csc(N3CC[C@@]4(C(=O)O)C[C@H]4C3)n2)c1] |
| 126 | 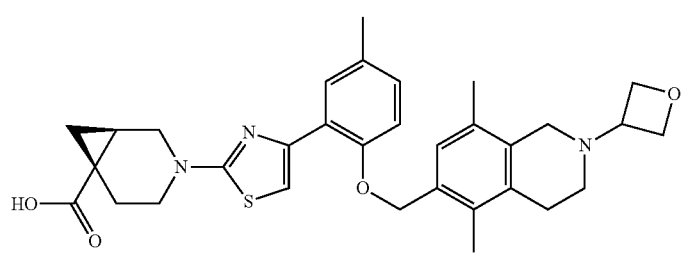 [SMILES: Cc1ccc(OCc2cc(C)c3c(c2C)CCN(C2COC2)C3)c(-c2csc(N3CC[C@@]4(C(=O)O)C[C@H]4C3)n2)c1] |
| 127 | 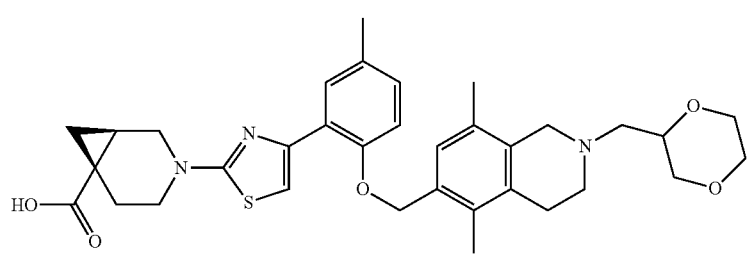 [SMILES: Cc1ccc(OCc2cc(C)c3c(c2C)CCN(CC2COCCO2)C3)c(-c2csc(N3CC[C@@]4(C(=O)O)C[C@H]4C3)n2)c1] |
| 128 | 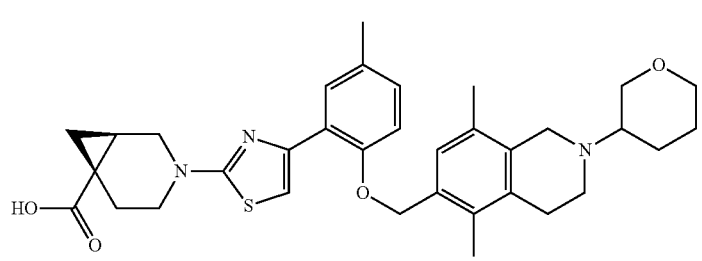 [SMILES: Cc1ccc(OCc2cc(C)c3c(c2C)CCN(C2CCCOC2)C3)c(-c2csc(N3CC[C@@]4(C(=O)O)C[C@H]4C3)n2)c1] |

TABLE 1-continued

| Cpd No | Structure |
|---|---|
| 129 | 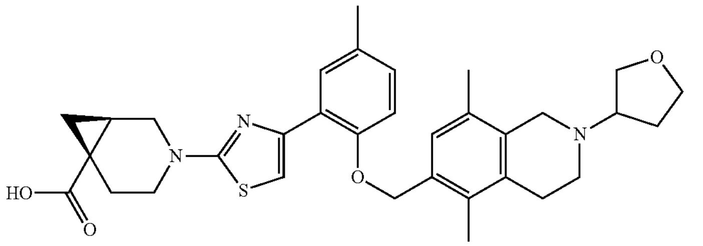 [SMILES: Cc1ccc(OCc2cc(C)c3c(c2C)CCN(C2CCOC2)C3)c(-c2csc(N3CC[C@@]4(C(=O)O)C[C@H]4C3)n2)c1] |
| 130 | 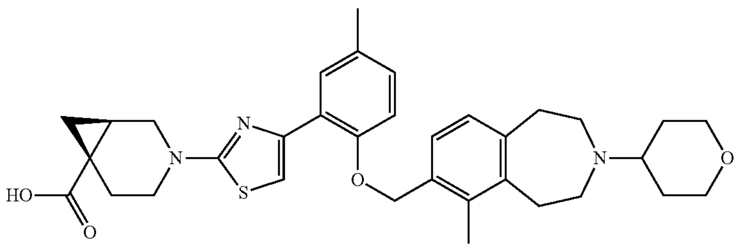 [SMILES: Cc1ccc(OCc2ccc3c(c2C)CCN(C2CCOCC2)CC3)c(-c2csc(N3CC[C@@]4(C(=O)O)C[C@H]4C3)n2)c1] |
| 131 | 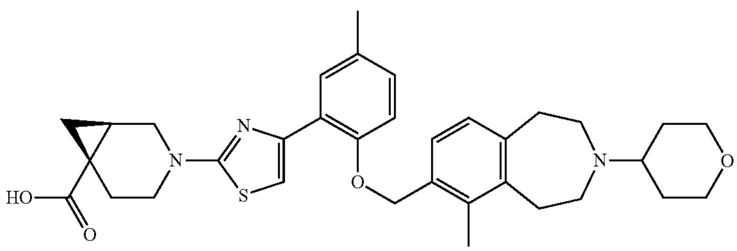 [SMILES: Cc1ccc(OCc2ccc3c(c2C)CCN(C2CCOCC2)CC3)c(-c2csc(N3CC[C@@]4(C(=O)O)C[C@H]4C3)n2)c1] |
| 132 | 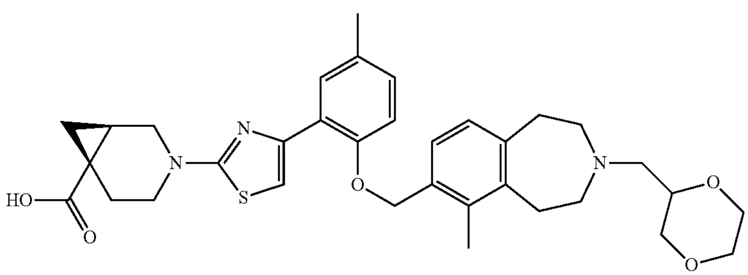 [SMILES: Cc1ccc(OCc2ccc3c(c2C)CCN(CC2COCCO2)CC3)c(-c2csc(N3CC[C@@]4(C(=O)O)C[C@H]4C3)n2)c1] |
| 133 | 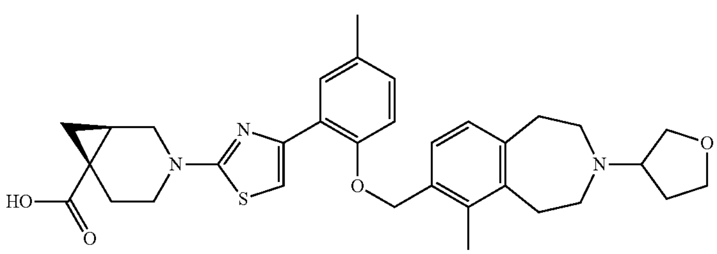 [SMILES: Cc1ccc(OCc2ccc3c(c2C)CCN(C2CCOC2)CC3)c(-c2csc(N3CC[C@@]4(C(=O)O)C[C@H]4C3)n2)c1] |
| 134 | 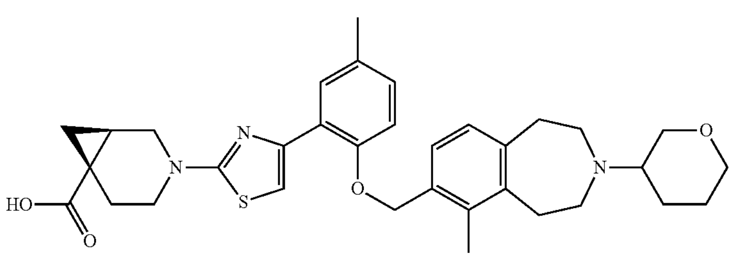 [SMILES: Cc1ccc(OCc2ccc3c(c2C)CCN(C2CCCOC2)CC3)c(-c2csc(N3CC[C@@]4(C(=O)O)C[C@H]4C3)n2)c1] |

TABLE 1-continued

| Cpd No | Structure |
|---|---|
| 135 | (structure) |
| 136 | (structure) |
| 137 | (structure) |
| 138 | (structure) |
| 139 | (structure) |
| 140 | (structure) |
| 141 | (structure) |

TABLE 1-continued

| Cpd No | Structure |
|---|---|
| 142 | 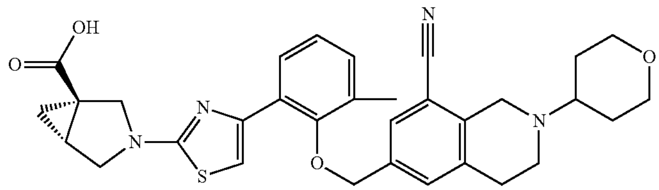 [SMILES: Cc1cccc(-c2csc(N3C[C@@H]4C[C@]4(C(=O)O)C3)n2)c1OCc1cc(C#N)c2c(c1)CCN(C1CCOCC1)C2] |
| 143 | 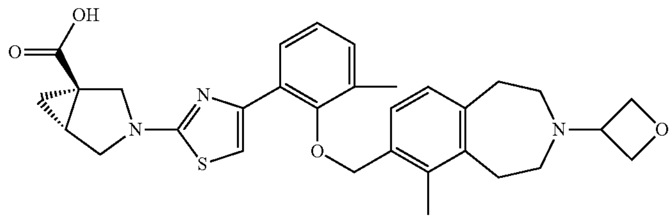 [SMILES: Cc1cccc(-c2csc(N3C[C@@H]4C[C@]4(C(=O)O)C3)n2)c1OCc1ccc2c(c1C)CCN(C1COC1)CC2] |
| 144 | 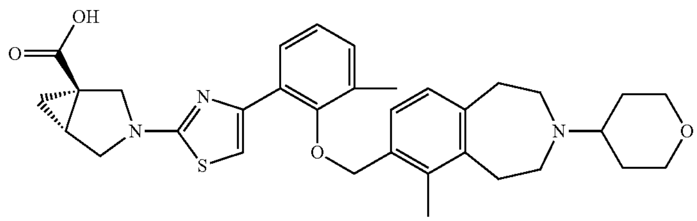 [SMILES: Cc1cccc(-c2csc(N3C[C@@H]4C[C@]4(C(=O)O)C3)n2)c1OCc1ccc2c(c1C)CCN(C1CCOCC1)CC2] |
| 145 | 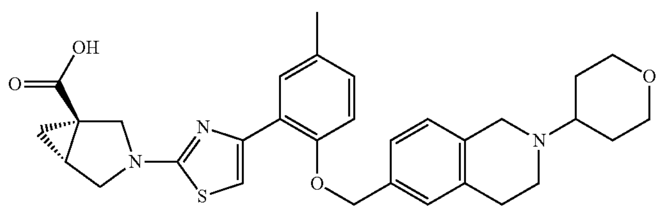 [SMILES: Cc1ccc(OCc2ccc3c(c2)CCN(C2CCOCC2)C3)c(-c2csc(N3C[C@@H]4C[C@]4(C(=O)O)C3)n2)c1] |
| 146 | 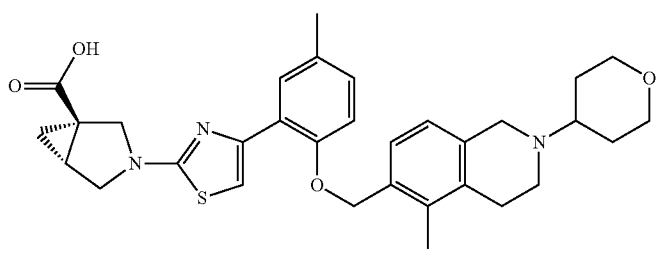 [SMILES: Cc1ccc(OCc2ccc3c(c2C)CCN(C2CCOCC2)C3)c(-c2csc(N3C[C@@H]4C[C@]4(C(=O)O)C3)n2)c1] |
| 147 | 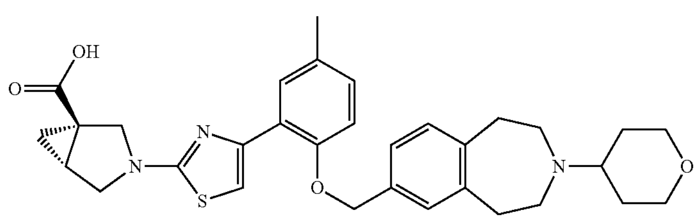 [SMILES: Cc1ccc(OCc2ccc3c(c2)CCN(C2CCOCC2)CC3)c(-c2csc(N3C[C@@H]4C[C@]4(C(=O)O)C3)n2)c1] |
| 148 | 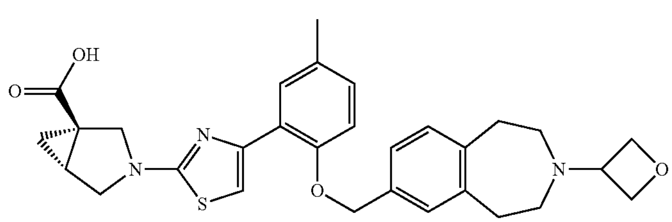 [SMILES: Cc1ccc(OCc2ccc3c(c2)CCN(C2COC2)CC3)c(-c2csc(N3C[C@@H]4C[C@]4(C(=O)O)C3)n2)c1] |

TABLE 1-continued

| Cpd No | Structure |
|---|---|
| 149 | 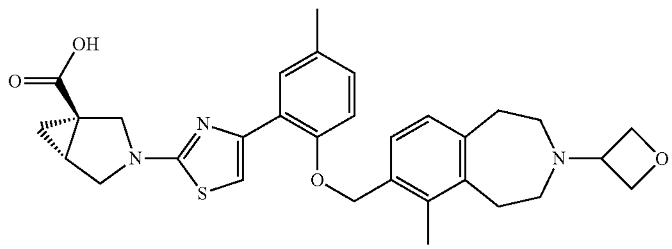 [SMILES: Cc1ccc(OCc2ccc3c(c2C)CCN(C2COC2)CC3)c(-c2csc(N3C[C@@H]4C[C@]4(C(=O)O)C3)n2)c1] |
| 150 | 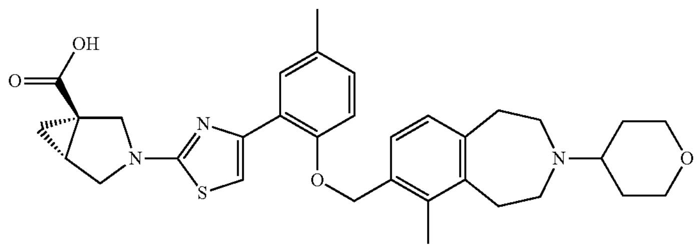 [SMILES: Cc1ccc(OCc2ccc3c(c2C)CCN(C2CCOCC2)CC3)c(-c2csc(N3C[C@@H]4C[C@]4(C(=O)O)C3)n2)c1] |
| 151 | 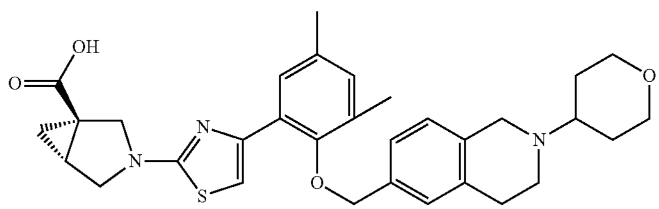 [SMILES: Cc1cc(C)c(OCc2ccc3c(c2)CCN(C2CCOCC2)C3)c(-c2csc(N3C[C@@H]4C[C@]4(C(=O)O)C3)n2)c1] |
| 152 | 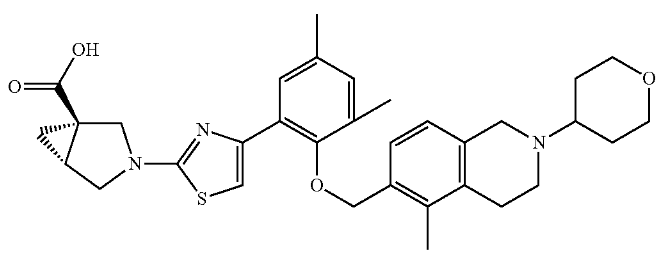 [SMILES: Cc1cc(C)c(OCc2ccc3c(c2C)CCN(C2CCOCC2)C3)c(-c2csc(N3C[C@@H]4C[C@]4(C(=O)O)C3)n2)c1] |
| 153 | 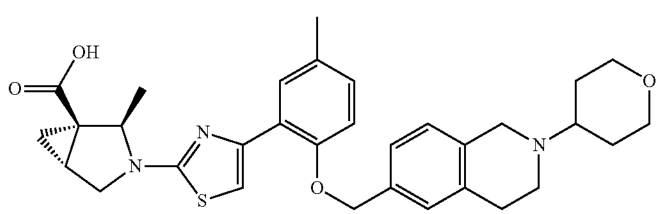 [SMILES: Cc1ccc(OCc2ccc3c(c2)CCN(C2CCOCC2)C3)c(-c2csc(N3C[C@@H]4C[C@]4(C(=O)O)[C@H]3C)n2)c1] |
| 154 | 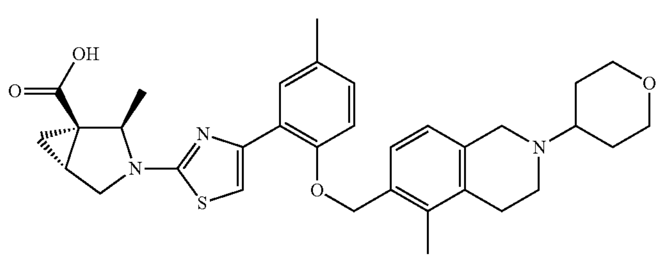 [SMILES: Cc1ccc(OCc2ccc3c(c2C)CCN(C2CCOCC2)C3)c(-c2csc(N3C[C@@H]4C[C@]4(C(=O)O)[C@H]3C)n2)c1] |

TABLE 1-continued

| Cpd No | Structure |
|---|---|
| 155 | 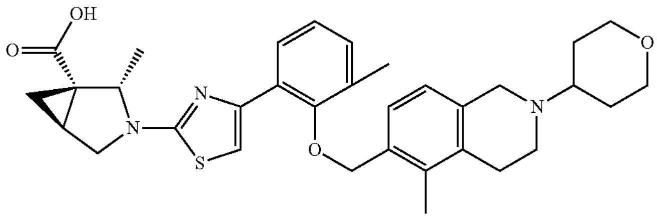 [SMILES: Cc1cccc(-c2csc(N3C[C@H]4C[C@@]4(C(=O)O)[C@@H]3C)n2)c1OCc1ccc2c(c1C)CCN(C1CCOCC1)C2] |
| 156 | 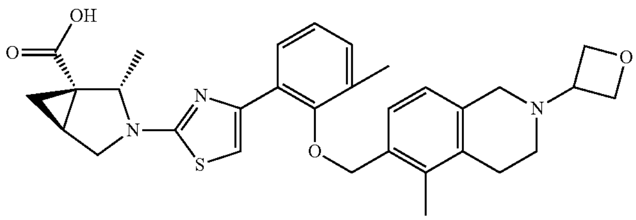 [SMILES: Cc1cccc(-c2csc(N3C[C@H]4C[C@@]4(C(=O)O)[C@@H]3C)n2)c1OCc1ccc2c(c1C)CCN(C1COC1)C2] |
| 157 | 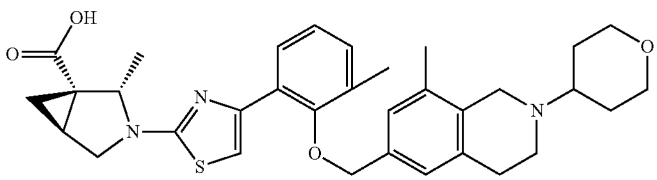 [SMILES: Cc1cc(COc2c(C)cccc2-c2csc(N3C[C@H]4C[C@@]4(C(=O)O)[C@@H]3C)n2)cc2c1CN(C1CCOCC1)CC2] |
| 158 | 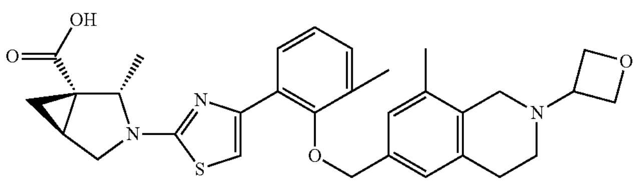 [SMILES: Cc1cc(COc2c(C)cccc2-c2csc(N3C[C@H]4C[C@@]4(C(=O)O)[C@@H]3C)n2)cc2c1CN(C1COC1)CC2] |
| 159 | 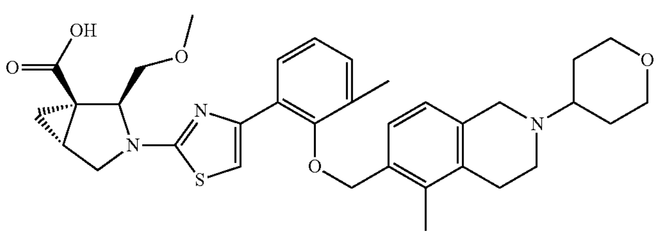 [SMILES: COC[C@H]1N(c2nc(-c3cccc(C)c3OCc3ccc4c(c3C)CCN(C3CCOCC3)C4)cs2)C[C@@H]2C[C@@]21C(=O)O] |
| 160 | 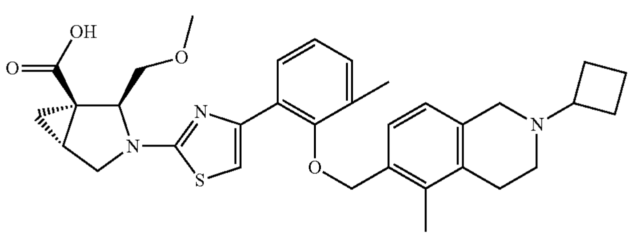 [SMILES: COC[C@H]1N(c2nc(-c3cccc(C)c3OCc3ccc4c(c3C)CCN(C3CCC3)C4)cs2)C[C@@H]2C[C@@]21C(=O)O] |
| 161 | 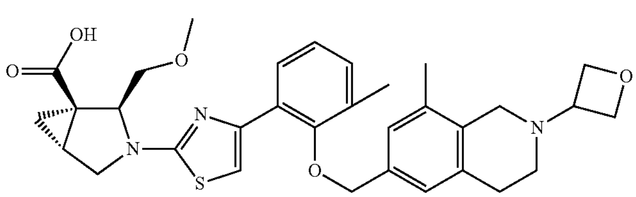 [SMILES: COC[C@H]1N(c2nc(-c3cccc(C)c3OCc3cc(C)c4c(c3)CCN(C3COC3)C4)cs2)C[C@@H]2C[C@@]21C(=O)O] |

TABLE 1-continued

| Cpd No | Structure |
|---|---|
| 162 | *(chemical structure)* |
| 163 | *(chemical structure)* |
| 164 | *(chemical structure)* |
| 165 | *(chemical structure)* |
| 166 | *(chemical structure)* |
| 167 | *(chemical structure)* |
| 168 | *(chemical structure)* |

TABLE 1-continued
| Cpd No | Structure |
|---|---|
| 169 | 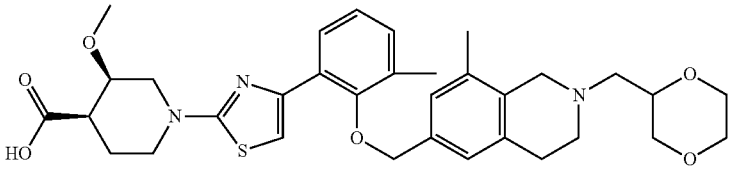 [SMILES: CO[C@H]1CN(c2nc(-c3cccc(C)c3OCc3cc(C)c4c(c3)CCN(CC3COCCO3)C4)cs2)CC[C@H]1C(=O)O] |
| 170 | 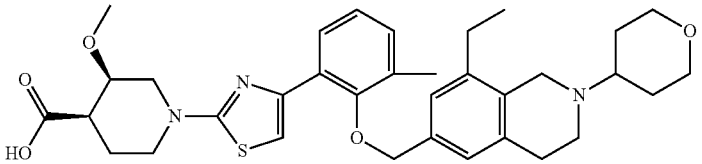 |
| 171 | 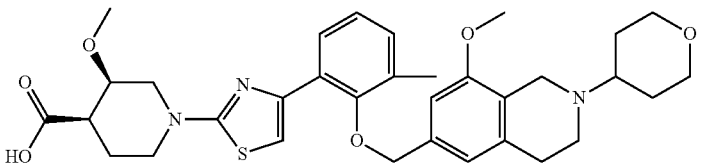 [SMILES: CCc1cc(COc2c(C)cccc2-c2csc(N3CC[C@@H](C(=O)O)[C@@H](OC)C3)n2)cc2c1CN(C1CCOCC1)CC2] |
| 172 | 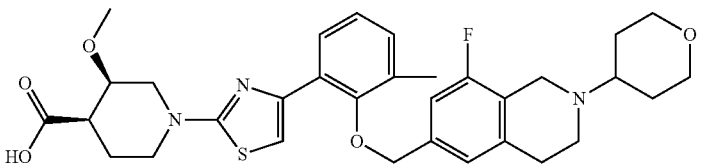 [SMILES: CO[C@H]1CN(c2nc(-c3cccc(C)c3OCc3cc(F)c4c(c3)CCN(C3CCOCC3)C4)cs2)CC[C@H]1C(=O)O] |
| 173 | 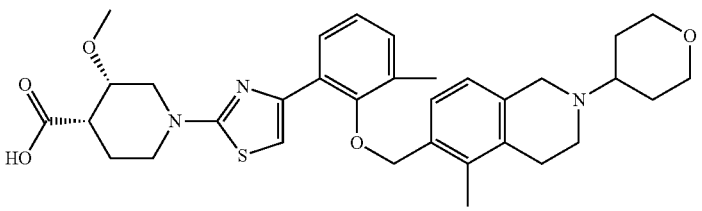 [SMILES: CO[C@@H]1CN(c2nc(-c3cccc(C)c3OCc3ccc4c(c3C)CCN(C3CCOCC3)C4)cs2)CC[C@@H]1C(=O)O] |
| 174 | 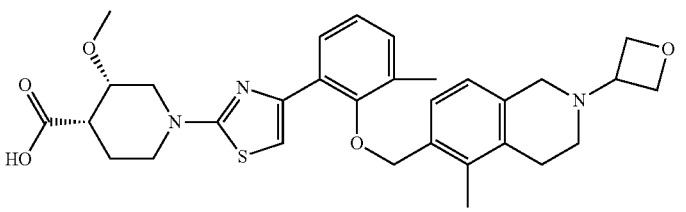 [SMILES: CO[C@@H]1CN(c2nc(-c3cccc(C)c3OCc3ccc4c(c3C)CCN(C3COC3)C4)cs2)CC[C@@H]1C(=O)O] |
| 175 | 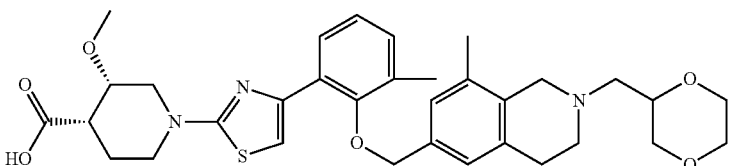 |
| 176 | 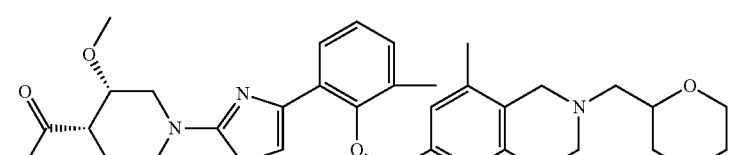 |

TABLE 1-continued
| Cpd No | Structure |
|---|---|
| 177 | 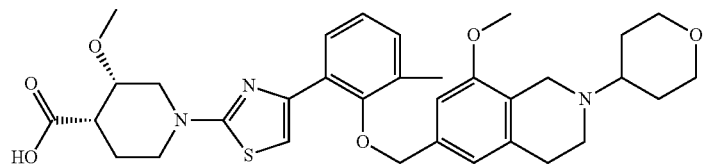 [SMILES: COc1cc(COc2c(C)cccc2-c2csc(N3CC[C@H](C(=O)O)[C@H](OC)C3)n2)cc2c1CN(C1CCOCC1)CC2] |
| 178 | 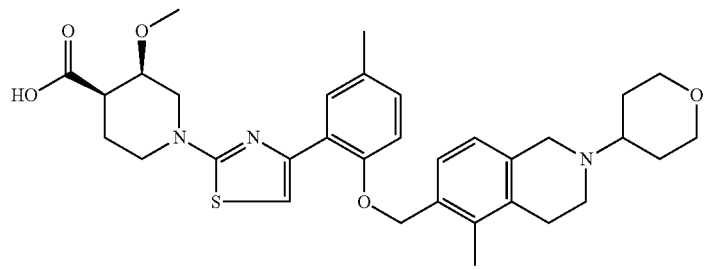 [SMILES: CO[C@H]1CN(c2nc(-c3cc(C)ccc3OCc3ccc4c(c3C)CCN(C3CCOCC3)C4)cs2)CC[C@H]1C(=O)O] |
| 179 | 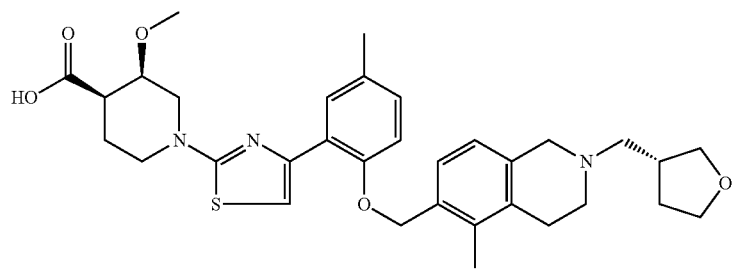 [SMILES: CO[C@H]1CN(c2nc(-c3cc(C)ccc3OCc3ccc4c(c3C)CCN(C[C@H]3CCOC3)C4)cs2)CC[C@H]1C(=O)O] |
| 180 | 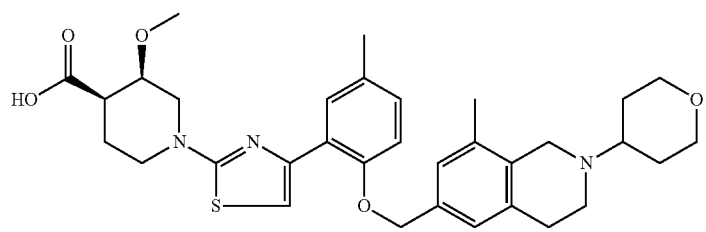 [SMILES: CO[C@H]1CN(c2nc(-c3cc(C)ccc3OCc3cc(C)c4c(c3)CCN(C3CCOCC3)C4)cs2)CC[C@H]1C(=O)O] |
| 181 | 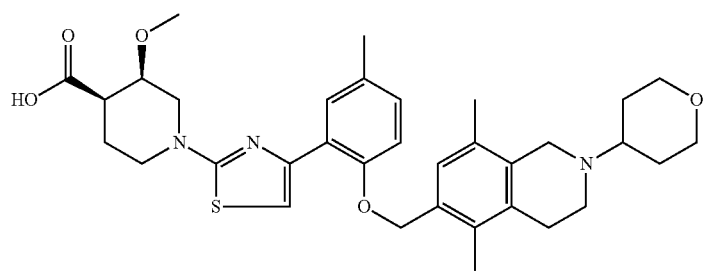 [SMILES: CO[C@H]1CN(c2nc(-c3cc(C)ccc3OCc3cc(C)c4c(c3C)CCN(C3CCOCC3)C4)cs2)CC[C@H]1C(=O)O] |
| 182 | 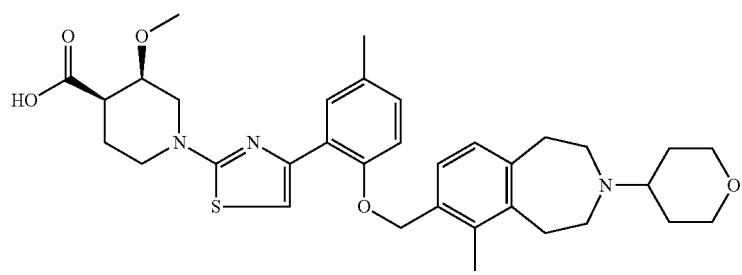 [SMILES: CO[C@H]1CN(c2nc(-c3cc(C)ccc3OCc3ccc4c(c3C)CCN(C3CCOCC3)CC4)cs2)CC[C@H]1C(=O)O] |

TABLE 1-continued

| Cpd No | Structure |
|---|---|
| 183 | 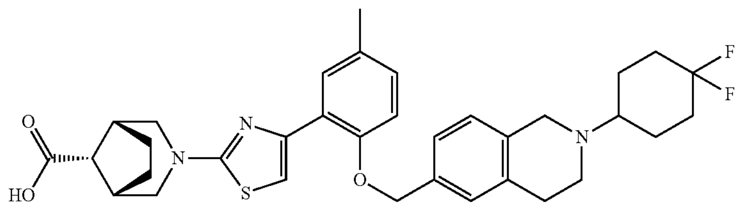 [SMILES: Cc1ccc(OCc2ccc3c(c2)CCN(C2CCC(F)(F)CC2)C3)c(-c2csc(N3C[C@H]4CC[C@@H](C3)[C@H]4C(=O)O)n2)c1] |
| 184 | 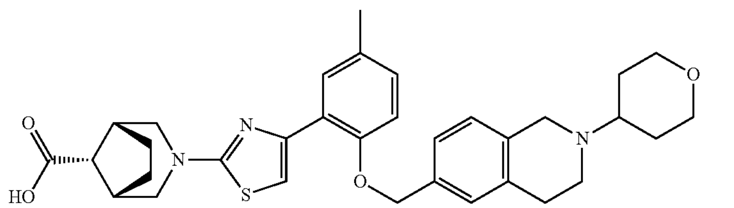 [SMILES: Cc1ccc(OCc2ccc3c(c2)CCN(C2CCOCC2)C3)c(-c2csc(N3C[C@H]4CC[C@@H](C3)[C@H]4C(=O)O)n2)c1] |
| 185 | 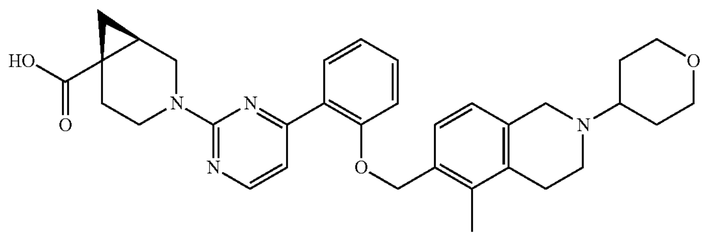 [SMILES: Cc1c(COc2ccccc2-c2ccnc(N3CC[C@@]4(C(=O)O)C[C@H]4C3)n2)ccc2c1CCN(C1CCOCC1)C2] |
| 186 | 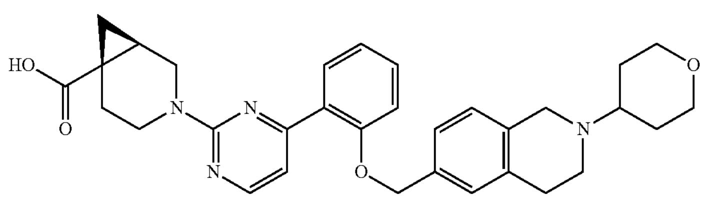 [SMILES: O=C(O)[C@@]12CCN(c3nccc(-c4ccccc4OCc4ccc5c(c4)CCN(C4CCOCC4)C5)n3)C[C@@H]1C2] |
| 187 | 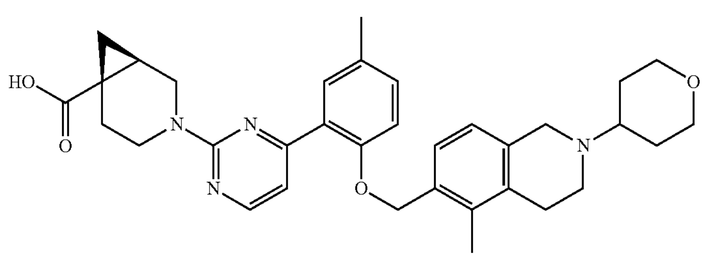 [SMILES: Cc1ccc(OCc2ccc3c(c2C)CCN(C2CCOCC2)C3)c(-c2ccnc(N3CC[C@@]4(C(=O)O)C[C@H]4C3)n2)c1] |
| 188 | 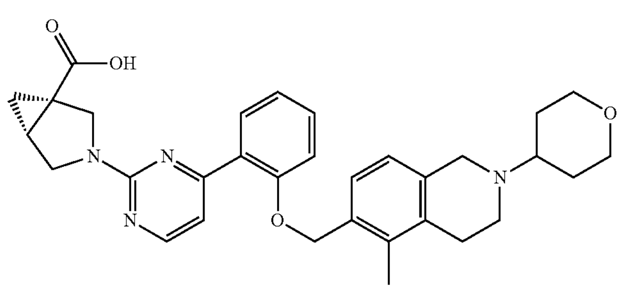 [SMILES: Cc1c(COc2ccccc2-c2ccnc(N3C[C@@H]4C[C@]4(C(=O)O)C3)n2)ccc2c1CCN(C1CCOCC1)C2] |

TABLE 1-continued

| Cpd No | Structure |
|---|---|
| 189 | 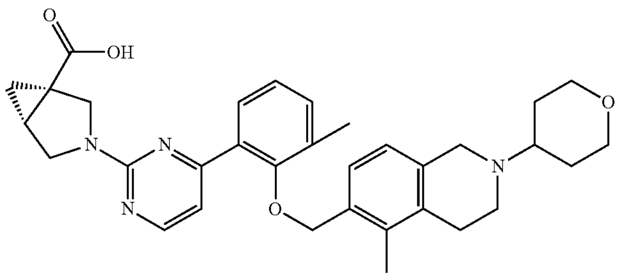 [SMILES: Cc1cccc(-c2ccnc(N3C[C@@H]4C[C@]4(C(=O)O)C3)n2)c1OCc1ccc2c(c1C)CCN(C1CCOCC1)C2] |
| 190 | 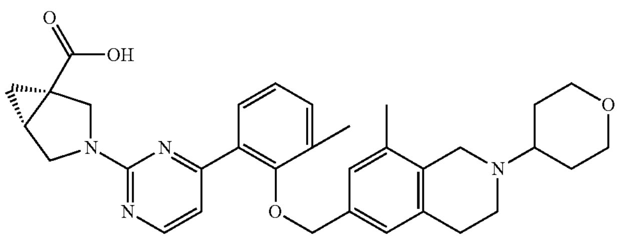 [SMILES: Cc1cc(COc2c(C)cccc2-c2ccnc(N3C[C@@H]4C[C@]4(C(=O)O)C3)n2)cc2c1CN(C1CCOCC1)CC2] |
| 191 | 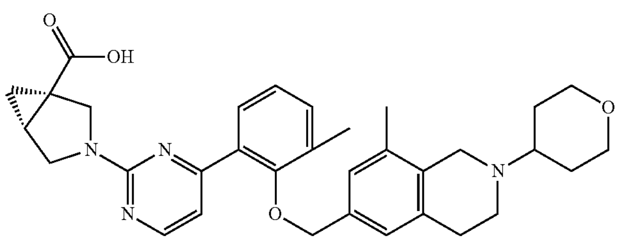 [SMILES: Cc1cc(COc2c(C)cccc2-c2ccnc(N3C[C@@H]4C[C@]4(C(=O)O)C3)n2)cc2c1CN(C1CCOCC1)CC2] |
| 192 | 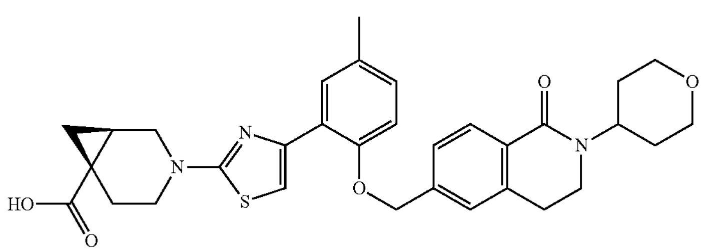 [SMILES: Cc1ccc(OCc2ccc3c(c2)CCN(C2CCOCC2)C3=O)c(-c2csc(N3CC[C@@]4(C(=O)O)C[C@H]4C3)n2)c1] |
| 193 | 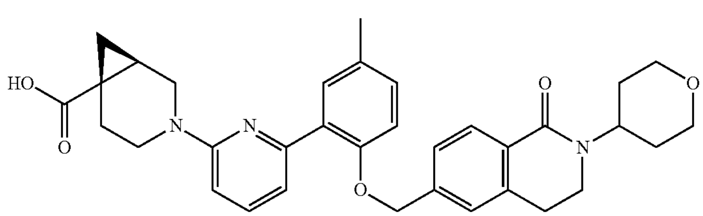 [SMILES: Cc1ccc(OCc2ccc3c(c2)CCN(C2CCOCC2)C3=O)c(-c2cccc(N3CC[C@@]4(C(=O)O)C[C@H]4C3)n2)c1] |
| 194 | 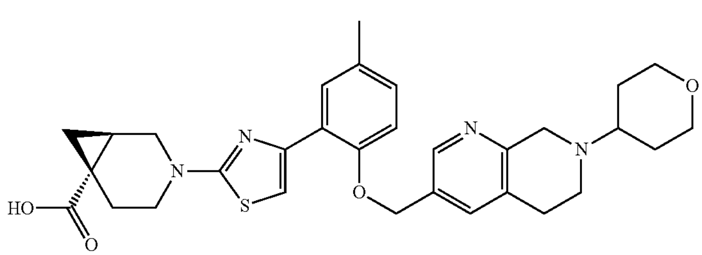 [SMILES: Cc1ccc(OCc2cnc3c(c2)CCN(C2CCOCC2)C3)c(-c2csc(N3CC[C@@]4(C(=O)O)C[C@H]4C3)n2)c1] |

TABLE 1-continued

| Cpd No | Structure |
|---|---|
| 195 | 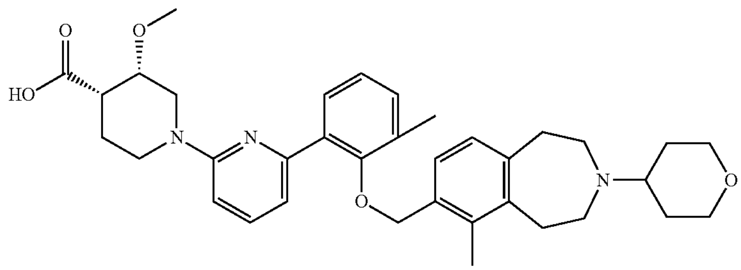 [SMILES: CO[C@@H]1CN(c2cccc(-c3cccc(C)c3OCc3ccc4c(c3C)CCN(C3CCOCC3)CC4)n2)CC[C@@H]1C(=O)O] |
| 196 | 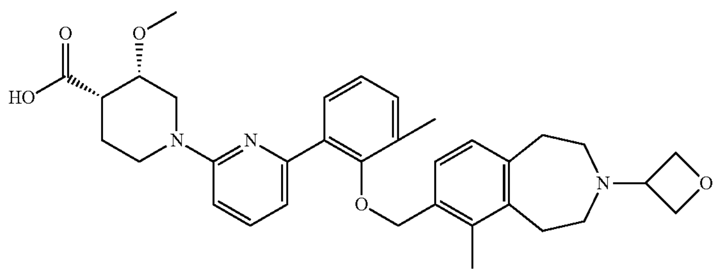 [SMILES: CO[C@@H]1CN(c2cccc(-c3cccc(C)c3OCc3ccc4c(c3C)CCN(C3COC3)CC4)n2)CC[C@@H]1C(=O)O] |
| 197 | 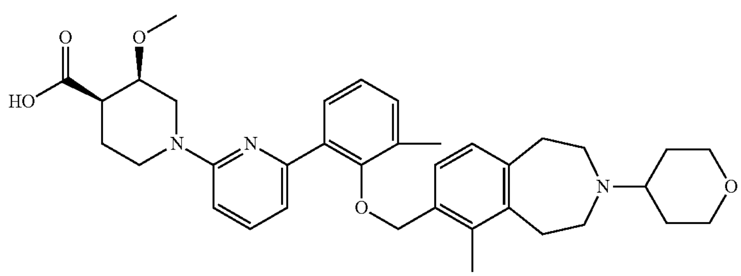 [SMILES: CO[C@H]1CN(c2cccc(-c3cccc(C)c3OCc3ccc4c(c3C)CCN(C3CCOCC3)CC4)n2)CC[C@H]1C(=O)O] |
| 198 | 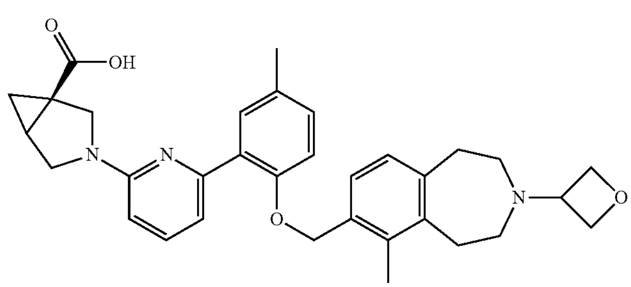 [SMILES: Cc1ccc(OCc2ccc3c(c2C)CCN(C2COC2)CC3)c(-c2cccc(N3CC4C[C@]4(C(=O)O)C3)n2)c1] |
| 199 | 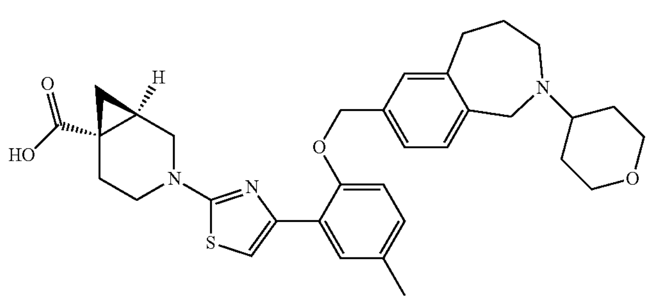 [SMILES: Cc1ccc(OCc2ccc3c(c2)CCCN(C2CCOCC2)C3)c(-c2csc(N3CC[C@@]4(C(=O)O)C[C@H]4C3)n2)c1] |

TABLE 1-continued

| Cpd No | Structure |
|---|---|
| 200 | 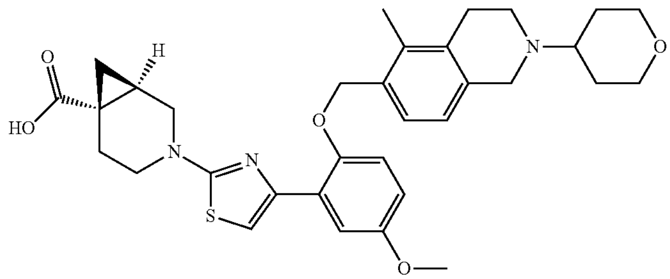 [SMILES: COc1ccc(OCc2ccc3c(c2C)CCN(C2CCOCC2)C3)c(-c2csc(N3CC[C@@]4(C(=O)O)C[C@H]4C3)n2)c1] |
| 201 | 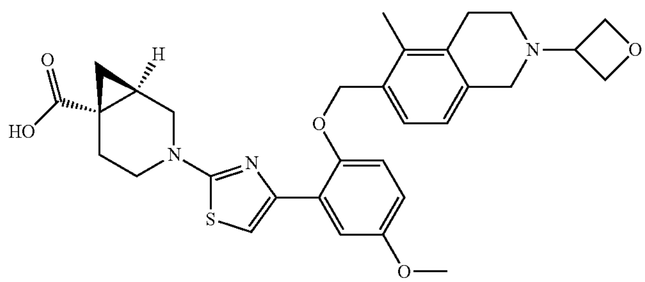 [SMILES: COc1ccc(OCc2ccc3c(c2C)CCN(C2COC2)C3)c(-c2csc(N3CC[C@@]4(C(=O)O)C[C@H]4C3)n2)c1] |
| 202 | 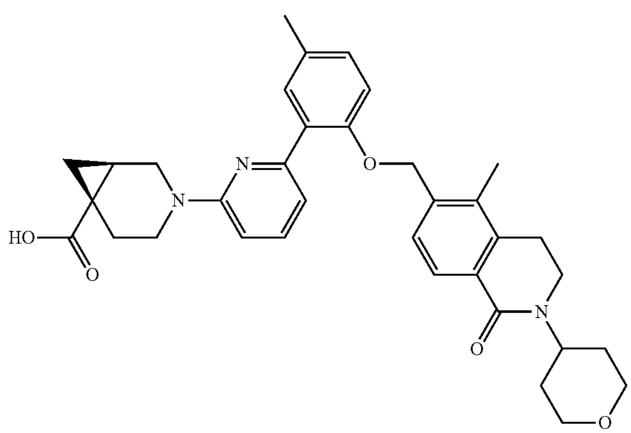 [SMILES: Cc1ccc(OCc2ccc3c(c2C)CCN(C2CCOCC2)C3=O)c(-c2cccc(N3CC[C@@]4(C(=O)O)C[C@H]4C3)n2)c1] |
| 203 | 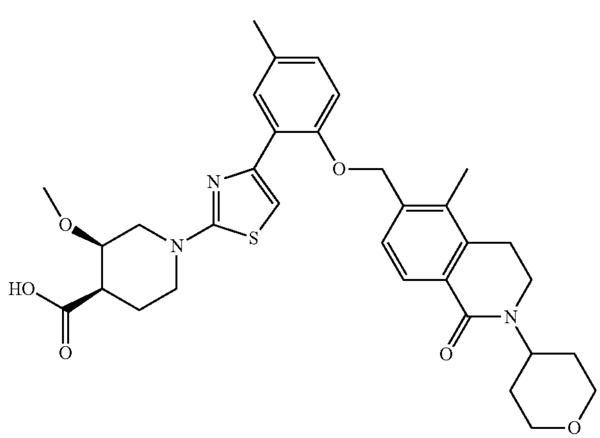 [SMILES: CO[C@H]1CN(c2nc(-c3cc(C)ccc3OCc3ccc4c(c3C)CCN(C3CCOCC3)C4=O)cs2)CC[C@H]1C(=O)O] |

TABLE 1-continued

| Cpd No | Structure |
|---|---|
| 204 | 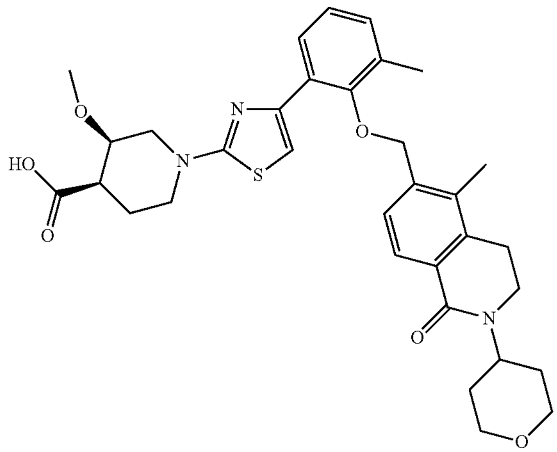 [SMILES: CO[C@H]1CN(c2nc(-c3cccc(C)c3OCc3ccc4c(c3C)CCN(C3CCOCC3)C4=O)cs2)CC[C@H]1C(=O)O] |
| 205 | 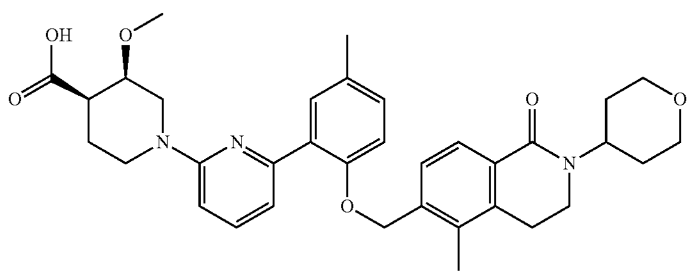 [SMILES: CO[C@H]1CN(c2cccc(-c3cc(C)ccc3OCc3ccc4c(c3C)CCN(C3CCOCC3)C4=O)n2)CC[C@H]1C(=O)O] |
| 206 | 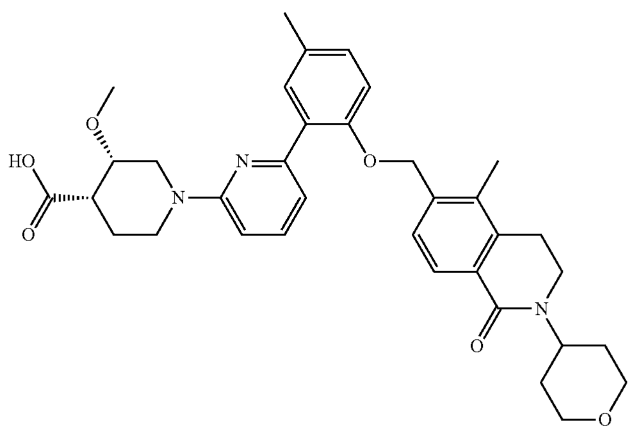 [SMILES: CO[C@@H]1CN(c2cccc(-c3cc(C)ccc3OCc3ccc4c(c3C)CCN(C3CCOCC3)C4=O)n2)CC[C@@H]1C(=O)O] |
| 207 | 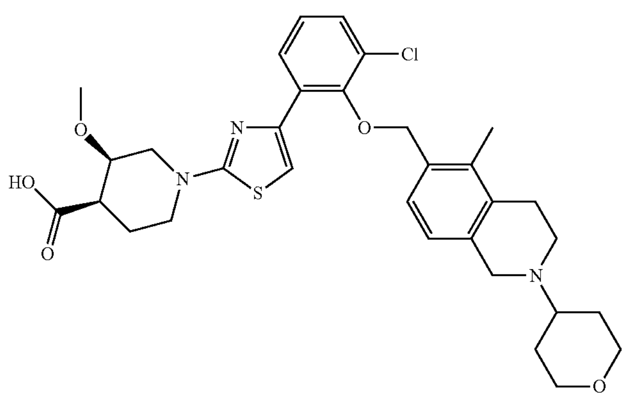 [SMILES: CO[C@H]1CN(c2nc(-c3cccc(Cl)c3OCc3ccc4c(c3C)CCN(C3CCOCC3)C4)cs2)CC[C@H]1C(=O)O] |

TABLE 1-continued
| Cpd No | Structure |
|---|---|
| 208 | 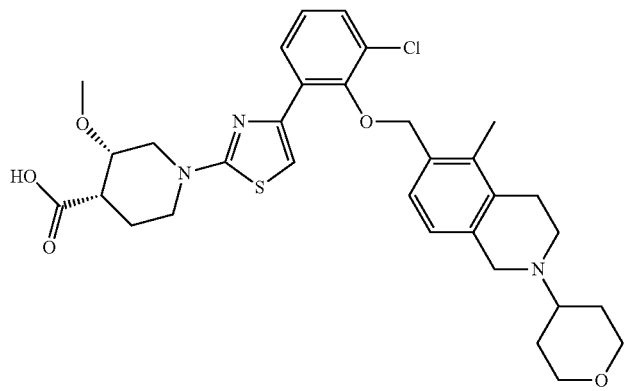 [SMILES: CO[C@@H]1CN(c2nc(-c3cccc(Cl)c3OCc3ccc4c(c3C)CCN(C3CCOCC3)C4)cs2)CC[C@@H]1C(=O)O] |
| 209 | 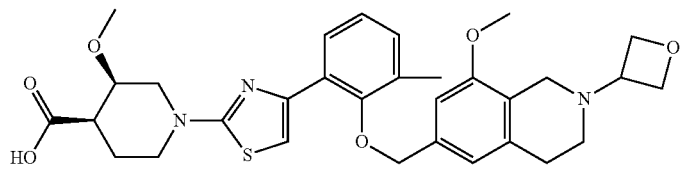 [SMILES: COc1cc(COc2c(C)cccc2-c2csc(N3CC[C@@H](C(=O)O)[C@@H](OC)C3)n2)cc2c1CN(C1COC1)CC2] |
| 210 | 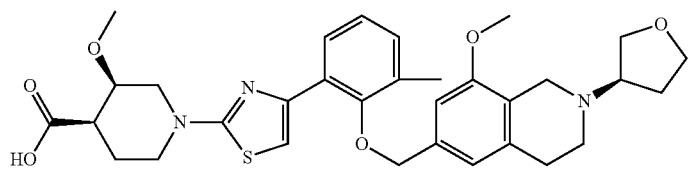 [SMILES: COc1cc(COc2c(C)cccc2-c2csc(N3CC[C@@H](C(=O)O)[C@@H](OC)C3)n2)cc2c1CN([C@@H]1CCOC1)CC2] |
| 211 | 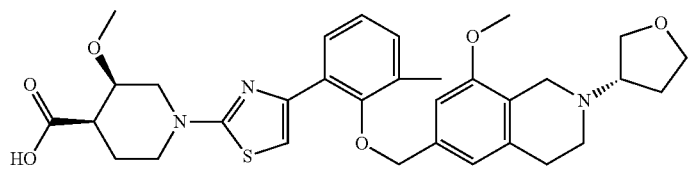 [SMILES: COc1cc(COc2c(C)cccc2-c2csc(N3CC[C@@H](C(=O)O)[C@@H](OC)C3)n2)cc2c1CN([C@H]1CCOC1)CC2] |
| 212 | 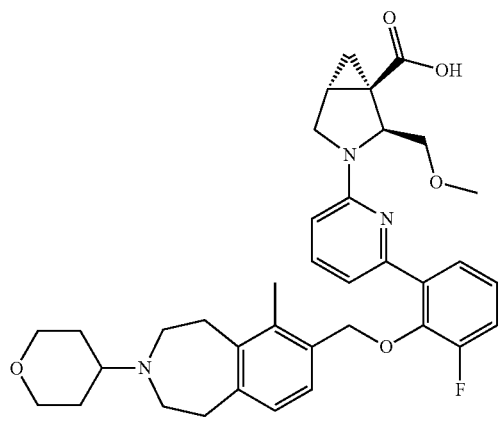 [SMILES: COC[C@H]1N(c2cccc(-c3cccc(F)c3OCc3ccc4c(c3C)CCN(C3CCOCC3)CC4)n2)C[C@@H]2C[C@@]21C(=O)O] |

… TABLE 1-continued
| Cpd No | Structure |
|---|---|
| 213 | 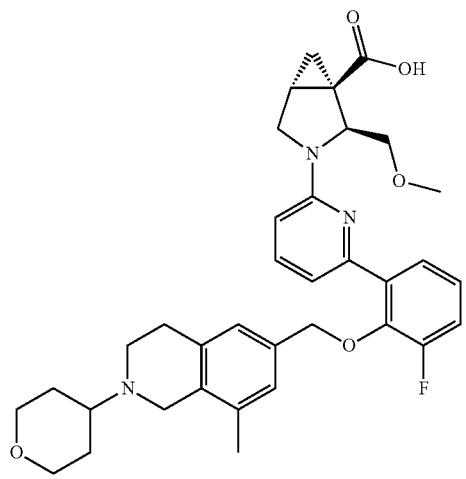 [SMILES: COC[C@H]1N(c2cccc(-c3cccc(F)c3OCc3cc(C)c4c(c3)CCN(C3CCOCC3)C4)n2)C[C@@H]2C[C@@]21C(=O)O] |
| 214 | 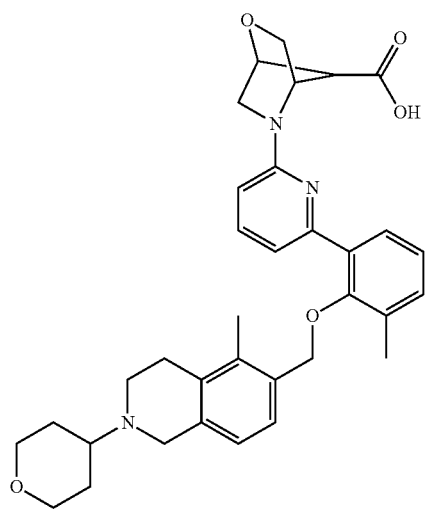 [SMILES: Cc1cccc(-c2cccc(N3CC4OCC3C4C(=O)O)n2)c1OCc1ccc2c(c1C)CCN(C1CCOCC1)C2] |
| 215 | 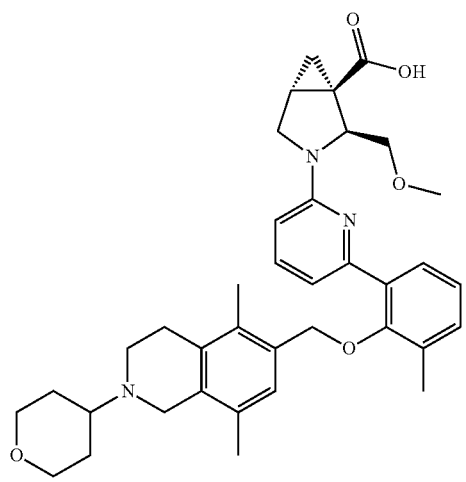 [SMILES: COC[C@H]1N(c2cccc(-c3cccc(C)c3OCc3cc(C)c4c(c3C)CCN(C3CCOCC3)C4)n2)C[C@@H]2C[C@@]21C(=O)O] |

TABLE 1-continued
| Cpd No | Structure |
|---|---|
| 216 | 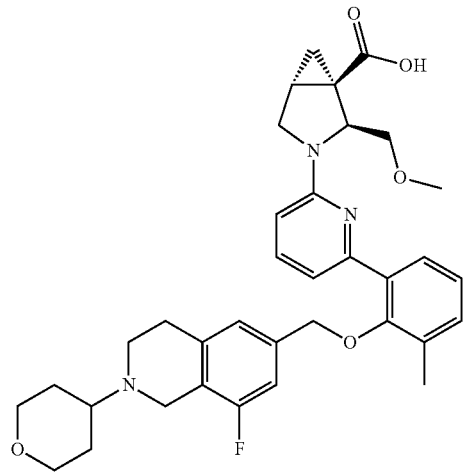 [SMILES: COC[C@H]1N(c2cccc(-c3cccc(C)c3OCc3cc(F)c4c(c3)CCN(C3CCOCC3)C4)n2)C[C@@H]2C[C@@]21C(=O)O] |
| 217 | 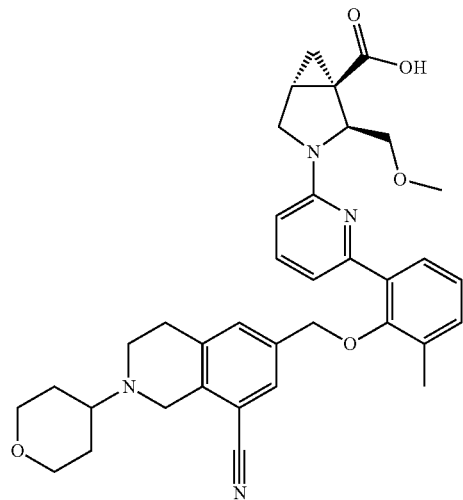 [SMILES: COC[C@H]1N(c2cccc(-c3cccc(C)c3OCc3cc(C#N)c4c(c3)CCN(C3CCOCC3)C4)n2)C[C@@H]2C[C@@]21C(=O)O] |
| 218 | 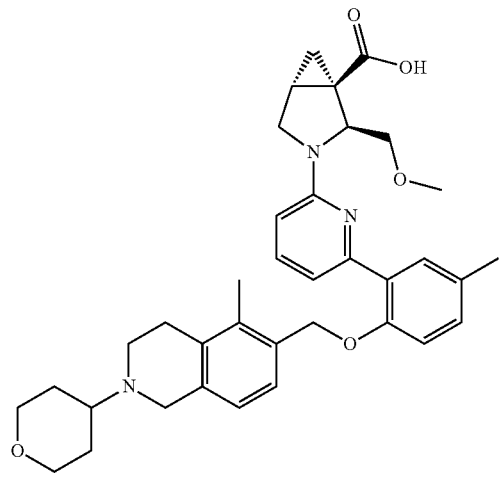 [SMILES: COC[C@H]1N(c2cccc(-c3cc(C)ccc3OCc3ccc4c(c3C)CCN(C3CCOCC3)C4)n2)C[C@@H]2C[C@@]21C(=O)O] |

TABLE 1-continued
| Cpd No | Structure |
|---|---|
| 219 | 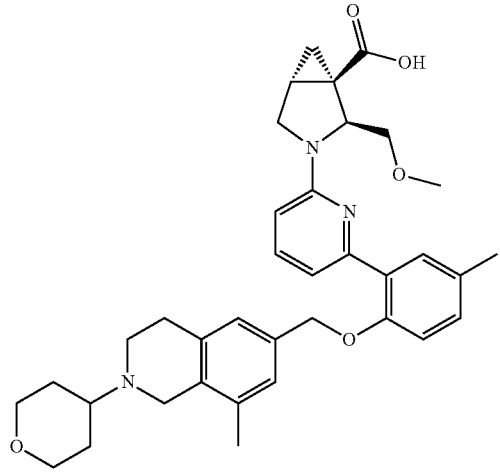 [SMILES: COC[C@H]1N(c2cccc(-c3cc(C)ccc3OCc3cc(C)c4c(c3)CCN(C3CCOCC3)C4)n2)C[C@@H]2C[C@@]21C(=O)O] |
| 220 | 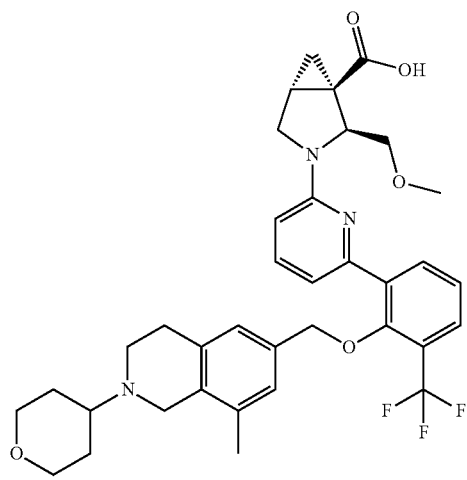 [SMILES: COC[C@H]1N(c2cccc(-c3cccc(C(F)(F)F)c3OCc3cc(C)c4c(c3)CCN(C3CCOCC3)C4)n2)C[C@@H]2C[C@@]21C(=O)O] |
| 221 | 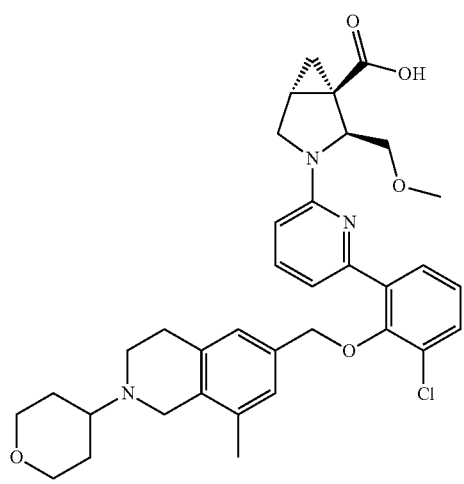 [SMILES: COC[C@H]1N(c2cccc(-c3cccc(Cl)c3OCc3cc(C)c4c(c3)CCN(C3CCOCC3)C4)n2)C[C@@H]2C[C@@]21C(=O)O] |

TABLE 1-continued
| Cpd No | Structure |
|---|---|
| 222 | 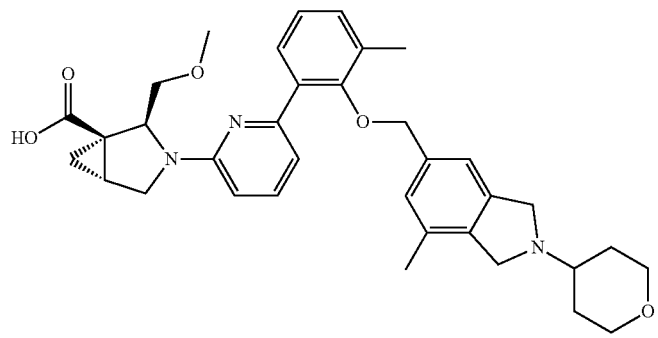 [SMILES: COC[C@H]1N(c2cccc(-c3cccc(C)c3OCc3cc(C)c4c(c3)CN(C3CCOCC3)C4)n2)C[C@@H]2C[C@@]21C(=O)O] |
| 223 | 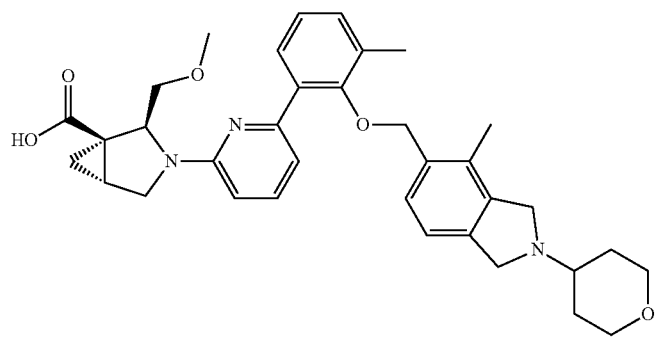 [SMILES: COC[C@H]1N(c2cccc(-c3cccc(C)c3OCc3ccc4c(c3C)CN(C3CCOCC3)C4)n2)C[C@@H]2C[C@@]21C(=O)O] |
| 224 | 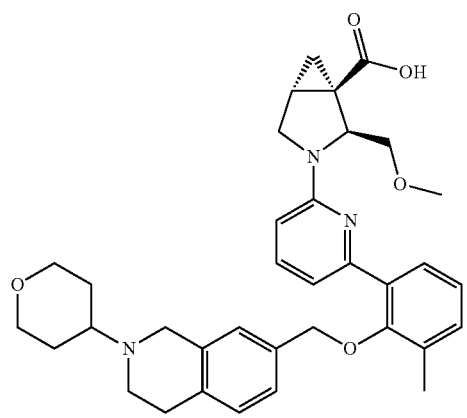 [SMILES: COC[C@H]1N(c2cccc(-c3cccc(C)c3OCc3ccc4c(c3)CN(C3CCOCC3)CC4)n2)C[C@@H]2C[C@@]21C(=O)O] |
| 225 | 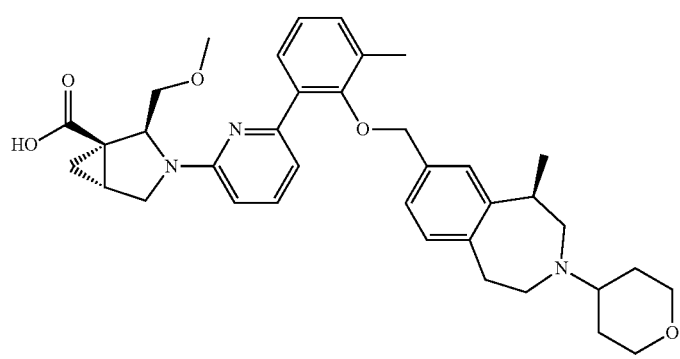 [SMILES: COC[C@H]1N(c2cccc(-c3cccc(C)c3OCc3ccc4c(c3)[C@@H](C)CN(C3CCOCC3)CC4)n2)C[C@@H]2C[C@@]21C(=O)O] |

TABLE 1-continued

| Cpd No | Structure |
|---|---|
| 226 | 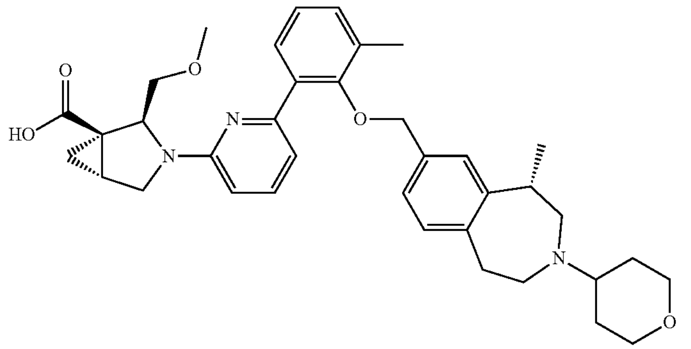 [SMILES: COC[C@H]1N(c2cccc(-c3cccc(C)c3OCc3ccc4c(c3)[C@H](C)CN(C3CCOCC3)CC4)n2)C[C@@H]2C[C@@]21C(=O)O] |
| 227 | 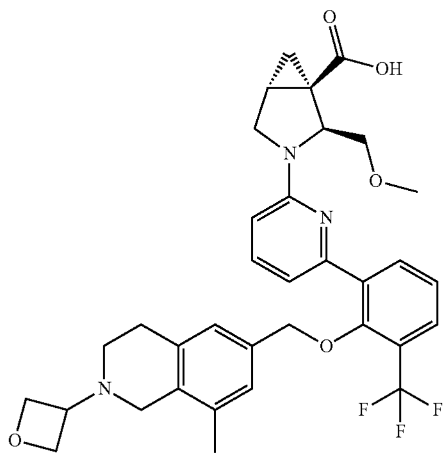 [SMILES: COC[C@H]1N(c2cccc(-c3cccc(C(F)(F)F)c3OCc3cc(C)c4c(c3)CCN(C3COC3)C4)n2)C[C@@H]2C[C@@]21C(=O)O] |
| 228 | 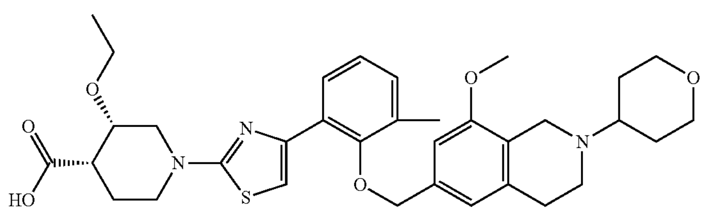 [SMILES: CCO[C@@H]1CN(c2nc(-c3cccc(C)c3OCc3cc4c(c(OC)c3)CN(C3CCOCC3)CC4)cs2)CC[C@@H]1C(=O)O] |
| 229 | 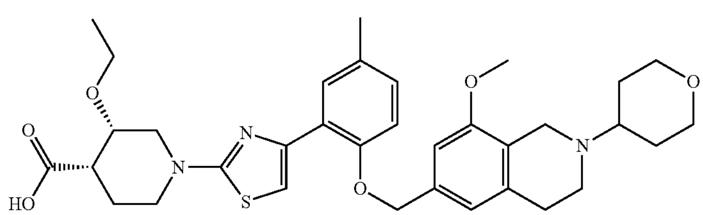 [SMILES: CCO[C@@H]1CN(c2nc(-c3cc(C)ccc3OCc3cc4c(c(OC)c3)CN(C3CCOCC3)CC4)cs2)CC[C@@H]1C(=O)O] |
| 230 | 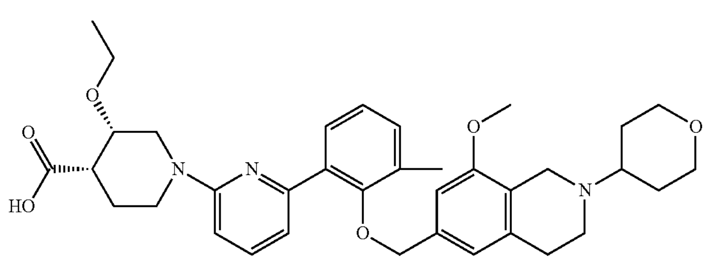 [SMILES: CCO[C@@H]1CN(c2cccc(-c3cccc(C)c3OCc3cc4c(c(OC)c3)CN(C3CCOCC3)CC4)n2)CC[C@@H]1C(=O)O] |

TABLE 1-continued
| Cpd No | Structure |
|---|---|
| 231 | 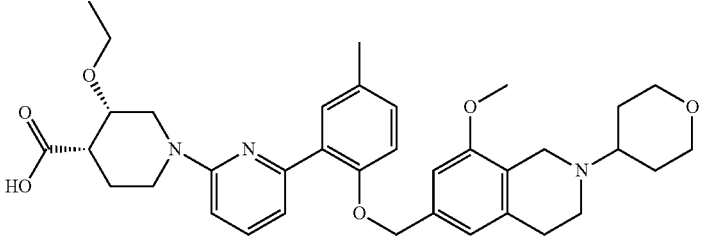 [SMILES: CCO[C@@H]1CN(c2cccc(-c3cc(C)ccc3OCc3cc4c(c(OC)c3)CN(C3CCOCC3)CC4)n2)CC[C@@H]1C(=O)O] |
| 232 | 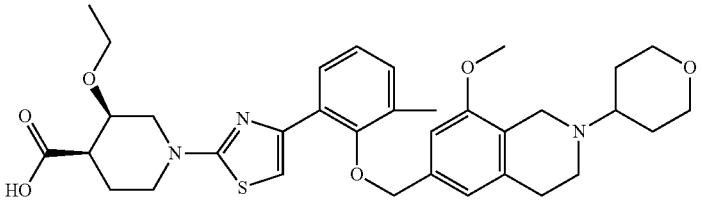 [SMILES: CCO[C@H]1CN(c2nc(-c3cccc(C)c3OCc3cc4c(c(OC)c3)CN(C3CCOCC3)CC4)cs2)CC[C@H]1C(=O)O] |
| 233 | 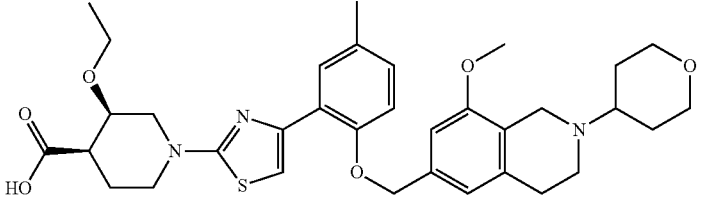 |
| 234 | 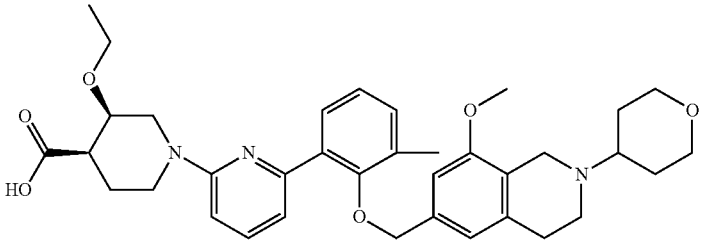 [SMILES: CCO[C@H]1CN(c2cccc(-c3cccc(C)c3OCc3cc4c(c(OC)c3)CN(C3CCOCC3)CC4)n2)CC[C@H]1C(=O)O] |
| 235 | 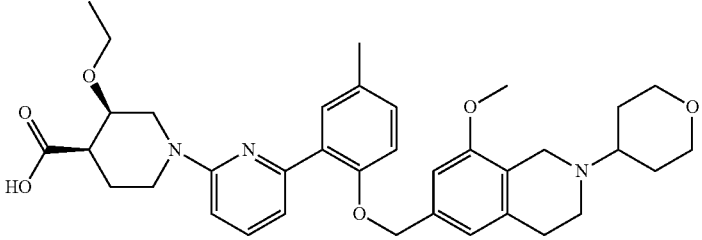 [SMILES: CCO[C@H]1CN(c2cccc(-c3cc(C)ccc3OCc3cc4c(c(OC)c3)CN(C3CCOCC3)CC4)n2)CC[C@H]1C(=O)O] |
| 236 | 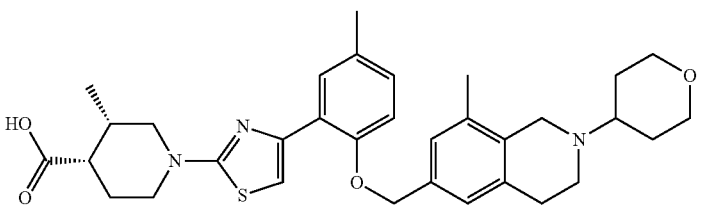 [SMILES: Cc1ccc(OCc2cc(C)c3c(c2)CCN(C2CCOCC2)C3)c(-c2csc(N3CC[C@H](C(=O)O)[C@H](C)C3)n2)c1] |

TABLE 1-continued
| Cpd No | Structure |
|---|---|
| 237 | 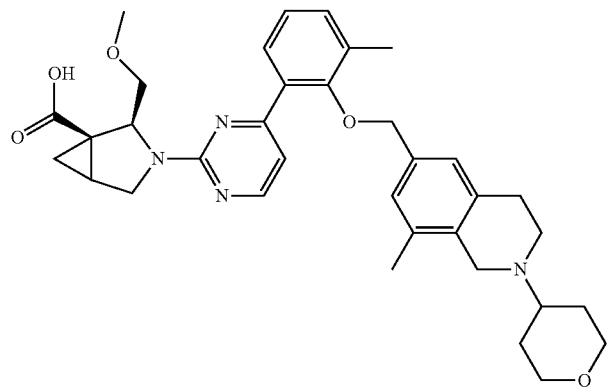 [SMILES: COC[C@H]1N(c2nccc(-c3cccc(C)c3OCc3cc(C)c4c(c3)CCN(C3CCOCC3)C4)n2)CC2C[C@@]21C(=O)O] |
| 238 | 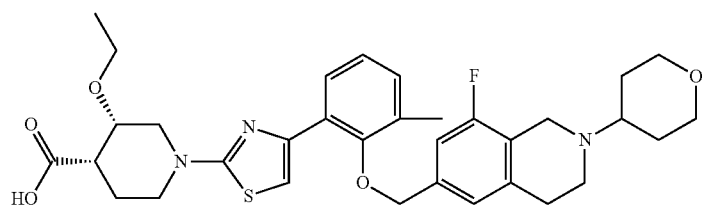 [SMILES: CCO[C@@H]1CN(c2nc(-c3cccc(C)c3OCc3cc(F)c4c(c3)CCN(C3CCOCC3)C4)cs2)CC[C@@H]1C(=O)O] |
| 239 | 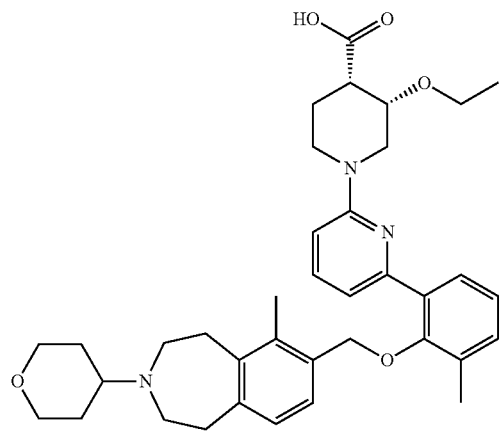 [SMILES: CCO[C@@H]1CN(c2cccc(-c3cccc(C)c3OCc3ccc4c(c3C)CCN(C3CCOCC3)CC4)n2)CC[C@@H]1C(=O)O] |
| 240 | 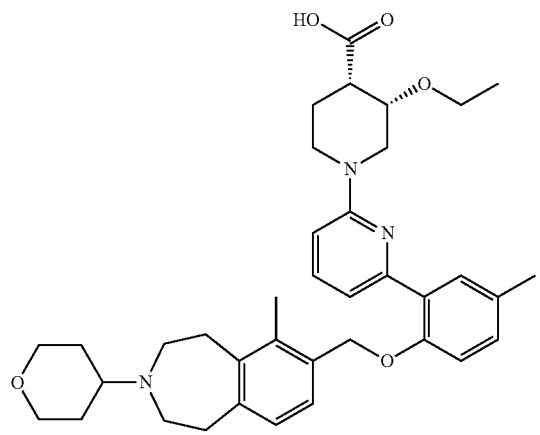 [SMILES: CCO[C@@H]1CN(c2cccc(-c3cc(C)ccc3OCc3ccc4c(c3C)CCN(C3CCOCC3)CC4)n2)CC[C@@H]1C(=O)O] |

TABLE 1-continued
| Cpd No | Structure |
|---|---|
| 241 | 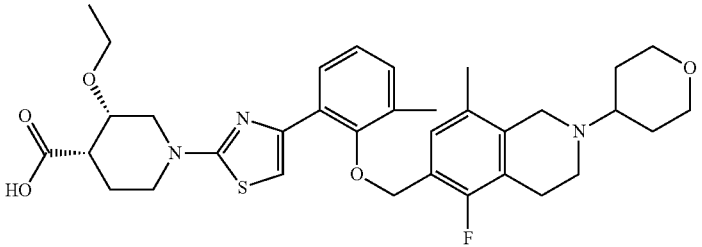 |
| 242 | 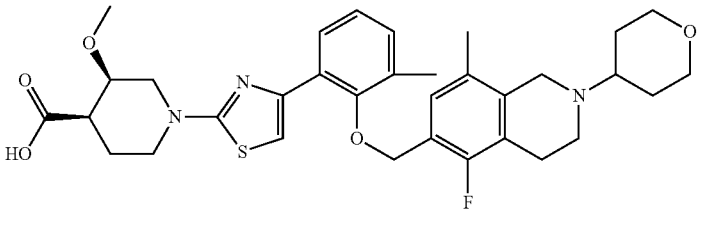 [SMILES: CO[C@H]1CN(c2nc(-c3cccc(C)c3OCc3cc(C)c4c(c3F)CCN(C3CCOCC3)C4)cs2)CC[C@H]1C(=O)O] |
| 243 | 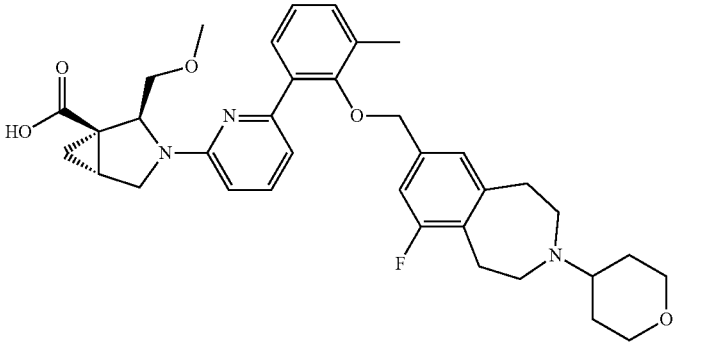 [SMILES: COC[C@H]1N(c2cccc(-c3cccc(C)c3OCc3cc(F)c4c(c3)CCN(C3CCOCC3)CC4)n2)C[C@@H]2C[C@@]21C(=O)O] |
| 244 | 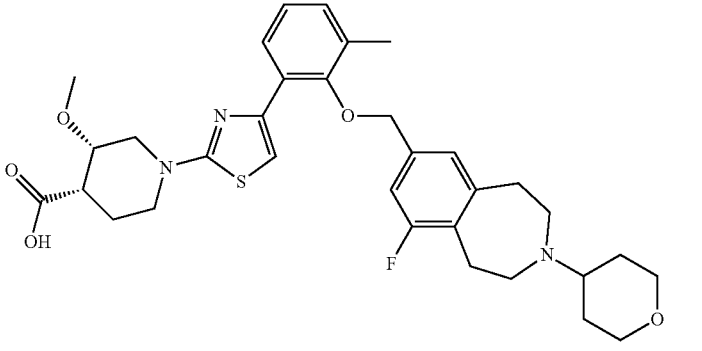 [SMILES: CO[C@@H]1CN(c2nc(-c3cccc(C)c3OCc3cc(F)c4c(c3)CCN(C3CCOCC3)CC4)cs2)CC[C@@H]1C(=O)O] |
| 245 | 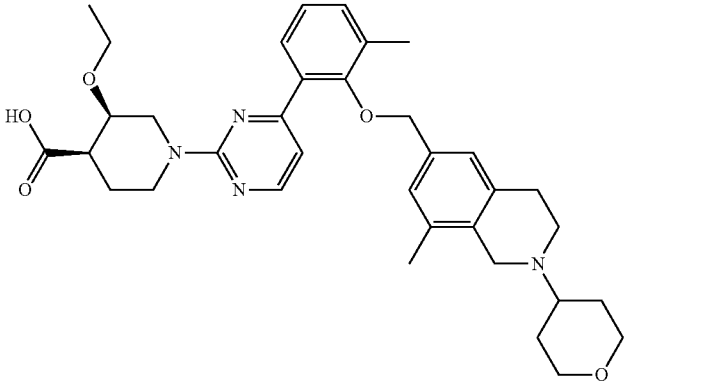 |

TABLE 1-continued

| Cpd No | Structure |
|---|---|
| 246 | 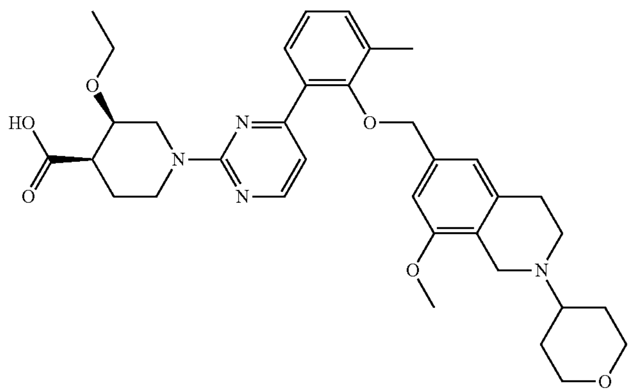 [SMILES: CCO[C@H]1CN(c2nccc(-c3cccc(C)c3OCc3cc(C)c4c(c3)CCN(C3CCOCC3)C4)n2)CC[C@H]1C(=O)O] |
| 247 | 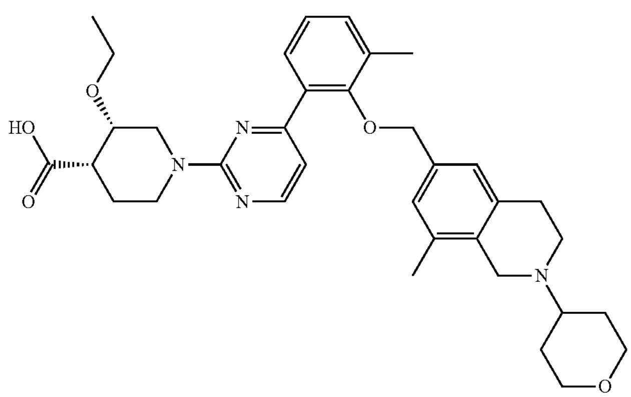 [SMILES: CCO[C@@H]1CN(c2nccc(-c3cccc(C)c3OCc3cc(C)c4c(c3)CCN(C3CCOCC3)C4)n2)CC[C@@H]1C(=O)O] |
| 248 | 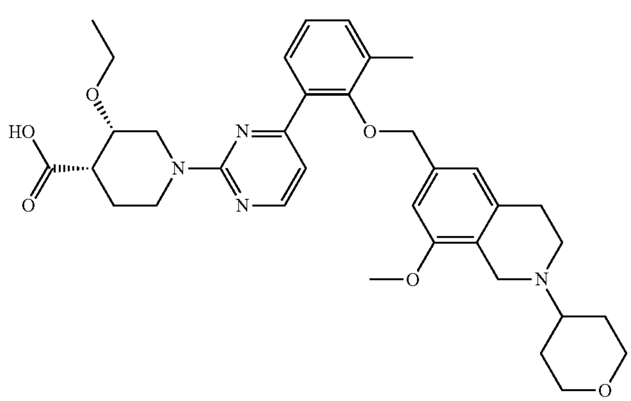 [SMILES: CCO[C@@H]1CN(c2nccc(-c3cccc(C)c3OCc3cc4c(c(OC)c3)CN(C3CCOCC3)CC4)n2)CC[C@@H]1C(=O)O] |
| 249 | 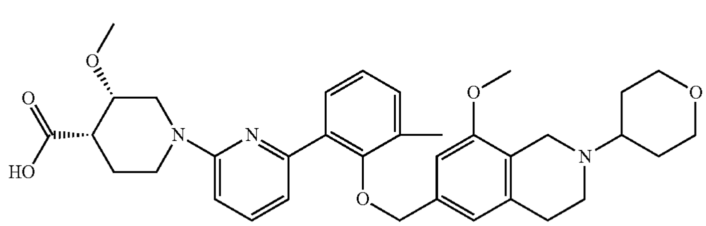 [SMILES: COc1cc(COc2c(C)cccc2-c2cccc(N3CC[C@H](C(=O)O)[C@H](OC)C3)n2)cc2c1CN(C1CCOCC1)CC2] |

TABLE 1-continued

| Cpd No | Structure |
|---|---|
| 250 | 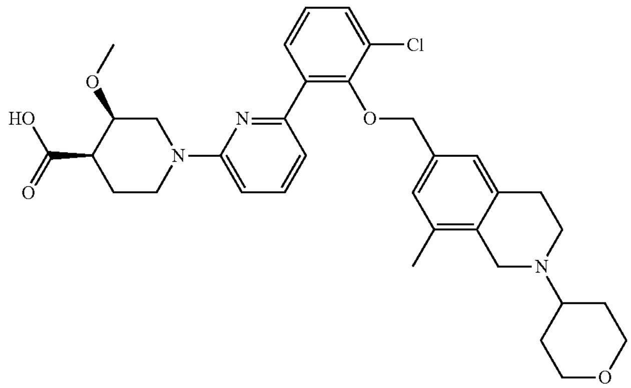 [SMILES: CO[C@H]1CN(c2cccc(-c3cccc(Cl)c3OCc3cc(C)c4c(c3)CCN(C3CCOCC3)C4)n2)CC[C@H]1C(=O)O] |
| 251 | 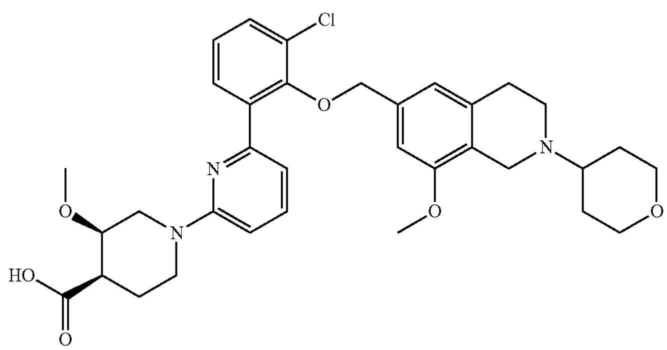 [SMILES: COc1cc(COc2c(Cl)cccc2-c2cccc(N3CC[C@@H](C(=O)O)[C@@H](OC)C3)n2)cc2c1CN(C1CCOCC1)CC2] |
| 252 | 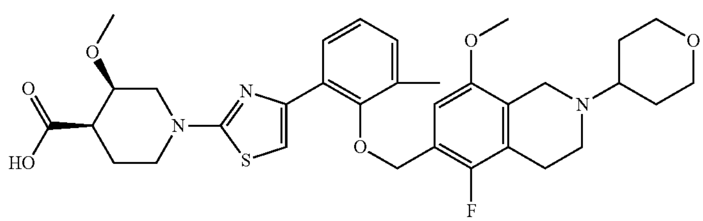 [SMILES: COc1cc(COc2c(C)cccc2-c2csc(N3CC[C@@H](C(=O)O)[C@@H](OC)C3)n2)c(F)c2c1CN(C1CCOCC1)CC2] |
| 253 | 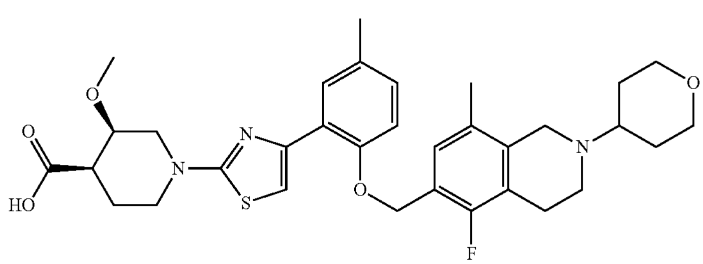 [SMILES: CO[C@H]1CN(c2nc(-c3cc(C)ccc3OCc3cc(C)c4c(c3F)CCN(C3CCOCC3)C4)cs2)CC[C@H]1C(=O)O] |
| 254 | 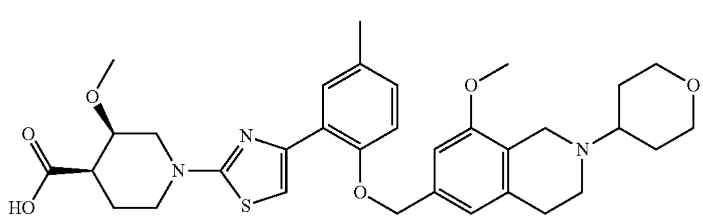 [SMILES: COc1cc(COc2ccc(C)cc2-c2csc(N3CC[C@@H](C(=O)O)[C@@H](OC)C3)n2)cc2c1CN(C1CCOCC1)CC2] |

TABLE 1-continued
| Cpd No | Structure |
|---|---|
| 255 | 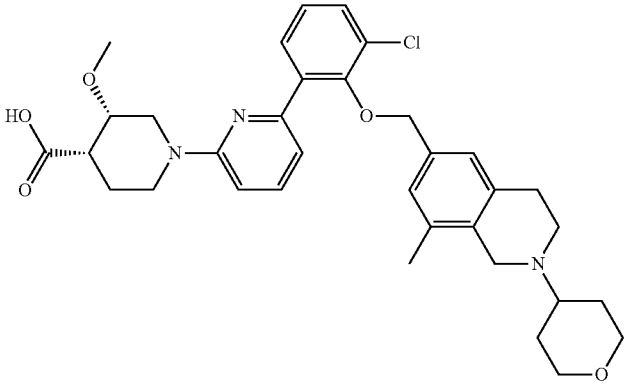 |
| 256 | 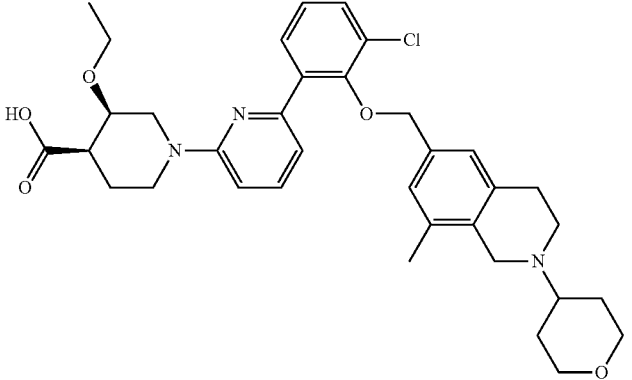 [SMILES: CCO[C@H]1CN(c2cccc(-c3cccc(Cl)c3OCc3cc(C)c4c(c3)CCN(C3CCOCC3)C4)n2)CC[C@H]1C(=O)O] |
| 257 | 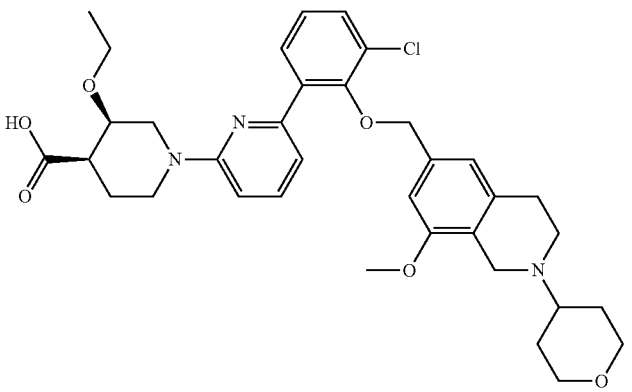 [SMILES: CCO[C@H]1CN(c2cccc(-c3cccc(Cl)c3OCc3cc4c(c(OC)c3)CN(C3CCOCC3)CC4)n2)CC[C@H]1C(=O)O] |
| 258 | 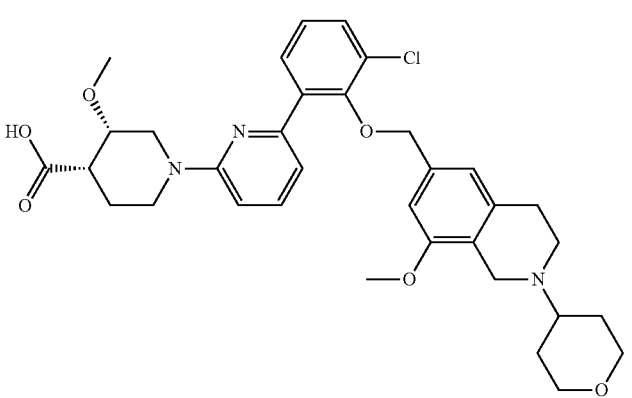 [SMILES: COc1cc(COc2c(Cl)cccc2-c2cccc(N3CC[C@H](C(=O)O)[C@H](OC)C3)n2)cc2c1CN(C1CCOCC1)CC2] |

TABLE 1-continued

| Cpd No | Structure |
|---|---|
| 259 | 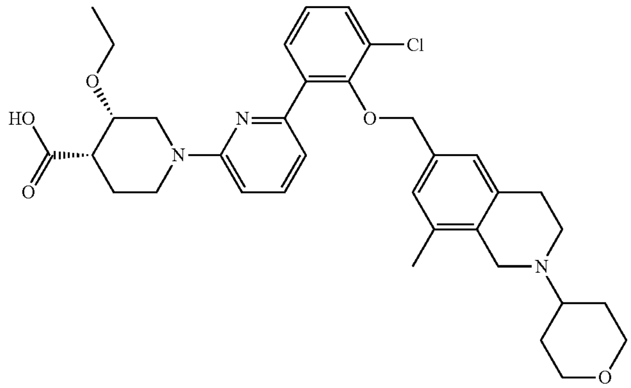 [SMILES: CCO[C@@H]1CN(c2cccc(-c3cccc(Cl)c3OCc3cc(C)c4c(c3)CCN(C3CCOCC3)C4)n2)CC[C@@H]1C(=O)O] |
| 260 | 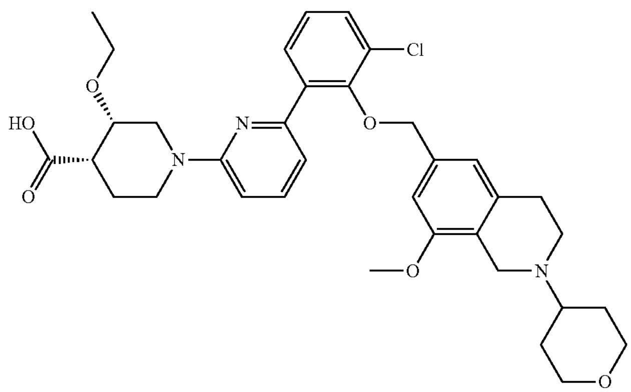 [SMILES: CCO[C@@H]1CN(c2cccc(-c3cccc(Cl)c3OCc3cc4c(c(OC)c3)CN(C3CCOCC3)CC4)n2)CC[C@@H]1C(=O)O] |
| 261 | 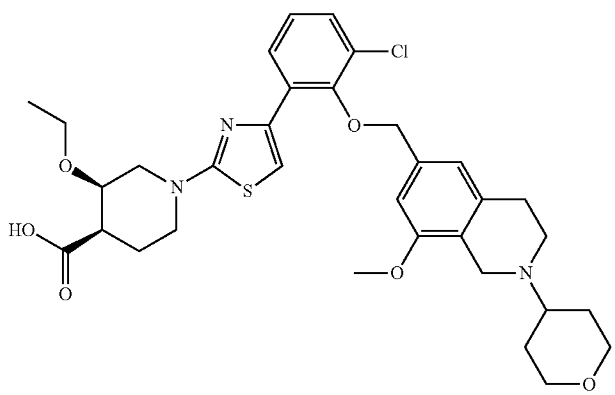 [SMILES: CCO[C@H]1CN(c2nc(-c3cccc(Cl)c3OCc3cc4c(c(OC)c3)CN(C3CCOCC3)CC4)cs2)CC[C@H]1C(=O)O] |
| 262 | 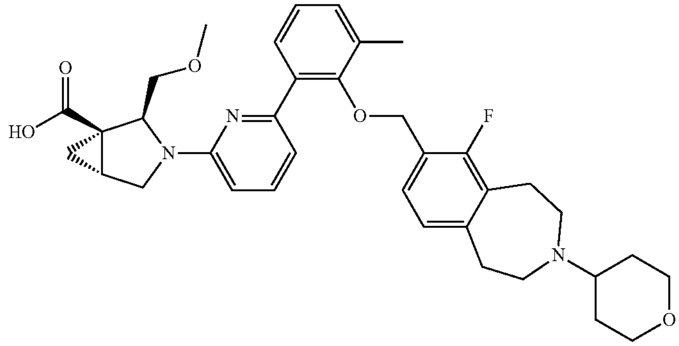 [SMILES: COC[C@H]1N(c2cccc(-c3cccc(C)c3OCc3ccc4c(c3F)CCN(C3CCOCC3)CC4)n2)C[C@@H]2C[C@@]21C(=O)O] |

TABLE 1-continued

| Cpd No | Structure |
|---|---|
| 263 | 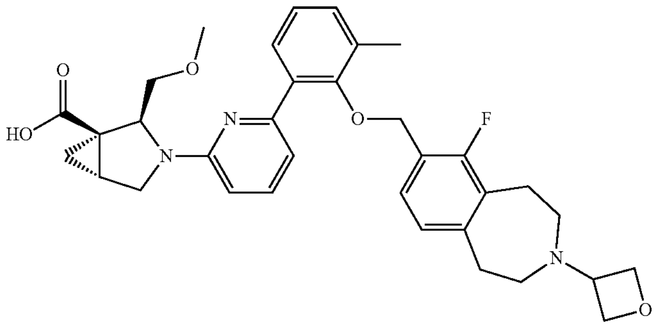 [SMILES: COC[C@H]1N(c2cccc(-c3cccc(C)c3OCc3ccc4c(c3F)CCN(C3COC3)CC4)n2)C[C@@H]2C[C@@]21C(=O)O] |
| 264 | 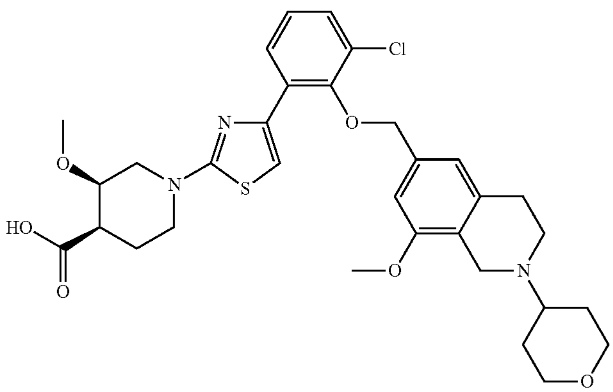 [SMILES: COc1cc(COc2c(Cl)cccc2-c2csc(N3CC[C@@H](C(=O)O)[C@@H](OC)C3)n2)cc2c1CN(C1CCOCC1)CC2] |
| 265 | 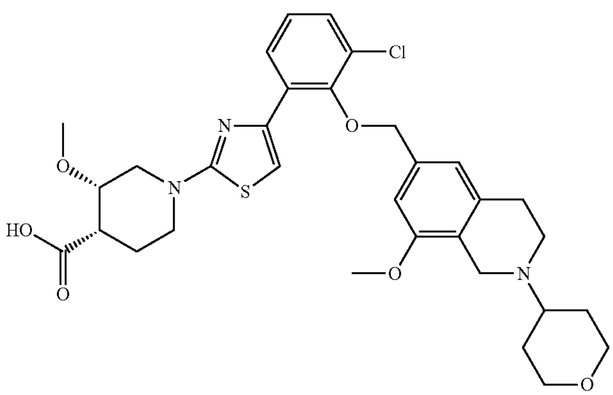 [SMILES: COc1cc(COc2c(Cl)cccc2-c2csc(N3CC[C@H](C(=O)O)[C@H](OC)C3)n2)cc2c1CN(C1CCOCC1)CC2] |
| 266 | 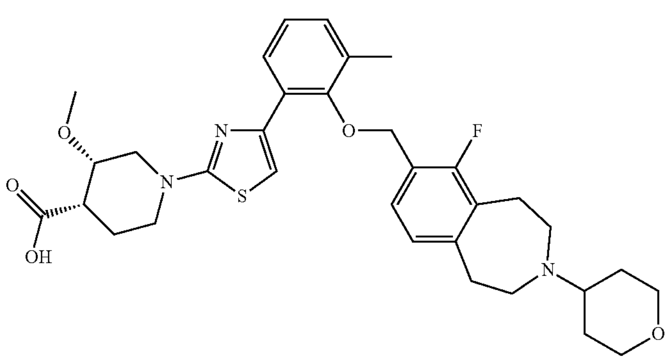 [SMILES: CO[C@@H]1CN(c2nc(-c3cccc(C)c3OCc3ccc4c(c3F)CCN(C3CCOCC3)CC4)cs2)CC[C@@H]1C(=O)O] |

TABLE 1-continued
| Cpd No | Structure |
|---|---|
| 267 | 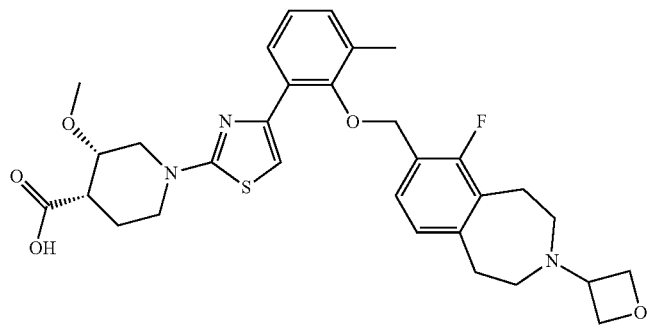 [SMILES: CO[C@@H]1CN(c2nc(-c3cccc(C)c3OCc3ccc4c(c3F)CCN(C3COC3)CC4)cs2)CC[C@@H]1C(=O)O] |
| 268 | 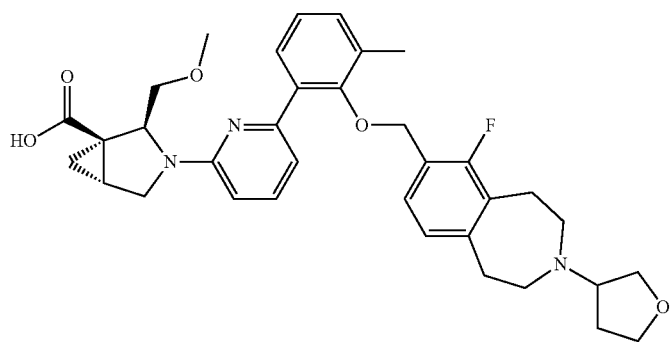 [SMILES: COC[C@H]1N(c2cccc(-c3cccc(C)c3OCc3ccc4c(c3F)CCN(C3CCOC3)CC4)n2)C[C@@H]2C[C@@]21C(=O)O] |
| 269 | 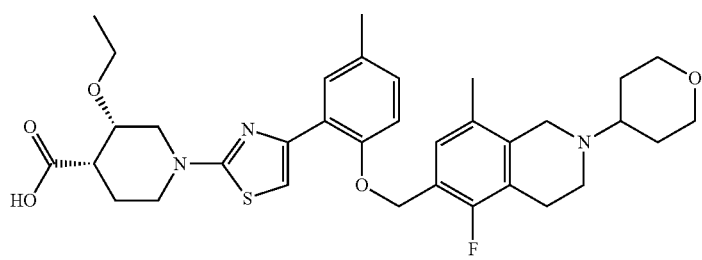 [SMILES: CCO[C@@H]1CN(c2nc(-c3cc(C)ccc3OCc3cc(C)c4c(c3F)CCN(C3CCOCC3)C4)cs2)CC[C@@H]1C(=O)O] |
| 270 | 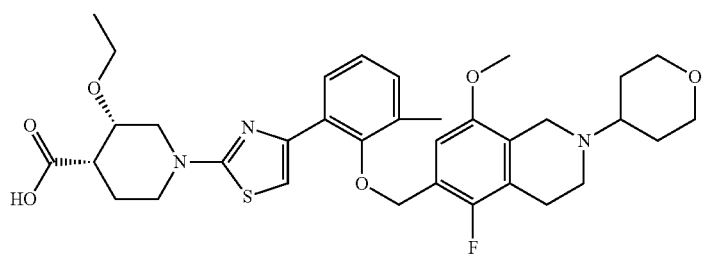 [SMILES: CCO[C@@H]1CN(c2nc(-c3cccc(C)c3OCc3cc(OC)c4c(c3F)CCN(C3CCOCC3)C4)cs2)CC[C@@H]1C(=O)O] |
| 271 | 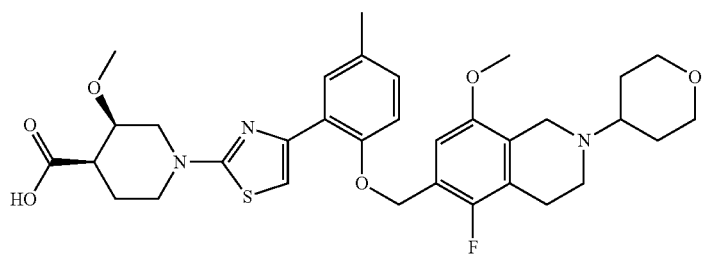 [SMILES: COc1cc(COc2ccc(C)cc2-c2csc(N3CC[C@@H](C(=O)O)[C@@H](OC)C3)n2)c(F)c2c1CN(C1CCOCC1)CC2] |

TABLE 1-continued
| Cpd No | Structure |
|---|---|
| 272 | 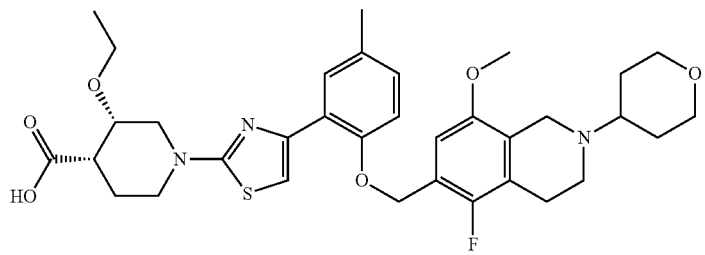 [SMILES: CCO[C@@H]1CN(c2nc(-c3cc(C)ccc3OCc3cc(OC)c4c(c3F)CCN(C3CCOCC3)C4)cs2)CC[C@@H]1C(=O)O] |
| 273 | 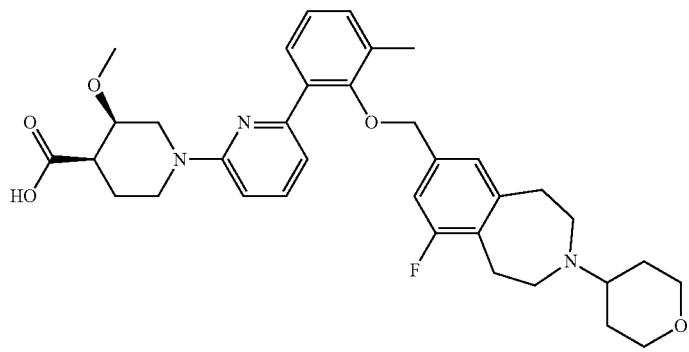 [SMILES: CO[C@H]1CN(c2cccc(-c3cccc(C)c3OCc3cc(F)c4c(c3)CCN(C3CCOCC3)CC4)n2)CC[C@H]1C(=O)O] |
| 274 | 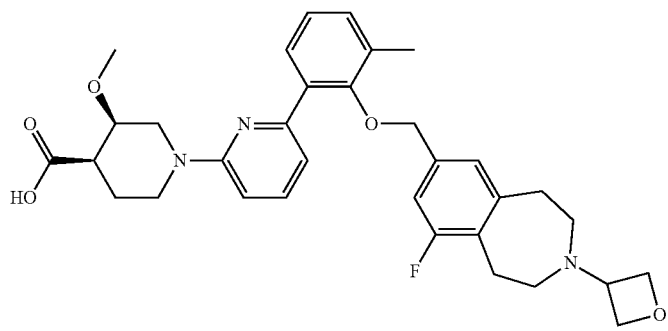 [SMILES: CO[C@H]1CN(c2cccc(-c3cccc(C)c3OCc3cc(F)c4c(c3)CCN(C3COC3)CC4)n2)CC[C@H]1C(=O)O] |
| 275 | 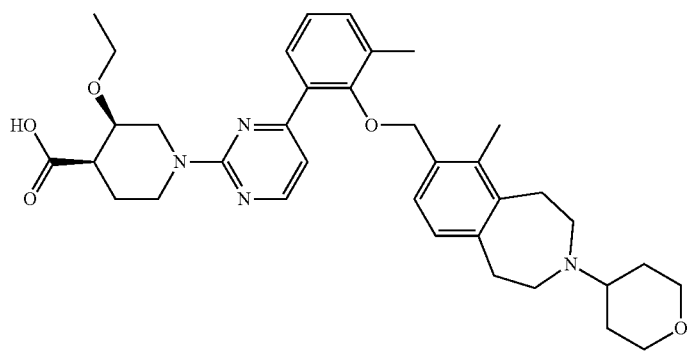 [SMILES: CCO[C@H]1CN(c2nccc(-c3cccc(C)c3OCc3ccc4c(c3C)CCN(C3CCOCC3)CC4)n2)CC[C@H]1C(=O)O] |

TABLE 1-continued
| Cpd No | Structure |
|---|---|
| 276 | 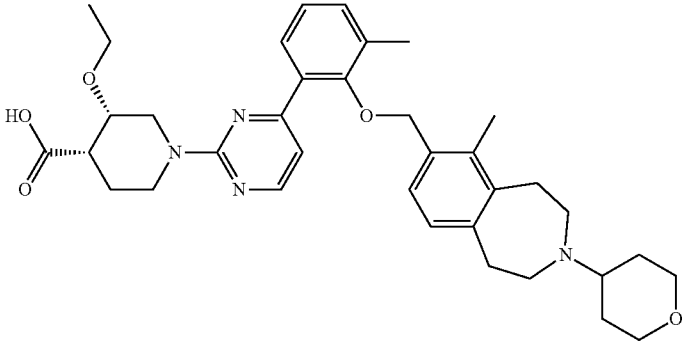 [SMILES: CCO[C@@H]1CN(c2nccc(-c3cccc(C)c3OCc3ccc4c(c3C)CCN(C3CCOCC3)CC4)n2)CC[C@@H]1C(=O)O] |
| 277 | 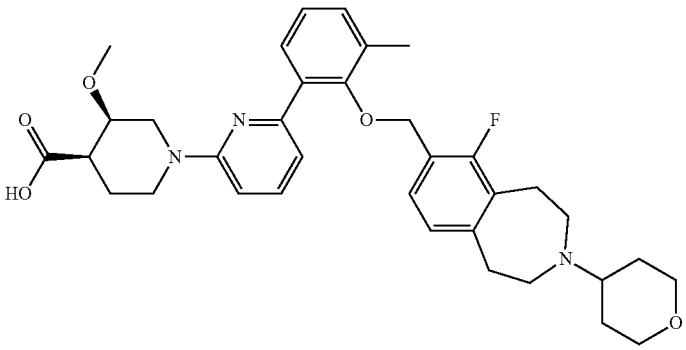 [SMILES: CO[C@H]1CN(c2cccc(-c3cccc(C)c3OCc3ccc4c(c3F)CCN(C3CCOCC3)CC4)n2)CC[C@H]1C(=O)O] |
| 278 | 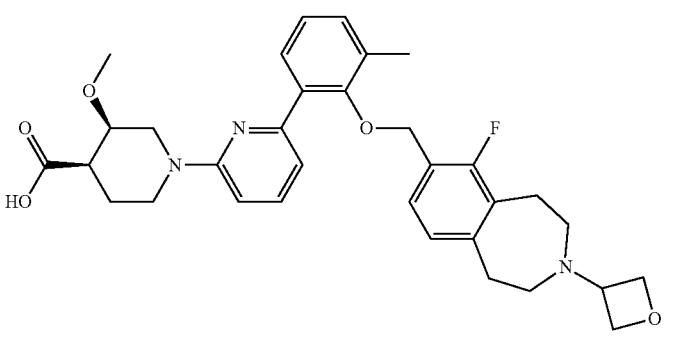 [SMILES: CO[C@H]1CN(c2cccc(-c3cccc(C)c3OCc3ccc4c(c3F)CCN(C3COC3)CC4)n2)CC[C@H]1C(=O)O] |
| 279 | 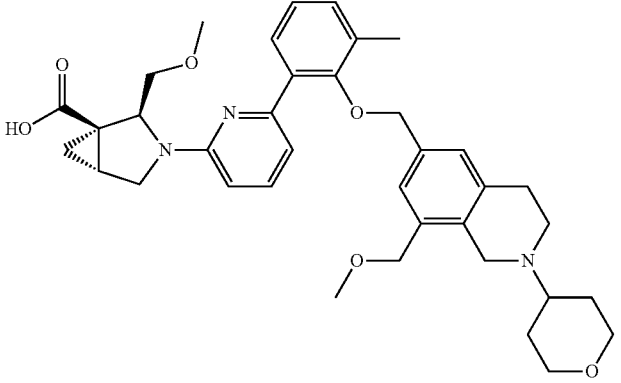 [SMILES: COCc1cc(COc2c(C)cccc2-c2cccc(N3C[C@@H]4C[C@]4(C(=O)O)[C@H]3COC)n2)cc2c1CN(C1CCOCC1)CC2] |

TABLE 1-continued
| Cpd No | Structure |
|---|---|
| 280 | 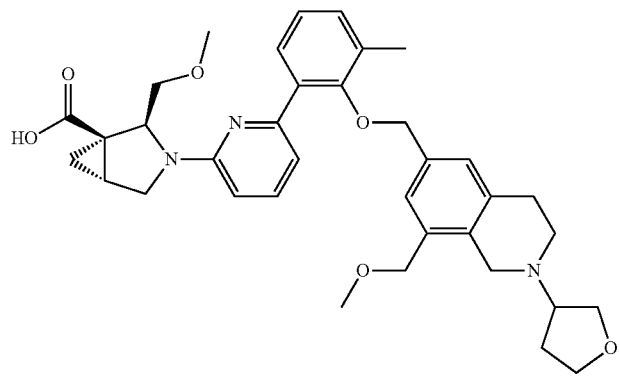 [SMILES: COCc1cc(COc2c(C)cccc2-c2cccc(N3C[C@@H]4C[C@]4(C(=O)O)[C@H]3COC)n2)cc2c1CN(C1CCOC1)CC2] |
| 281 | 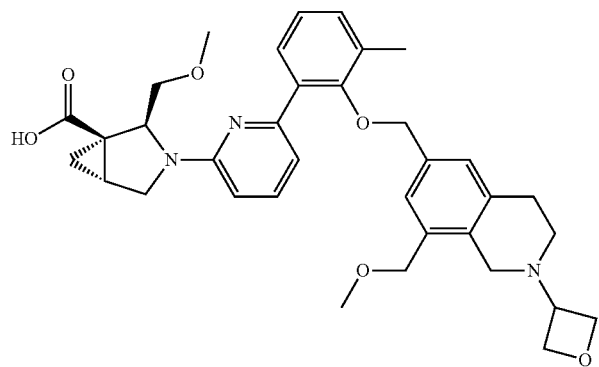 [SMILES: COCc1cc(COc2c(C)cccc2-c2cccc(N3C[C@@H]4C[C@]4(C(=O)O)[C@H]3COC)n2)cc2c1CN(C1COC1)CC2] |
| 282 | 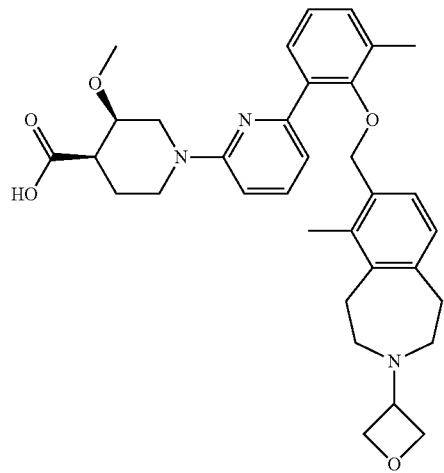 [SMILES: CO[C@H]1CN(c2cccc(-c3cccc(C)c3OCc3ccc4c(c3C)CCN(C3COC3)CC4)n2)CC[C@H]1C(=O)O] |

TABLE 1-continued
| Cpd No | Structure |
|---|---|
| 283 | 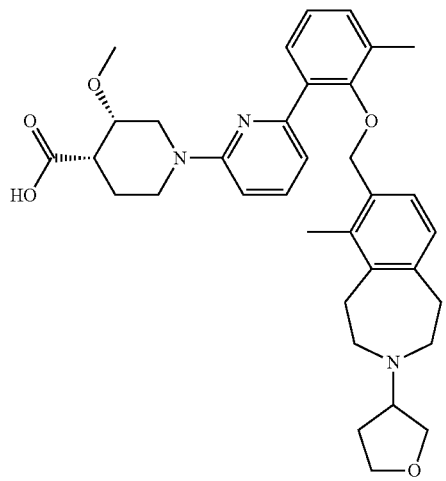 [SMILES: CO[C@@H]1CN(c2cccc(-c3cccc(C)c3OCc3ccc4c(c3C)CCN(C3CCOC3)CC4)n2)CC[C@@H]1C(=O)O] |
| 284 | 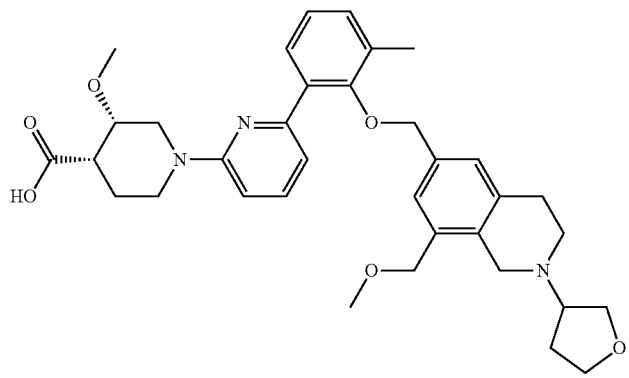 [SMILES: COCc1cc(COc2c(C)cccc2-c2cccc(N3CC[C@H](C(=O)O)[C@H](OC)C3)n2)cc2c1CN(C1CCOC1)CC2] |
| 285 | 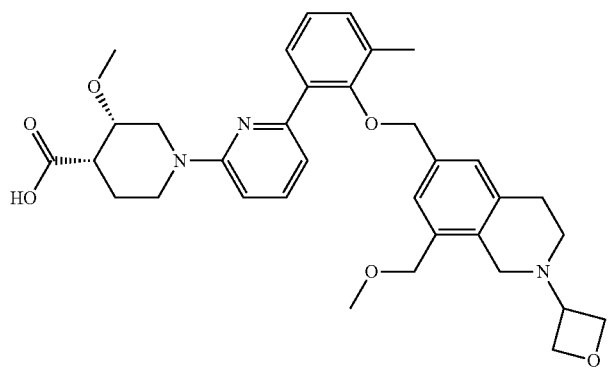 [SMILES: COCc1cc(COc2c(C)cccc2-c2cccc(N3CC[C@H](C(=O)O)[C@H](OC)C3)n2)cc2c1CN(C1COC1)CC2] |

TABLE 1-continued
| Cpd No | Structure |
|---|---|
| 286 | 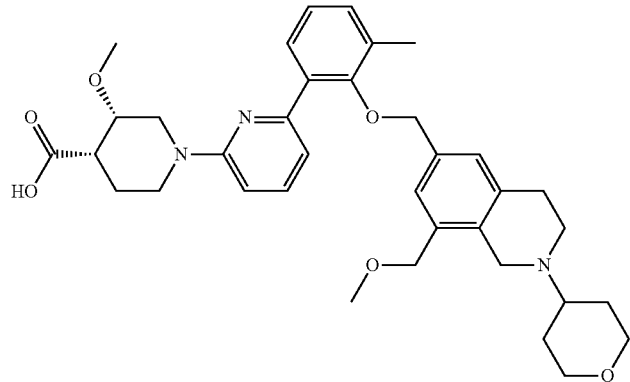 [SMILES: COCc1cc(COc2c(C)cccc2-c2cccc(N3CC[C@H](C(=O)O)[C@H](OC)C3)n2)cc2c1CN(C1CCOCC1)CC2] |
| 287 | 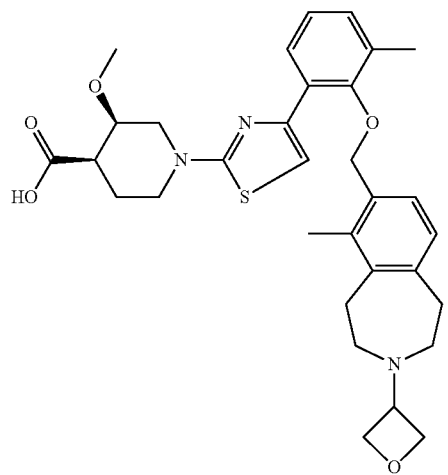 [SMILES: CO[C@H]1CN(c2nc(-c3cccc(C)c3OCc3ccc4c(c3C)CCN(C3COC3)CC4)cs2)CC[C@H]1C(=O)O] |
| 288 | 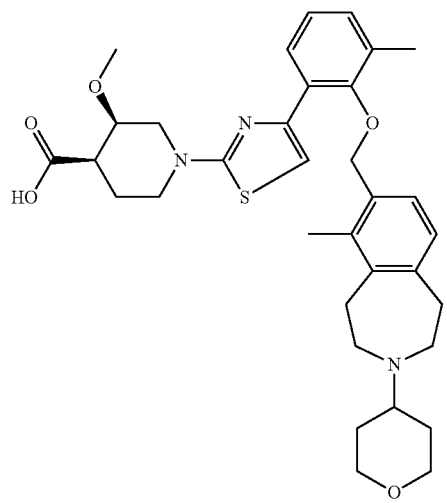 [SMILES: CO[C@H]1CN(c2nc(-c3cccc(C)c3OCc3ccc4c(c3C)CCN(C3CCOCC3)CC4)cs2)CC[C@H]1C(=O)O] |

TABLE 1-continued
| Cpd No | Structure |
|---|---|
| 289 | 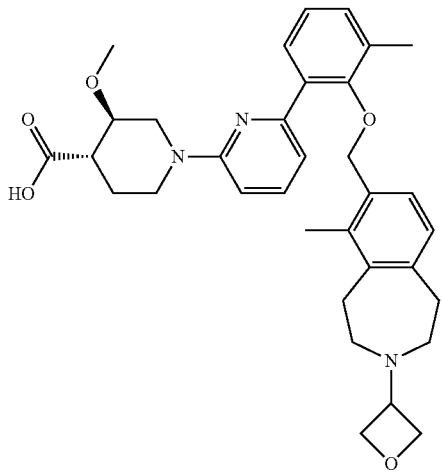 [SMILES: CO[C@H]1CN(c2cccc(-c3cccc(C)c3OCc3ccc4c(c3C)CCN(C3COC3)CC4)n2)CC[C@@H]1C(=O)O] |
| 290 | 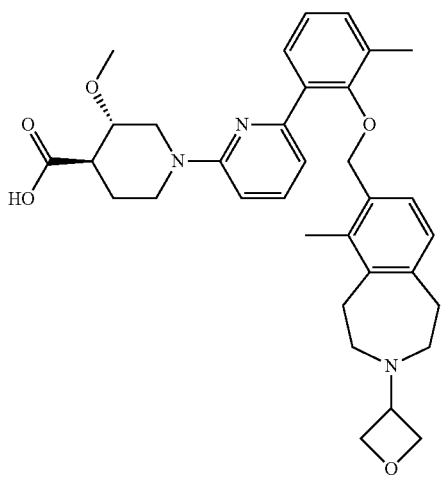 [SMILES: CO[C@@H]1CN(c2cccc(-c3cccc(C)c3OCc3ccc4c(c3C)CCN(C3COC3)CC4)n2)CC[C@H]1C(=O)O] |
| 291 | 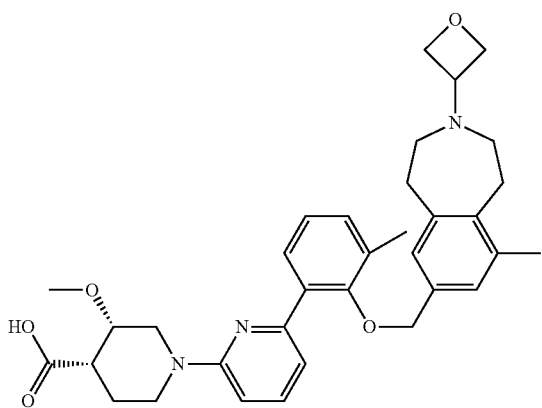 [SMILES: CO[C@@H]1CN(c2cccc(-c3cccc(C)c3OCc3cc(C)c4c(c3)CCN(C3COC3)CC4)n2)CC[C@@H]1C(=O)O] |

TABLE 1-continued

| Cpd No | Structure |
|---|---|
| 292 | 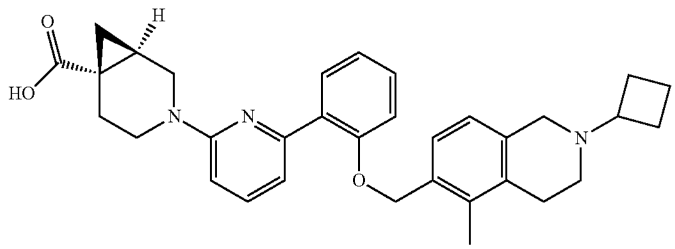 [SMILES: Cc1c(COc2ccccc2-c2cccc(N3CC[C@@]4(C(=O)O)C[C@H]4C3)n2)ccc2c1CCN(C1CCC1)C2] |
| 293 | 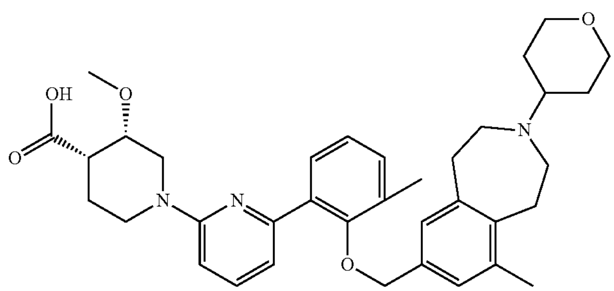 [SMILES: CO[C@@H]1CN(c2cccc(-c3cccc(C)c3OCc3cc(C)c4c(c3)CCN(C3CCOCC3)CC4)n2)CC[C@@H]1C(=O)O] |
| 294 | 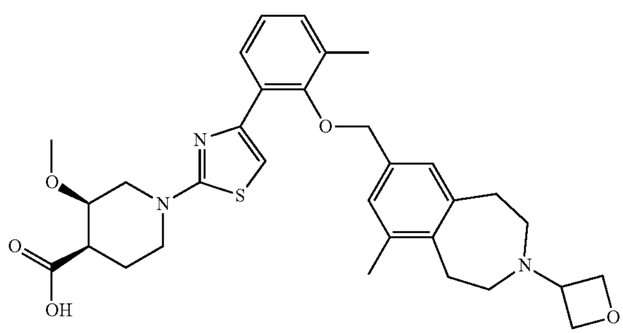 [SMILES: CO[C@H]1CN(c2nc(-c3cccc(C)c3OCc3cc(C)c4c(c3)CCN(C3COC3)CC4)cs2)CC[C@H]1C(=O)O] |
| 295 | 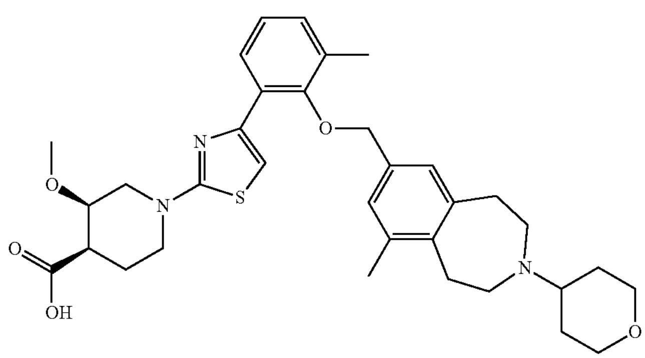 [SMILES: CO[C@H]1CN(c2nc(-c3cccc(C)c3OCc3cc(C)c4c(c3)CCN(C3CCOCC3)CC4)cs2)CC[C@H]1C(=O)O] |

TABLE 1-continued
| Cpd No | Structure |
|---|---|
| 296 | 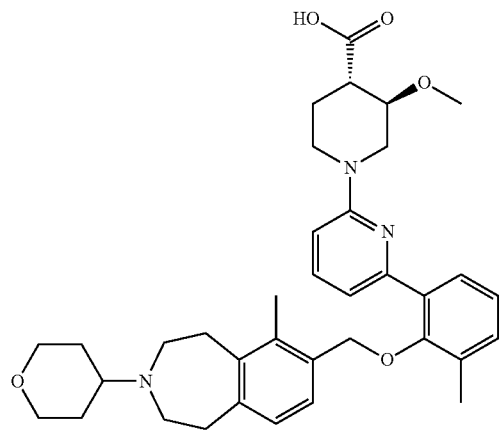 [SMILES: CO[C@H]1CN(c2cccc(-c3cccc(C)c3OCc3ccc4c(c3C)CCN(C3CCOCC3)CC4)n2)CC[C@@H]1C(=O)O] |
| 297 | 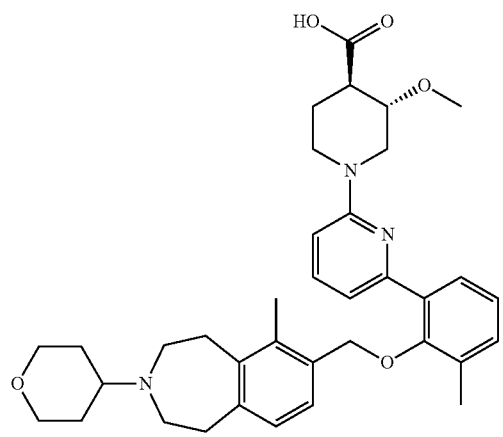 [SMILES: CO[C@@H]1CN(c2cccc(-c3cccc(C)c3OCc3ccc4c(c3C)CCN(C3CCOCC3)CC4)n2)CC[C@H]1C(=O)O] |
| 298 | 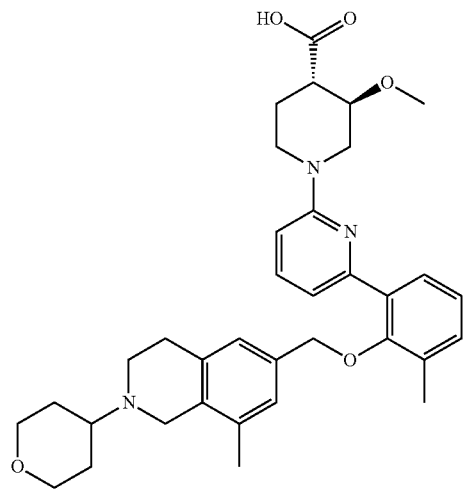 [SMILES: CO[C@H]1CN(c2cccc(-c3cccc(C)c3OCc3cc(C)c4c(c3)CCN(C3CCOCC3)C4)n2)CC[C@@H]1C(=O)O] |

TABLE 1-continued
| Cpd No | Structure |
|---|---|
| 299 | 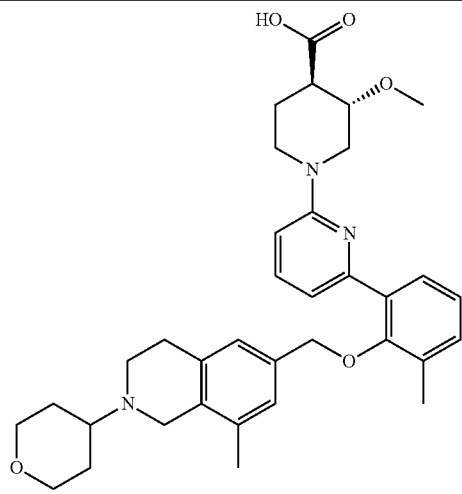 |
| 300 | 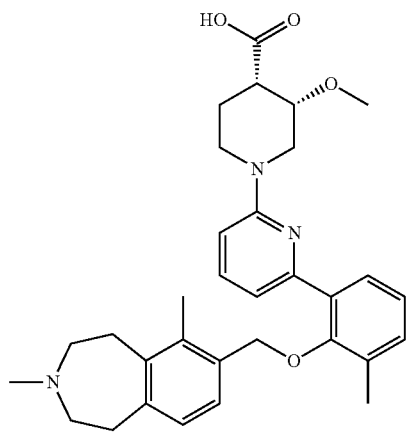 [SMILES: CO[C@@H]1CN(c2cccc(-c3cccc(C)c3OCc3ccc4c(c3C)CCN(C)CC4)n2)CC[C@@H]1C(=O)O] |
| 301 | 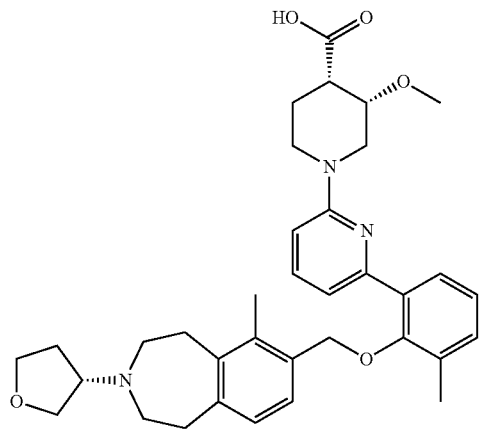 [SMILES: CO[C@@H]1CN(c2cccc(-c3cccc(C)c3OCc3ccc4c(c3C)CCN([C@H]3CCOC3)CC4)n2)CC[C@@H]1C(=O)O] |

TABLE 1-continued
| Cpd No | Structure |
|---|---|
| 302 | 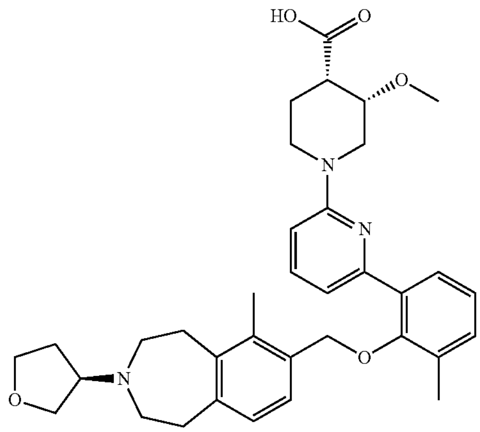 [SMILES: CO[C@@H]1CN(c2cccc(-c3cccc(C)c3OCc3ccc4c(c3C)CCN([C@@H]3CCOC3)CC4)n2)CC[C@@H]1C(=O)O] |
| 303 | 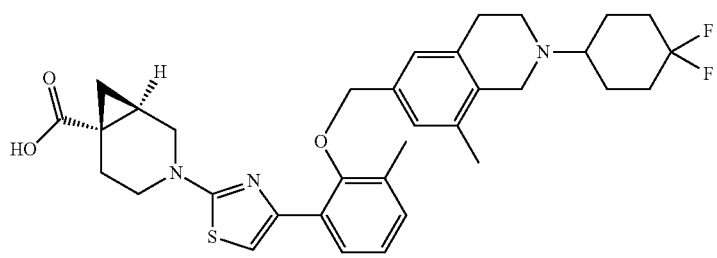 [SMILES: Cc1cc(COc2c(C)cccc2-c2csc(N3CC[C@@]4(C(=O)O)C[C@H]4C3)n2)cc2c1CN(C1CCC(F)(F)CC1)CC2] |
| 304 | 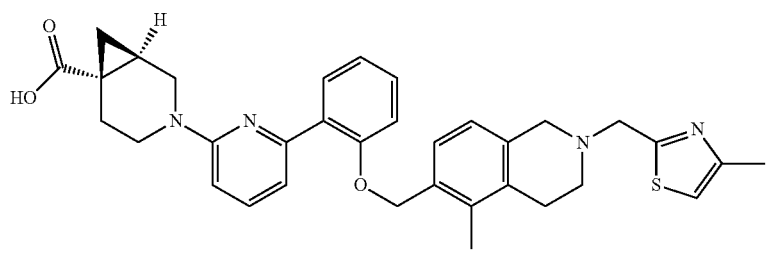 [SMILES: Cc1csc(CN2CCc3c(ccc(COc4ccccc4-c4cccc(N5CC[C@@]6(C(=O)O)C[C@H]6C5)n4)c3C)C2)n1] |
| 305 | 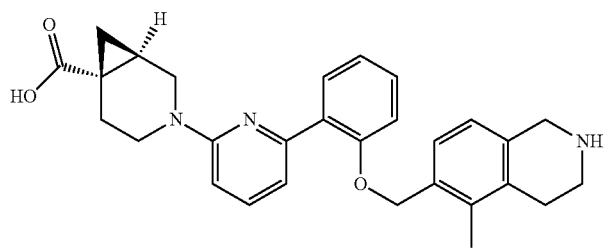 [SMILES: Cc1c(COc2ccccc2-c2cccc(N3CC[C@@]4(C(=O)O)C[C@H]4C3)n2)ccc2c1CCNC2] |
| 306 | 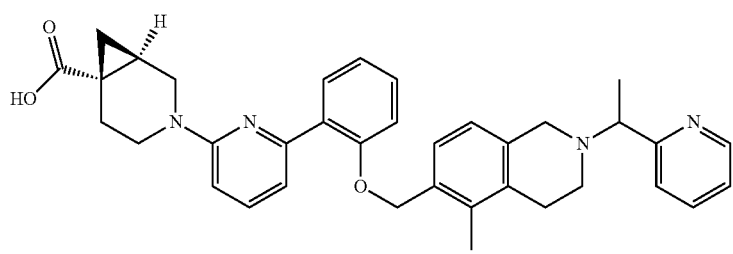 [SMILES: Cc1c(COc2ccccc2-c2cccc(N3CC[C@@]4(C(=O)O)C[C@H]4C3)n2)ccc2c1CCN(C(C)c1ccccn1)C2] |

TABLE 1-continued
| Cpd No | Structure |
|---|---|
| 307 | 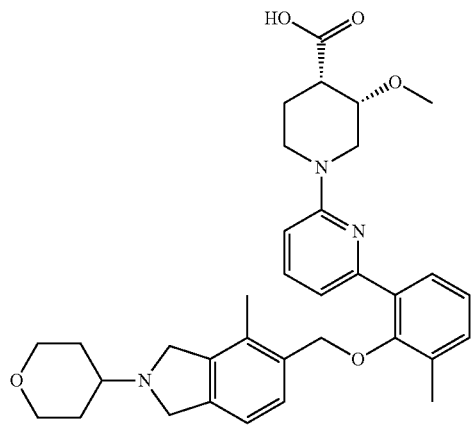 [SMILES: CO[C@@H]1CN(c2cccc(-c3cccc(C)c3OCc3ccc4c(c3C)CN(C3CCOCC3)C4)n2)CC[C@@H]1C(=O)O] |
| 308 | 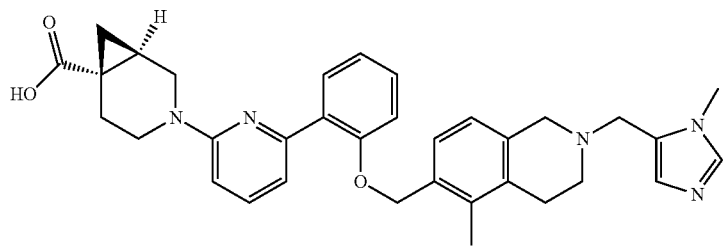 [SMILES: Cc1c(COc2ccccc2-c2cccc(N3CC[C@@]4(C(=O)O)C[C@H]4C3)n2)ccc2c1CCN(Cc1cncn1C)C2] |
| 309 | 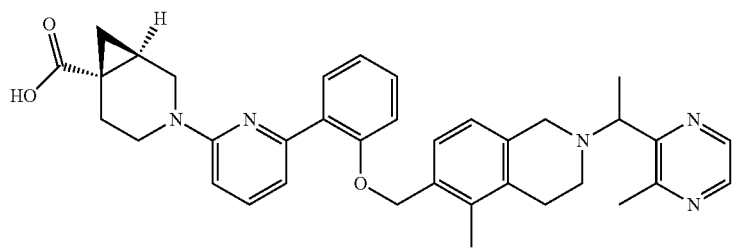 [SMILES: Cc1nccnc1C(C)N1CCc2c(ccc(COc3ccccc3-c3cccc(N4CC[C@@]5(C(=O)O)C[C@H]5C4)n3)c2C)C1] |
| 310 | 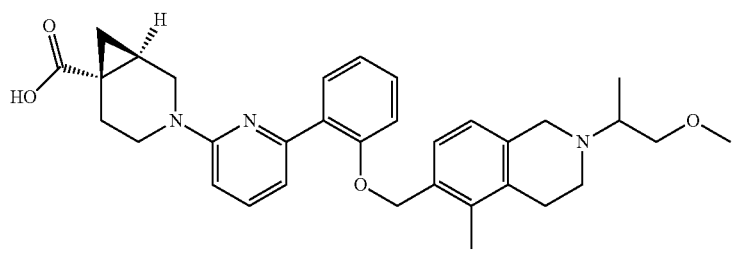 [SMILES: COCC(C)N1CCc2c(ccc(COc3ccccc3-c3cccc(N4CC[C@@]5(C(=O)O)C[C@H]5C4)n3)c2C)C1] |
| 311 | 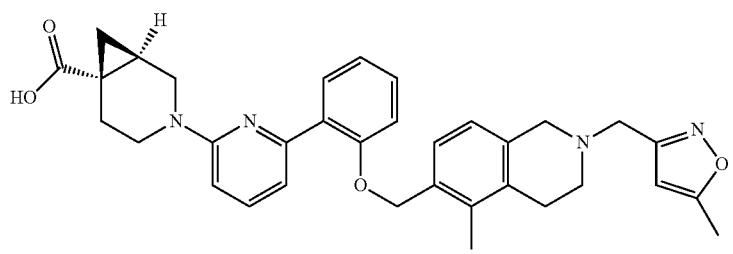 [SMILES: Cc1cc(CN2CCc3c(ccc(COc4ccccc4-c4cccc(N5CC[C@@]6(C(=O)O)C[C@H]6C5)n4)c3C)C2)no1] |

TABLE 1-continued

| Cpd No | Structure |
|---|---|
| 312 | 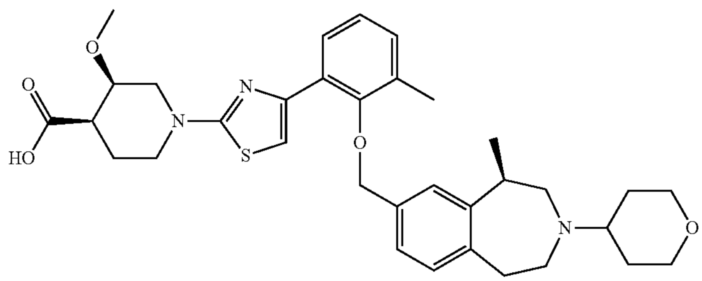 [SMILES: CO[C@H]1CN(c2nc(-c3cccc(C)c3OCc3ccc4c(c3)[C@@H](C)CN(C3CCOCC3)CC4)cs2)CC[C@H]1C(=O)O] |
| 313 | 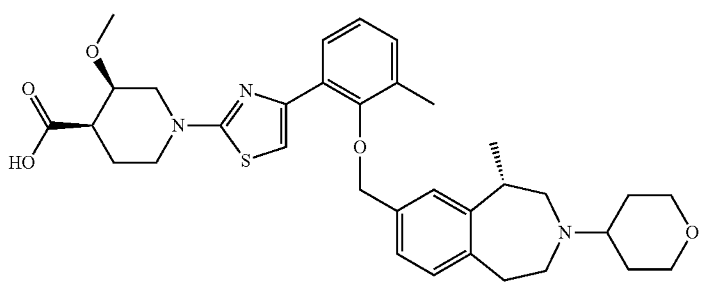 [SMILES: CO[C@H]1CN(c2nc(-c3cccc(C)c3OCc3ccc4c(c3)[C@H](C)CN(C3CCOCC3)CC4)cs2)CC[C@H]1C(=O)O] |
| 314 | 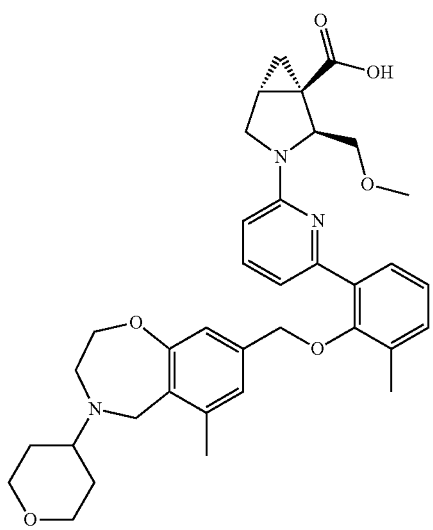 [SMILES: COC[C@H]1N(c2cccc(-c3cccc(C)c3OCc3cc(C)c4c(c3)OCCN(C3CCOCC3)C4)n2)C[C@@H]2C[C@@]21C(=O)O] |
| 315 | 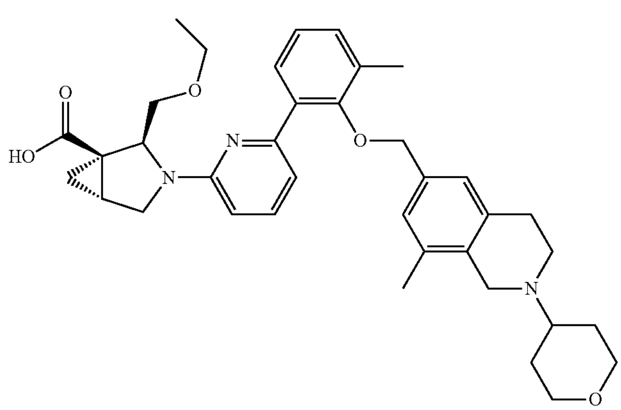 [SMILES: CCOC[C@H]1N(c2cccc(-c3cccc(C)c3OCc3cc(C)c4c(c3)CCN(C3CCOCC3)C4)n2)C[C@@H]2C[C@@]21C(=O)O] |

TABLE 1-continued

| Cpd No | Structure |
|---|---|
| 316 | 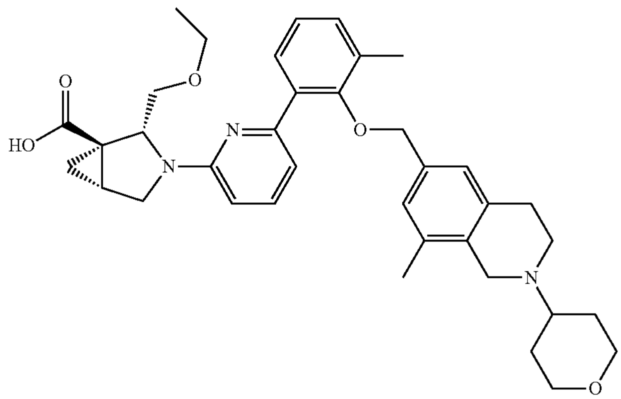 [SMILES: CCOC[C@@H]1N(c2cccc(-c3cccc(C)c3OCc3cc(C)c4c(c3)CCN(C3CCOCC3)C4)n2)C[C@@H]2C[C@@]21C(=O)O] |
| 317 | 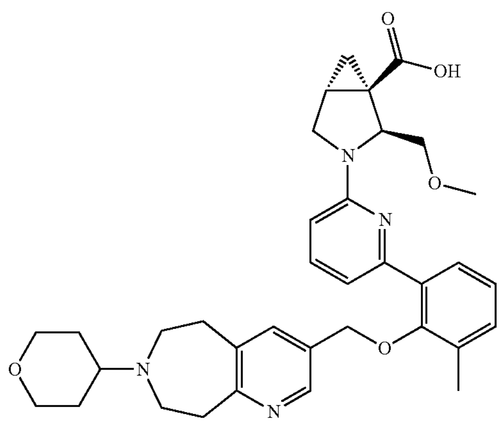 [SMILES: COC[C@H]1N(c2cccc(-c3cccc(C)c3OCc3cnc4c(c3)CCN(C3CCOCC3)CC4)n2)C[C@@H]2C[C@@]21C(=O)O] |
| 318 | 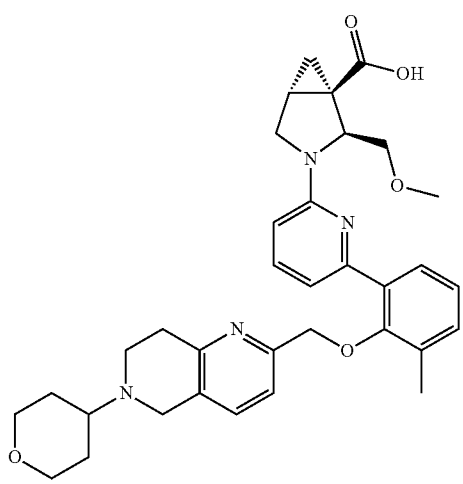 [SMILES: COC[C@H]1N(c2cccc(-c3cccc(C)c3OCc3ccc4c(n3)CCN(C3CCOCC3)C4)n2)C[C@@H]2C[C@@]21C(=O)O] |
| 319 | 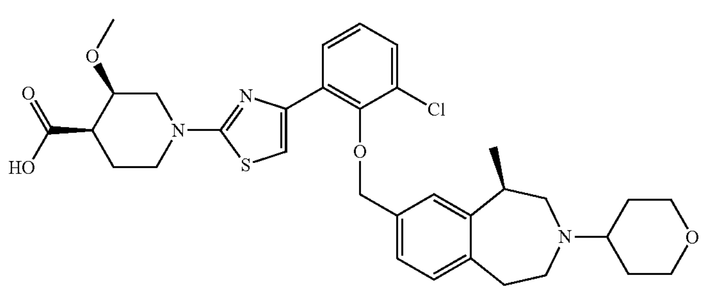 [SMILES: CO[C@H]1CN(c2nc(-c3cccc(Cl)c3OCc3ccc4c(c3)[C@@H](C)CN(C3CCOCC3)CC4)cs2)CC[C@H]1C(=O)O] |

TABLE 1-continued

| Cpd No | Structure |
|---|---|
| 320 | 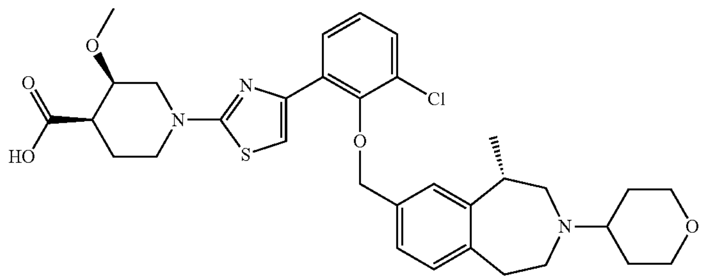 |
| 321 | 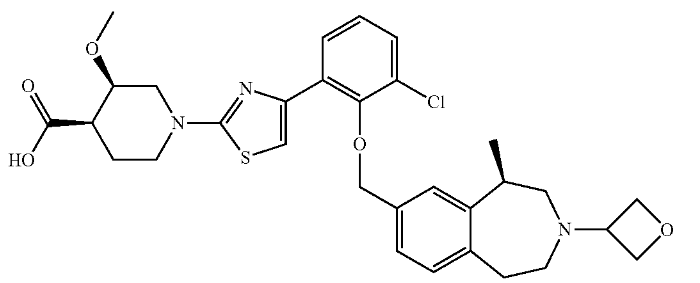 [SMILES: CO[C@H]1CN(c2nc(-c3cccc(Cl)c3OCc3ccc4c(c3)[C@@H](C)CN(C3COC3)CC4)cs2)CC[C@H]1C(=O)O] |
| 322 | 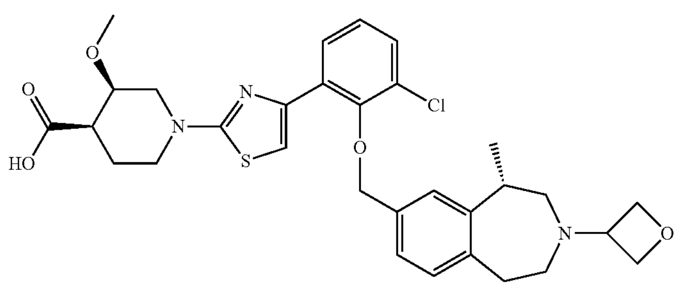 [SMILES: CO[C@H]1CN(c2nc(-c3cccc(Cl)c3OCc3ccc4c(c3)[C@H](C)CN(C3COC3)CC4)cs2)CC[C@H]1C(=O)O] |
| 323 | 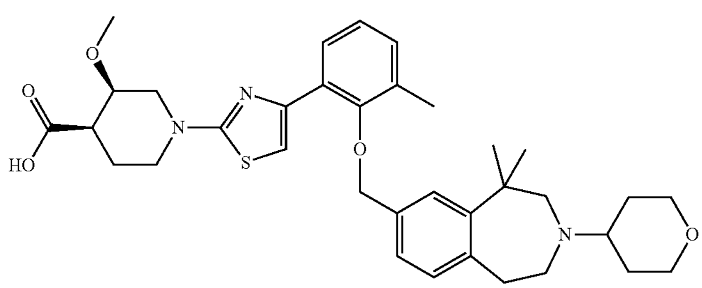 [SMILES: CO[C@H]1CN(c2nc(-c3cccc(C)c3OCc3ccc4c(c3)C(C)(C)CN(C3CCOCC3)CC4)cs2)CC[C@H]1C(=O)O] |
| 324 | 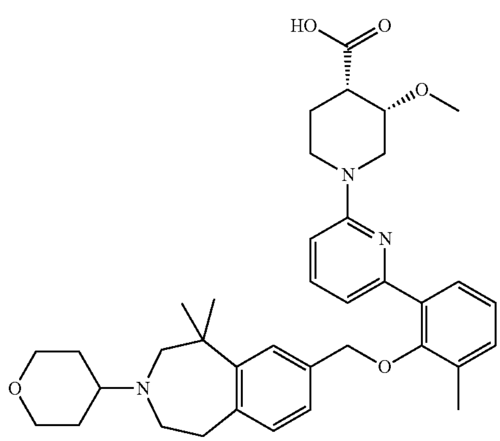 [SMILES: CO[C@@H]1CN(c2cccc(-c3cccc(C)c3OCc3ccc4c(c3)C(C)(C)CN(C3CCOCC3)CC4)n2)CC[C@@H]1C(=O)O] |

TABLE 1-continued
| Cpd No | Structure |
|---|---|
| 325 | 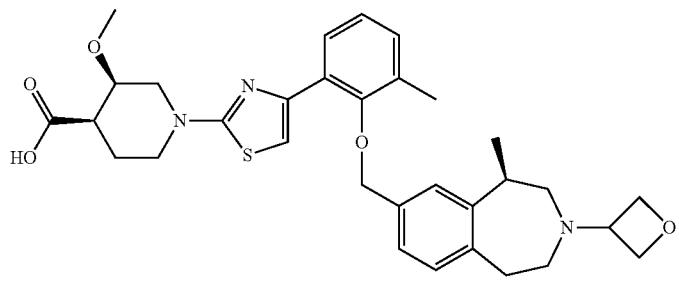 [SMILES: CO[C@H]1CN(c2nc(-c3cccc(C)c3OCc3ccc4c(c3)[C@@H](C)CN(C3COC3)CC4)cs2)CC[C@H]1C(=O)O] |
| 326 | 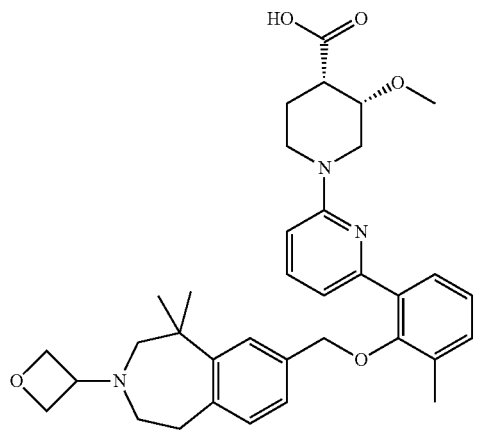 [SMILES: CO[C@@H]1CN(c2cccc(-c3cccc(C)c3OCc3ccc4c(c3)C(C)(C)CN(C3COC3)CC4)n2)CC[C@@H]1C(=O)O] |
| 327 | 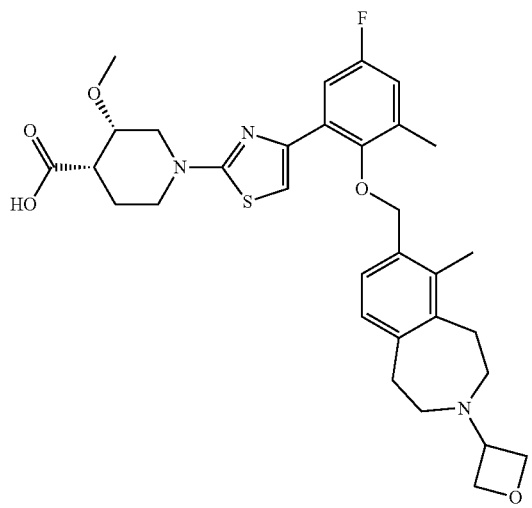 [SMILES: CO[C@@H]1CN(c2nc(-c3cc(F)cc(C)c3OCc3ccc4c(c3C)CCN(C3COC3)CC4)cs2)CC[C@@H]1C(=O)O] |

TABLE 1-continued
| Cpd No | Structure |
|---|---|
| 328 | 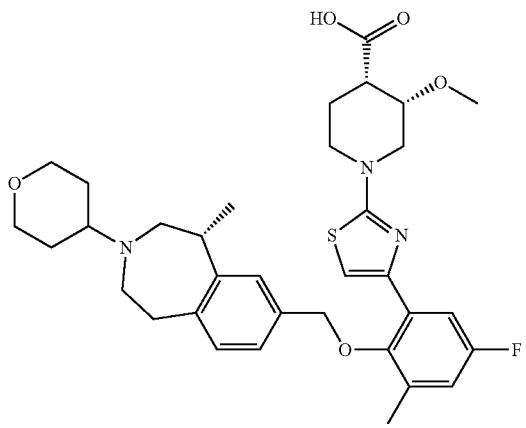 [SMILES: CO[C@@H]1CN(c2nc(-c3cc(F)cc(C)c3OCc3ccc4c(c3)[C@@H](C)CN(C3CCOCC3)CC4)cs2)CC[C@@H]1C(=O)O] |
| 329 | 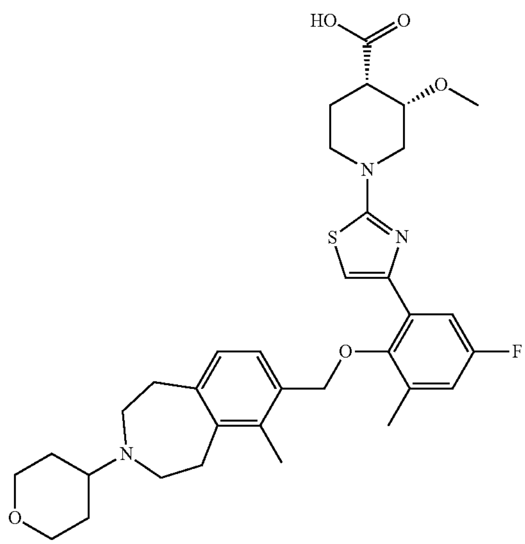 [SMILES: CO[C@@H]1CN(c2nc(-c3cc(F)cc(C)c3OCc3ccc4c(c3C)CCN(C3CCOCC3)CC4)cs2)CC[C@@H]1C(=O)O] |
| 330 | 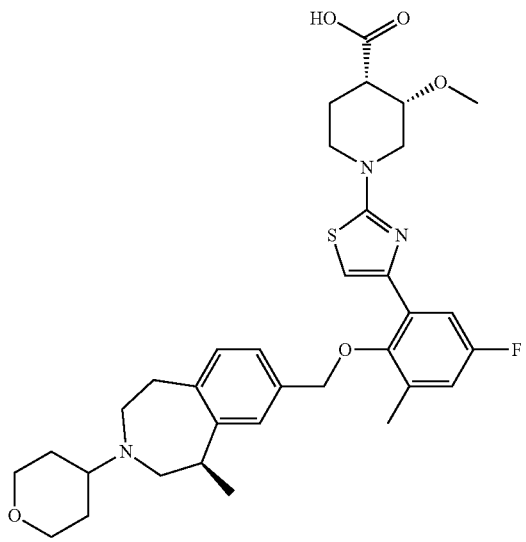 [SMILES: CO[C@@H]1CN(c2nc(-c3cc(F)cc(C)c3OCc3ccc4c(c3)[C@@H](C)CN(C3CCOCC3)CC4)cs2)CC[C@@H]1C(=O)O] |

TABLE 1-continued

| Cpd No | Structure |
|---|---|
| 331 | 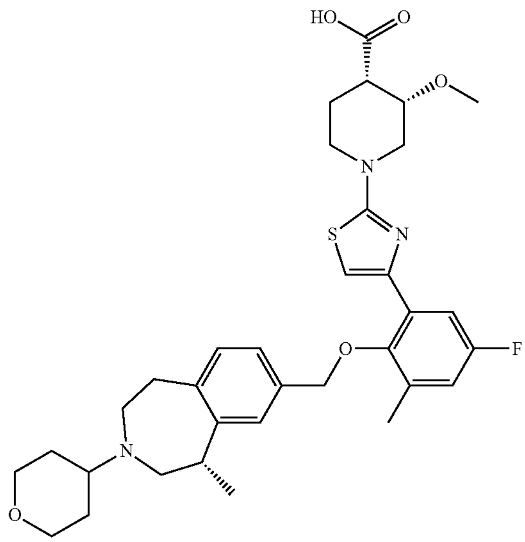 [SMILES: CO[C@@H]1CN(c2nc(-c3cc(F)cc(C)c3OCc3ccc4c(c3)[C@H](C)CN(C3CCOCC3)CC4)cs2)CC[C@@H]1C(=O)O] |
| 332 | 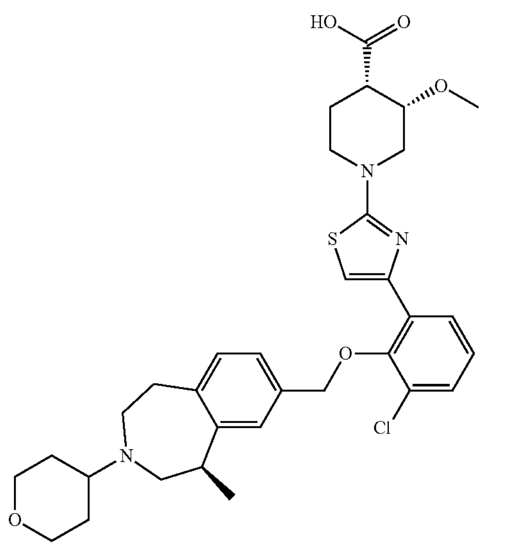 [SMILES: CO[C@@H]1CN(c2nc(-c3cccc(Cl)c3OCc3ccc4c(c3)[C@@H](C)CN(C3CCOCC3)CC4)cs2)CC[C@@H]1C(=O)O] |
| 333 | 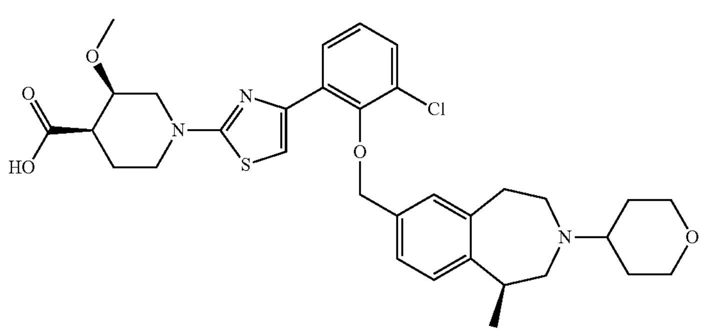 [SMILES: CO[C@H]1CN(c2nc(-c3cccc(Cl)c3OCc3ccc4c(c3)CCN(C3CCOCC3)C[C@H]4C)cs2)CC[C@H]1C(=O)O] |

TABLE 1-continued
| Cpd No | Structure |
|---|---|
| 334 | 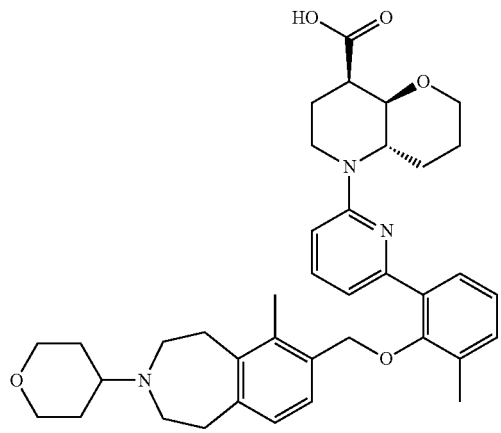 [SMILES: Cc1cccc(-c2cccc(N3CC[C@@H](C(=O)O)[C@H]4OCCC[C@@H]43)n2)c1OCc1ccc2c(c1C)CCN(C1CCOCC1)CC2] |
| 335 | 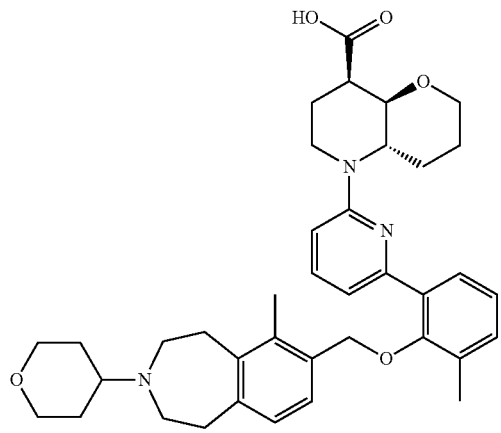 [SMILES: Cc1cccc(-c2cccc(N3CC[C@@H](C(=O)O)[C@H]4OCCC[C@@H]43)n2)c1OCc1ccc2c(c1C)CCN(C1CCOCC1)CC2] |
| 336 | 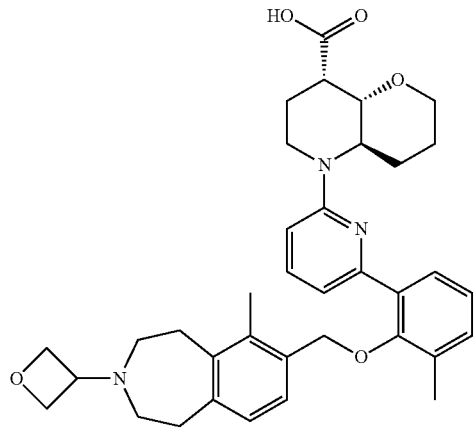 [SMILES: Cc1cccc(-c2cccc(N3CC[C@H](C(=O)O)[C@@H]4OCCC[C@H]43)n2)c1OCc1ccc2c(c1C)CCN(C1COC1)CC2] |

TABLE 1-continued

| Cpd No | Structure |
|---|---|
| 337 | (structure) |
| 338 | (structure) |

In one embodiment, the invention relates to any of the compounds depicted in Table 1 above and the pharmaceutically acceptable salts thereof.

In another embodiment the invention relates to the group of compounds depicted in Table 1 consisting of compounds 1-198.

In another embodiment the invention relates to the group of compounds depicted in Table 1 consisting of compounds 198-338.

In another embodiment the invention relates to the group of compounds depicted in Table 1 consisting of compounds 43, 44, 45, 46, 47, 48, 49, 53, 55, 56, 57, 58, 59, 60, 61, 161, 162, 163, 164, 212, 213, 215, 216, 217, 218, 219, 220, 221, 222, 223, 224, 225, 226, 227, 237, 243, 262, 263, 268, 279, 280, 281, 314, 316, 317, and 318.

In another embodiment the invention relates to the group of compounds depicted in Table 1 consisting of compounds 64, 65, 66, 67, 68, 69, 70, 71, 72, 74, 75, 76, 77, 78, 79, 80, 165, 166, 167, 168, 169, 170, 171, 172, 173, 174, 175, 176, 177, 181, 182, 195, 196, 197, 203, 204, 205, 206, 207, 208, 209, 210, 211, 228, 229, 230, 231, 232, 233, 234, 235, 238, 239, 240, 241, 242, 244, 245, 246, 247, 248, 249, 250, 251, 252, 253, 254, 255, 256, 257, 258, 259, 260, 261, 264, 265, 266, 267, 269, 270, 271, 272, 273, 274, 275, 276, 277, 278, 282, 283, 284, 285, 286, 287, 288, 289, 290, 291, 293, 294, 295, 296, 297, 298, 299, 300, 301, 302, 307, 312, 313, 319, 320, 321, 322, 323, 324, 325, 326, 327, 328, 329, 330, 331, 332, 333 and 338.

In another embodiment the invention relates to the group of compounds depicted in Table 1 consisting of compounds 1, 2, 3, 4, 5, 6, 7, 8, 9, 10, 11, 12, 13, 14, 15, 16, 17, 18, 19, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 185, 186, 187, 192, 193, 194, 199, 200, 201, 202, 292, 303, 304, 305, 306, 308, 309, 310, and 311

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula I can exist in more than one tautomeric form. The invention includes methods for using all such tautomers.

The invention includes pharmaceutically acceptable derivatives of compounds of formula I. A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula I.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula I. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

For all compounds disclosed herein above in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_2CH_3))$—, —$(CHCH(CH_3)_2)$— and —$C(CH_3)(CH_2CH_3)$—.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3] heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —$CH_2CHF_2$, —$CF_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl, likewise, —S—$R_a$ may be represented as phenyl-S(O)$_m$— when $R_a$ is phenyl and where m is 0, 1 or 2.

General Synthetic Methods

The compounds of the invention may be prepared by the general methods and examples presented below and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

The methods described below and in the Synthetic Examples section may be used to prepare the compounds of formula I.

Compounds of formula I may be prepared as described in Scheme 1

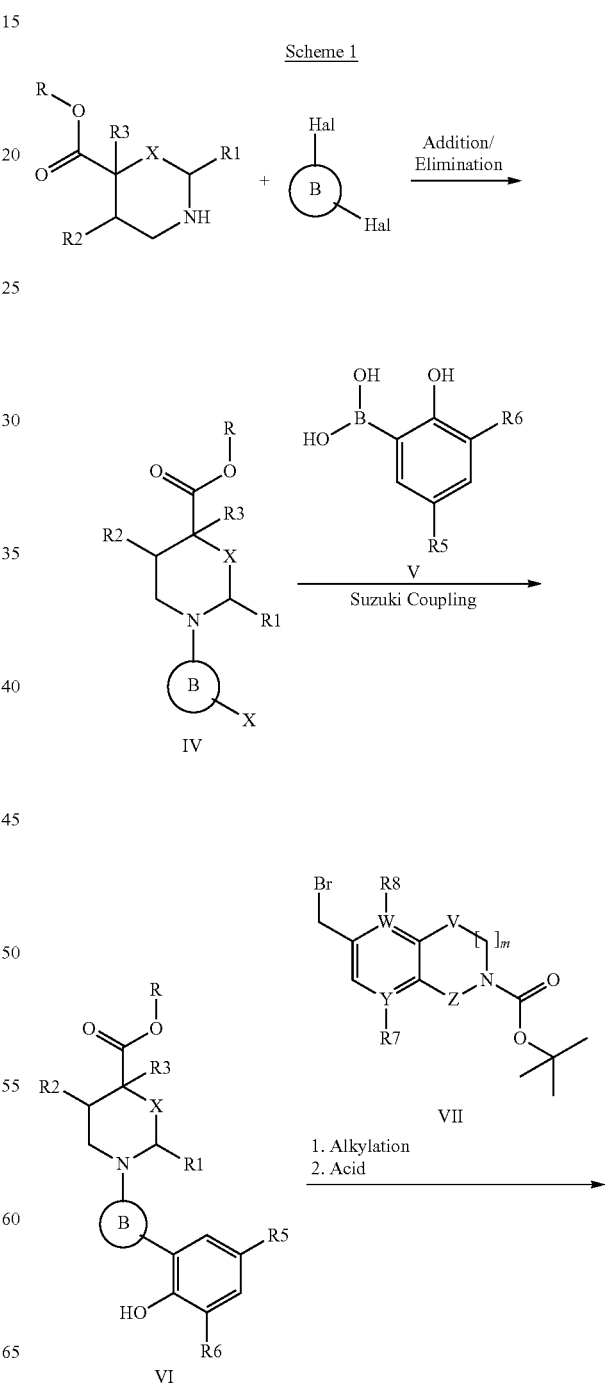

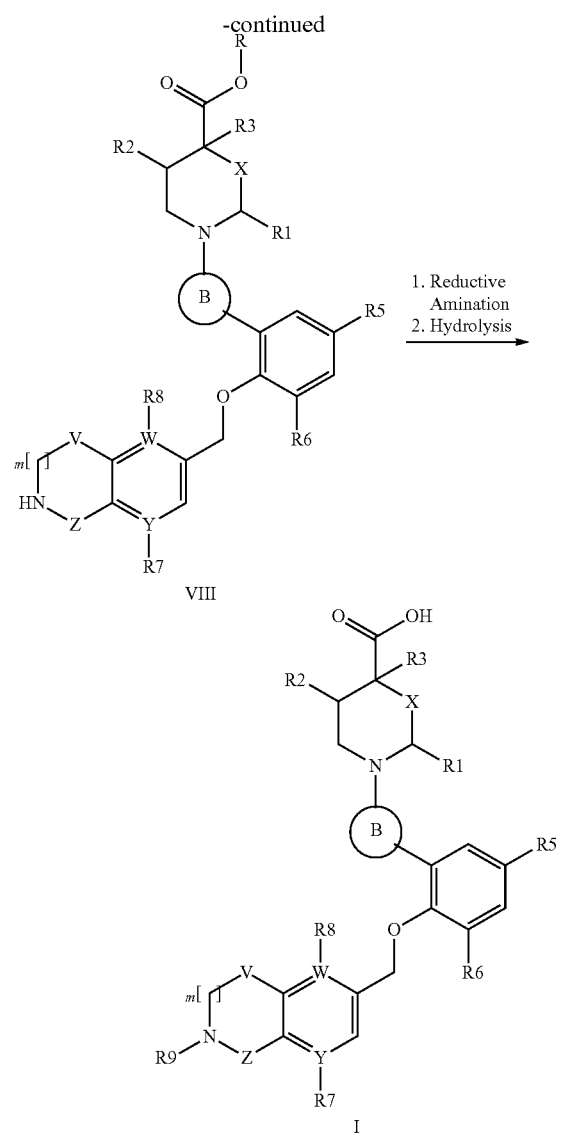

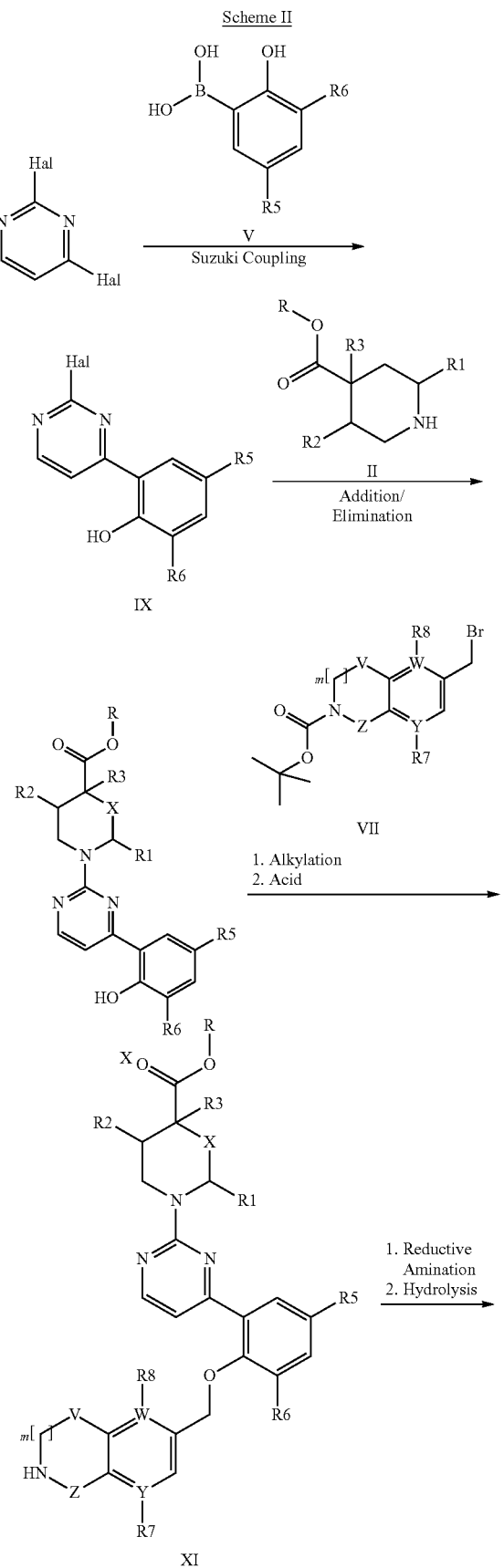

As illustrated in Scheme I above, amine II (X=CH₂ or bond, R=Me, Et or tert-butyl) and dihalo heterocycle (B=2,6 pyridyl or 2,5-thiazole; Hal=Cl or Br) III are refluxed in a suitable solvent such as N,N-dimethylformamide with a suitable base such as potassium carbonate (K₂CO₃) yielding heteroaryl IV. Compound IV is coupled with boron species, V, in the presence of a palladium catalyst such as tetrakis(triphenyl)phosphine (0) and a suitable base such as Na₂CO₃ in aqueous 1,4-dioxane at about 80° C. to provide VI. Alkylation of the phenol intermediate, VI with alkyl bromide VII, using a base such as cesium carbonate (Cs₂CO₃) in a solvent such as acetone. Subsequent deprotection of the Boc group with a suitable acid such as trifluoroacetic acid (TFA) provides compound VIII. Reductive amination of amine, VIII, with the desired ketone or aldehyde using an appropriate hydride source such as NaBH₃CN in a solvent such as MeOH containing an organic acid such as AcOH at about 50° C., followed by in situ hydrolysis with a base such as aqueous LiOH (where R4=Me or Et), or using formic acid (where R4=tert-butyl), affords the desired compound of formula I.

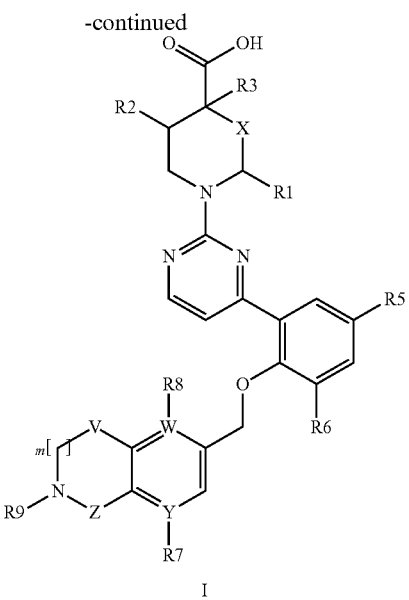

I

Alternatively, as illustrated in Scheme II when B is a 2,6 disubstituted pyrimidine ring, the starting 2,6-dihalopyrimidine (Cl or Br) is coupled with boron species, V, in the presence of a palladium catalyst such as tetrakis(triphenyl)phosphine (0) and a suitable base such as Na$_2$CO$_3$ in aqueous 1,4-dioxane at 80° C. to provide IX. Amine II (X=CH$_2$ or bond, R$^4$=Me, Et, or tert-butyl) and IX are refluxed in a suitable solvent such as N,N-dimethylformamide with a suitable base such as potassium carbonate (K$_2$CO$_3$) yielding aminopyrimidine X. This is followed by alkylation of the phenol intermediate, X with alkyl bromide VII, using a base such as cesium carbonate (Cs$_2$CO$_3$) in a solvent such as acetone. Subsequent deprotection of the Boc group with a suitable acid such as trifluoroacetic acid (TFA) provides compound XI. Reductive amination of amine, XI, with the desired ketone or aldehyde using an appropriate hydride source such as NaBH$_3$CN in a solvent such as MeOH containing an organic acid such as AcOH at about 50° C., followed by in situ hydrolysis with a base such as aqueous LiOH (where R4=Me or Et), or using formic acid (where R4=tert-butyl), affords the desired compound of formula I.

UPLC/MS Methods

Retention times (RT) reported for compounds in the Synthetic Examples section are obtained by UPLC/MS using one of the following methods:

For each of the methods, the following are identical:

UPLC/MS system components—Acquity UPLC with PDA, SQ and ELS detectors.

PDA conditions—Detection: 210 to 400 nm. Sampling rate: 20 pts/sec. Filter response: fast.

ELSD conditions—Gain: 1000. Sampling rate: 20 pts/sec. Drift tube temp: 55° C. Nebulizer mode: cooling. Gas pressure: 41 psi.

MS conditions—Instrument: Acquity SQD with ESCi source. Ionization mode: ESI+/−. Capillary voltage: 3.5 kV. Cone voltage: 5 V. Extractor: 1.3 V. Source temp: 150° C. Desolvation temp: 350° C. Desolvation gas: 800 L/hr. Cone gas: 50 L/hr.

Conditions specific to each method are as follows

Method A1

Column—Waters BEH C18, 2.1×50 mm, 1.7 um particle diameter.

Description and Gradient: Medium polar fast gradient method. ESI+/− ion mode 80-1000 Da. Gradient: 90% A to 95% B in 1.19 min hold at 95% B to 1.70 min. Flow rate 0.8 mL/min. A=(95% Water 5% Acetonitrile 0.05% Formic Acid) B=(Acetonitrile 0.05% Formic Acid). Sample Injection Volume: 1 uL Method A2

Column: HSS T3 2.1×100 mm, 1.8 um particle diameter.

Description and Gradient: Polar gradient method. ESI+/− ion mode 80-1000 Da. Gradient: 95% A to 95% B in 3.65 min hold at 95% B to 4.95 min. Flow rate 0.6 mL/min. A=(95% Water 5% Acetonitrile 0.05% Formic Acid) B=(Acetonitrile 0.05% Formic Acid).

Sample Injection Volume: 1 uL

Method A3

Column: BEH 2.1×50 mm C18, 1.7 um particle diameter.

Description and Gradient: Medium polar long gradient method. ESI+/− ion mode 80-1000 Da. Gradient: 90% A to 95% B in 4.45 min hold at 95% B to 4.58 min. Flow rate 0.8 mL/min. A=(95% Water 5% Acetonitrile+0.05% Formic Acid) B=(Acetonitrile+0.05% Formic Acid)

Sample Injection Volume: 1 uL

Method A4

Column: BEH 2.1×50 mm C18, 1.7 um particle diameter.

Description and Gradient: Base buffered medium polar fast gradient method. ESI+/− ion mode 80-1000 Da. Gradient: 90% A to 95% B in 1.19 min hold at 95% B to 1.70 min. Flow rate 0.8 mL/min. A=(95% Water 5% Acetonitrile 2.5 mM Ammonium Bicarbonate) B=(Acetonitrile).

Sample Injection Volume: 1 uL

Method A1 is used for all of the compounds except where noted.

SYNTHETIC EXAMPLES

Final compounds are designated by compound numbers corresponding to the compound numbers in Table 1. Intermediates are given hyphenated numbers corresponding to the figures and numbers shown in the scheme for each example.

Synthesis of Intermediates

Example 1

Preparation of intermediate (S)-3-Aza-bicyclo[4.1.0]heptane-6-carboxylic acid ethyl ester (A-1)

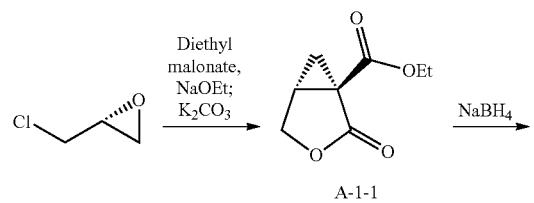

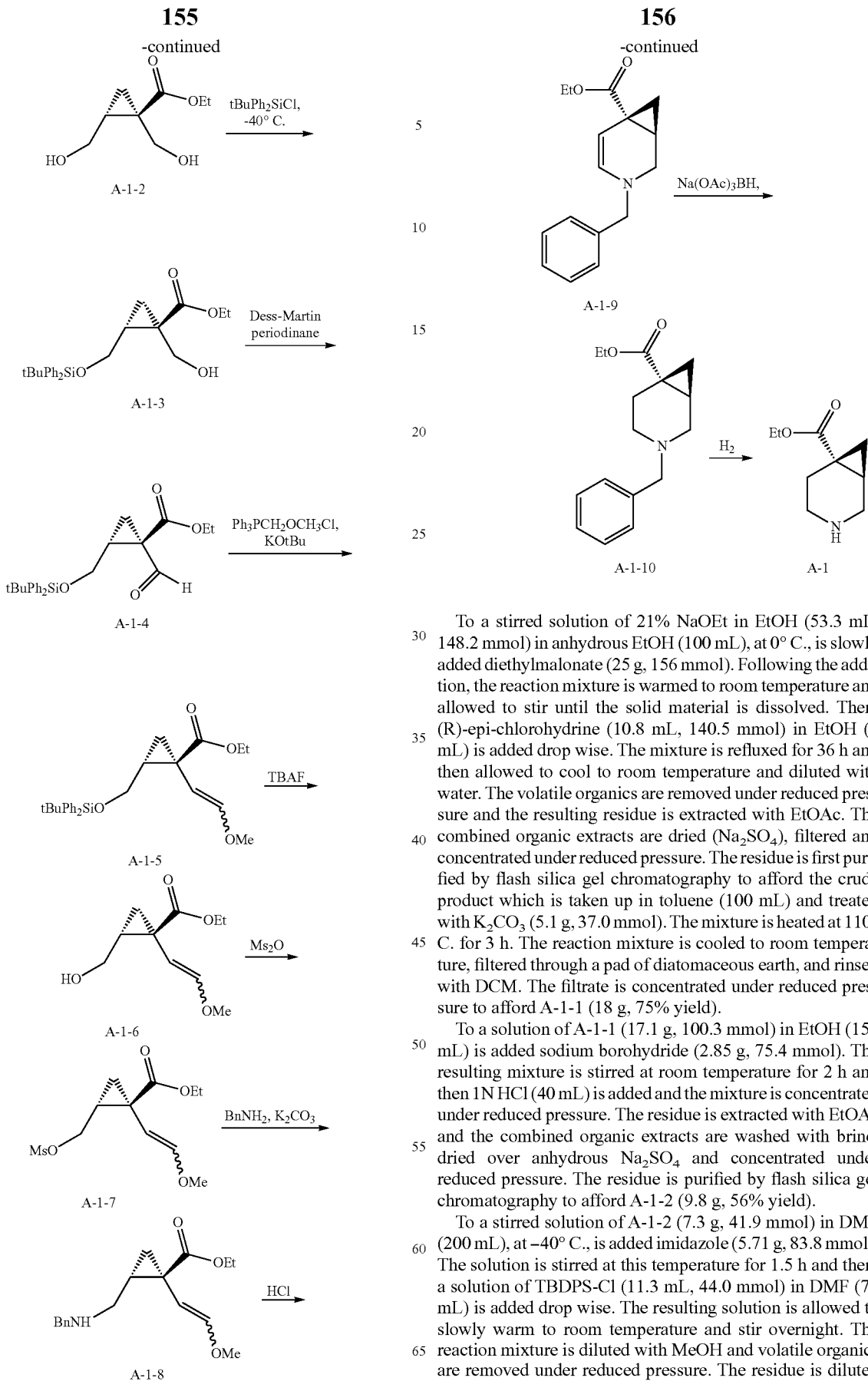

To a stirred solution of 21% NaOEt in EtOH (53.3 mL, 148.2 mmol) in anhydrous EtOH (100 mL), at 0° C., is slowly added diethylmalonate (25 g, 156 mmol). Following the addition, the reaction mixture is warmed to room temperature and allowed to stir until the solid material is dissolved. Then, (R)-epi-chlorohydrine (10.8 mL, 140.5 mmol) in EtOH (5 mL) is added drop wise. The mixture is refluxed for 36 h and then allowed to cool to room temperature and diluted with water. The volatile organics are removed under reduced pressure and the resulting residue is extracted with EtOAc. The combined organic extracts are dried ($Na_2SO_4$), filtered and concentrated under reduced pressure. The residue is first purified by flash silica gel chromatography to afford the crude product which is taken up in toluene (100 mL) and treated with $K_2CO_3$ (5.1 g, 37.0 mmol). The mixture is heated at 110° C. for 3 h. The reaction mixture is cooled to room temperature, filtered through a pad of diatomaceous earth, and rinsed with DCM. The filtrate is concentrated under reduced pressure to afford A-1-1 (18 g, 75% yield).

To a solution of A-1-1 (17.1 g, 100.3 mmol) in EtOH (150 mL) is added sodium borohydride (2.85 g, 75.4 mmol). The resulting mixture is stirred at room temperature for 2 h and then 1N HCl (40 mL) is added and the mixture is concentrated under reduced pressure. The residue is extracted with EtOAc and the combined organic extracts are washed with brine, dried over anhydrous $Na_2SO_4$ and concentrated under reduced pressure. The residue is purified by flash silica gel chromatography to afford A-1-2 (9.8 g, 56% yield).

To a stirred solution of A-1-2 (7.3 g, 41.9 mmol) in DMF (200 mL), at −40° C., is added imidazole (5.71 g, 83.8 mmol). The solution is stirred at this temperature for 1.5 h and then, a solution of TBDPS-Cl (11.3 mL, 44.0 mmol) in DMF (70 mL) is added drop wise. The resulting solution is allowed to slowly warm to room temperature and stir overnight. The reaction mixture is diluted with MeOH and volatile organics are removed under reduced pressure. The residue is diluted with EtOAc and washed with water followed by brine. The organic phase is concentrated under reduced pressure and the residue is purified by flash silica gel chromatography to afford A-1-3 (12.2 g, 71% yield).

To a stirred solution of A-1-3 (11.4 g, 27.6 mmol) in DCM (150 mL), at 0° C., is added Dess-Martin periodinane (14.1 g, 33.2 mmol). Following 30 min at 0° C., the cooling bath is removed and stirring is maintained for an additional hour. The reaction medium is neutralized with aqueous NaHCO₃. The mixture is diluted with EtOAc, washed with water, followed by brine then concentrated under reduced pressure. The residue is purified by flash silica gel chromatography to afford A-1-4 (10.5 g, 93% yield).

A suspension of methoxymethyltriphenylphosphine chloride (10.4 g, 30.4 mmol) and potassium tert-butoxide (3.4 g, 30.4 mmol) in THF (120 mL) is stirred at 0° C. for 30 min. To this suspension is added, dropwise, a solution of A-1-4 (10.4 g, 25.3 mmol) in THF (20 mL). The reaction mixture is stirred at 0° C. for 1 h then warmed to room temperature and stirred overnight. The reaction mixture is diluted with water and extracted with EtOAc. The organic phase is washed with brine then concentrated under reduced pressure. The residue is purified by flash silica gel chromatography to afford A-1-5 as a mixture of two isomers (10.0 g, 90% yield).

To a stirred solution of A-1-5 (10.0 g, 22.8 mmol) in THF (100 mL), cooled to 0° C., is added TBAF (27.4 mL, 27.4 mmol). The solution is warmed to room temperature and stirred for 1.5 h. The mixture is concentrated under reduced pressure and the residue is purified by flash silica gel chromatography to afford A-1-6 as a mixture of two isomers (4.2 g, 92% yield).

To a stirred solution of A-1-6 (2.8 g, 14.0 mmol) in DCM (30 mL), cooled to 0° C., is added TEA (5.3 mL, 42.0 mmol) followed by methane sulfonic anhydride (3.7 g, 21.0 mmol). The solution is warmed to room temperature and stirred for 2 h. To the mixture is added a saturated aqueous solution of NaHCO₃ (100 mL). The phases are separated and the aqueous layer is extracted with DCM. The combined organic extracts are dried over anhydrous MgSO₄, filtered and concentrated under reduced pressure to afford A-1-7 (3.8 g, 98% yield).

To a solution of A-1-7 (3.8 g, 13.7 mmol) in ACN (30 mL) is added benzyl amine (2.2 mL, 20.5 mmol), followed by K₂CO₃ (5.7 g, 41.0 mmol). The mixture is heated at 80° C. overnight then cooled to room temperature. A precipitate is formed which is removed by filtration and the filter pad is rinsed thoroughly with ACN. The filtrate is concentrated under reduced pressure and the residue is purified by flash silica gel chromatography to afford A-1-8 (2.6 g, 66% yield).

To a stirred solution of A-1-8 (2.6 g, 9.0 mmol) in THF (30 mL), at 0° C., is added 6N HCl (4.5 mL, 27 mmol). After 20 min, the cooling bath is removed and the reaction mixture is allowed to stir for an additional 5 h. The reaction mixture is then neutralized with a saturated aqueous solution of Na₂CO₃ and extracted with EtOAc. The organic phase is washed with brine and concentrated under reduced pressure to give A-1-9.

To a stirred solution of A-1-9 in DCE (50 mL), 0° C., is added sodium triacetoxyborohydride (3.6 g, 17.1 mmol). The reaction mixture is stirred at 0° C. for 2 h then excess reagents are consumed by the addition of a saturated aqueous solution of Na₂CO₃. The mixture is extracted with EtOAc and the organic phase is washed with brine and concentrated under reduced pressure. The residue is purified by flash silica gel chromatography to afford A-1-10 (1.4 g, 62% yield from A-1-8).

A flask is charged with 10% palladium on carbon (0.25 g, 0.23 mmol) and the atmosphere is evacuated and refilled with Argon three times. To this is added a solution of A-1-10 (1.00 g, 3.86 mmol) in EtOH (40 mL). The reaction mixture is placed under an atmosphere of hydrogen, stirred at room temperature for three days, then filtered through diatomaceous earth and concentrated under reduced pressure to provide A-1 (0.72 g, quant.).

Example 2

Preparation of intermediate (R)-3-Aza-bicyclo[3.1.0]hexane-1-carboxylic acid methyl ester (A-2)

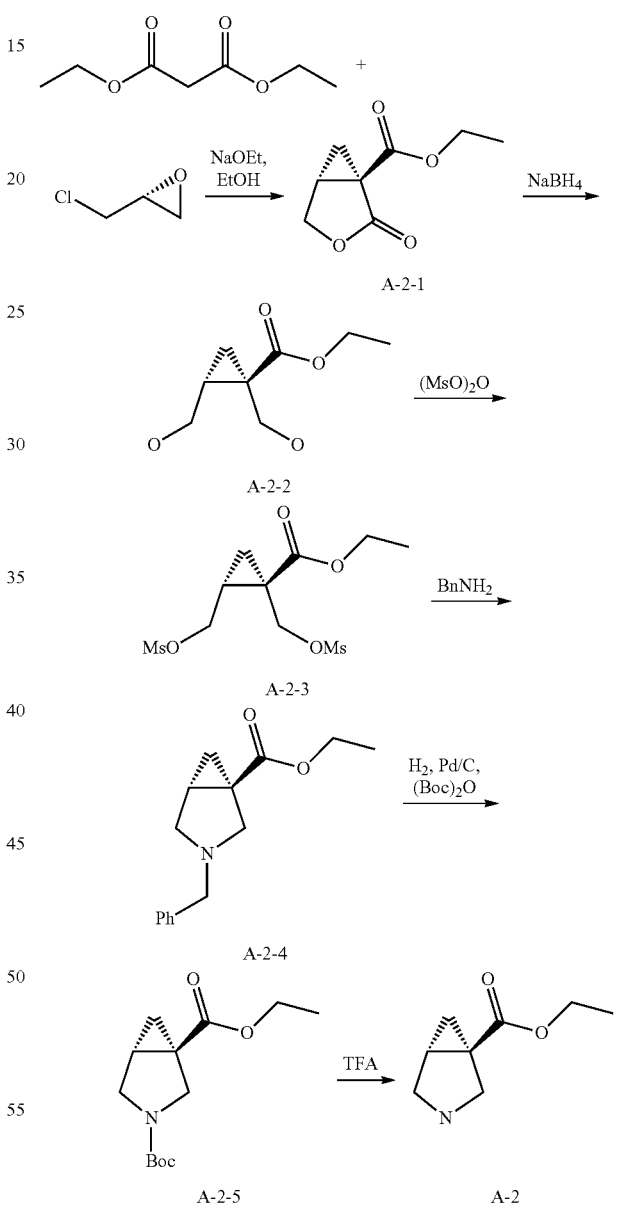

To a solution of 21% NaOEt solution (53 mL, 150 mmol) in EtOH (100 mL), cooled to 0° C., is added diethylmalonate (25 g, 16 mmol). When the mixture becomes thick, additional EtOH (50 mL) is added and the mixture is warmed to room temperature and kept stirring until all solids have dissolved. To the mixture is added, drop wise, a solution of (R)-epichlorohydrin (10.8 mL, 140 mmol) in EtOH (5 mL). After the addition, the mixture is heated to reflux for 36 h and then, cooled to room temperature and diluted with water. The solution is extracted with EtOAc and the combined extracts are dried over anhydrous Na₂SO₄ and concentrated under reduced pressure. The residue is purified by flash silica gel chromatography to afford A-2-1 (13.5 g, 51% yield).

To a solution of A-2-1 (11.5 g, 68 mmol) in EtOH (150 mL) is added sodium borohydride (1.9 g, 51 mmol). The resulting mixture is stirred at room temperature for 2 h. Excess reactants are consumed by the addition of 1N solution of HCl (40 mL). The mixture is concentrated under reduced pressure then diluted with water and extracted with EtOAc. The combined extracts are washed with brine, dried over anhydrous Na₂SO₄ and concentrated under reduced pressure. The residue is purified by flash silica gel chromatography to afford A-2-2 (8.5 g, 72% yield).

To a solution of A-2-2 (8.2 g, 47 mmol) in DCM (100 mL), cooled to 0° C., is added TEA (25 mL, 190 mmol) followed by sulfonic anhydride (20 g, 120 mmol). After the addition, the solution is warmed to room temperature and stirred for 2 h. To the mixture is added a saturated aqueous solution of NaHCO₃ (100 mL). The phases are separated and the aqueous layer is extracted with DCM. The combined organic extracts are dried over anhydrous MgSO₄ and concentrated under reduced pressure to provide A-2-3 (15.5 g, 96% yield).

A solution of A-2-3 (15.5 g, 45 mmol), benzyl amine (7.7 mL, 70 mmol), and K₂CO₃ (19 g, 140 mmol) in ACN (150 mL) is heated to 80° C. for 36 h. After cooling to room temperature a precipitate is separated by filtration and the filter pad is rinsed with ACN. The filtrate is concentrated under reduced pressure. The residue is purified by flash silica gel chromatography to afford A-2-4 (8.4 g, 73% yield).

A mixture of amine A-2-4 (1.4 g, 6.0 mmol), Boc₂O (2.0 g, 9.0 mmol) and 5% Pd/C (200 mg) in MeOH (60 mL) is stirred under an atmosphere of hydrogen for 3 h. The mixture is filtered and the filtrate is concentrated under reduced pressure. The residue is purified by flash silica gel chromatography to afford A-2-5 (1.5 g, 100% yield).

To a solution of A-2-5 (1.4 g, 5.8 mmol) in DCM (15 mL), at 0° C., is added TFA (4.4 mL, 58 mmol). The ice bath is removed immediately following the addition of TFA and the reaction is maintained at room temperature for 3 h. Then solvents are removed under reduced pressure and the residue is diluted with DCM. The mixture is cooled to 0° C. and neutralized with a saturated aqueous solution of NaHCO₃. The resultant heterogeneous mixture is allowed to warm to room temperature and stirred for 1 h. The mixture is filtered through a phase separator and the retained aqueous phase is washed thoroughly with DCM. The solvent is concentrated under reduced pressure to afford A-2 (0.85 g, 98% yield).

Example 3

Preparation of intermediate (1R,2R)-2-Methyl-3-azabicyclo[3.1.0]hexane-1-carboxylic acid methyl ester (A-3) and (1R,2S)-2-Methyl-3-aza-bicyclo[3.1.0]hexane-1-carboxylic acid methyl ester (A-4)

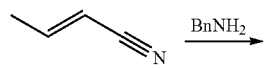

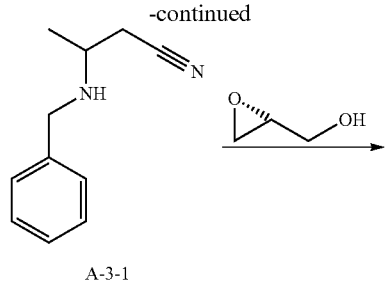

A-3-1

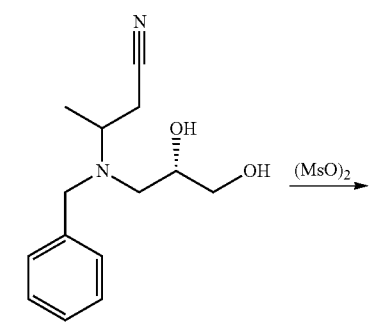

A-3-2

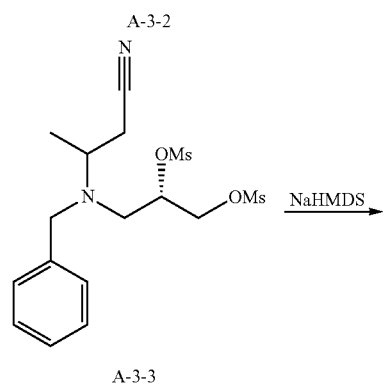

A-3-3

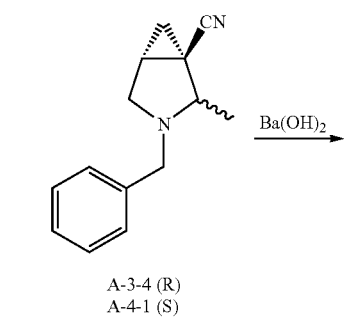

A-3-4 (R)
A-4-1 (S)

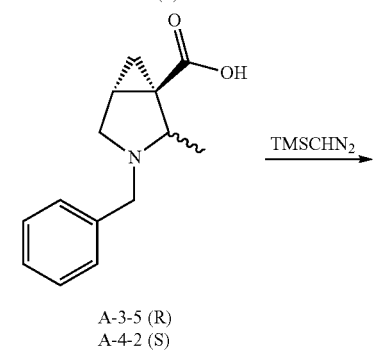

A-3-5 (R)
A-4-2 (S)

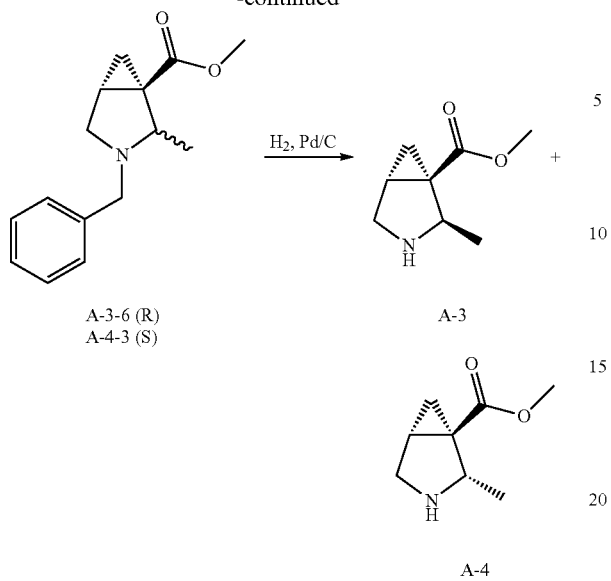

A-3-6 (R)
A-4-3 (S)

A-3

A-4

A solution of benzyl amine (11.2 g, 104 mmol) and crotonitrile (7.0 g, 110 mmol) in EtOH (125 mL) is heated to reflux for 24 h. The mixture is cooled to room temperature and concentrated under reduced pressure. The residue is purified by flash silica gel chromatography to afford A-3-1 (13 g, 73% yield).

A solution of A-3-1 (13 g, 74 mmol) and (R)-glycidol (11 g, 150 mmol) in EtOH (100 mL) is heated to reflux for 2 days. The mixture is cooled to room temperature and concentrated under reduced pressure. The residue is purified by flash silica gel chromatography to afford A-3-2 (13 g, 71% yield).

To a solution of diol A-3-2 (11.5 g, 46.0 mmol) in DCM (150 mL), cooled to 0° C., is added TEA (29 mL, 232 mmol) followed by sulfonic anhydride (24 g, 140 mmol). The solution is warmed to room temperature and stirred for 2 h. To the mixture is added a saturated aqueous solution of NaHCO$_3$ (100 mL). The mixture is separated and the aqueous layer is extracted with DCM. The combined organic extracts are dried over anhydrous MgSO$_4$ and concentrated under reduced pressure to afford A-3-3 (18.5 g, 100% yield).

To a flask containing THF (250 mL) is added a 1N solution of NaHMDS (100 mL, 100 mmol) in THF. The solution is cooled to 0° C. and a solution of A-3-3 (18.5 g, 46 mmol) in THF (50 mL) is added drop wise. The mixture is stirred at 0° C. for 10 min, then the cooling bath is removed and the stirring is continued at room temperature for 2 h. Excess reactants are consumed by the addition of a saturated aqueous solution of NaHCO$_3$. The mixture is extracted with EtOAc and the combined organic extracts are washed with brine and concentrated under reduced pressure. The residue is purified by flash silica gel chromatography to afford compound A-3-4 (2.4 g, 24% yield), and compound A-4-1 (2.7 g, 28% yield).

The mixture of nitrile A-3-4 (2.4 g, 11 mmol) and Ba(OH)$_2$.8H$_2$O (5.3 g, 17 mmol) in water (100 mL) is heated to reflux for 5 days. The mixture is cooled to room temperature and the solution is acidified by the addition of a 6N solution of HCl. The mixture is concentrated under reduced pressure and the residue is suspended in EtOH. The mixture is filtered and the filtrate is concentrated under reduced pressure. The residue is purified by flash silica gel chromatography to afford A-3-5 (2.6 g, 99% yield).

To a solution of A-3-5 (2.6 g, 11 mmol) in MeOH (50 mL), cooled to 0° C., is added TMSCHN$_2$ until a yellowish color persists. The mixture is stirred at stirred at 0° C. for 30 min and then, excess reagents are consumed by the addition of acetic acid. The solution is concentrated under reduced pressure and the residue is purified by flash silica gel chromatography to afford the A-3-6 (1.8 g, 65% yield).

A mixture of A-3-6 (1.8 g, 7.3 mmol) and 5% Pd/C (0.50 g) in MeOH (20 mL) is stirred at ambient temperature overnight under an atmosphere of hydrogen. The mixture is filtered through a pad of diatomaceous earth and the filter pad is rinsed with MeOH. The filtrate is concentrated under reduced pressure to afford A-3 (1.1 g, 97% yield).

Intermediate A-4 can be prepared in a similar way from A-4-1.

Example 4

Preparation of intermediate (1R,2S)-2-Methoxymethyl-3-aza-bicyclo[3.1.0]hexane-1-carboxylic acid methyl ester (A-5) and (1R,2R)-2-Methoxymethyl-3-aza-bicyclo[3.1.0]hexane-1-carboxylic acid methyl ester (A-6)

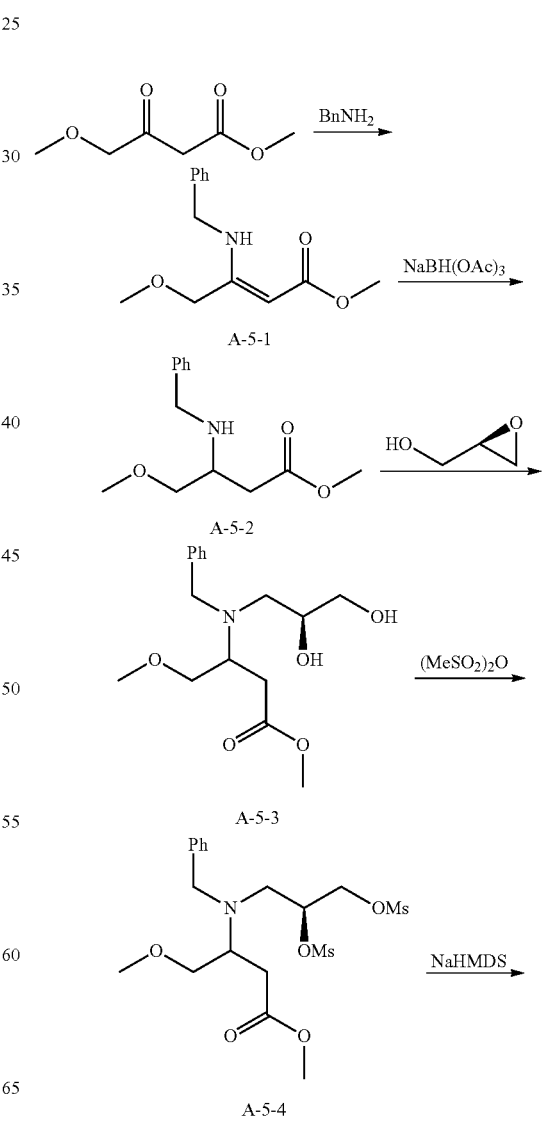

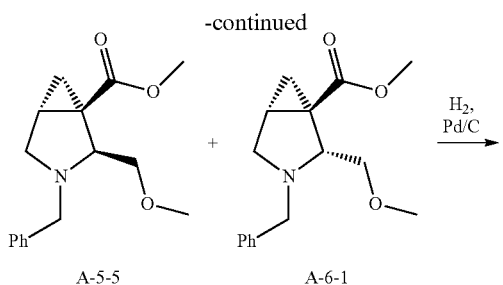

A-5-5      A-6-1

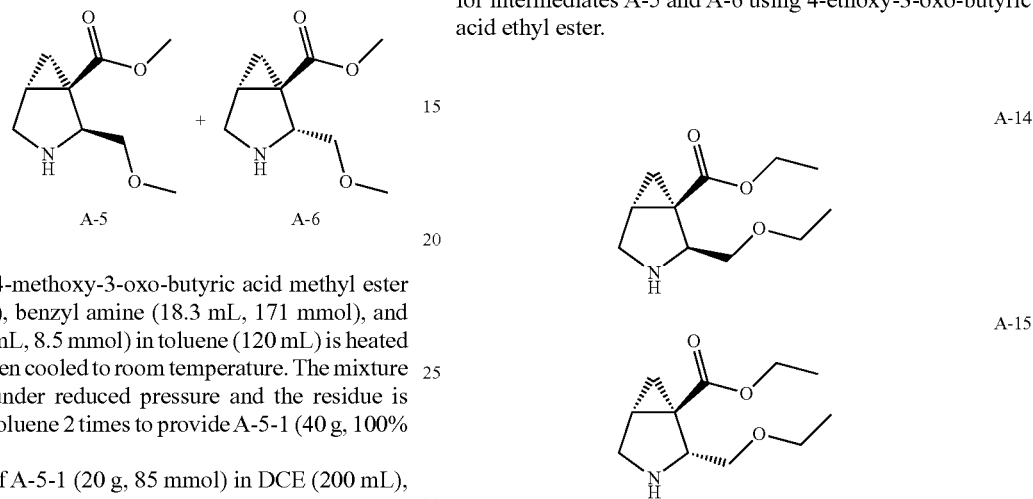

A-5      A-6

A solution of 4-methoxy-3-oxo-butyric acid methyl ester (25 g, 170 mmol), benzyl amine (18.3 mL, 171 mmol), and acetic acid (0.50 mL, 8.5 mmol) in toluene (120 mL) is heated at 60° C. for 5 h then cooled to room temperature. The mixture is concentrated under reduced pressure and the residue is azeotroped with toluene 2 times to provide A-5-1 (40 g, 100% yield).

To a solution of A-5-1 (20 g, 85 mmol) in DCE (200 mL), cooled to 0° C., is added acetic acid (25 mL, 420 mmol) and sodium triacetoxyborohydride (54 g, 250 mmol). The mixture is stirred at 0° C. for 2 h, then warmed to room temperature and stirred for an additional 2 h. The mixture is concentrated under reduced pressure and the residue is diluted with EtOAc. The mixture is made alkaline by the addition of a saturated aqueous solution of Na$_2$CO$_3$. The organic phase is separated and the aqueous phase is extracted with EtOAc. The combined extracts are dried over anhydrous Na$_2$SO$_4$ and concentrated under reduced pressure. The residue is purified by flash silica gel chromatography to afford A-5-2 (18 g, 89% yield).

The solution of A-5-2 (18 g, 75 mmol), and (R)-(+)-glycidol (11 g, 150 mmol) in MeOH (100 mL) is heated to reflux for 2 days then cooled to room temperature and concentrated under reduced pressure. The residue is purified by flash silica gel chromatography to afford A-5-3 (14 g, 59% yield).

To a solution of A-5-3 (10 g, 32 mmol) in DCM (100 mL), cooled to 0° C., is added TEA (20 mL, 160 mmol), followed by sulfonic anhydride (17 g, 96 mmol). The solution is warmed to room temperature and stirred for 2 h. The mixture is diluted with a saturated aqueous solution of NaHCO$_3$ (100 mL) and extracted with EtOAc. The combined organic extracts are washed with brine, dried over anhydrous MgSO$_4$, and concentrated under reduced pressure to provide A-5-4 (15 g, 100% yield).

A flask is charge with THF (150 mL) followed by a 1N solution of NaHMDS in THF (70 mL, 70 mmol). The solution is cooled to −20° C. then a solution of A-5-4 (15 g, 32 mmol) in THF (30 mL) is added drop wise. The mixture is stirred at −20° C. for 1 h then allowed to slowly warm to room temperature and the stirring for an additional 2 h. The reaction is quenched by the addition of a saturated aqueous solution of NaHCO$_3$, extracted with EtOAc. The combined extracts are washed with brine and concentrated under reduced pressure. The residue is purified by flash silica gel chromatography to afford A-5-5 (1 g, 11% yield) and A-6-1 (2.1 g, 21% yield).

A mixture of A-5-5 (1.6 g, 5.8 mmol) and 5% Pd/C (0.50 g) in MeOH (10 mL) is stirred overnight at ambient temperature under an atmosphere of hydrogen. The mixture is filtered through a pad of diatomaceous earth and the filter pad is rinsed with MeOH. The filtrate is concentrated under reduced pressure to afford A-5 (1.1 g, 100% yield)

Intermediate A-6 can be prepared in a similar way from A-6-1.

Intermediates A-14 and A-15 can be prepared as described for intermediates A-5 and A-6 using 4-ethoxy-3-oxo-butyric acid ethyl ester.

A-14

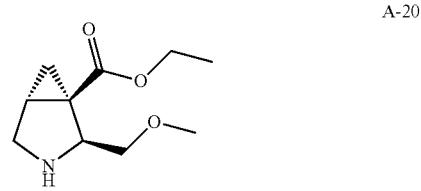

A-15

Racemic intermediate A-20 can be prepared as described for intermediates A-5 using racemic glycidol.

A-20

Example 5

Preparation of intermediate cis tert-butyl 3-methoxypiperidine-4-carboxylate acetic acid salt (A-7)

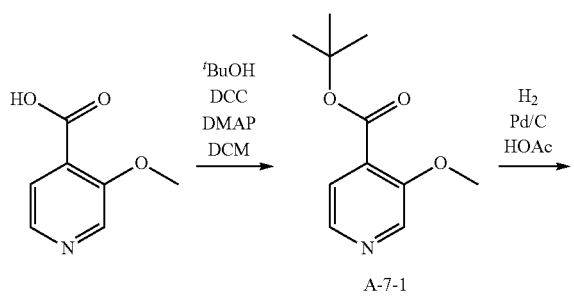

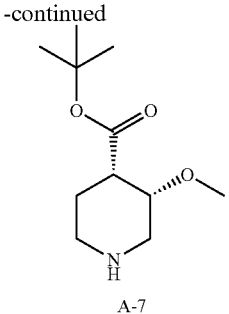 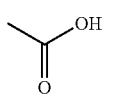

A-7

To a solution of 3-methoxypyridine-4-carboxylic acid (10.0 g, 65.3 mmol) in DCM (400 mL) is added tert-butyl alcohol (15.6 mL, 163 mmol), DCC (21.6 g, 104 mmol) and DMAP (16.0 g, 131 mmol). The mixture is stirred at room temperature for 3 days. The solid is filtered and the filtrate is concentrated to dryness under reduced pressure. The crude is purified first by flash silica gel chromatography then triturated with 10% EtOAc in heptane. The solid is filtered and the filtrate is concentrated under reduced pressure to afford A-7-1 (9.7 g, 70% yield).

A solution of A-7-1 (4.96 g, 23.7 mmol) in HOAc (100 mL) is hydrogenated on an H-cube hydrogenator using a 10% Pd/C cartridge under 30 bar hydrogen pressure at 80° C. with recirculation at 0.5 mL/min for 6 days. The solution is concentrated to dryness under reduced pressure. The residue is dissolved in MeCN/water (1:1) and freeze-dried to afford A-7 (5.6 g, 86% yield).

The following intermediate can be prepared in a similar fashion using the appropriate reagents.

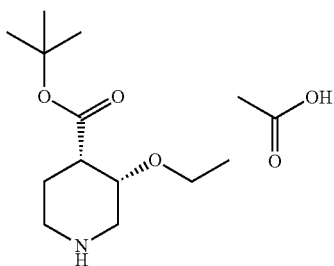

A-13

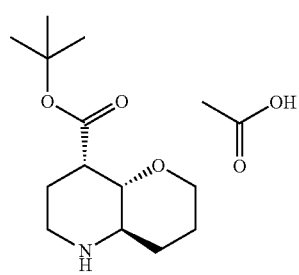

A-17

Example 6

Preparation of intermediate 3-[4-(2-hydroxy-5-methyl-phenyl)-thiazol-2-yl]-3-aza-bicyclo[3.2.1]octane-8(syn)-carboxylic acid methyl ester (A-8)

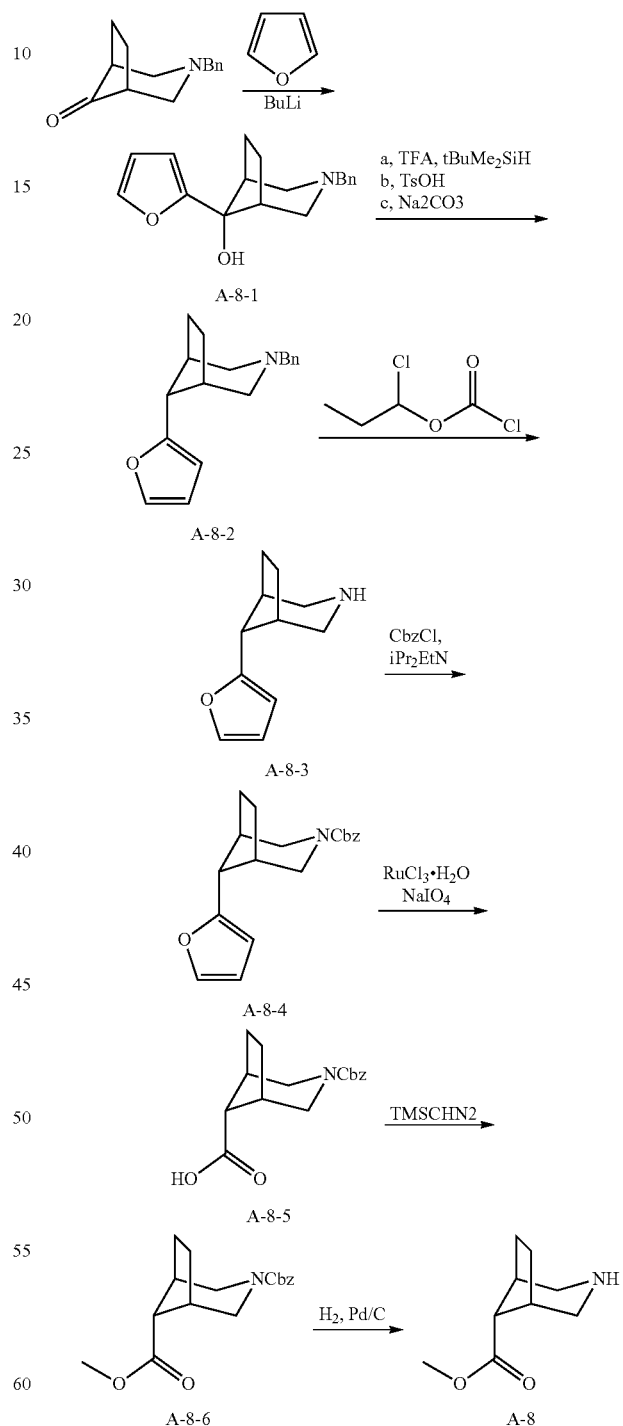

To a stirred solution of furan (63 mmol, 4.5 mL) in THF (30 mL), under argon and cooled to −20° C., is added a solution of n-BuLi in pentane (2.0N, 69 mmol, 34.5 mL). The mixture is warmed up to ambient temperature and stirred for 1 h. The mixture is then cooled to 0° C. and a solution of 3-aza-bicyclo[3.2.1]octan-8-one (13 mmol, 2.7 g) in THF (5 mL) is added. The mixture is warmed to ambient temperature and stirred overnight. The mixture is diluted with water, extracted with ethyl acetate, washed with brine, and then concentrated to afford A-8-1 (3.5 g, 100% yield).

To a solution of A-8-1 (8.8 mmol, 2.5 g) in DCM (30 mL) is added TFA (88 mmol, 6.7 mL) and t-butyldimethylethylsilane (44 mmol, 7.3 mL). The mixture is stirred at 35° C. overnight. The reaction mixture is concentrated under reduced pressure and the residue is dissolved in ethyl acetate, washed successively with aqueous NaHCO₃, water, and brine. The mixture is then concentrated under reduced pressure. The residue is dissolved in DCM (30 mL) then TsOH (8.8 mmol, 1.7 g) is added. After a clear solution is obtained the solvent is concentrated under reduced pressure. The residue is recrystallized from an isopropanol:heptanes mixture and collected by filtration. The isolated solid is dissolved in methylene chloride and then, washed with an aqueous sodium carbonate solution followed by brine. The mixture is then dried over anhydrous sodium sulfate and concentrated to give A-8-2 (1.7 g, 68% yield).

To the stirred solution of A-8-2 (3.2 mmol, 0.85 g,) in DCE is added 1-chloroethyl chloroformate (9.6 mmol, 1.0 mL). The resulting solution is stirred at ambient temperature for 10 min, then heated to 80° C. for 3 h. The solution is then cooled down to ambient temperature and concentrated under reduced pressure. Methanol is added to the residue and the mixture is heated to reflux for 1 h then cooled to ambient temperature and concentrated under reduced pressure to afford A-8-3 which is used directly.

The above crude A-8-3 is dissolved in DCM and then Hunig's base (13 mmol, 2.4 mL) and benzyl chloroformate (6.4 mmol, 0.9 mL) are added successively. The resulting solution is stirred at ambient temperature for 2 h and then concentrated under reduced pressure. The residue is dried in a vacuum oven at 40° C. overnight to afford A-8-4 (4.0 g, quantitative yield from A-8-2).

To a solution of A-8-4 (3.8 mmol, 1.2 g) in a 2:2:3 mixture of acetonitrile:carbon tetrachloride:water (50 mL) is added sodium periodate (38 mmol, 8.2 g). After 10 min, ruthenium trichloride (0.2 mmol, 43 mg) is added. The mixture is stirred for 20 min then diluted with water, extracted with ethyl acetate, washed with brine, dried over anhydrous sodium sulfate, and concentrated under reduced pressure to provide A-8-5 which is used directly.

The isolated A-8-5 is dissolved in MeOH and the solution is cooled to 0° C. To this mixture is added trimethylsilyldiazomethane (2.0N in ether, ca. 12 mL), drop wise, until a yellowish color is persistent. Stirring is continued for 30 min then excess reactants are consumed by the addition of acetic acid. The solution is concentrated under reduced pressure and the residue is purified by flash silica gel chromatography to afford the A-8-6 (0.81 g, 70% yield from A-8-4).

A suspension of A-8-6 (2.2 mmol, 0.66 g) and 5% palladium on carbon (0.10 g) in MeOH (5 mL) is stirred under a hydrogen atmosphere for 3 h. The mixture is filtered through a pad of diatomaceous earth, rinsed with a 10% MeOH in DCM mixture and the filtrate is concentrated under reduced pressure to afford A-8 (0.34 g, 92% yield).

Example 7

Preparation of intermediate (1S,2S)-2-Methyl-3-aza-bicyclo[3.1.0]hexane-1-carboxylic acid methyl ester (A-9) and (1S,2R)-2-Methyl-3-aza-bicyclo[3.1.0]hexane-1-carboxylic acid methyl ester (A-10)

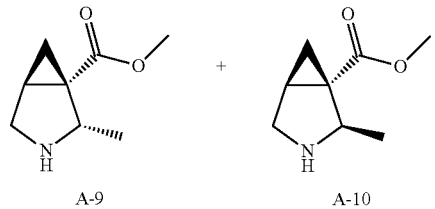

A-9                           A-10

Intermediates A-9 and A-10 can be prepared as described for intermediates A-3 and A-4 in Example 3 using (S)-(−)-glycidol.

Example 8

Preparation of intermediate (1S,2R)-2-Methoxymethyl-3-aza-bicyclo[3.1.0]hexane-1-carboxylic acid methyl ester (A-11) and (1S,2S)-2-Methoxymethyl-3-aza-bicyclo[3.1.0]hexane-1-carboxylic acid methyl ester (A-12)

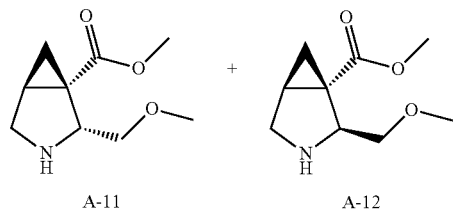

A-11                          A-12

Intermediates A-11 and A-12 can be prepared as described for intermediates A-5 and A-6 in Example 4 using (S)-(−)-glycidol.

Example 9

Preparation of intermediate (1R,6S)-3-(6-Bromo-pyridin-2-yl)-3-aza-bicyclo[4.1.0]heptane-6-carboxylic acid ethyl ester (B-1)

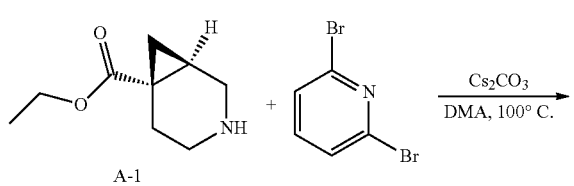

-continued

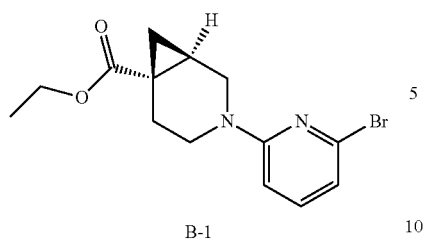

B-1

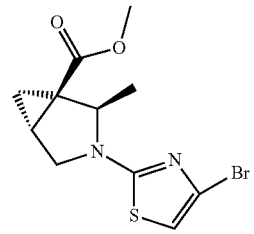

B-9

To a solution of A-1 (2.01 g, 11.8 mmol), in DMA (30 mL), is added 2,6-dibromopyridine (3.65 g, 15.4) followed by cesium carbonate (8.11 g, 24.9 mmol). The reaction mixture is heated at 100° C. overnight and then, cooled to room temperature and diluted with water and MTBE. The organic phase is separated and the aqueous phase is extracted with MTBE. The combined organic extracts are washed with brine, dried over anhydrous $Na_2SO_4$, filtered, and concentrated under reduced pressure. The crude material is purified via flash silica gel chromatography to afford B-1 (2.6 g, 68% yield).

The following intermediates can be prepared in a similar fashion using the appropriate reagents.

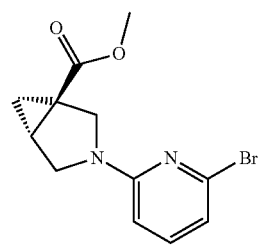

B-2

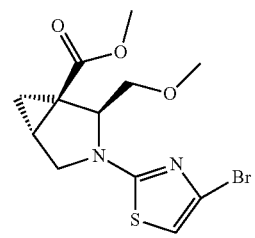

B-10

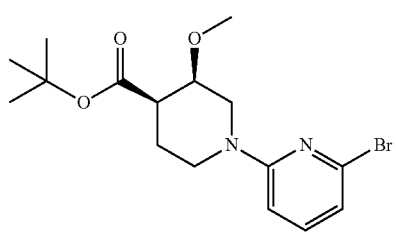

B-6

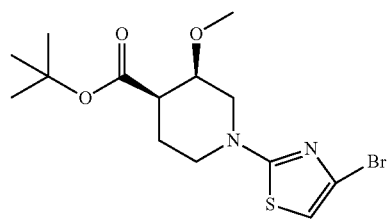

B-11

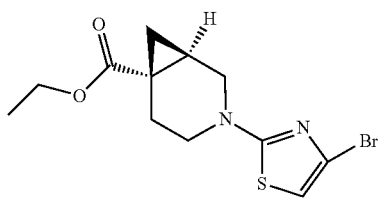

B-7

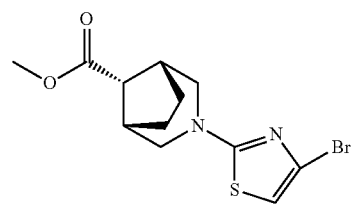

B-12

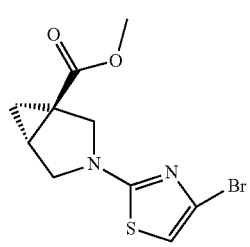

B-8

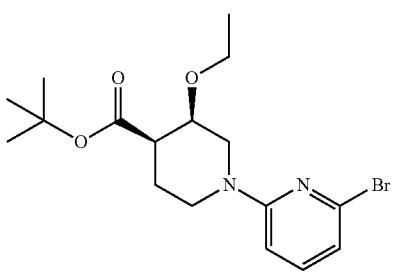

B-13

B-18

-continued

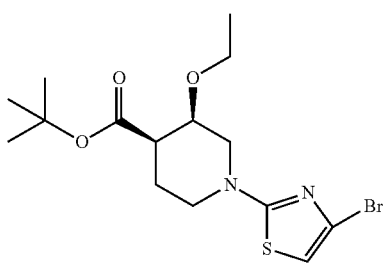
B-19

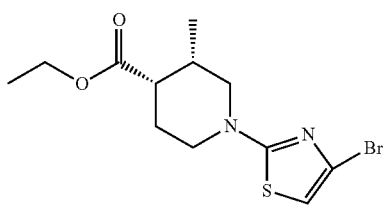
B-20

The following intermediates is isolated as a minor component during the generation of B-6

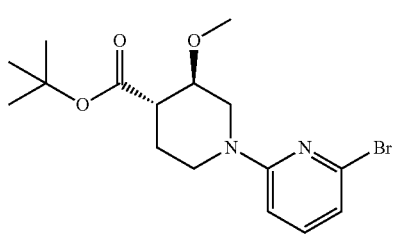
B-25

Example 10

Preparation of intermediate (1R,2S)-3-(6-Bromo-pyridin-2-yl)-2-methoxymethyl-3-aza-bicyclo[3.1.0]hexane-1-carboxylic acid methyl ester (B-3)

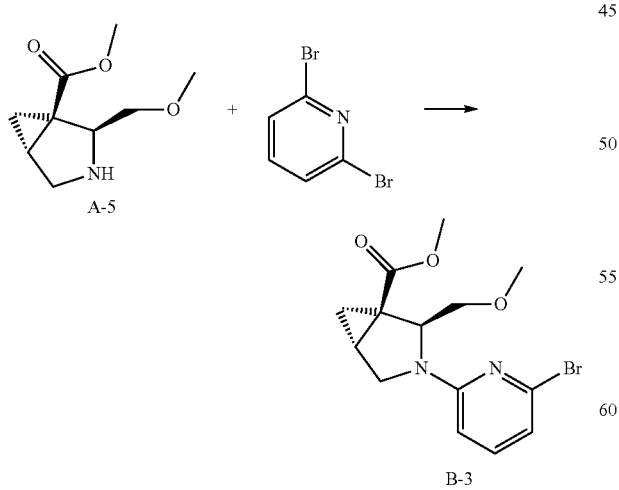
B-3

A suspension of A-5 (1.1 g, 5.8 mmol) and 2,6-dibromopyridine (4.2 g, 17 mmol) in 2,2,6,6-tetramethylpiperidine (3.5 mL, 17 mmol) is heated at 130° C. for 48 h. The reaction mixture is cooled to ambient temperature and diluted with EtOAc. The mixture is washed with a saturated aqueous solution of NaHCO₃ followed by brine and then, concentrated under reduced pressure. The residue is purified by flash silica gel chromatography to afford B-3 (1.7 g, 84% yield).

The following intermediates can be prepared in a similar fashion using the appropriate reagents. Intermediate B-26 is racemic and is generated from the racemic intermediate A-20.

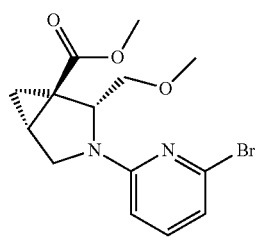
B-4

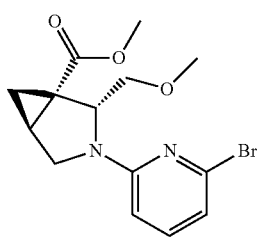
B-5

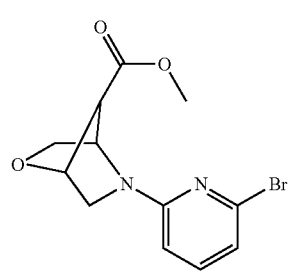
B-17

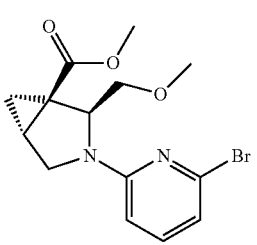
B-21

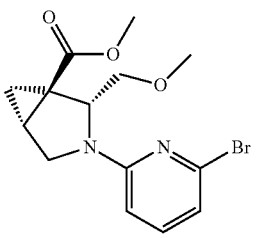
B-22

B-26

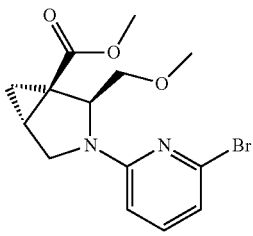

Example 11

Preparation of intermediate 2-(2-Chloro-pyrimidin-4-yl)-6-methyl-phenol (B-16)

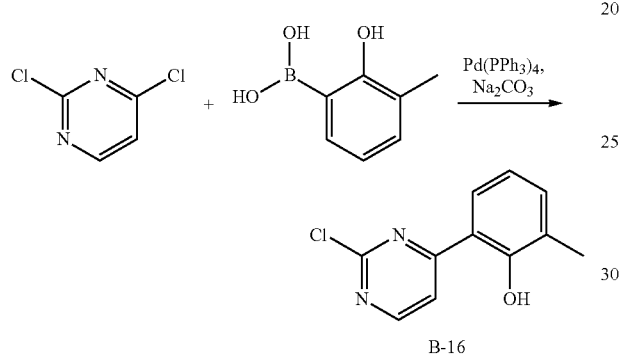

B-16

To a solution of 3.0 g (20 mmol) of 2,4-dichloro-pyrimidine in a 10:1 mixture of dioxane:water (220 mL) is added 3.3 g (22 mmol) of 2-hydroxy-3-methyl-phenyl boronic acid followed by 6.0 g (57 mmol) of sodium carbonate. Argon is bubbled through the solution for 15 min then 2.4 g (2.1 mmol) of tetrakis(triphenylphosphine)palladium (0) is added. The reaction is heated overnight at 100° C. then cooled to ambient temperature and filtered through diatomaceous earth. The filter pad is washed with EtOAc then placed on a new receiving flask and washed with a 1:1 mixture of MeOH:DCM. The filtrate is concentrated under reduced pressure to B-16 (1.60 g, 36.0%)

The following intermediates can be prepared in a similar fashion using the appropriate reagents.

B-14

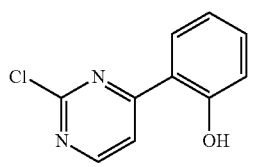

B-15

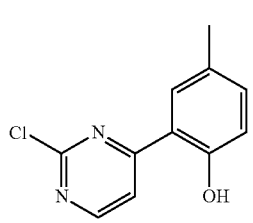

Example 12

Preparation of intermediates (4aS,8R,8aR)-5-(6-Bromo-pyridin-2-yl)-octahydro-pyrano[3,2-b]pyridine-8-carboxylic acid tert-butyl ester (B-23) & (4aR,8S,8aS)-5-(6-Bromo-pyridin-2-yl)-octahydro-pyrano[3,2-b]pyridine-8-carboxylic acid tert-butyl ester (B-24)

2-Bromo-6-fluoropyridine (0.97 g, 5.5 mmol) is added to a solution of A-17 (1.0 g, 3.3 mmol) in DMSO. The resulting mixture is heated at 120° C. for 18 h. Half the volume of DMSO is removed under reduced pressure, and the remaining solution is purified first by flash reverse phase chromatography to provide a mixture of diasteromers. The diastereomeric mixture is resolved by flash silica gel chromatography using a gradient elution of 5-45% EtOAc in heptane to afford intermediate B-23 (0.183 g, 14%) and B-24 (182 g, 14%) respectively.

Intermediates B-23 and B-24 may be recrystallized from hot heptane/EtOAc to afford white needles. The relative stereochemistry of intermediates B-23 and B-24 are assigned on the basis of single crystal X-ray results. The absolute stereochemistry was not determined and the structures drawn are arbitrarily assigned.

Example 13

Preparation of intermediate (1R,6S)-3-[6-(2-Hydroxy-phenyl)-pyridin-2-yl]-3-aza-bicyclo[4.1.0]heptane-6-carboxylic acid (C-1)

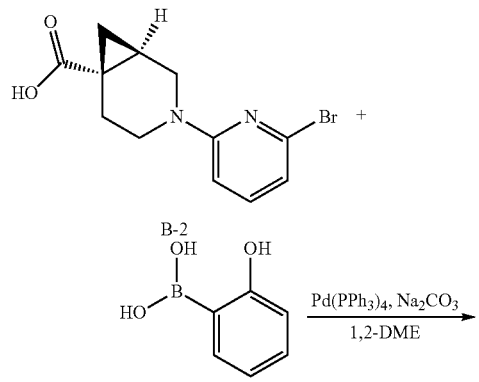

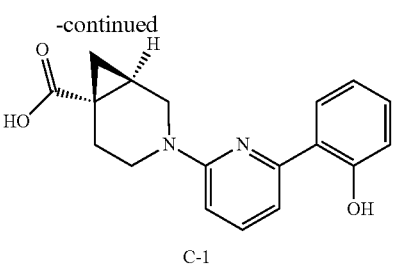

C-1

A solution of B-1 (0.204 g, 0.628 mmol) and 2-hydroxyphenylboronic acid (0.113 g, 0.816 mmol) in 1,2-DME (12 mL) is sparged with nitrogen for approximately 10 min. Then, tetrakis(triphenylphosphine)palladium (0.849 g, 0.0735 mmol) is introduced, followed by a 20% aqueous solution of sodium carbonate (1.0 mL, 2.0 mmol). The reaction mixture is sparged with nitrogen for an additional 15 min and then, heated in a microwave reactor at 125° C. for 30 min. The crude material is purified by flash silica gel column chromatography to afford (0.20 g, 96% yield) of C-1.

The following intermediates can be prepared in a similar fashion using the appropriate reagents.

| Intermediate | Prepared From | Structure |
|---|---|---|
| C-2 | B-1 | 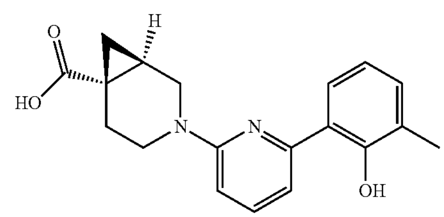 [SMILES: Cc1cccc(-c2cccc(N3CC[C@@]4(C(=O)O)C[C@H]4C3)n2)c1O] |
| C-3 | B-1 | 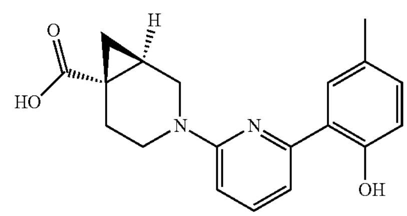 [SMILES: Cc1ccc(O)c(-c2cccc(N3CC[C@@]4(C(=O)O)C[C@H]4C3)n2)c1] |
| C-4 | B-2 | 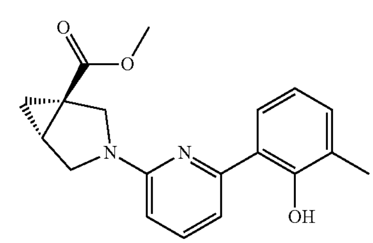 [SMILES: COC(=O)[C@]12C[C@H]1CN(c1cccc(-c3cccc(C)c3O)n1)C2] |

-continued
| Intermediate | Prepared From | Structure |
|---|---|---|
| C-5 | B-2 | 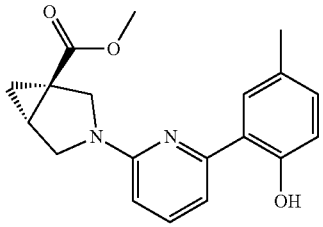 [SMILES: COC(=O)[C@]12C[C@H]1CN(c1cccc(-c3cc(C)ccc3O)n1)C2] |
| C-6 | B-3 | 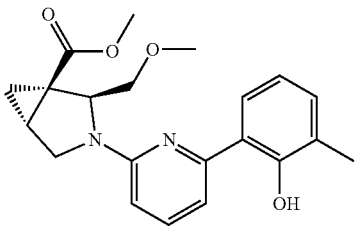 [SMILES: COC[C@H]1N(c2cccc(-c3cccc(C)c3O)n2)C[C@@H]2C[C@@]21C(=O)OC] |
| C-7 | B-4 | 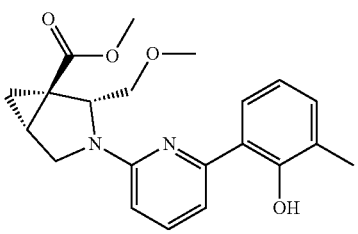 [SMILES: COC[C@@H]1N(c2cccc(-c3cccc(C)c3O)n2)C[C@@H]2C[C@@]21C(=O)OC] |
| C-8 | B-5 | 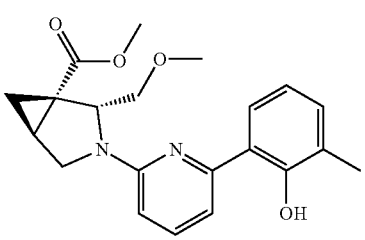 [SMILES: COC[C@@H]1N(c2cccc(-c3cccc(C)c3O)n2)C[C@H]2C[C@]21C(=O)OC] |
| C-13 | B-7 | 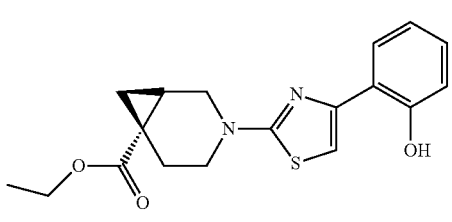 |
| C-14 | B-7 | 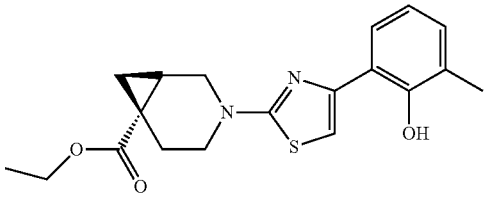 |

-continued
| Intermediate | Prepared From | Structure |
|---|---|---|
| C-15 | B-7 | 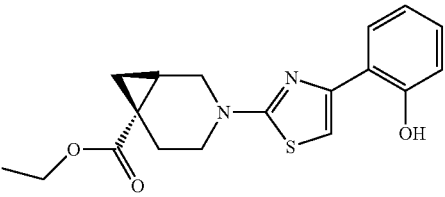 |
| C-16 | B-8 | 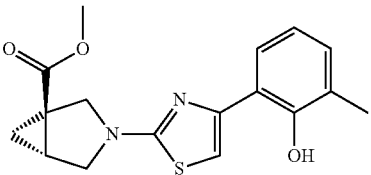 |
| C-17 | B-8 | 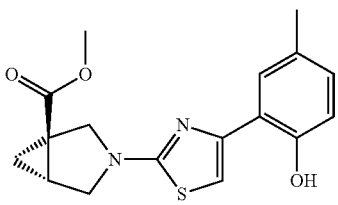 |
| C-18 | B-8 | 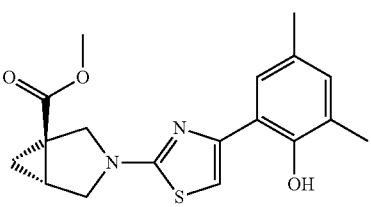 |
| C-19 | B-9 | 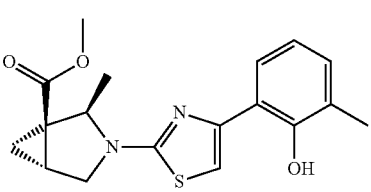 |
| C-20 | B-10 | 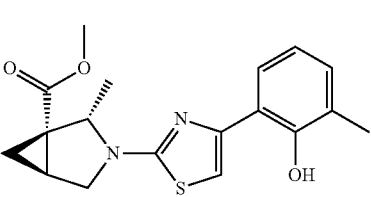 [SMILES: COC(=O)[C@@]12C[C@@H]1CN(c1nc(-c3cccc(C)c3O)cs1)[C@H]2C] |
| C-21 | B-11 | 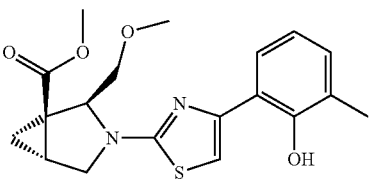 |

-continued

| Intermediate | Prepared From | Structure |
|---|---|---|
| C-22 | B-11 | 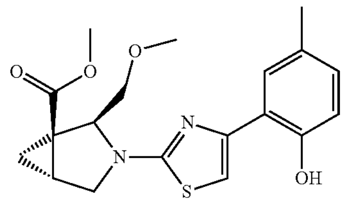 |
| C-27 | B-13 | 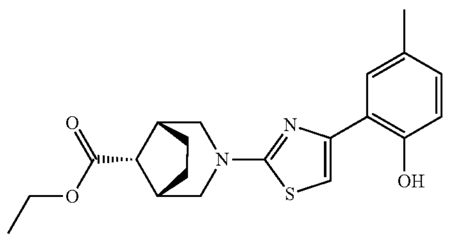 [SMILES: CCOC(=O)[C@H]1[C@@H]2CC[C@H]1CN(c1nc(-c3cc(C)ccc3O)cs1)C2] |
| C-33 | B-7 | 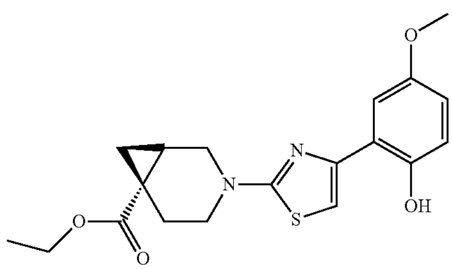 |
| C-34 | B-3 | 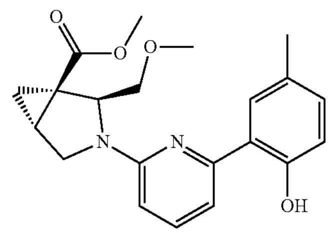 [SMILES: COC[C@H]1N(c2cccc(-c3cc(C)ccc3O)n2)C[C@@H]2C[C@@]21C(=O)OC] |
| C-35 | B-3 | 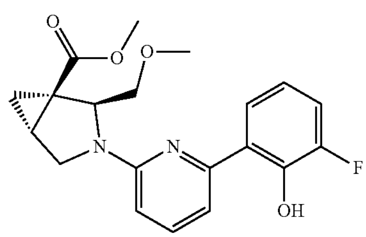 [SMILES: COC[C@H]1N(c2cccc(-c3cccc(F)c3O)n2)C[C@@H]2C[C@@]21C(=O)OC] |
| C-36 | B-3 | 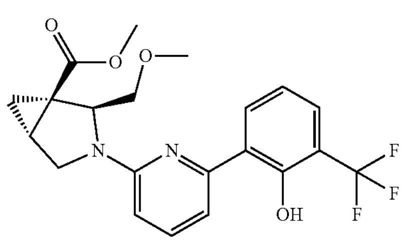 [SMILES: COC[C@H]1N(c2cccc(-c3cccc(C(F)(F)F)c3O)n2)C[C@@H]2C[C@@]21C(=O)OC] |

-continued

| Intermediate | Prepared From | Structure |
|---|---|---|
| C-37 | B-3 | 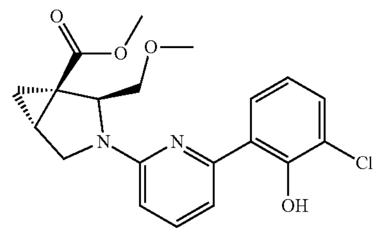 [SMILES: COC[C@H]1N(c2cccc(-c3cccc(Cl)c3O)n2)C[C@@H]2C[C@@]21C(=O)OC] |
| C-45 | B-17 | 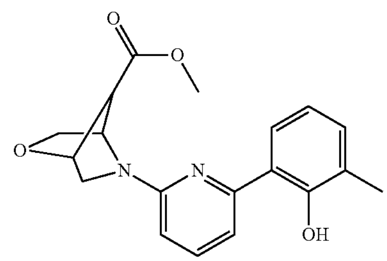 [SMILES: COC(=O)C1C2CN(c3cccc(-c4cccc(C)c4O)n3)C1CO2] |
| C-59 | B-20 | 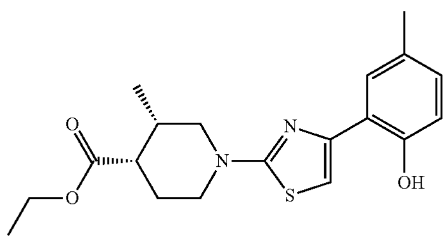 [SMILES: CCOC(=O)[C@H]1CCN(c2nc(-c3cc(C)ccc3O)cs2)C[C@H]1C] |
| C-60 | B-21 | 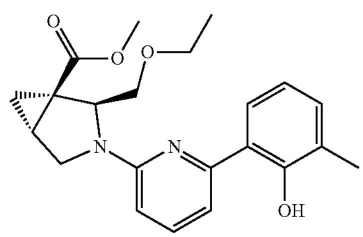 [SMILES: CCOC[C@H]1N(c2cccc(-c3cccc(C)c3O)n2)C[C@@H]2C[C@@]21C(=O)OC] |
| C-61 | B-22 | 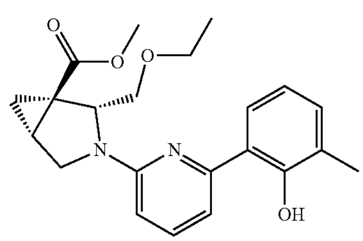 [SMILES: CCOC[C@@H]1N(c2cccc(-c3cccc(C)c3O)n2)C[C@@H]2C[C@@]21C(=O)OC] |
| C-62 | B-23 | 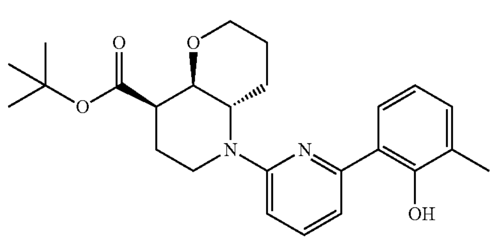 [SMILES: Cc1cccc(-c2cccc(N3CC[C@@H](C(=O)OC(C)(C)C)[C@H]4OCCC[C@@H]43)n2)c1O] |

| Intermediate | Prepared From | Structure |
|---|---|---|
| C-63 | B-24 | 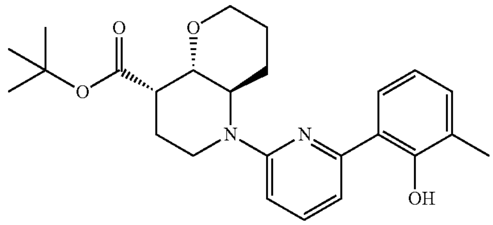 [SMILES: Cc1cccc(-c2cccc(N3CC[C@H](C(=O)OC(C)(C)C)[C@@H]4OCCC[C@H]43)n2)c1O] |
| C-65 | B-26 | 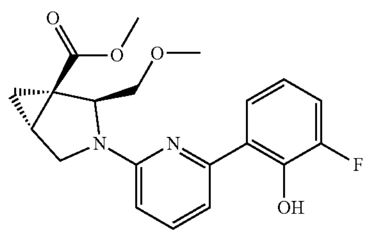 [SMILES: COC[C@H]1N(c2cccc(-c3cccc(F)c3O)n2)C[C@@H]2C[C@@]21C(=O)OC] |

Example 14

Preparation of intermediate (3S,4S)-1-[4-(2-Hydroxy-5-methyl-phenyl)-thiazol-2-yl]-3-methoxy-piperidine-4-carboxylic acid tert-butyl ester (C-25) and (3R,4R)-1-[4-(2-Hydroxy-5-methyl-phenyl)-thiazol-2-yl]-3-methoxy-piperidine-4-carboxylic acid tert-butyl ester (C-26)

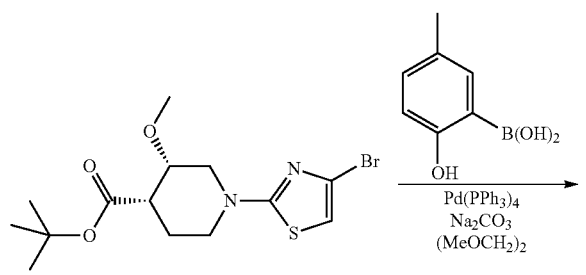

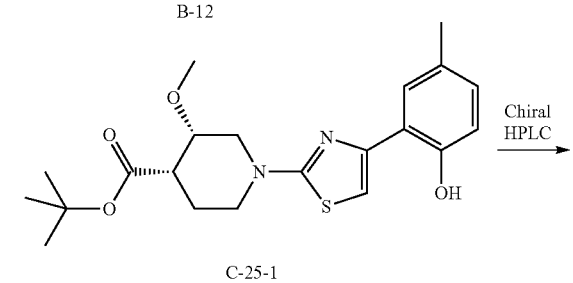

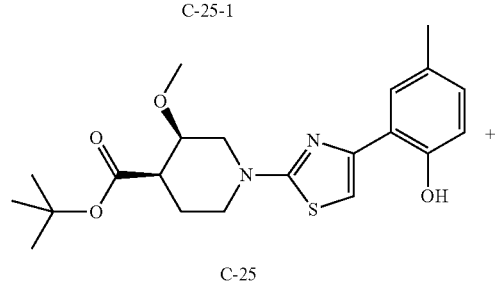

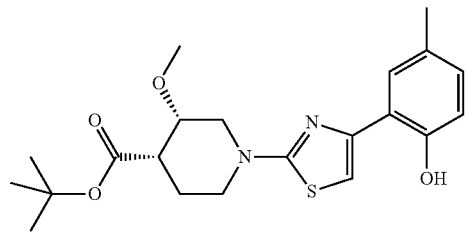

To a solution of B-12 (3.28 g, 8.69 mmol) in DME (35 mL) is added 2-hydroxy-5-methylphenylboronic acid (1.65 g, 10.87 mmol), tetrakis(triphenylphosphine)palladium (1.0 g, 0.87 mmol) and a 2M aqueous solution of $Na_2CO_3$ (13.0 mL, 26.0 mmol). The mixture is heated at reflux for 3 h then cooled to room temperature and diluted with water (50 mL). The mixture is extracted with EtOAc and the combined organic layers are washed with brine then concentrated under reduced pressure. The residue is purified by flash silica gel column chromatography to afford C-25-1 (2.73 g, 77% yield).

The racemate is resolved on a Chiralpak IA column (21× 250 mm) using 25% MeOH in super critical $CO_2$ at 80 mL/min under 100 bar at 40° C. to afford C-25 (1.05 g, 30% yield) and C-26 (1.05 g, 30% yield). The absolute stereochemistry is confirmed using single crystal X-ray diffraction.

The following intermediates can be prepared from intermediate B-12 in a similar fashion using the appropriate reagents. The absolute stereochemistry for C-23 and C-24 is confirmed using single crystal X-ray diffraction. The absolute stereochemistry for C-42, C-43 and C-44 is not determined and the structures drawn are arbitrarily assigned.

C-23
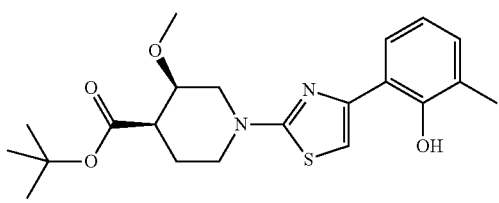

C-24
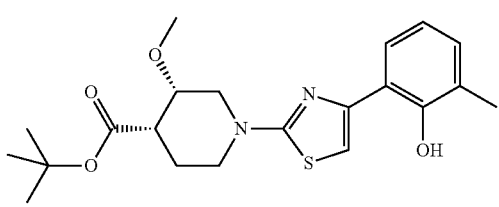

C-42
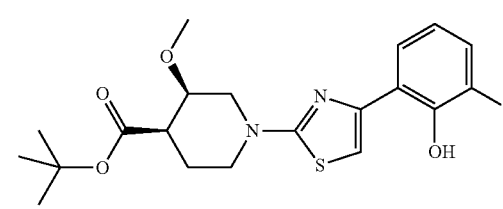

C-43

C-44
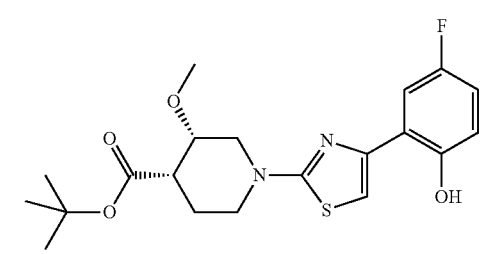

The following intermediates can be prepared from intermediate B-6 in a similar fashion using the appropriate reagents. The absolute stereochemistry for C-9, C-10, C-11 and C-12 is confirmed using single crystal X-ray diffraction. The absolute stereochemistry for C-38 and C-39 is not determined and the structures drawn are arbitrarily assigned.

C-9
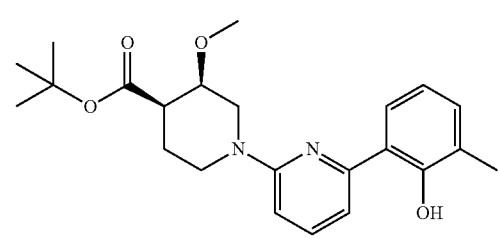

C-10
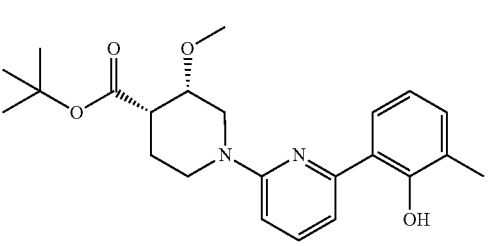

C-11

C-12

C-38

C-39

The following intermediates were isolated during the generation of C-9 and C-10. The relative stereochemistry is confirmed by $^1$H-NMR experiments. The absolute stereochemistry is not determined and the structures drawn are arbitrarily assigned.

C-40

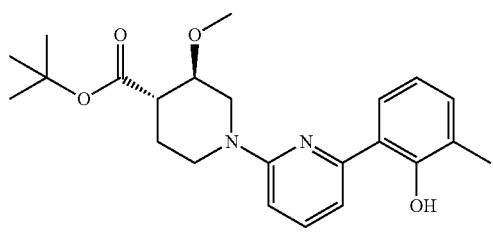

C-49

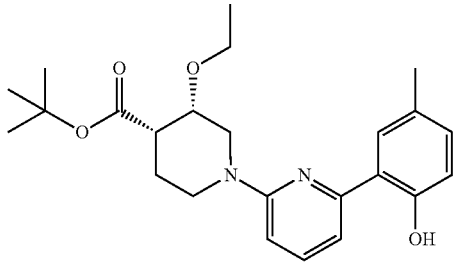

C-41

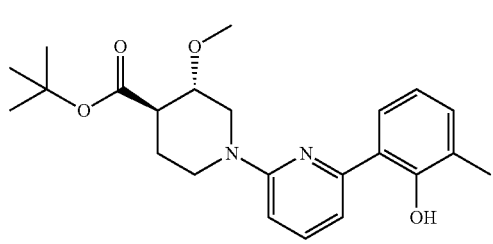

The following intermediates can be prepared from intermediate B-18 in a similar fashion using the appropriate reagents. The absolute stereochemistry is not determined and the structures drawn are arbitrarily assigned.

C-50

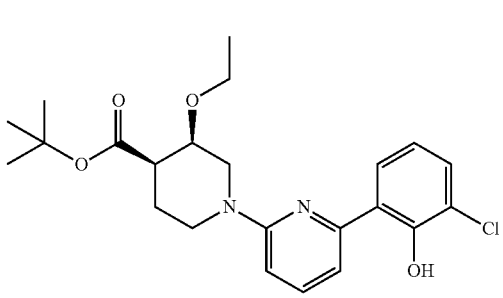

C-51

C-46

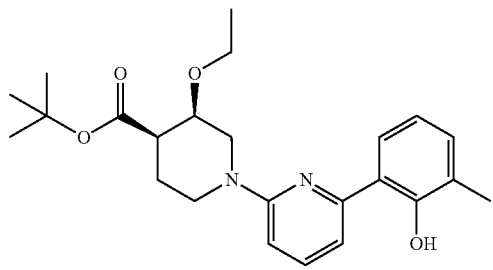

The following intermediates can be prepared from intermediate B-19 in a similar fashion using the appropriate reagents. The absolute stereochemistry is not determined and the structures drawn are arbitrarily assigned.

C-47

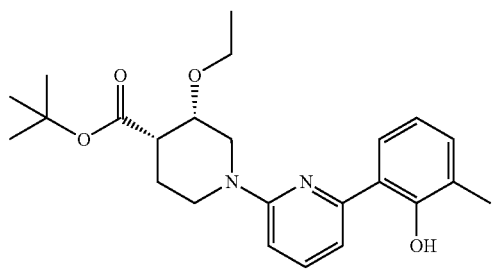

C-52

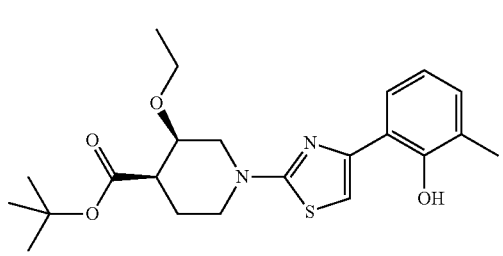

C-48

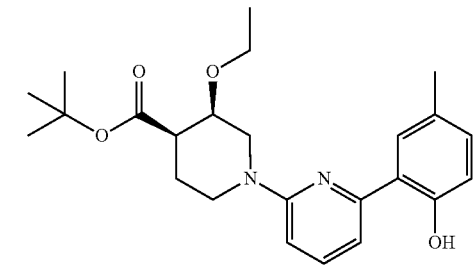

C-53

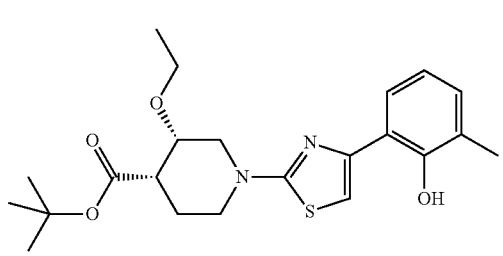

-continued

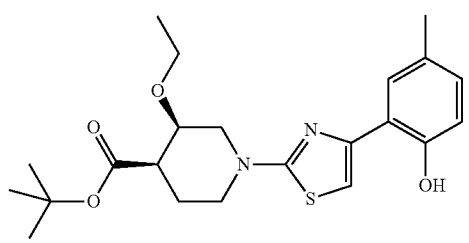
C-54

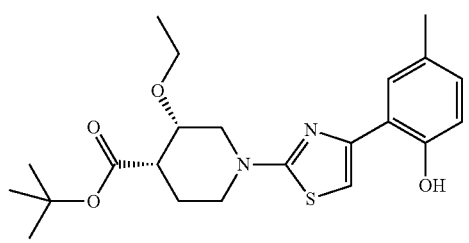
C-55

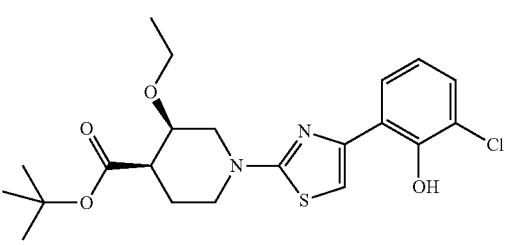
C-56

Example 15

Preparation of intermediate (1R,6S)-3-[4-(2-hydroxy-phenyl)-pyrimidin-2-yl]-3-aza-bicyclo[4.1.0]heptane-6-carboxylic acid ethyl ester (C-29)

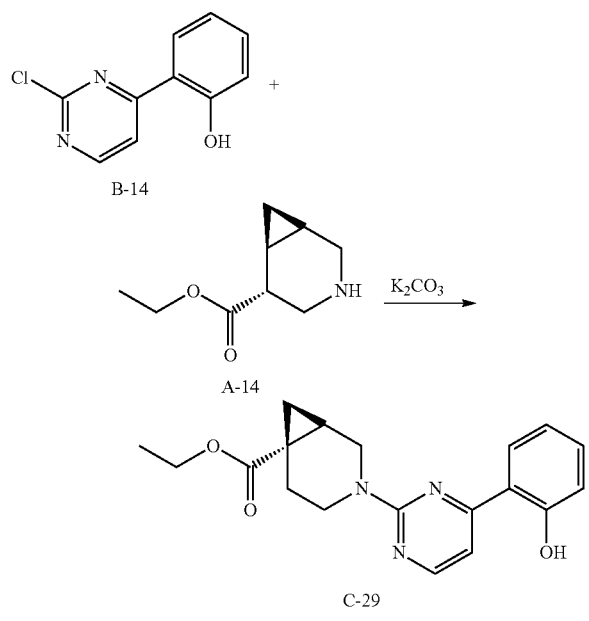

To a solution of 0.200 g (0.968 mmol) of B-14 in DMF (5 mL) is added 0.35 g (2.1 mmol) of A-14 followed by 1.0 g (7.2 mmol) of potassium carbonate. The mixture is heated at 80° C. for 2 days then cooled to room temperature and diluted with water. The mixture is extracted with EtOAc. The combined organic extract is washed with water followed by brine then dried over anhydrous sodium sulfate and concentrated under reduced pressure. The residue is purified by flash silica gel chromatography to afford C-29 (0.221 g, 67.3%).

The following intermediate can be prepared from intermediates B-13 and A-14 in a similar fashion using the appropriate reagents.

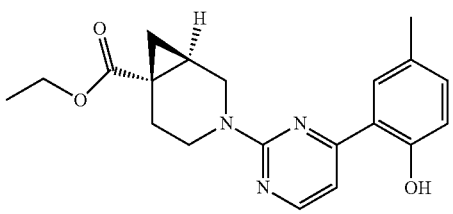
C-30

The following intermediate can be prepared from intermediates B-14 and A-2 in a similar fashion using the appropriate reagents.

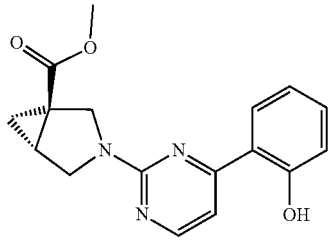
C-31

The following intermediate can be prepared from intermediates B-16 and A-2 in a similar fashion using the appropriate reagents.

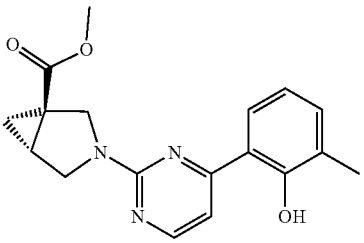
C-32

The following intermediate can be prepared from intermediates B-16 and A-4 in a similar fashion using the appropriate reagents.

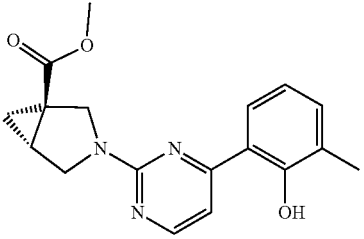
C-32

The following intermediates can be prepared from intermediate B-16 and A-13 in a similar fashion using the appropriate reagents. The racemate is resolved on a Chiralpak IA column (21×250 mm) using 25% MeOH in super critical CO$_2$ at 80 mL/min under 100 bar at 40° C. to afford C-57 and C-58 (1.05 g, 30% yield). The absolute stereochemistry was not determined and the stereochemistry drawn is arbitrarily assigned.

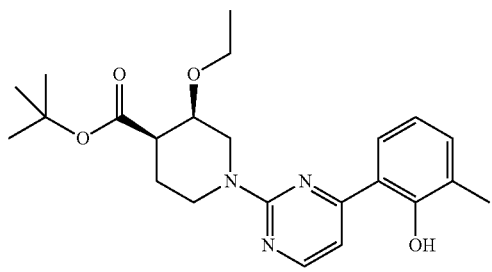

C-57

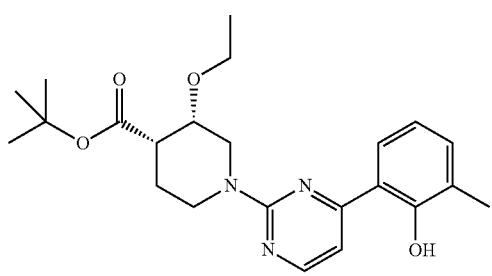

C-58

Example 16

Preparation of intermediate 6-bromomethyl-3,4-dihydro-1H-isoquinoline-2-carboxylic acid tert-butyl ester (D-1)

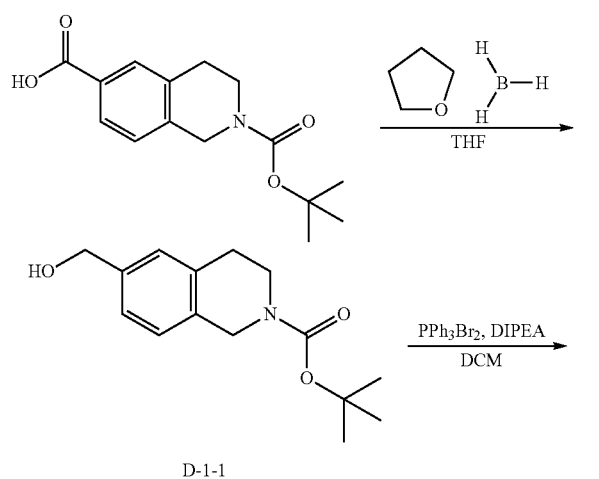

D-1-1

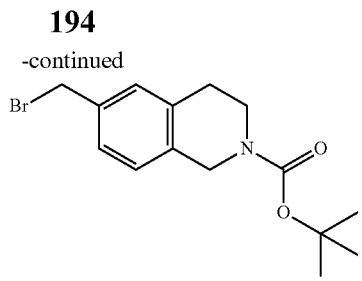

D-1

To a solution of 3,4-dihydro-1H-isoquinoline-2,6-dicarboxylic acid 2-tert-butyl ester (12.50 g, 45.08 mmol) in dry THF (125.0 mL), under nitrogen at 25° C., is added via syringe borane THF complex (99.17 mL, 99.17 mmol) The mixture is stirred at 25° C. for 16 h then water (10.0 mL) is slowly added followed by 2.0 M Na$_2$CO$_3$ (15.0 mL). This mixture is stirred for 15 min and then is diluted with EtOAc and the organic layers are collected. The organics are rinsed with 1M HCl, dried over MgSO$_4$, and concentrated under reduced pressure to afford an oil. The oil is purified by silica gel chromatography to yield D-1-1 (11.8 g, 99.3% yield), as a white solid.

To a solution of alcohol, D-1-1, (9.50 g, 36.1 mmol) and N,N-diisopropylethylamine (9.43 mL, 54.1 mmol) in dichloromethane (200.0 mL) is added triphenylphosphine dibromide (23.79 g, 54.11 mmol) at 0° C. The reaction is stirred for 1 h then concentrated under reduced pressure. The resulting residue is purified by silica gel chromatography to yield D-1 (8.74 g, 74% yield), as a white solid.

The following intermediates are synthesized in similar fashion from the appropriate reagents:

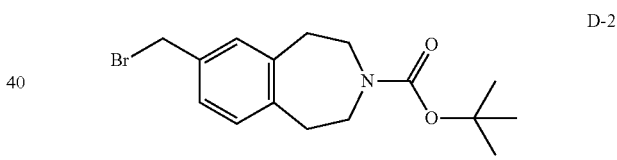

D-2

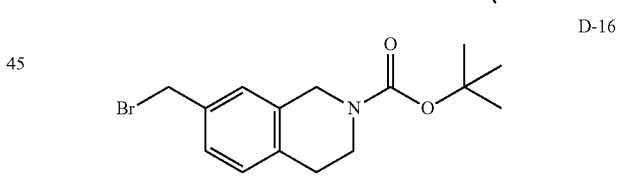

D-16

Example 17

Preparation of intermediate 6-bromomethyl-5-methyl-3,4-dihydro-1H-isoquinoline-2-carboxylic acid tert-butyl ester (D-3)

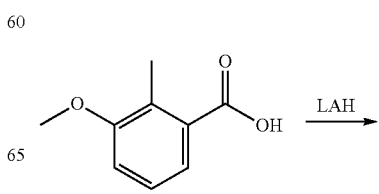

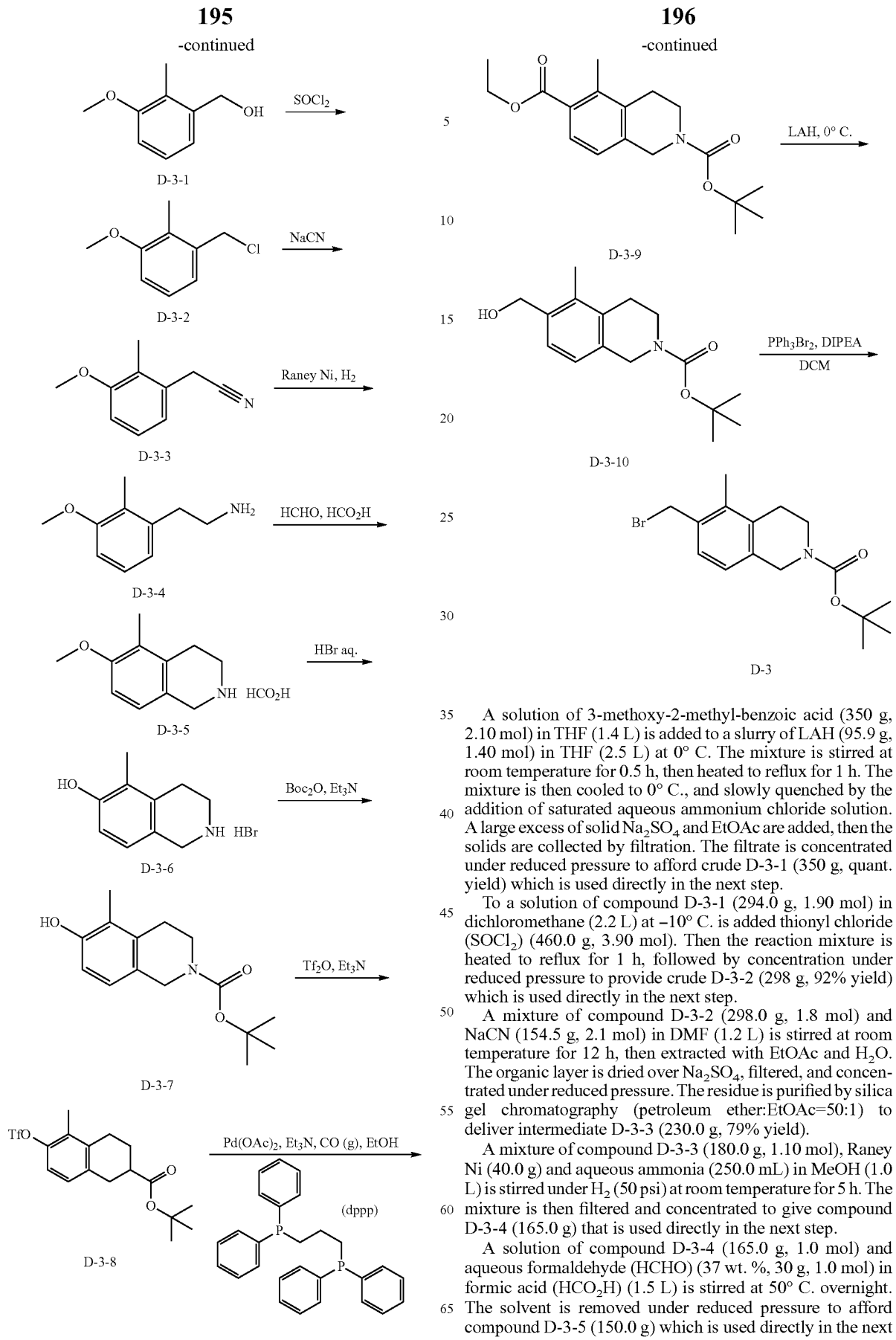

A solution of 3-methoxy-2-methyl-benzoic acid (350 g, 2.10 mol) in THF (1.4 L) is added to a slurry of LAH (95.9 g, 1.40 mol) in THF (2.5 L) at 0° C. The mixture is stirred at room temperature for 0.5 h, then heated to reflux for 1 h. The mixture is then cooled to 0° C., and slowly quenched by the addition of saturated aqueous ammonium chloride solution. A large excess of solid $Na_2SO_4$ and EtOAc are added, then the solids are collected by filtration. The filtrate is concentrated under reduced pressure to afford crude D-3-1 (350 g, quant. yield) which is used directly in the next step.

To a solution of compound D-3-1 (294.0 g, 1.90 mol) in dichloromethane (2.2 L) at −10° C. is added thionyl chloride ($SOCl_2$) (460.0 g, 3.90 mol). Then the reaction mixture is heated to reflux for 1 h, followed by concentration under reduced pressure to provide crude D-3-2 (298 g, 92% yield) which is used directly in the next step.

A mixture of compound D-3-2 (298.0 g, 1.8 mol) and NaCN (154.5 g, 2.1 mol) in DMF (1.2 L) is stirred at room temperature for 12 h, then extracted with EtOAc and $H_2O$. The organic layer is dried over $Na_2SO_4$, filtered, and concentrated under reduced pressure. The residue is purified by silica gel chromatography (petroleum ether:EtOAc=50:1) to deliver intermediate D-3-3 (230.0 g, 79% yield).

A mixture of compound D-3-3 (180.0 g, 1.10 mol), Raney Ni (40.0 g) and aqueous ammonia (250.0 mL) in MeOH (1.0 L) is stirred under $H_2$ (50 psi) at room temperature for 5 h. The mixture is then filtered and concentrated to give compound D-3-4 (165.0 g) that is used directly in the next step.

A solution of compound D-3-4 (165.0 g, 1.0 mol) and aqueous formaldehyde (HCHO) (37 wt. %, 30 g, 1.0 mol) in formic acid ($HCO_2H$) (1.5 L) is stirred at 50° C. overnight. The solvent is removed under reduced pressure to afford compound D-3-5 (150.0 g) which is used directly in the next step.

Compound D-3-5 (150.0 g, 847 mmol) is suspended in aqueous HBr (48%, 1.0 L), then heated to 100° C. overnight. Removal of the solvent under reduced pressure provides compound D-3-6 (195.0 g) which is used directly in the next step.

To a solution of compound D-3-6 (195.0 g, 799 mmol) in THF (1.0 L) and H₂O (1.0 L) is added Et₃N (242.0 g, 2.4 mol) and Boc₂O (174.0 g, 799 mmol). The resulting mixture is stirred at room temperature overnight, then extracted with EtOAc. The combined organic phases are washed with brine, dried over Na₂SO₄, filtered and concentrated under reduced pressure. The crude product is purified by silica gel chromatography (using 10:1 petroleum ether:EtOAc) to provide compound D-3-7 (100.0 g, 56% yield over 4 steps).

To a solution of compound D-3-7 (100 g, 380 mmol) and Et₃N (76.8 g, 760 mmol) in dichloromethane (1.5 L), cooled to 0° C., is added triflic anhydride (Tf₂O) (107.0 g, 380 mmol) via an addition funnel. Upon complete addition of Tf₂O the solution is then warmed to room temperature for 5 h. The reaction mixture is then treated with H₂O and dichloromethane and the organic phase is separated. The organic phase is washed with brine and dried over anhydrous Na₂SO₄. The mixture is then filtered and concentrated under reduced pressure. The residue is purified by flash silica gel chromatography (using 20:1 petroleum ether:EtOAc) to provide compound D-3-8 (105 g, 70% yield).

Compound D-3-8 (50.0 g, 127 mmol) is combined with palladium (II) acetate (5.0 g), dppp (5.0 g) and Et₃N (25.7 g, 254 mmol) in EtOH (1.0 L). The mixture is then stirred at 80° C. overnight under an atmosphere of CO at a pressure of 4 MPa. The mixture is cooled to room temperature and the solids are removed by filtration. The filtrate is concentrated under reduced pressure and the residue is purified by flash silica gel chromatography (using 20:1 petroleum ether:EtOAc) to provide compound D-3-9 (25.0 g, 62% yield).

To a solution of LAH (12.5 g, 330 mmol) in THF (400 mL), cooled to −30° C., is added, drop wise over 30 min, a solution of compound D-3-9 (35.0 g, 110 mmol) in THF (400 mL). After addition, the reaction mixture is stirred at 0° C. for 30 min, then treated with H₂O and dichloromethane. The organic phase is: separated, washed with brine, dried over anhydrous Na₂SO₄, filtered, and then concentrated under reduced pressure. The crude product is purified by flash silica gel chromatography (using 10:1 petroleum ether:EtOAc) to provide the desired intermediate D-3-10 (21.1 g, 69% yield).

To a solution of alcohol D-3-10, (6.00 g, 21.6 mmol) and N,N-diisopropylethylamine (5.65 mL, 32.5 mmol) in dichloromethane (200 mL) is added triphenylphosphine dibromide (14.3 g, 32.5 mmol) at 0° C. The reaction is stirred for 1 h and then, concentrated under reduced pressure. The resulting residue is purified by flash silica gel chromatography to afford D-3 (6.60 g, 90% yield), as a white solid.

Example 18

Preparation of intermediate 6-Bromomethyl-8-methyl-3,4-dihydro-1H-isoquinoline-2-carboxylic acid tert-butyl ester (D-4)

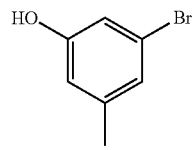

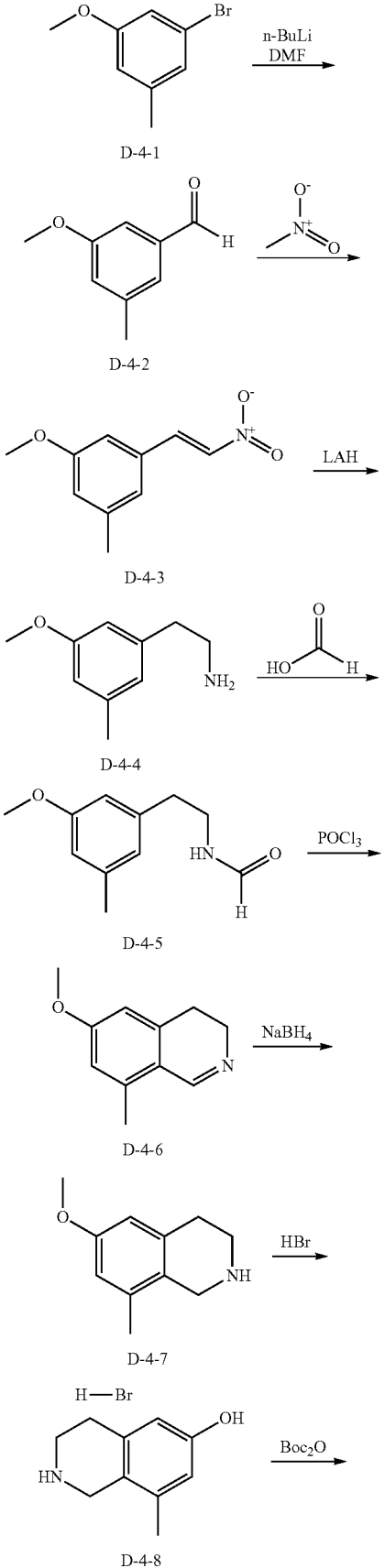

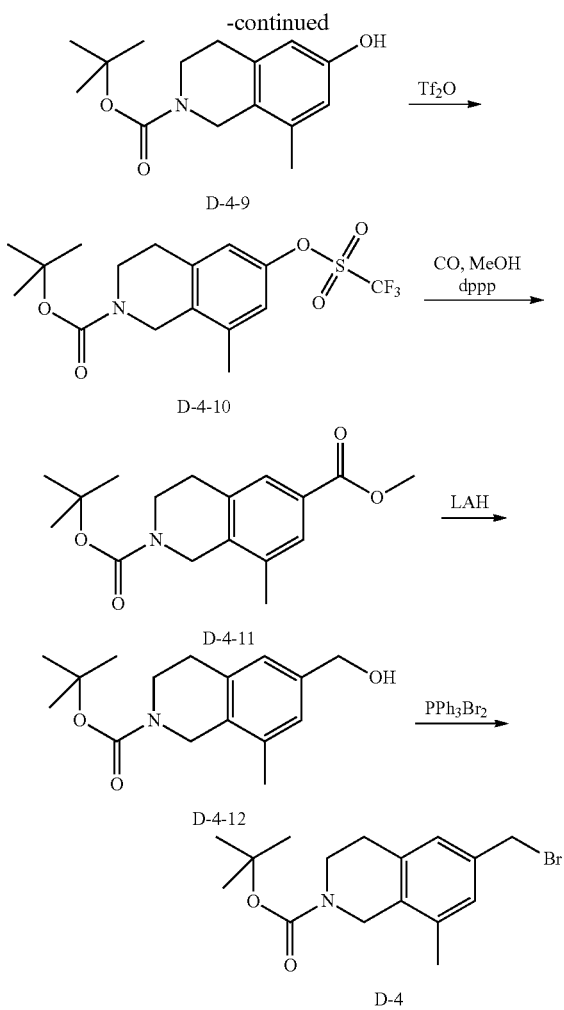

The mixture is cooled to 0° C., quenched slowly with water (78 mL) followed by a 15% wt. solution of NaOH (78 mL) and then with additional water (235 mL). After filtration, the mixture is concentrated under reduced pressure to afford D-4-4 (40 g, 60% yield) as a light yellow oil.

The mixture of compound D-4-4 (66 g, 0.40 mol) and formic acid (73.5 g, 1.60 mol) in dioxane (600 mL) is stirred for 16 h at 90° C. The mixture is concentrated under reduced pressure to afford D-4-5 (77 g, 90% yield) as yellow solid.

To a solution of D-4-5 (76.0 g, 0.354 mol) in dichloromethane (2.5 L), at 15° C., is added $POCl_3$ (155 g, 1.01 mol). After addition the mixture is refluxed for 3 h then cooled to ambient temperature. The solution is concentrated under reduced pressure. To the residue is added water (1.5 L), toluene (1.5 L) and 20% NaOH (500 mL). The mixture is then refluxed for 1 h then cooled to ambient temperature. The mixture is diluted with EtOAc and washed with water followed by brine. The combined organic phase is dried over anhydrous $Na_2SO_4$ and then, concentrated under reduced pressure. The residue is purified by flash silica gel column (PE:EtOAc=10:1) to afford D-4-6 (58.5 g, 94% yield) as brown oil.

To a solution of D-4-6 (58.5 g, 0.334 mol) in MeOH (500 mL), at 0° C., is added $NaBH_4$ (63.3 g, 1.67 mol). The mixture is maintained at 0° C. for 4 h. The solution is quenched with 1N HCl (100 mL). The pH is adjusted to pH 8 by addition of $NaHCO_3$. The mixture is extracted with DCM. The combined organic extracts are dried over anhydrous $Na_2SO_4$ and concentrated to afford D-4-7 as brown oil.

A solution of crude D-4-7 (83 g, 0.47 mol) in a solution of HBr (40% in water, 500 mL) is heated to 90° C. for 12 h. The solution is concentrated under reduced pressure to obtain D-4-8 which is used directly in the next reaction.

To a solution of crude D-4-8 in DCM (1 L) is added $Boc_2O$ (72 g, 0.33 mol) and triethylamine (63 g, 0.62 mol). The resulting mixture is stirred for 12 h at 15° C., then diluted with DCM (1500 mL) and water (100 mL). The organics layer is separated and washed with 0.5 N HCl (100 mL) followed by brine (100 mL). The organic phase is dried over anhydrous $Na_2SO_4$ and concentrated under reduced pressure. The residue is purified by flash silica gel column chromatography to afford D-4-9 (33.4 g, 34% yield from D-4-6) as a white solid.

To a solution of D-4-9 (33 g; 0.113 mol) and pyridine (20.1 g, 0.254 mol) in dry dichloromethane (300 mL), at −30° C., is added $Tf_2O$ (39.4 g, 0.139 mol) drop-wise. The mixture is stirred for 1 h at −30° C. then warmed to 15° C. and stirred for 8 h. The mixture is diluted with dichloromethane (500 mL) and water (100 mL). The organic phase is concentrated under reduced pressure and the residue purified by flash silica gel chromatography to afford D-4-10 (43 g, 96% yield) as a white solid.

A solution of D-4-10 (43 g, 0.109 mol), $Et_3N$ (33.0 g, 0.327 mol), DPPP (4.53 g) and $Pd(OAc)_2$ (5 g) in MeOH (500 mL) is stirred under 3 MPa pressure of CO at 90° C. for 2 days. After filtration and concentration the residue is purified by silica gel chromatography (PE:EtOAc=50:1) to afford 8-Methyl-3,4-dihydro-1H-isoquinoline-2,6-dicarboxylic acid 2-tert-butyl ester 6-methyl ester, D-4-11 (21 g, 64% yield) as a colorless oil.

To a solution of D-4-11 (21 g, 0.0693 mol) in dry THF (500 mL), at −50'C, is added $LiAlH_4$ (7.4 g, 208 mmol). The mixture is stirred at −50° C. for 1 h and then warned to 0° C. and stirred for an additional 30 min. The reaction is slowly quenched with water (7.4 mL), 15% NaOH (7.4 mL), and additional water (22.2 mL). The mixture is filtered and the filtrate is concentrated under reduced pressure. The residue is To a mixture of 3-bromo-5-methyl-phenol (185 g; 0.940 mol) and $K_2CO_3$ (437 g, 3.17 mol) in acetone (2 L) is added MeI (424 g, 2.99 mol). The mixture is stirred at 40° C. for 16 h. The mixture is cooled to ambient temperature, filtered, and concentrated under reduced pressure. After filtration, the mixture is purified by flash silica gel chromatography to afford 1-Bromo-3-methoxy-5-methyl-benzene, D-4-1 (189 g, quant. yield) as a light yellow oil.

To a mixture of D-4-1 (200 g, 0.995 mol) in dry THF (1.7 L), at −70° C., is added drop wise a solution of n-BuLi in hexanes (438 ml; 1.09 mol). After stirring for 1 h at −70° C., dry DMF (76.3 g, 1.04 mol) is added drop wise at −70° C. Following this, the mixture is stirred for 1 h at −70° C. The mixture is poured into $NH_4Cl$ (1 L) and extracted with EtOAc. The combined extracted are washed with brine, dried over anhydrous $Na_2SO_4$ and concentrated under reduced pressure to afford D-4-2 (147 g, 98% yield) as a yellow oil.

The mixture of D-4-2 (150 g, 0.999 mol) and $NH_4OAc$ (30.8 g, 0.40 mol) in $MeNO_2$ (1.5 L) is refluxed for 16 h. The mixture is concentrated then diluted with EtOAc (1000 mL) and washed sequentially with water (1 L) followed by brine (100 mL). The organic phase is dried over anhydrous $Na_2SO_4$ and concentrated under reduced pressure. The mixture is triturated with PE:EtOAc=10:1 for 10 min and the solid collected by filtration to afford D-4-3 (80 g, 42% yield) as yellow solid.

To a mixture of $LiAlH_4$ (78.6 g, 2.00 mol) in dry THF (1 L), at 0° C., is added a solution of D-4-3 (78 g, 0.404 mol) in THF (200 mL). The mixture is heated to 70° C. and stirred for 16 h.

purified by prep-HPLC. The eluent is concentrated under reduced pressure to remove volatile organics. The remaining aqueous mixture residue is extracted with dichloromethane. The combined organic extracts are dried over $Na_2SO_4$ and concentrated under reduced pressure to afford D-4-12 (14.8 g, 77% yield) as a colorless oil.

To a solution of D-4-12 (13.4 g, 0.0485 mol) and DIEA (11.8 mL, 0.679 mol) in dichloromethane (200 mL), at −30° C., is added triphenylphosphine dibromide (26.6 g, 0.606 mol). The resulting mixture is stirred 1 h, over which time cold bath is allowed to warm to −10° C. Volatiles are stripped from the −10° C. mixture, the residue is suspended in dichloromethane (50 mL), and the filtrate is purified by flash silica gel chromatography to afford D-4 (16.2 g, quant. yield) as a white solid.

Example 19

Preparation of intermediate 6-Bromomethyl-5,8-dimethyl-3,4-dihydro-1H-isoquinoline-2-carboxylic acid tert-butyl ester (D-5)

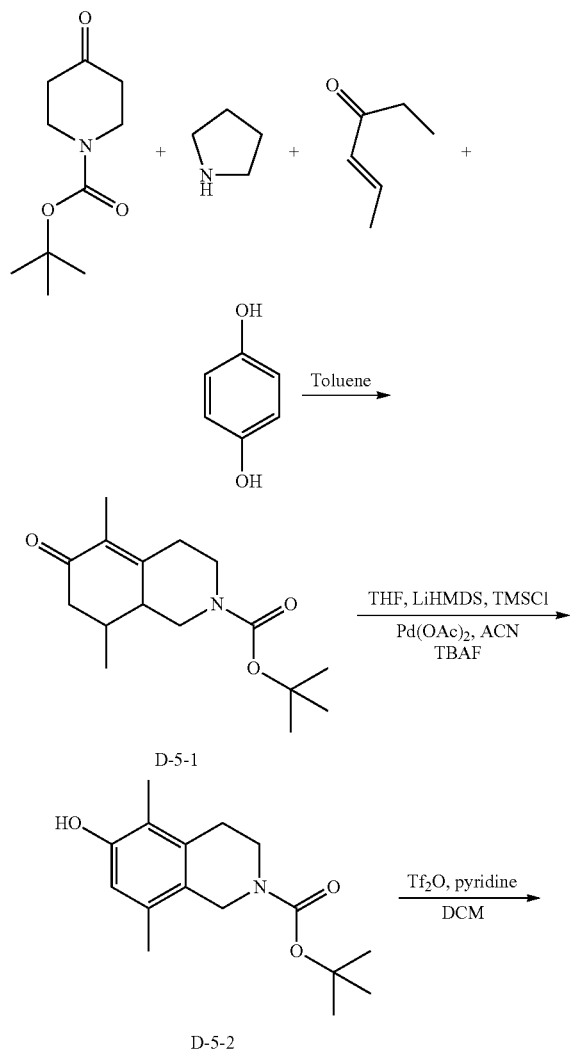

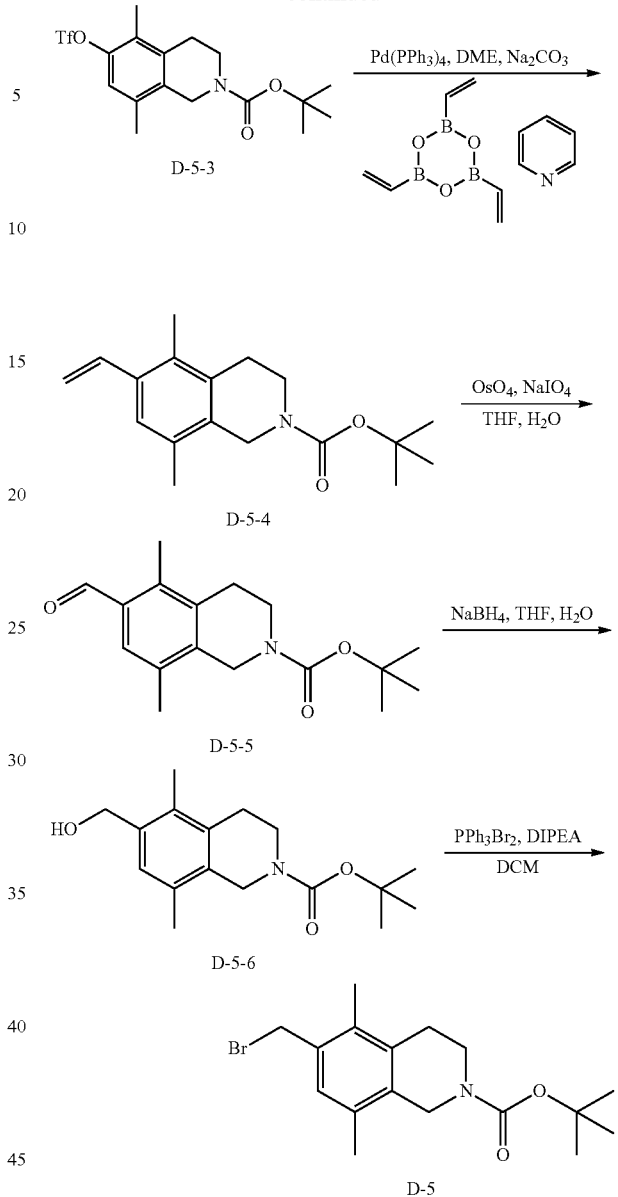

A solution of boc-4-piperidinone (14.0 g, 70.3 mmol) and pyrrolidine (8.71 mL, 106 mmol) in toluene (60 mL) is refluxed under Dean Stark conditions for 24 h. The reaction is then concentrated under reduced pressure. The resulting residue is dissolved in toluene (60 mL) and treated with 4-hexen-3-one (8.32 mL, 70.3 mmol) and hydroquinone (0.080 g, 0.73 mmol). The solution is heated to reflux for 24 h then cooled to ambient temperature. The mixture is diluted with EtOAc and washed with 1N HCl. The combined organics are dried and concentrated under reduced pressure to afford a viscous oil. The material is purified by flash silica gel chromatography afford D-5-1 as a yellow solid (11.7 g, 60% yield).

A 1.0 M LiHMDS solution in THF (43 mL) is added drop wise to a solution of D-5-1 (10.00 g, 35.79 mmol) in THF (50.0 mL) at −78° C. This mixture is stirred at −78° C. for 30 min then TMS-Cl (5.45 mL, 42.9 mmol) is added drop wise. The mixture is stirred at −78° C. for an additional 2 h then warmed to room temperature and diluted with diethyl ether (200 mL). This mixture is added to a saturated Na₂CO₃ solution and the phases are separated. The combined organics are dried and concentrated under reduced pressure. The residue is dissolved in MeCN (50.0 mL) and Pd(OAc)₂ (8.04 g, 35.8 mmol) is added. The resulting mixture is cooled in a water bath to maintain reaction temp below 35° C. and stirred overnight. The reaction is filtered through diatomaceous earth and the filtrate is concentrated under reduced pressure. The residue is taken up in 200 mL EtOAc then treated with 1.0 M TBAF solution (50.0 mL). This mixture is stirred for 30 min and then washed sequentially with a 1N HCl and 10% sodium thiosulfate solution. The organics are dried and concentrated. The material is purified by silica gel chromatography afford D-5-2 as an off-white solid (6.11 g, 62% yield).

To a solution of D-5-2 (1.50 g, 5.41 mmol) in dichloromethane (25 mL) at room temperature is added pyridine (0.87 mL, 11 mmol). The solution is cooled to −30° C. and Tf₂O (1.00 mL, 5.95 mmol) is added drop wise. The reaction is stirred at −30° C. for 1 h and then warmed to room temperature. The mixture is concentrated under reduced pressure and the residue is diluted with EtOAc then washed sequentially with solution of a 1N HCl, saturated NaHCO₃, and then brine. The mixture is dried over anhydrous MgSO₄ and concentrated under reduced pressure. The resulting material is purified by flash silica gel chromatography to afford D-5-3 as a white solid (1.61 g, 73% yield).

Triflate D-5-3 (1.00 g, 2.44 mmol) is combined with the boronate (0.647 g, 2.69 mmol) and Pd(PPh₃)₄ (0.144 g, 0.124 mmol) in a mixture of DME (15.0 mL) and 2.0 M Na₂CO₃ (1.27 mL). The reaction is irradiated in a microwave reactor at 120° C. for 40 min. The mixture is concentrated under reduced pressure and the residue purified by flash silica gel chromatography to afford D-5-4 a white solid (0.662 g, 94% yield).

Substrate D-5-4 (1.03 g, 3.58 mmol), NaIO₄ (2.34 g, 10.9 mmol), 2.5 wt. % OsO₄ in t-BuOH (1.0 mL), THF (12.4 mL) and H₂O (2.4 mL) are combined at room temperature. The mixture is stirred overnight in the dark then diluted with water and dichloromethane. The phases is separated using a hydrophobic frit. The organic phase is dried over Na₂SO₄, filtered, and concentrated under reduced pressure. The residue is purified by flash silica gel chromatography to afford D-5-5 as an amber oil (0.786 g, 76% yield).

Aldehyde D-5-5 (0.785 g, 2.71 mmol) is dissolved in THF (5.0 mL) and MeOH (5.0 mL). The mixture is cooled to 0° C. and NaBH₄ (0.156 g, 4.07 mmol) is added. The reaction is stirred at room temperature for 30 min. Excess reactants are consumed by the addition of an aqueous solution of NH₄Cl and the mixture is stirred at room temperature for 10 min. The mixture is extracted with EtOAc and the organic phase is washed with a solution of NH₄Cl followed by brine. The organic phase is then dried over anhydrous MgSO₄ and concentrated under reduced pressure. The resulting material is purified by flash silica gel chromatography to afford D-5-6 (0.626 g, 79% yield) as a white solid.

To a solution of alcohol D-5-6 (0.300 g, 1.03 mmol) and N,N-diisopropylethylamine (0.269 mL, 1.54 mmol) in dichloromethane (10.0 mL), at 0 C, is added triphenylphosphine dibromide (0.679 g, 1.54 mmol). The reaction is stirred for 2 h and concentrated under reduced pressure. The resulting residue is purified by silica gel chromatography to afford D-5 (0.338 g, 93% yield) as a white solid.

Example 20

Preparation of intermediate tert-Butyl 8-ethyl-6(bromomethyl)-3,4-dihydroisoquinoline-2(1H)-carboxylate (D-6)

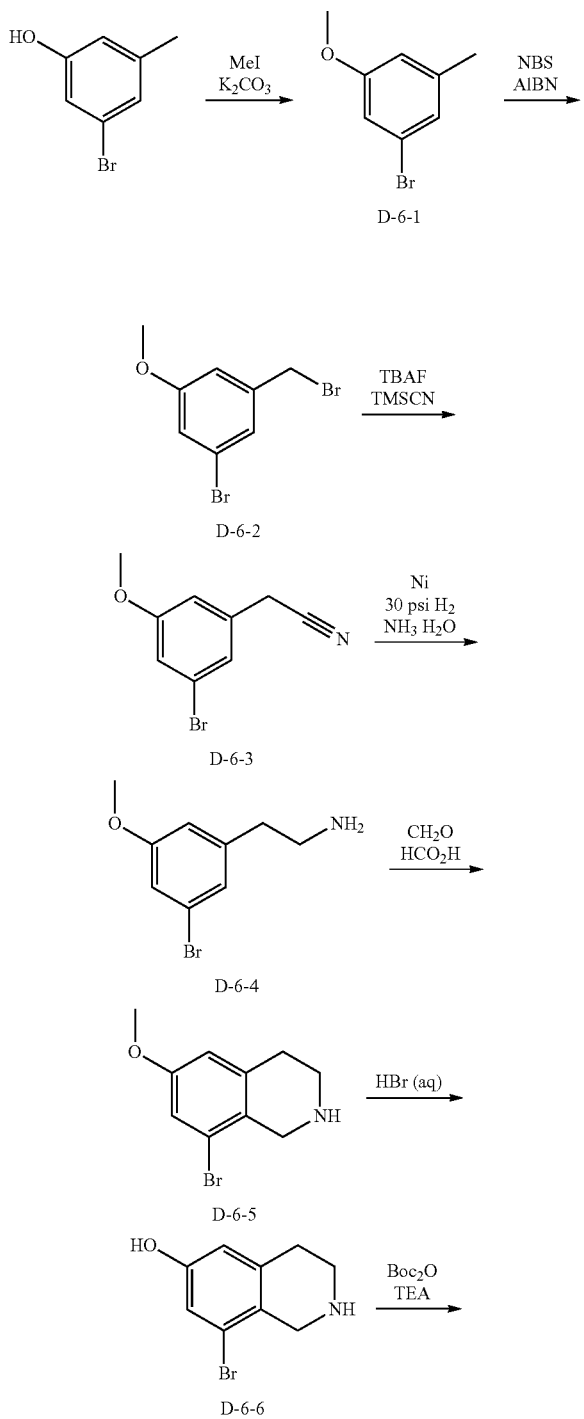

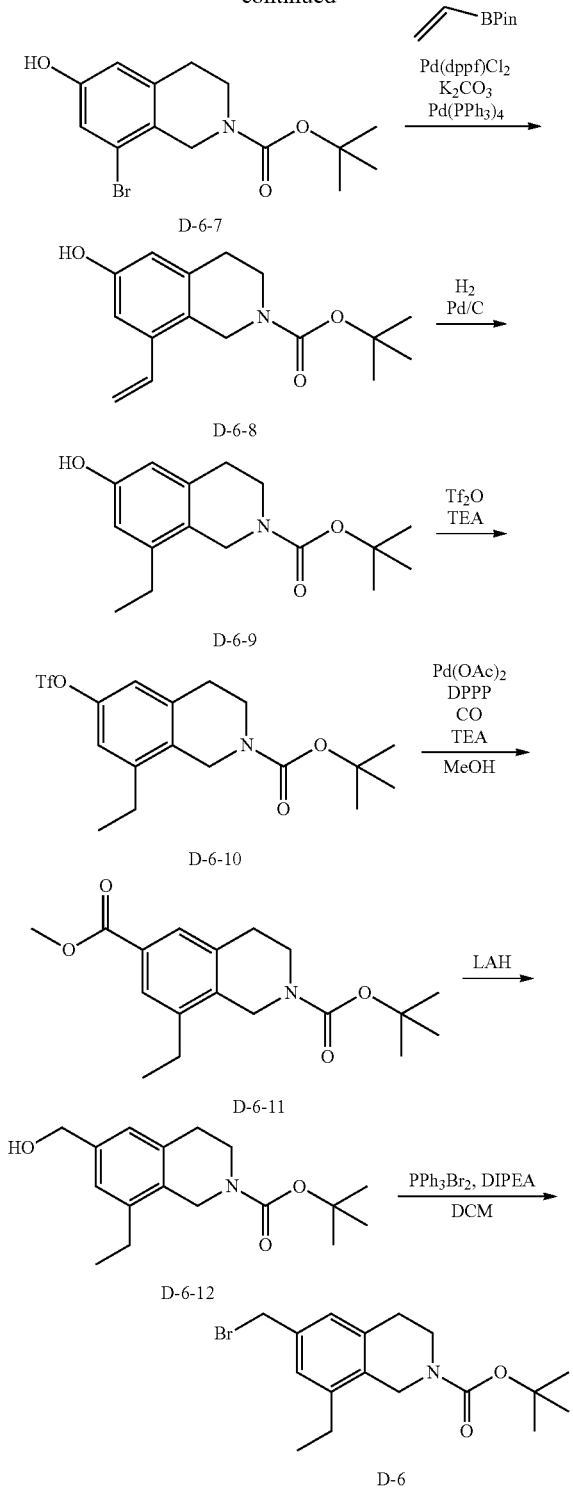

To the mixture of 3-bromo-5-methylphenol (300 g, 1.60 mol) and $K_2CO_3$ (665 g, 4.8 mol) in DMF (2000 mL) at room temperature is added MeI (250 g, 1.8 mol) drop wise. The mixture is stirred overnight then diluted with $H_2O$ and extracted with EtOAc. The organic layer is dried over anhydrous sodium sulfate and concentrated under reduced pressure. The residue is purified by flash silica gel chromatography on silica gel to afford D-6-1 (165 g, 52.0% yield).

A mixture of D-6-1 (100 g, 497 mmol), NBS (88.5 g, 497 mmol), and AIBN (10 g, 50 mmol) in $CCl_4$ (700 mL) is heated to reflux for 12 h. The mixture is cooled to ambient temperature, diluted with $H_2O$, and extracted with EtOAc. The organic layer is separated, dried over anhydrous sodium sulfate, and concentrated under reduced pressure. The residue is purified by flash silica gel chromatography to afford D-6-2 (48 g, 42% yield).

A solution of compound D-6-2 (80.0 g, 286 mmol) and TMSCN (28.2 g, 286 mmol) in MeCN (600 ml) is stirred at room temperature for 0.5 h. The mixture is cooled to 0° C. and TBAF (74.6 g, 286 mmol) is added. The mixture is stirred for 12 h then diluted with water and extracted with EtOAc. The organic layer is separated, dried over anhydrous sodium sulfate, and concentrated under reduced pressure. The residue is purified by flash silica gel chromatography to afford D-6-3 (39 g, 60% yield).

A solution of D-6-3 (12 g, 53 mmol) and Ni(s) (10 g) in a mixture of MeOH (80 ml) and ammonium hydroxide (80 ml) is stirred at room temperature for 5 hours under an 50 psi atmosphere of hydrogen. The mixture is filtered and the filtrate concentrated under reduced pressure to afford D-6-4 (8 g) which is used directly in the next step.

A mixture of D-6-4 (75 g, 330 mmol) and formaldehyde (8.8 g, 290 mmol) in formic acid (500 ml) is stirred overnight under $N_2$ at 50° C. The solvent is removed under reduced pressure and the residue purified by flash silica gel chromatography To afford D-6-5 (54 g, 64% yield for 2 steps).

A mixture of D-6-5 (45 g, 186 mmol) in an aqueous HBr solution (400 ml) is stirred at 90° C. for 12 h. The solvent is removed under reduced pressure and the residue is purified by silica gel chromatography to afford D-6-6 (21 g, 53% yield).

A mixture of D-6-6 (20 g, 88 mmol), $Boc_2O$ (19.1 g, 87.7 mmol), and TEA (17.7 g, 175 mmol) in a 1:1 mixture of THF:water (200 ml) is stirred at room temperature for 3 h. The mixture is diluted with water and extracted with EtOAc. The organic layer is dried over anhydrous sodium sulfate and concentrated under reduced pressure. The residue is purified by flash silica gel chromatography to afford D-6-7 (20 g, 70% yield).

A mixture of D-6-7 (14 g, 43 mmol), $K_2CO_3$ (17.7 g, 128 mmol), Pd(dppf)$Cl_2$ (2.5 g), Pd (PPh$_3$)$_4$ (2.5 g), and the vinyl boronic ester (7.22 g, 46.9 mmol) in DMF (150 ml) is stirred at reflux overnight. The mixture is filtered and the filtrate concentrate under reduced pressure. The residue is purified by flash silica gel chromatography to afford D-6-8 (7.2 g, 61% yield).

A mixture of D-6-8 (7.2 g, 26.2 mmol) and 10% Pd—C (2 g) in MeOH (100 ml) is stirred at ambient temperature under a 50 psi atmosphere of $H_2$ for 12 h. The mixture is filtered through diatomaceous earth and the filtrate is concentrated to give crude product which is purified by flash silica gel chromatography to afford D-6-9 (5.8 g, 80% yield).

A mixture of D-6-9 (5.8 g, 20.9 mmol), Tf$_2$O (5.9 g, 20.9 mmol) and TEA (6.3 g, 62.7 mmol) in DCM (70 ml) is stirred at room temperature for 3 h. The reaction is diluted with $H_2O$ and extracted with EtOAc. The organic layer is dried over $Na_2SO_4$ and concentrated under reduced pressure. The residue is purified by flash silica gel chromatography to provide D-6-10 (7.0 g, 82% yield).

A mixture of D-6-10 (7.0 g, 17 mmol), Pd(OAc)$_2$ (1.4 g), dppp (1.4 g) and Et$_3$N (5.2 g, 51.3 mmol) in MeOH (80 mL) is stirred for 2 days at 80° C. under an atmosphere of 3 MPa of CO. The mixture is filtered through diatomaceous earth and the filtrate is concentrated under reduced pressure. The residue is purified by flash silica gel chromatography to afford D-6-11 (4.8 g, 88% yield).

To a solution of LiAlH₄ (1.1 g, 30.1 mmol) in THF (10 mL), at −50° C., is added, drop wise over a 30 minute period, a solution of D-6-11 (4.8 g, 15 mmol) in THF (50 mL). After addition, the reaction mixture is stirred at 0° C. for 2.5 h then diluted with H₂O followed by DCM. The organic layer is separated, washed with brine then dried over Na₂SO₄ and concentrated under reduced pressure. The residue is purified by flash silica gel chromatography to provide D-6-12 (4.1 g, 92% yield).

To a solution of alcohol, D-6-12, (3.12 g, 10.7 mmol) and N,N-diisopropylethylamine (2.80 mL, 16.1 mmol) in dichloromethane (57 mL), at 0 C, is added triphenylphosphine dibromide (6.92 g, 16.1 mmol). The reaction is stirred at 0° C. for 2 h then concentrated under reduced pressure. The resulting residue is purified by silica gel chromatography to yield D-6 (2.90 g, 76% yield).

Example 21

Preparation of intermediate tert-Butyl 8-cyano-6-(bromomethyl)-3,4-dihydroisoquinoline-2(1H)-carboxylate (D-7)

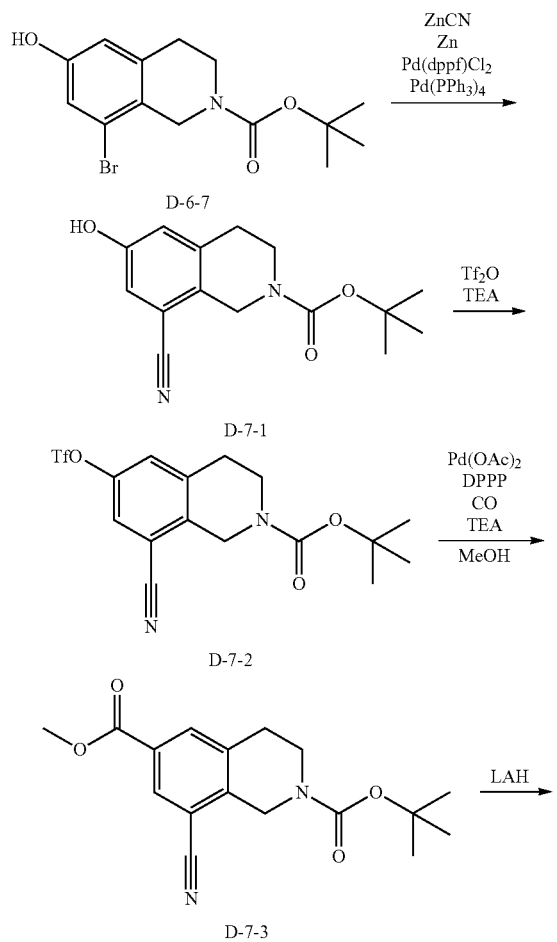

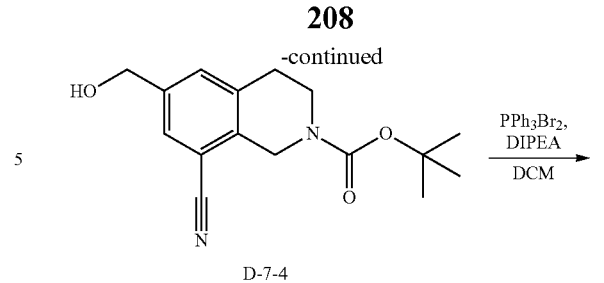

A solution of compound D-6-7 (11 g, 35 mmol), Pd(dppf)Cl₂ (2.5 g), Pd (PPh₃)₄ (2.5 g), ZnCN (2.8 g, 31.3 mmol), Zn (1.1 g, 17.4 mmol) in DMF (110 ml) is stirred at reflux overnight. The mixture is filtered through diatomaceous earth and the filtrate is concentrate under reduced pressure. The residue is purified by flash silica gel chromatography to afford D-7-1 (6.5 g, 71% yield).

A solution of D-7-1 (12 g, 44 mmol), Tf₂O (12 g, 44 mmol) and TEA (13.3 g, 131 mmol) in DCM (120 ml) is stirred at room temperature for 3 h. The reaction is diluted with H₂O and extracted with EtOAc. The organic layer is dried over anhydrous Na₂SO₄, filtered and concentrated under reduced pressure. The residue is purified by flash silica gel chromatography to provide D-7-2 (9.0 g, 51% yield).

A mixture of D-7-2 (9.5 g, 23.4 mmol), Pd(OAc)₂ (1.9 g), dppp (1.9 g) and Et₃N (7.1 g, 70.1 mmol) in MeOH (90 mL) is stirred at 80° C. under an atmosphere of 3 MPa of CO for 2 d. The solid is filtered off and the filtrate concentrated under reduced pressure. The residue is purified by flash silica gel chromatography to afford D-7-3 (6.0 g, 80% yield).

To a solution of LiAlH₄ (1.4 g, 38 mmol) in THF (10 mL), at −50° C., is added over 30 min, a solution of D-7-3 (6.0 g, 19 mmol) in THF (50 mL). After addition, the reaction mixture is stirred at −20° C. for 4.5 h then treated with H₂O followed DCM. The organic layer is separated, washed with brine, dried over Na₂SO₄, and concentrated under reduced pressure. The residue is purified by flash silica gel chromatography on silica gel to provide D-7-4 (4.1 g, 74% yield).

To a solution of alcohol, D-7-4, (1.00 g, 3.47 mmol) and N,N-diisopropylethylamine (1.00 mL, 5.74 mmol) in dichloromethane (50 mL), at 0 C, is added triphenylphosphine dibromide (2.50 g, 5.69 mmol). The reaction is stirred for 1 h then concentrated under reduced pressure. The resulting residue is purified by silica gel chromatography to yield D-7 (0.900 g, 74% yield).

Example 22

Preparation of intermediate 6-Bromomethyl-8-methoxy-3,4-dihydro-1H-isoquinoline-2-carboxylic acid tert-butyl ester (D-8)

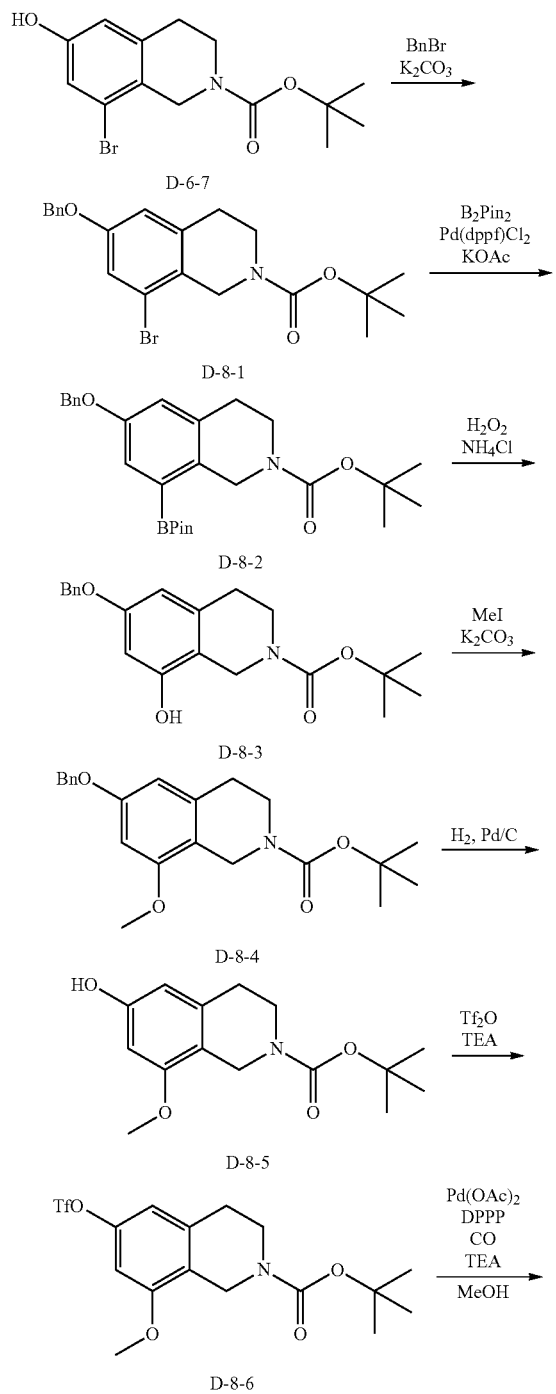

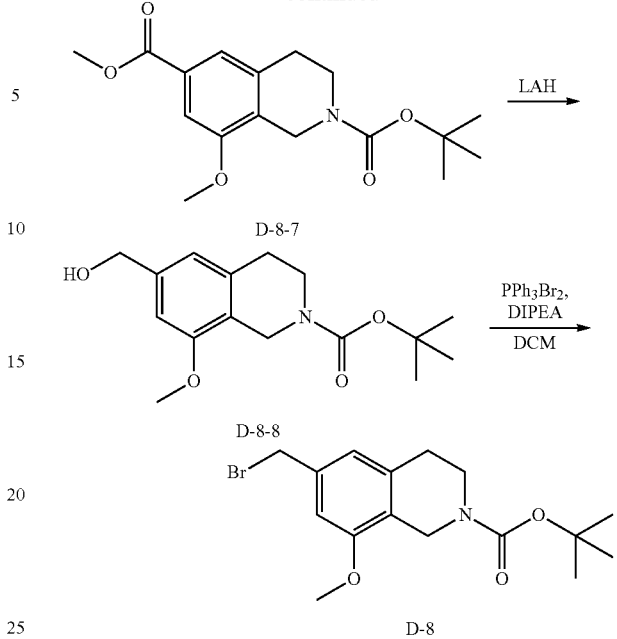

A solution of D-8-3 (22.5 g, 68.6 mmol) and K₂CO₃ (28.4 g, 205.7 mmol) in DMF (200 ml) is stirred at room temperature for 2 h. Then BnBr (11.7 g, 68.6 mmol) is added into the reaction mixture. The mixture is stirred at room temperature overnight. The reaction is diluted with water and extracted with EtOAc. The organic layer is dried, filtered and concentrated under reduced pressure. The crude product is purified by flash silica gel chromatography to afford D-8-1 (20 g, 70% yield).

A solution of D-8-1 (10 g, 24 mmol), B₂Pin₂ (7.2 g, 29 mmol), KOAc (7.0 g, 71 mmol) and Pd(dppf)Cl₂ (2 g) in dioxane (100 ml) is stirred at 90° C. overnight. After filtration, the filtrate is concentrate under reduced pressure and the residue is purified by flash silica gel chromatography to afford D-8-2 (5.4 g, 67% yield).

A solution of D-8-2 (15 g, 32 mmol), NH₄Cl (1.7 g, 120 mmol) and H₂O₂ (11 g, 30%, 97 mmol) in THF/H₂O=1:1 (150 ml) is stirred at room temperature for 12 h. The reaction is quenched by addition of an aqueous NaS₂O₄ solution and extracted with EtOAc. The organic layer is dried, filtered and concentrated under reduced pressure. The residue is purified by flash silica gel chromatography to afford D-8-3 (9.0 g, 79% yield).

To a mixture of D-8-3 (9 g, 25.3 mmol) and K₂CO₃ (10.5 g, 76.0 mmol) in DMF (80 mL) is added MeI (3.6 g, 25 mmol) at room temperature. The mixture is stirred overnight at ambient temperature then diluted with H₂O and extracted with EtOAc. The organic layer is dried, filtered and concentrated under reduced pressure. The crude produce is purified by flash silica gel chromatography to afford D-8-4 (7.5 g, 80% yield).

A mixture of D-8-4 (12 g, 32 mmol) and Pd—C(12 g) in MeOH (100 ml) is stirred under a 50 psi atmosphere of H₂ at room temperature for 12 h. The mixture is filtered through diatomaceous earth and the filtrate is concentrated under reduced pressure. The crude product is purified by flash silica gel chromatography to afford D-8-5 (7.6 g, 85% yield).

A solution of D-8-5 (7.0 g, 25 mmol), Tf₂O (7.1 g, 25 mmol) and TEA (7.6 g, 75 mmol) in DCM (70 ml) is stirred at room temperature for 3 h. The reaction is dilute with H₂O and extracted with EtOAc. The organic layer is dried, filtered and concentrated under reduced pressure. The crude product is purified by flash silica gel chromatography to afford D-8-6 (7.3 g, 73% yield).

A mixture of D-8-6 (9 g, 22 mmol), Pd(OAc)$_2$ (1.8 g), dppp (1.8 g) and Et$_3$N (6.6 g, 65.6 mmol) in MeOH (80 mL) is stirred overnight at 80° C. under a 3 MPa atmosphere of CO. The solid is filtered off and the filtrate is concentrated under reduced pressure. The residue is purified by flash silica gel chromatography to afford D-8-7 (6.8 g, 85% yield).

To a solution of LiAlH$_4$ (1.6 g, 42 mmol) in THF (10 mL) at −50° C. is added, drop wise over 30 min, a solution of D-8-7 (6.8 g, 21 mmol) in THF (70 mL). After addition, the reaction mixture is stirred at 0° C. for 2.5 h then treated with H$_2$O and DCM. The organic layer is separated, washed with brine, dried over Na$_2$SO$_4$, and concentrated under reduced pressure. The residue is purified by flash silica gel chromatography to afford D-8-8 (5.9 g, 90% yield).

To a solution of alcohol, D-8-8, (6.37 g, 21.7 mmol) and N,N-diisopropylethylamine (5.30 mL, 30.4 mmol) in dichloromethane (mL), cooled to −45 C, is added triphenylphosphine dibromide (11.9 g, 27.1 mmol). The reaction is warmed to 0° C. stirred for 3 h then concentrated under reduced pressure. The resulting residue is purified by silica gel chromatography to yield D-8 (6.58 g, 85% yield).

Example 23

Preparation of intermediate 6-Bromomethyl-8-fluoro-3,4-dihydro-1H-isoquinoline-2-carboxylic acid tert-butyl ester (D-9)

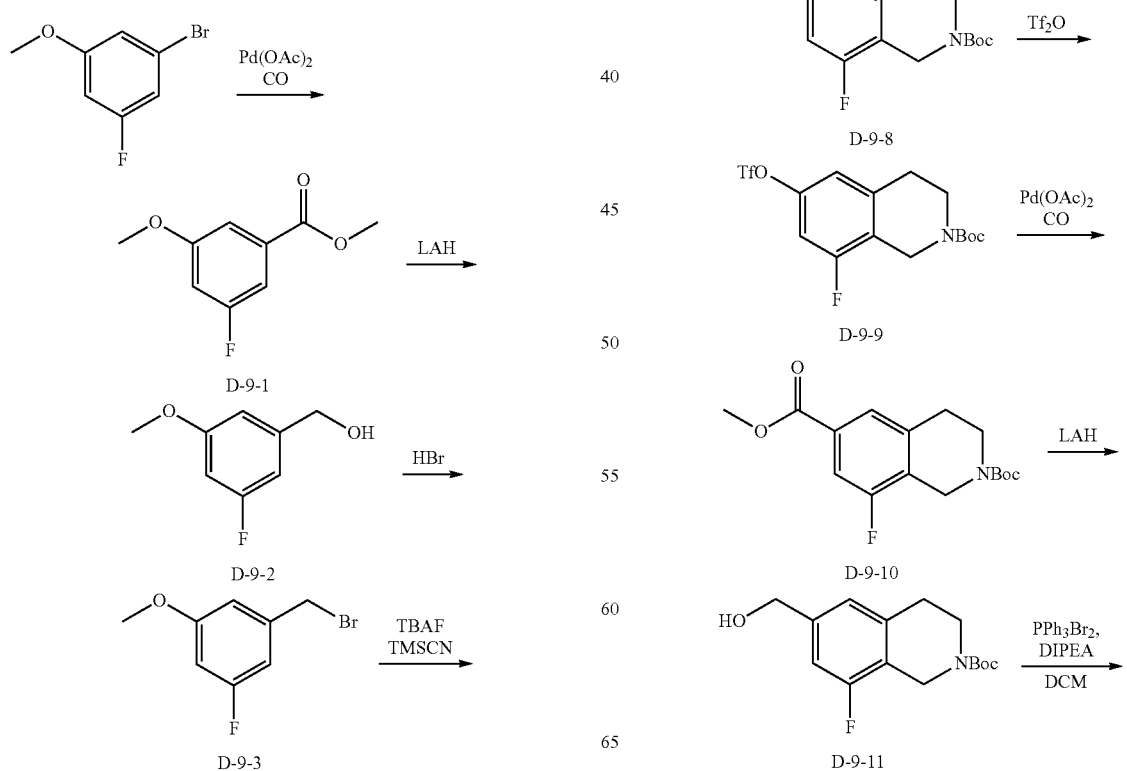

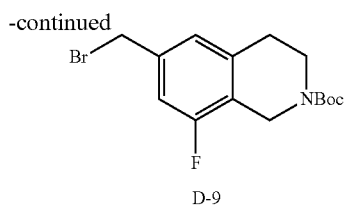

D-9

A mixture of 1-bromo-3-fluoro-5-methoxy-benzene (80 g, 0.39 mol), TEA (118 g, 1.17 mol), Pd(OAc)$_2$ (16 g, 20%) and DPPP (16 g, 20%) in MeOH (800 mL) is stirred under a 3 Mpa atmosphere of CO for 2 days. The mixture is filtered and the filtrate is concentrated under reduced pressure. The crude is purified by flash silica gel chromatography to afford compound D-9-1 (42 g, 59% yield).

To a solution of D-9-1 (250 g, 1.4 mol) in THF (2000 mL), cooled to −50 C, is added LAH (77 g, 2.0 mol). The mixture is slowly warmed to 0° C. and stirred for 3 h. Excess reactants are consumed by the addition of a aqueous solution of NH$_4$Cl and the mixture is extracted with EtOAc. The organic phase is dried over sodium sulfate and concentrated under reduced pressure. The crude product is purified by flash silica gel chromatography to afford D-9-2 (100 g, 47% yield).

A mixture of D-9-2 (50 g, 320 mmol), aqueous solution of HBr (200 mL), and toluene (200 ml) is stirred at room temperature for 1 day. The reaction is diluted with H$_2$O and extracted with DCM. The organic layers are dried over anhydrous sodium sulfate and concentrated under reduced pressure. The crude product is purified by flash silica gel chromatography to afford D-9-3 (45 g, 64% yield).

A solution of D-9-3 (60 g, 270 mmol) and TMSCN (28 g, 300 mmol) in ACN (600 mL) is stirred at room temperature for 0.5 h. To this is added TBAF (79 g, 300 mmol) and the reaction mixture is stirred at room temperature overnight. The reaction is diluted with H$_2$O and extracted with DCM. The organic layer is dried over anhydrous sodium sulfate and concentrated under reduced pressure. The crude product is purified by flash silica gel chromatography to afford D-9-4 (36 g, 78% yield).

A mixture of D-9-4 (12 g, 73 mmol), Ni (12 g), NH$_3$.H$_2$O (80 ml), and MeOH (80 mL) is stirred under a 30 Psi atmosphere of H$_2$ at room temperature for 5 h. The mixture is filtered and the filtrate is concentrate under reduced pressure to afford the crude product containing D-9-5 which is used directly without further purification.

A mixture of the crude product containing D-9-5 (45 g, 270 mmol) and HCHO (7.25 g, 239 mmol) in HCO$_2$H (500 mL) is stirred at 50° C. overnight. The solvent is removed under reduced pressure and the crude product is purified by flash silica gel chromatography to afford D-9-6 (40 g, 62% yield over 2 steps).

A solution of D-9-6 (40 g, 220 mmol) in an aqueous solution of HBr (400 mL) is stirred at 90° C. for 2 days. The solvent is removed under reduced pressure and the crude product is taken up in a saturated aqueous solution of NaHCO$_3$ then extracted with DCM. The organic layers are concentrated under reduced pressure and the crude product is purified by flash silica gel chromatography to afford D-9-7 (19 g, 52% yield).

A mixture of D-9-7 (38 g, 230 mmol), TEA (46 g, 450 mmol), and Boc$_2$O (49.1 g, 227 mmol) in THF/H$_2$O (1:1) (400 mL) is stirred at room temperature for 3 h. The reaction is diluted with H$_2$O and extracted with DCM. The organic layer is dried over anhydrous sodium sulfate, filtered and concentrated under reduced pressure. The crude product is purified by flash silica gel chromatography to afford D-9-8 (28 g, 46% yield).

A mixture of D-9-8 (14 g, 52 mmol), Tf$_2$O (14.8 g, 52.4 mmol), and TEA (15.8 g, 157 mmol) in DCM (60 mL) is stirred at room temperature for 3 h. The reaction is diluted with H$_2$O and extracted with DCM. The organic layer is dried over anhydrous sodium sulfate, filtered and concentrated under reduced pressure. The crude product is purified by flash silica gel chromatography to afford D-9-9 (10 g, 59% yield).

A mixture of D-9-9 (18 g, 45 mmol), TEA (13.6 g, 135 mmol), Pd(OAc)$_2$ (3.6 g), and DPPP (3.6 g) in MeOH (150 mL) is stirred under a 3 MPa atmosphere of CO at 90° C. for 2 days. The mixture is filtered and the filtrate is concentrated under reduced pressure. The crude product is purified by flash silica gel chromatography to afford D-9-10 (11.8 g, 85% yield).

To a solution of D-9-10 (11.8 g, 38.2 mmol) in THF (100 mL), cooled to −50 C, is added LAH (2.17 g, 57.3 mmol). Then the reaction mixture is stirred at 0° C. for 3 h. Excess reactants are consumed by the addition of a saturated aqueous solution of NH$_4$Cl. The mixture is extracted with DCM and the organic layer is dried over anhydrous sodium sulfate, filtered and concentrated under reduced pressure. The crude product is purified by flash silica gel chromatography to afford D-9-11 (9.8 g, 92% yield).

To a solution of alcohol, D-9-11, (4.00 g, mmol) and pyridine (2.25 mL, 21.3 mmol) in dichloromethane (66 mL), at 0 C, is added triphenylphosphine dibromide (9.00 g, 21.3 mmol). The reaction is stirred for 3 h then concentrated under reduced pressure. The resulting residue is purified by silica gel chromatography to yield D-9 (2.49 g, 49% yield).

Example 24

Preparation of intermediate 6-Bromomethyl-5-fluoro-8-methyl-3,4-dihydro-1H-isoquinoline-2-carboxylic acid tert-butyl ester (D-10)

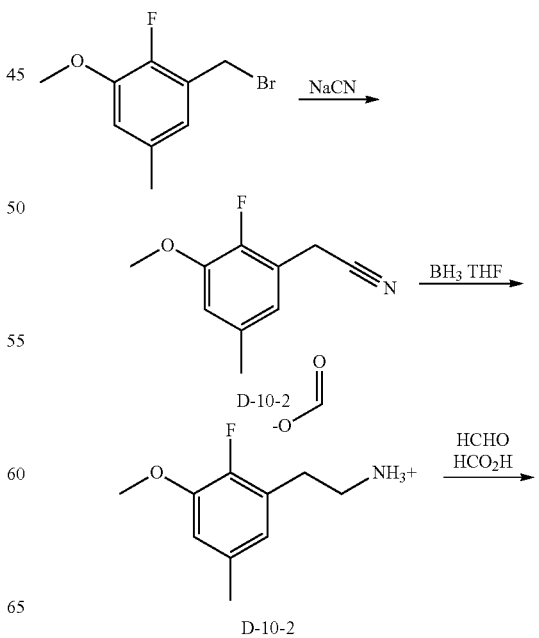

D-10-2

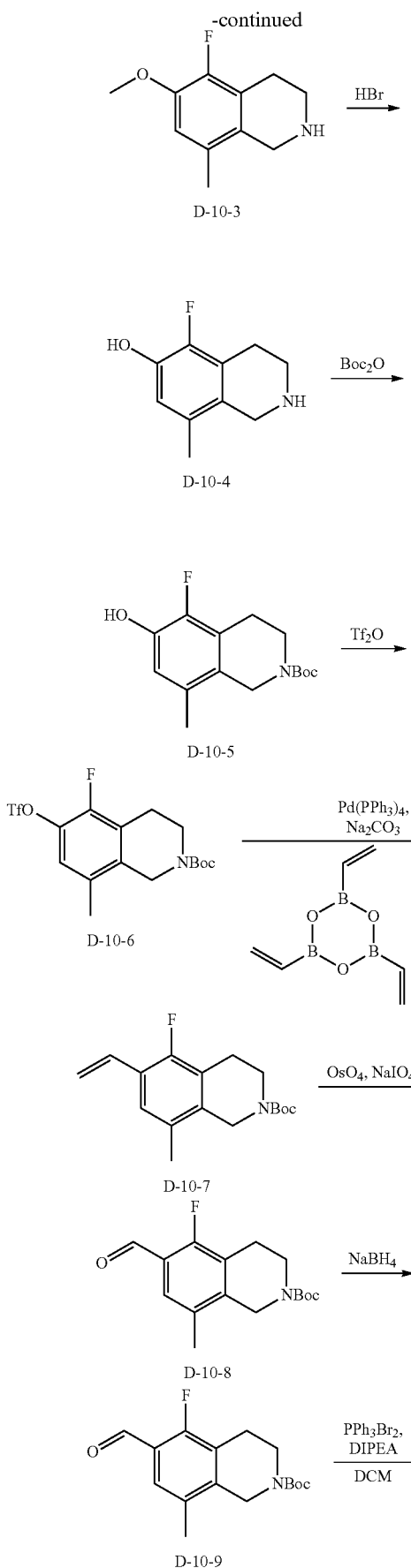

1-Bromomethyl-2-fluoro-3-methoxy-5-methyl-benzene (1.3 g, 5.4 mmol) and NaCN (0.29 g, 5.9 mmol) are combined in DMF (15 mL) then stirred at 45° C. for 2 h. The mixture is diluted with EtOAc/water (100 mL/200 mL) and the layers are separated. The organic phase is dried over anhydrous sodium sulfate, then filtered and concentrated under reduced pressure. The crude material is purified by flash silica gel chromatography to afford D-10-1 (0.926 g, 96% yield).

To a solution of D-10-1 (0.92 g, 5.2 mmol) in THF is added, drop wise via syringe, a solution of borane-THF complex (1.0 M, 11 mL, 11 mmol). Upon complete addition, the mixture is heated to 55° C. and stirred overnight. The resulting mixture is cooled to ambient temperature and excess reactants are consumed by the addition of water (3 mL). After 5 min, conc. HCl (3 mL) is added. After stirring for 1 h, water (10 mL) and solid NaOH are added until the mixture becomes alkaline. DCM (50 mL) is then added and the layers are separated with a hydrophobic frit. The organic phase is additionally dried over anhydrous sodium sulfate, filtered, and concentrated under reduced pressure. The crude residue is purified by flash reverse phase chromatography using a MeCN/water mixture with +0.1% formic acid. The eluent is removed under reduced pressure and the isolated product azeotroped with MTBE to afford D-10-2 (0.777 g, 66%) as the formate salt.

A mixture of D-10-2 (0.775 g, 3.49 mmol) and $CH_2O$ (37% in $H_2O$, 0.26 mL, 3.5 mmol) in HCOOH (10 mL) is stirred at 60° C. for 16 hours. The solvent is removed under reduced pressure and the crude solid is azeotroped with toluene to afford the crude D-10-3 which is not purified but used immediately in the next reaction.

The crude D-10-3 is suspended a 48% aqueous solution of HBr (15 mL) and then heated to 95° C. and stirred overnight. The mixture is cooled to ambient temperature, concentrated under reduced pressure, and then azeotroped with toluene to afford the crude D-10-4 which is not purified further but used immediately in the next reaction.

The crude D-10-4 is slurried at room temperature in a 4:1 mixture of DCM/DMF (25 mL) containing 4-DMAP (0.040 g, 0.3 mmol) and $Et_3N$ (2.1 mL, 15 mmol). To this mixture is added $Boc_2O$ (0.665 g, 3.04 mmol) in one portion. The mixture is stirred overnight then a saturated solution of $NH_4Cl$ (50 mL) is added and the layers are separated with a hydrophobic frit. The organic phase is concentrated under reduced pressure and the crude product is purified by flash silica gel chromatography to afford D-10-5. An additional amount of N,O-Diboc protected product is also isolated. This material is treated with LiOH (100 mg) in a mixture of THF/MeOH/H2O (2:1:1, 10 mL). The hydrolysis reaction is concentrated and purified by flash silica gel chromatography to afford additional D-10-5. The combined product fractions are combined to afford D-10-5 (0.290 g, 30%).

A mixture of D-10-5 (0.290 g, 1.03 mmol), 4-DMAP (13 mg, 0.11 mmol) and $Et_3N$ in DCM (8 ml) is cooled to 0 C, and then treated with $Tf_2O$ (0.21 mL, 1.2 mmol). The mixture is allowed to warm to ambient temperature and stirred overnight. The mixture is diluted with a saturated aqueous solution of NaHCO₃ (10 mL). The layers are separated using a hydrophobic frit, and the organic phase is concentrated under reduced pressure. The crude residue is purified by flash silica gel chromatography to afford D-10-6 (0.35 g, 81%).

A mixture of the D-10-6 (0.29 g, 0.70 mmol), vinylboronic acid-pyridine complex (0.18 g, 0.75 mmol) and a 2.0 M solution of Na₂CO₃ (0.70 mL, 1.4 mmol) in 1,2-DME (4 mL) is charged with Pd[P(Ph₃)₄] and then irradiated in a microwave reactor at 120° C. for 40 min. The mixture is diluted with water (5 mL) and DCM (15 mL). After vigorous mixing, the layers are separated using a hydrophobic frit. The organic layer is concentrated under reduced pressure and the crude product purified by flash silica gel chromatography to afford D-10-7 which is used immediately in the next reaction.

A mixture of D-10-7 and NaIO₄ (0.55 g, 2.6 mmol) in a 4:1 mixture of THF:H₂O (20 mL) is treated with a 4 wt. % aqueous solution of OsO₄ (0.34 mL, 0.04 mmol). The resulting slurry is stirred overnight at ambient temperature in the absence of light. The slurry is filtered and the filtrate concentrated under reduced pressure to remove volatile organics. The remaining aqueous phase is diluted with DCM (20 mL) and then partitioned using a hydrophobic frit. The mixture is concentrated under reduced pressure to afford the crude D-10-8 which is not purified but used immediately in the next reaction.

The crude D-10-8 is dissolved in 1:1 mixture of THF:MeOH (20 mL) and treated with solid NaBH₄ (50 mg, 1.3 mmol). The mixture is stirred at ambient temperature for 30 min then concentrated under reduced pressure. The residue is diluted with DCM (20 mL) and a saturated aqueous solution of NH₄Cl (40 mL). The solution is stirred vigorously for 15 min and then the phases are separated using a hydrophobic frit. The organic phase is concentrated under reduced pressure and the residue purified by flash silica gel chromatography to afford D-10-9 (0.174 g, 69% over 3 steps).

A mixture D-10-9 (0.174 g, 0.589 mmol) and N,N-diisopropylethylamine (0.18 mL, 1.0 mmol) in DCM (15 mL), cooled to 0 C, is treated with dibromotriphenolphosphorane (0.39 g, 0.89 mmol) in one portion. The mixture is stirred at ambient temperature for 1 hour then concentrated under reduced pressure. The crude residue is purified by flash silica gel chromatography to afford D-10 (0.210 g, 100%).

Example 25

Preparation of intermediate 7-Bromomethyl-6-methyl-1,2,4,5-tetrahydro-benzo[d]azepine-3-carboxylic acid tert-butyl ester (D-11)

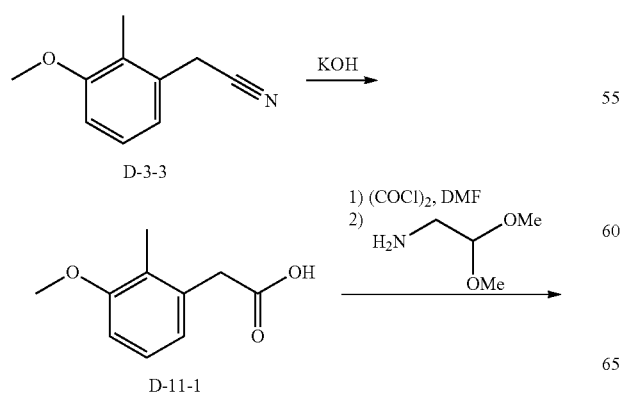

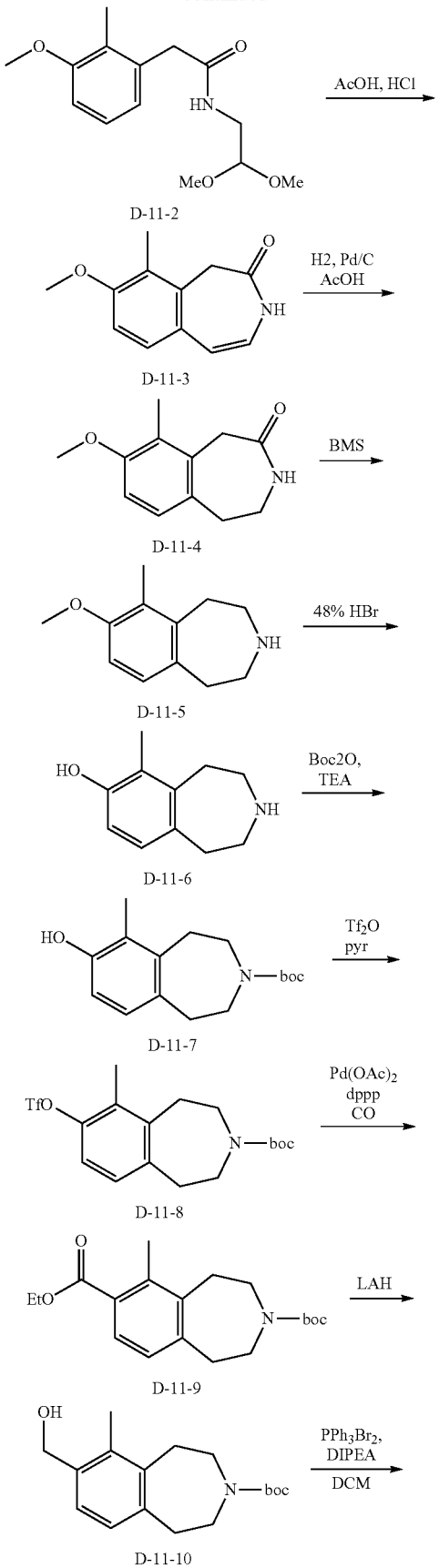

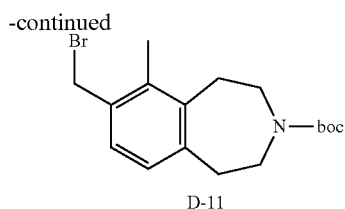

D-11

A mixture of D-3-3 (1608 g, 9.975 mol) and KOH (1117 g, 19.95 mol) in EtOH_ (15 L) is heated to reflux for 5 h. The solvent is removed under reduced pressure. The pH of the residue is adjusted to pH 1. The mixture is filtered and the filter cake is dried to yield D-11-1 (1474 g, 86% yield).

To a stirred solution of $(COCl)_2$ (8.18 mol) and DMF (70.000 ml) in DCM (7.5 L) is added D-11-1 (737 g, 4.09 mol). The mixture is stirred at room temperature for 2 h then concentrated under reduced pressure. The residue is added to a stirred solution of 2,2-dimethoxyethyl-1-amine (430 g, 4.09 mol) and TEA (454 g, 4.50 mol) in DCM (1000 ml). The mixture is stirred at room temperature for 2 h then concentrated under reduced pressure. The residue is purified by flash silica gel column chromatography to afford D-11-2 (1474 g, 96% yield).

A solution of D-11-2 (1053 g, 3.939 mol) in a mixture of AcOH (2 L) and concentrated hydrochloric acid (2 L) is stirred at room temperature for 16 h. The mixture is concentrated under reduced pressure. The residue is crystallized, washed with water and EtOH, collected by filtration, and dried to afford D-11-3 (358 g, 45% yield).

A mixture of Pd/C (4 g) and D-11-3 (40.0 g, 0.197 mol) in AcOH (2 L) is stirred at room temperature under an atmosphere of $H_2$ for 16 h. The mixture is filtered through diatomaceous earth and concentrated under reduced pressure. The residue is recrystallized from EtOH and the formed solid is collected by filtration and dried to give afford D-11-4 (37 g, 92% yield).

To a stirred solution of D-11-4 (130 g, 0.633 mol) in THF (1300 ml) is added BMS_(127 ml, 1.27 mol), slowly under $N_2$ atmosphere, while the temperature is maintained below $-5°$ C. The reaction mixture is stirred for 16 h. Excess reactants are consumed by the additional of concentrated hydrochloric acid and the mixture is refluxed for 2 h. The solvent is removed under reduced pressure and the residue is diluted with water and washed with DCM. The aqueous phase is adjusted to pH=9 and the formed solid is collected by filtration and dried to afford D-11-5 (37 g, 92% yield).

A solution of D-11-5 (220 g, 1.15 mol) in a 48% aqueous solution of HBr (1800 ml) is stirred at 110° C. for 4 h under a $N_2$ atmosphere. The mixture is concentrated under reduced pressure to afford the crude D-11-6 which is used without further purification.

A mixture of D-11-6 (267 g, 1.51 mol), $Boc_2O$ (492 g, 2.26 mol) and TEA (380 g, 3.77 mol) in dichloromethane (2670 ml) is stirred at room temperature for 2 h. The reaction mixture is concentrated under reduce pressure and the residue purified by flash silica gel column chromatography to afford D-11-7 (230 g, 64% from D-11-5 yield).

A mixture of compound D-11-7 (267 g, 0.963 mol) and $Tf_2O$ (271 g, 0.963 mol) in DCM (2670 ml) is stirred at room temperature for 2 h under an atmosphere of $N_2$. The reaction mixture is concentrated under reduce pressure and the residue is purified by flash silica gel column chromatography to afford D-11-8 (220 g, 56% yield).

A mixture of D-11-8 (20 g, 0.049 mol), dppp (2.0 g), $Pd(OAc)_2$ (2.0 g), and TEA (9.9 g, 0.098 mol) in EtOH (400.000 ml) is stirred at 80° C. for 12 h under an atmosphere of CO. The reaction mixture is concentrated under reduce pressure and the residue is purified by flash silica gel column chromatography to afford D-11-9 (8 g, 50% yield).

To a stirred solution of D-11-9 (22 g, 0.066 mol) in THF (300 ml), cooled to −40 C, is slowly added LAH (2.5 g, 0.066 mol). After addition is completed the mixture is stirred at room temperature for 2 h. Excess reactants are consumed by the addition of water. The mixture is concentrated under reduced pressure and the residue is taken back up in water and extracted with DCM. The organic phase is dried over anhydrous sodium sulfate and concentrated under reduced pressure. The residue is purified by flash silica gel column chromatography to afford D-11-10 (14 g, 71% yield).

To a solution of alcohol, D-11-10, (19.0 g, 65.2 mmol) and N,N-diisopropylethylamine (13.0 mL, 74.6 mmol) in dichloromethane (340 mL). at 0 C, is added triphenylphosphine dibromide (30.0 g, 68.2 mmol). The reaction is stirred for 1 h then concentrated under reduced pressure. The resulting residue is purified by silica gel chromatography to yield D-11 (22.4 g, 97% yield).

Example 26

Preparation of intermediate 3-Hydroxymethyl-5,8-dihydro-6H-[1,7]naphthyridine-7-carboxylic acid tert-butyl ester (D-12)

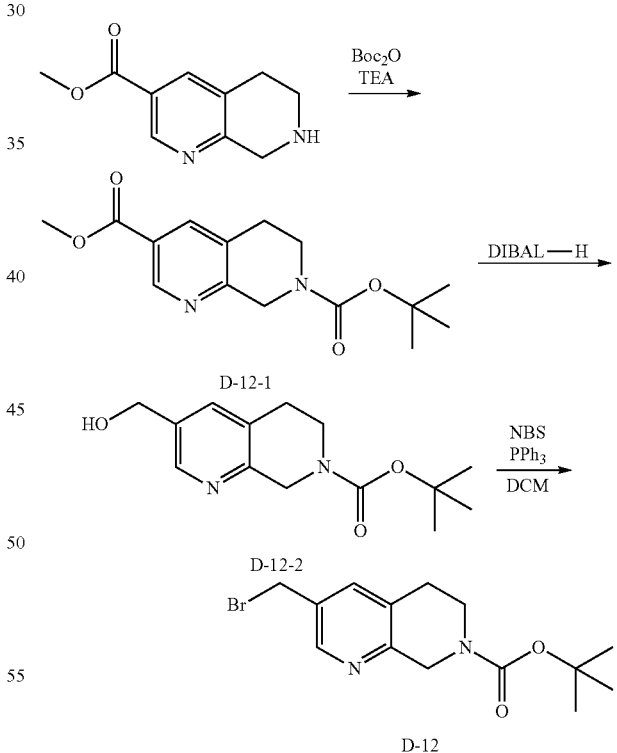

To a solution of 5,6,7,8-tetrahydro-[1,7]naphthyridine-3-carboxylic acid methyl ester (232.8 mg, 1.018 mmol) and Boc anhydride (379.4 mg, 1.738 mmol) at 0° C. in THF (3.4 mL) is added TEA (0.500 mL). DCM (1.0 mL) is added and the reaction mixture is stirred at room temperature overnight. The reaction mixture is diluted with water and the aqueous phase is extracted with EtOAc. The combined organic extracts are washed with brine, dried over anhydrous sodium sulfate, and concentrated under reduced pressure. The crude material is purified by flash silica gel column chromatography to afford D-12-1 (0.169 g, 57% yield).

To a 0° C. solution of the starting ester (0.169 g, 0.576 mmol) in THF (5 mL) is added 1.0 M DiBAl-H in toluene (3.4 mL, 3.4 mmol) over the span of 15 min. The ice bath is removed approximately 2 h later. The reaction mixture is allowed to gradually warm to room temperature and is maintained at room temperature for the next 2 h. Finally, the reaction mixture is cooled to 0° C. and Rochelle's salt (6 mL) is introduced. The resultant heterogeneous mixture is allowed to warm to room temperature and stir at this temperature (for the duration of the weekend). Then, the mixture is diluted with water and EtOAc. The aqueous phase is extracted with EtOAc (×3). The combined organic extracts are washed with brine, dried (Na$_2$SO$_4$), filtered and concentrated under reduced pressure to give D-12-2 which is not purified but used directly in the next reaction.

To a 0° C. solution of D-12-2 (0.261 mg, 0.987 mmol) in DCM is added NBS (0.211 g, 1.19 mmol), followed by PPh$_3$ (0.311 g, 1.19 mmol). The reaction mixture is allowed to stir at 0° C. for 1 h then is concentrated under reduced pressure without warming. The crude material is purified by flash silica gel chromatography to afford D-12 (0.22 g, 68% yield) as a white solid.

Example 27

Preparation of intermediate Methanesulfonic acid 1-oxo-2-(tetrahydro-pyran-4-yl)-1,2,3,4-tetrahydro-isoquinolin-6-ylmethyl ester (D-13)

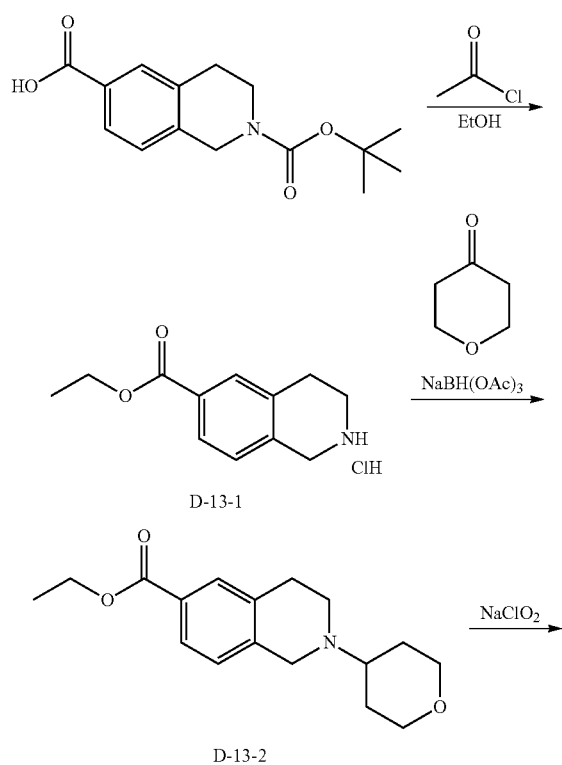

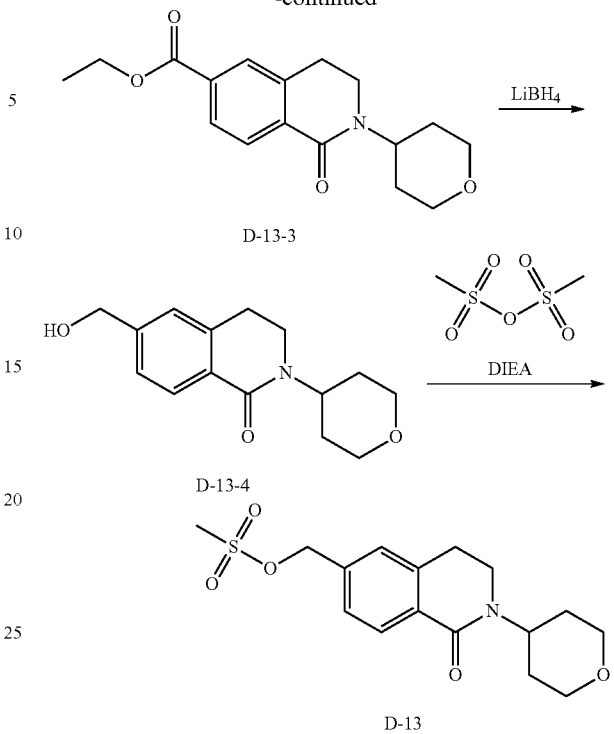

To a flask charged with ethanol (180 mL), cooled to 0 C, is added 4.0 mL (56 mmol) of acetyl chloride. The mixture is stirred at 0° C. for 30 min then 5.00 g (18.0 mmol) of 3,4-dihydro-1H-isoquinoline-2,6-dicarboxylic acid 2-tert-butyl ester is added. The mixture is heated to 70° C. and stirred for 2 days. The mixture is cooled to room temperature and filtered through diatomaceous earth. The filtrate is concentrated under reduced pressure to provide D-13-1 (3.47 g, 79.6%) as a white powder.

To a solution of 3.45 g (14.3 mmol) of D-13-1 in DCM (150 mL) is added 2.0 g (20 mmol) of tetrahydro-pyran-4-one. The mixture is stirred at room temperature for 30 min then 12 g (56 mmol) of sodium triacetoxyborohydride is added. The mixture is stirred at room temperature for 4 days then diluted with a saturated aqueous solution of sodium bicarbonate. The mixture is separated and the aqueous phase extracted with DCM. The combined organic phase is dried over anhydrous sodium sulfate and concentrated under reduced pressure. The residue is purified by flash silica gel chromatography to afford D-13-2 (2.51 g, 45%).

To a solution of 2.51 g (8.67 mmol) of D-13-2 in a 4:1 mixture of 1,1,2,2,-tetrachloroethane:water is added 2.4 g (26 mmol) of sodium chlorite. The mixture is heated overnight at 55° C. then cooled to room temperature. Excess reactants are consumed by the addition of a 10% solution of sodium bisulfite. The mixture is diluted with water and extracted with DCM. The combined organic phase is washed with a 2N solution of HCl, dried over anhydrous sodium sulfate, and concentrated under reduced pressure. The residue is purified by flash silica gel chromatography to afford D-13-3 (0.64 g, 24%).

To a solution of 0.640 g (2.11 mmol) of D-13-3 in THF (20 mL) is added 2.5 mL (5.0 mmol) of lithium borohydride as a 2M solution in THF. The mixture is stirred overnight at room temperature then excess reagents are consumed by the slow addition of water. The mixture is diluted with water and extracted with EtOAc. The combined organic phase are washed with brine, dried over anhydrous sodium sulfate, and concentrated under reduced pressure. The residue is purified by flash silica gel chromatography to afford D-13-4 (0.090 g, 16%)

To a solution of 0.090 g (0.34 mmol) of D-13-4 in DCM (5 mL) is added 0.070 g (0.40 mmol) of methanesulfonic anhydride followed by 0.075 mL (0.43 mmol) of DIEA. The mixture is stirred overnight at room temperature then washed with water, dried over anhydrous sodium sulfate and concentrated under reduced pressure to provide D-13 0.16 g (100%) as a clear oil that is used directly without further purification.

Example 28

Preparation of intermediates 5-Bromomethyl-4-methyl-1,3-dihydro-isoindole-2-carboxylic acid tert-butyl ester (D-14) and 6-Bromomethyl-4-methyl-1,3-dihydro-isoindole-2-carboxylic acid tert-butyl ester (D-15)

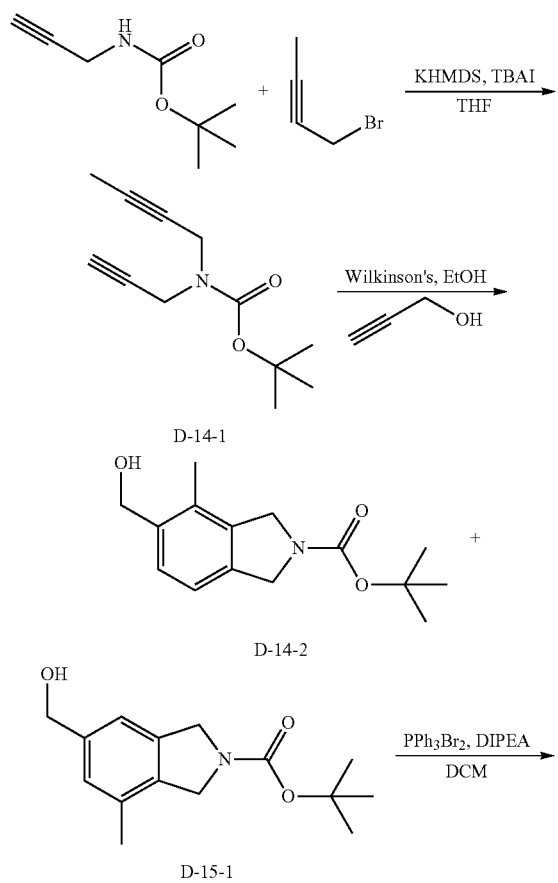

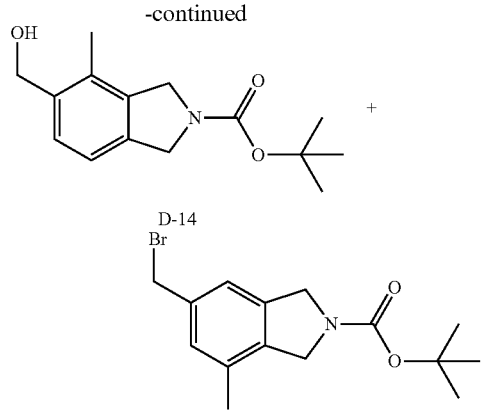

To a stirred solution of Boc-propargyl amine (2.00 g, 12.9 mmol) in THF (30.0 mL) and tetrabutylammonium iodide (0.476 g, 1.29 mmol) is added a 0.5 M KHMDS solution (25.8 mL, 12.9 mmol) in THF and the mixture is stirred for 30 min at room temperature. The bromide (1.69 mL, 19.3 mmol) is added dropwise and the mixture is stirred for 30 min at room temperature and then is refluxed for 2 h. The reaction is diluted with saturated NH$_4$Cl and extracted with EtOAc. The combined organics are dried with MgSO$_4$ and concentrated under reduced pressure. The crude material is purified by flash silica gel chromatography to afford D-14-1 (2.13 g) as a colorless oil.

Propargyl alcohol (2.39 mL, 41.1 mmol) is added dropwise at 0° C. to a solution of D-14-1 (2.13 g, 10.28 mmol) in anhydrous ethanol (50.0 mL). Wilkinson's catalyst (0.95 g, 1.0 mmol) is added and the mixture is stirred overnight at room temperature. The crude reaction mixture is concentrated under reduced pressure and the residue is purified by flash silica gel chromatography to afford a mixture of D-14-2 and D-15-1 (1.93 g). The mixture is not separated but carried on to the next step.

To a solution of the mixture containing D-14-2 and D-15-1 (1.93 g, 7.33 mmol) and N,N-diisopropylethylamine (1.91 mL, 11.0 mmol) in dichloromethane (50.0 mL), at 0° C., is added triphenylphosphine dibromide (4.73 g, 11.0 mmol). The reaction is stirred for 2 h then concentrated under reduced pressure. The residue is purified by flash silica gel chromatography to yield the mixture of regioisomers D-14 and D-15 (2.12 g) as a white solid.

Example 29

Preparation of intermediates (R)-8-Bromomethyl-1-methyl-1,2,4,5-tetrahydro-benzo[d]azepine-3-carboxylic acid tert-butyl ester (D-17) and (S)-8-Bromomethyl-1-methyl-1,2,4,5-tetrahydro-benzo[d]azepine-3-carboxylic acid tert-butyl ester (D-18)

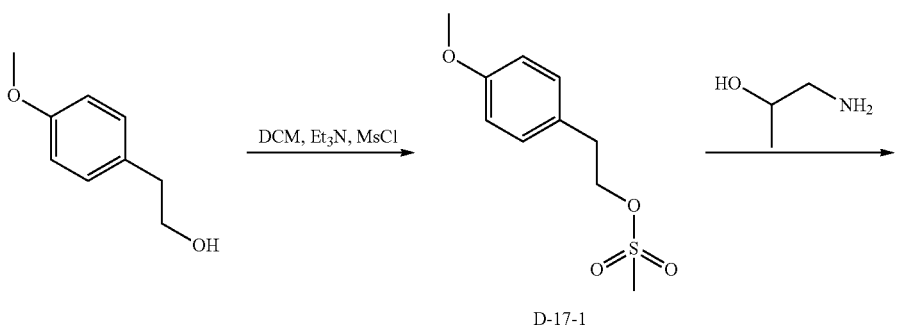

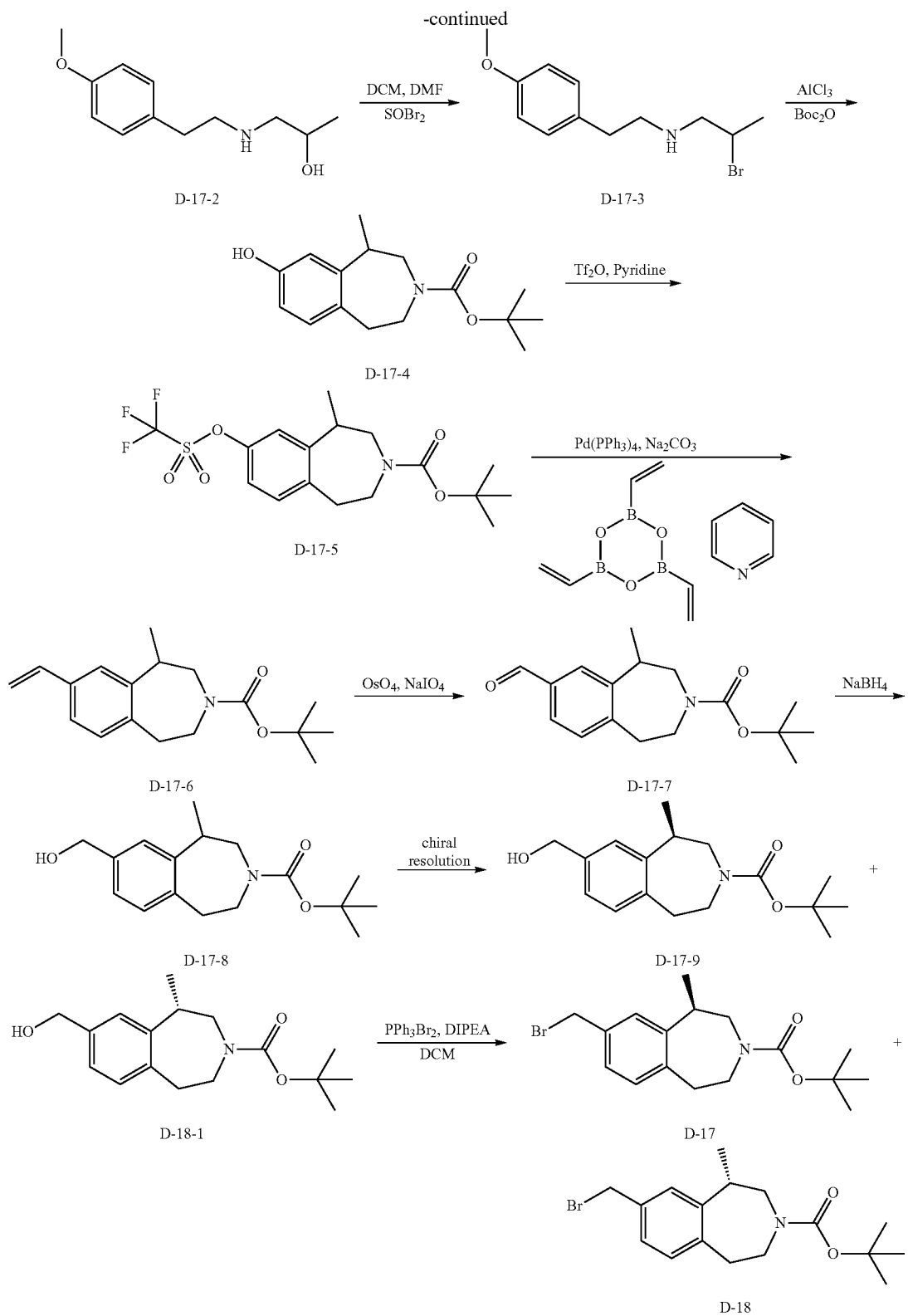

To a solution of 4-methoxyphenethyl alcohol (2.50 g, 16.4 mmol) in DCM (20.0 mL) is added Et3N (2.75 mL, 19.7 mmol) followed by methanesulfonyl chloride (1.53 mL, 19.7 mmol). The mixture is stirred at room temperature overnight then extracted with DCM, washed with brine, dried over MgSO4, and concentrated under reduced pressure to provide 17-1 (3.75). The material is carried without further purification.

The crude 17-1 (3.75 g, 16.3 mmol) is treated with neat 1-amino-2-propanol (20 mL) and heated to reflux for 3 h. The mixture is diluted with water (50 mL) and extracted with EtOAc. The combined organics are washed with brine, dried with Na$_2$SO$_4$, filtered and concentrated under reduced pressure. The crude amine is dissolved in DCM (20 ml) and 2.0 M HCl in ether (5 ml, 10 mmol) is added to form a white precipitate. The formed solid is which is collected by filtration and dried on the filter pad to provide 17-2 (2.63 g) which was used without further purification.

To a solution of 17-2, (2.63 g, 12.5 mmol) in DCM (60 mL), at 0° C., is added dimethyl formamide (0.49 mL, 6.3 mmol) followed by thionyl bromide (1.26 mL, 16.3 mmol). The mixture is stirred for 14 h while warming to 20° C. Cold diethyl ether (30 mL, 0° C.) is added and the reaction cooled to 0° C. causing a solid to precipitate from solution. The formed solid is collected by filtration and dried on the filter pad to yield 17-3 as an off-white solid (3.31 g).

To a flask containing 17-3 (1.00 g, 3.67 mmol) is added aluminum chloride (0.882 g, 4.40 mmol). The mixture is heated to 150° C. for 20 h. While the reaction is still warm, water (20 mL) is added, after 5 min EtOAc:DCM is added and the reaction is allowed to cool to 20° C. with stirring. To this is added saturated NaHCO$_3$ (25 mL) to give an emulsion. The layers are separated. To the aqueous layer is added tetrahydrofuran (50 mL) and ditertbuyldicarbonate and the mixture is stirred overnight. The reaction is partitioned between EtOAc and saturated citric acid. The layers are separated and the organics are washed with brine, dried over MgSO$_4$, filtered, and concentrated under reduced pressure to furnish 17-4 as a white solid (0.625 g).

To a solution of 17-4 (0.625 g, 2.25 mmol) in DCM (20.0 mL) at room temperature is added pyridine (0.36 mL, 4.5 mmol). The solution is cooled to −30° C. and trifluoromethanesulfonic anhydride (0.42 mL, 2.5 mmol) is added dropwise. The reaction is stirred at −30° C. for 1 hour then allowed to warm to room temperature. It is concentrated under reduced pressure. The residue is diluted with EtOAc and washed with 1 N HCl followed by saturated NaHCO$_3$, and brine. The mixture is dried over MgSO$_4$ and concentrated under reduced pressure. The resulting material is purified by flash silica gel chromatography to afford 17-5 (0.850 g).

The triflate (0.850 g, 2.08 mmol) is combined with the boronate (0.600 g, 2.49 mmol) and Pd(PPh$_3$)$_4$ (0.12 g, 0.11 mmol) in a mixture of DME (15.0 mL) and 2.0 M Na$_2$CO$_3$ (1.09 mL). The reaction is heated in a microwave reactor at 120° C. for 40 minutes. The reaction is concentrated and purified by flash silica gel chromatography to afford 17-6 as an oil (0.519 g).

To a solution of 17-6 (0.519 g, 1.81 mmol) in a mixture of THF (7.0 mL) and H$_2$O (1.50 mL) is added NaIO$_4$ (1.18 g, 5.52 mmol). The mixture is stirred at room temperature overnight in the dark then diluted with a mixture of water and DCM. The layers are separated with a hydrophobic frit and the organic is dried over MgSO$_4$ then filtered and concentrated under reduced pressure. The residue is purified by flash silica gel chromatography to afford 17-7 as a dark oil (0.390 g).

To a solution of 17-7 (0.390 g, 1.35 mmol) in a mixture of THF (5 mL) and MeOH (5 mL), cooled to 0° C., is added NaBH$_4$ (0.077 g, 2.0 mmol). The reaction is warmed to room temperature and stirred for 30 min. The reaction is diluted with a aq. NH$_4$Cl solution and stirred for 10 minutes. The mixture is extracted with EtOAc and the combined organic phase is washed with NH$_4$Cl followed by brine then dried over MgSO4 and concentrated under reduced pressure. The resulting material is purified by flash silica gel chromatography to afford 17-8 (0.326 g).

The racemic 17-8 is resolved on a ChiralCel 10 u (300×50 mm) using 20% IPA in super critical CO$_2$ at 200 mL/min under 100 bar at 38° C. to afford 17-9 (first eluting peak) and 18-1 (second eluting peak). The absolute stereochemistry is not established and the structures are drawn arbitrarily.

To a solution of 17-9 (1.58 g, 5.44 mmol) in DCM (30 mL), cooled to 0° C., is added N,N-diisopropylethylamine (1.42 mL, 8.16 mmol) followed by triphenylphosphine dibromide (3.514 g, 8.159 mmol). The reaction is stirred for 2 h and concentrated under reduced pressure. The resulting residue is purified by flash silica gel chromatography to afford the title compound D-17 (1.79 g).

To a solution of 18-1 (1.64 g, 5.64 mmol) in DCM (30 mL), cooled to 0° C., is added N,N-diisopropylethylamine (1.47 mL, 8.45 mmol) followed by triphenylphosphine dibromide (3.64 g, 8.45 mmol) at 0° C. The reaction is stirred for 2 h and concentrated under reduced pressure. The resulting residue is purified by flash silica gel chromatography to afford the title compound D-18 (1.86 g).

The following intermediate is synthesized in similar fashion from the appropriate reagents:

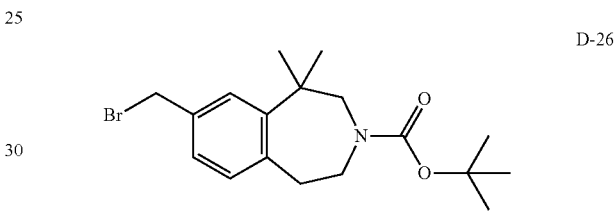

D-26

Example 30

Preparation of intermediate 7-Bromomethyl-6-fluoro-1,2,4,5-tetrahydro-benzo[d]azepine-3-carboxylic acid tert-butyl ester (D-20)

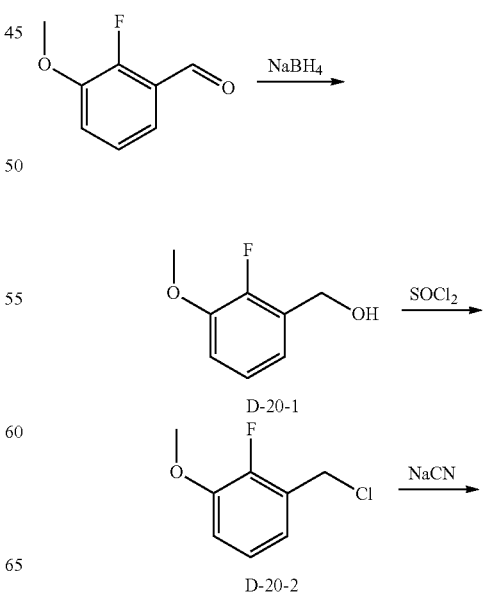

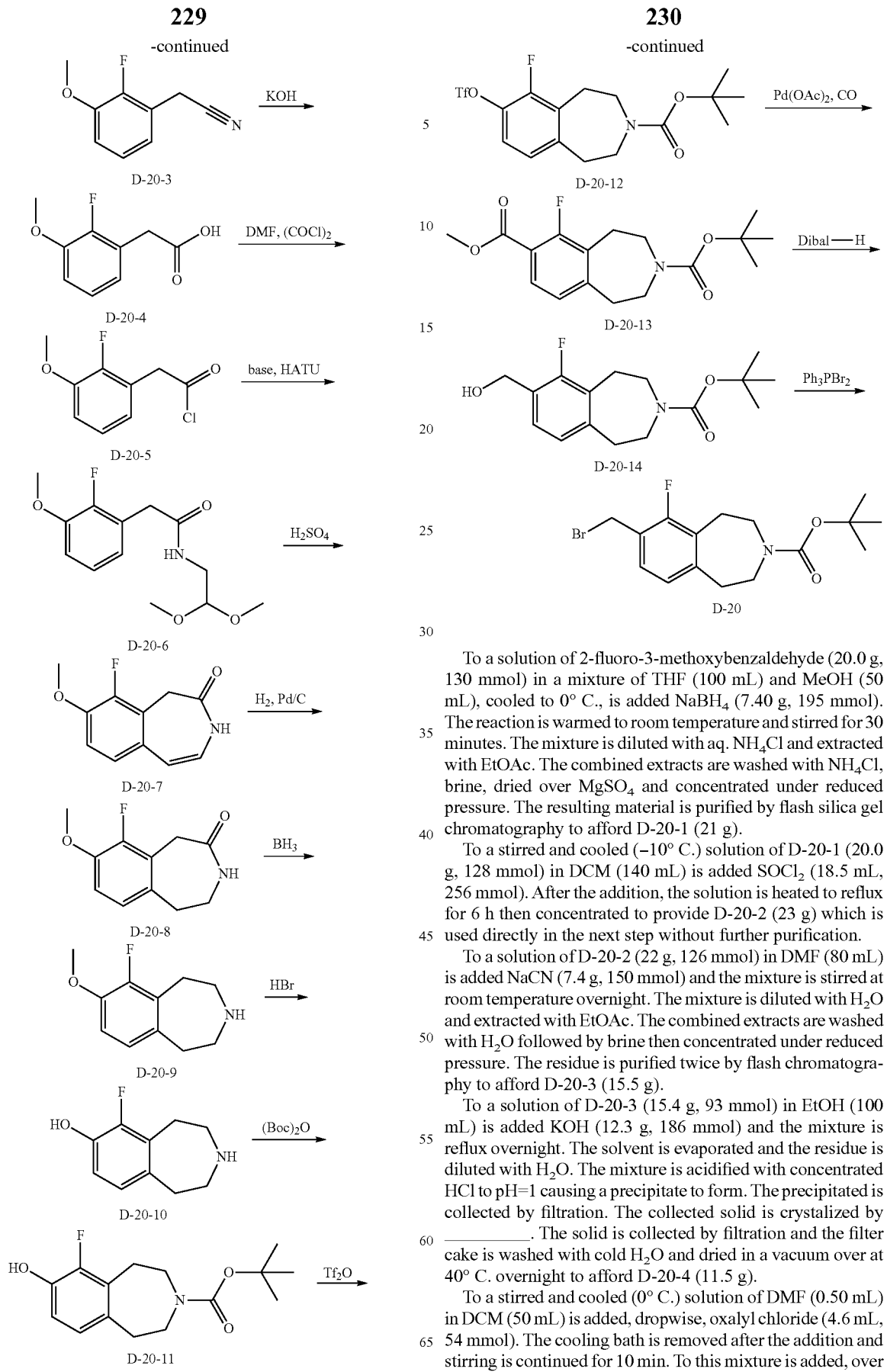

To a solution of 2-fluoro-3-methoxybenzaldehyde (20.0 g, 130 mmol) in a mixture of THF (100 mL) and MeOH (50 mL), cooled to 0° C., is added NaBH$_4$ (7.40 g, 195 mmol). The reaction is warmed to room temperature and stirred for 30 minutes. The mixture is diluted with aq. NH$_4$Cl and extracted with EtOAc. The combined extracts are washed with NH$_4$Cl, brine, dried over MgSO$_4$ and concentrated under reduced pressure. The resulting material is purified by flash silica gel chromatography to afford D-20-1 (21 g).

To a stirred and cooled (−10° C.) solution of D-20-1 (20.0 g, 128 mmol) in DCM (140 mL) is added SOCl$_2$ (18.5 mL, 256 mmol). After the addition, the solution is heated to reflux for 6 h then concentrated to provide D-20-2 (23 g) which is used directly in the next step without further purification.

To a solution of D-20-2 (22 g, 126 mmol) in DMF (80 mL) is added NaCN (7.4 g, 150 mmol) and the mixture is stirred at room temperature overnight. The mixture is diluted with H$_2$O and extracted with EtOAc. The combined extracts are washed with H$_2$O followed by brine then concentrated under reduced pressure. The residue is purified twice by flash chromatography to afford D-20-3 (15.5 g).

To a solution of D-20-3 (15.4 g, 93 mmol) in EtOH (100 mL) is added KOH (12.3 g, 186 mmol) and the mixture is reflux overnight. The solvent is evaporated and the residue is diluted with H$_2$O. The mixture is acidified with concentrated HCl to pH=1 causing a precipitate to form. The precipitated is collected by filtration. The collected solid is crystalized by _____. The solid is collected by filtration and the filter cake is washed with cold H$_2$O and dried in a vacuum over at 40° C. overnight to afford D-20-4 (11.5 g).

To a stirred and cooled (0° C.) solution of DMF (0.50 mL) in DCM (50 mL) is added, dropwise, oxalyl chloride (4.6 mL, 54 mmol). The cooling bath is removed after the addition and stirring is continued for 10 min. To this mixture is added, over multiple portions, D-20-4 (5.0 g, 27 mmol). Stirring is continued for a further 2.5 h then the solvent is evaporated to afford D-20-5 (5.7 g) which is used directly in the next step.

To a stirred solution of D-20-5 (2.50 g, 13.6 mmol) in DMF (50 mL) are added successively DIEA (5.9 mL, 34 mmol), HATU (6.4 g, 16 mmol) and amine (1.7 mL, 16 mmol). The mixture is stirred at room temperature overnight. The solvent is removed under reduced pressure and the residue is purified by flash silica gel chromatography to afford D-20-6 (2.1 g).

A mixture of D-20-6 (1.6 g, 5.9 mmol) in concentrated $H_2SO_4$ (6.60 mL, 118 mmol) is stirred at room temperature for 1 h then poured onto ice and neutralized with $Na_2CO_3$. The mixture is extracted with EtOAc and the combined extracts are concentrated under reduced pressure. The residue is purified by flash silica gel chromatography to afford D-20-7 (0.530 g).

A mixture of D-20-7 (2.4 g, 11 mmol) and 10% Pd/C (0.200 g) in acetic acid (10 mL) is stirred overnight under an atmosphere of hydrogen. The mixture is filtered through Celite and the filtrate is concentrated under reduced pressure to afford D-20-8 (2.5 g) which is used directly in the next step without further purification.

To a stirred and cooled (0° C.) solution of D-20-8 (2.4 g, 11 mmol) in THF (40 mL) is added, dropwise, a solution of borane in THF (11 mL, 2.0 M, 22 mmol). After the addition, the solution is stirred for 15 h then the solution is heated to reflux for 2 h. The solution is cooled to room temperature and a 10% HCl (20 mL) solution is added slowly. The mixture is reflux for another 2 h then cooled to room temperature. The solvent is concentrated under reduced pressure and the residue is washed with ether then the PH is adjusted to pH 9 by addition of a 10% solution of NaOH. The mixture is extracted with DCM, the combined extracted are dried ($Na_2SO_4$) and concentrated under reduced pressure to afford D-20-9 (1.7 g) which is used directly in the next step.

A mixture of D-20-9 (1.5 g, 7.7 mmol) in 48% HBr is heated at 100° C. for 3 h. After cooling down to room temperature, the solvent is concentrated under reduced pressure to afford D-20-10 (2.1 g) which is used directly in the next step.

To a stirred and cooled (0° C.) solution of D-20-10 (2.1 g, 12 mmol) in DCM are added successively DIEA (6.4 mL, 35 mmol) and Boc anhydride (3.0 g, 14 mmol). The mixture is stirred for 3 h then the solvent is concentrated under reduced pressure and the residue is purified by flash silica gel chromatography to afford D-20-11 (1.2 g).

To a stirred and cooled (0° C.) solution of D-20-11 (1.0 g, 3.5 mmol) in DCM (10 mL) are added successively TEA (1.2 mL, 8.9 mmol) and $Tf_2O$ (0.7 mL, 4.3 mmol). The mixture is stirred at 0° C. for 2 h then diluted with a saturated $NaHCO_3$ solution and extracted with EtOAc. The combined extracts are washed with saturated $NaHCO_3$ followed by brine then dried ($Na_2SO_4$) and concentrated under reduced pressure to afford D-20-12 which is used directly in the next step.

A mixture of the crude D-20-12, Pd(OAc)2 (0.082 g, 0.37 mmol), dppp (0.15 g, 0.36 mmol) in a mixture of MeOH (6.0 mL) and DMSO (9.0 mL) is flushed with CO for 5 min. To this mixture is added TEA (1.5 mL, 11 mmol). The mixture is heated at 70° C. overnight under an atmosphere of CO atmosphere. The mixture is cooled to room temperature and volatile organics are removed under reduced pressure. The residue is purified by flash silica gel chromatography to afford D-20-13 (0.710 g).

To a stirred and cooled (−78° C.) solution of D-20-13 (0.71 g, 2.2 mmol) in DCM (20 mL) is added a solution of Dibal-H (6.6 mL, 1.0 M, 6.6 mmol). After 20 min of stirring, the cooling bath is removed and the stirring is continued for 3 h.

To this mixture is added MeOH followed by $Na_2SO_4.12H_2O$. The stirring is continued for 2 h then the mixture is filtered through a pad of Celite and the filter pad is rinsed with 10% MeOH/DCM. The filtrate is concentrated under reduced pressure. The residue is purified by flash silica gel chromatography to afford D-20-14 (0.325 g).

A mixture of D-20-14 (0.32 g, 1.1 mmol) and DIEA (0.28 mL, 1.6 mmol) in DCM (10 mL) is cooled to −30° C. To this is added $Ph_3PBr_2$ (0.595 g, 1.30 mmol) in one portion. After stirring for 1 h at this temperature the solution is slowly warmed up to 0 C over 1 h. The reaction is concentrated under reduced pressure and the solid residue is diluted with DCM to give a slurry, which is purified by flash silica gel chromatography to afford the title compound D-20 (0.351 g).

The following intermediate is synthesized in similar fashion from the appropriate reagents:

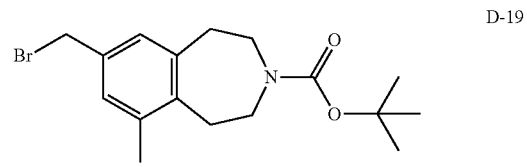 [SMILES: Cc1cc(CBr)cc2c1CCN(C(=O)OC(C)(C)C)CC2]

D-19

Example 31

Preparation of intermediate 6-Bromomethyl-8-methoxymethyl-3,4-dihydro-1H-isoquinoline-2-carboxylic acid tert-butyl ester (D-21)

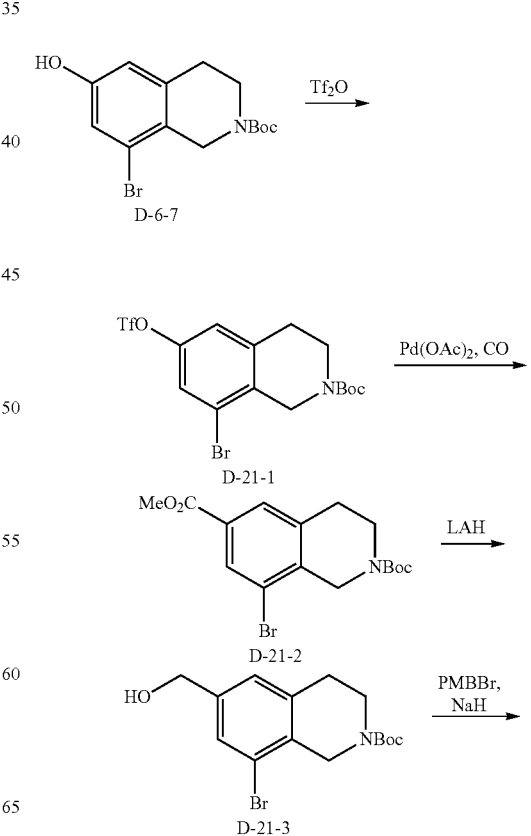

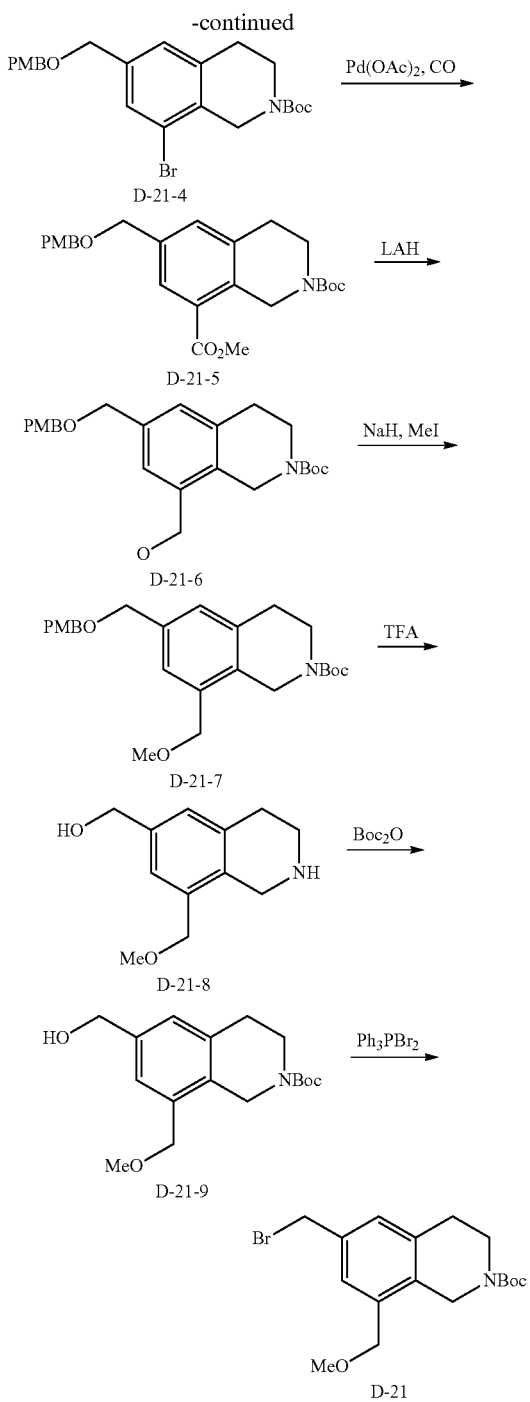

To a mixture of D-6-6 (60.0 g, 183 mmol) and TEA (55 g, 550 mmol) in DCM (600 mL) is added Tf$_2$O (51.6 g, 183 mmol). The mixture is stirred at room temperature for 3 h then diluted with H$_2$O and extracted with DCM. The organic layer is dried of Na$_2$SO$_4$, filtered and concentrated under reduced pressure. The residue is purified by flash silica gel chromatography to afford D-21-1 (60 g).

A mixture of D-21-1 (60 g, 130 mmol), TEA (39.5 g, 391 mmol), Pd(OAc)$_2$ (12 g) and DPPP (12 g) in dry MeOH (600 mL) is stirred under an atmosphere of 50 psi CO at 65° C. for 4 h. The mixture is filtered and the filtrate is concentrated under reduced pressed. The residue is purified by flash silica gel chromatography to afford D-21-2 (40 g).

To a solution of D-21-2 (40.0 g, 108 mmol) in THF (400 mL), cooled to −50° C., is added LAH (6.1 g, 160 mmol). The mixture is stirred at −50° C. for 3 h. Excess reactants are consumed by the addition of saturated aqueous NH$_4$Cl. The mixture is extracted with EtOAc. The organic layer is dried, filtered and concentrated under reduced pressure. The residue is purified by flash silica gel chromatography to afford D-21-3 (25 g).

To a solution of D-21-3 (25 g, 73 mmol) in DCM (250 mL), at 0° C., is added NaH (4.38 g, 110 mmol, 60% dispersion in mineral oil). To this mixture is added PMBBr (16.1 g, 80.4 mmol). The mixture is warmed to room temperature and stirred for 1 h. Excess reactants are consumed by the addition of saturated aqueous solution of NH$_4$Cl. The mixture is extracted with DCM. The organic layer is dried, filtered and concentrated under reduced pressure. The residue is purified by flash silica gel chromatography to afford D-21-4 (27 g).

A mixture of D-21-4 (27 g, 58 mmol), TEA (17.7 g, 175 mmol), Pd(OAc)$_2$ (5.4 g) and DPPP (5.4 g) in dry MeOH (300 mL) is stirred under an atmosphere of 50 psi CO at 65° C. for 3 days. The mixture is filtered and the filtrate is concentrated under reduced pressed. The residue is purified by flash silica gel chromatography to afford D-21-5 (20 g).

To a solution of LAH (2.6 g, 68 mmol) in THF (60 mL), at −50° C., is added dropwise a solution of D-21-5 (20.0 g, 45.3 mmol) in THF (130 mL) over 30 min. After addition, the reaction mixture is stirred at 0° C. for 4.5 h. The reaction mixture was treated with a mixture of saturated aqueous NH$_4$Cl and DCM. The organic layer is separated, washed with brine, dried over Na$_2$SO$_4$, filtered and concentrated under reduced pressure. The residue is purified by flash silica gel chromatography afford D-21-6 (14 g).

To a suspension of NaH (0.43 g, 60% dispersion in mineral oil, 10.6 mmol) in DMF (15 mL) is added D-21-6 (4.0 g, 9.7 mmol), followed by MeI (0.80 mL, 13 mmol). The mixture is stirred at 20° C. for 16 hours. Water is added and the mixture is extracted with EtOAc. The organic layers are washed with brine, dried (Na$_2$SO$_4$) and concentrated under reduced pressure. The residue is purified by flash silica gel chromatography to afford D-21-7 (2.7 g).

A mixture of D-21-7 (3.8 g, 8.9 mmol) and TFA (6.7 mL, 89 mmol) in DCM (20 mL) is stirred at 0° C. for 3 h. The reaction is diluted with aqueous NaHCO$_3$ and extracted with EtOAc. The combined organic phase is dried (Na$_2$SO$_4$) and concentrated under reduced pressure to afford D-21-8 which was used directly in the next step.

To a solution of the crude D-21-8 in DCM (20 mL), at 0° C., is added DIEA (2.5 mL, 14 mmol) followed by Boc$_2$O (1.9 g, 9 mmol). The solution is stirred at 0° C. for 2 h then concentrated under reduced pressure. The residue is purified by flash silica gel chromatography to afford D-21-9 (1.1 g)

To a solution of D-21-9 (1.1 g, 4.0 mmol) in DCM, cooled to −30 C, is added DIEA (0.90 mL, 5.4 mmol) followed by Ph$_3$PBr$_2$ (2.0 g, 4.5 mmol) in one portion. The mixture is stirred at −30 C for 1 h then warmed up over a 1 hour period to 0° C. The mixture is concentrated under reduced pressure and the resulting residue is diluted with DCM to give a slurry which is purified by flash silica gel chromatography to afford the title compound D-21 (1.1 g).

Example 32

Preparation of intermediate 8-Bromomethyl-6-methyl-2,3-dihydro-5H-benzo[f][1,4]oxazepine-4-carboxylic acid tert-butyl ester (D-22)

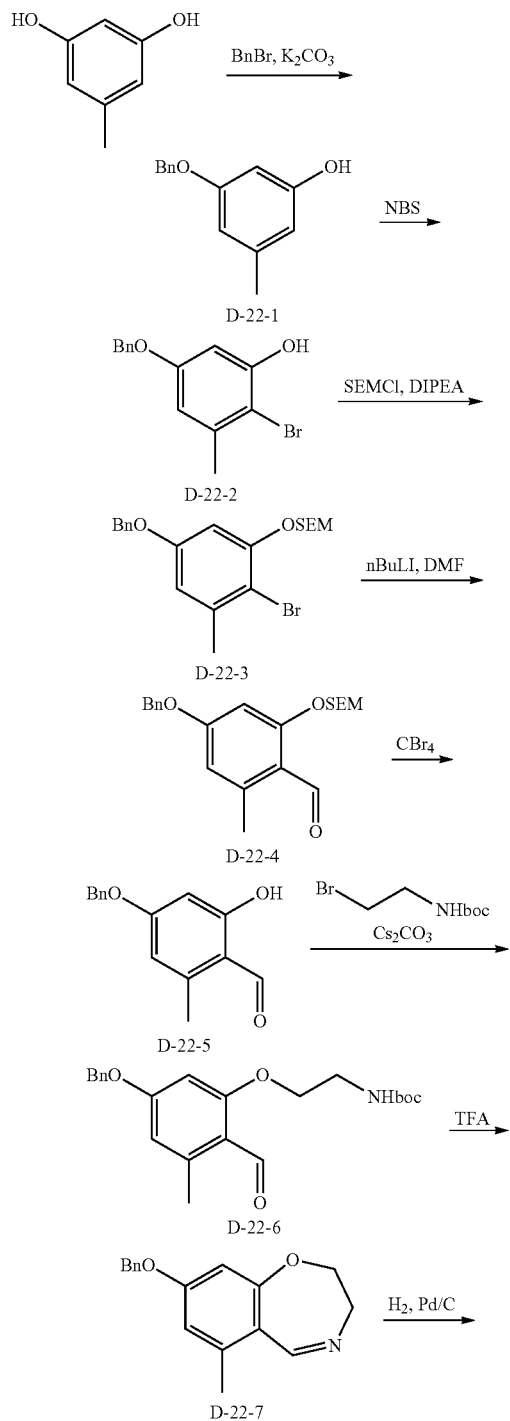

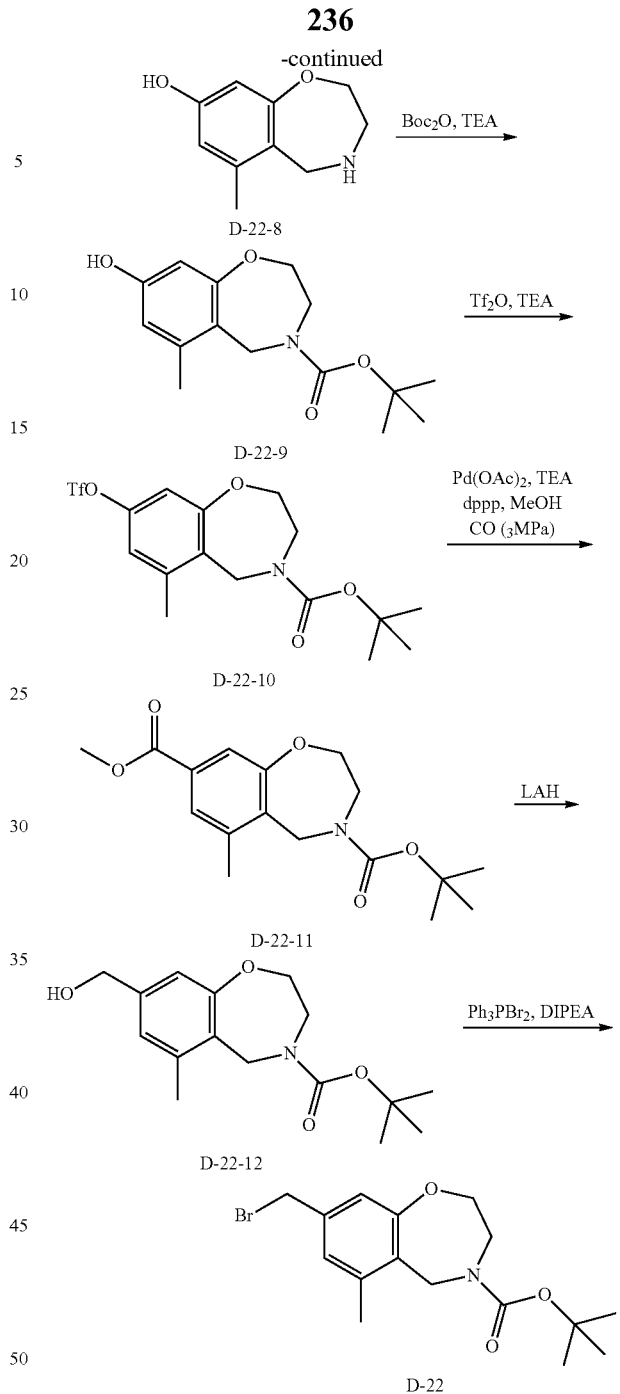

To the mixture of compound 5-Methyl-benzene-1,3-dio (200 g, 1.61 mol) and $K_2CO_3$ (448 g, 3.22 mol) in DMF (2000 mL) is added BnBr (248 g, 1.45 mol) dropwise at room temperature. The mixture is stirred for 12 h then diluted with $H_2O$ and extracted with EtOAc. The organic layer was dried, filtered, and evaporated under reduced pressure. The crude product was purified by chromatography on silica gel to afford D-22-1 (137.5 g).

To a solution of compound D-22-1 (220 g, 1.02 mol) in DCM (2200 mL), at −50° C. under $N_2$, is added NBS (146 g, 0.82 mol). The mixture is stirred for 0.5 h at −50° C. then diluted with $H_2O$ and extracted with DCM. The organic layer was dried, filtered and evaporated under reduced pressure. The crude product is purified by chromatography on silica gel to afford D-22-2 (108 g).

To the solution of D-22-2 (108 g, 0.37 mol) and DIPEA (143 g, 1.10 mol) in DCM (1000 mL), at 0° C., is added SEMCl (74 g, 0.44 mol) dropwise. The mixture is stirred at room temperature for 3 h then diluted with H₂O and extracted with DCM. The organic layer is dried, filtered and evaporated under reduced pressure. The crude product is purified by chromatography on silica gel to afford D-22-3 (101 g).

To a solution of D-22-3 (110 g, 0.24 mol) in THF (1000 mL), at −78° C. under N₂ is added n-BuLi (120 mL, 0.29 mol) dropwise. The mixture is stirred for 0.5 h at −78° C. and then DMF (26 g, 0.36 mol) is added into the mixture dropwise. The mixture was stirred for 1.5 h then diluted with aq. NH₄Cl solution and extracted with EtOAc. The organic layer is dried, filtered and evaporated under reduced pressure. The crude product is purified by chromatography on silica gel to afford D-22-4 (53 g).

A solution of D-22-4 (106.5 g, 0.30 mol) and CBr₄ (100 g, 0.30 mol) in i-PrOH (1000 mL) is stirred at 80° C. for 3 h. The solvent was removed under reduced pressure and the crude product is purified by chromatography on silica gel to afford D-22-5 (52 g).

A solution of D-22-5 (50 g, 0.21 mol), (2-bromo-ethyl)-carbamic acid tert-butyl ester (46 g, 0.21 mol), and Cs₂CO₃ (203 g, 0.63 mol) in DMF (500 mL) is stirred at room temperature for 10 min under N₂. Then the mixture is stirred at 80° C. for 12 h. The solvent is removed under reduced pressure and the crude product is purified by chromatography on silica gel to afford D-22-6 (60.5 g).

To a solution of D-22-6 (60 g, 0.16 mol) in DCM (600 mL) is added TFA (100 g) dropwise under N₂. The mixture is stirred at room temperature for 1 h then diluted with H₂O and extracted with EtOAc. The organic layer was dried, filtered and evaporated under reduced pressure. The crude product is purified by chromatography on silica gel to afford D-22-7 (28.3 g).

A mixture of D-22-7 (28.3 g, 0.11 mol) and Pd—C(dry, 5 g) in MeOH (250 mL) is stirred at room temperature under and atmosphere of H₂ (50 Psi) for 8 h. The reaction is filtered and the solvent evaporated under reduced pressure to afford D-22-8 (19 g) which was used directly without further purification.

A solution of D-22-8 (19 g, 0.087 mol), TEA (26.4 g, 0.26 mol) and Boc₂O (15.6 g, 0.087 mol) in DCM (200 mL) is stirred at room temperature for 0.5 h. The reaction is diluted with H₂O and extracted with DCM. The organic layer is dried, filtered and evaporated under reduced pressure. The crude product is purified by chromatography on silica gel to afford D-22-9 (13.3 g).

To a solution of D-22-9 (11 g, 39 mmol) and TEA (11.9 g, 118 mmol) in DCM (110 mL) is added Tf₂O (11.1 g, 39 mmol) dropwise at room temperature under N₂. The mixture is stirred at room temperature for 3 h then diluted with H₂O and extracted with DCM. The organic layer is dried, filtered and evaporated under reduced pressure. The crude product is purified by chromatography on silica gel to afford D-22-10 (13.1 g).

A mixture of D-22-10 (13.1 g, 32 mmol), TEA (9.7 g, 96 mmol), Pd(OAc)₂ (2.6 g, 20%) and DPPP (2.6 g, 20%) in MeOH (130 mL) is stirred under an atmosphere of CO (3 MPa) at 90° C. for 2 days. The mixture is filtered and the filtrate evaporated under reduced pressure. The crude product is purified by chromatography on silica gel to afford D-22-11 (9.2 g).

To a solution of LAH (1.6 g, 43 mmol) in THF (46 mL), at −50° C., was added a solution of D-22-11 (9.2 g, 29 mmol) in THF (46 mL) dropwise over 30 min. After addition, the reaction mixture is stirred at 0° C. for 4.5 h. The reaction mixture is diluted with H₂O and extracted DCM. The organic layer is dried, filtered and evaporated under reduced pressure. The crude product is purified by chromatography on silica gel to afford D-22-12 (6.7 g).

To a solution of D-22-12 (1.61 g, 5.48 mmol) in dichloromethane (30 mL), at 0° C., is added DIEA (1.4 mL, 8.2 mmol). To this solution is added triphenylphosphine dibromide (3.54 g, 8.21 mmol) in batches (×4) over the span of 10 minutes. The reaction is maintained at 0° C. for approximately 2 h then the ice bath is removed and the reaction mixture is allowed to warm to room temperature over the span of an additional 1.5 h. The reaction mixture is concentrated under reduced pressure and the residue is purified by flash silica gel chromatography to afford the title compound, D-22 (1.73 g) as a white solid.

Example 33

Preparation of intermediate 3-Bromomethyl-5,6,8,9-tetrahydro-pyrido[2,3-d]azepine-7-carboxylic acid tert-butyl ester (D-23)

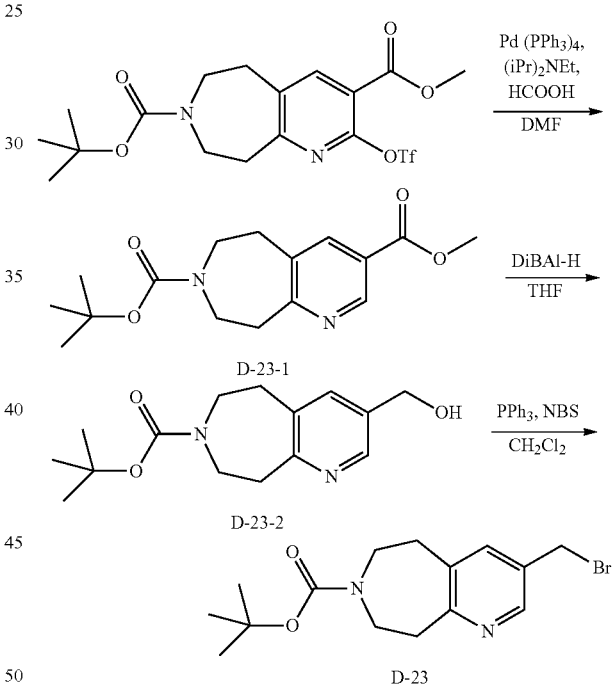

To a solution of the starting triflate (0.523 g, 1.15 mmol) in DMF (20 mL) is added Pd(PPh₃)₄ (0.200 g, 0.173 mmol) and DIEA (0.650 mL, 3.73 mmol) followed by formic acid (0.065 mL, 1.7 mmol). The resultant mixture is heated at 60° C. for 3.5 h then cooled to room temperature. Water and EtOAc are added to the reaction mixture. The aqueous phase is separated from the organic phase and then, extracted with EtOAc (×3). The combined organic extracts are washed with brine, dried (Na₂SO₄), filtered and concentrated under reduced pressure. The crude material is purified via flash silica gel column chromatography to afford D-23-1 (0.3627 g).

To a 0° C. solution D-23-1 (0.4507 g, 1.471 mmol) in THF (15 mL) is added a 1.0 M DiBAl-H solution in toluene (4.6 mL, 4.6 mmol) over the span of 5 minutes. The reaction mixture is maintained at 0° C. for a total of 2 h and 45 minutes.

The reaction mixture, still at 0° C., is treated with Rochelle's salt (15 mL). The resultant heterogeneous mixture is allowed to warm to room temperature and stir at this temperature overnight. The mixture is diluted with water and EtOAc. The aqueous phase is extracted with EtOAc (×4). The combined organic extracts are washed with brine, dried (Na₂SO₄), filtered and concentrated under reduced pressure. The crude material is purified by flash silica gel chromatography to afford D-23-2 (0.2784 mg).

To a 0° C. solution of D-23-2 (0.2062 g, 0.7408 mmol) in DCM (5 mL) is added NBS (0.1726 g, 0.9698 mmol), followed by PPh₃ (0.255 g, 0.972 mmol). The reaction mixture is allowed to stir at 0° for 1.5 h. The reaction mixture is partially concentrated under reduced pressure (without warming). The crude material is purified by flash silica gel column chromatography to afford the title compound D-23 (0.1844 g).

Example 34

Preparation of intermediate 2-Bromomethyl-7,8-dihydro-5H-[1,6]naphthyridine-6-carboxylic acid tert-butyl ester (D-24)

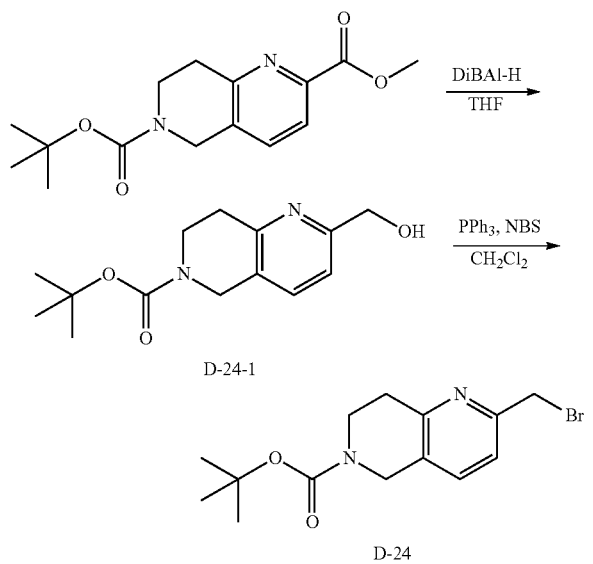

To a 0° C. solution of the starting ester (1.06 g, 3.63 mmol) in THF (33 mL) is added 1.0 M DiBAl-H in toluene (11 mL, 11 mmol). The reaction mixture is allowed to stir at 0° C. for 2.5 h then the reaction mixture is treated with Rochelle's salt (35 mL). The resultant heterogeneous mixture is allowed to warm to room temperature and stir at this temperature for 2 days. The mixture is diluted with water and EtOAc and the aqueous phase is extracted with EtOAc (×4). The combined organic extracts are washed with brine, dried (Na₂SO₄), filtered and concentrated under reduced pressure. The crude material is purified by flash silica gel chromatography to afford D-24-1 (0.459 g).

To a 0° C. solution of D-24-1 (0.459 g, 1.74 mmol) in DCM (12 mL) is added NBS (0.371 g, 2.08 mmol), followed by PPh₃ (0.557 g, 2.12 mmol). The reaction mixture is allowed to stir at 0° for 1 h and 40 minutes. The reaction mixture is partially concentrated under reduced pressure (without warming) and the residue is purified by flash silica gel column chromatography to afford the title compound, D-24 (0.422 g).

Example 35

Preparation of intermediate 8-Bromomethyl-6-methyl-1,2,4,5-tetrahydro-benzo[d]azepine-3-carboxylic acid tert-butyl ester (D-25)

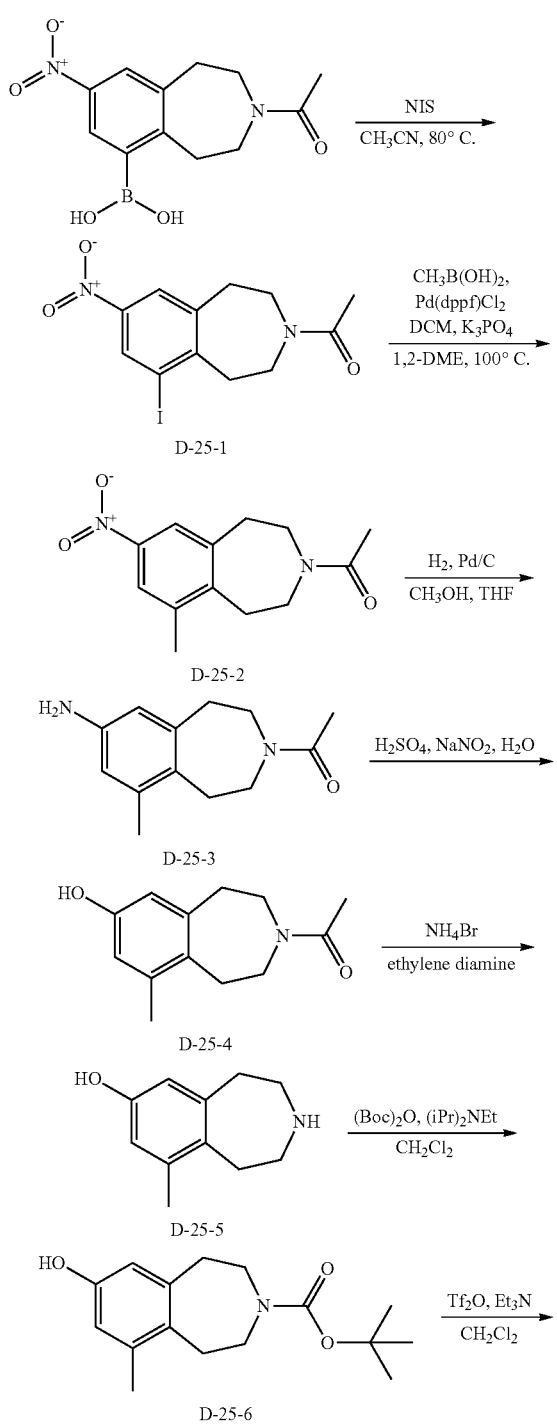

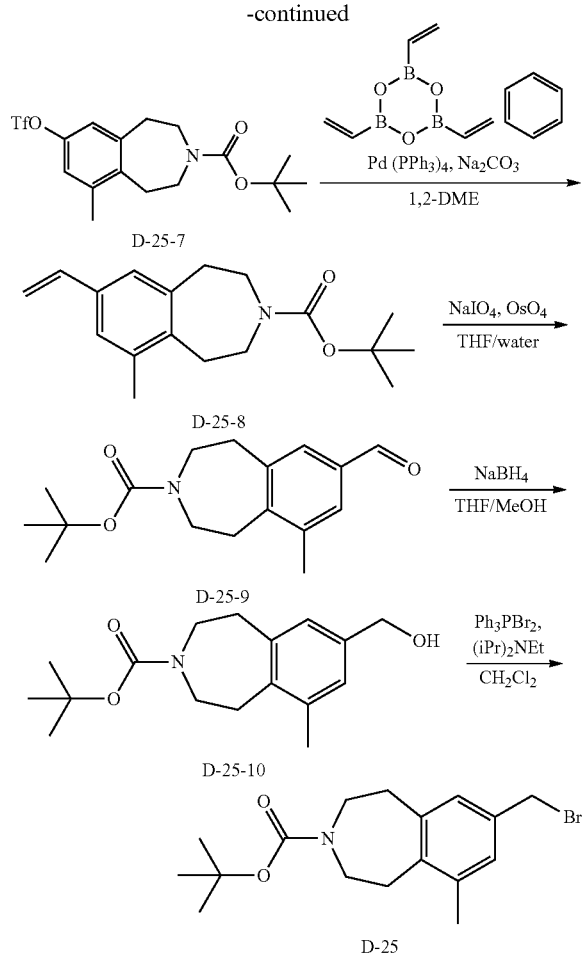

A heterogeneous mixture of the starting boronic acid (4.98 g, 17.9 mmol) and NIS (8.06 g, 35.8 mmol) in acetonitrile (103 mL) is heated at 80° C. under a stream of N₂ for approximately 19 h. Then, the reaction mixture is diluted with brine and DCM. The aqueous phase is extracted with DCM (×3). The combined organic extracts are washed with 1.0 M NaHSO₃, followed by a second portion of brine, dried (Na₂SO₄), filtered and concentrated under reduced pressure to a reduced volume. The remaining solution is poured directly onto a column for purification. The crude material is purified flash silica gel chromatography to afford D-25-1 (6.24 g).

A mixture of D-25-1 (5.01 g, 13.9 mmol), methylboronic acid (2.18 g, 36.5 mmol) and K₃PO₄ (7.49 g, 35.3 mmol) in 1,2-DME (135 mL) is sparged with N₂ for 15 minutes prior to the addition of the Pd catalyst (approximately 1.2 g, 1.5 mmol). The resultant reaction mixture is sparged with N₂ for an additional 15 minutes. Then, the reaction mixture is heated in a 350 mL pressure flask in a heating block at 100° C. for 24 h. Then, it is allowed to cool to room temperature and diluted with EtOAc and water. The aqueous phase is extracted with EtOAc (×3). The combined organic extracts are washed with brine, dried (Na₂SO₄), filtered and concentrated under reduced pressure to give the crude material. The crude material is purified by flash silica gel chromatography to afford D-25-2 (2.46 g).

A solution of D-25-2 (2.96 g, 11.9 mmol) in MeOH (70 mL) and THF (30 mL) is hydrogenated over Pd/C at room temperature and atmospheric pressure for approximately 24 h. The reaction mixture is filtered through a pad of Celite and washed thoroughly with MeOH. The resultant solution is concentrated under reduced pressure to afford D-25-3 (2.52 g) which was used as is used for the subsequent transformation.

A 0° C. solution of concentrated H₂SO₄ (10 mL) in H₂O (38 mL) is added to D-25-3 (2.52 g, 11.5 mmol) at 0° C. Approximately 20 minutes later, a solution of NaNO₂ (0.800 g, 11.6 mmol) in H₂O (13 mL) is added dropwise over the span of 35 minutes. After 40 minutes at this temperature, the reaction mixture is warmed to room temperature and maintained at this temperature for 1.5 h. Then, H₂O (40 mL) is added and the resultant solution is heated at reflux for approximately 2 h then cooled to room temperature. The solution is saturated with NaCl and extracted with EtOAc (×4). The combined organic extracts are dried (Na₂SO₄), filtered and concentrated under reduced pressure to give a thick oil. The crude material is purified by flash silica gel chromatography to afford D-25-4 (1.63 g) as a pale yellow solid.

A mixture of D-25-4 (0.524 g, 2.39 mmol) and ammonium bromide (0.265 g, 2.70 mmol) in ethylene diamine (0.800 mL, 12.0 mmol) is heated at 100° C. for approximately 4 d. The reaction mixture is cooled to room temperature and diluted with a small quantity of water and then acidified to pH 6 with glacial acetic acid. This material is purified by flash C18 reverse phase column chromatography using a eluent of water and acetonitrile with 0.1% TFA additive. Separation of the product from the unreacted starting material is not achieved and the mixture containing D-25-5 is used as is in the following reaction.

To a 0° C. mixture of mixture containing D-25-5 in DCM (50 mL) is added excess N,N-diisopropylethylamine (approximately 7.0 mL, 40.2 mmol), followed by excess (Boc)₂O (5.48 g, 25.1 mmol). The ice bath is removed immediately after the addition and the reaction mixture is maintained at room temperature for approximately 48 h. The reaction mixture is concentrated under reduced pressure to a reduced volume and then, purified by flash silica gel chromatography to afford D-25-6 (0.439 g).

To a 0° C. solution of D-25-6 in DCM (7 mL) is added TEA (0.600 mL, 4.30 mmol) followed by Tf₂O (0.320 mL, 1.90 mmol) over the span of 5 minutes. The reaction mixture is allowed to stir at 0° C. for 2.5 h. The mixture is diluted with saturated aqueous NaHCO₃ (10 mL). The aqueous phase is extracted with EtOAc (×3). The combined organic extracts are washed with saturated aqueous NaHCO₃, brine, dried (Na₂SO₄) and concentrated under reduced pressure to afford D-25-7 which was used without further purification.

A solution of D-25-7 (0.686 g, 1.68 mmol) and the starting boronate (0.520 g, 2.16 mmol) in DME (12 mL) is sparged with N₂ for 10 minutes prior to the addition of the Pd catalyst (0.206 g, 0.178 mmol) and aqueous Na₂CO₃ (2.0 M, 2.1 mL). The reaction mixture is sparged with N₂ for an additional 5 minutes prior to being heated in a microwave reactor at 120° C. for 40 minutes. The reaction mixture is diluted with water and EtOAc. The aqueous phase is extracted with EtOAc (×3). The combined organic extracts are washed with brine, dried (Na₂SO₄), filtered and concentrated under reduced pressure. The crude material is purified by flash silica gel column chromatography to afford D-25-8 (0.2804 g) as a colorless oil.

To a solution of D-25-8 in THF (10 mL) and water (3 mL) is added sodium periodate (0.661 g, 3.09 mmol). The heterogeneous mixture is allowed to stir for 10 minutes prior to the introduction of osmium tetraoxide (4 wt % in water, approximately 0.4 mL). The very thick slurry is stirred vigorously overnight (20 h). The reaction flask is wrapped in aluminum foil to exclude light. The reaction mixture is diluted with DCM (40 mL) and water (40 mL). The heterogeneous mixture is allowed to stir vigorously for 45 minutes then passed through a phase separator. The retained aqueous phase is washed thoroughly with DCM. The organic phase is dried ($Na_2SO_4$), filtered and concentrated under reduced pressure. The crude material is purified by flash silica gel column chromatography to afford D-25-9 (0.2308 g).

To a 0° C. solution of D-25-9 in a mixture of THF (4 mL) and MeOH (4 mL) is added $NaBH_4$ (0.0504 g, 1.33 mmol) in one single batch. The ice bath is removed approximately 10 minutes later and the reaction mixture is maintained at room temperature for 1 h and 15 minutes. Additional $NaBH_4$ (0.0281 g) is added to the 0° C. reaction mixture 1 h and 25 minutes after the initiation of the reaction to drive the reaction to completion. Finally, the reaction mixture is quenched with saturated aqueous $NH_4Cl$ (2 h and 40 minutes, total reaction time). The reaction mixture is allowed to stir at room temperature for approximately 1 extracted with EtOAc (×3). The combined organic extracts are washed with saturated aqueous $NH_4Cl$, brine, dried ($MgSO_4$), filtered and concentrated under reduced pressure. The crude material is purified by flash silica gel column chromatography to afford D-25-10 (0.208 g).

To a 0° C. solution of D-25-10 (0.208 g, 0.715 mmol) and DIEA (0.200 mL, 1.15 mmol) is added triphenylphosphine dibromide (0.480 g, 1.14 mmol) in batches (×3) over the span of 5 minutes. The clear, colorless solution turned yellow upon the addition of the dibromide. The reaction mixture is stirred at room temperature for 1 hour then concentrated to a reduced volume. The remaining solution is purified by flash silica gel column chromatography to afford the title compound, D-25 (0.2185 g).

Example 36

Preparation of intermediate tert-butyl 6-(bromomethyl)-5-fluoro-8-methoxy-3,4-dihydro-1H-isoquinoline-2-carboxylate (D-28)

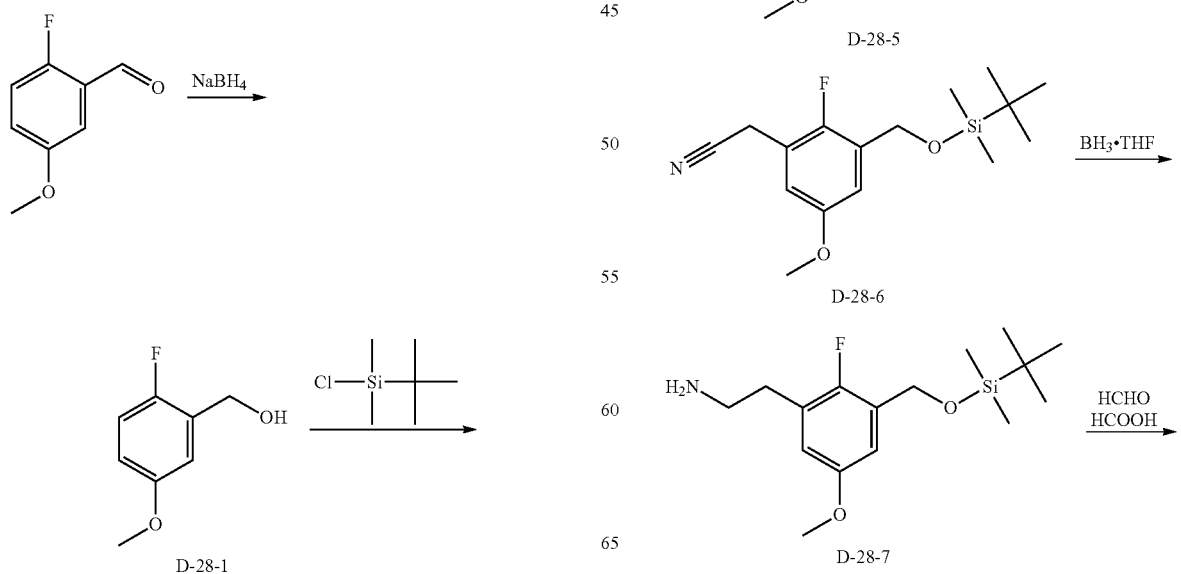

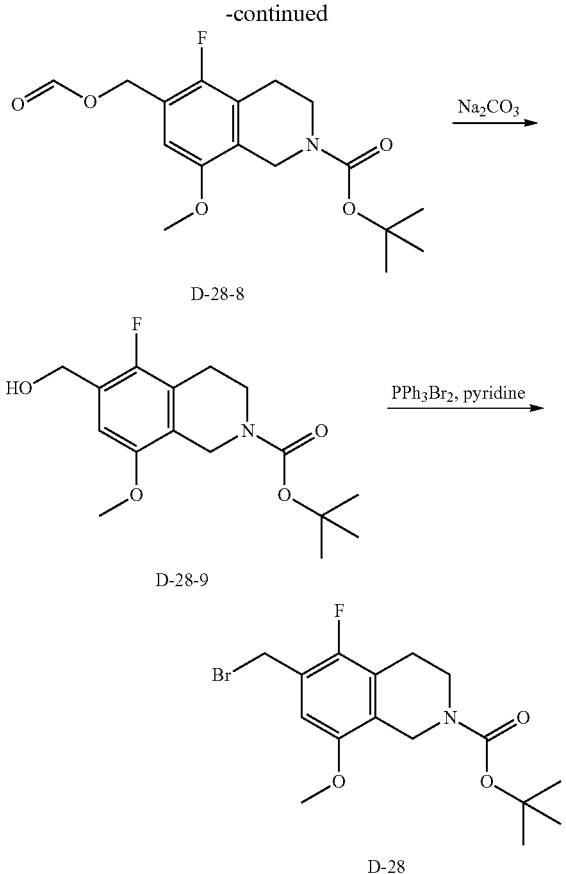

To a solution of 2-fluoro-5-methoxybenzaldehyde (5.00 g, 32.4 mmol) in MeOH (90 mL) is added NaBH$_4$ (1.93 g, 50.9 mmol). The mixture is stirred at room temperature for 1 h then water (50 mL) is added. The resulting mixture is stirred for 15 min and concentrated under reduced pressure. The residue is dissolved in water (50 mL) and extracted with dichloromethane (2×50 mL). The combined organic layers are washed with brine (50 mL), passed through a phase separator and concentrated under reduced pressure to afford compound D-28-1 (4.88 g).

A mixture of D-28-1 (4.88 g, 31.2 mmol), t-butyldimethylsilyl chloride (7.06 g, 46.8 mmol), imidazole (4.25 g, 62.44 mmol) and THF (130 mL) is stirred at room temperature for 16 h then concentrated under reduced pressure. The residue is dissolved in water (50 mL). The mixture is extracted with MTBE (50 mL). The organic layer is sequentially washed with a 1 N aqueous HCl solution (50 mL) and brine (50 mL), then dried over Na$_2$SO$_4$ and concentrated under reduced pressure. The residue was purified by flash chromatography to afford compound D-28-2 (8.23 g).

To a solution of D-28-2 (8.23 g, 30.4 mmol) in THF (150 mL) cooled under argon at −78° C. is added a solution of 1.4 M s-BuLi in cyclohexane (mL, mmol). The mixture is stirred at −78° C. for 1.5 h then DMF (5.16 mL, 67.0 mmol) is added. The resulting mixture is stirred at −78° C. for 30 min then at room temperature for 45 min. Water (50 mL) is added, the layers are separated and the aqueous layer is extracted with EtOAc (2×100 mL). The combined organic layers are washed with brine (100 mL) and then concentrated under reduced pressure. The crude is purified by flash silica gel chromatography to afford compound D-28-3 (4.67 g).

To a solution of compound D-28-3 (4.67 g) in MeOH (60 mL) is added NaBH$_4$ (0.93 g, 24.6 mmol). The mixture is stirred at room temperature for 1 h then water (50 mL) is added. The resulting mixture is stirred for 20 min then concentrated under reduced pressure. The residue is dissolved in water (50 mL) and extracted with dichloromethane (2×55 mL). The combined organic layers are passed through a phase separator and concentrated under reduced pressure. The crude is purified by flash silica gel chromatography to afford compound D-28-4 (2.15 g).

To a solution of D-28-4 (2.15 g, 7.16 mmol) and pyridine (0.94 mL, 8.95 mmol) in dichlormethane (35 mL) is added dibromotriphenylposphorane (3.47 g, 8.23 mmol) at 0° C. The mixture is stirred at 0° C. for 1.5 h then concentrated under reduced pressure. The residue is triturated with 20% EtOAc in heptane (100 mL) and filtered. The filtrate is concentrated under reduced pressure and the crude is purified by flash silica gel chromatography to afford compound D-28-5 (2.20 g).

A mixture of D-28-5 (2.20 g, 6.05 mmol) and NaCN (0.33 g, 6.7 mmol) in DMF (16 mL) is stirred at 45° C. for 2 h and diluted with MTBE (75 mL) and water (100 mL). The aqueous layer is extracted with MTBE (75 mL). The combined organic layers are washed with water (2×75 mL), then brine (75 mL) and concentrated under reduced pressure. The crude is purified by flash silica gel chromatography to afford compound D-28-6 (1.71 g).

To a solution of compound D-28-6 (1.71 g, 5.53 mmol) in THF (22 mL) is added a 1.0 M solution of borane-THF complex in THF (12.16 mL, 12.16 mmol) under argon at room temperature. The mixture is heated at 55° C. for 1 h then cooled to room temperature. Water (10 mL) is added and the resulting mixture is stirred for 15 min then concentrated under reduced pressure. The crude is purified by reverse phase C18 flash chromatography to afford compound D-28-7 (1.10 g).

A mixture of compound D-28-7 (1.10 g, 3.06 mmol), 15 wt % formaldehyde in water (0.25 mL) and formic acid (8.80 mL) is stirred at 60° C. for 5.5 h. The mixture is then concentrated under reduced pressure and the residue is azeotroped with toluene (2×50 mL). The residue is taken up in DCM (16.6 mL) and to this is added DMAP (37.4 mg, 0.31 mmol), triethylamine (1.90 mL, 13.52 mmol), and Boc$_2$O (667.8 mg, 3.06 mmol). The mixture is stirred at room temperature for 2 h then concentrated under reduced pressure. The crude is purified by flash silica gel chromatography to afford compound D-28-8 (0.26 g).

A mixture of D-28-8 (0.26 g, 0.77 mmol), and Na$_2$CO$_3$ (438.5 mg, 4.14 mmol) in MeOH (6.20 mL) is stirred at room temperature overnight. The solvent is evaporated under reduced pressure. The residue is dissolved in water (20 mL) and the mixture is extracted with DCM (3×20 mL). The combined organic layers are concentrated under reduced pressure and the crude is purified by flash silica gel chromatography to afford compound D-28-9 (0.2307 g).

To a solution of D-28-9 (0.230 g, 0.74 mmol) and pyridine (0.09 mL, 0.85 mmol) in DCM (7.6 mL), at 0° C., is added dibromotriphenylposphorane (0.3586 g, 0.85 mmol). The mixture is stirred at 0° C. for 1 h then concentrated under reduced pressure. The residue is triturated with 20% EtOAc in heptane (50 mL) and filtered. The filtrate is concentrated under reduced pressure and the crude is purified by flash silica gel chromatography to afford the title compound D-28 (0.2107 g).

Example 37

Preparation of intermediates (R)-7-Bromomethyl-1-methyl-1,2,4,5-tetrahydro-benzo[d]azepine-3-carboxylic acid tert-butyl ester (D-29) and (R)-7-Bromomethyl-1-methyl-1,2,4,5-tetrahydro-benzo[d]azepine-3-carboxylic acid tert-butyl ester (D-30)

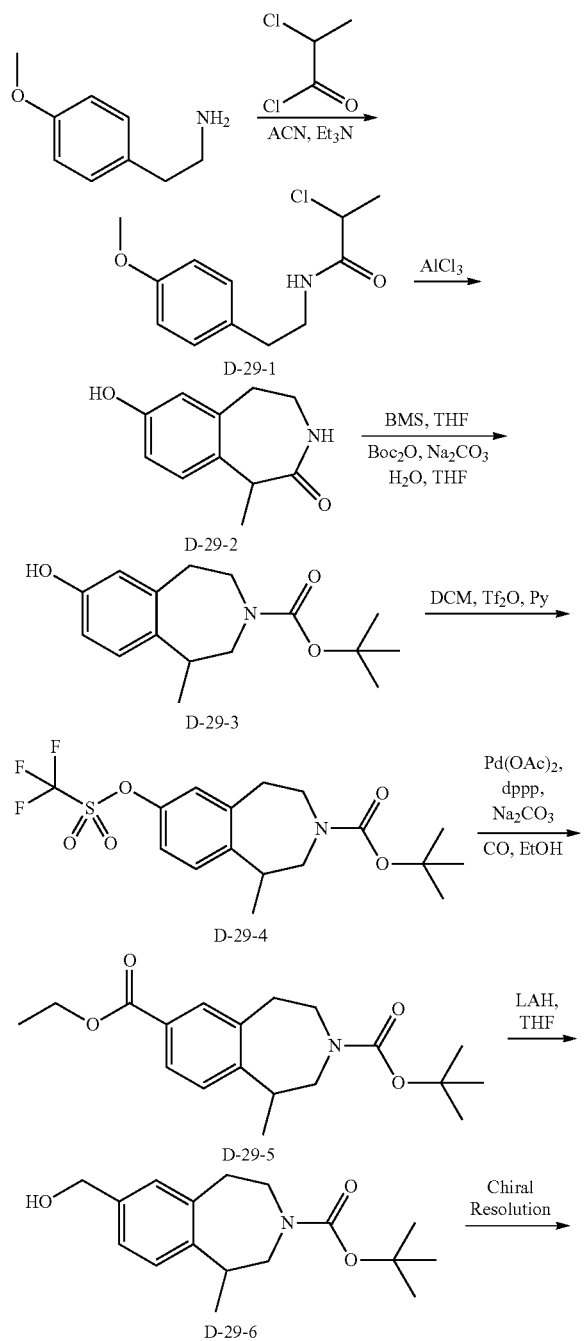

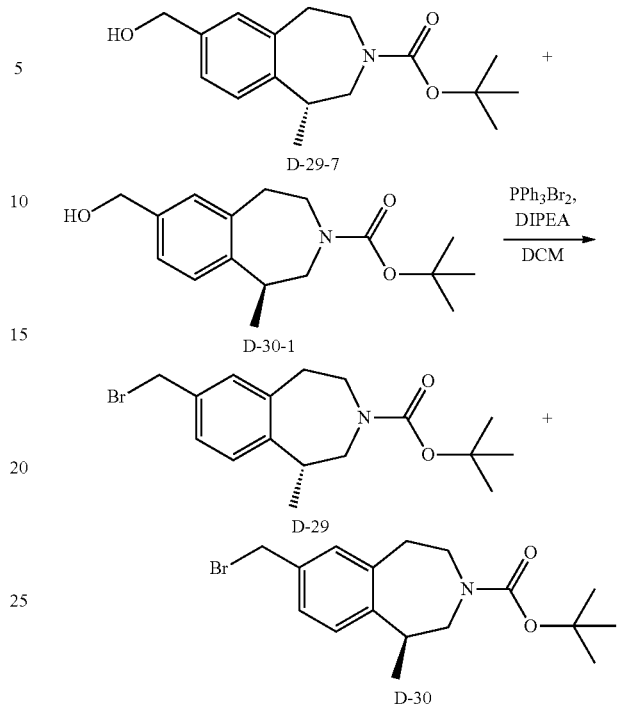

2-Chloro-propionyl chloride (109 g, 0.860 mol) is added dropwise to a stirred solution of 2-(4-methoxy-phenyl)-ethylamine (130 g, 0.860 mol) and TEA (174 g, 1.72 mol) in ACN (2 L) at 0° C. under $N_2$. The solution is warmed to 20° C. for 2 h then evaporated and extracted with EtOAc. The combined organics are washed with brine, dried with anhydrous $Na_2SO_4$, filtered and concentrated to give D-29-1 (190 g).

A mixture of D-29-1 (100.00 g, 413.71 mmol) and $AlCl_3$ (165 g, 1.24 mol) is heated to 150° C. under $N_2$ for 12 h. The reaction is cooled to room temperature, diluted with water and extracted with EtOAc. The combined organics are washed with brine, dried over anhydrous $Na_2SO_4$, filtered and concentrated under reduced pressure. The residue is purified by flash silica gel column chromatography to yield D-29-2 (55.0 g).

To a mixture of D-29-2 (77.0 g, 0.403 mol) in THF (770 mL) is slowly added borane dimethyl sulfide (10 M, 89 mL) at room temperature under $N_2$. The mixture is stirred for 10 min and then is heated to 65° C. for 16 h. The mixture is cooled to room temperature and is quenched with HCl (10%) and stirred for 20 min. The pH of the mixture made basic by addition of $Na_2CO_3$. To this is added $(Boc)_2O$ (88 g, 0.403 mol) and the reaction stirred at room temperature for 16 h. The mixture is extracted with EtOAc, washed with brine, dried with anhydrous $Na_2SO_4$, filtered and concentrated under reduced pressure. The residue is purified by flash silica gel column chromatography to afford D-29-3 (57.0 g) as a yellow solid.

To a mixture of D-29-3 (135 g, 0.487 mol) and pyridine (77 g, 0.97 mol) in DCM (1350 ml), at −50° C. under $N_2$, is added $Tf_2O$ (151 g, 0.535 mol) dropwise over 10 min. The reaction mixture is allowed to warm to room temperature for 2 h and then is concentrated under reduced pressure. The resulting residue is diluted with EtOAc, washed with 1 N HCl, followed by saturated $NaHCO_3$ and brine then dried over $Na_2SO_4$ and concentrated under reduced pressure. This residue is purified by flash silica gel column chromatography to afford D-29-4 (165 g).

A mixture of D-29-4 (140 g, 0.342 mol), dppp (14 g), Pd(OAc)$_2$ (14 g), TEA (69 g, 0.684 mol) in EtOH (2800 mL) is stirred at 80° C. under and atmosphere of CO (4 MPa) for 12 h. The reaction mixture is cooled to room temperature and concentrated under reduced pressure. The resulting residue is purified by flash silica gel column chromatography to give D-29-5 (108 g).

To a stirred solution of D-29-5 (5.00 g, 15.0 mmol) in THF (100 mL), at −40° C., is slowly added lithium aluminum hydride (0.597 g, 15.7 mmol) keeping the temperature at −40° C. After addition is completed, the mixture is warmed to room temperature and stirred for 2 h. The solvent is removed under reduced pressure and the residue is separated with dichloromethane and H$_2$O. The organic phase is dried over anhydrous Na$_2$SO$_4$ and concentrated under reduced pressure. The residue is purified by flash silica gel column chromatography to give D-29-6 (4.0 g) as an oil.

The racemic D-29-6 is resolved on a LUX 5 u cellulose (30×250 mm) using 10% IPA in super critical CO$_2$ at 85 g/min under 140 bar at 40° C. to afford D-29-7 (first eluting peak, 0.980 g) and D-30-1 (second eluting peak, 1.118 g). The absolute stereochemistry was not established and the structures drawn are arbitrarily assigned.

To a solution of alcohol D-29-7 (0.980 g, 3.36 mmol) and N,N-diisopropylethylamine (0.879 mL, 5.04 mmol) in DCM (30.0 mL), at 0° C., is added triphenylphosphine dibromide (2.173 g, 5.045 mmol). The reaction is stirred for 2 h then concentrated under reduced pressure. The resulting residue is purified by flash silica gel column chromatography to afford the title compound D-29 (0.786 g).

To a solution of alcohol D-30-1 (1.118 g, 3.837 mmol) and N,N-diisopropylethylamine (1.003 mL, 5.755 mmol) in DCM (30.0 mL), at 0° C., is added triphenylphosphine dibromide (2.479 g, 5.755 mmol). The reaction is stirred for 2 h then concentrated under reduced pressure. The resulting residue is purified by flash silica gel column chromatography to afford the title compound D-30 (0.948 g).

Example 38

Preparation of intermediate 6-{2-[6-((1R,6S)-6-Carboxy-3-aza-bicyclo[4.1.0]hept-3-yl)-pyridin-2-yl]-phenoxymethyl}-3,4-dihydro-1H-isoquinoline-2-carboxylic acid tert-butyl ester (E-1)

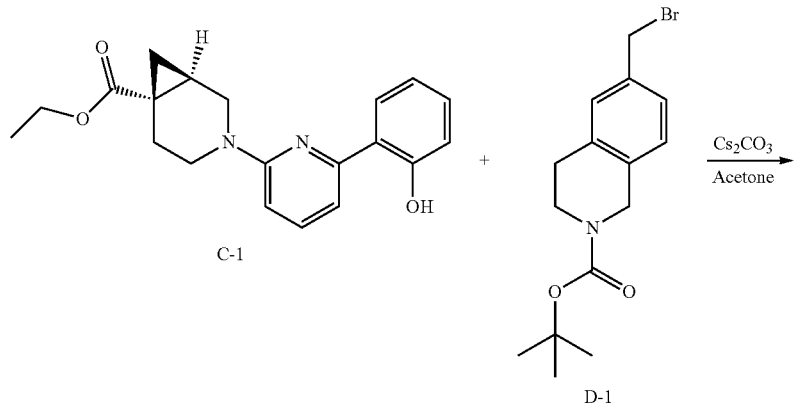

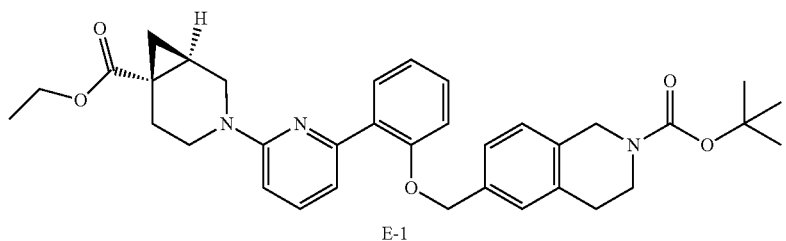

To a solution of 0.109 g (0.322 mmol) of C-1 in acetone (15 mL) is added 0.11 g (0.34 mmol) of D-1 followed by 0.35 g (1.1 mmol) of cesium carbonate. The mixture is stirred at ambient temperature for 4 days then filtered to remove insoluble inorganics and concentrated under reduced pressure. The residue is purified by flash silica gel chromatography to afford E-1 (0.065 g, 35% yield).

The following intermediates can be prepared from intermediate C-1 in a similar fashion using the appropriate reagents.

| Intermediate | Prepared From | Structure |
|---|---|---|
| E-2 | C-1 | 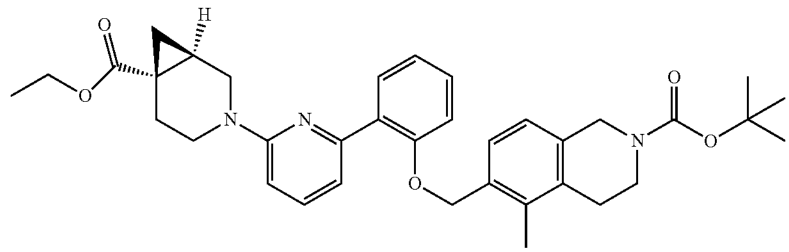 [SMILES: CCOC(=O)[C@@]12CCN(c3cccc(-c4ccccc4OCc4ccc5c(c4C)CCN(C(=O)OC(C)(C)C)C5)n3)C[C@@H]1C2] |
| E-3 | C-1 | 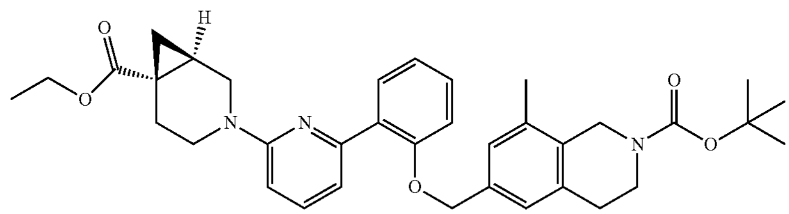 [SMILES: CCOC(=O)[C@@]12CCN(c3cccc(-c4ccccc4OCc4cc(C)c5c(c4)CCN(C(=O)OC(C)(C)C)C5)n3)C[C@@H]1C2] |
| E-4 | C-2 | 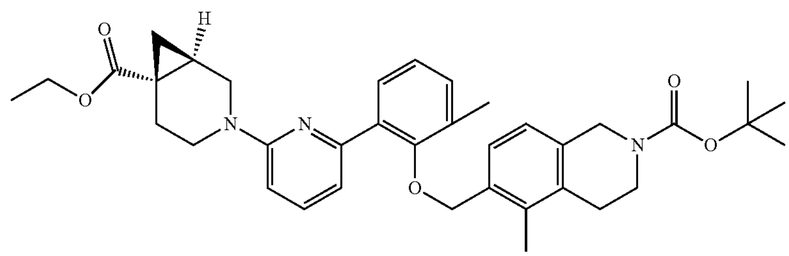 [SMILES: CCOC(=O)[C@@]12CCN(c3cccc(-c4cccc(C)c4OCc4ccc5c(c4C)CCN(C(=O)OC(C)(C)C)C5)n3)C[C@@H]1C2] |
| E-5 | C-2 | 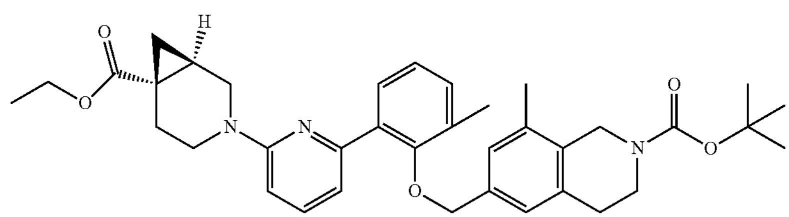 [SMILES: CCOC(=O)[C@@]12CCN(c3cccc(-c4cccc(C)c4OCc4cc(C)c5c(c4)CCN(C(=O)OC(C)(C)C)C5)n3)C[C@@H]1C2] |
| E-7 | C-3 | 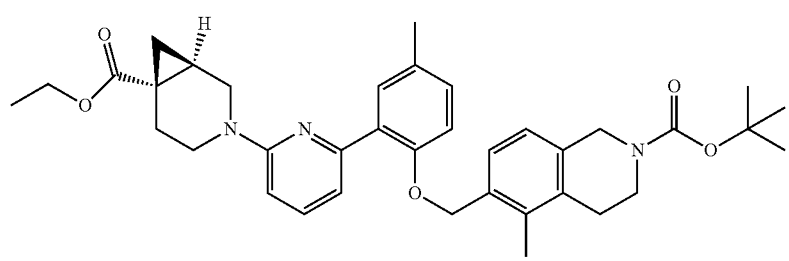 [SMILES: CCOC(=O)[C@@]12CCN(c3cccc(-c4cc(C)ccc4OCc4ccc5c(c4C)CCN(C(=O)OC(C)(C)C)C5)n3)C[C@@H]1C2] |
| E-8 | C-3 | 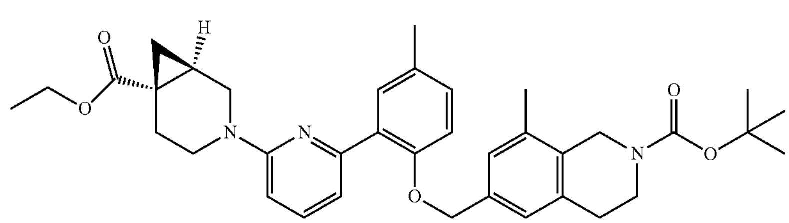 [SMILES: CCOC(=O)[C@@]12CCN(c3cccc(-c4cc(C)ccc4OCc4cc(C)c5c(c4)CCN(C(=O)OC(C)(C)C)C5)n3)C[C@@H]1C2] |

-continued
| Intermediate | Prepared From | Structure |
|---|---|---|
| E-9 | C-4 | 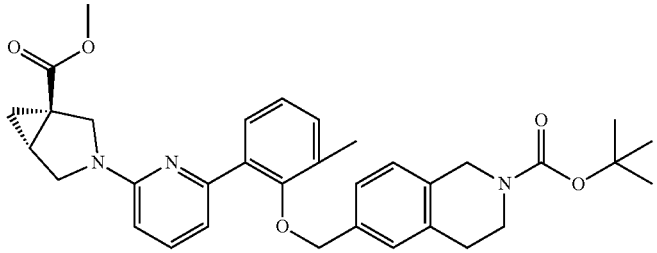 [SMILES: COC(=O)[C@]12C[C@H]1CN(c1cccc(-c3cccc(C)c3OCc3ccc4c(c3)CCN(C(=O)OC(C)(C)C)C4)n1)C2] |
| E-10 | C-4 | 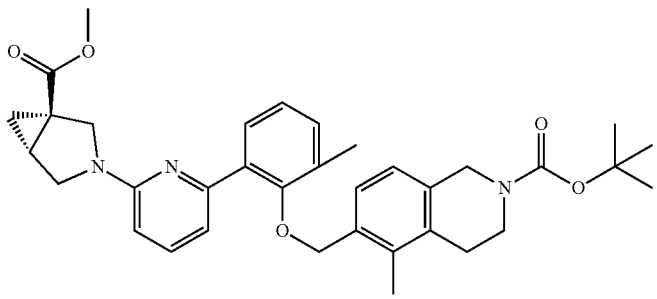 [SMILES: COC(=O)[C@]12C[C@H]1CN(c1cccc(-c3cccc(C)c3OCc3ccc4c(c3C)CCN(C(=O)OC(C)(C)C)C4)n1)C2] |
| E-11 | C-4 | 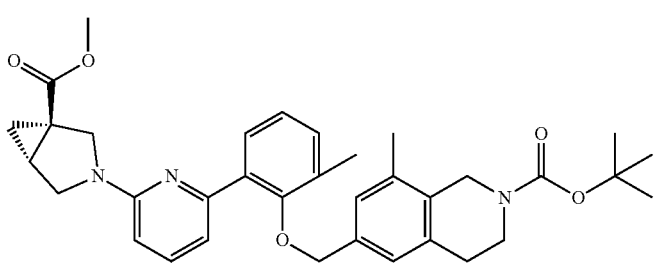 [SMILES: COC(=O)[C@]12C[C@H]1CN(c1cccc(-c3cccc(C)c3OCc3cc(C)c4c(c3)CCN(C(=O)OC(C)(C)C)C4)n1)C2] |
| E-12 | C-4 | 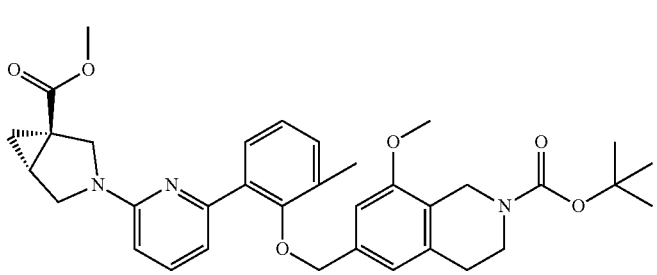 [SMILES: COC(=O)[C@]12C[C@H]1CN(c1cccc(-c3cccc(C)c3OCc3cc4c(c(OC)c3)CN(C(=O)OC(C)(C)C)CC4)n1)C2] |
| E-13 | C-4 | 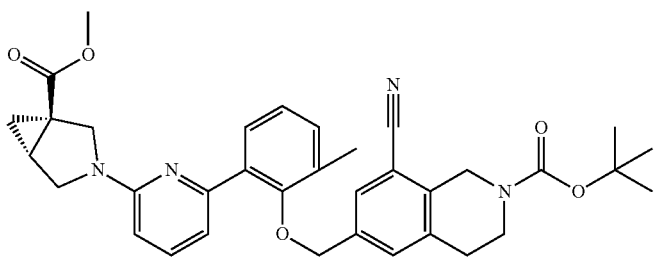 [SMILES: COC(=O)[C@]12C[C@H]1CN(c1cccc(-c3cccc(C)c3OCc3cc(C#N)c4c(c3)CCN(C(=O)OC(C)(C)C)C4)n1)C2] |

-continued
| Intermediate | Prepared From | Structure |
|---|---|---|
| E-14 | C-4 | 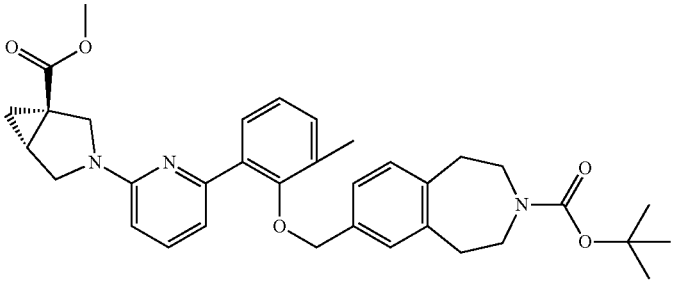 [SMILES: COC(=O)[C@]12C[C@H]1CN(c1cccc(-c3cccc(C)c3OCc3ccc4c(c3)CCN(C(=O)OC(C)(C)C)CC4)n1)C2] |
| E-15 | C-4 | 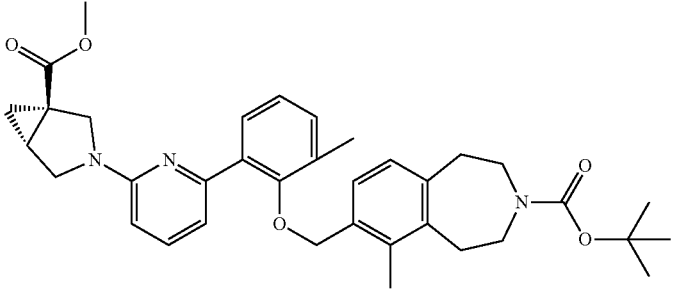 [SMILES: COC(=O)[C@]12C[C@H]1CN(c1cccc(-c3cccc(C)c3OCc3ccc4c(c3C)CCN(C(=O)OC(C)(C)C)CC4)n1)C2] |
| E-16 | C-5 | 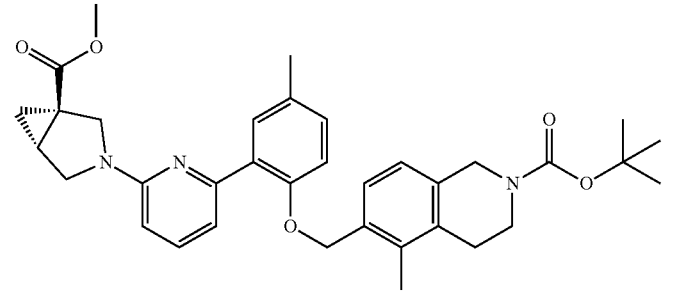 [SMILES: COC(=O)[C@]12C[C@H]1CN(c1cccc(-c3cc(C)ccc3OCc3ccc4c(c3C)CCN(C(=O)OC(C)(C)C)C4)n1)C2] |
| E-17 | C-5 | 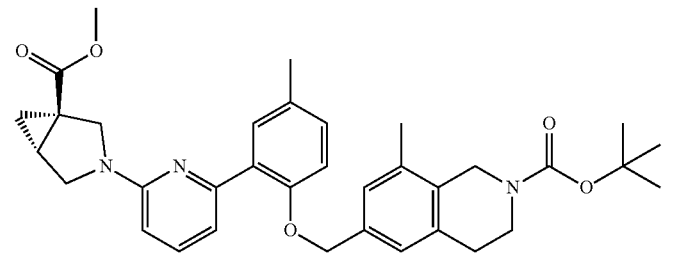 [SMILES: COC(=O)[C@]12C[C@H]1CN(c1cccc(-c3cc(C)ccc3OCc3cc(C)c4c(c3)CCN(C(=O)OC(C)(C)C)C4)n1)C2] |
| E-18 | C-5 | 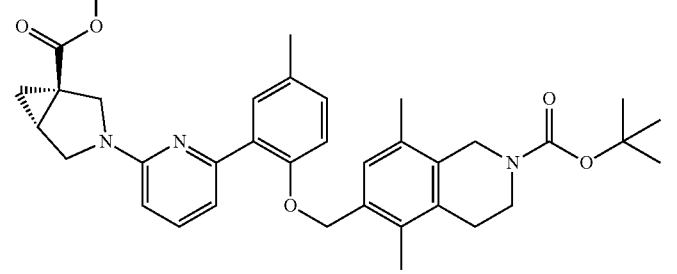 |

-continued
| Intermediate | Prepared From | Structure |
|---|---|---|
| E-19 | C-5 | 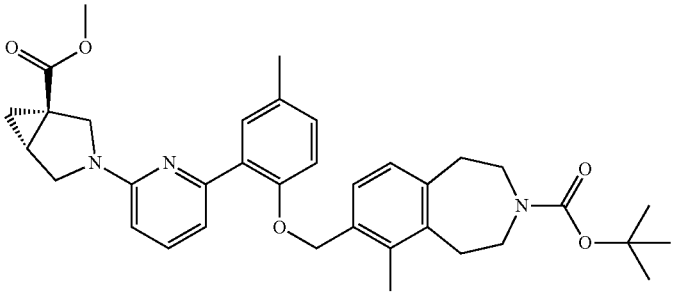 [SMILES: COC(=O)[C@]12C[C@H]1CN(c1cccc(-c3cc(C)ccc3OCc3ccc4c(c3C)CCN(C(=O)OC(C)(C)C)CC4)n1)C2] |
| E-20 | C-6 | 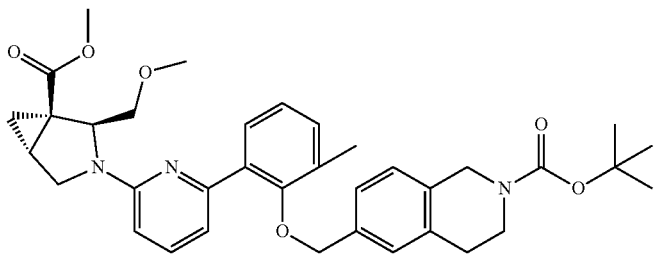 [SMILES: COC[C@H]1N(c2cccc(-c3cccc(C)c3OCc3ccc4c(c3)CCN(C(=O)OC(C)(C)C)C4)n2)C[C@@H]2C[C@@]21C(=O)OC] |
| E-21 | C-6 | 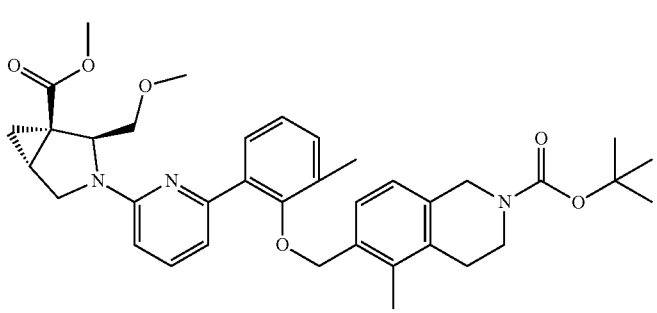 [SMILES: COC[C@H]1N(c2cccc(-c3cccc(C)c3OCc3ccc4c(c3C)CCN(C(=O)OC(C)(C)C)C4)n2)C[C@@H]2C[C@@]21C(=O)OC] |
| E-22 | C-6 | 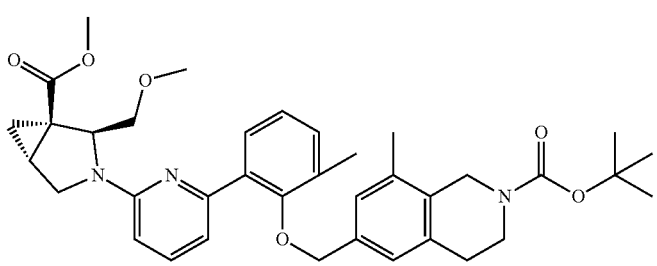 [SMILES: COC[C@H]1N(c2cccc(-c3cccc(C)c3OCc3cc(C)c4c(c3)CCN(C(=O)OC(C)(C)C)C4)n2)C[C@@H]2C[C@@]21C(=O)OC] |
| D-23 | C-6 | 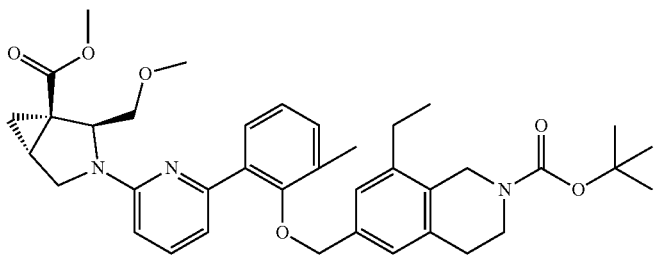 [SMILES: CCc1cc(COc2c(C)cccc2-c2cccc(N3C[C@@H]4C[C@]4(C(=O)OC)[C@H]3COC)n2)cc2c1CN(C(=O)OC(C)(C)C)CC2] |

-continued
| Intermediate | Prepared From | Structure |
|---|---|---|
| E-24 | C-6 | 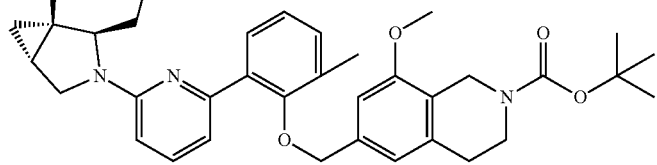 |
| E-25 | C-6 | 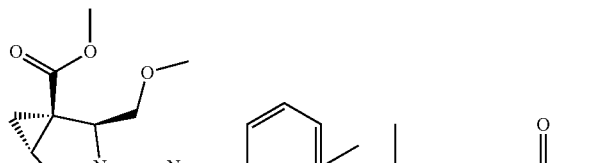 |
| E-26 | C-6 | 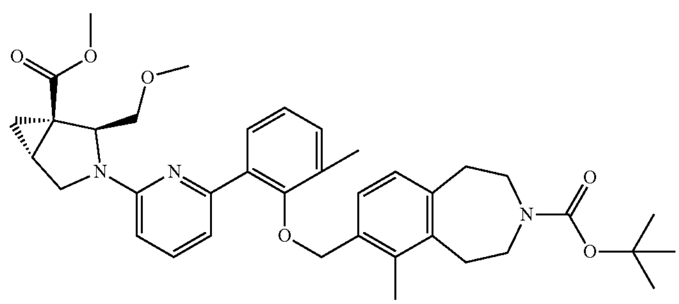 [SMILES: COC[C@H]1N(c2cccc(-c3cccc(C)c3OCc3ccc4c(c3C)CCN(C(=O)OC(C)(C)C)CC4)n2)C[C@@H]2C[C@@]21C(=O)OC] |
| E-27 | C-7 | 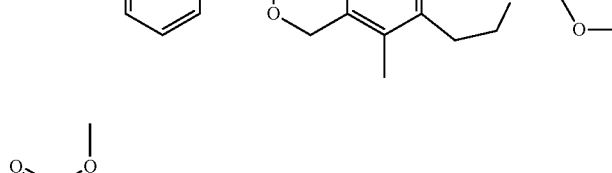 |
| E-28 | C-8 | 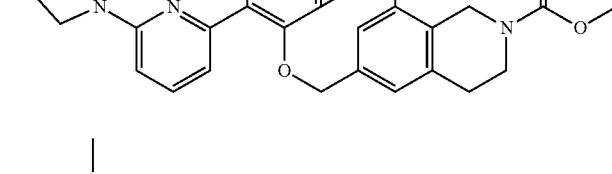 |

-continued

| Intermediate | Prepared From | Structure |
|---|---|---|
| E-29 | C-9 | 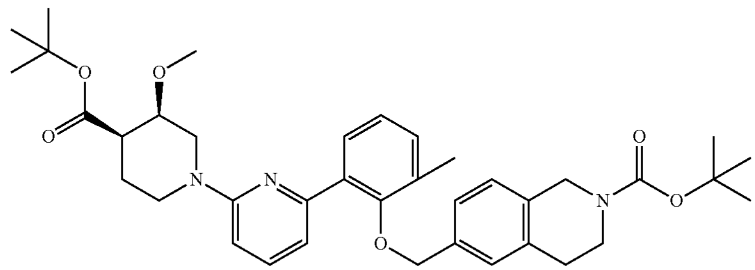 [SMILES: CO[C@H]1CN(c2cccc(-c3cccc(C)c3OCc3ccc4c(c3)CCN(C(=O)OC(C)(C)C)C4)n2)CC[C@H]1C(=O)OC(C)(C)C] |
| E-30 | C-9 | 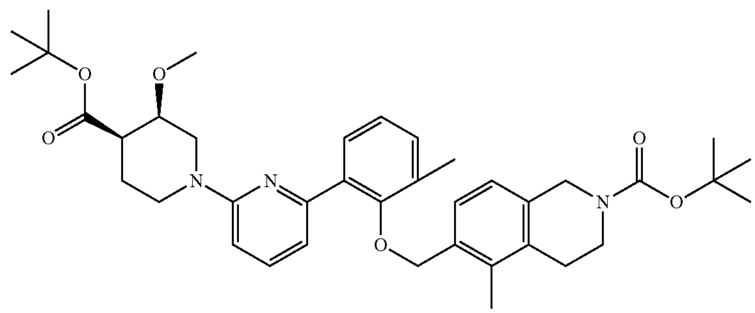 [SMILES: CO[C@H]1CN(c2cccc(-c3cccc(C)c3OCc3ccc4c(c3C)CCN(C(=O)OC(C)(C)C)C4)n2)CC[C@H]1C(=O)OC(C)(C)C] |
| E-31 | C-10 | 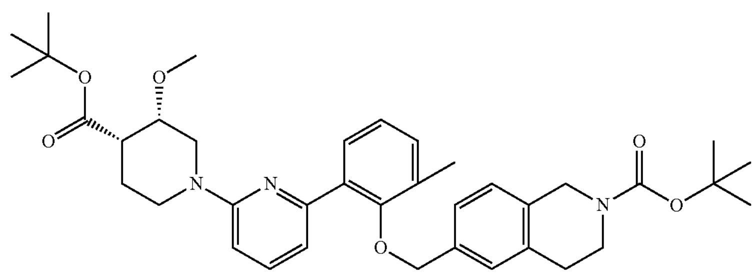 [SMILES: CO[C@@H]1CN(c2cccc(-c3cccc(C)c3OCc3ccc4c(c3)CCN(C(=O)OC(C)(C)C)C4)n2)CC[C@@H]1C(=O)OC(C)(C)C] |
| E-32 | C-10 | 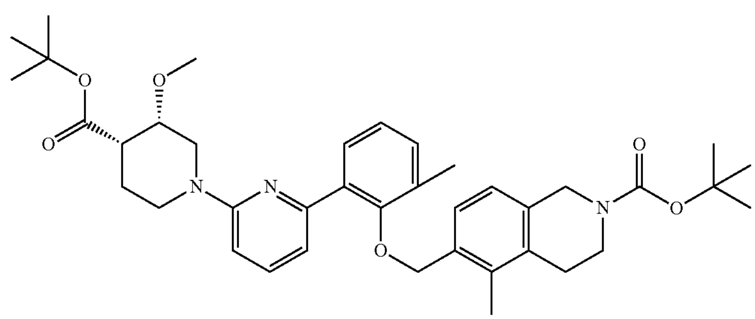 [SMILES: CO[C@@H]1CN(c2cccc(-c3cccc(C)c3OCc3ccc4c(c3C)CCN(C(=O)OC(C)(C)C)C4)n2)CC[C@@H]1C(=O)OC(C)(C)C] |
| E-33 | C-11 | 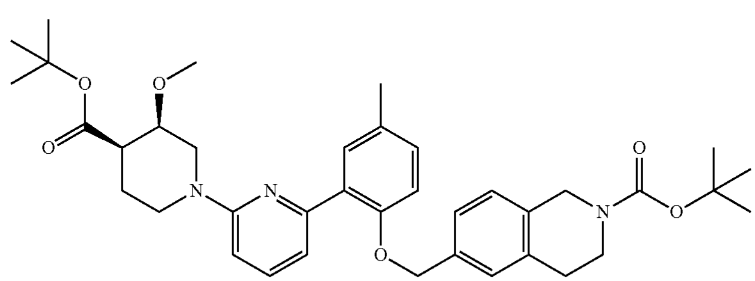 [SMILES: CO[C@H]1CN(c2cccc(-c3cc(C)ccc3OCc3ccc4c(c3)CCN(C(=O)OC(C)(C)C)C4)n2)CC[C@H]1C(=O)OC(C)(C)C] |

| Intermediate | Prepared From | Structure |
|---|---|---|
| E-34 | C-11 | 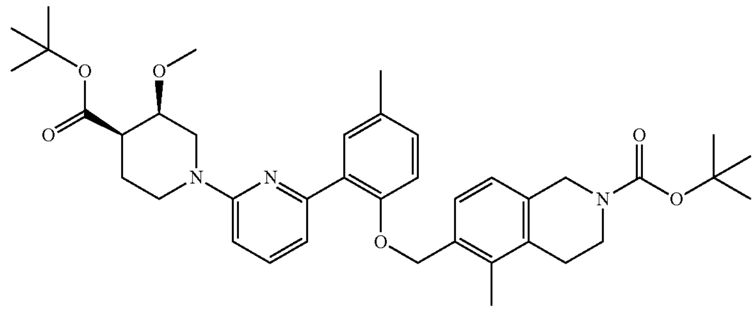 [SMILES: CO[C@H]1CN(c2cccc(-c3cc(C)ccc3OCc3ccc4c(c3C)CCN(C(=O)OC(C)(C)C)C4)n2)CC[C@H]1C(=O)OC(C)(C)C] |
| E-35 | C-11 | 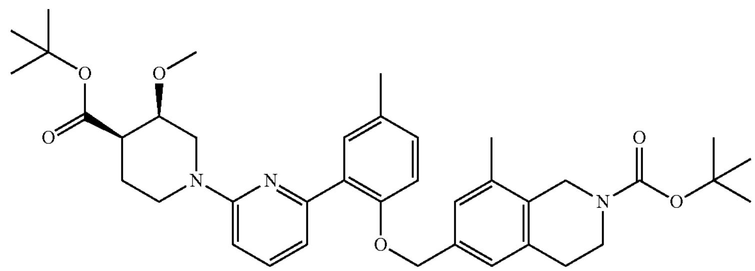 [SMILES: CO[C@H]1CN(c2cccc(-c3cc(C)ccc3OCc3cc(C)c4c(c3)CCN(C(=O)OC(C)(C)C)C4)n2)CC[C@H]1C(=O)OC(C)(C)C] |
| E-36 | C-11 | 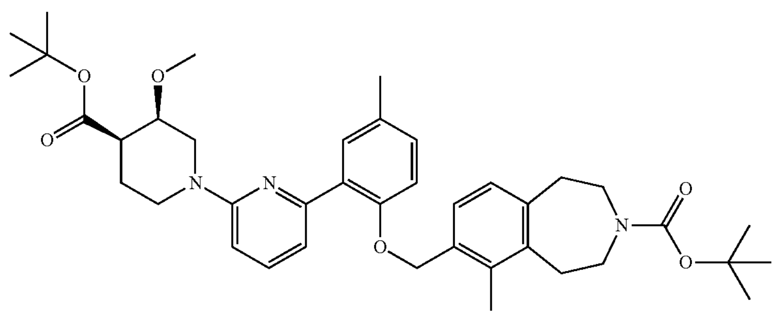 [SMILES: CO[C@H]1CN(c2cccc(-c3cc(C)ccc3OCc3ccc4c(c3C)CCN(C(=O)OC(C)(C)C)CC4)n2)CC[C@H]1C(=O)OC(C)(C)C] |
| E-37 | C-12 | 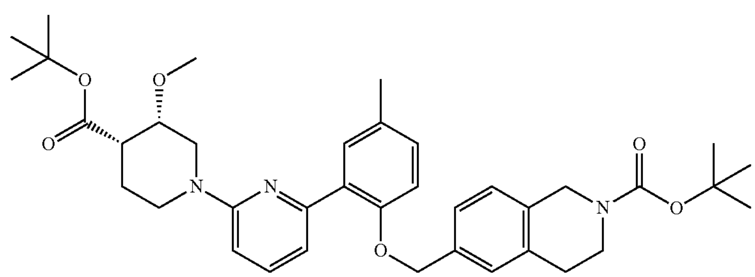 [SMILES: CO[C@@H]1CN(c2cccc(-c3cc(C)ccc3OCc3ccc4c(c3)CCN(C(=O)OC(C)(C)C)C4)n2)CC[C@@H]1C(=O)OC(C)(C)C] |
| E-38 | C-12 | 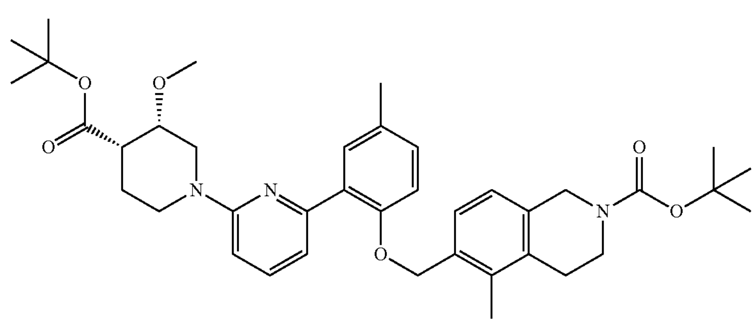 [SMILES: CO[C@@H]1CN(c2cccc(-c3cc(C)ccc3OCc3ccc4c(c3C)CCN(C(=O)OC(C)(C)C)C4)n2)CC[C@@H]1C(=O)OC(C)(C)C] |

-continued

| Intermediate | Prepared From | Structure |
|---|---|---|
| E-39 | C-12 | 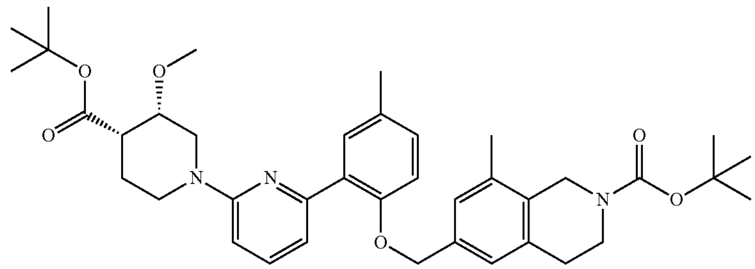 [SMILES: CO[C@@H]1CN(c2cccc(-c3cc(C)ccc3OCc3cc(C)c4c(c3)CCN(C(=O)OC(C)(C)C)C4)n2)CC[C@@H]1C(=O)OC(C)(C)C] |
| E-40 | C-12 | 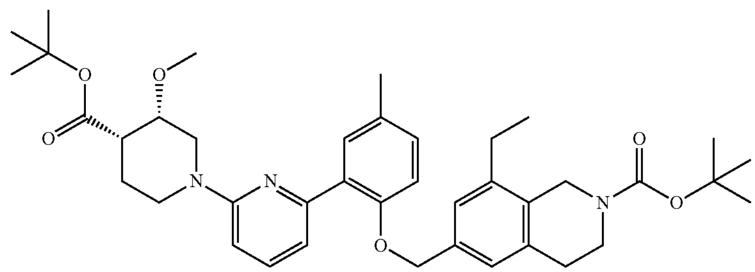 [SMILES: CCc1cc(COc2ccc(C)cc2-c2cccc(N3CC[C@H](C(=O)OC(C)(C)C)[C@H](OC)C3)n2)cc2c1CN(C(=O)OC(C)(C)C)CC2] |
| E-41 | C-12 | 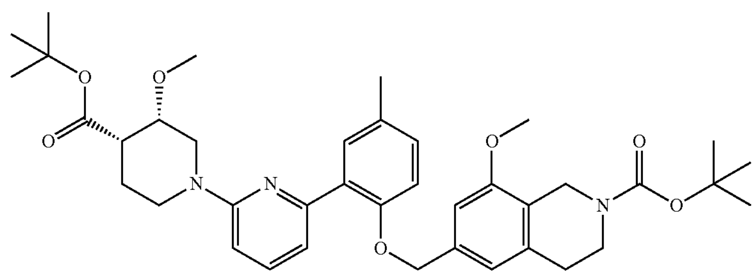 [SMILES: COc1cc(COc2ccc(C)cc2-c2cccc(N3CC[C@H](C(=O)OC(C)(C)C)[C@H](OC)C3)n2)cc2c1CN(C(=O)OC(C)(C)C)CC2] |
| E-42 | C-12 | 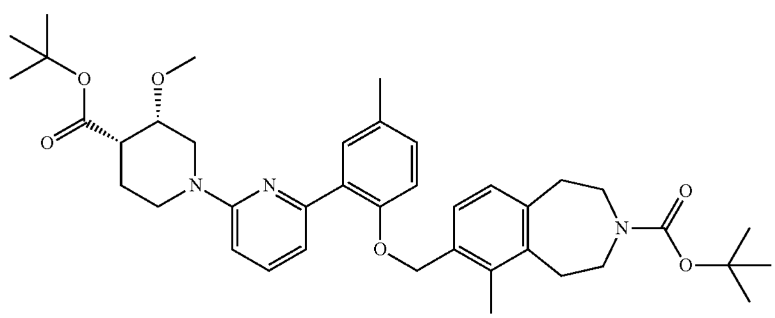 [SMILES: CO[C@@H]1CN(c2cccc(-c3cc(C)ccc3OCc3ccc4c(c3C)CCN(C(=O)OC(C)(C)C)CC4)n2)CC[C@@H]1C(=O)OC(C)(C)C] |
| E-43 | C-13 | 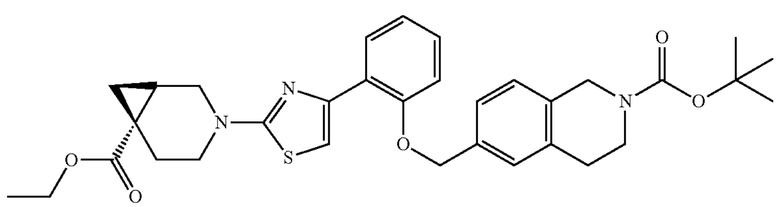 |
| E-44 | C-13 | 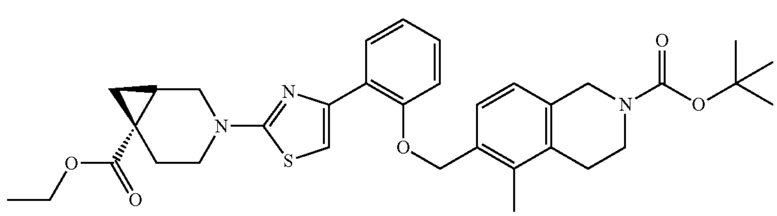 |

| Intermediate | Prepared From | Structure |
|---|---|---|
| E-45 | C-14 | 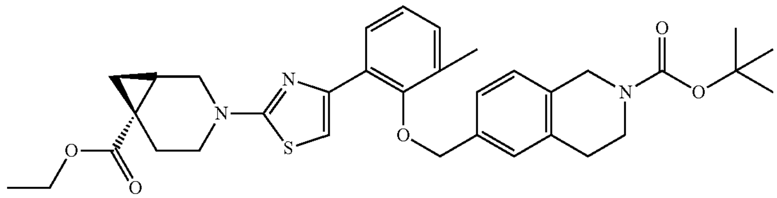 |
| E-46 | C-14 | 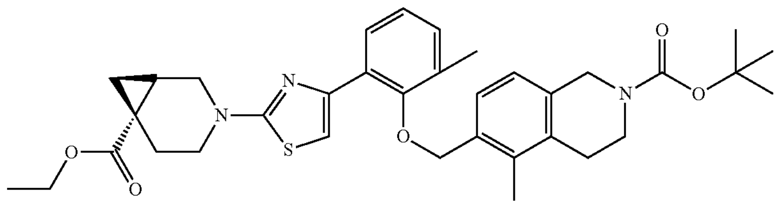 |
| E-47 | C-14 | 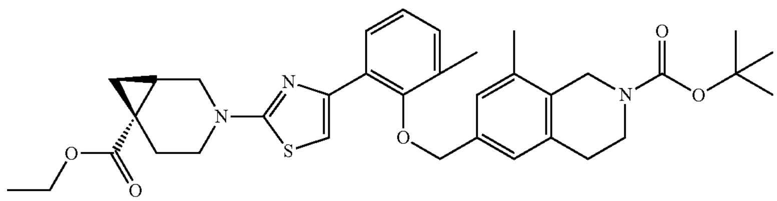 |
| E-48 | C-14 | 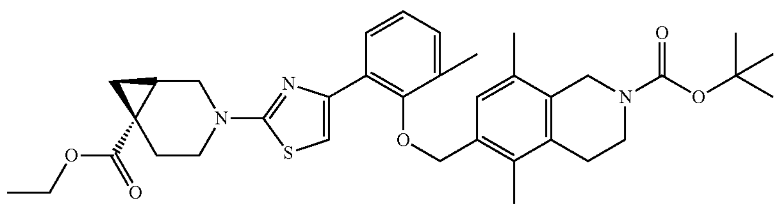 |
| E-49 | C-14 | 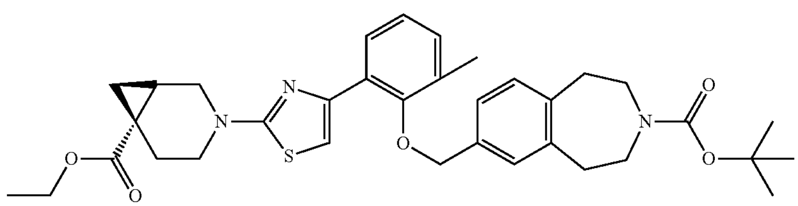 |
| E-50 | C-14 | 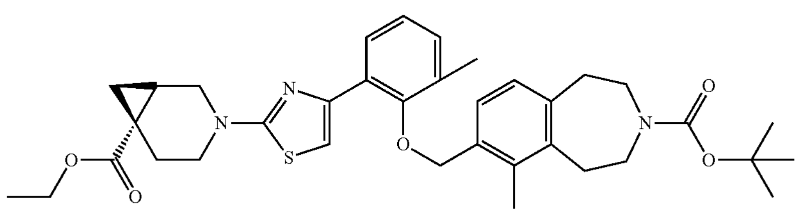 |
| E-51 | C-14 | 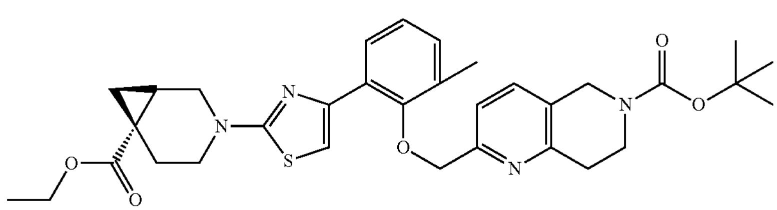 |

-continued

| Intermediate | Prepared From | Structure |
|---|---|---|
| E-52 | C-15 | 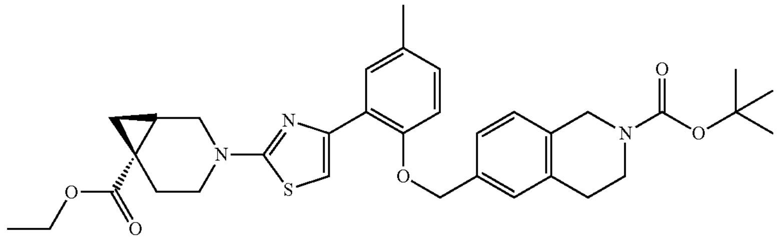 |
| E-53 | C-15 | 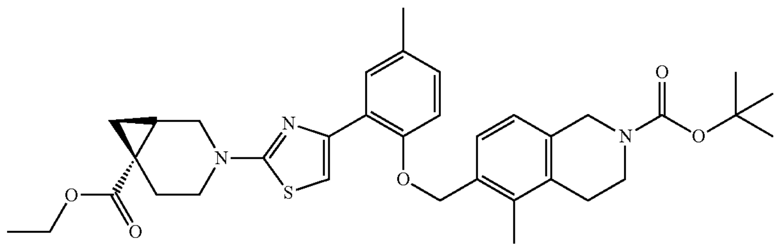 |
| E-54 | C-15 | 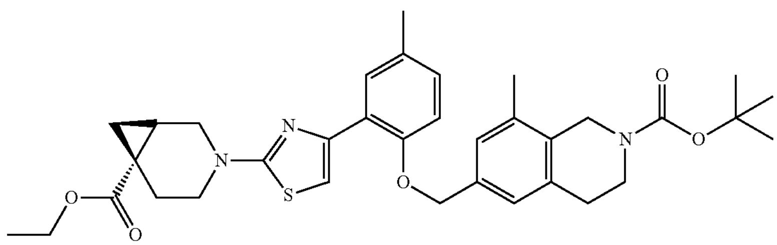 |
| E-55 | C-15 | 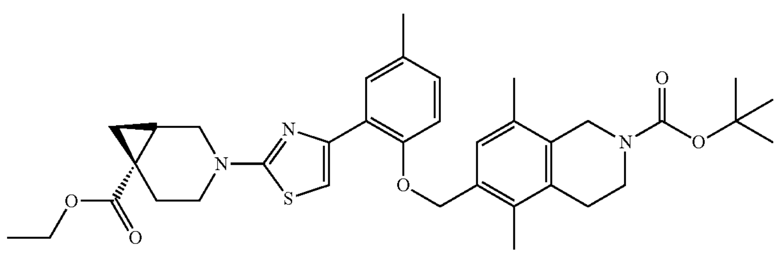 |
| E-56 | C-15 | 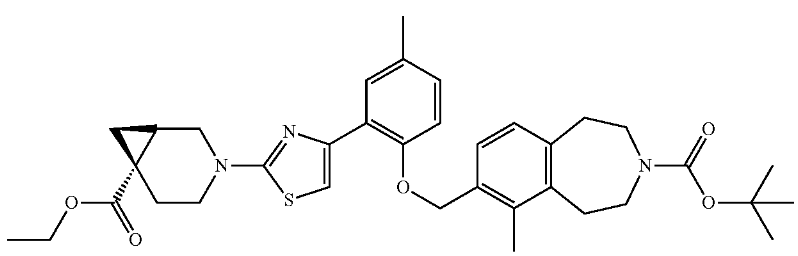 |
| E-57 | C-16 | 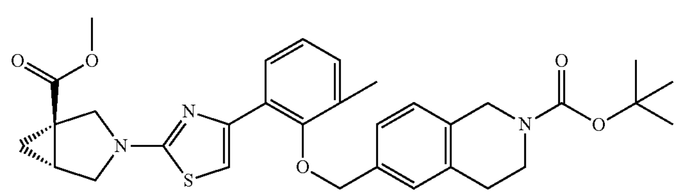 [SMILES: COC(=O)[C@]12C[C@H]1CN(c1nc(-c3cccc(C)c3OCc3ccc4c(c3)CCN(C(=O)OC(C)(C)C)C4)cs1)C2] |

-continued

| Intermediate | Prepared From | Structure |
|---|---|---|
| E-58 | C-16 | 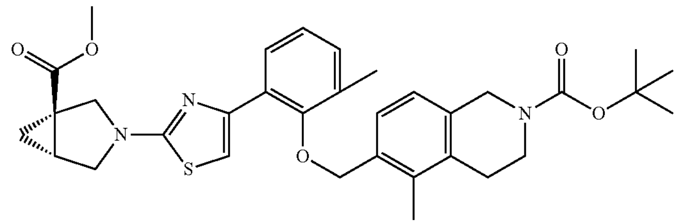 [SMILES: COC(=O)[C@]12C[C@H]1CN(c1nc(-c3cccc(C)c3OCc3ccc4c(c3C)CCN(C(=O)OC(C)(C)C)C4)cs1)C2] |
| E-59 | C-16 | 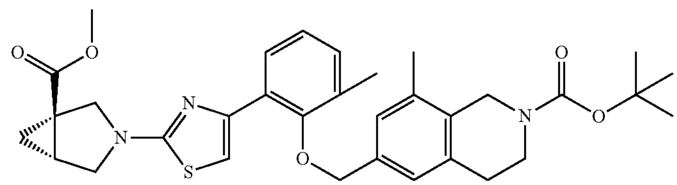 [SMILES: COC(=O)[C@]12C[C@H]1CN(c1nc(-c3cccc(C)c3OCc3cc(C)c4c(c3)CCN(C(=O)OC(C)(C)C)C4)cs1)C2] |
| E-60 | C-16 | 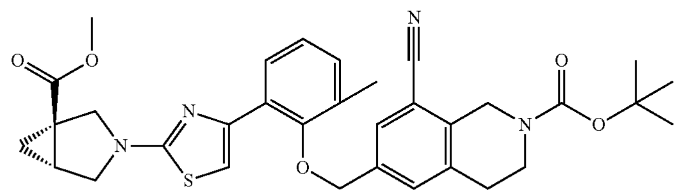 [SMILES: COC(=O)[C@]12C[C@H]1CN(c1nc(-c3cccc(C)c3OCc3cc(C#N)c4c(c3)CCN(C(=O)OC(C)(C)C)C4)cs1)C2] |
| E-61 | C-16 | 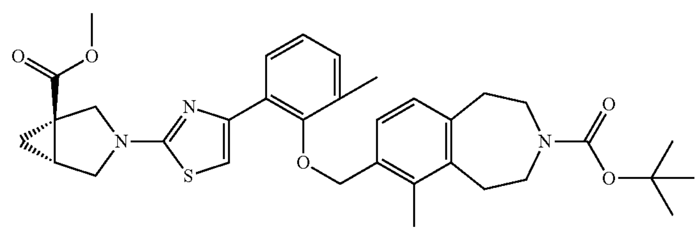 [SMILES: COC(=O)[C@]12C[C@H]1CN(c1nc(-c3cccc(C)c3OCc3ccc4c(c3C)CCN(C(=O)OC(C)(C)C)CC4)cs1)C2] |
| E-62 | C-17 | 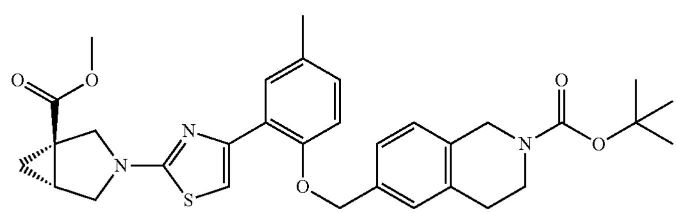 [SMILES: COC(=O)[C@]12C[C@H]1CN(c1nc(-c3cc(C)ccc3OCc3ccc4c(c3)CCN(C(=O)OC(C)(C)C)C4)cs1)C2] |
| E-63 | C-17 | 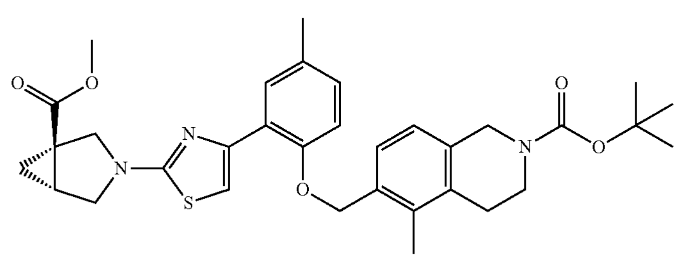 [SMILES: COC(=O)[C@]12C[C@H]1CN(c1nc(-c3cc(C)ccc3OCc3ccc4c(c3C)CCN(C(=O)OC(C)(C)C)C4)cs1)C2] |
| E-64 | C-17 | 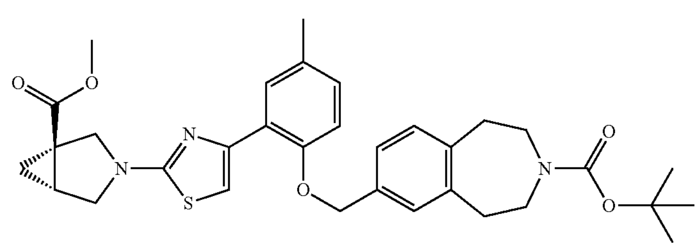 [SMILES: COC(=O)[C@]12C[C@H]1CN(c1nc(-c3cc(C)ccc3OCc3ccc4c(c3)CCN(C(=O)OC(C)(C)C)CC4)cs1)C2] |

-continued
| Intermediate | Prepared From | Structure |
|---|---|---|
| E-65 | C-17 | 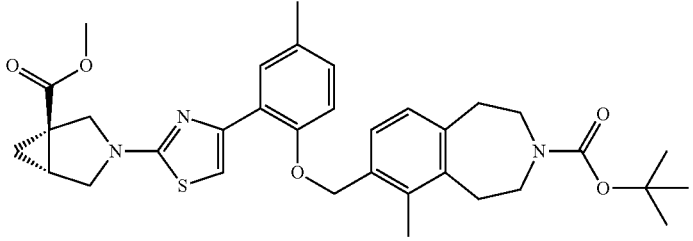 [SMILES: COC(=O)[C@]12C[C@H]1CN(c1nc(-c3cc(C)ccc3OCc3ccc4c(c3C)CCN(C(=O)OC(C)(C)C)CC4)cs1)C2] |
| E-66 | C-18 | 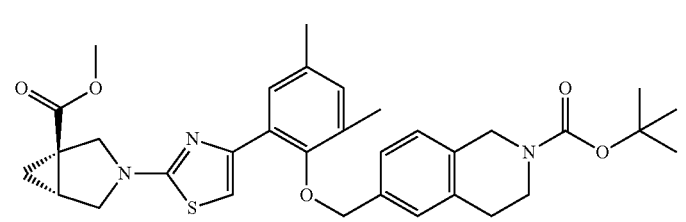 [SMILES: COC(=O)[C@]12C[C@H]1CN(c1nc(-c3cc(C)cc(C)c3OCc3ccc4c(c3)CCN(C(=O)OC(C)(C)C)C4)cs1)C2] |
| E-67 | C-18 | 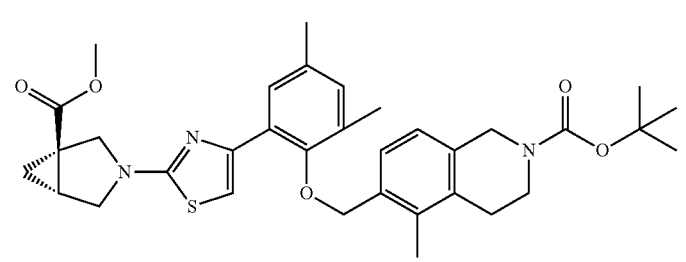 [SMILES: COC(=O)[C@]12C[C@H]1CN(c1nc(-c3cc(C)cc(C)c3OCc3ccc4c(c3C)CCN(C(=O)OC(C)(C)C)C4)cs1)C2] |
| E-68 | C-19 | 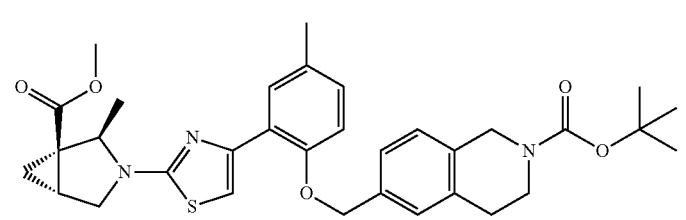 [SMILES: COC(=O)[C@]12C[C@H]1CN(c1nc(-c3cc(C)ccc3OCc3ccc4c(c3)CCN(C(=O)OC(C)(C)C)C4)cs1)[C@@H]2C] |
| E-69 | C-19 | 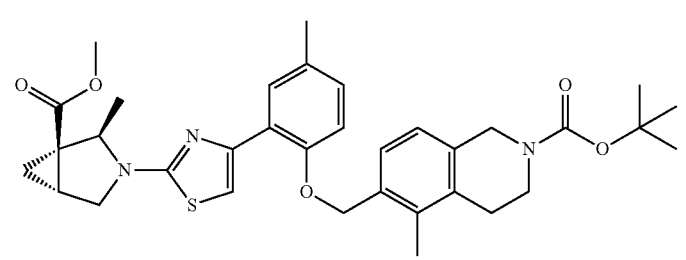 [SMILES: COC(=O)[C@]12C[C@H]1CN(c1nc(-c3cc(C)ccc3OCc3ccc4c(c3C)CCN(C(=O)OC(C)(C)C)C4)cs1)[C@@H]2C] |
| E-70 | C-20 | 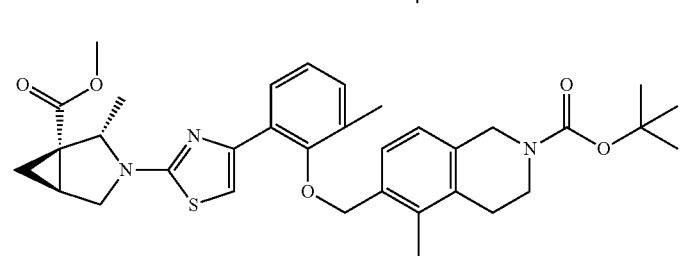 |

| Intermediate | Prepared From | Structure |
|---|---|---|
| E-71 | C-20 | 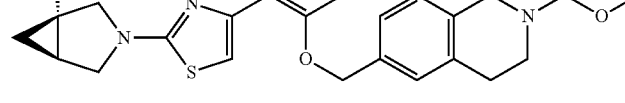 |
| E-72 | C-21 | 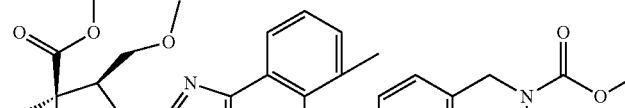 |
| E-73 | C-21 | 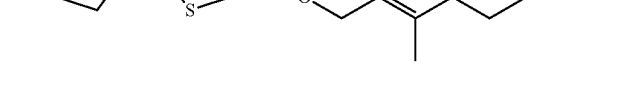 |
| E-74 | C-22 | 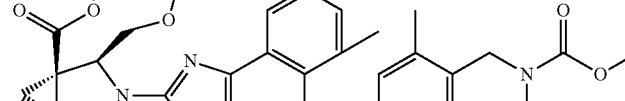 |
| E-75 | C-22 | 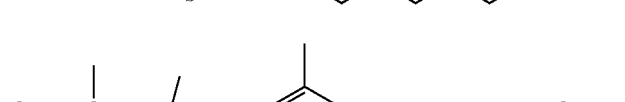 |
| E-76 | C-23 | 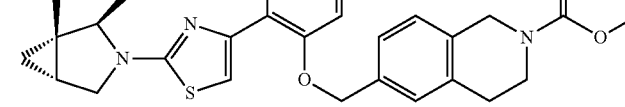 |
| E-77 | C-23 | 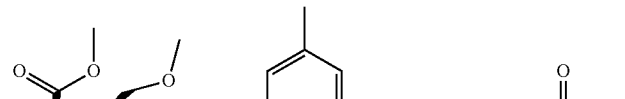 |

-continued

| Intermediate | Prepared From | Structure |
|---|---|---|
| E-78 | C-23 | 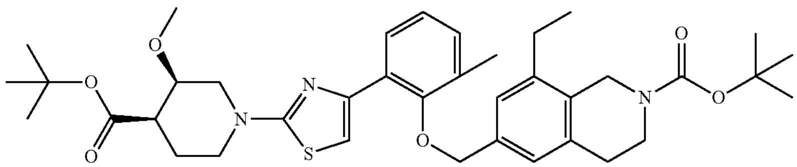 [SMILES: CCc1cc(COc2c(C)cccc2-c2csc(N3CC[C@@H](C(=O)OC(C)(C)C)[C@@H](OC)C3)n2)cc2c1CN(C(=O)OC(C)(C)C)CC2] |
| E-79 | C-23 | 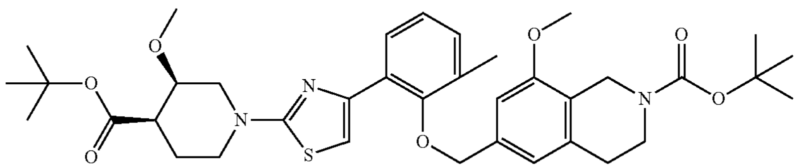 [SMILES: COc1cc(COc2c(C)cccc2-c2csc(N3CC[C@@H](C(=O)OC(C)(C)C)[C@@H](OC)C3)n2)cc2c1CN(C(=O)OC(C)(C)C)CC2] |
| E-80 | C-23 | 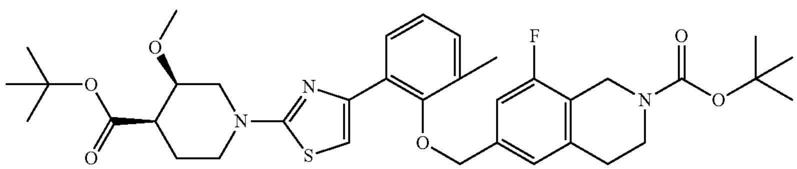 [SMILES: CO[C@H]1CN(c2nc(-c3cccc(C)c3OCc3cc(F)c4c(c3)CCN(C(=O)OC(C)(C)C)C4)cs2)CC[C@H]1C(=O)OC(C)(C)C] |
| E-81 | C-24 | 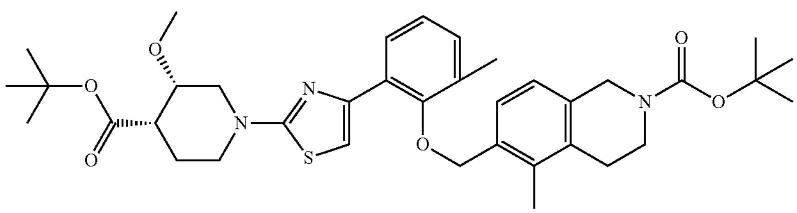 [SMILES: CO[C@@H]1CN(c2nc(-c3cccc(C)c3OCc3ccc4c(c3C)CCN(C(=O)OC(C)(C)C)C4)cs2)CC[C@@H]1C(=O)OC(C)(C)C] |
| E-82 | C-24 | 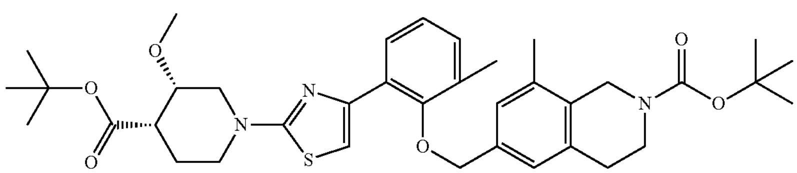 [SMILES: CO[C@@H]1CN(c2nc(-c3cccc(C)c3OCc3cc(C)c4c(c3)CCN(C(=O)OC(C)(C)C)C4)cs2)CC[C@@H]1C(=O)OC(C)(C)C] |
| E-83 | C-24 | 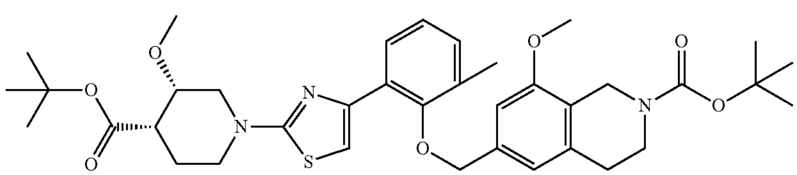 [SMILES: COc1cc(COc2c(C)cccc2-c2csc(N3CC[C@H](C(=O)OC(C)(C)C)[C@H](OC)C3)n2)cc2c1CN(C(=O)OC(C)(C)C)CC2] |
| E-84 | C-25 | 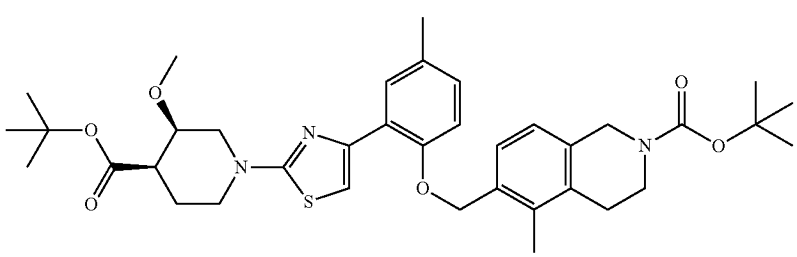 [SMILES: CO[C@H]1CN(c2nc(-c3cc(C)ccc3OCc3ccc4c(c3C)CCN(C(=O)OC(C)(C)C)C4)cs2)CC[C@H]1C(=O)OC(C)(C)C] |
| E-85 | C-25 | 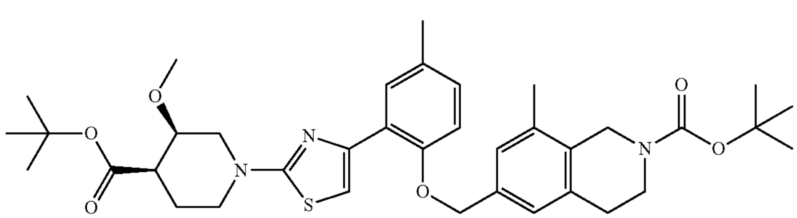 [SMILES: CO[C@H]1CN(c2nc(-c3cc(C)ccc3OCc3cc(C)c4c(c3)CCN(C(=O)OC(C)(C)C)C4)cs2)CC[C@H]1C(=O)OC(C)(C)C] |

-continued

| Intermediate | Prepared From | Structure |
|---|---|---|
| E-86 | C-25 | 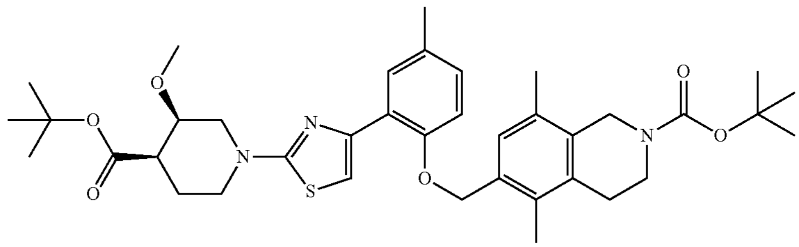 [SMILES: CO[C@H]1CN(c2nc(-c3cc(C)ccc3OCc3cc(C)c4c(c3C)CCN(C(=O)OC(C)(C)C)C4)cs2)CC[C@H]1C(=O)OC(C)(C)C] |
| E-87 | C-25 | 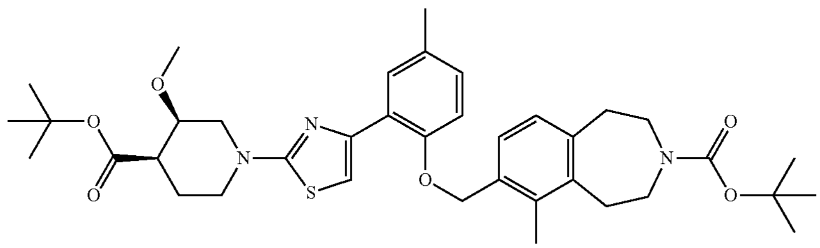 [SMILES: CO[C@H]1CN(c2nc(-c3cc(C)ccc3OCc3ccc4c(c3C)CCN(C(=O)OC(C)(C)C)CC4)cs2)CC[C@H]1C(=O)OC(C)(C)C] |
| E-88 | C-27 | 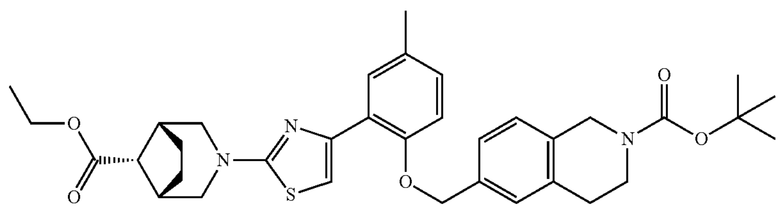 [SMILES: CCOC(=O)[C@H]1[C@@H]2CC[C@H]1CN(c1nc(-c3cc(C)ccc3OCc3ccc4c(c3)CCN(C(=O)OC(C)(C)C)C4)cs1)C2] |
| E-89 | C-29 | 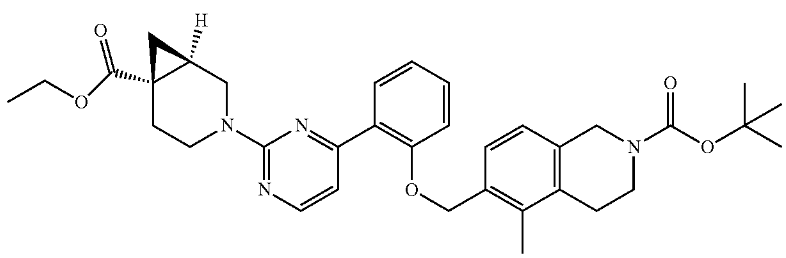 [SMILES: CCOC(=O)[C@@]12CCN(c3nccc(-c4ccccc4OCc4ccc5c(c4C)CCN(C(=O)OC(C)(C)C)C5)n3)C[C@@H]1C2] |
| E-90 | C-29 | 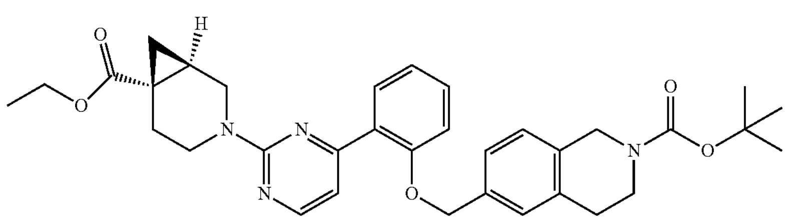 [SMILES: CCOC(=O)[C@@]12CCN(c3nccc(-c4ccccc4OCc4ccc5c(c4)CCN(C(=O)OC(C)(C)C)C5)n3)C[C@@H]1C2] |
| E-91 | C-30 | 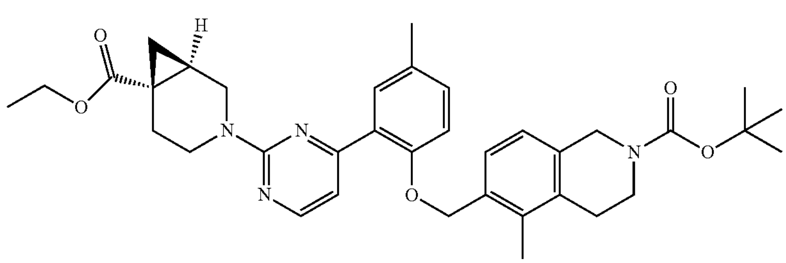 [SMILES: CCOC(=O)[C@@]12CCN(c3nccc(-c4cc(C)ccc4OCc4ccc5c(c4C)CCN(C(=O)OC(C)(C)C)C5)n3)C[C@@H]1C2] |

-continued

| Intermediate | Prepared From | Structure |
|---|---|---|
| E-92 | C-31 | 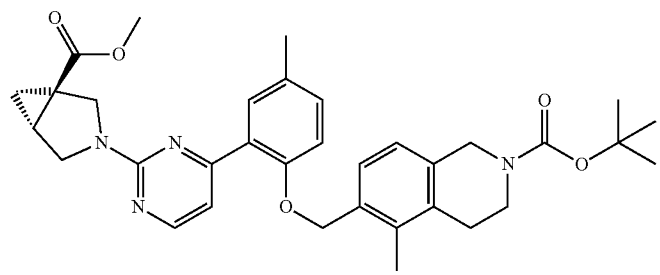 |
| E-93 | C-32 | 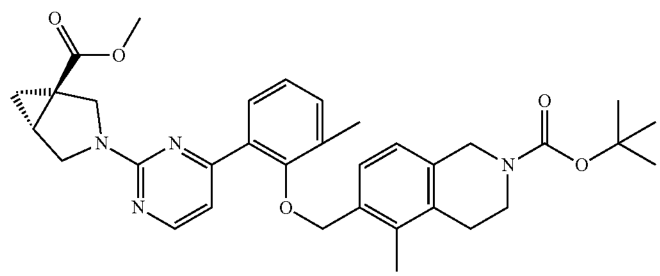 |
| E-94 | C-32 | 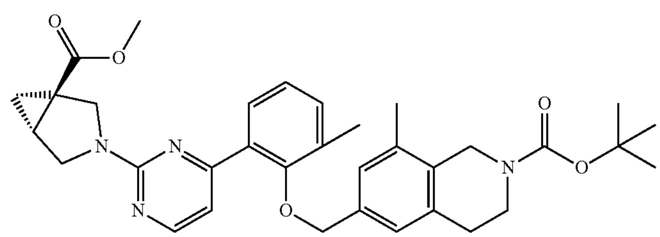 |
| E-96 | C-15 | 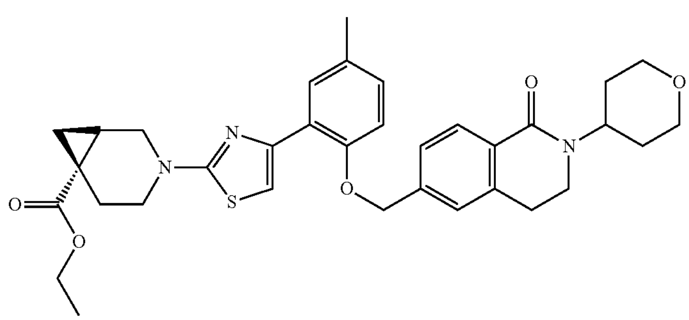 |
| E-97 | C-3 | 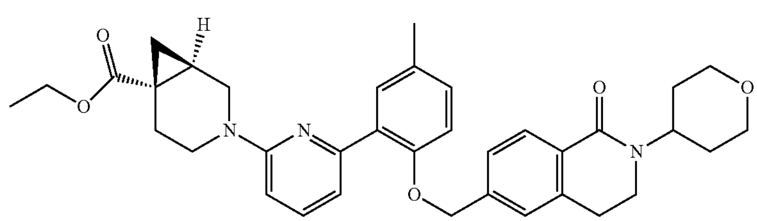 [SMILES: CCOC(=O)[C@@]12CCN(c3cccc(-c4cc(C)ccc4OCc4ccc5c(c4)CCN(C4CCOCC4)C5=O)n3)C[C@@H]1C2] |

-continued
| Intermediate | Prepared From | Structure |
|---|---|---|
| E-98 | C-10 | 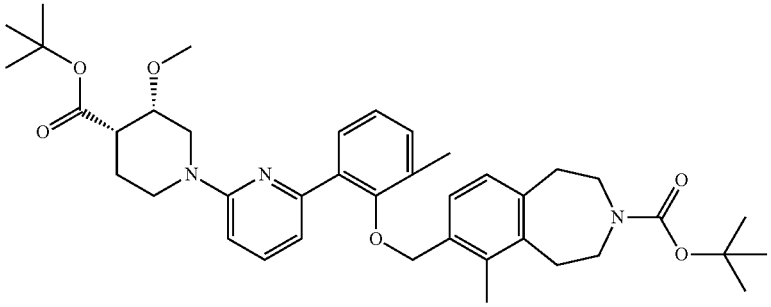 [SMILES: CO[C@@H]1CN(c2cccc(-c3cccc(C)c3OCc3ccc4c(c3C)CCN(C(=O)OC(C)(C)C)CC4)n2)CC[C@@H]1C(=O)OC(C)(C)C] |
| E-99 | C-9 | 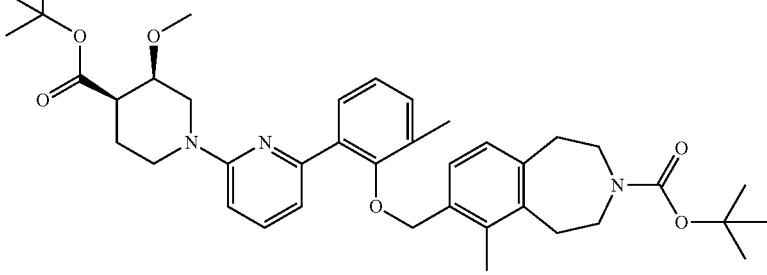 |
| E-100 | C-33 | 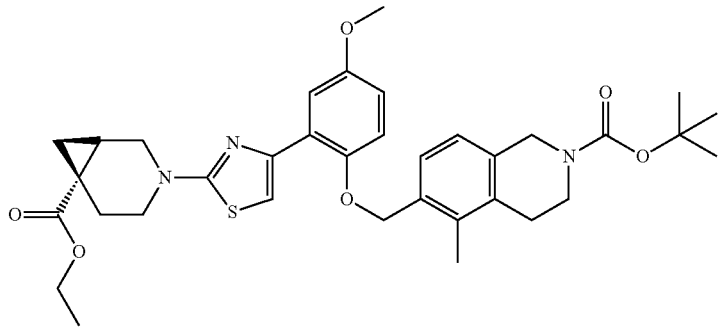 |
| E-101 | C-6 | 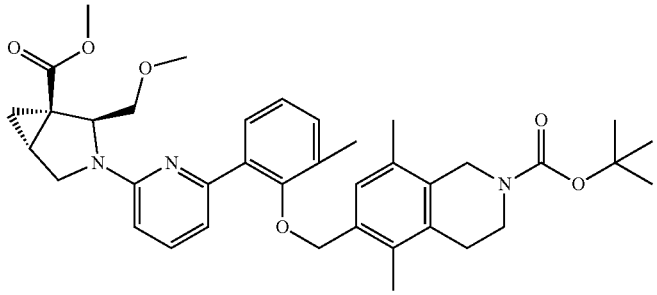 [SMILES: COC[C@H]1N(c2cccc(-c3cccc(C)c3OCc3cc(C)c4c(c3C)CCN(C(=O)OC(C)(C)C)C4)n2)C[C@@H]2C[C@@]21C(=O)OC] |
| E-102 | C-6 | 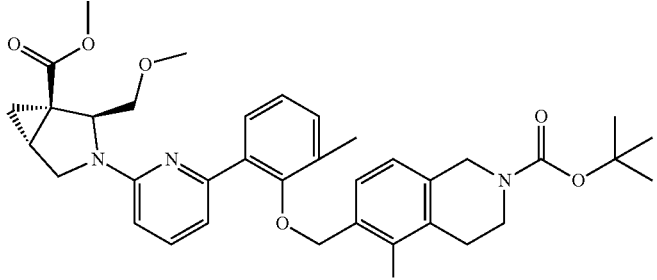 |

-continued
| Intermediate | Prepared From | Structure |
|---|---|---|
| E-103 | C-6 | 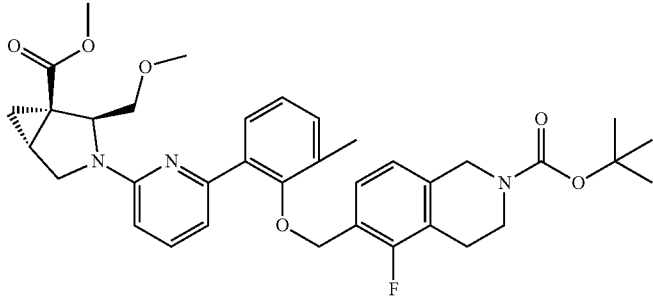 [SMILES: COC[C@H]1N(c2cccc(-c3cccc(C)c3OCc3ccc4c(c3F)CCN(C(=O)OC(C)(C)C)C4)n2)C[C@@H]2C[C@@]21C(=O)OC] |
| E-104 | C-6 | 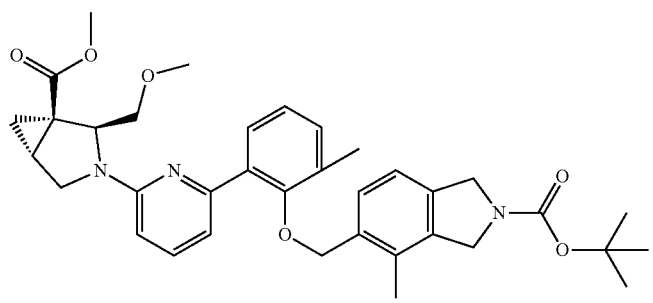 [SMILES: COC[C@H]1N(c2cccc(-c3cccc(C)c3OCc3ccc4c(c3C)CN(C(=O)OC(C)(C)C)C4)n2)C[C@@H]2C[C@@]21C(=O)OC] |
| E-105 | C-6 | 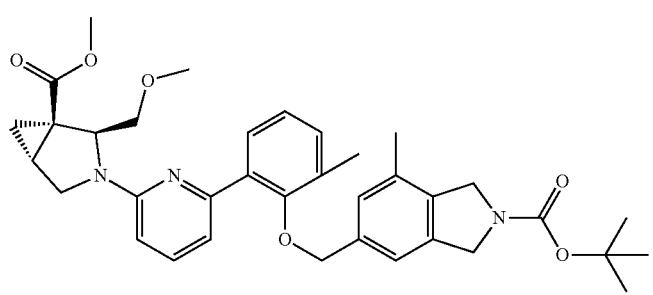 [SMILES: COC[C@H]1N(c2cccc(-c3cccc(C)c3OCc3cc(C)c4c(c3)CN(C(=O)OC(C)(C)C)C4)n2)C[C@@H]2C[C@@]21C(=O)OC] |
| E-106 | C-6 | 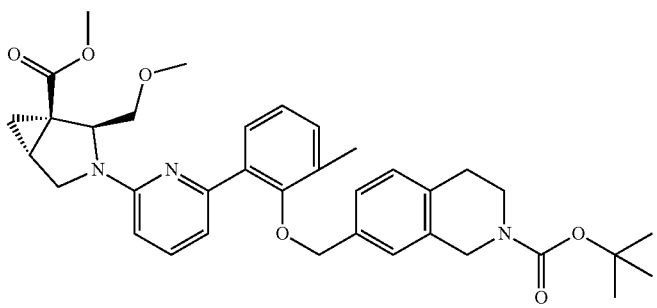 [SMILES: COC[C@H]1N(c2cccc(-c3cccc(C)c3OCc3ccc4c(c3)CN(C(=O)OC(C)(C)C)CC4)n2)C[C@@H]2C[C@@]21C(=O)OC] |
| E-107 | C-6 | 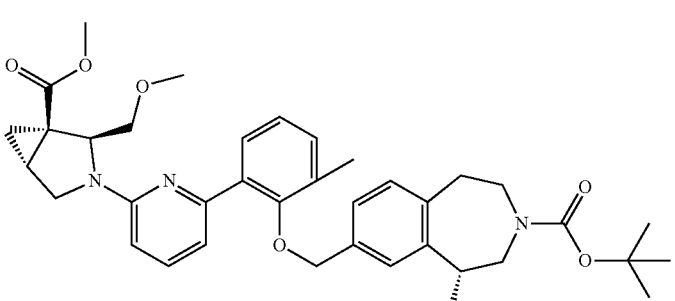 |

-continued

| Intermediate | Prepared From | Structure |
|---|---|---|
| E-108 | C-6 | 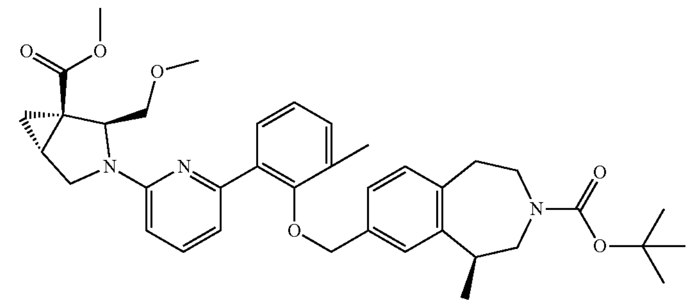 [SMILES: COC[C@H]1N(c2cccc(-c3cccc(C)c3OCc3ccc4c(c3)[C@H](C)CN(C(=O)OC(C)(C)C)CC4)n2)C[C@@H]2C[C@@]21C(=O)OC] |
| E-109 | C-6 | 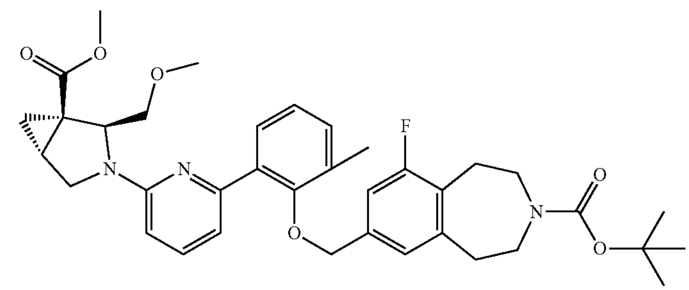 [SMILES: COC[C@H]1N(c2cccc(-c3cccc(C)c3OCc3cc(F)c4c(c3)CCN(C(=O)OC(C)(C)C)CC4)n2)C[C@@H]2C[C@@]21C(=O)OC] |
| E-110 | C-6 | 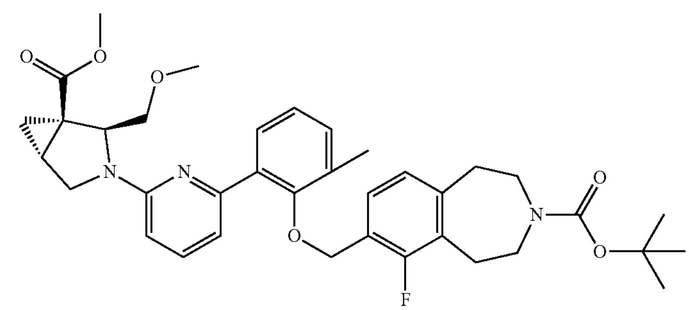 [SMILES: COC[C@H]1N(c2cccc(-c3cccc(C)c3OCc3ccc4c(c3F)CCN(C(=O)OC(C)(C)C)CC4)n2)C[C@@H]2C[C@@]21C(=O)OC] |
| E-111 | C-6 | 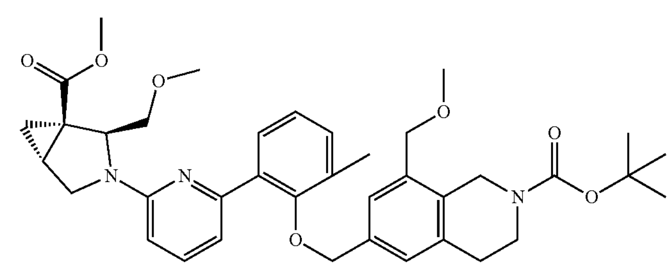 [SMILES: COCc1cc(COc2c(C)cccc2-c2cccc(N3C[C@@H]4C[C@]4(C(=O)OC)[C@H]3COC)n2)cc2c1CN(C(=O)OC(C)(C)C)CC2] |
| E-112 | C-6 | 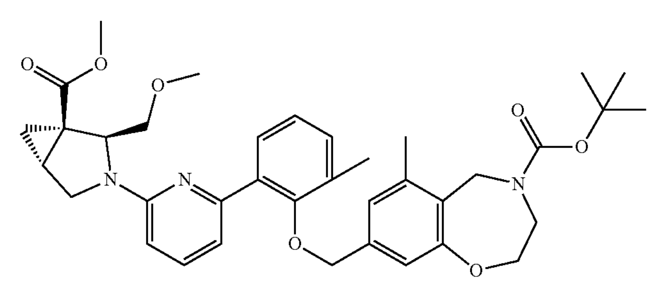 [SMILES: COC[C@H]1N(c2cccc(-c3cccc(C)c3OCc3cc(C)c4c(c3)OCCN(C(=O)OC(C)(C)C)C4)n2)C[C@@H]2C[C@@]21C(=O)OC] |

| Intermediate | Prepared From | Structure |
|---|---|---|
| E-113 | C-6 | 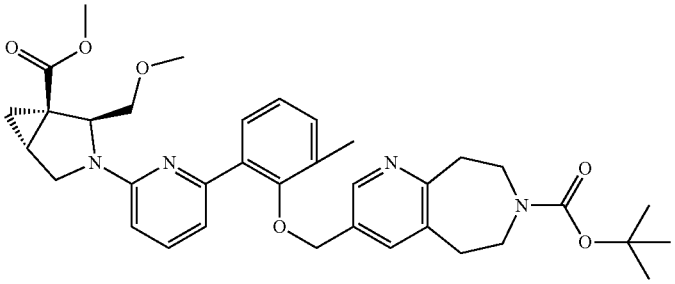 [SMILES: COC[C@H]1N(c2cccc(-c3cccc(C)c3OCc3cnc4c(c3)CCN(C(=O)OC(C)(C)C)CC4)n2)C[C@@H]2C[C@@]21C(=O)OC] |
| E-114 | C-6 | 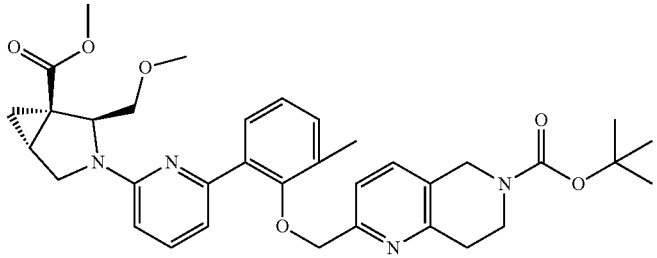 [SMILES: COC[C@H]1N(c2cccc(-c3cccc(C)c3OCc3ccc4c(n3)CCN(C(=O)OC(C)(C)C)C4)n2)C[C@@H]2C[C@@]21C(=O)OC] |
| E-115 | C-9 | 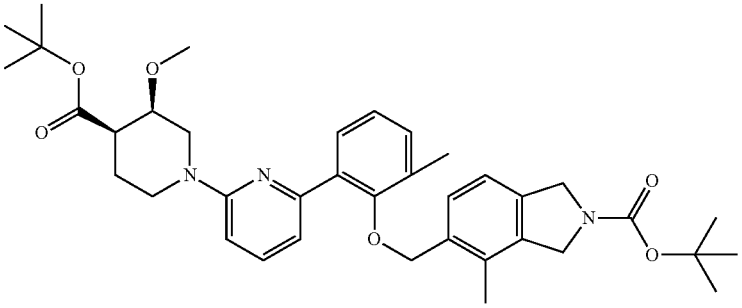 [SMILES: CO[C@H]1CN(c2cccc(-c3cccc(C)c3OCc3ccc4c(c3C)CN(C(=O)OC(C)(C)C)C4)n2)CC[C@H]1C(=O)OC(C)(C)C] |
| E-116 | C-9 | 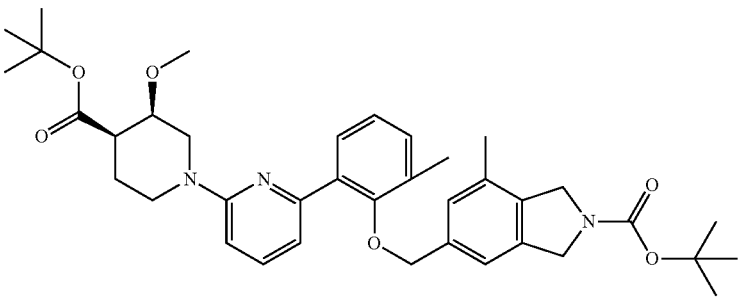 [SMILES: CO[C@H]1CN(c2cccc(-c3cccc(C)c3OCc3cc(C)c4c(c3)CN(C(=O)OC(C)(C)C)C4)n2)CC[C@H]1C(=O)OC(C)(C)C] |
| E-117 | C-9 | 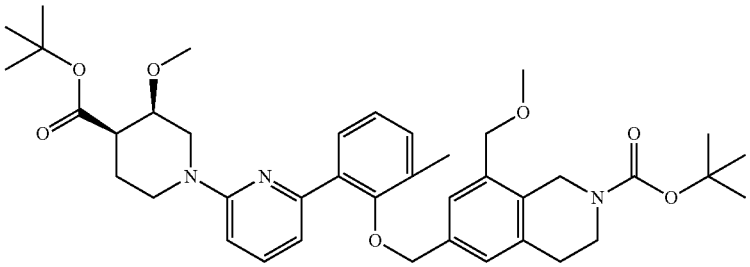 [SMILES: COCc1cc(COc2c(C)cccc2-c2cccc(N3CC[C@@H](C(=O)OC(C)(C)C)[C@@H](OC)C3)n2)cc2c1CN(C(=O)OC(C)(C)C)CC2] |

-continued

| Intermediate | Prepared From | Structure |
|---|---|---|
| E-118 | C-9 | 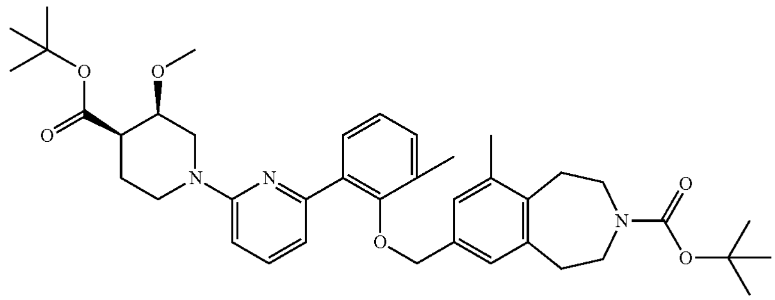 [SMILES: CO[C@H]1CN(c2cccc(-c3cccc(C)c3OCc3cc(C)c4c(c3)CCN(C(=O)OC(C)(C)C)CC4)n2)CC[C@H]1C(=O)OC(C)(C)C] |
| E-119 | C-10 | 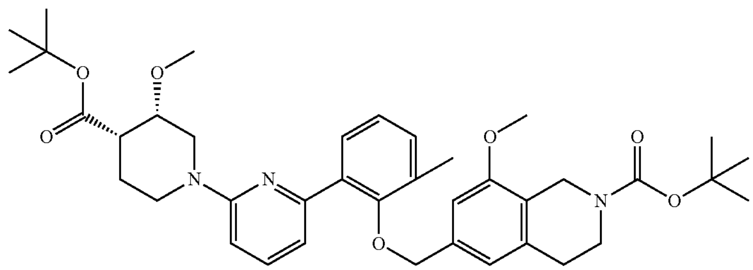 [SMILES: COc1cc(COc2c(C)cccc2-c2cccc(N3CC[C@H](C(=O)OC(C)(C)C)[C@H](OC)C3)n2)cc2c1CN(C(=O)OC(C)(C)C)CC2] |
| E-120 | C-10 | 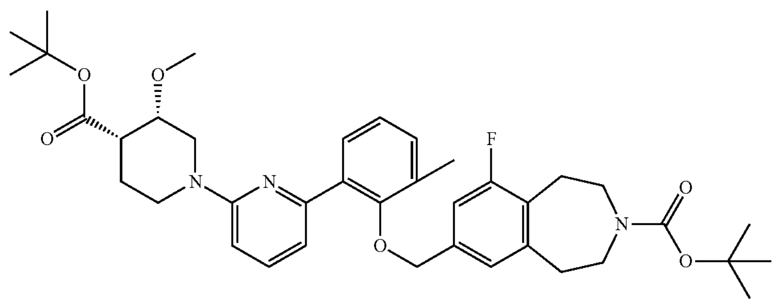 [SMILES: CO[C@@H]1CN(c2cccc(-c3cccc(C)c3OCc3cc(F)c4c(c3)CCN(C(=O)OC(C)(C)C)CC4)n2)CC[C@@H]1C(=O)OC(C)(C)C] |
| E-121 | C-10 | 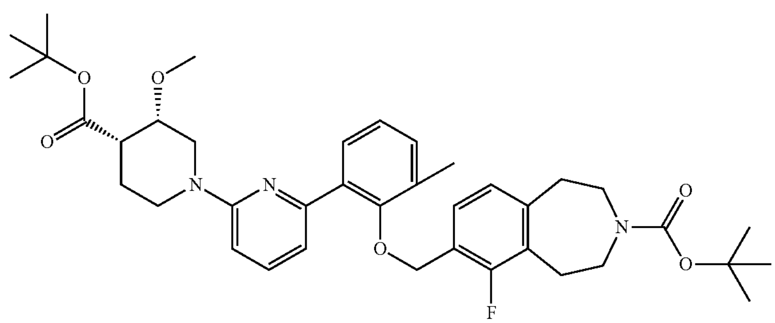 [SMILES: CO[C@@H]1CN(c2cccc(-c3cccc(C)c3OCc3ccc4c(c3F)CCN(C(=O)OC(C)(C)C)CC4)n2)CC[C@@H]1C(=O)OC(C)(C)C] |
| E-122 | C-9 | 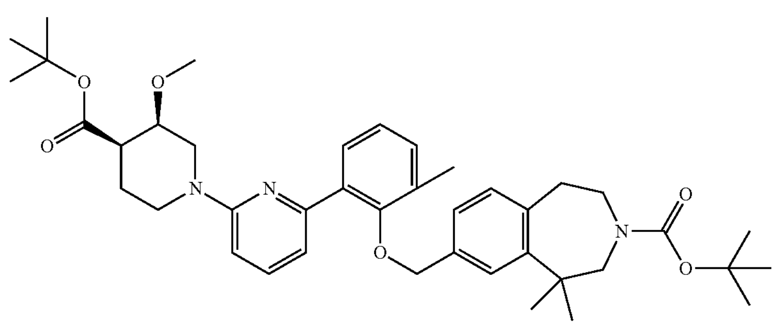 [SMILES: CO[C@H]1CN(c2cccc(-c3cccc(C)c3OCc3ccc4c(c3)C(C)(C)CN(C(=O)OC(C)(C)C)CC4)n2)CC[C@H]1C(=O)OC(C)(C)C] |

-continued

| Intermediate | Prepared From | Structure |
|---|---|---|
| E-123 | C-15 | 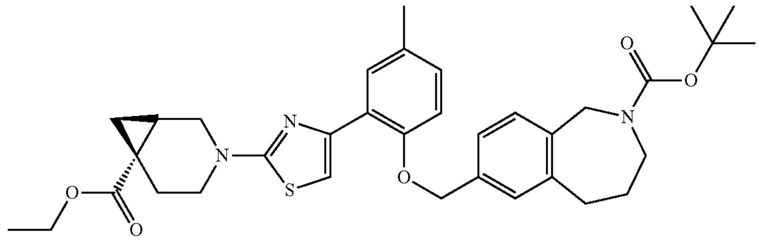 |
| E-124 | C-23 | 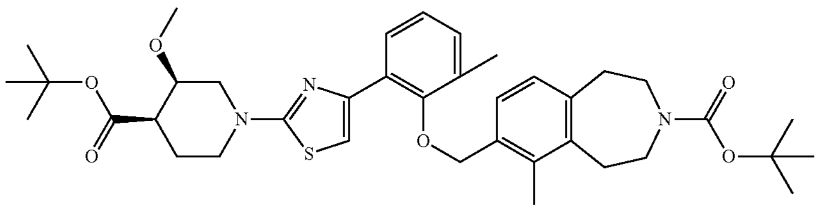 [SMILES: CO[C@H]1CN(c2nc(-c3cccc(C)c3OCc3ccc4c(c3C)CCN(C(=O)OC(C)(C)C)CC4)cs2)CC[C@H]1C(=O)OC(C)(C)C] |
| E-125 | C-23 | 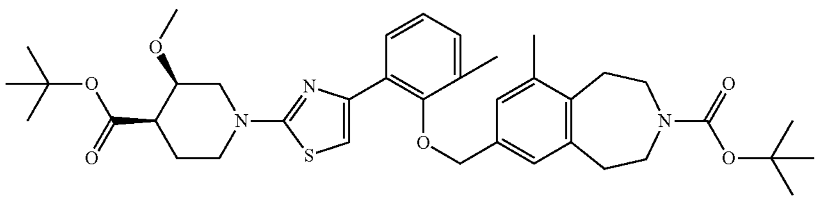 [SMILES: CO[C@H]1CN(c2nc(-c3cccc(C)c3OCc3cc(C)c4c(c3)CCN(C(=O)OC(C)(C)C)CC4)cs2)CC[C@H]1C(=O)OC(C)(C)C] |
| E-126 | C-23 | 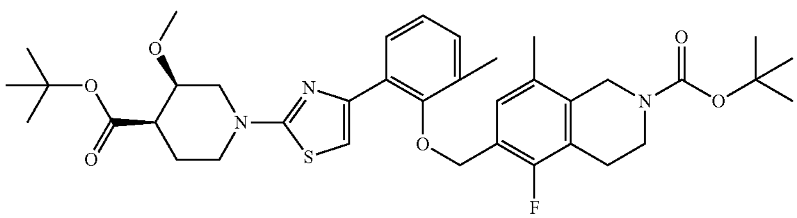 [SMILES: CO[C@H]1CN(c2nc(-c3cccc(C)c3OCc3cc(C)c4c(c3F)CCN(C(=O)OC(C)(C)C)C4)cs2)CC[C@H]1C(=O)OC(C)(C)C] |
| E-127 | C-23 | 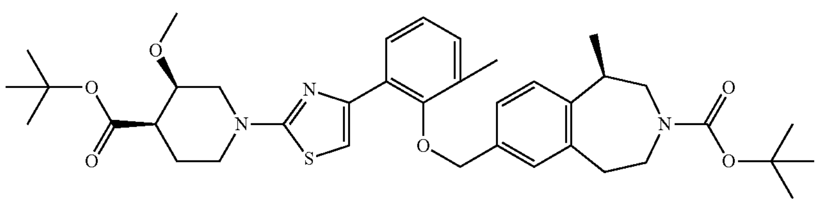 [SMILES: CO[C@H]1CN(c2nc(-c3cccc(C)c3OCc3ccc4c(c3)CCN(C(=O)OC(C)(C)C)C[C@@H]4C)cs2)CC[C@H]1C(=O)OC(C)(C)C] |
| E-128 | C-23 | 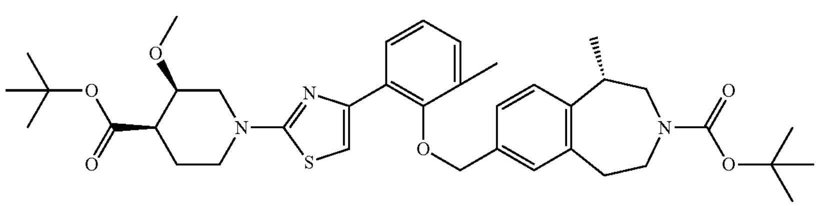 [SMILES: CO[C@H]1CN(c2nc(-c3cccc(C)c3OCc3ccc4c(c3)CCN(C(=O)OC(C)(C)C)C[C@H]4C)cs2)CC[C@H]1C(=O)OC(C)(C)C] |
| E-129 | C-24 | 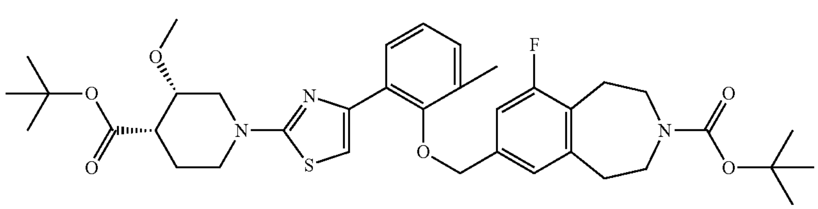 [SMILES: CO[C@@H]1CN(c2nc(-c3cccc(C)c3OCc3cc(F)c4c(c3)CCN(C(=O)OC(C)(C)C)CC4)cs2)CC[C@@H]1C(=O)OC(C)(C)C] |

-continued

| Intermediate | Prepared From | Structure |
|---|---|---|
| E-130 | C-24 | 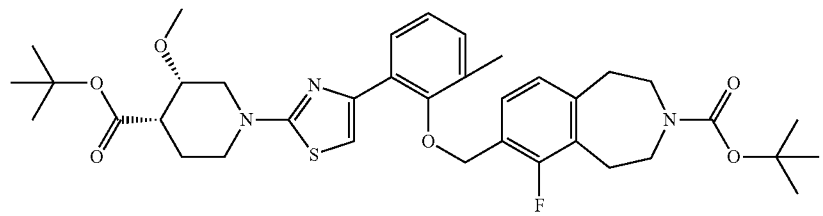 [SMILES: CO[C@@H]1CN(c2nc(-c3cccc(C)c3OCc3ccc4c(c3F)CCN(C(=O)OC(C)(C)C)CC4)cs2)CC[C@@H]1C(=O)OC(C)(C)C] |
| E-131 | C-24 | 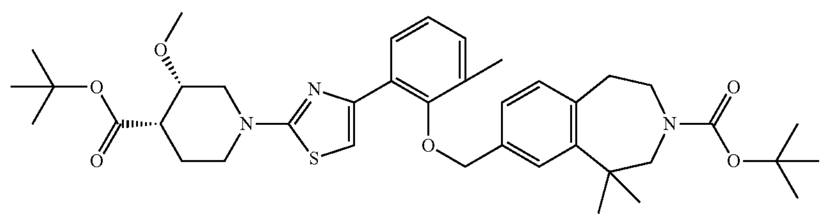 [SMILES: CO[C@@H]1CN(c2nc(-c3cccc(C)c3OCc3ccc4c(c3)C(C)(C)CN(C(=O)OC(C)(C)C)CC4)cs2)CC[C@@H]1C(=O)OC(C)(C)C] |
| E-132 | C-25 | 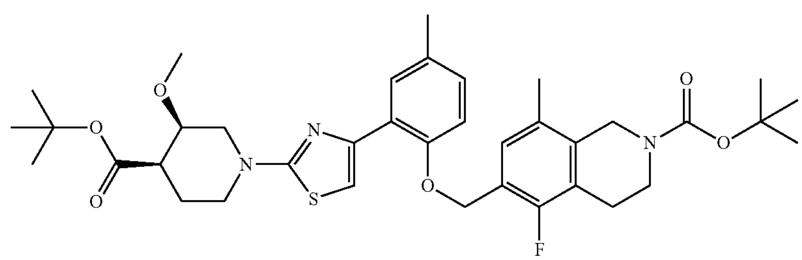 [SMILES: CO[C@H]1CN(c2nc(-c3cc(C)ccc3OCc3cc(C)c4c(c3F)CCN(C(=O)OC(C)(C)C)C4)cs2)CC[C@H]1C(=O)OC(C)(C)C] |
| E-133 | C-25 | 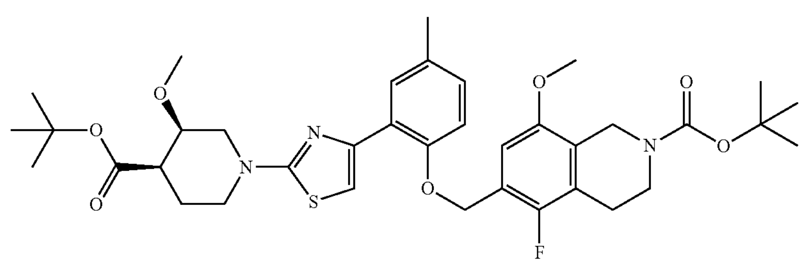 [SMILES: COc1cc(COc2ccc(C)cc2-c2csc(N3CC[C@@H](C(=O)OC(C)(C)C)[C@@H](OC)C3)n2)c(F)c2c1CN(C(=O)OC(C)(C)C)CC2] |
| E-134 | C-23 | 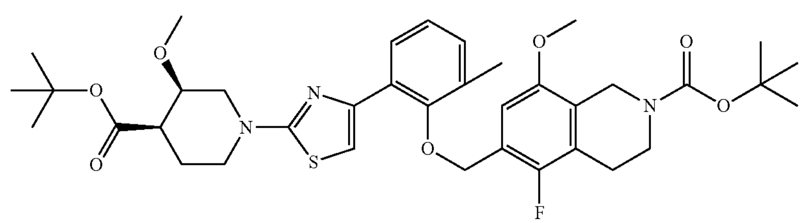 [SMILES: COc1cc(COc2c(C)cccc2-c2csc(N3CC[C@@H](C(=O)OC(C)(C)C)[C@@H](OC)C3)n2)c(F)c2c1CN(C(=O)OC(C)(C)C)CC2] |
| E-135 | C-25 | 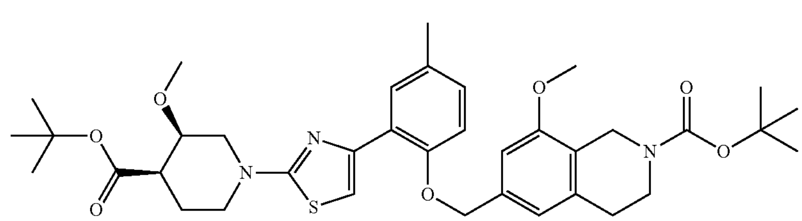 [SMILES: COc1cc(COc2ccc(C)cc2-c2csc(N3CC[C@@H](C(=O)OC(C)(C)C)[C@@H](OC)C3)n2)cc2c1CN(C(=O)OC(C)(C)C)CC2] |

-continued

| Intermediate | Prepared From | Structure |
|---|---|---|
| E-136 | C-34 | 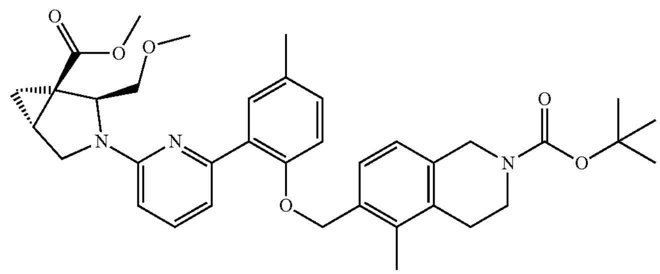 |
| E-137 | C-34 | 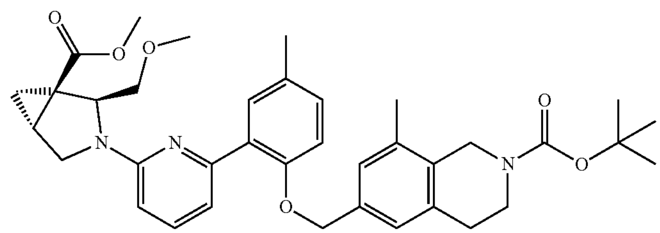 |
| E-138 | C-35 | 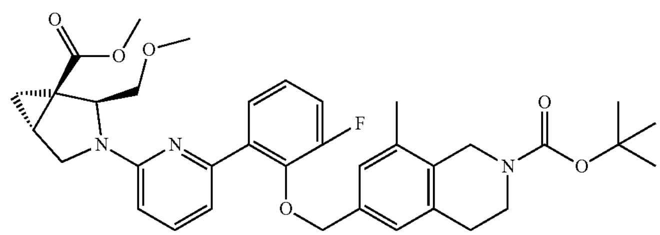 |
| E-139 | C-65 | 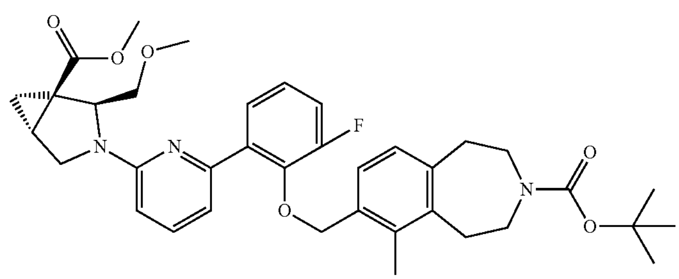 |
| E-140 | C-36 | 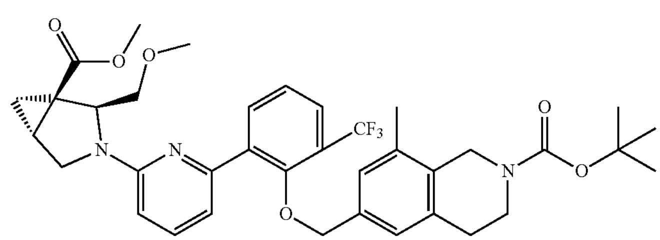 |
| E-141 | C-37 | 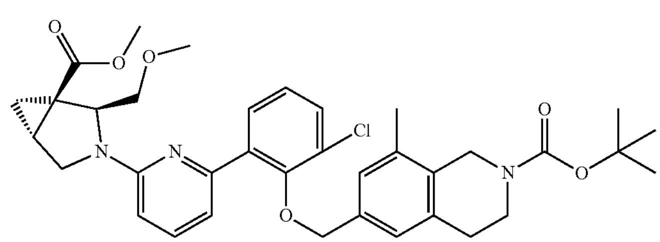 |

| Intermediate | Prepared From | Structure |
|---|---|---|
| E-142 | C-46 | 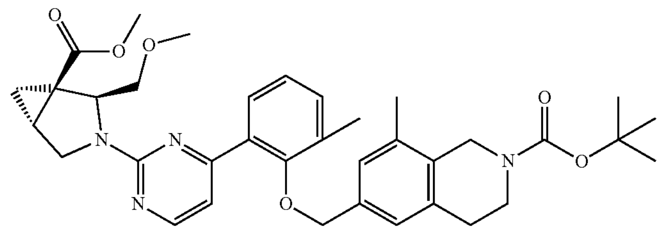 |
| E-143 | C-38 | 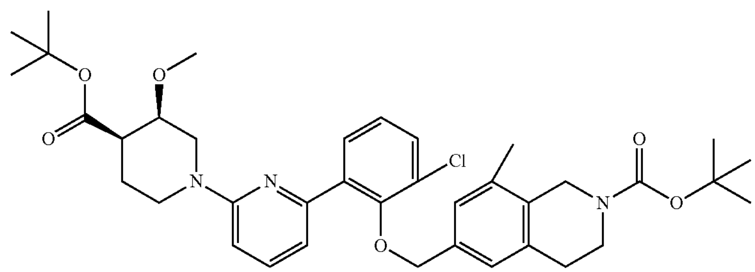 [SMILES: CO[C@H]1CN(c2cccc(-c3cccc(Cl)c3OCc3cc(C)c4c(c3)CCN(C(=O)OC(C)(C)C)C4)n2)CC[C@H]1C(=O)OC(C)(C)C] |
| E-144 | C-38 | 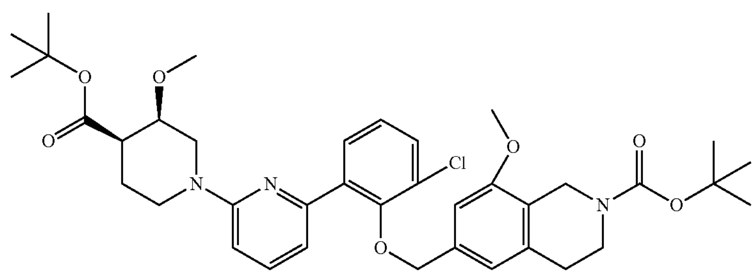 [SMILES: COc1cc(COc2c(Cl)cccc2-c2cccc(N3CC[C@@H](C(=O)OC(C)(C)C)[C@@H](OC)C3)n2)cc2c1CN(C(=O)OC(C)(C)C)CC2] |
| E-145 | C-39 | 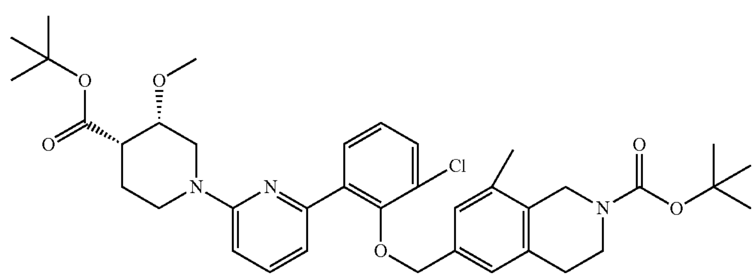 [SMILES: CO[C@@H]1CN(c2cccc(-c3cccc(Cl)c3OCc3cc(C)c4c(c3)CCN(C(=O)OC(C)(C)C)C4)n2)CC[C@@H]1C(=O)OC(C)(C)C] |
| E-146 | C-39 | 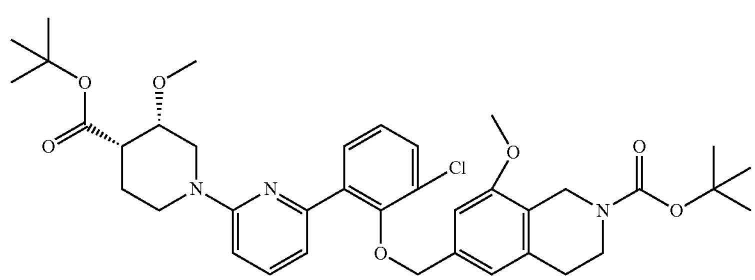 [SMILES: COc1cc(COc2c(Cl)cccc2-c2cccc(N3CC[C@H](C(=O)OC(C)(C)C)[C@H](OC)C3)n2)cc2c1CN(C(=O)OC(C)(C)C)CC2] |

-continued

| Intermediate | Prepared From | Structure |
|---|---|---|
| E-147 | C-40 | 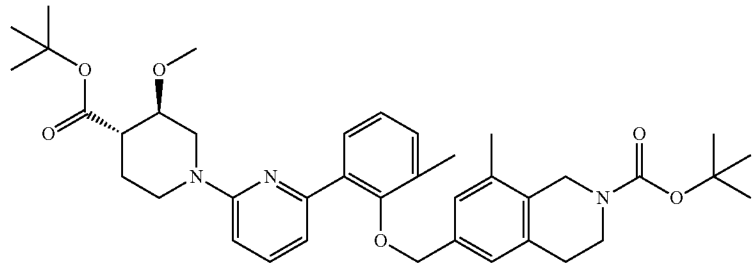 [SMILES: CO[C@H]1CN(c2cccc(-c3cccc(C)c3OCc3cc(C)c4c(c3)CCN(C(=O)OC(C)(C)C)C4)n2)CC[C@@H]1C(=O)OC(C)(C)C] |
| E-148 | C-40 | 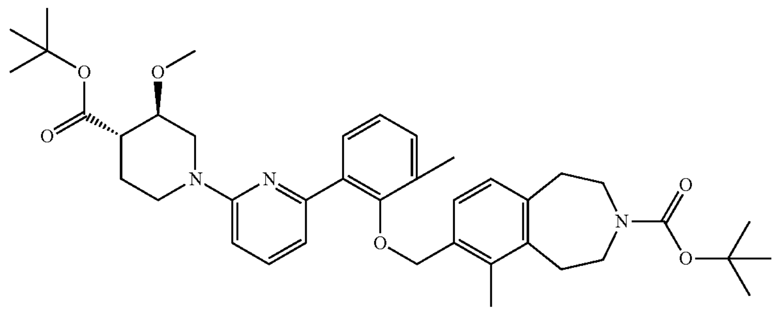 [SMILES: CO[C@H]1CN(c2cccc(-c3cccc(C)c3OCc3ccc4c(c3C)CCN(C(=O)OC(C)(C)C)CC4)n2)CC[C@@H]1C(=O)OC(C)(C)C] |
| E-149 | C-41 | 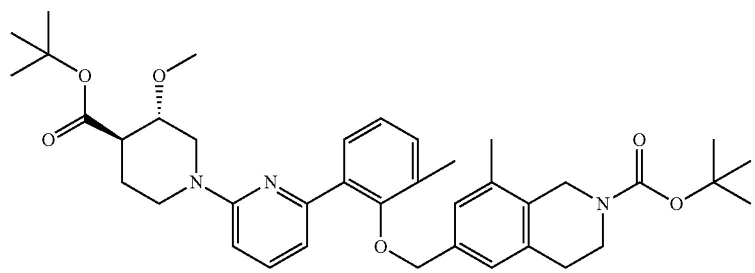 [SMILES: CO[C@@H]1CN(c2cccc(-c3cccc(C)c3OCc3cc(C)c4c(c3)CCN(C(=O)OC(C)(C)C)C4)n2)CC[C@H]1C(=O)OC(C)(C)C] |
| E-150 | C-41 | 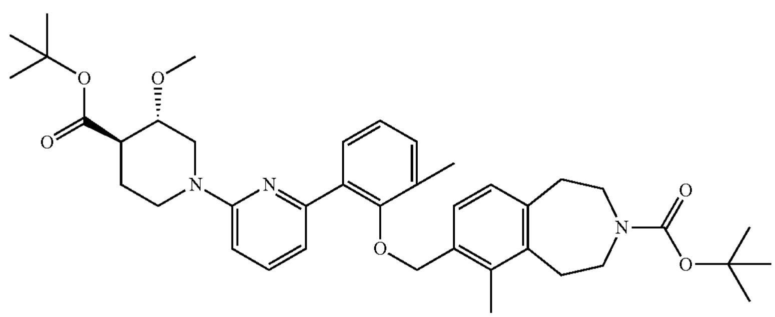 [SMILES: CO[C@@H]1CN(c2cccc(-c3cccc(C)c3OCc3ccc4c(c3C)CCN(C(=O)OC(C)(C)C)CC4)n2)CC[C@H]1C(=O)OC(C)(C)C] |
| E-151 | C-42 | 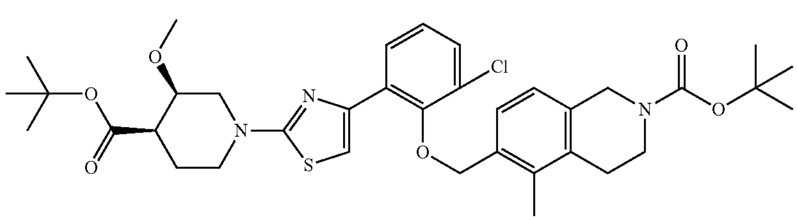 [SMILES: CO[C@H]1CN(c2nc(-c3cccc(Cl)c3OCc3ccc4c(c3C)CCN(C(=O)OC(C)(C)C)C4)cs2)CC[C@H]1C(=O)OC(C)(C)C] |
| E-152 | C-42 | 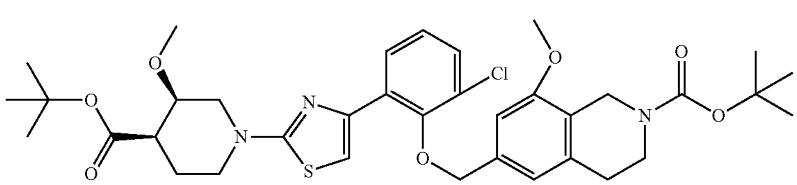 [SMILES: COc1cc(COc2c(Cl)cccc2-c2csc(N3CC[C@@H](C(=O)OC(C)(C)C)[C@@H](OC)C3)n2)cc2c1CN(C(=O)OC(C)(C)C)CC2] |

-continued

| Intermediate | Prepared From | Structure |
|---|---|---|
| E-153 | C-42 | 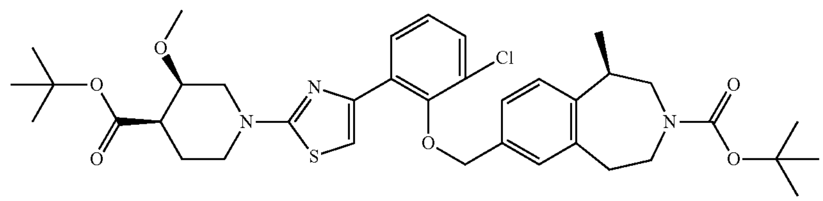 [SMILES: CO[C@H]1CN(c2nc(-c3cccc(Cl)c3OCc3ccc4c(c3)CCN(C(=O)OC(C)(C)C)C[C@@H]4C)cs2)CC[C@H]1C(=O)OC(C)(C)C] |
| E-154 | C-42 | 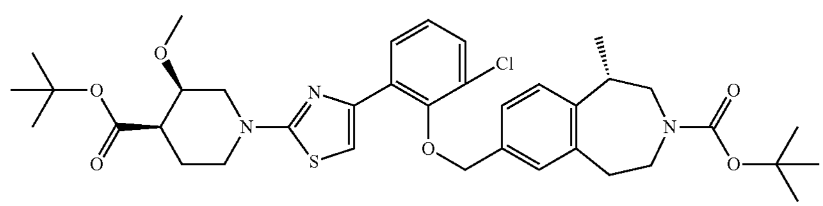 [SMILES: CO[C@H]1CN(c2nc(-c3cccc(Cl)c3OCc3ccc4c(c3)CCN(C(=O)OC(C)(C)C)C[C@H]4C)cs2)CC[C@H]1C(=O)OC(C)(C)C] |
| E-155 | C-42 | 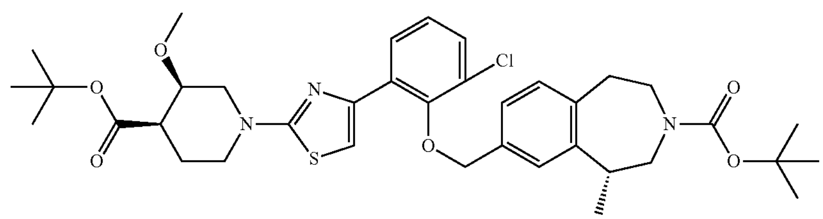 [SMILES: CO[C@H]1CN(c2nc(-c3cccc(Cl)c3OCc3ccc4c(c3)[C@@H](C)CN(C(=O)OC(C)(C)C)CC4)cs2)CC[C@H]1C(=O)OC(C)(C)C] |
| E-156 | C-42 | 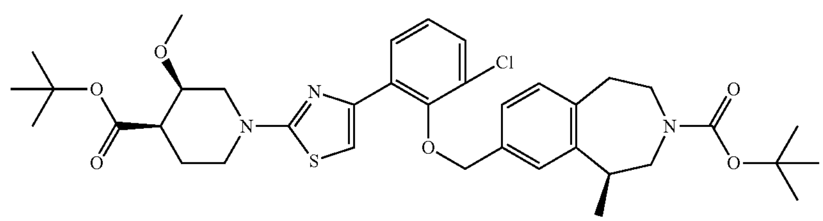 [SMILES: CO[C@H]1CN(c2nc(-c3cccc(Cl)c3OCc3ccc4c(c3)[C@H](C)CN(C(=O)OC(C)(C)C)CC4)cs2)CC[C@H]1C(=O)OC(C)(C)C] |
| E-157 | C-43 | 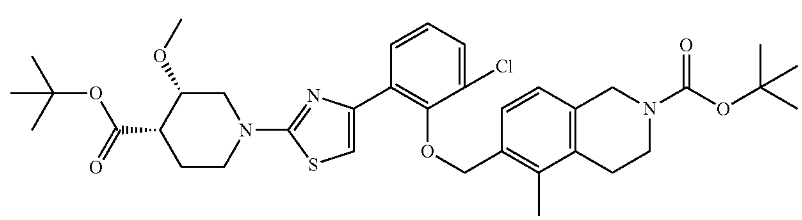 [SMILES: CO[C@@H]1CN(c2nc(-c3cccc(Cl)c3OCc3ccc4c(c3C)CCN(C(=O)OC(C)(C)C)C4)cs2)CC[C@@H]1C(=O)OC(C)(C)C] |
| E-158 | C-44 | 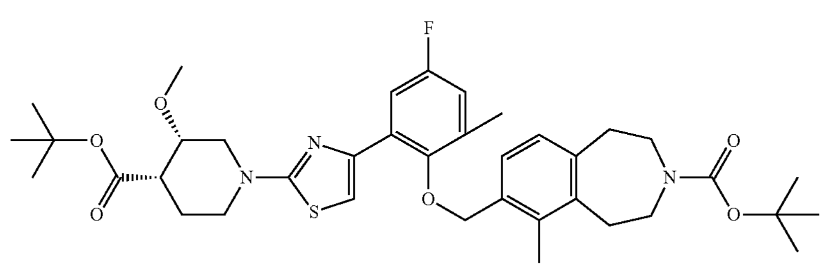 [SMILES: CO[C@@H]1CN(c2nc(-c3cc(F)cc(C)c3OCc3ccc4c(c3C)CCN(C(=O)OC(C)(C)C)CC4)cs2)CC[C@@H]1C(=O)OC(C)(C)C] |

-continued
| Intermediate | Prepared From | Structure |
|---|---|---|
| E-159 | C-44 | 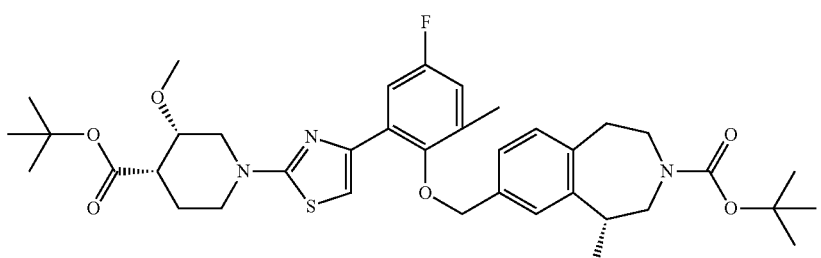 |
| E-160 | C-44 | 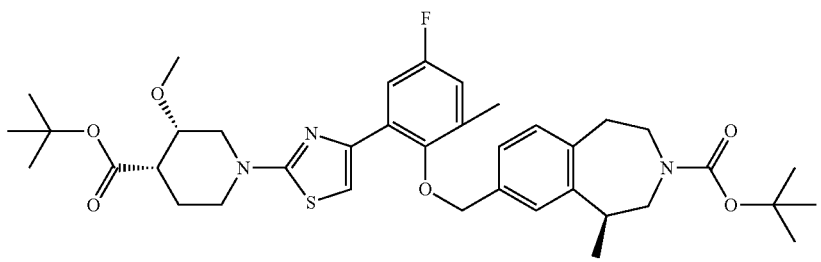 [SMILES: CO[C@@H]1CN(c2nc(-c3cc(F)cc(C)c3OCc3ccc4c(c3)[C@H](C)CN(C(=O)OC(C)(C)C)CC4)cs2)CC[C@@H]1C(=O)OC(C)(C)C] |
| E-161 | C-45 | 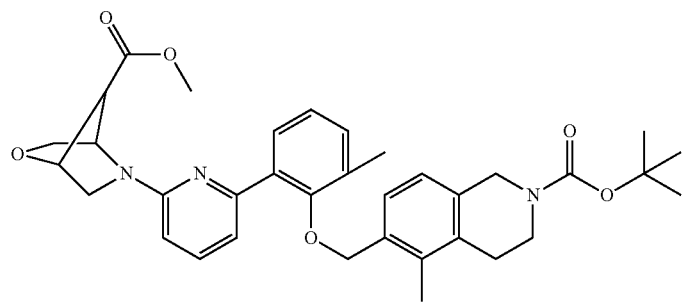 [SMILES: COC(=O)C1C2CN(c3cccc(-c4cccc(C)c4OCc4ccc5c(c4C)CCN(C(=O)OC(C)(C)C)C5)n3)C1CO2] |
| E-162 | C-46 | 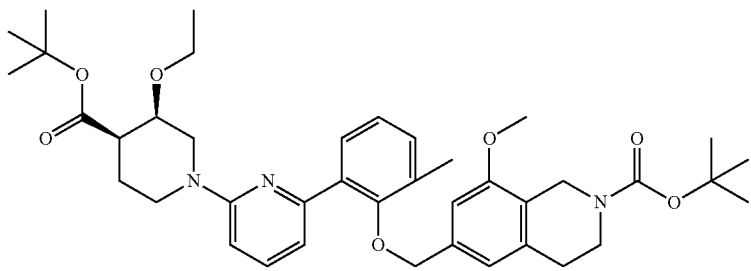 [SMILES: CCO[C@H]1CN(c2cccc(-c3cccc(C)c3OCc3cc4c(c(OC)c3)CN(C(=O)OC(C)(C)C)CC4)n2)CC[C@H]1C(=O)OC(C)(C)C] |
| E-163 | C-47 | 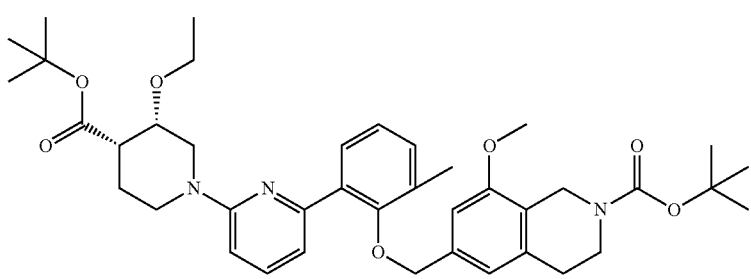 [SMILES: CCO[C@@H]1CN(c2cccc(-c3cccc(C)c3OCc3cc4c(c(OC)c3)CN(C(=O)OC(C)(C)C)CC4)n2)CC[C@@H]1C(=O)OC(C)(C)C] |

-continued
| Intermediate | Prepared From | Structure |
|---|---|---|
| E-164 | C-47 | 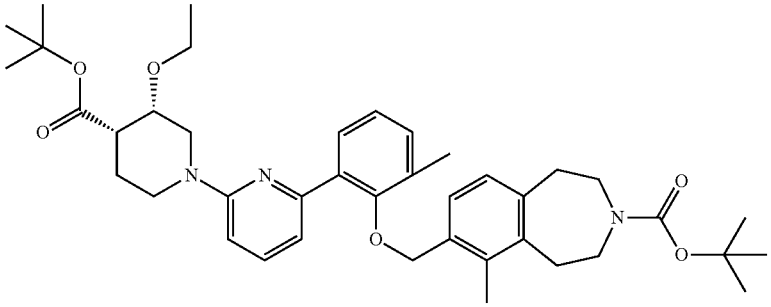 |
| E-165 | C-48 | 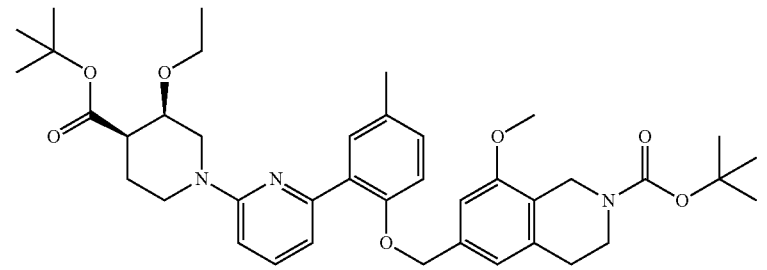 [SMILES: CCO[C@H]1CN(c2cccc(-c3cc(C)ccc3OCc3cc4c(c(OC)c3)CN(C(=O)OC(C)(C)C)CC4)n2)CC[C@H]1C(=O)OC(C)(C)C] |
| E-166 | C-49 | 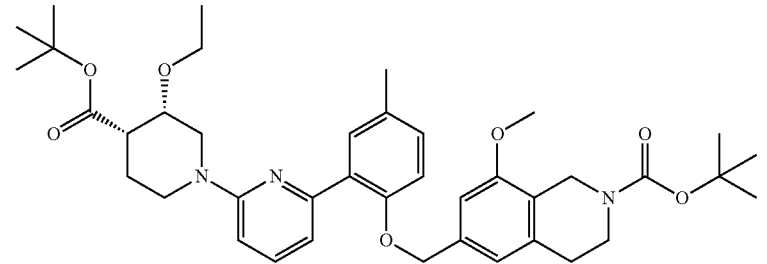 |
| E-167 | C-49 | 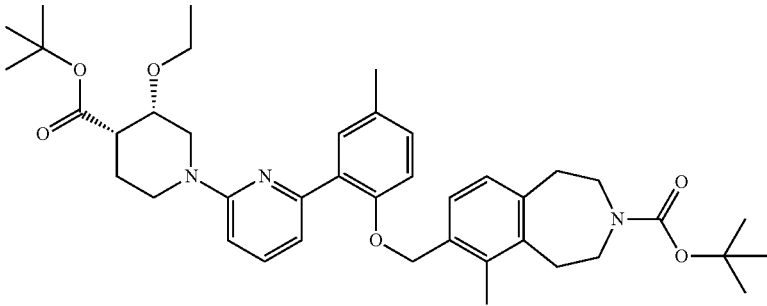 [SMILES: CCO[C@@H]1CN(c2cccc(-c3cc(C)ccc3OCc3ccc4c(c3C)CCN(C(=O)OC(C)(C)C)CC4)n2)CC[C@@H]1C(=O)OC(C)(C)C] |
| E-168 | C-50 | 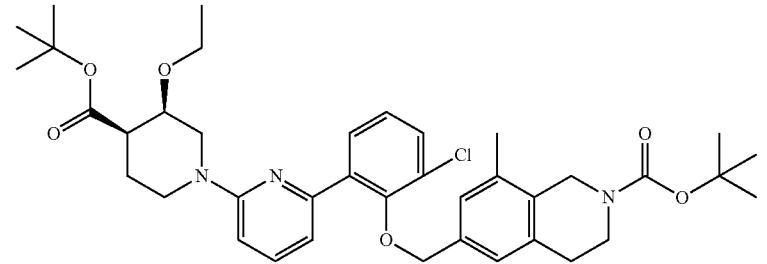 [SMILES: CCO[C@H]1CN(c2cccc(-c3cccc(Cl)c3OCc3cc(C)c4c(c3)CCN(C(=O)OC(C)(C)C)C4)n2)CC[C@H]1C(=O)OC(C)(C)C] |

-continued

| Intermediate | Prepared From | Structure |
|---|---|---|
| E-169 | C-50 | 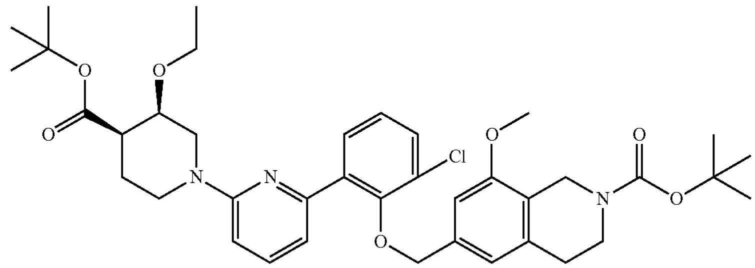 [SMILES: CCO[C@H]1CN(c2cccc(-c3cccc(Cl)c3OCc3cc4c(c(OC)c3)CN(C(=O)OC(C)(C)C)CC4)n2)CC[C@H]1C(=O)OC(C)(C)C] |
| E-170 | C-51 | 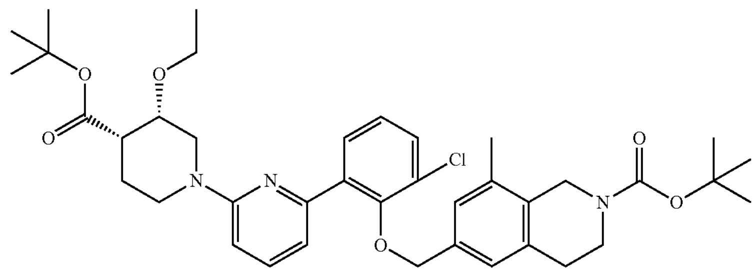 [SMILES: CCO[C@@H]1CN(c2cccc(-c3cccc(Cl)c3OCc3cc(C)c4c(c3)CCN(C(=O)OC(C)(C)C)C4)n2)CC[C@@H]1C(=O)OC(C)(C)C] |
| E-171 | C-51 | 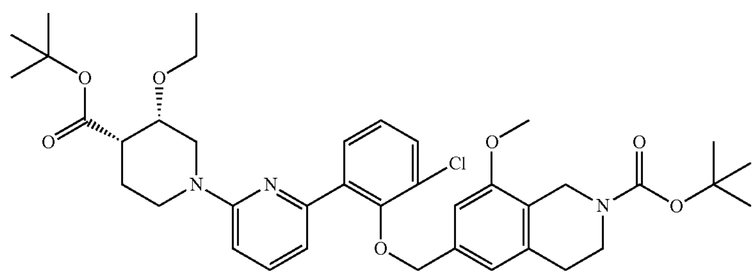 [SMILES: CCO[C@@H]1CN(c2cccc(-c3cccc(Cl)c3OCc3cc4c(c(OC)c3)CN(C(=O)OC(C)(C)C)CC4)n2)CC[C@@H]1C(=O)OC(C)(C)C] |
| E-172 | C-52 | 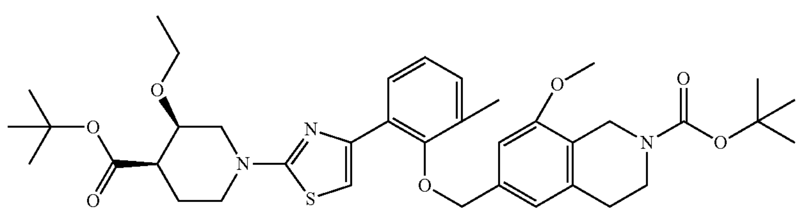 [SMILES: CCO[C@H]1CN(c2nc(-c3cccc(C)c3OCc3cc4c(c(OC)c3)CN(C(=O)OC(C)(C)C)CC4)cs2)CC[C@H]1C(=O)OC(C)(C)C] |
| E-173 | C-53 | 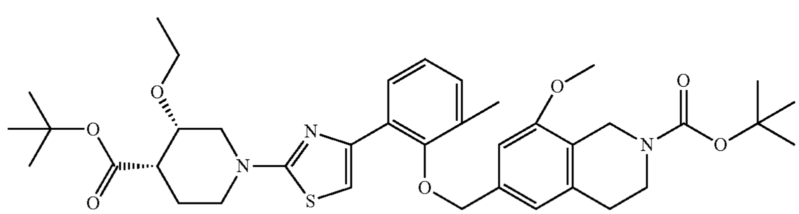 [SMILES: CCO[C@@H]1CN(c2nc(-c3cccc(C)c3OCc3cc4c(c(OC)c3)CN(C(=O)OC(C)(C)C)CC4)cs2)CC[C@@H]1C(=O)OC(C)(C)C] |
| E-174 | C-53 | 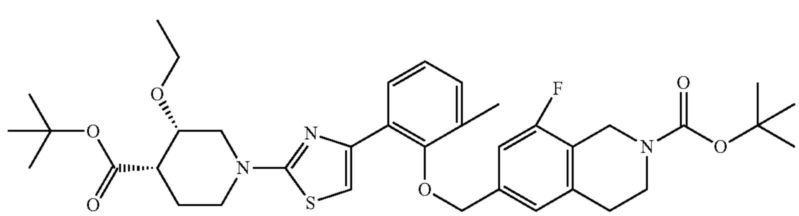 [SMILES: CCO[C@@H]1CN(c2nc(-c3cccc(C)c3OCc3cc(F)c4c(c3)CCN(C(=O)OC(C)(C)C)C4)cs2)CC[C@@H]1C(=O)OC(C)(C)C] |

-continued

| Intermediate | Prepared From | Structure |
|---|---|---|
| E-175 | C-53 | 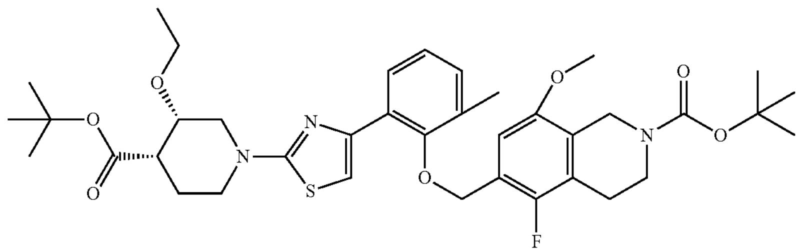 [SMILES: CCO[C@@H]1CN(c2nc(-c3cccc(C)c3OCc3cc(OC)c4c(c3F)CCN(C(=O)OC(C)(C)C)C4)cs2)CC[C@@H]1C(=O)OC(C)(C)C] |
| E-176 | C-53 | 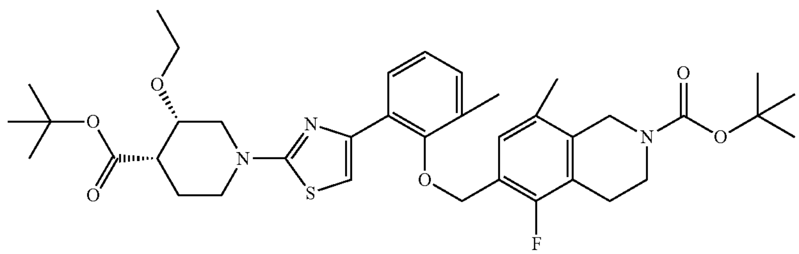 [SMILES: CCO[C@@H]1CN(c2nc(-c3cccc(C)c3OCc3cc(C)c4c(c3F)CCN(C(=O)OC(C)(C)C)C4)cs2)CC[C@@H]1C(=O)OC(C)(C)C] |
| E-177 | C-54 | 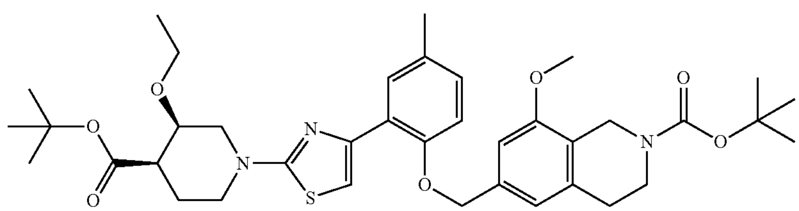 [SMILES: CCO[C@H]1CN(c2nc(-c3cc(C)ccc3OCc3cc4c(c(OC)c3)CN(C(=O)OC(C)(C)C)CC4)cs2)CC[C@H]1C(=O)OC(C)(C)C] |
| E-178 | C-55 | 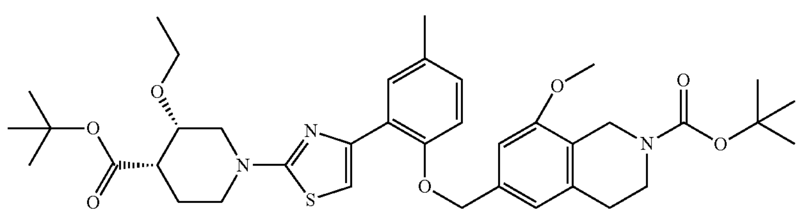 [SMILES: CCO[C@@H]1CN(c2nc(-c3cc(C)ccc3OCc3cc4c(c(OC)c3)CN(C(=O)OC(C)(C)C)CC4)cs2)CC[C@@H]1C(=O)OC(C)(C)C] |
| E-179 | C-55 | 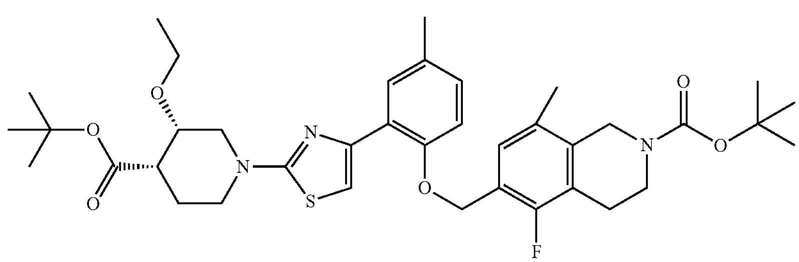 [SMILES: CCO[C@@H]1CN(c2nc(-c3cc(C)ccc3OCc3cc(C)c4c(c3F)CCN(C(=O)OC(C)(C)C)C4)cs2)CC[C@@H]1C(=O)OC(C)(C)C] |
| E-180 | C-55 | 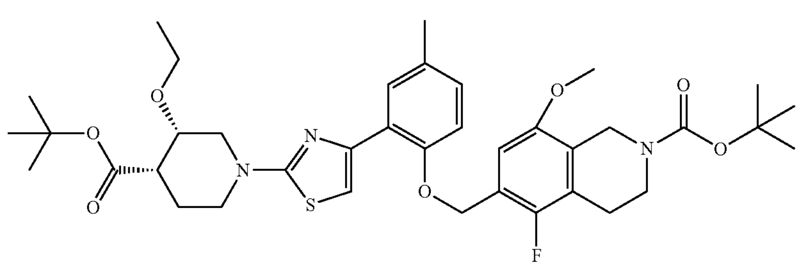 [SMILES: CCO[C@@H]1CN(c2nc(-c3cc(C)ccc3OCc3cc(OC)c4c(c3F)CCN(C(=O)OC(C)(C)C)C4)cs2)CC[C@@H]1C(=O)OC(C)(C)C] |

-continued

| Intermediate | Prepared From | Structure |
|---|---|---|
| E-181 | C-56 | 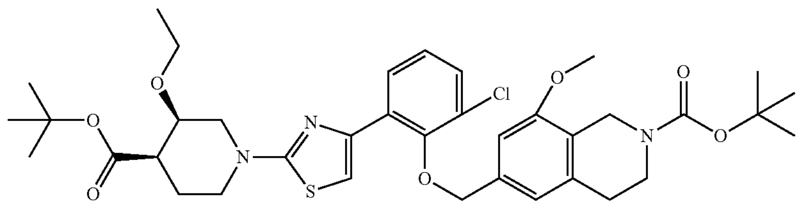 [SMILES: CCO[C@H]1CN(c2nc(-c3cccc(Cl)c3OCc3cc4c(c(OC)c3)CN(C(=O)OC(C)(C)C)CC4)cs2)CC[C@H]1C(=O)OC(C)(C)C] |
| E-182 | C-57 | 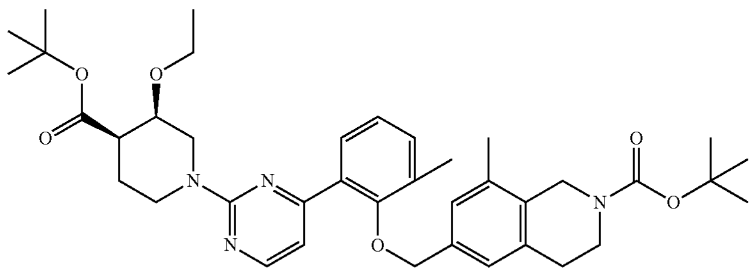 [SMILES: CCO[C@H]1CN(c2nccc(-c3cccc(C)c3OCc3cc(C)c4c(c3)CCN(C(=O)OC(C)(C)C)C4)n2)CC[C@H]1C(=O)OC(C)(C)C] |
| E-183 | C-57 | 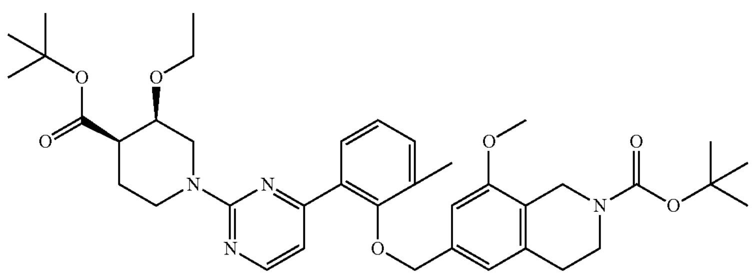 [SMILES: CCO[C@H]1CN(c2nccc(-c3cccc(C)c3OCc3cc4c(c(OC)c3)CN(C(=O)OC(C)(C)C)CC4)n2)CC[C@H]1C(=O)OC(C)(C)C] |
| E-184 | C-57 | 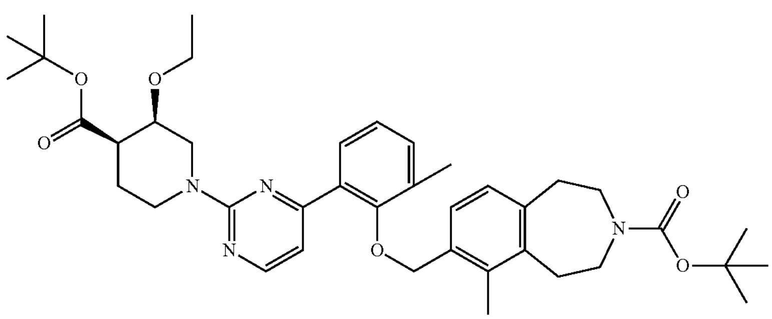 [SMILES: CCO[C@H]1CN(c2nccc(-c3cccc(C)c3OCc3ccc4c(c3C)CCN(C(=O)OC(C)(C)C)CC4)n2)CC[C@H]1C(=O)OC(C)(C)C] |
| E-185 | C-58 | 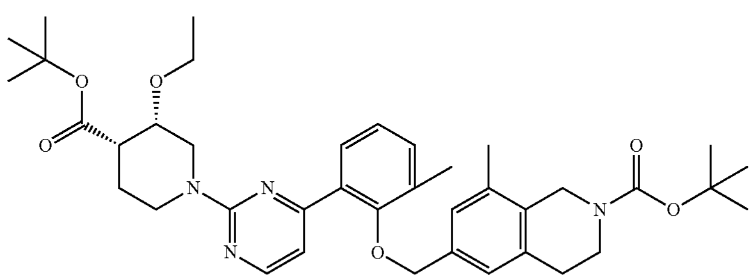 [SMILES: CCO[C@@H]1CN(c2nccc(-c3cccc(C)c3OCc3cc(C)c4c(c3)CCN(C(=O)OC(C)(C)C)C4)n2)CC[C@@H]1C(=O)OC(C)(C)C] |

-continued

| Intermediate | Prepared From | Structure |
|---|---|---|
| E-186 | C-58 | 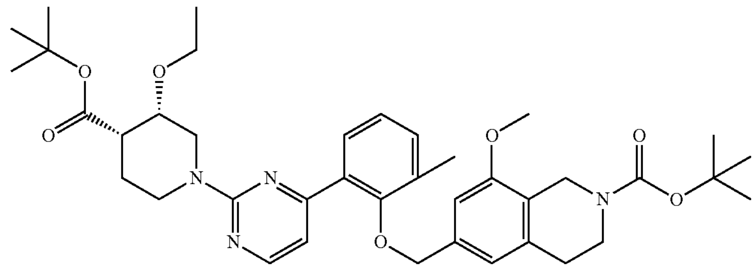 [SMILES: CCO[C@@H]1CN(c2nccc(-c3cccc(C)c3OCc3cc4c(c(OC)c3)CN(C(=O)OC(C)(C)C)CC4)n2)CC[C@@H]1C(=O)OC(C)(C)C] |
| E-187 | C-58 | 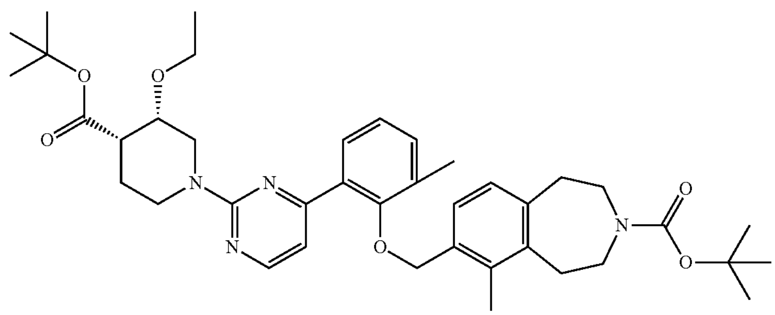 [SMILES: CCO[C@@H]1CN(c2nccc(-c3cccc(C)c3OCc3ccc4c(c3C)CCN(C(=O)OC(C)(C)C)CC4)n2)CC[C@@H]1C(=O)OC(C)(C)C] |
| E-188 | C-59 | 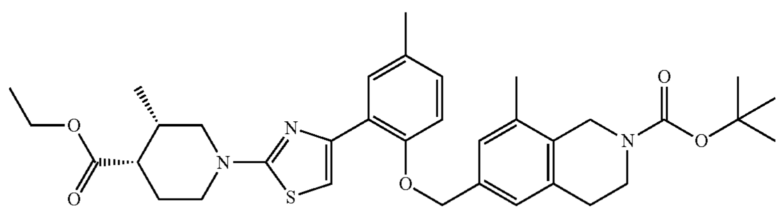 [SMILES: CCOC(=O)[C@H]1CCN(c2nc(-c3cc(C)ccc3OCc3cc(C)c4c(c3)CCN(C(=O)OC(C)(C)C)C4)cs2)C[C@H]1C] |
| E-189 | C-60 | 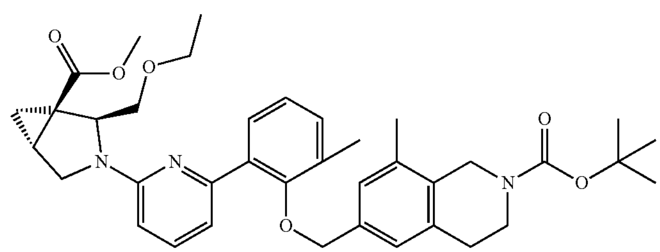 |
| E-190 | C-61 | 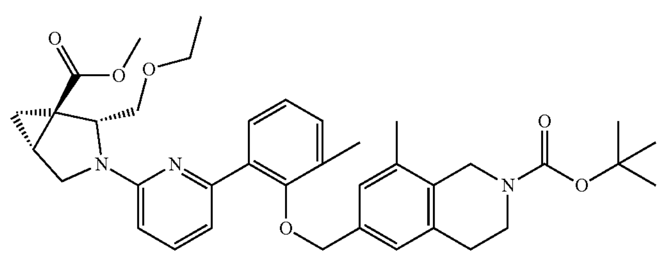 |

| Intermediate | Prepared From | Structure |
|---|---|---|
| E-191 | C-62 | 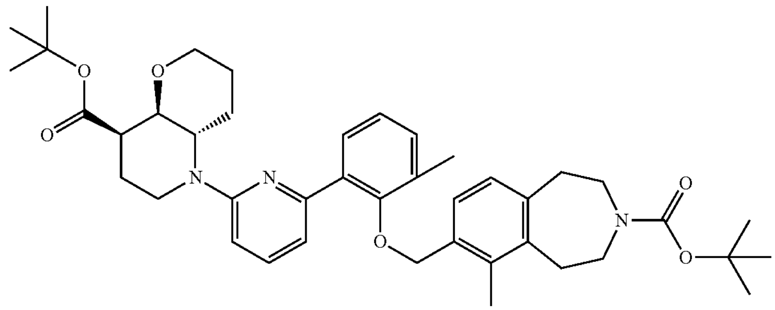 [SMILES: Cc1cccc(-c2cccc(N3CC[C@@H](C(=O)OC(C)(C)C)[C@H]4OCCC[C@@H]43)n2)c1OCc1ccc2c(c1C)CCN(C(=O)OC(C)(C)C)CC2] |
| E-192 | C-63 | 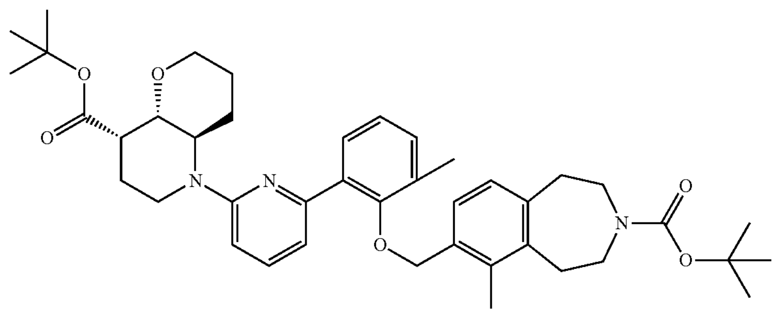 [SMILES: Cc1cccc(-c2cccc(N3CC[C@H](C(=O)OC(C)(C)C)[C@@H]4OCCC[C@H]43)n2)c1OCc1ccc2c(c1C)CCN(C(=O)OC(C)(C)C)CC2] |
| E-193 | C-43 | 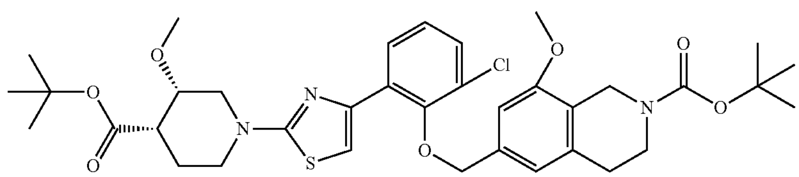 [SMILES: COc1cc(COc2c(Cl)cccc2-c2csc(N3CC[C@H](C(=O)OC(C)(C)C)[C@H](OC)C3)n2)cc2c1CN(C(=O)OC(C)(C)C)CC2] |

Example 39

Preparation of intermediate 6-{2-[6-((1R,6S)-6-Carboxy-3-aza-bicyclo[4.1.0]hept-3-yl)-pyridin-2-yl]-phenoxymethyl}-3,4-dihydro-1H-isoquinoline-2-carboxylic acid tert-butyl ester (E-95)

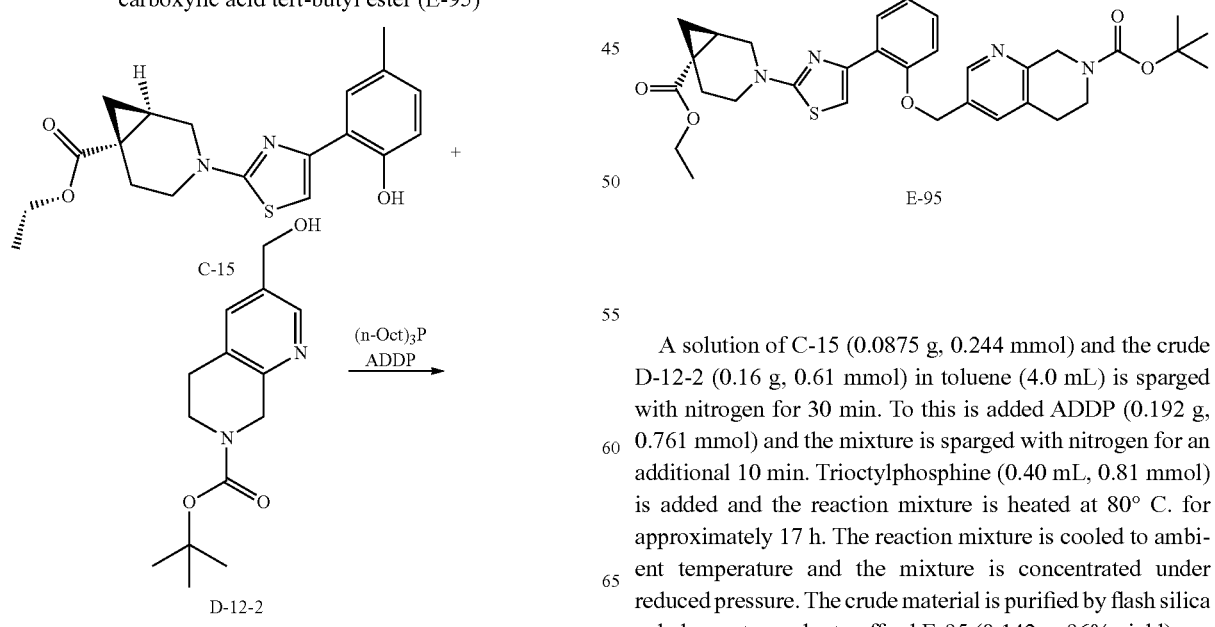

A solution of C-15 (0.0875 g, 0.244 mmol) and the crude D-12-2 (0.16 g, 0.61 mmol) in toluene (4.0 mL) is sparged with nitrogen for 30 min. To this is added ADDP (0.192 g, 0.761 mmol) and the mixture is sparged with nitrogen for an additional 10 min. Trioctylphosphine (0.40 mL, 0.81 mmol) is added and the reaction mixture is heated at 80° C. for approximately 17 h. The reaction mixture is cooled to ambient temperature and the mixture is concentrated under reduced pressure. The crude material is purified by flash silica gel chromatography to afford E-95 (0.142 g, 96% yield).

Example 40
Preparation of intermediate (1R,6S)-3-(6-{5-Methyl-2-[5-methyl-1-oxo-2-(tetrahydro-pyran-4-yl)-1,2,3,4-tetrahydro-isoquinolin-6-ylmethoxy]-phenyl}-pyridin-2-yl)-3-aza-bicyclo[4.1.0]heptane-6-carboxylic acid ethyl ester (E-194)
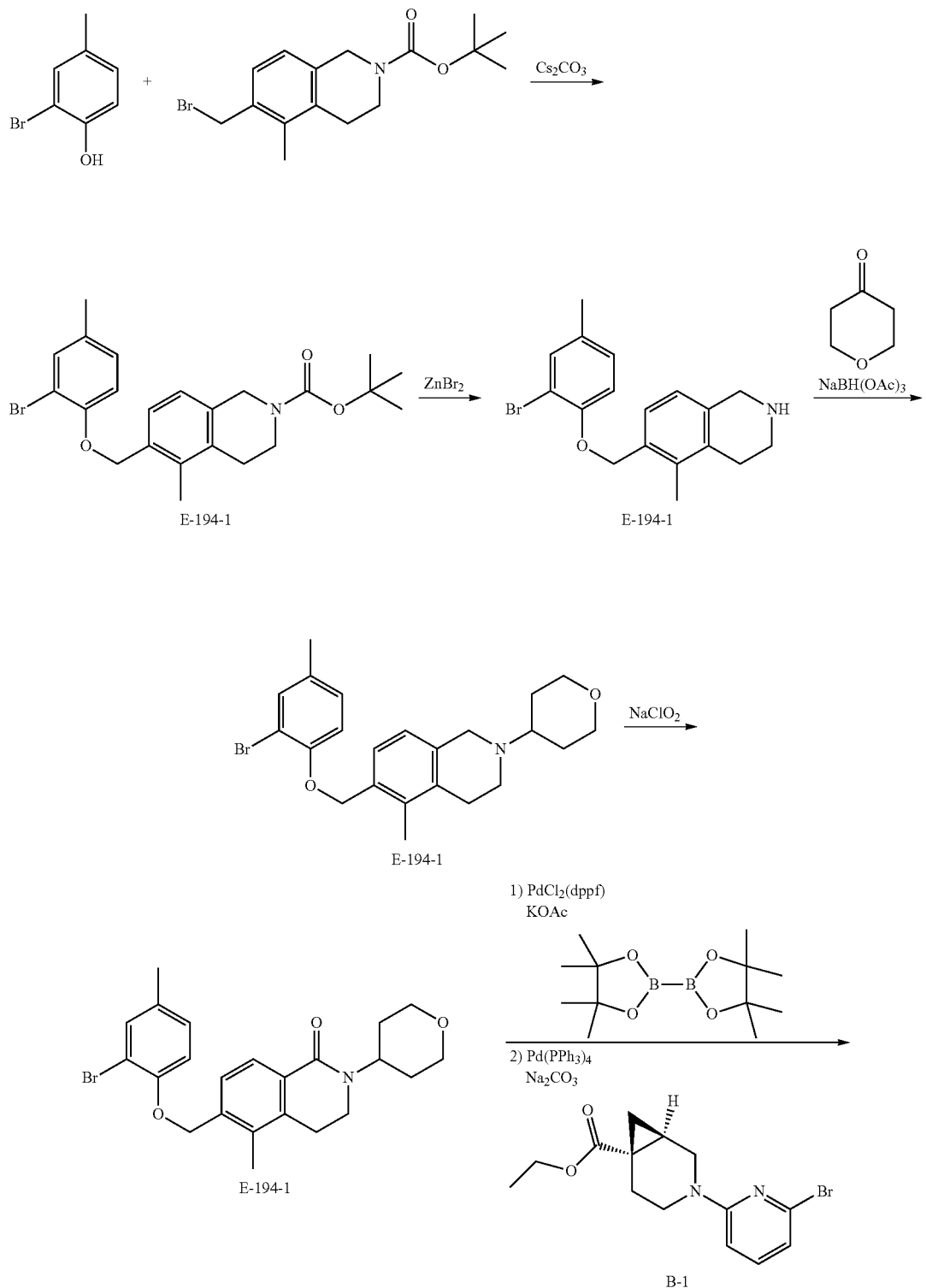

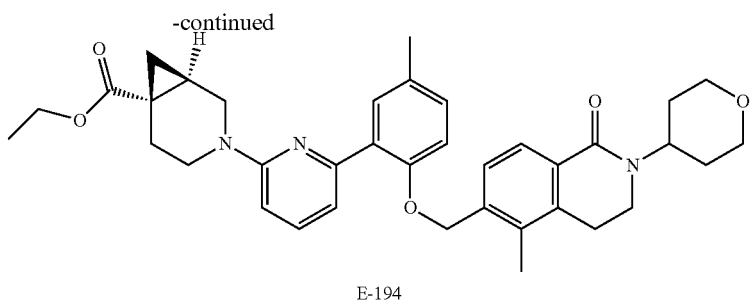

E-194

To a solution of 2-bromo-4-methyl-phenol (0.200 g, 1.07 mmol) in acetone (10 mL) is added 0.40 g (1.2 mmol) of D-3 followed by 1.0 g (3.1 mmol) of cesium carbonate. The mixture is stirred overnight at room temperature then filtered and concentrated under reduced pressure. The residue is purified by flash silica gel chromatography and the eluent removed under reduced pressure to provide E-194-1 (0.34 g)

To a solution of E-194-1 (0.34 g, 0.76 mmol) in DCM (10 mL) was added 0.70 g (3.1 mmol) of zinc bromide. The mixture is stirred at room temperature for 3 days then diluted with an aqueous solution of sodium carbonate and extracted with DCM. The combined organic phase is washed with brine, dried over anhydrous sodium sulfate and concentrated under reduced pressure to provide E-194-2 (0.25 g) as a clear film. No further purification was performed.

To a solution of the crude reaction product containing E-194-2 in DCM (25 mL) is added 0.30 g (3.0 mmol) of tetrahydro-pyran-4-one followed by 1.5 g (7.1 mmol) of sodium triacetoxyborohydride. The mixture is stirred for 2 days at room temperature then diluted with a saturated aqueous solution of sodium carbonate and extracted with DCM. The combined organic phase is dried over anhydrous sodium sulfate and concentrated under reduced pressure. The residue is purified by flash silica gel chromatography and the eluent was removed under reduced pressure to provide E-194-3 (1.00 g) as a white powder.

To a solution of 0.80 g (1.86 mmol) of E-194-3 in a 4:1 mixture of chloroform: water (20 mL) is added 0.60 g (6.6 mmol) of sodium chlorite. The mixture is heated at 55 C overnight then cooled to room temperature and concentrated under reduced pressure. The residue is purified by C18 reverse phase chromatography using a gradient of ACN in water with 0.1% TFA additive. The eluent was removed under reduced pressure to provide E-194-4 (0.235 g) as a white powder.

To a solution of 0.100 g (0.225 mmol) of E-194-4 in 1,4-dioxane (6 mL) is added 0.25 g (0.98 mmol) of 4,4,5,5,4',4',5',5'-octamethyl-[2,2']bi[[1,3,2]dioxaborolanyl] followed by 0.15 g (1.5 mmol) of potassium acetate and 0.050 g (0.068 mmol) of palladium(II)dichloride(dppf). Argon gas is bubbled through the solution for 10 minutes then the mixture is heated to 100 C and stirred overnight then cooled to room temperature. To this mixture is added water (1 mL), 0.10 g (0.31 mmol) of B-1, 0.050 g (0.043 mmol) of tetrakis(triphenylphosphine)palladium (0), and 0.10 g (0.94 mmol) of sodium carbonate. The mixture is heated overnight at 100 C then cooled to room temperature and diluted with water. The mixture is extracted with EtOAc and the combined organic phase is dried over anhydrous sodium sulfate and concentrated under reduced pressure. The residue is purified by flash silica gel chromatography and the eluent is removed under reduced pressure to afford the title compound E-194 (0.100 g).

The following intermediates can be prepared from intermediate B-12 in a similar fashion using the appropriate reagents.

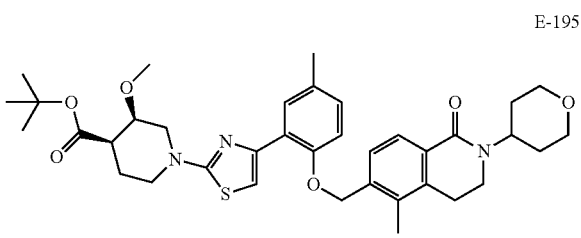

E-195

E-196

The following intermediates can be prepared from intermediate B-6 in a similar fashion using the appropriate reagents.

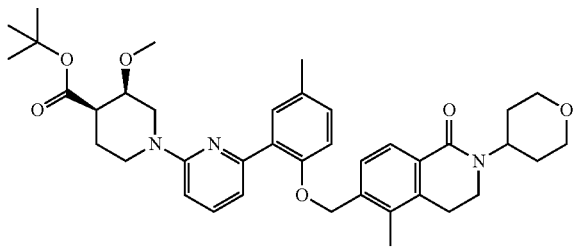

E-197

Example 41

Preparation of intermediate (1R,6S)-3-{6-[2-(1,2,3,4-Tetrahydro-isoquinolin-6-ylmethoxy)-phenyl]-pyridin-2-yl}-3-aza-bicyclo[4.1.0]heptane-6-carboxylic acid ethyl ester trifluoroacetic acid salt (F-1)

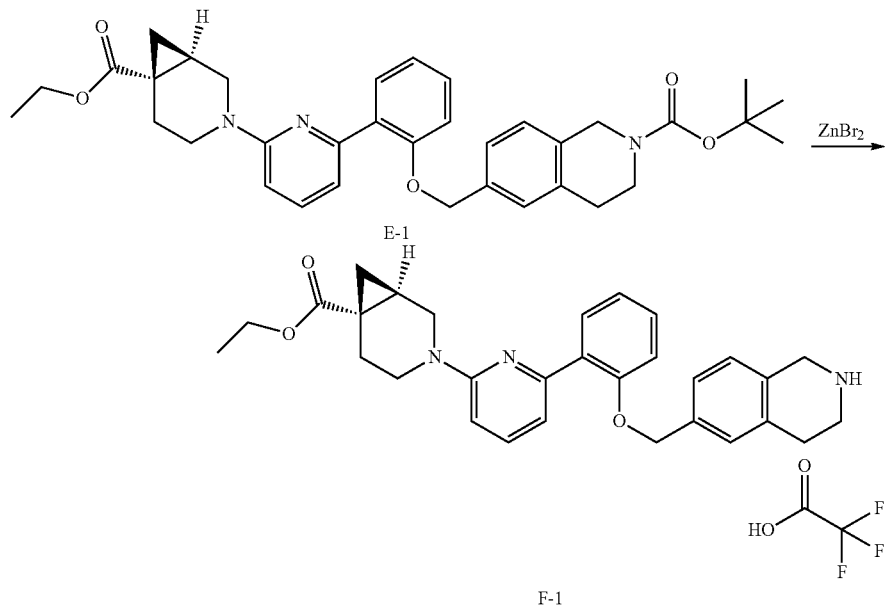

To a solution of 0.065 g (0.11 mmol) of E-1 in DCM (1 mL) is added 0.15 g (0.67 mmol) of zinc dibromide. The mixture is stirred overnight at ambient temperature then filtered and concentrated under reduced pressure. The residue is purified by reverse phase flash chromatography with 0.1% TFA additive. The eluent is concentrated under reduced pressure to provide F-1 which is used directly in the next reaction sequence.

The following intermediates can be prepared from in a similar fashion using the appropriate reagents.

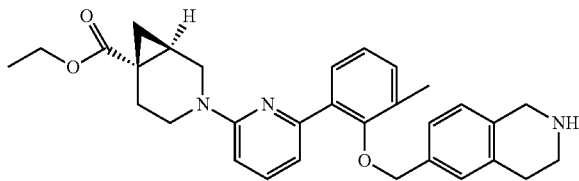

-continued

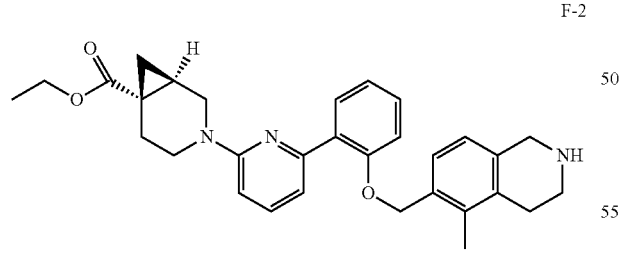

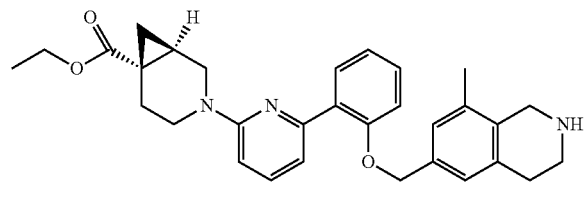

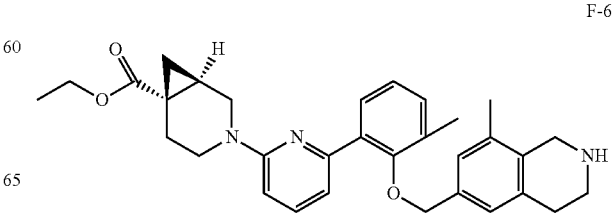

F-7
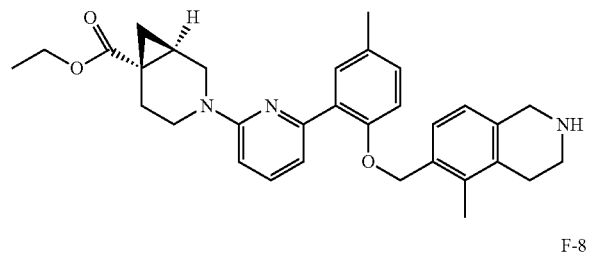
F-8
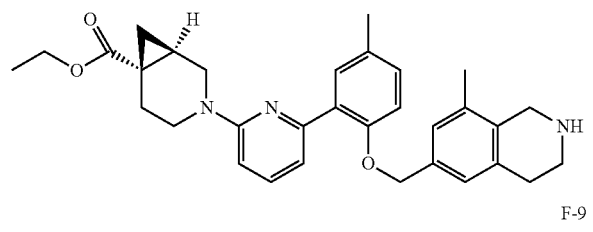
F-9
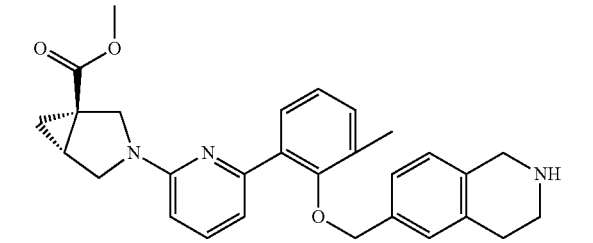
F-10
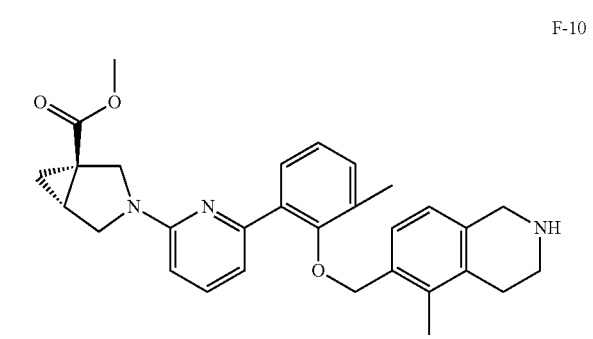
F-11
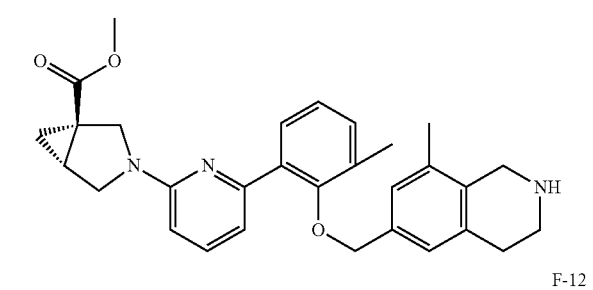
F-12
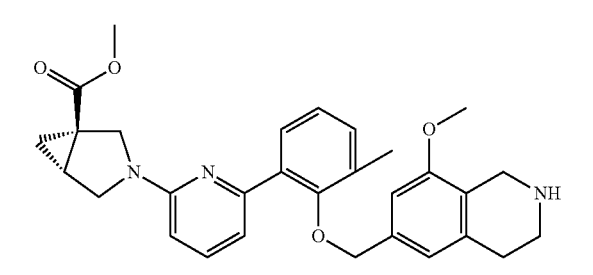
F-13
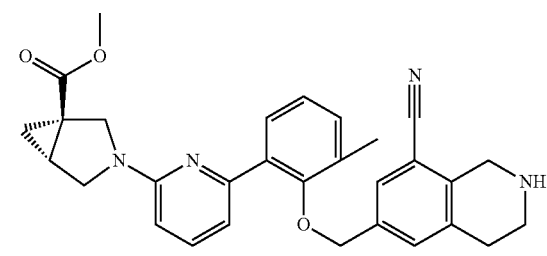
F-14
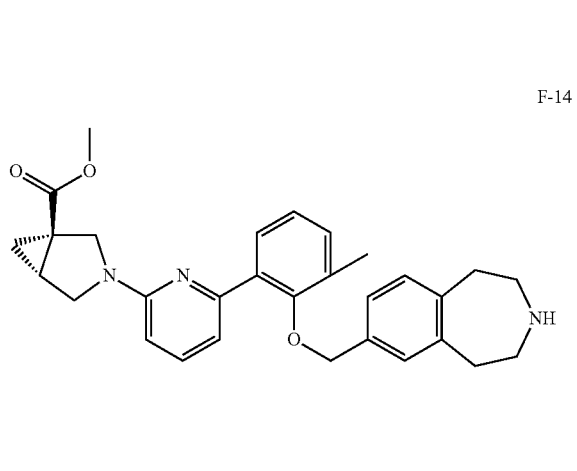
F-15
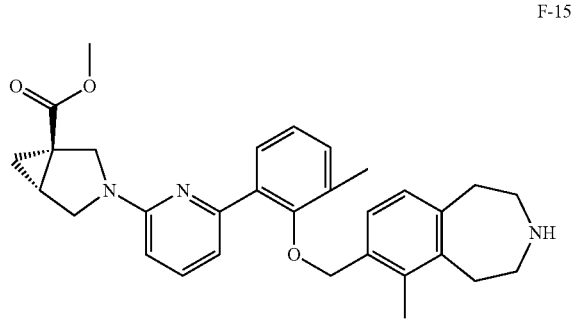
F-16
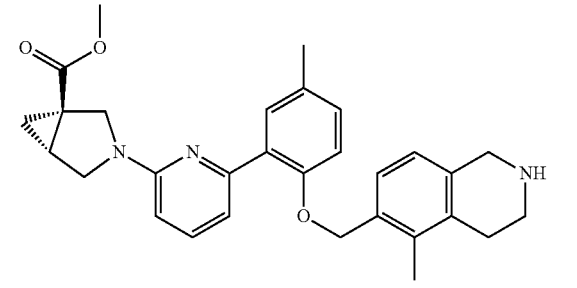
F-17
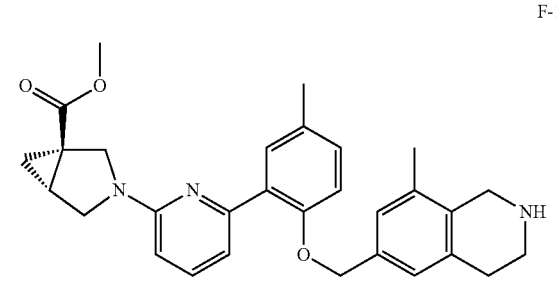

| 327 -continued | 328 -continued |
|---|---|
| F-18 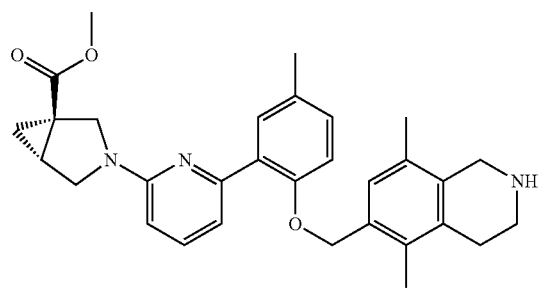 | F-23 |
| F-19 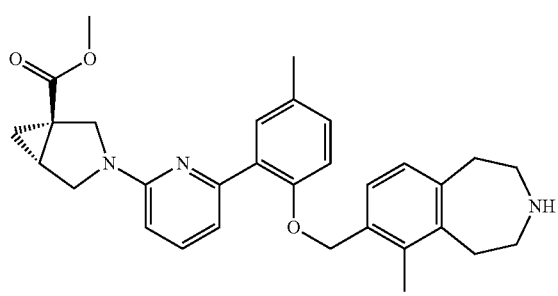 | F-24 |
| F-20 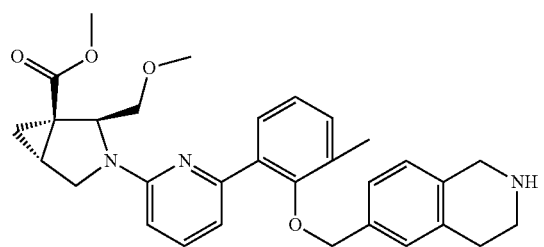 | F-25 |
| F-21 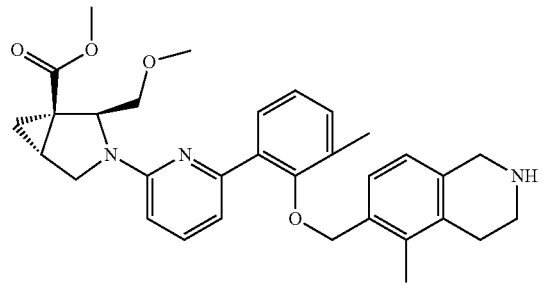 | F-26 |
| F-22 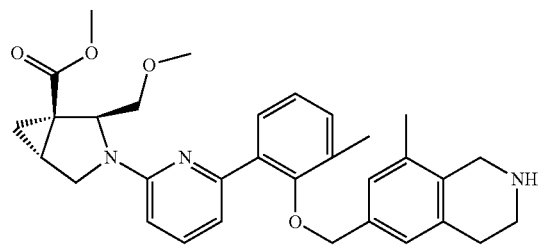 | F-27 |

-continued

F-28, F-43, F-44, F-45, F-46, F-47, F-48, F-49, F-50, F-51, F-52, F-53, F-54, F-55

F-56
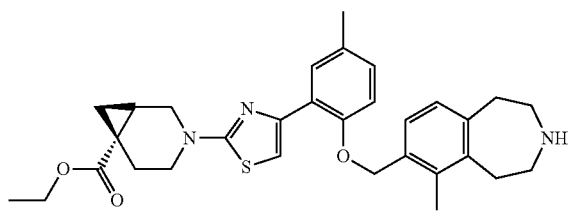
F-57
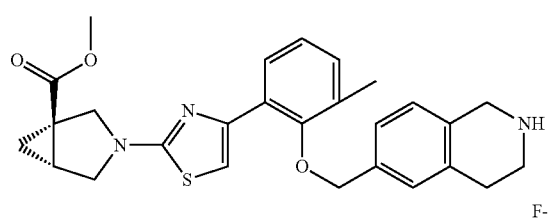
F-58
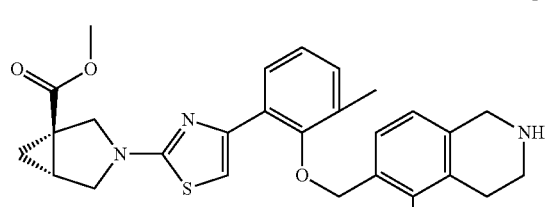
F-59
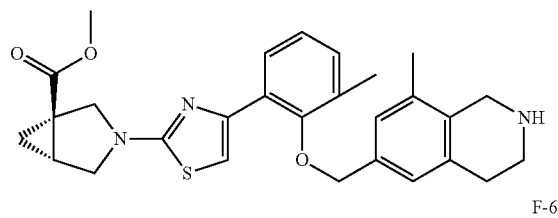
F-60
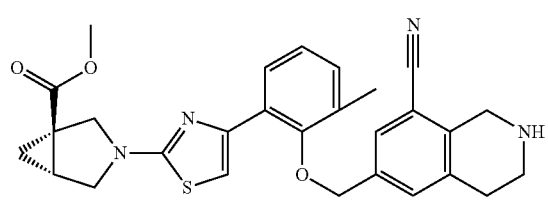
F-61
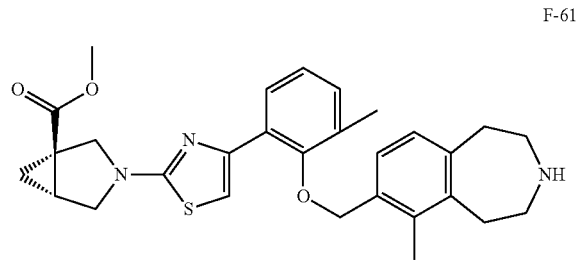
F-62
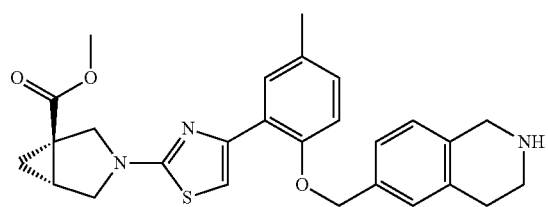
F-63
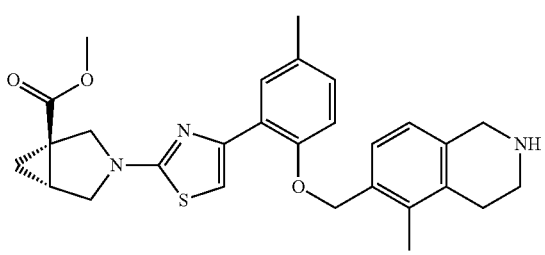
F-64
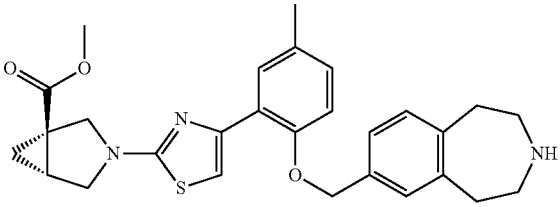
F-65
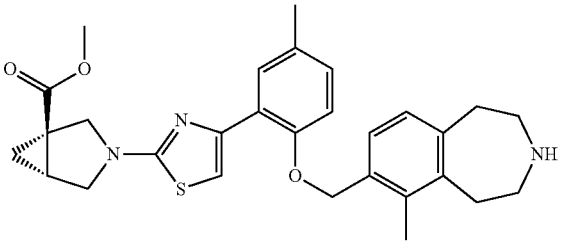
F-66
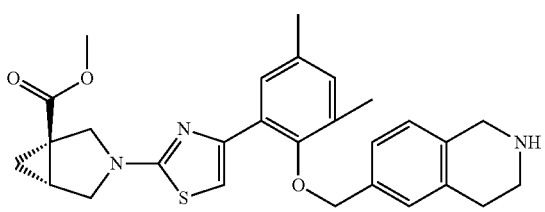
F-67
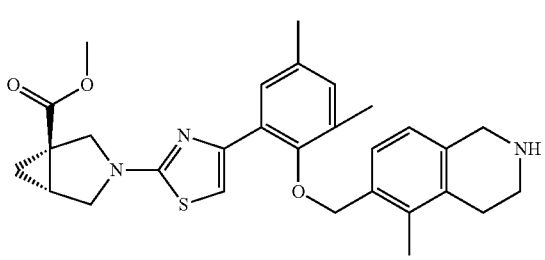
F-68
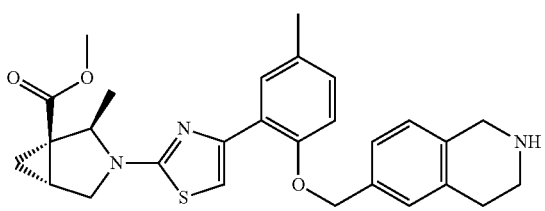

-continued
F-69
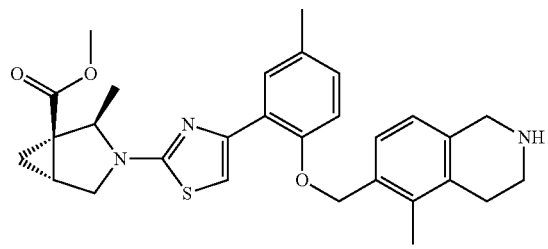
F-70
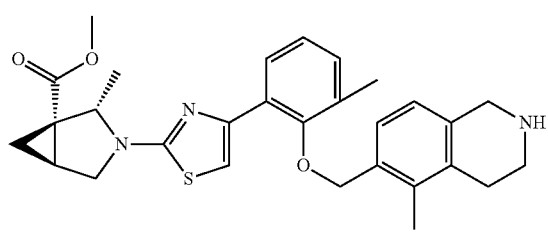
F-71
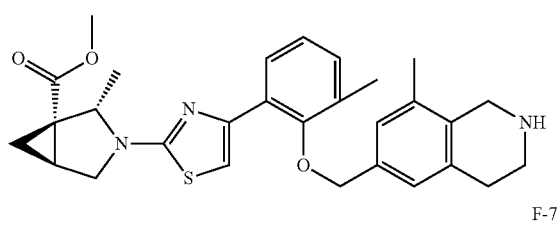
F-72
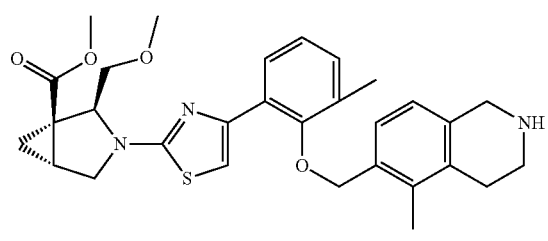
F-73
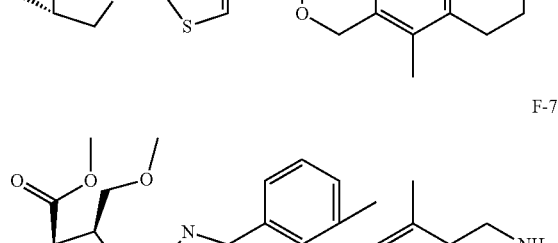
F-74
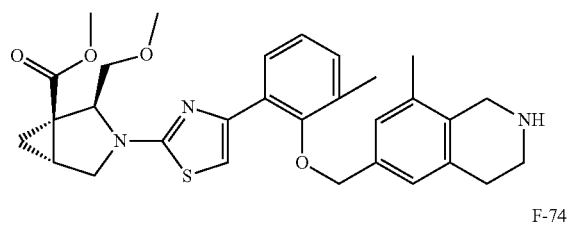
-continued
F-75
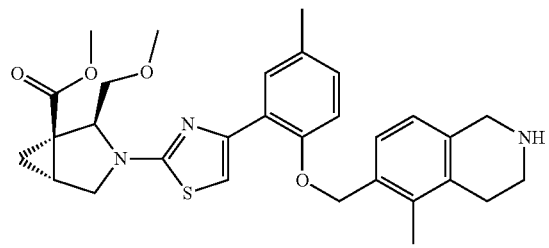
F-88
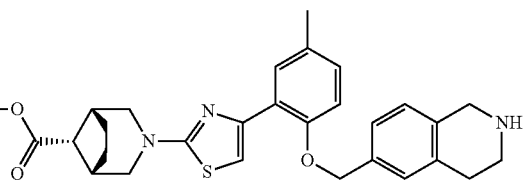
F-89
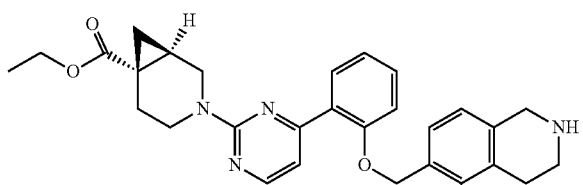
F-90
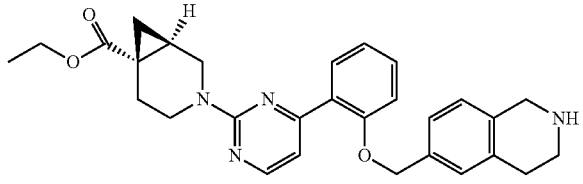
F-91
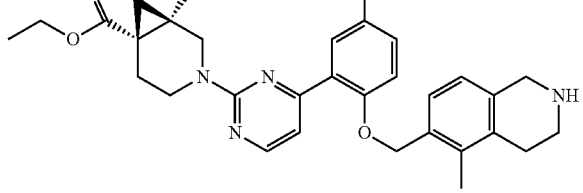
F-92
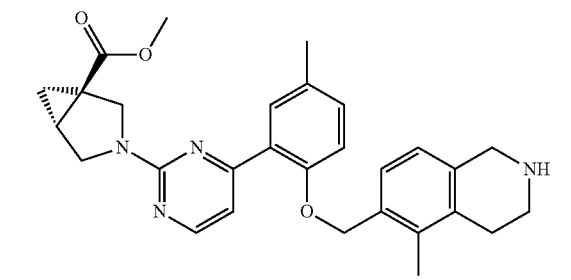

F-93
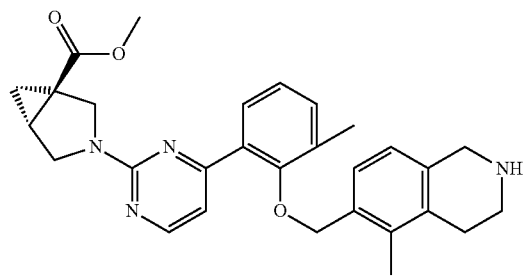
F-94
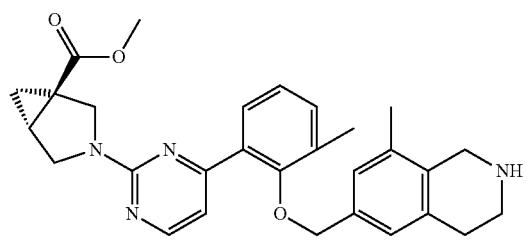
F-98
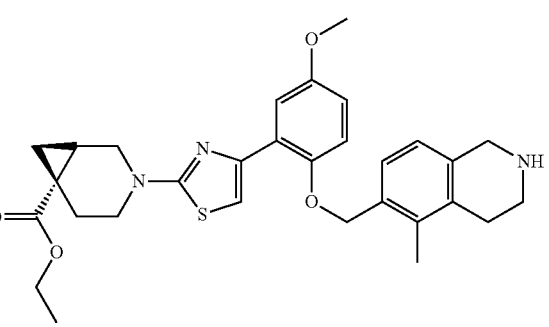
F-99
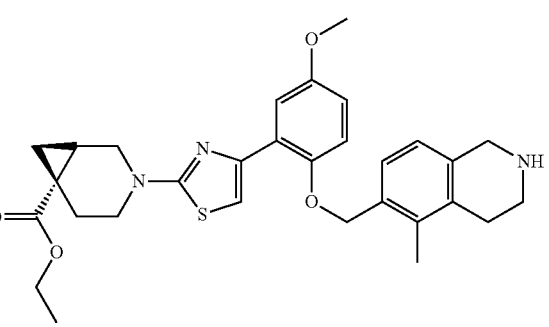
F-100
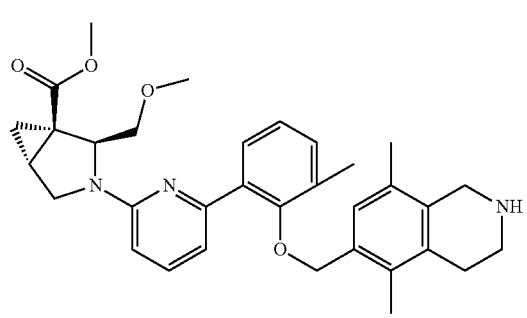
F-101
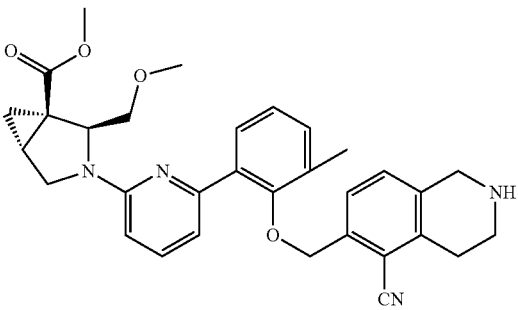
F-102
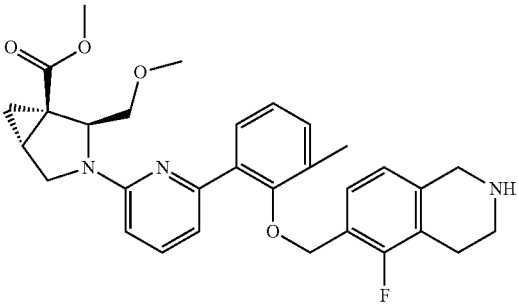
F-103
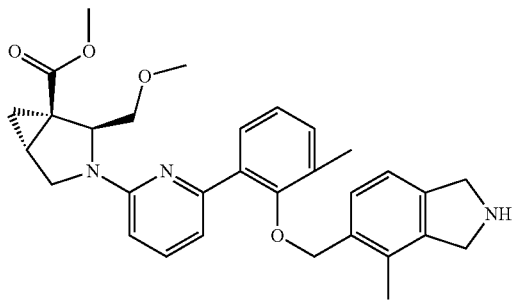
F-104
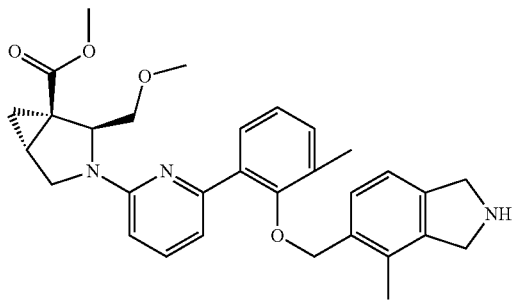
F-105
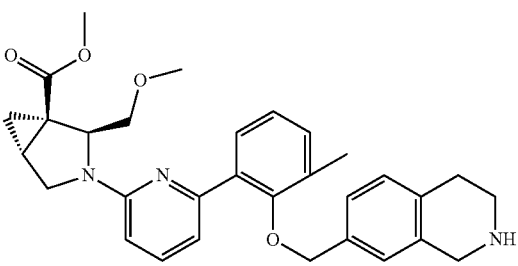

F-106
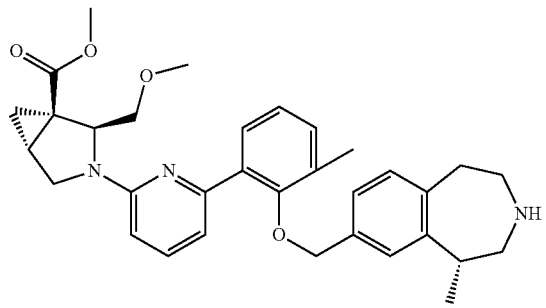
F-107
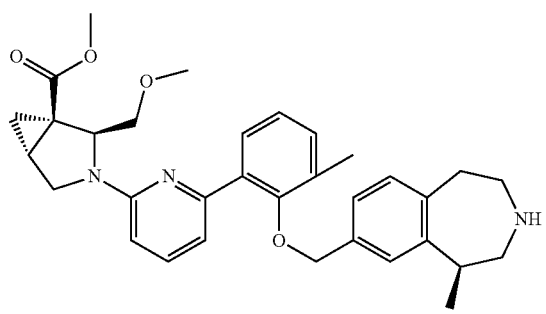
F-108
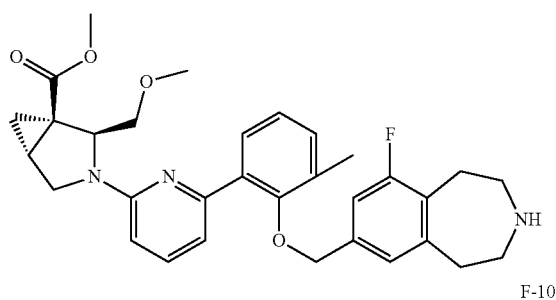
F-109
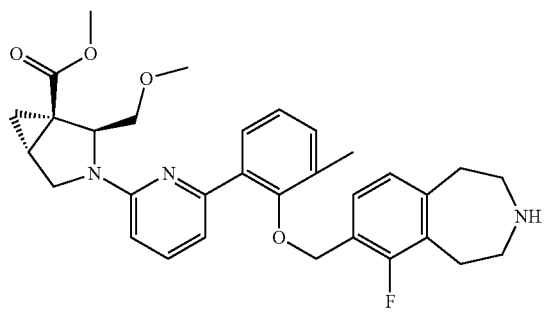
F-110
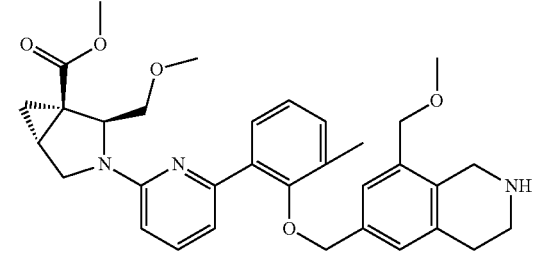
F-111
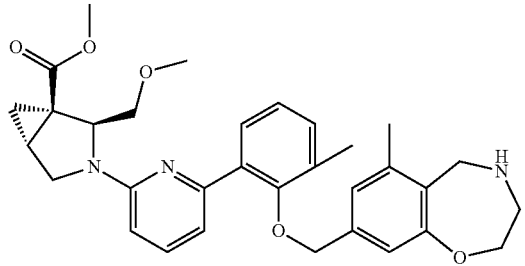
F-112
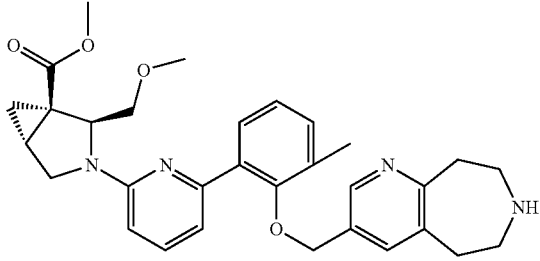
F-113
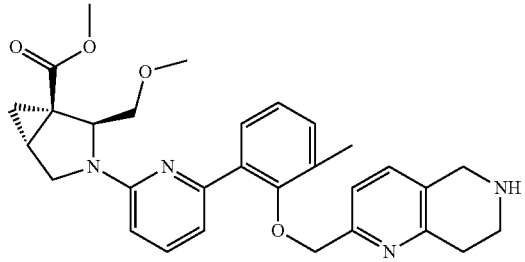
F-122
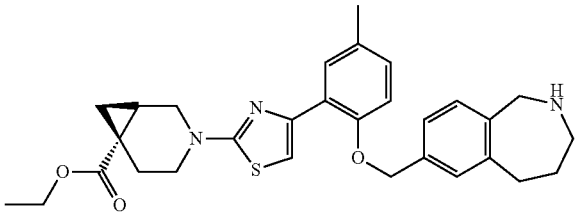
F-135
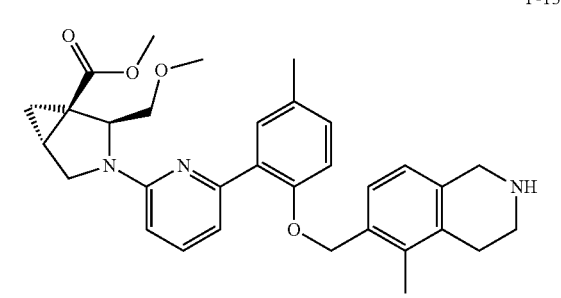

F-136
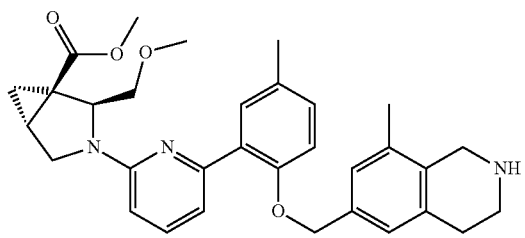
F-137
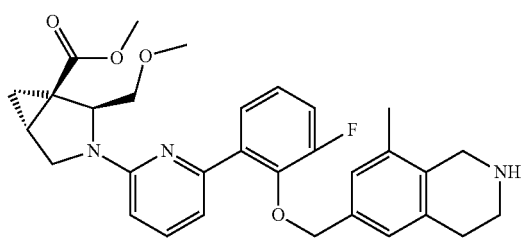
F-138
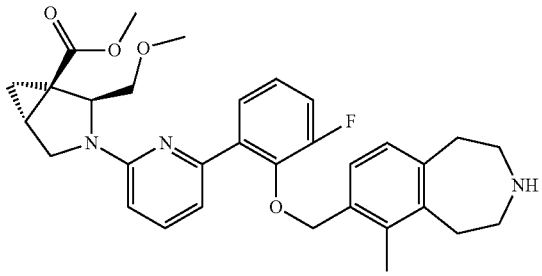
F-139
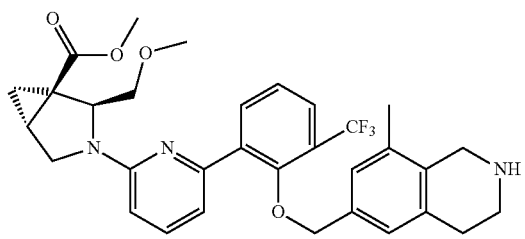
F-140
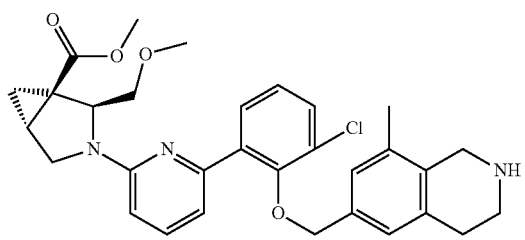
F-141
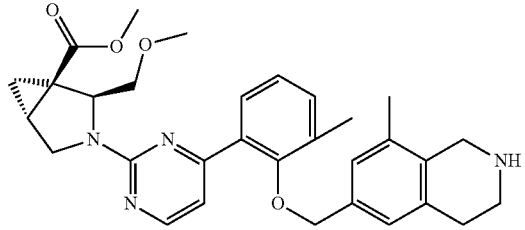
F-160
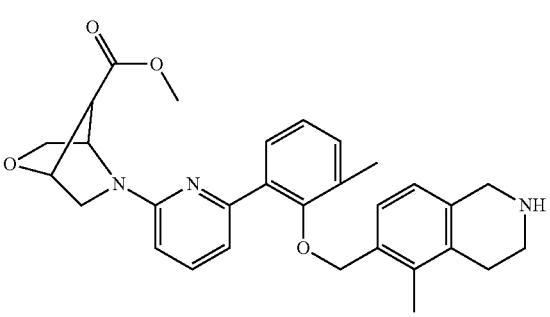
F-187
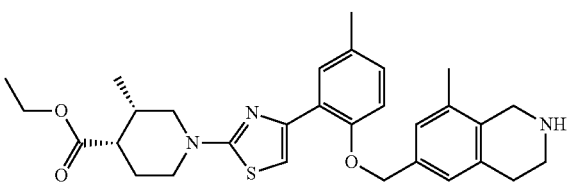
F-188
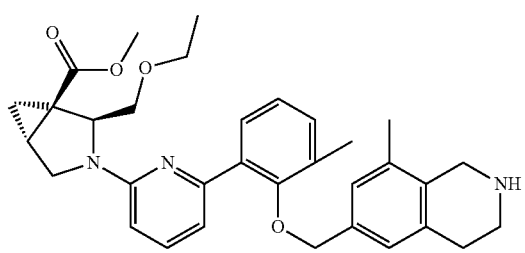
F-189
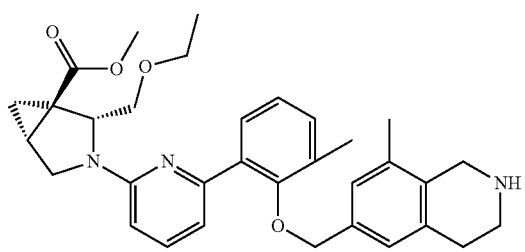

Example 42

Preparation of intermediate (1R,6S)-3-{6-[2-(1,2,3,4-Tetrahydro-isoquinolin-6-ylmethoxy)-phenyl]-pyridin-2-yl}-3-aza-bicyclo[4.1.0]heptane-6-carboxylic acid ethyl ester trifluoroacetic acid salt (F-29)

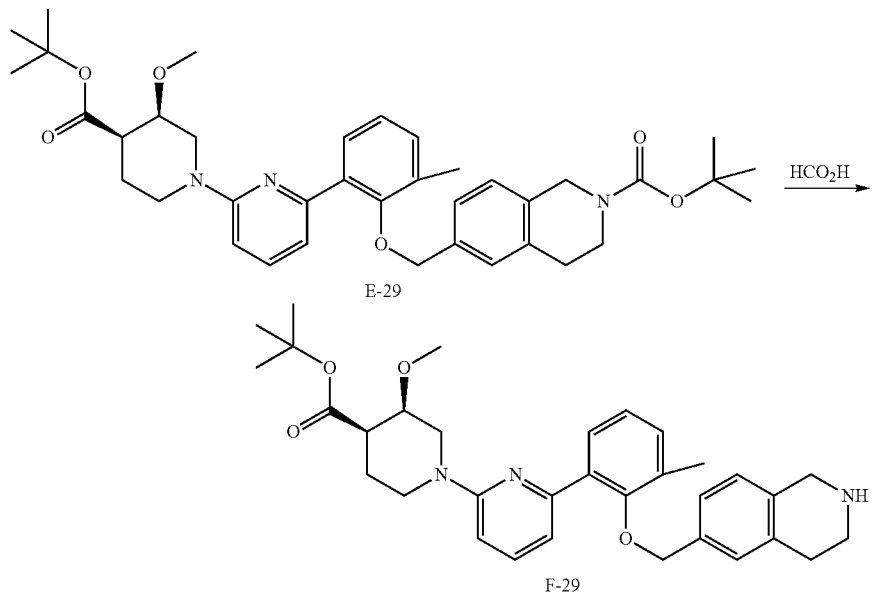

A solution of 0.163 g (0.254 mmol) of E-29 in formic (0.5 mL) is stirred at 35° C. for 3 hours. The mixture is diluted with EtOAc and washed with saturated aqueous sodium bicarbonate followed by brine. The organic phase is concentrated under reduced pressure to afford F-29 which is used directly in the next reaction sequence.

The following intermediates can be prepared from in a similar fashion using the appropriate reagents.

F-30

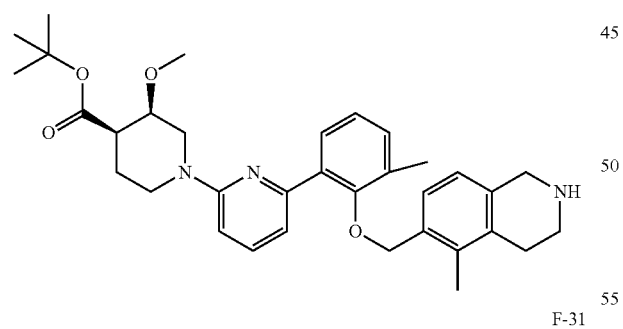

F-31

-continued

F-32

F-33

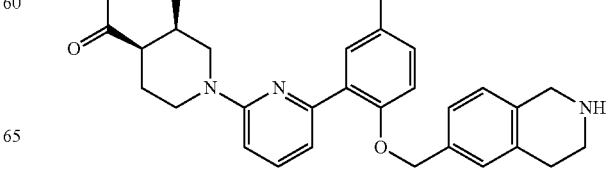

F-34
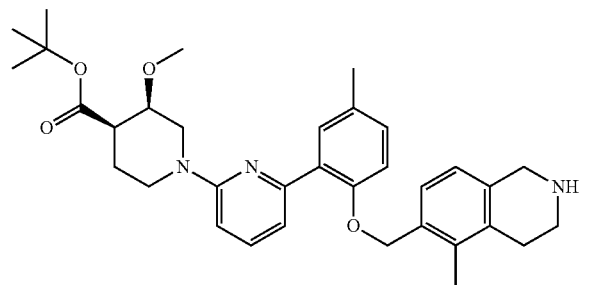
F-35
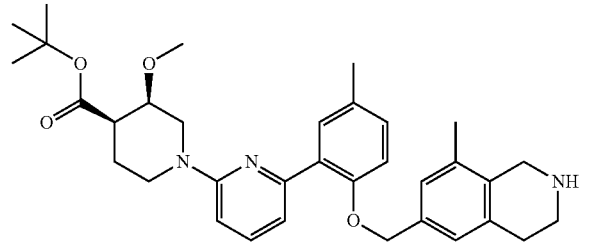
F-36
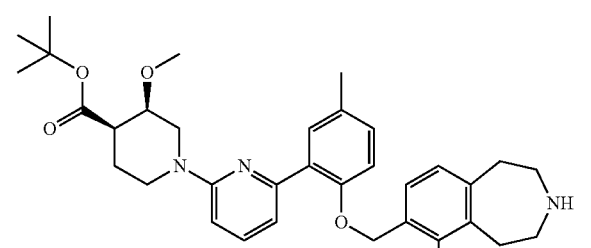
F-37
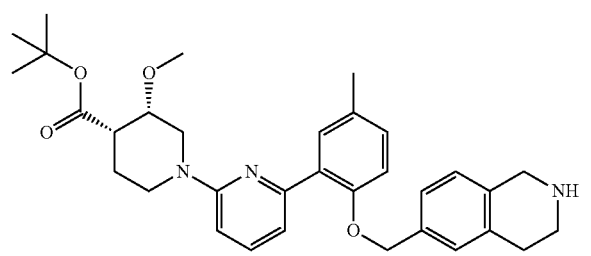
F-38
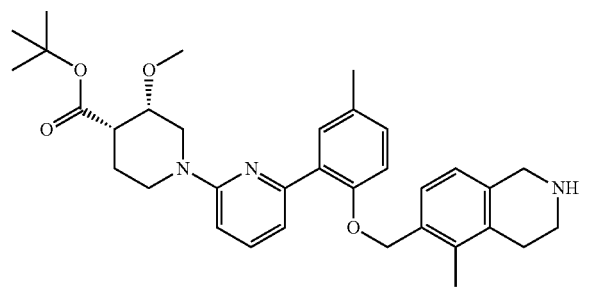
F-39
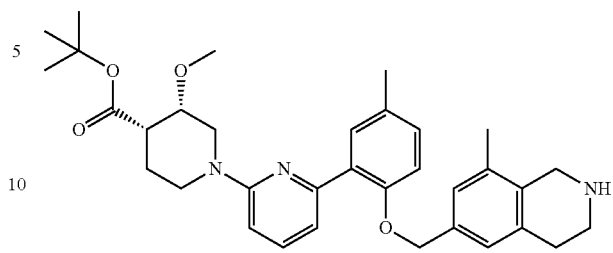
F-40
F-41
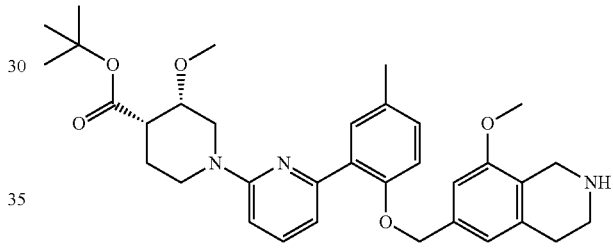
F-42
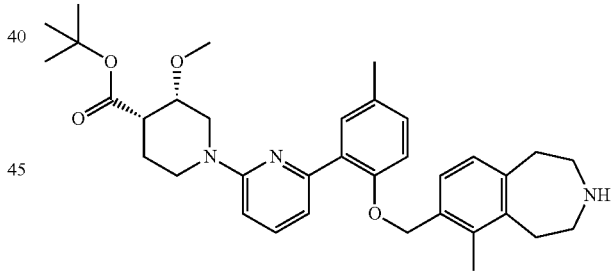
F-76
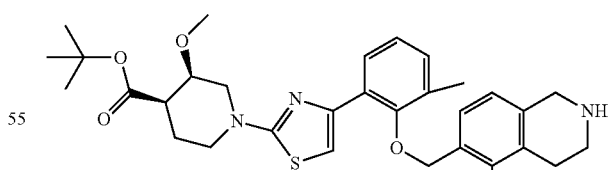
F-77
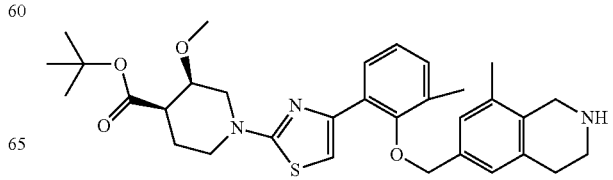

F-78
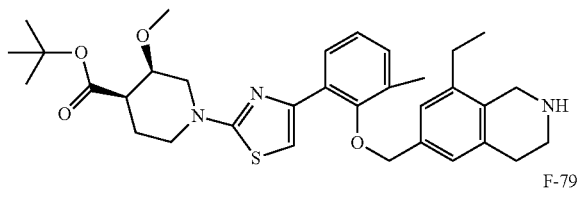
F-79
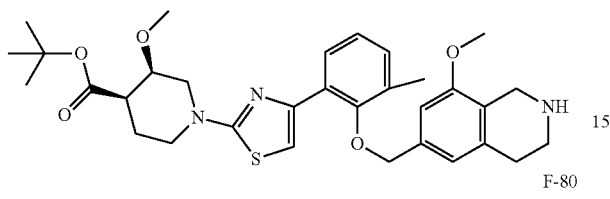
F-80
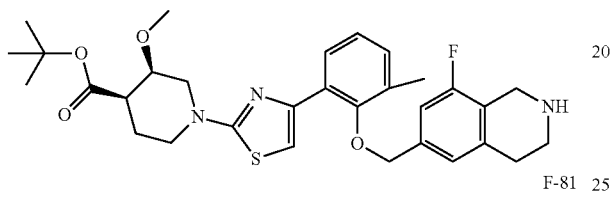
F-81
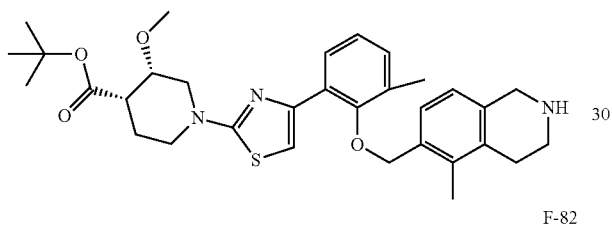
F-82
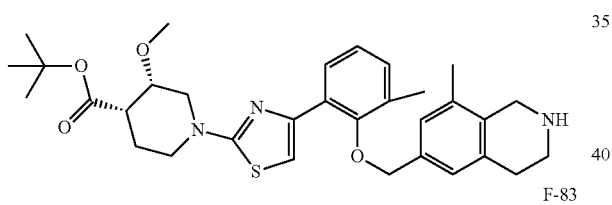
F-83
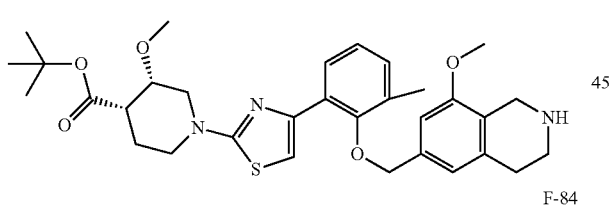
F-84
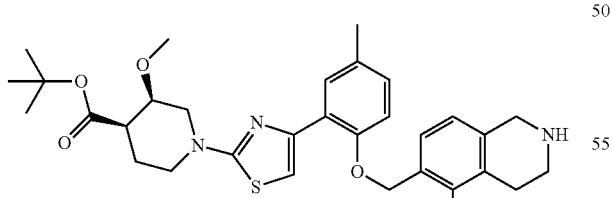
F-85
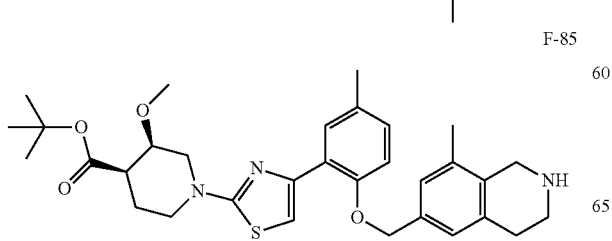
F-86
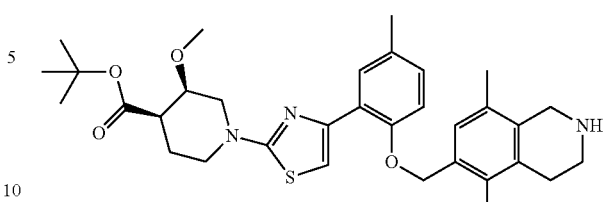
F-87
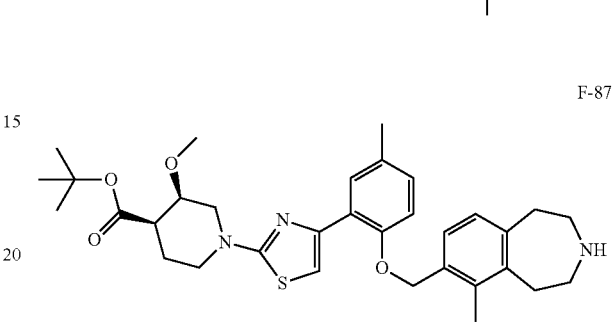
F-96
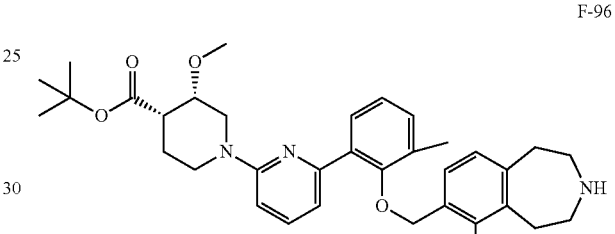
F-97
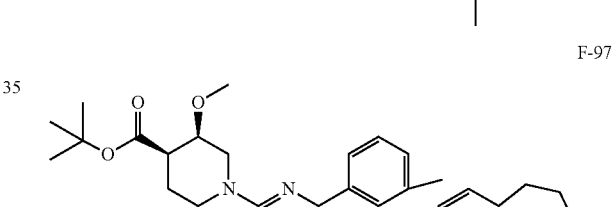
F-114
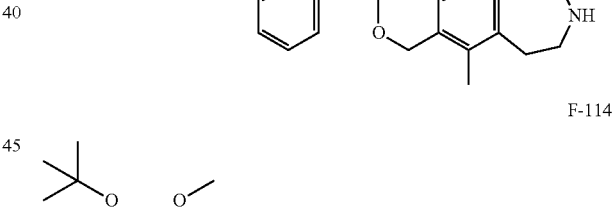
F-115
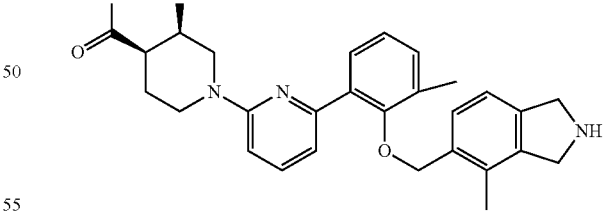
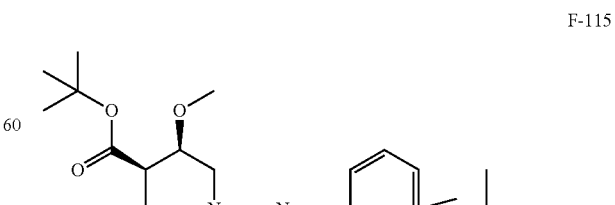
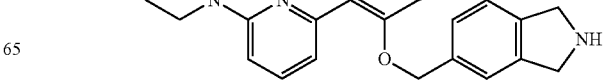

347
-continued
F-116
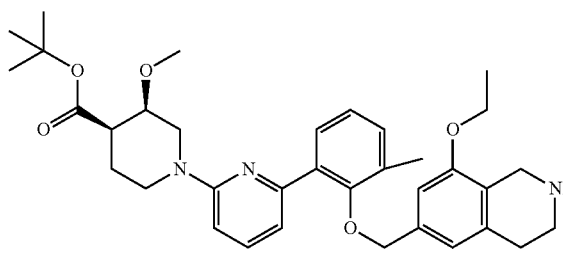
F-117
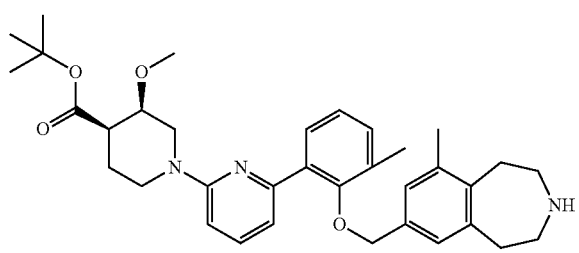
F-118
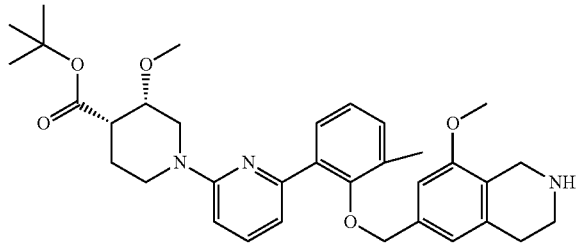
F-119
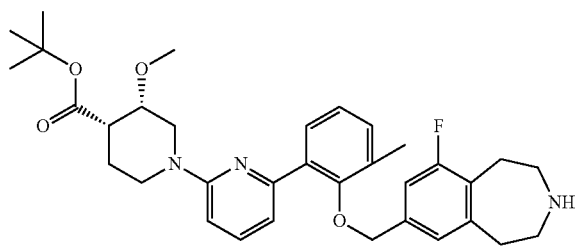
F-120
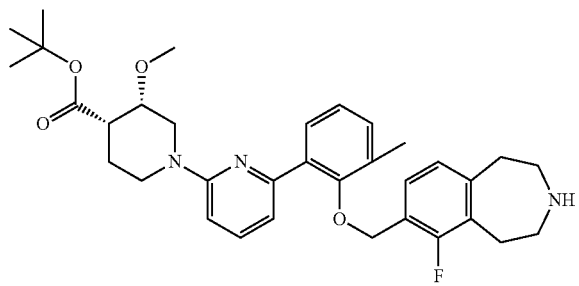
348
-continued
F-121
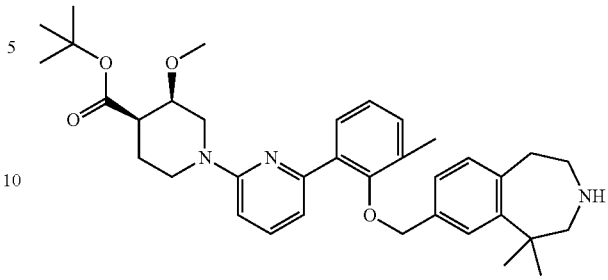
F-123
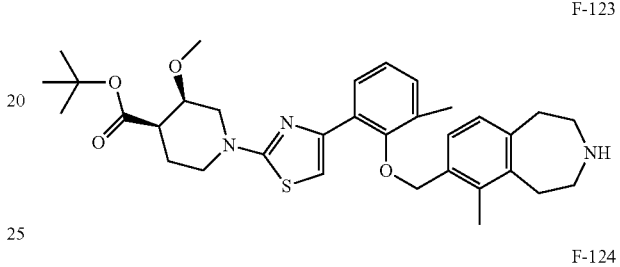
F-124
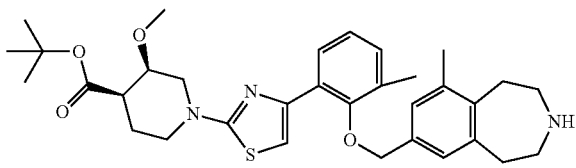
F-125
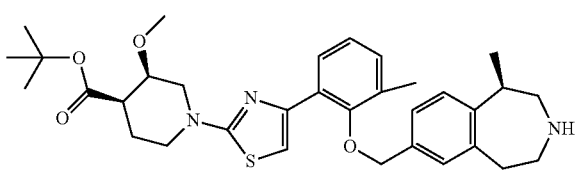
F-126
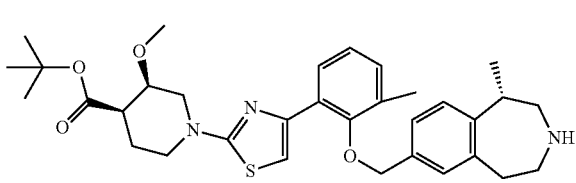
F-127
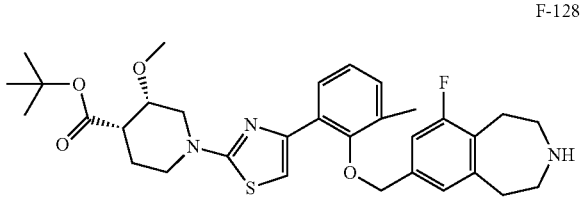 [SMILES: CO[C@H]1CN(c2nc(-c3cccc(C)c3OCc3cc(C)c4c(c3)CCNCC4)cs2)CC[C@H]1C(=O)OC(C)(C)C]
F-128
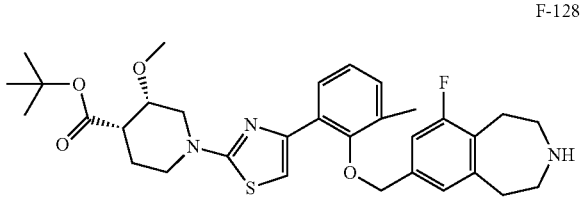 [SMILES: CO[C@H]1CN(c2nc(-c3cccc(C)c3OCc3cc(C)c4c(c3)CCNCC4)cs2)CC[C@H]1C(=O)OC(C)(C)C]

F-129
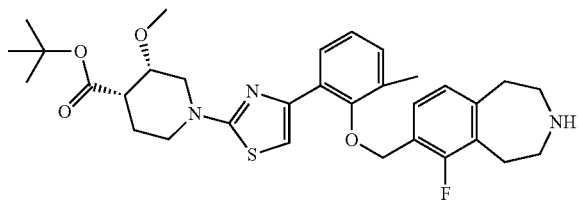
F-130
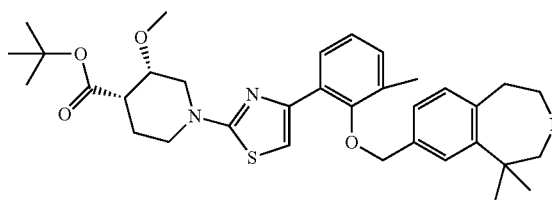
F-131
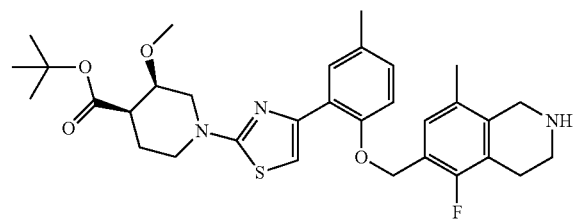
F-132
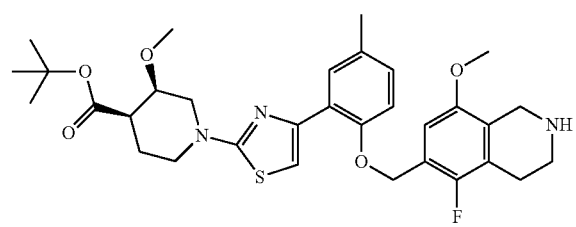
F-133
F-134
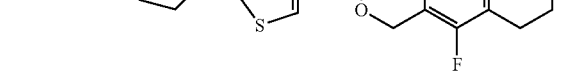
F-142
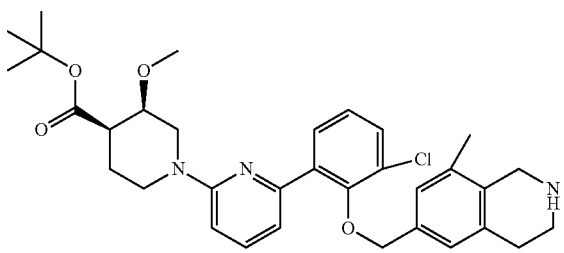
F-143
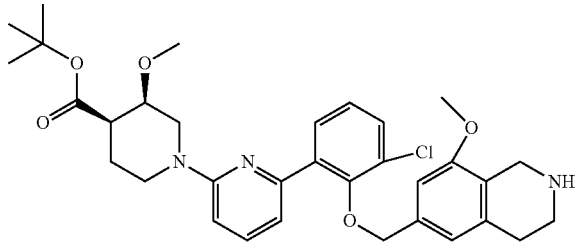
F-144
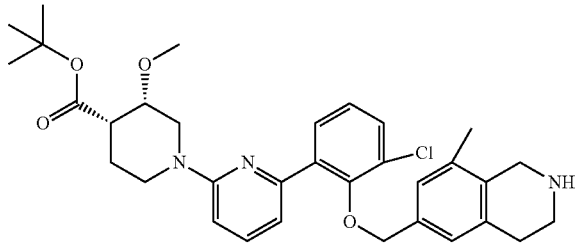
F-145
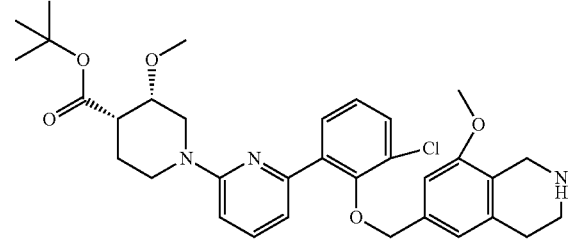
F-146
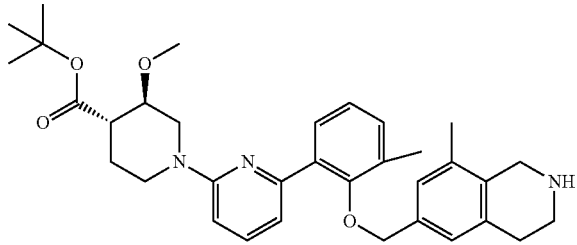

F-147
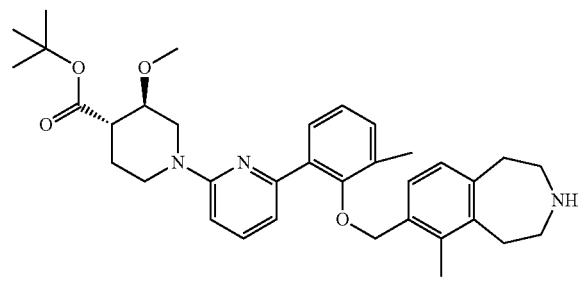
F-148
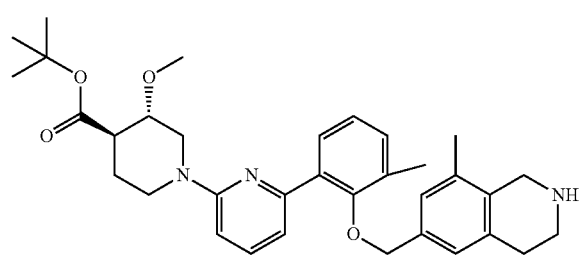
F-149
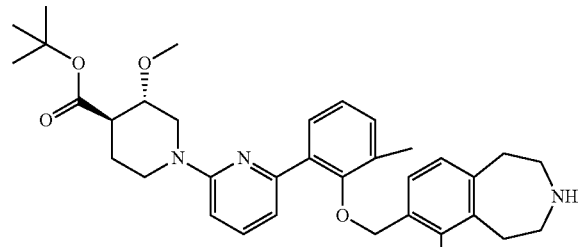
F-150
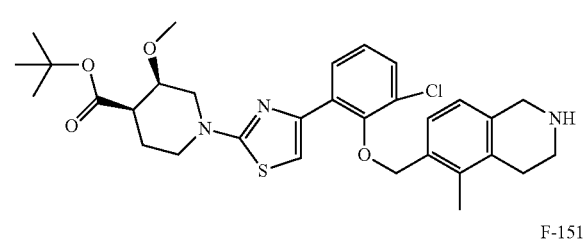
F-151
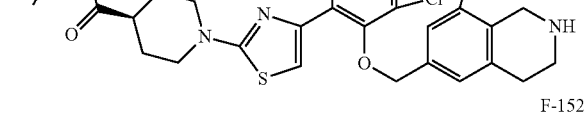
F-152
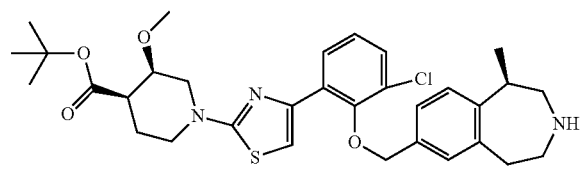
F-153
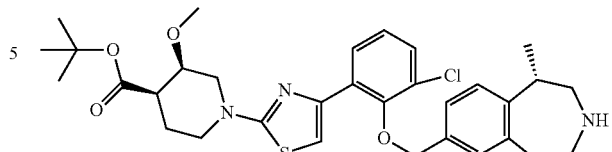
F-154
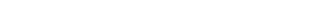
F-155
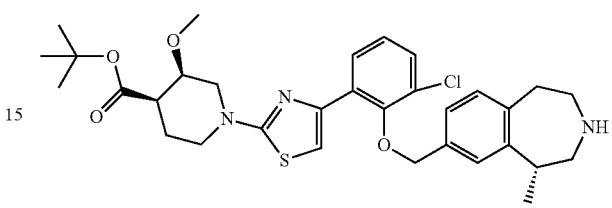
F-156
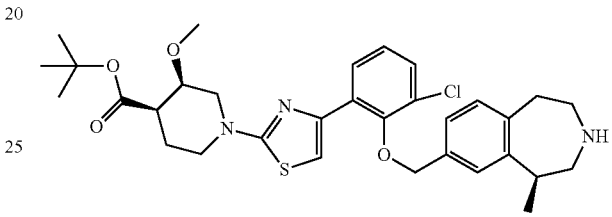
F-157
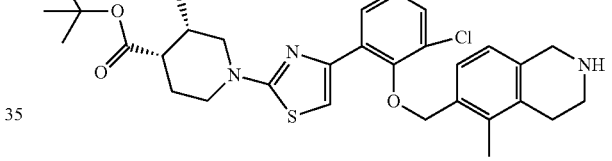
F-158
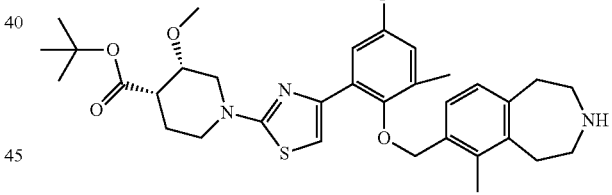
F-159
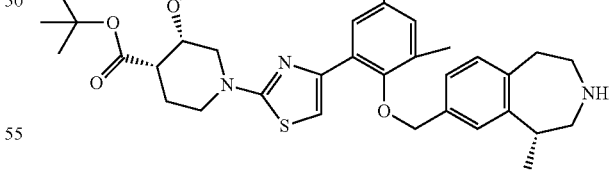
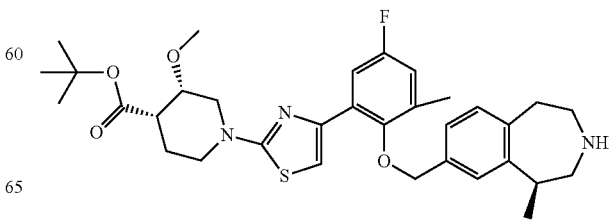

353
-continued
F-161
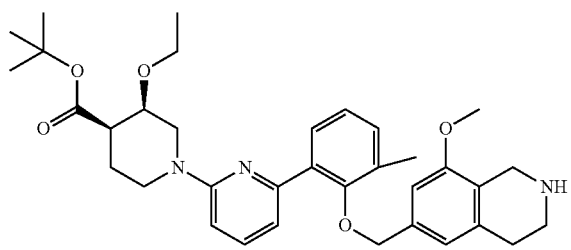
F-162
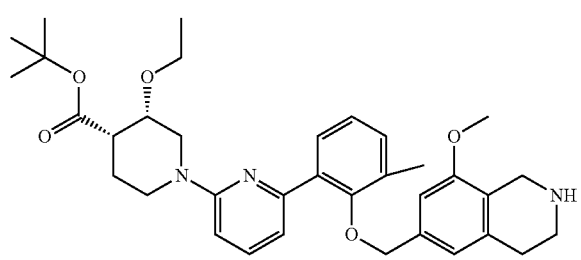
F-163
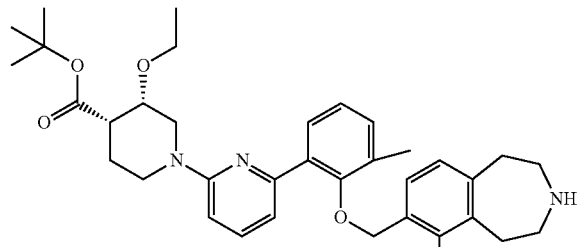
F-164
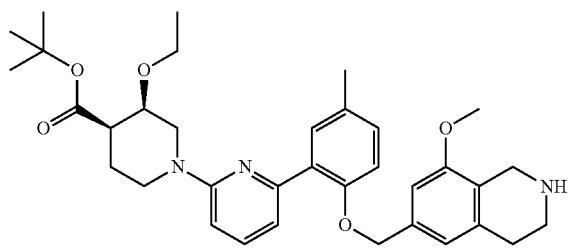
F-165
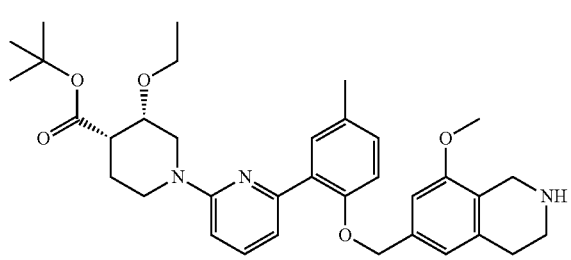
354
-continued
F-166
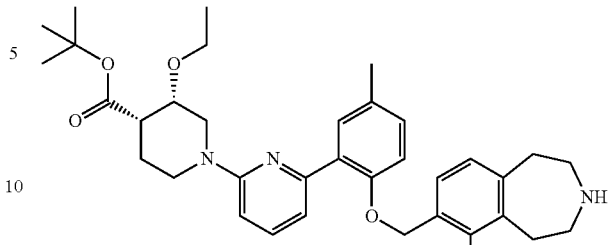
F-167
F-168
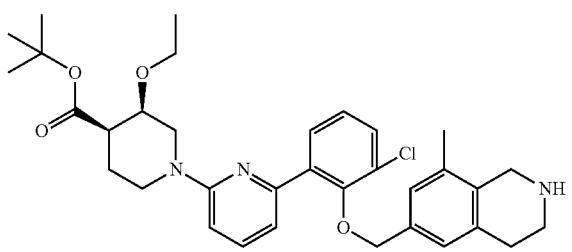
F-169
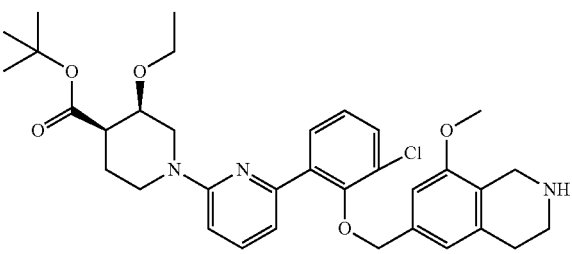
F-170
F-171
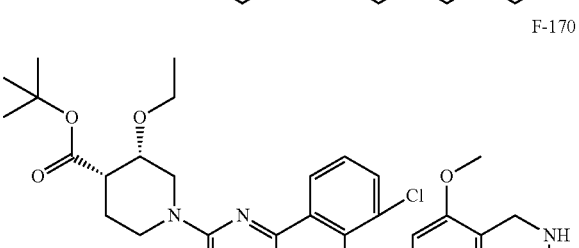
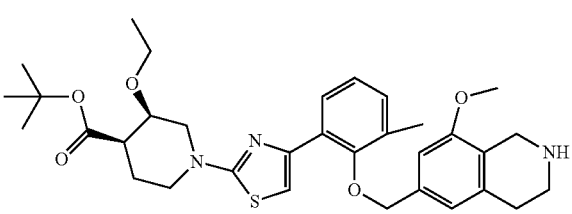

F-172
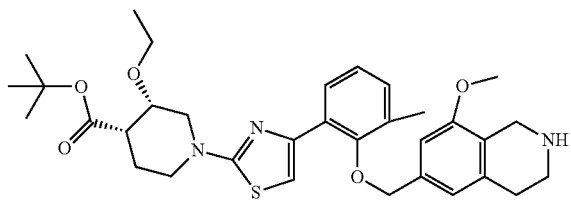
F-173
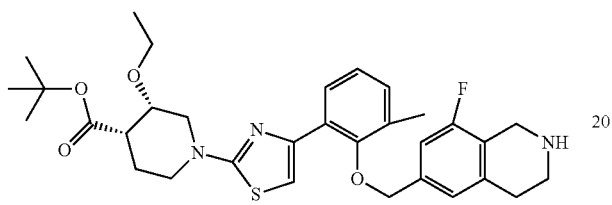
F-174
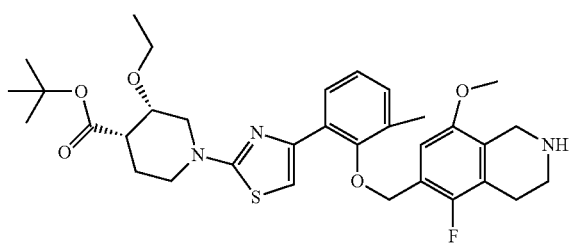
F-175
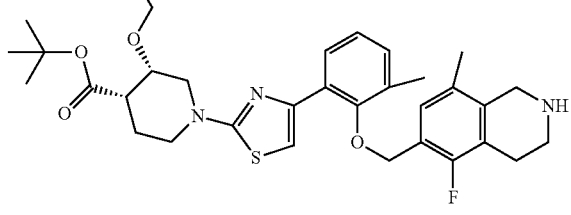
F-176
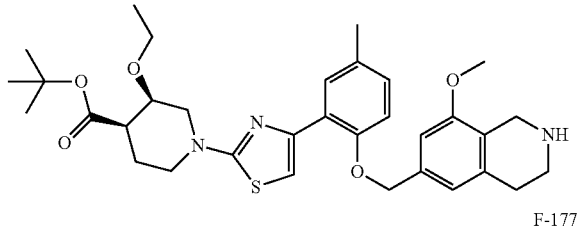
F-177
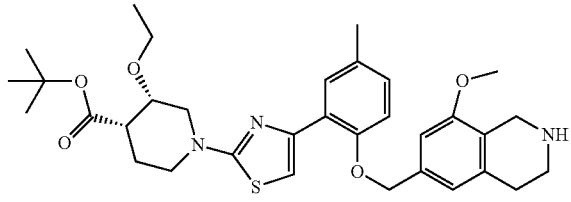
F-178
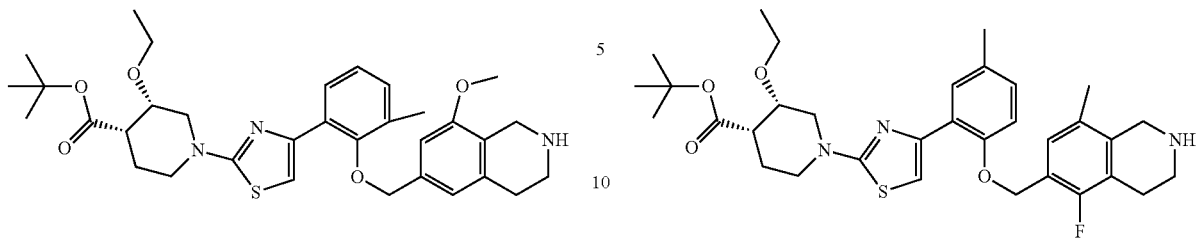
F-179
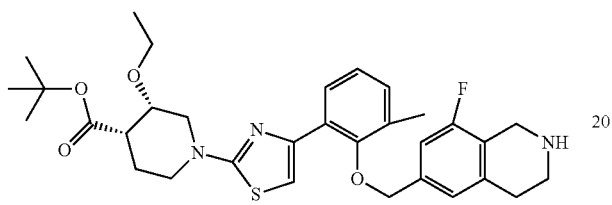
F-180
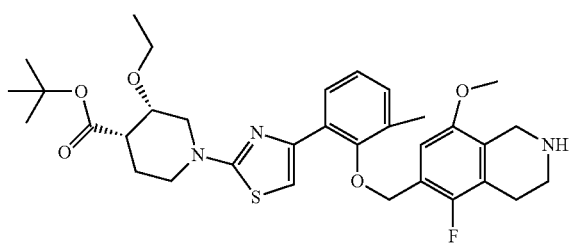
F-181
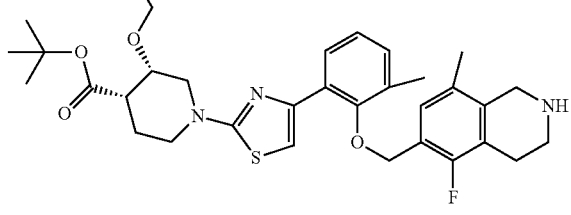
F-182
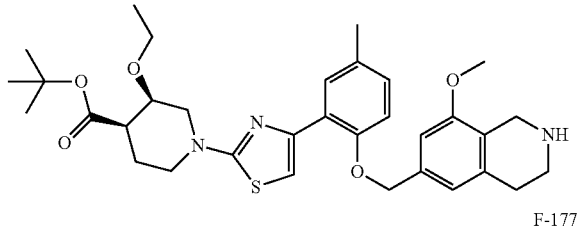
F-183
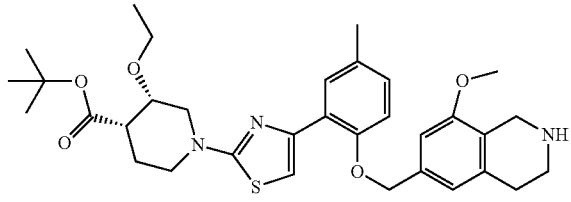

357
-continued
F-184
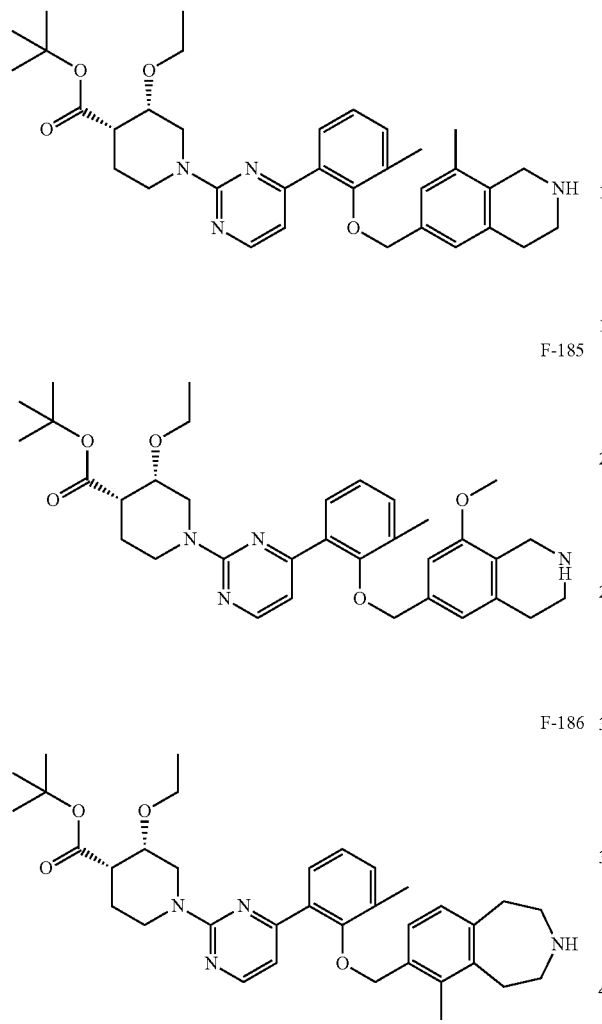
F-185
F-186
358
-continued
F-190
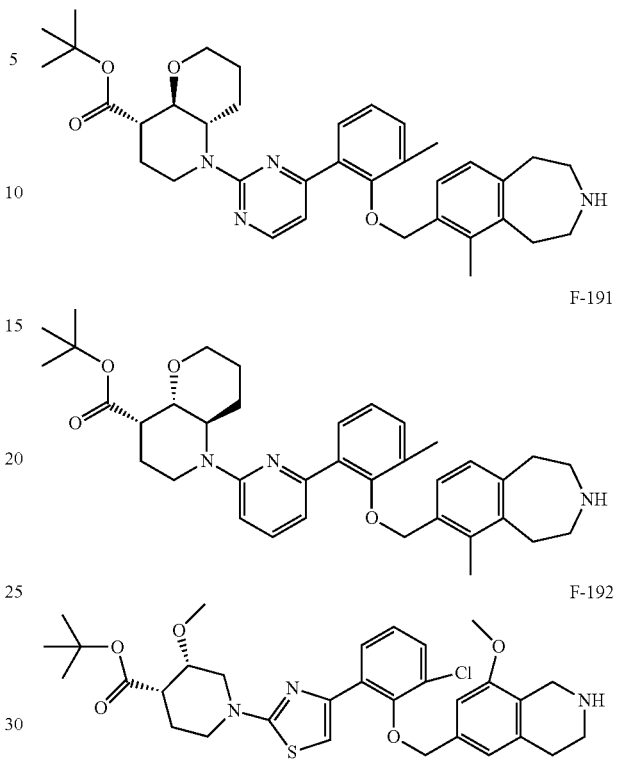
F-191
F-192
Synthesis of Final Compounds
Example 43
Preparation of (1R,6S)-3-(6-{2-[2-(Tetrahydro-pyran-4-yl)-1,2,3,4-tetrahydro-isoquinolin-6-yl-methoxy]-phenyl}-pyridin-2-yl)-3-aza-bicyclo[4.1.0]heptane-6-carboxylic acid (1)
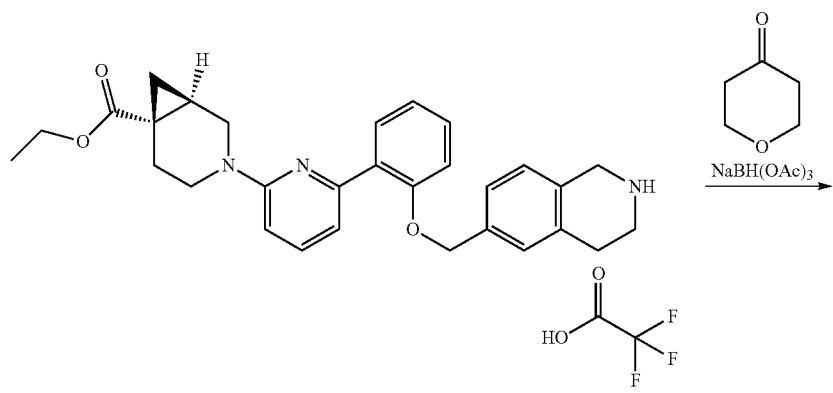
F-1

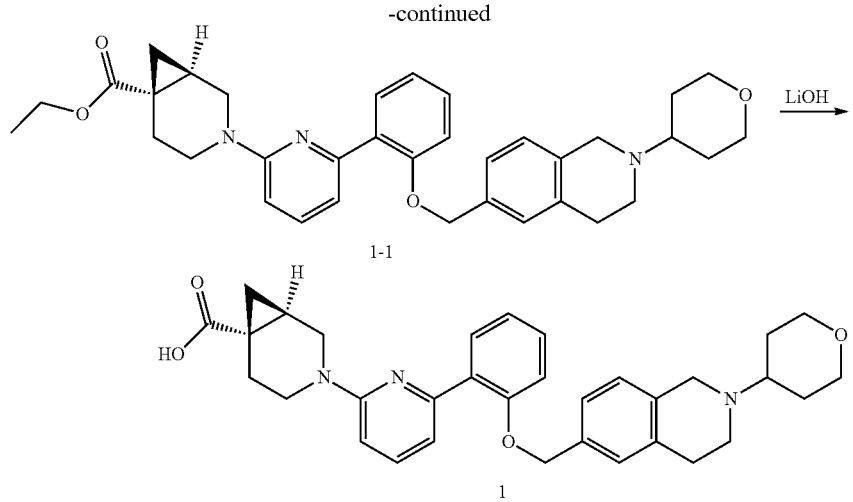

To a solution of F-1 in DCM (10 mL) is added 0.050 mL (0.54 mmol) of tetrahydro-pyran-4-one followed by 0.10 g (0.42 mmol) of sodium triacetoxyborohydride. The mixture is stirred overnight at room temperature then diluted with methanol and concentrated under reduced pressure. The residue is purified by flash silica gel chromatography to afford 0.020 g (32% over two steps) of 1-1.

To a solution of 0.020 g (0.035 mmol) of 1-1 in a 1:1:1 mixture of water: MeOH: THF (15 mL) is added 0.020 g (0.48 mmol) of lithium hydroxide monohydrate. The mixture is stirred overnight at room temperature then concentrated under reduced pressure. The residue is purified by reverse phase flash chromatography with 0.1% TFA additive. The eluent is removed under reduced pressure to afford 1 (0.020 g, 74) as the TFA salt. MS, electrospray, m/z=540.4[M+H], RT 1.11 min.

The following compounds can be prepared from the F-intermediate indicated in a similar fashion using the appropriate reagents.

| Compound Number | From Intermediate F- | Mass [M + H]+ | Method | Retention Time | Comment |
| --- | --- | --- | --- | --- | --- |
| 2 | 1 | 512.3 | A2 | 1.40 | |
| 3 | 2 | 554.3 | A3 | 0.46 | |
| 4 | 2 | 526.3 | A3 | 0.54 | |
| 5 | 2 | 570.3 | A1 | 0.36 | |
| 6 | 2 | 554.2 | A2 | 1.37 | |
| 7 | 2 | 540.2 | A2 | 1.32 | |
| 8 | 2 | 540.2 | A2 | 1.35 | |
| 9 | 2 | 570.2 | A2 | 1.40 | |
| 10 | 2 | 570.2 | A2 | 1.40 | |
| 11 | 2 | 554.2 | A2 | 1.38 | |
| 12 | 3 | 554.4 | A2 | 1.38 | |
| 13 | 4 | 554.3 | A1 | 0.66 | |
| 14 | 5 | 568.3 | A1 | 0.68 | |
| 15 | 6 | 568.3 | A1 | 0.65 | |
| 16 | 7 | 554.2 | A1 | 0.47 | |
| 17 | 7 | 526.3 | A1 | 0.70 | |
| 19 | 8 | 540.3 | A1 | 0.72 | |
| 20 | 9 | 540.3 | A1 | 0.63 | |
| 21 | 10 | 554.3 | A1 | 0.43 | |
| 22 | 11 | 554.7 | A1 | 0.29 | |
| 23 | 11 | 526.5 | A1 | 0.46 | |
| 24 | 11 | 540.4 | A1 | 0.27 | Mixture of diastereomers |
| 27 | 12 | 570.5 | A1 | 0.27 | |
| 28 | 12 | 542.5 | A1 | 0.28 | |
| 29 | 13 | 537.6 | A1 | 0.64 | |
| 30 | 13 | 565.4 | A1 | 0.47 | |
| 31 | 14 | 554.4 | A1 | 0.49 | |
| 32 | 14 | 526.3 | A1 | 0.48 | |
| 33 | 15 | 568.4 | A1 | 0.44 | |
| 34 | 15 | 540.4 | A1 | 0.41 | |
| 35 | 16 | 554.4 | A1 | 0.26 | |
| 36 | 16 | 526.4 | A1 | 0.27 | |
| 37 | 17 | 554.3 | A1 | 0.26 | |
| 38 | 17 | 526.4 | A1 | 0.28 | |
| 39 | 18 | 568.4 | A1 | 0.38 | |
| 40 | 18 | 540.8 | A1 | 0.49 | |
| 41 | 19 | 568.4 | A1 | 0.27 | |
| 42 | 19 | 540.4 | A1 | 0.27 | |
| 43 | 20 | 556.2 | A2 | 1.60 | |
| 44 | 20 | 584.3 | A2 | 1.60 | |
| 45 | 20 | 570.2 | A2 | 1.58 | Mixture of diastereomers |
| 46 | 21 | 598.2 | A1 | 0.51 | |
| 47 | 21 | 570.2 | A1 | 0.53 | |
| 48 | 22 | 598.5 | A1 | 0.41 | |
| 49 | 22 | 570.4 | A1 | 0.66 | |
| 53 | 23 | 612.3 | A2 | 1.84 | |
| 54 | 23 | 584.2 | A2 | 1.93 | |
| 55 | 23 | 598.2 | A2 | 1.83 | |
| 56 | 23 | 628.2 | A2 | 1.86 | |
| 57 | 24 | 614.5 | A1 | 0.49 | |
| 58 | 24 | 586.1 | A1 | 0.50 | |
| 59 | 25 | 616.3 | A1 | 0.76 | |
| 60 | 26 | 584.4 | A1 | 0.51 | |
| 61 | 26 | 612.4 | A1 | 0.53 | |
| 62 | 27 | 598.3 | A3 | 0.58 | |
| 63 | 28 | 598.3 | A3 | 0.82 | |
| 82 | 43 | 546.6 | A1 | 0.51 | |
| 83 | 44 | 560.1 | A1 | 0.76 | |
| 84 | 45 | 560.3 | A1 | 0.66 | |
| 85 | 45 | 532.3 | A3 | 1.44 | |
| 86 | 46 | 590.5 | A4 | 0.76 | |
| 87 | 46 | 574.5 | A4 | 0.78 | |
| 88 | 46 | 560.3 | A4 | 0.74 | |
| 89 | 46 | 590.5 | A4 | 0.77 | |
| 90 | 46 | 574.5 | A4 | 0.80 | |
| 91 | 47 | 590.5 | A4 | 0.77 | |

| Compound Number | From Intermediate F- | Mass [M + H]+ | Method | Retention Time | Comment |
|---|---|---|---|---|---|
| 92 | 47 | 560.5 | A4 | 0.75 | |
| 93 | 47 | 590.5 | A4 | 0.76 | |
| 94 | 47 | 574.5 | A4 | 0.79 | |
| 95 | 47 | 560.4 | A4 | 0.75 | |
| 96 | 47 | 574.5 | A4 | 0.77 | |
| 97 | 47 | 564.4 | A4 | 0.72 | |
| 98 | 48 | 604.5 | A4 | 0.79 | |
| 99 | 48 | 588.5 | A4 | 0.81 | |
| 100 | 48 | 574.5 | A4 | 0.77 | |
| 101 | 48 | 588.5 | A4 | 0.79 | |
| 102 | 48 | 560.5 | A4 | 0.74 | |
| 103 | 49 | 588.5 | A4 | 0.81 | |
| 104 | 49 | 574.5 | A4 | 0.77 | |
| 105 | 50 | 560.5 | A4 | 0.76 | |
| 106 | 50 | 574.5 | A4 | 0.78 | Mixture of diastereomers |
| 107 | 50 | 546.4 | A4 | 0.73 | |
| 108 | 51 | 590.5 | A4 | 0.77 | |
| 109 | 51 | 574.5 | A4 | 0.79 | Mixture of diastereomers |
| 110 | 52 | 560.4 | A4 | 0.75 | |
| 111 | 52 | 574.5 | A4 | 0.77 | |
| 112 | 52 | 576.5 | A4 | 0.74 | Mixture of diastereomers |
| 113 | 52 | 560.4 | A4 | 0.77 | Mixture of diastereomers |
| 114 | 52 | 546.5 | A4 | 0.72 | Mixture of diastereomers |
| 115 | 53 | 574.3 | A1 | 0.77 | |
| 116 | 53 | 546.3 | A3 | 1.49 | |
| 117 | 53 | 590.5 | A4 | 0.77 | Mixture of diastereomers |
| 118 | 53 | 574.5 | A4 | 0.80 | Mixture of diastereomers |
| 119 | 53 | 560.5 | A4 | 0.75 | Mixture of diastereomers |
| 120 | 54 | 590.5 | A4 | 0.78 | Mixture of diastereomers |
| 121 | 54 | 574.5 | A4 | 0.81 | Mixture of diastereomers |
| 122 | 54 | 560.5 | A4 | 0.76 | Mixture of diastereomers |
| 123 | 54 | 574.5 | A4 | 0.78 | |
| 124 | 54 | 546.4 | A4 | 0.73 | |
| 125 | 55 | 588.3 | A3 | 1.62 | |
| 126 | 55 | 560.3 | A3 | 1.64 | |
| 127 | 55 | 604.5 | A4 | 0.81 | Mixture of diastereomers |
| 128 | 55 | 588.5 | A4 | 0.83 | Mixture of diastereomers |
| 129 | 55 | 574.5 | A4 | 0.79 | Mixture of diastereomers |
| 130 | 56 | 588.3 | A3 | 1.62 | |
| 131 | 56 | 560.3 | A3 | 1.50 | |
| 132 | 56 | 604.3 | A3 | 1.64 | Mixture of diastereomers |
| 133 | 56 | 574.3 | A3 | 1.61 | Mixture of diastereomers |
| 134 | 56 | 588.3 | A3 | 1.69 | Mixture of diastereomers |
| 135 | 57 | 546.1 | A1 | 0.61 | |
| 136 | 58 | 560.5 | A1 | 0.62 | |
| 137 | 58 | 530.4 | A1 | 0.57 | |
| 138 | 58 | 532.3 | A1 | 0.63 | |
| 139 | 59 | 532.3 | A1 | 0.60 | |
| 140 | 59 | 560.4 | A1 | 0.60 | |
| 141 | 60 | 543.3 | A1 | 0.85 | |
| 142 | 60 | 571.3 | A1 | 0.58 | |
| 143 | 61 | 546.4 | A1 | 0.61 | |
| 144 | 61 | 574.3 | A1 | 0.62 | |
| 145 | 62 | 546.3 | A1 | 0.76 | |
| 146 | 63 | 560.3 | A1 | 0.79 | |
| 147 | 64 | 560.0 | A1 | 0.63 | |
| 148 | 64 | 532.4 | A1 | 0.62 | |
| 149 | 65 | 546.3 | A1 | 0.61 | |
| 150 | 65 | 574.3 | A1 | 0.66 | |
| 151 | 66 | 560.4 | A1 | 0.67 | |
| 152 | 67 | 574.3 | A1 | 0.68 | |
| 153 | 68 | 560.3 | A1 | 0.80 | |
| 154 | 69 | 574.2 | A1 | 0.91 | |
| 155 | 70 | 574.4 | A1 | 0.81 | |
| 156 | 70 | 546.3 | A1 | 0.87 | |
| 157 | 71 | 574.4 | A1 | 0.83 | |
| 158 | 71 | 546.3 | A1 | 0.89 | |
| 159 | 72 | 604.4 | A1 | 0.63 | |
| 160 | 72 | 574.3 | A1 | 0.63 | |
| 161 | 73 | 576.4 | A1 | 0.86 | |
| 162 | 73 | 604.4 | A1 | 0.81 | |
| 163 | 74 | 590.3 | A1 | 0.64 | |
| 164 | 75 | 604.7 | A1 | 0.66 | |
| 183 | 88 | 608/2 | A3 | 1.68 | |
| 184 | 88 | 574.2 | A3 | 1.46 | |
| 185 | 89 | 555.2 | A1 | 0.62 | |
| 186 | 90 | 555.2 | A1 | 0.66 | |
| 187 | 91 | 567.3 | A1 | 0.69 | |
| 188 | 92 | 541.2 | A1 | 0.58 | |
| 189 | 93 | 555.2 | A1 | 0.60 | |
| 190 | 94 | 555.1 | A1 | 0.61 | |
| 191 | 94 | 527.4 | A1 | 0.73 | |
| 194 | 95 | 561.3 | A3 | 0.96 | |
| 198 | 98 | 600.3 | A1 | 0.27 | |
| 199 | 122 | 574.3 | A2 | 2.20 | |
| 200 | 99 | 590.3 | A2 | 1.38 | |
| 201 | 99 | 562.2 | A2 | 1.35 | |
| 212 | 138 | 616.2 | A1 | 0.54 | |
| 213 | 137 | 602.4 | A1 | 1.96 | |
| 214 | 160 | 570.3 | A1 | 0.56 | |
| 215 | 100 | 612.5 | A1 | 0.52 | |
| 216 | 102 | 602.4 | A2 | 1.72 | |
| 217 | 101 | 609.3 | A3 | 0.86 | |
| 218 | 135 | 598.4 | A3 | 0.65 | |
| 219 | 136 | 598.4 | A3 | 0.73 | |
| 220 | 139 | 652.0 | A3 | 1.52 | |
| 221 | 140 | 618.3 | A1 | 0.59 | |
| 222 | 104 | 584.3 | A1 | 0.48 | |
| 223 | 103 | 584.3 | A1 | 0.47 | |
| 224 | 105 | 584.4 | A1 | 0.46 | |
| 225 | 106 | 612.4 | A3 | 0.85 | |
| 226 | 107 | 612.4 | A3 | 0.85 | |
| 227 | 139 | 624.3 | A1 | 0.72 | |
| 236 | 187 | 576.10 | A1 | 0.66 | |
| 237 | 141 | 599.10 | A1 | 0.64 | |
| 243 | 108 | 616.1 | A1 | 0.57 | |
| 262 | 109 | 616.3 | A1 | 0.49 | |
| 263 | 109 | 588.1 | A1 | 0.50 | |
| 268 | 109 | 602.3 | A1 | 0.49 | |
| 279 | 110 | 628.6 | A1 | 0.52 | |
| 280 | 110 | 614.6 | A1 | 0.52 | |
| 281 | 110 | 600.6 | A1 | 0.54 | |
| 292 | 2 | 524.6 | A3 | 0.73 | |
| 304 | 2 | 581.6 | A1 | 0.58 | |
| 305 | 2 | 470.6 | A2 | 1.19 | |
| 306 | 2 | 575.7 | A2 | 0.73 | |
| 308 | 2 | 564.6 | A2 | 1.17 | |
| 309 | 2 | 590.6 | A2 | 1.34 | |
| 310 | 2 | 542.7 | A2 | 1.30 | |
| 311 | 2 | 565.6 | A2 | 1.52 | |
| 314 | 111 | 614.3 | A3 | 0.79 | |
| 315 | 188 | 612.4 | A3 | 0.83 | |
| 316 | 189 | 612.3 | A3 | 0.66 | |
| 317 | 112 | 599.3 | A1 | 0.46 | |
| 318 | 113 | 585.4 | A1 | 0.45 | |

The following compounds from Table 1 are prepared in a similar fashion to the procedure described in Example 43, using intermediate F-11 and the appropriate reagents. The diastereomers are separated prior to the final synthetic step.

The absolute configuration of the diastereomeric center is not determined:

Compound 25: MS, electrospray, m/z=540.4 [M+1-1], RT 0.27 min;

Compound 26: MS, electrospray, m/z=540.5 [M+1-1], RT 0.27 min;

The following compounds from Table 1 are prepared in a similar fashion to the procedure described in Example 43, using intermediate F-22 and the appropriate reagents. The diastereomers are separated prior to the final synthetic step. The absolute configuration of the diastereomeric center is not determined:

Compound 51: MS, electrospray, m/z=584.4 [M+1-1], RT 0.52 min;

Compound 52: MS, electrospray, m/z=584.4 [M+1-1], RT 0.54 min;

Example 44

Preparation of (3R,4R)-3-Methoxy-6'-{3-methyl-2-[2-(tetrahydro-pyran-4-yl)-1,2,3,4-tetrahydro-isoquinolin-6-ylmethoxy]-phenyl}-3,4,5,6-tetrahydro-2H-[1,2']bipyridinyl-4-carboxylic acid (64)

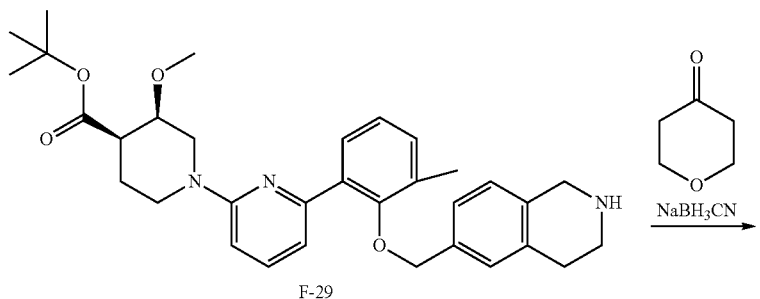

F-29

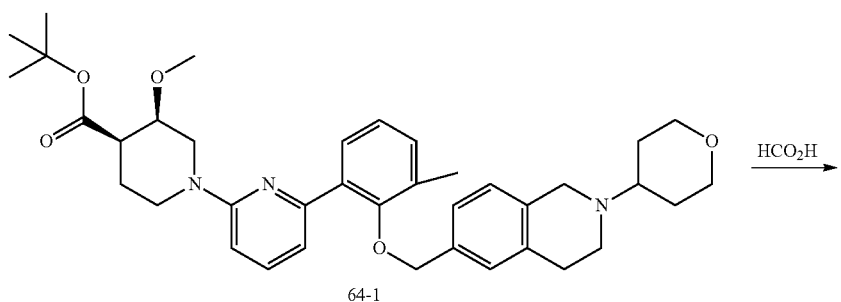

64-1

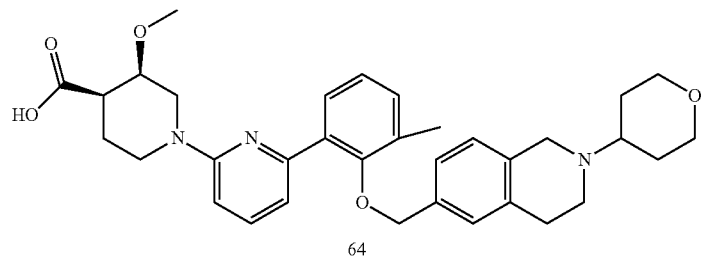

64

To a solution of 0.102 g (0.188 mmol) of F-29 in MeOH (1 mL) is added 0.022 mL (0.38 mmol) of acetic acid followed by 0.034 mL (0.38 mmol) of tetrahydro-pyran-4-one, and 0.047 g (0.75 mmol) of sodium cyanoborohydride. The mixture is stirred at 50° C. for 3 days then purified by flash silica gel chromatography to afford 0.13 g (quant %) of 64-1.

A solution of 0.13 g (0.20 mmol) of 64-1 in formic acid (0.5 mL) is heated overnight at 50 C. The residue is purified by reverse phase flash chromatography with 0.1% formic acid additive. The eluent is removed under reduced pressure to afford 64 (0.079 g, 67%) as the formate salt. MS, electrospray, m/z=572.4 [M+H], RT 1.66 min.

The following compounds from Table 1 are prepared in a similar fashion to the procedure described in Example 44,

| Compound Number | From Intermediate F- | Mass [M + H]+ | Method | Retention Time |
|---|---|---|---|---|
| 65 | 30 | 586.1 | A2 | 1.69 |
| 66 | 30 | 558.6 | A2 | 1.60 |
| 67 | 31 | 572.1 | A2 | 1.65 |
| 68 | 32 | 586.1 | A2 | 1.59 |
| 69 | 32 | 558.6 | A2 | 1.60 |
| 70 | 33 | 573.3 | A2 | 1.41 |
| 71 | 34 | 586.2 | A1 | 0.51 |
| 72 | 35 | 586.1 | A2 | 1.48 |
| 73 | 36 | 600.2 | A1 | 0.53 |
| 74 | 37 | 573.3 | A2 | 1.41 |
| 75 | 38 | 586.2 | A1 | 0.50 |
| 76 | 39 | 586.7 | A2 | 1.49 |
| 79 | 40 | 600.4 | A1 | 0.56 |
| 80 | 41 | 602.4 | A1 | 0.52 |
| 81 | 42 | 600.2 | A1 | 0.53 |
| 165 | 76 | 592.3 | A1 | 0.61 |
| 166 | 76 | 564.3 | A1 | 0.60 |
| 167 | 77 | 592.3 | A1 | 0.68 |
| 170 | 78 | 606.3 | A1 | 0.68 |
| 171 | 79 | 608.3 | A1 | 0.67 |
| 172 | 80 | 596.3 | A1 | 0.65 |
| 173 | 81 | 592.4 | A1 | 0.57 |
| 174 | 81 | 564.3 | A1 | 0.63 |
| 177 | 83 | 608.4 | A1 | 0.67 |
| 178 | 84 | 592.1 | A1 | 0.66 |
| 179 | 84 | 592.3 | A1 | 0.62 |
| 180 | 85 | 592.1 | A1 | 0.67 |
| 181 | 86 | 606.2 | A1 | 0.70 |
| 182 | 87 | 606.1 | A1 | 0.69 |
| 195 | 96 | 606.6 | A1 | 0.53 |
| 196 | 96 | 572.3 | A1 | 0.50 |
| 197 | 97 | 600.3 | A1 | 0.51 |
| 207 | 150 | 612.3 | A1 | 0.67 |
| 208 | 156 | 612.3 | A1 | 0.67 |
| 209 | 79 | 580.3 | A1 | 0.66 |
| 210 | 79 | 594.3 | A1 | 0.64 |
| 211 | 79 | 594.3 | A1 | 0.63 |
| 228 | 172 | 622.4 | A1 | 0.63 |
| 229 | 177 | 622.2 | A1 | 0.66 |
| 230 | 162 | 616.3 | A1 | 0.56 |
| 231 | 165 | 616.3 | A1 | 0.52 |
| 232 | 171 | 622.2 | A1 | 0.65 |
| 233 | 176 | 622.2 | A1 | 0.65 |
| 234 | 161 | 616.3 | A1 | 0.54 |
| 235 | 164 | 616.3 | A1 | 0.51 |
| 238 | 173 | 610.2 | A1 | 0.68 |
| 239 | 163 | 614.4 | A1 | 0.54 |
| 240 | 166 | 614.3 | A1 | 0.50 |
| 241 | 175 | 624.4 | A1 | 0.68 |
| 242 | 125 | 610.0 | A1 | 0.64 |
| 244 | 128 | 610.1 | A1 | 0.64 |
| 245 | 181 | 601.2 | A1 | 0.65 |
| 246 | 182 | 617.1 | A1 | 0.65 |
| 247 | 184 | 601.10 | A1 | 0.66 |
| 248 | 185 | NA | NA | NA |
| 249 | 118 | 602.3 | A1 | 0.50 |
| 250 | 142 | 606.4 | A1 | 0.60 |
| 251 | 143 | 622.3 | A1 | 0.61 |
| 252 | 133 | 626.2 | A1 | 0.61 |
| 253 | 131 | 610.2 | A1 | 0.62 |
| 254 | 134 | 608.0 | A1 | 0.62 |
| 255 | 144 | 606.3 | A1 | 0.60 |
| 256 | 167 | 620.4 | A1 | 0.64 |
| 257 | 168 | 636.4 | A1 | 0.64 |
| 258 | 145 | 622.4 | A1 | 0.61 |
| 259 | 169 | 620.4 | A1 | 0.64 |
| 260 | 170 | 636.4 | A1 | 0.64 |
| 261 | 180 | 643.3 | A1 | 0.69 |
| 264 | 151 | NA | NA | NA |
| 265 | 192 | NA | NA | NA |
| 266 | 129 | 610.4 | A1 | 0.62 |
| 267 | 129 | 582.1 | A1 | 0.63 |
| 269 | 178 | 624.1 | A1 | 0.67 |
| 270 | 174 | 640.2 | A1 | 0.66 |
| 271 | 132 | 626.4 | A1 | 0.62 |
| 272 | 179 | 640.2 | A1 | 0.64 |
| 273 | 119 | 604.5 | A1 | 0.53 |
| 274 | 119 | 576.5 | A1 | 0.53 |
| 275 | 183 | 615.4 | A1 | 0.66 |
| 276 | 186 | 615.5 | A1 | 0.66 |
| 277 | 120 | 604.4 | A1 | 0.48 |
| 278 | 120 | 576.3 | A1 | 0.48 |
| 282 | 96 | 572.3 | A1 | 0.46 |
| 283 | 97 | 586.4 | A1 | 0.49 |
| 284 | 116 | 602.4 | A1 | 0.48 |
| 285 | 116 | 588.4 | A1 | 0.49 |
| 286 | 116 | 616.4 | A1 | 0.49 |
| 287 | 123 | 578.3 | A1 | 0.60 |
| 288 | 123 | 606.4 | A1 | 0.61 |
| 289 | 147 | 572.30 | A1 | 0.54 |
| 290 | 149 | 572.3 | A1 | 0.53 |
| 291 | 117 | 572.3 | A2 | 1.65 |
| 293 | 117 | 600.2 | A3 | 0.89 |
| 294 | 124 | 578.6 | A2 | 1.26 |
| 295 | 124 | 606.6 | A2 | 1.32 |
| 296 | 147 | 600.4 | A1 | 0.53 |
| 297 | 149 | 600.4 | A1 | 0.53 |
| 298 | 146 | 586.4 | A1 | 0.53 |
| 299 | 148 | 586.4 | A1 | 0.53 |
| 300 | 97 | 530.3 | A1 | 0.46 |
| 301 | 97 | 586.9 | A1 | 0.51 |
| 302 | 97 | 586.6 | A1 | 0.51 |
| 307 | 114 | 572.7 | A3 | 0.75 |
| 312 | 126 | 606.3 | A3 | 1.25 |
| 313 | 127 | 606.3 | A3 | 1.25 |
| 319 | 152 | 626.3 | A3 | 1.54 |
| 320 | 153 | 626.3 | A3 | 1.54 |
| 321 | 152 | 598.2 | A3 | 1.53 |
| 322 | 153 | 598.2 | A3 | 1.53 |
| 323 | 130 | 620.4 | A3 | 1.42 |
| 324 | 121 | 614.5 | A3 | 1.01 |
| 325 | 126 | 578.4 | A3 | 1.36 |
| 326 | 121 | 586.4 | A3 | 1.02 |
| 327 | 157 | 596.6 | A3 | 1.45 |
| 328 | 158 | 624.4 | A1 | 0.70 |
| 329 | 157 | 624.6 | A3 | 1.49 |
| 330 | 158 | 596.1 | A3 | 1.66 |
| 331 | 159 | 610.6 | A1 | 1.50 |
| 332 | 154 | 626.6 | A3 | 1.51 |
| 333 | 155 | 626.6 | A1 | 1.51 |
| 334 | 190 | 596.7 | A3 | 0.97 |
| 335 | 190 | 626.8 | A3 | 1.02 |
| 336 | 191 | 598.6 | A3 | 0.96 |
| 337 | 191 | 626.7 | A3 | 1.03 |
| 338 | 115 | 572.7 | A3 | 0.72 |

The following compounds from Table 1 are prepared in a similar fashion to the procedure described in Example 44, using intermediate F-39 and the appropriate reagents. The diastereomers are separated prior to the final synthetic step.

The absolute configuration of the diastereomeric center is not determined:

Compound 77: MS, electrospray, m/z=572.3 [M+H], RT 0.56 min;

Compound 78: MS, electrospray, m/z=572.3 [M+H], RT 0.56 min;

The following compounds from Table 1 are prepared in a similar fashion to the procedure described in Example 44, using intermediate F-77 and the appropriate reagents. The diastereomers are separated prior to the final synthetic step. The absolute configuration of the diastereomeric center is not determined:

Compound 168: MS, electrospray, m/z=608.3 [M+H], RT 0.72 min;

Compound 169: MS, electrospray, m/z=608.3 [M+H], RT 0.71 min;

The following compounds from Table 1 are prepared in a similar fashion to the procedure described in Example 44, using intermediate F-82 and the appropriate reagents. The diastereomers are separated prior to the final synthetic step. The absolute configuration of the diastereomeric center is not determined:

Compound 175: MS, electrospray, m/z=608.4 [M+H], RT 0.72 min;

Compound 176: MS, electrospray, m/z=608.3 [M+H], RT 0.72 min;

Example 45

Preparation of (1R,6S)-3-(4-{5-Methyl-2-[1-oxo-2-(tetrahydro-pyran-4-yl)-1,2,3,4-tetrahydro-isoquinolin-6-ylmethoxy]-phenyl}-thiazol-2-yl)-3-aza-bicyclo[4.1.0]heptane-6-carboxylic acid (192)

The following compounds from Table 1 are prepared in a similar fashion to the procedure described above.

Compound 193: MS, electrospray, m/z=568.3 [M+H], RT 0.58 min;

Compound 202: MS, electrospray, m/z=582.40 [M+H], RT 0.76 min;

Compound 203: MS, electrospray, m/z=606.30 [M+H], RT 1.19 min;

Compound 204: MS, electrospray, m/z=606.30 [M+H], RT 1.15 min;

The following compounds from Table 1 are prepared in a similar fashion to the procedure described in Example 45. The racemic compound was resolved on a Chiralpak AD-H (20×250 mm) using 65% IPA in heptane at 5 mL/min at 40° C. to afford 205 (first eluting peak) and 206 (second eluting peak). The absolute stereochemistry is not established and the structures are drawn arbitrarily.

Compound 205: MS, electrospray, m/z=600.40 [M+H], RT 0.77 min;

Compound 206: MS, electrospray, m/z=600.40 [M+H], RT 0.77 min;

Assessment of Biological Activity

Cellular Assay

The sGC cellular activator assay is performed in the presence and absence of 50% human serum (HS) using Chinese hamster ovary cells that have been stably transfected to express the human soluble guanylate cyclase alpha 1 and beta 1 subunits (sGC). Cells are preincubated with 40 microM 1H-[1,2,4]oxadiazolo[4,3-a]quinoxalin-1-one (ODQ), an sGC inhibitor, for one h in buffer containing 0.1% bovine serum albumin and 3-isobutyl-1-methylxanthine (IBMX). Concentration response curves are prepared for test compounds in DMSO. An intermediate dilution of the compounds

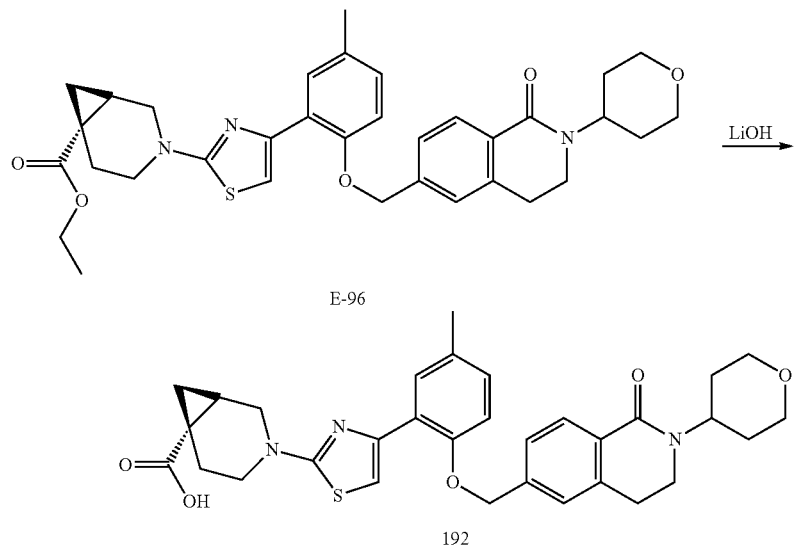

To a solution of 0.040 g (0.066 mmol) of E-96 in a 1:1:1 mixture of MeOH:THF:water (3 mL) is added 0.050 g (1.2 mmol) of lithium hydroxide monohydrate. The mixture is stirred at ambient temperature for 4 days then concentrated under reduced pressure. The residue is purified by reverse phase flash chromatography with 0.1% TFA additive to afford 192 (0.015 g, 39%). MS, electrospray, m/z=574.3 [M+H], RT 0.99 min.

is performed in either buffer containing IBMX or type AB HS containing IBMX. Diluted compounds are added to cells and they are incubated at room temperature for thirty min. cGMP is measured using a CisBio homogeneous time resolved fluorescence kit and the $EC_{50}$ is calculated for each compound.

Representative compounds of the present invention were tested for activity the above assay. Preferred compounds have an $EC_{50}$ of <1,000 nM in the above assay and more preferred compounds have an $EC_{50}$<200 nM. As examples, data for representative compounds from Table 1 are shown in Table 2.

TABLE 2

| Compound Number | $EC_{50\ (nM)}$ |
|---|---|
| 1 | 7 |
| 2 | 11 |
| 3 | 3 |
| 4 | 4 |
| 5 | 3 |
| 6 | 3 |
| 7 | 11 |
| 8 | 12 |
| 9 | 1 |
| 10 | 9 |
| 11 | 4 |
| 12 | 12 |
| 13 | 6 |
| 14 | 3 |
| 15 | 2 |
| 16 | 8 |
| 17 | 22 |
| 18 | 2 |
| 19 | 8 |
| 20 | 21 |
| 21 | 11 |
| 22 | 6 |
| 23 | 6 |
| 24 | 6 |
| 25 | 16 |
| 26 | 9 |
| 27 | 16 |
| 28 | 19 |
| 29 | 18 |
| 30 | 8 |
| 31 | 7 |
| 32 | 4 |
| 33 | 4 |
| 34 | 2 |
| 35 | 45 |
| 36 | 120 |
| 37 | 299 |
| 38 | 354 |
| 39 | 50 |
| 40 | 38 |
| 41 | 16 |
| 42 | 50 |
| 43 | 63 |
| 44 | 58 |
| 45 | 76 |
| 46 | 18 |
| 47 | 17 |
| 48 | 18 |
| 49 | 12 |
| 50 | 8 |
| 51 | 27 |
| 52 | 12 |
| 53 | 9 |
| 54 | 16 |
| 55 | 10 |
| 56 | 26 |
| 57 | 21 |
| 58 | 30 |
| 59 | 8 |
| 60 | 6 |
| 61 | 8 |
| 62 | 465 |
| 63 | 96 |
| 64 | 36 |
| 65 | 29 |
| 66 | 20 |
| 67 | 23 |
| 68 | 14 |
| 69 | 16 |
| 70 | 120 |
| 71 | 110 |
| 72 | 64 |
| 73 | 57 |
| 74 | 20 |
| 75 | 15 |
| 76 | 25 |
| 77 | 71 |
| 78 | 26 |
| 79 | 25 |
| 80 | 23 |
| 81 | 30 |
| 82 | 10 |
| 83 | 4 |
| 84 | 27 |
| 85 | 28 |
| 86 | 2 |
| 87 | 2 |
| 88 | 4 |
| 89 | 11 |
| 90 | 17 |
| 91 | 3 |
| 92 | 11 |
| 93 | 2 |
| 94 | 3 |
| 95 | 2 |
| 96 | 2 |
| 97 | 2 |
| 98 | 1 |
| 99 | 3 |
| 100 | 3 |
| 101 | 3 |
| 102 | 3 |
| 103 | 10 |
| 104 | 11 |
| 105 | 2 |
| 106 | 5 |
| 107 | 6 |
| 108 | 209 |
| 109 | 453 |
| 110 | 17 |
| 111 | 73 |
| 112 | 2 |
| 113 | 5 |
| 114 | 7 |
| 115 | 11 |
| 116 | 35 |
| 117 | 2 |
| 118 | 4 |
| 119 | 3 |
| 120 | 6 |
| 121 | 10 |
| 122 | 11 |
| 123 | 10 |
| 124 | 14 |
| 125 | 23 |
| 126 | 44 |
| 127 | 3 |
| 128 | 9 |
| 129 | 6 |
| 130 | 6 |
| 131 | 10 |
| 132 | 22 |
| 133 | 18 |
| 134 | 11 |
| 135 | 39 |
| 136 | 18 |
| 137 | 67 |
| 138 | 18 |
| 139 | 7 |
| 140 | 5 |
| 141 | 34 |
| 142 | 23 |
| 143 | 9 |
| 144 | 10 |
| 145 | 162 |
| 146 | 57 |
| 147 | 49 |
| 148 | 67 |
| 149 | 34 |
| 150 | 24 |

TABLE 2-continued

| Compound Number | EC$_{50\,(nM)}$ |
|---|---|
| 151 | 135 |
| 152 | 71 |
| 153 | 14 |
| 154 | 4 |
| 155 | 46 |
| 156 | 387 |
| 157 | 28 |
| 158 | 37 |
| 159 | 44 |
| 160 | 105 |
| 161 | 7 |
| 162 | 4 |
| 163 | 345 |
| 164 | 108 |
| 165 | 12 |
| 166 | 17 |
| 167 | 10 |
| 168 | 53 |
| 169 | 29 |
| 170 | 5 |
| 171 | 10 |
| 172 | 7 |
| 173 | 21 |
| 174 | 44 |
| 175 | 155 |
| 176 | 64 |
| 177 | 47 |
| 178 | 14 |
| 179 | 17 |
| 180 | 46 |
| 181 | 23 |
| 182 | 26 |
| 183 | 80 |
| 184 | 68 |
| 185 | 21 |
| 186 | 32 |
| 187 | 12 |
| 188 | 150 |
| 189 | 43 |
| 190 | 17 |
| 191 | 18 |
| 192 | 29 |
| 193 | 22 |
| 194 | 63 |
| 195 | 6 |
| 196 | 3 |
| 197 | 9 |
| 198 | 50 |
| 199 | 145 |
| 200 | 25 |
| 201 | 40 |
| 202 | 9 |
| 203 | 33 |
| 205 | 52 |
| 207 | 8 |
| 208 | 16 |
| 209 | 14 |
| 210 | 16 |
| 211 | 18 |
| 212 | 34 |
| 213 | 134 |
| 214 | 243 |
| 215 | 10 |
| 216 | 14 |
| 217 | 40 |
| 218 | 81 |
| 219 | 263 |
| 220 | 9 |
| 221 | 12 |
| 222 | 23 |
| 223 | 23 |
| 224 | 51 |
| 225 | 5 |
| 226 | 6 |
| 227 | 9 |
| 228 | 6 |
| 229 | 4 |

TABLE 2-continued

| Compound Number | EC$_{50\,(nM)}$ |
|---|---|
| 230 | 6 |
| 231 | 13 |
| 232 | 330 |
| 233 | 190 |
| 234 | 257 |
| 235 | 680 |
| 236 | 66 |
| 237 | 42 |
| 238 | 4 |
| 239 | 5 |
| 240 | 5 |
| 241 | 2 |
| 242 | 4 |
| 243 | 3 |
| 244 | 4 |
| 245 | 23 |
| 246 | 15 |
| 247 | 659 |
| 248 | 578 |
| 249 | 13 |
| 250 | 7 |
| 251 | 6 |
| 252 | 2 |
| 253 | 9 |
| 254 | 14 |
| 255 | 7 |
| 256 | 3 |
| 257 | 3 |
| 259 | 65 |
| 260 | 56 |
| 261 | 3 |
| 262 | 3 |
| 263 | 7 |
| 264 | 4 |
| 265 | 15 |
| 266 | 5 |
| 267 | 7 |
| 268 | 4 |
| 269 | 6 |
| 270 | 2 |
| 271 | 5 |
| 272 | 2 |
| 273 | 5 |
| 274 | 4 |
| 275 | 32 |
| 276 | 150 |
| 277 | 4 |
| 278 | 6 |
| 279 | 65 |
| 280 | 140 |
| 281 | 267 |
| 282 | 14 |
| 283 | 4 |
| 284 | 231 |
| 285 | 359 |
| 286 | 160 |
| 287 | 13 |
| 288 | 18 |
| 289 | 235 |
| 290 | 228 |
| 291 | 2 |
| 292 | 3 |
| 293 | 1 |
| 296 | 363 |
| 297 | 150 |
| 298 | 578 |
| 299 | 152 |
| 300 | 154 |
| 301 | 1 |
| 302 | 3 |
| 303 | 2 |
| 304 | 0 |
| 305 | 340 |
| 306 | 3 |
| 307 | 19 |
| 308 | 10 |
| 309 | 18 |

TABLE 2-continued

| Compound Number | EC$_{50\ (nM)}$ |
|---|---|
| 310 | 5 |
| 311 | 3 |
| 312 | 3 |
| 313 | 7 |
| 314 | 529 |
| 315 | 18 |
| 316 | 222 |
| 317 | 245 |
| 318 | 739 |
| 319 | 1 |
| 320 | 4 |
| 321 | 3 |
| 322 | 7 |
| 323 | 2 |
| 324 | 2 |
| 325 | 7 |
| 326 | 1 |
| 327 | 5 |
| 328 | 2 |
| 329 | 13 |
| 330 | 5 |
| 331 | 11 |
| 332 | 15 |
| 333 | 10 |
| 335 | 80 |
| 336 | 54 |
| 337 | 130 |
| 338 | 24 |

Assessment of Solubility

Solubility is measured by the following method.

1. Sample Preparation:

100 uL, 10 mM DMSO stock solution of each compound is prepared in a 96 well plate format. The experiment is done in single determination at 3 pH values (2.2, 4.5 and 6.8). For each pH and one reference, 40 uL of each compound is needed.

Buffer Preparation:

McIlvaine pH 2.2: To 2.076 g citric acid monohydrate and 0.043 g Na$_2$HPO$_4$×2H$_2$O add 100 ml deionized water McIlvaine pH 4.5: To 1.166 g citric acid monohydrate and 1.585 g Na$_2$HPO$_4$×2H$_2$O add 100 ml deionized water McIlvaine pH 6.8: To 0.476 g citric acid monohydrate and 2.753 g Na$_2$HPO$_4$×2H$_2$O add 100 ml deionized water With a suitable liquid handling device (Multipette® or a liquid handler) 390 uL of each buffer solution and 10 uL of compound is added to each well of a 96 deep well plate. The plates are covered firmly and shaken for 24 h on an over head shaker (at 54 RPM) at room temperature. The DMSO content in the final buffer is 2.5% v/v.

After 24 h the plates are centrifuged to remove droplets on the lid before opening (for ~5 min at 2500 RPM).

The filtration is done under vacuum with Millipore 96 well filter plate. Filtrate is collected in a deep well plate and transferred to a suitable plate for UPLC analysis.

The reference plate is prepared by adding 10 uL of compound to 390 uL of 50:50 acetonitrile/water in a 96 deep well plate and transferred to a suitable plate for UPLC analysis. Wells are checked visually for precipitation, any presence noted under comments in reported results.

2. Sample Measurement

The samples are measured with UPLC-UV using the chromatographic method described below.

| stationary phase | Waters ACQUITY UPLC ® BEH C18 1.7 µm 2.5 × 50 mm |
|---|---|
| mobile phase | |
| solvent A | 0.1% formic acid (pH 3) |
| solvent B | acetonitrile with 0.1% formic acid |
| Gradient | |
| 0 min | 5% B |
| 1.0 min | 95% B |
| 1.3 min | 95% B |
| 1.4 min | 5% B |
| 1.7 min | 5% B |
| column temperature | 40° C. |
| Flow | 0.8 mL/min |
| duration/cycle time | 1.7 min/2.7 min |
| injection volume | 2 µL |
| sample temperature | 20° C. |
| PDA detection | Enable 3D data |
| wavelength | 254 nm |
| sampling rate | 40 points/sec |
| resolution | 4.8 nm |

Waters Empower®2 software is used for generating Sample Sets (according to the plate layout), Sample Set Methods and Instrument Methods.

One Sample Set comprises the methods for three 96 well plates (one reference plate and two sample plates, and includes one Sample Set Method and one Instrument Method).

3. Data Processing and Analysis

The UV chromatograms collected at 254 nm are integrated and processed.

It is assumed that the compound is completely dissolved in the reference solution (50:50 acetonitrile/water)

Solubility data (µg/mL) for compounds from Table 1 is shown in Table 3 below.

TABLE 3

| Number | (pH 2.2) | (pH 4.5) | (pH 6.8) |
|---|---|---|---|
| 1 | 140 | 120 | 57 |
| 2 | 110 | 90 | 58 |
| 3 | 140 | 120 | 60 |
| 4 | 140 | 120 | 65 |
| 5 | 160 | 140 | 79 |
| 6 | 160 | 130 | 60 |
| 7 | 150 | 120 | 59 |
| 8 | 150 | 110 | 44 |
| 9 | 130 | 110 | 53 |
| 10 | 130 | 110 | 55 |
| 11 | 140 | 110 | 46 |
| 12 | 110 | 90 | 33 |
| 13 | 140 | 120 | 71 |
| 14 | 120 | 94 | 53 |
| 15 | 110 | 90 | 51 |
| 16 | 130 | 96 | 41 |
| 17 | 100 | 83 | 39 |
| 18 | 130 | 99 | 38 |
| 19 | 110 | 82 | 32 |
| 20 | 110 | 96 | 64 |
| 21 | 120 | 110 | 70 |
| 22 | 110 | 90 | 60 |
| 23 | 100 | 88 | 69 |
| 24 | 110 | 98 | 69 |
| 25 | 100 | 89 | 62 |
| 26 | 110 | 90 | 67 |
| 27 | 110 | 95 | 68 |

TABLE 3-continued

| Number | (pH 2.2) | (pH 4.5) | (pH 6.8) |
|---|---|---|---|
| 28 | 110 | 90 | 73 |
| 29 | 110 | 76 | 79 |
| 30 | 110 | 84 | 62 |
| 31 | 110 | 95 | 67 |
| 32 | 120 | 88 | 50 |
| 33 | 110 | 93 | 68 |
| 34 | 110 | 97 | 67 |
| 35 | 100 | 93 | 6.4 |
| 36 | 100 | 84 | 48 |
| 37 | 100 | 93 | 50 |
| 38 | 100 | 85 | 59 |
| 39 | 100 | 91 | 45 |
| 40 | 98 | 79 | 52 |
| 41 | 100 | 84 | 45 |
| 42 | 96 | 87 | 58 |
| 43 | 140 | 120 | 97 |
| 44 | 130 | 110 | 86 |
| 45 | 140 | 100 | 81 |
| 46 | 110 | 96 | 77 |
| 47 | 110 | 95 | 84 |
| 48 | 110 | 69 | 83 |
| 49 | 120 | 95 | 82 |
| 50 | 120 | 96 | 77 |
| 51 | 110 | 94 | 74 |
| 52 | 110 | 93 | 76 |
| 53 | 130 | 110 | 80 |
| 54 | 130 | 90 | 81 |
| 55 | 150 | 110 | 82 |
| 56 | 140 | 120 | 88 |
| 57 | 120 | 99 | 78 |
| 58 | 110 | 90 | 80 |
| 59 | 120 | 99 | 74 |
| 60 | 120 | 100 | 79 |
| 61 | 110 | 96 | 74 |
| 62 | 130 | 130 | 130 |
| 63 | 130 | 130 | 130 |
| 64 | 100 | 88 | 69 |
| 65 | 130 | 110 | 80 |
| 66 | 100 | 84 | 64 |
| 67 | 100 | 92 | 71 |
| 68 | 140 | 120 | 93 |
| 69 | 130 | 110 | 89 |
| 70 | 130 | 120 | 83 |
| 71 | 130 | 110 | 81 |
| 72 | 120 | 100 | 74 |
| 73 | 110 | 93 | 69 |
| 74 | 120 | 100 | 80 |
| 75 | 120 | 110 | 74 |
| 76 | 130 | 110 | 80 |
| 77 | 110 | 95 | 64 |
| 78 | 110 | 91 | 63 |
| 79 | 140 | 120 | 91 |
| 80 | 150 | 130 | 92 |
| 81 | >160 | >160 | 91 |
| 82 | 100 | 40 | 22 |
| 83 | 120 | 47 | 13 |
| 84 | 120 | 70 | 53 |
| 85 | 120 | 52 | 55 |
| 86 | 120 | 71 | 57 |
| 87 | 120 | 67 | 28 |
| 88 | 120 | 69 | 48 |
| 89 | 130 | 58 | 41 |
| 90 | 130 | 54 | 56 |
| 91 | 120 | 68 | 41 |
| 92 | 150 | 85 | 63 |
| 93 | 140 | 70 | 51 |
| 94 | 120 | 55 | 19 |
| 95 | 120 | 66 | 31 |
| 96 | 120 | 68 | 52 |
| 97 | 120 | 37 | 57 |
| 98 | 120 | 75 | 31 |
| 99 | 120 | 69 | 14 |
| 100 | 130 | 68 | 27 |
| 101 | 120 | 79 | 38 |
| 102 | 130 | 41 | 54 |
| 103 | 140 | 73 | 63 |
| 104 | 130 | 62 | 47 |
| 105 | 120 | 72 | 56 |
| 106 | 130 | 66 | 44 |
| 107 | 140 | 65 | 40 |
| 108 | 130 | 75 | 74 |
| 109 | 130 | 69 | 84 |
| 110 | 110 | 54 | 0.58 |
| 111 | 120 | 9.2 | 16 |
| 112 | 120 | 55 | 8.1 |
| 113 | 130 | 36 | 2.7 |
| 114 | 120 | 38 | 5.0 |
| 115 | 130 | 36 | 5.1 |
| 116 | 140 | 11 | 6.0 |
| 117 | 120 | 42 | 3.4 |
| 118 | 120 | 21 | <0.1 |
| 119 | 120 | 18 | 1.3 |
| 120 | 130 | 27 | 2.2 |
| 121 | 110 | 14 | 0.69 |
| 122 | 120 | 18 | 1.6 |
| 123 | 120 | 32 | 3.3 |
| 124 | 120 | 3.7 | 4.9 |
| 125 | 140 | 20 | 1.2 |
| 126 | 130 | 2.8 | 1.8 |
| 127 | 130 | 17 | 0.77 |
| 128 | 120 | 6.3 | 0.3 |
| 129 | 120 | 7.7 | 0.49 |
| 130 | 120 | 20 | 2.9 |
| 131 | 140 | 15 | 1.9 |
| 132 | 110 | 23 | 3.1 |
| 133 | 90 | 12 | 1.6 |
| 134 | 110 | 8.5 | 0.95 |
| 135 | 100 | 70 | 56 |
| 136 | 110 | 76 | 62 |
| 137 | 100 | 71 | 51 |
| 138 | 100 | 59 | 65 |
| 139 | 96 | 58 | 59 |
| 140 | 100 | 73 | 60 |
| 141 | 110 | 38 | 81 |
| 142 | 110 | 69 | 69 |
| 143 | 110 | 70 | 56 |
| 144 | 110 | 74 | 62 |
| 145 | 110 | 62 | 28 |
| 146 | 110 | 59 | 9.9 |
| 147 | >140 | <0.1 | <0.1 |
| 148 | 93 | 8.4 | 1.1 |
| 149 | 98 | 37 | 35 |
| 150 | 100 | 44 | 9.7 |
| 151 | 110 | 71 | 54 |
| 152 | 110 | 70 | 53 |
| 153 | 120 | 72 | 47 |
| 154 | 110 | 65 | 25 |
| 155 | 96 | 69 | 61 |
| 156 | >140 | 0.5 | 8.9 |
| 157 | 97 | 72 | 63 |
| 158 | 94 | 53 | 65 |
| 159 | 120 | 95 | 89 |
| 160 | 120 | <0.1 | 75 |
| 161 | 110 | 62 | 76 |
| 162 | 120 | 82 | 75 |
| 163 | 110 | 77 | 65 |
| 164 | 120 | 75 | 59 |
| 165 | 120 | 86 | 77 |
| 166 | 110 | 74 | 82 |
| 167 | 110 | 84 | 82 |
| 168 | 130 | 87 | 81 |
| 169 | 130 | 96 | 90 |
| 170 | 130 | 90 | 79 |
| 171 | 140 | 100 | 99 |
| 172 | 130 | 98 | 85 |
| 173 | 120 | 71 | 75 |
| 174 | 120 | 79 | 83 |
| 175 | 140 | 100 | 95 |
| 176 | 140 | 95 | 89 |
| 177 | 140 | 100 | 96 |
| 178 | 110 | 72 | 5.1 |
| 180 | 120 | 4.3 | 0.73 |
| 181 | 120 | 53 | 5.0 |
| 182 | 120 | 61 | 55 |

TABLE 3-continued

| Number | (pH 2.2) | (pH 4.5) | (pH 6.8) |
|---|---|---|---|
| 185 | 100 | 43 | 42 |
| 186 | 95 | 34 | 34 |
| 187 | 99 | 36 | 36 |
| 188 | 110 | 50 | 54 |
| 189 | 110 | 66 | 66 |
| 190 | 99 | 71 | 74 |
| 191 | 100 | 68 | 79 |
| 192 | 48 | <0.1 | 9.2 |
| 194 | 140 | 70 | 57 |
| 195 | 121 | 119 | 114 |
| 196 | 117 | 114 | 107 |
| 197 | 110 | 73 | 53 |
| 198 | 96 | 87 | 58 |
| 199 | 134.2 | 51.6 | 23.8 |
| 200 | 130.3 | 43.6 | 10.5 |
| 201 | 131.8 | 10.1 | 19.5 |
| 202 | 84.0 | 10.0 | 0.1 |
| 203 | 56.8 | 0.1 | 1.6 |
| 205 | 109.2 | 42.6 | 10.8 |
| 207 | 143.4 | 88.6 | 76.8 |
| 208 | 139.3 | 88.9 | 77.1 |
| 209 | 127.7 | 83.9 | 88.7 |
| 210 | 136.3 | 88.2 | 75.0 |
| 211 | 133.1 | 83.4 | 76.5 |
| 212 | 136.3 | 96.6 | 72.7 |
| 213 | 144.1 | 108.8 | 81.3 |
| 214 | 118.1 | 107.5 | 87.9 |
| 215 | 142.6 | 135.0 | 129.0 |
| 216 | 144.5 | 139.1 | 134.3 |
| 217 | 167.0 | 162.2 | 157.8 |
| 218 | 143.8 | 139.1 | 133.9 |
| 219 | 146.2 | 142.2 | 136.9 |
| 220 | 166.6 | 136.0 | 132.6 |
| 221 | 155.1 | 144.2 | 131.5 |
| 222 | 132.3 | 129.7 | 118.6 |
| 223 | 144.9 | 139.5 | 132.2 |
| 224 | 150.2 | 145.3 | 136.3 |
| 225 | 135.9 | 134.6 | 129.1 |
| 226 | 144.7 | 141.6 | 134.1 |
| 227 | 142.0 | 127.7 | 137.8 |
| 228 | 148.5 | 114.0 | 106.7 |
| 229 | 122.0 | 116.1 | 114.5 |
| 230 | 130.9 | 128.4 | 119.7 |
| 231 | 126.4 | 126.2 | 120.8 |
| 232 | 142.5 | 131.4 | 131.3 |
| 233 | 134.8 | 124.1 | 122.5 |
| 234 | 127.5 | 123.7 | 116.8 |
| 235 | 127.8 | 126.8 | 118.9 |
| 236 | 141.1 | 131.1 | 129.3 |
| 237 | 155.6 | 136.1 | 142.6 |
| 238 | 111.8 | 109.1 | 108.7 |
| 239 | 126.0 | 123.0 | 117.2 |
| 240 | 122.7 | 118.2 | 116.6 |
| 241 | 128.9 | 98.5 | 92.2 |
| 242 | 125.5 | 116.5 | 115.0 |
| 243 | 130.8 | 123.5 | 106.9 |
| 244 | 117.8 | 108.6 | 107.2 |
| 246 | 117.2 | 113.5 | 85.4 |
| 248 | 91.2 | 88.9 | 88.1 |
| 249 | 128.8 | 126.7 | 119.8 |
| 250 | 147.0 | 82.2 | 51.9 |
| 251 | 154.7 | 90.7 | 66.6 |
| 252 | 132.9 | 81.7 | 72.9 |
| 253 | 127.0 | 7.7 | 1.1 |
| 254 | 118.2 | 67.5 | 2.9 |
| 255 | 169.5 | 69.5 | 37.7 |
| 256 | 150.9 | 82.0 | 57.1 |
| 257 | 164.3 | 88.2 | 59.0 |
| 259 | 149.6 | 86.8 | 58.0 |
| 260 | 148.4 | 83.9 | 58.3 |
| 261 | 115.7 | 40.7 | 38.9 |
| 262 | 132.6 | 94.9 | 67.4 |
| 263 | 121.5 | 82.8 | 54.4 |
| 264 | 134.8 | 56.6 | 51.8 |
| 265 | 117.2 | 53.7 | 46.7 |
| 266 | 109.3 | 63.1 | 59.4 |
| 267 | 115.9 | 60.3 | 59.6 |
| 268 | 119.3 | 88.6 | 57.8 |
| 269 | 114.9 | 35.1 | 3.0 |
| 270 | 114.4 | 73.4 | 64.0 |
| 271 | 133.9 | 66.6 | 32.8 |
| 272 | 128.4 | 54.1 | 18.5 |
| 273 | 119.5 | 80.7 | 64.3 |
| 274 | 113.8 | 72.0 | 65.5 |
| 275 | 117.1 | 81.3 | 84.5 |
| 276 | 126.4 | 84.8 | 90.6 |
| 277 | 133.0 | 97.1 | 74.4 |
| 278 | 122.0 | 85.1 | 68.0 |
| 279 | 127.7 | 100.3 | 82.8 |
| 280 | 120.1 | 91.0 | 79.3 |
| 281 | 120.0 | 87.4 | 83.1 |
| 282 | 137.4 | 99.6 | 80.5 |
| 283 | 123.9 | 89.4 | 68.4 |
| 284 | 129.3 | 102.9 | 83.5 |
| 285 | 145.5 | 110.7 | 97.6 |
| 286 | 148.9 | 119.1 | 88.5 |
| 287 | 119.6 | 72.7 | 71.7 |
| 288 | 116.8 | 75.5 | 71.8 |
| 289 | 123.2 | 82.4 | 69.9 |
| 290 | 118.9 | 80.0 | 66.5 |
| 291 | 127.8 | 84.7 | 62.3 |
| 292 | 113.2 | 43.5 | 6.2 |
| 293 | 115.6 | 82.3 | 63.1 |
| 294 | 107.9 | 77.7 | 77.9 |
| 295 | 109.3 | 80.5 | 79.2 |
| 296 | 131.6 | 77.2 | 68.8 |
| 297 | 134.3 | 93.7 | 77.3 |
| 298 | 131.3 | 98.1 | 80.1 |
| 299 | 134.4 | 90.8 | 70.8 |
| 300 | 116.5 | 82.3 | 62.3 |
| 301 | 141.4 | 105.2 | 91.1 |
| 302 | 147.8 | 111.5 | 85.5 |
| 303 | 140.7 | 16.4 | 1.0 |
| 304 | 156.7 | 153.7 | 146.0 |
| 305 | 108.5 | 81.2 | 0.7 |
| 306 | 141.3 | 97.1 | 5.2 |
| 307 | 127.3 | 100.6 | 81.2 |
| 308 | 134.8 | 97.5 | 0.1 |
| 309 | 162.9 | 116.0 | 23.8 |
| 310 | 93.0 | 73.7 | 5.2 |
| 311 | 99.5 | 61.6 | 0.5 |
| 312 | 154.9 | 142.8 | 146.4 |
| 313 | 141.1 | 136.5 | 132.6 |
| 314 | 115.1 | 109.8 | 98.8 |
| 315 | 137.3 | 135.1 | 119.0 |
| 316 | 146.7 | 148.7 | 142.0 |
| 317 | 157.7 | 151.6 | 139.0 |
| 318 | 150.8 | 123.3 | 73.7 |
| 319 | 108.6 | 60.2 | 55.4 |
| 320 | 115.3 | 60.6 | 46.4 |
| 321 | 112.1 | 41.5 | 50.5 |
| 322 | 109.9 | 36.4 | 60.2 |
| 323 | 130.9 | 84.3 | 65.2 |
| 324 | 133.8 | 102.9 | 77.5 |
| 325 | 131.4 | 69.1 | 67.4 |
| 326 | 129.1 | 91.1 | 71.6 |
| 327 | 99.8 | 51.8 | 59.1 |
| 328 | 97.4 | 59.4 | 56.8 |
| 329 | 102.6 | 63.9 | 68.0 |
| 330 | 112.6 | 48.0 | 64.9 |
| 331 | 121.9 | 74.8 | 68.2 |
| 332 | 126.7 | 86.6 | 76.8 |
| 333 | 108.6 | 68.3 | 66.7 |
| 336 | 69.9 | 37.6 | 30.0 |
| 337 | 113.4 | 80.5 | 78.0 |
| 338 | 131.6 | 105.9 | 73.6 |

Assessment of Metabolic Stability

Objective

The 5 time point, high-throughput human liver microsome (HLM) metabolic stability assay is designed to determine in vitro compound metabolism. Compounds are incubated with HLMs at a concentration of 1 uM, at 37° C., for a total of 60 min. The percent of compound remaining at 5, 15, 30, and 60 min is used to calculate the t1/2 (min), $CL_{int}$ (mL/min/kg), $CL_h$ (mL/min/kg), and % $Q_h$. The assay is based on a 96-well format and can accommodate up to 92 compounds per plate (n=1).

Incubation

Using the 96-well multi-channel head, the Biomek FX, equipped with a Peltier heating block/shaker, is programmed to accomplish the following steps:
1. Pipette 175 uL of 1.15 mg/mL microsomes into each of the 96 conical inserts (Analytical Sales and Products, catalog number 96PL05) that fit into the plate of the Peltier heating block/shaker (the incubation plate)
2. Add 5 uL of compounds from the assay plate to the microsomes and shake the mixture at 600 rpm at 42.1° C. for 10 min (a setting of 42.1° C. on the Peltier is required for the samples to incubate at 37° C.)
3. After 10 min, prompt the user to add the NADPH plate to the deck and add 20 uL from the NADPH plate to the incubation plate to start the reaction
4. Add 215 uL of 100%, cold acetonitrile containing an internal standard(s) to a 0 minute, 5 minute, 15 minute, 30 minute, and 60 minute "quench" plate
5. At 0 min, 5 min, 15 min, 30 min, and 60 min into the incubation, aspirate 12 uL from the incubation mixture and add it to the quench solution to stop the reaction
6. Add 185 uL HPLC grade water to each well of the 0, 5, 15, 30 and 60 minute quench plates to dilute compounds to the appropriate concentration for the mass spectrometer After all time points are collected, the quench plates are sealed with 96-well pierceable plate mats or heat sealing foil and centrifuged at 3000 rpm for 15 min to pellet the microsomes.

Analysis

The plates are analyzed using LC/MS/MS with electron spray ionization (ESI) and the previously determined MRM transitions. The LC method includes the following parameters:

Injection volume: 5 uL
Mobile Phases: 0.1% Formic Acid in Water (A) and 0.1% Formic Acid in Acetonitrile (B) (HPLC grade)
Left and Right Temperature: 35° C.
Run Time: 4.0 min
Column: Thermo Scientific, Aquasil C18, 50×2.1 mm, 5µ, part number 77505-052130, or equivalent
LC Pump Gradient:

| Total Time (min) | Flow Rate (uL/min) | % A | % B |
|---|---|---|---|
| 0 | 500 | 90.0 | 10.0 |
| 0.5 | 500 | 90.0 | 10.0 |
| 1.5 | 500 | 1.0 | 99.0 |
| 2.5 | 500 | 1.0 | 99.0 |
| 3.3 | 500 | 90.0 | 10.0 |
| 4.0 | 500 | 90.0 | 10.0 |

If peak shape is poor and cannot be integrated properly, the following LC method can be used:
Injection volume: 5 uL
Mobile Phases: 2.5 mM Ammonium Bicarbonate (A) and 100% Acetonitrile (B) (HPLC grade)
Aqueous Wash: 90% Water, 10% Acetonitrile (HPLC grade)
Organic Wash: 90% Acetonitrile, 10% Water (HPLC grade)
Left and Right Temperature: 35° C.
Run Time: 4.5 min
Column: Phenomex Luna 3 u C18(2) 100 A, 50×2.00 mm
LC Pump Gradient:

| Total Time (min) | Flow Rate (uL/min) | % A | % B |
|---|---|---|---|
| 0 | 500 | 90.0 | 10.0 |
| 0.5 | 500 | 90.0 | 10.0 |
| 1.5 | 500 | 1.0 | 99.0 |
| 2.5 | 500 | 1.0 | 99.0 |
| 3.30 | 500 | 90.0 | 10.0 |
| 4.50 | 500 | 90.0 | 10.0 |

Using an Excel template in Activitybase, the peak areas corresponding to 5, 15, 30 and 60 min are compared to the peak area at 0 min to calculate the percent of remaining compound using the following equation:

Percent compound remaining=(AUC at Time t min/AUC at Time 0 min)×100 where t=0, 5, 15, 30 or 60 min.

Time (min) is plotted against the natural logarithm (Ln) of the percent compound remaining to determine the slope. The slope is used to calculate t1/2 (min) using the equation, t1/2=0.693/slope.

Clint, Intrinsic clearance
0.693/t1/2*Avg liver wt in g/avg body wt in kg*f(u)/protein concentration in incubation in mg/mL*mg microsomal protein/g liver
0.693/t1/2*26 g/kg*1/1.0 mg/mL*45 mg/g
Clh, Hepatic clearance
Hepatic flow*f(u)*Clint/(hepatic flow+f(u)*Clint)
Qh, % Hepatic blood flow
(Clh/Hepatic flow)*100

Metabolic stability data (% Qh) for compounds from Table 1 is shown in Table 4 below. Preferred compounds have % Qh values of less than 24.

TABLE 4

| Number | (Qh %) |
|---|---|
| 1 | <24 |
| 2 | <24 |
| 3 | <24 |
| 4 | <24 |
| 5 | 35 |
| 6 | 54 |
| 7 | 45 |
| 8 | 49 |
| 9 | 37 |
| 10 | 32 |
| 11 | 53 |
| 12 | <24 |
| 13 | 42 |
| 14 | 61 |
| 15 | 51 |
| 16 | 28 |
| 17 | 33 |
| 18 | 34 |
| 19 | 63 |
| 20 | <24 |
| 21 | <24 |
| 22 | <24 |
| 23 | <24 |
| 24 | <24 |
| 25 | <24 |
| 26 | <24 |
| 27 | <24 |
| 28 | <24 |

TABLE 4-continued

| Number | (Qh %) |
|---|---|
| 29 | <24 |
| 30 | <24 |
| 31 | <24 |
| 32 | <24 |
| 33 | <24 |
| 34 | <24 |
| 35 | <24 |
| 36 | <24 |
| 37 | <24 |
| 38 | <24 |
| 39 | <24 |
| 40 | <24 |
| 41 | <24 |
| 42 | 76 |
| 43 | <24 |
| 44 | <24 |
| 45 | <24 |
| 46 | <24 |
| 47 | <24 |
| 48 | <24 |
| 49 | <24 |
| 50 | 26 |
| 51 | 28 |
| 52 | 38 |
| 53 | <24 |
| 54 | 39 |
| 55 | <24 |
| 56 | <24 |
| 57 | <24 |
| 58 | <24 |
| 59 | <24 |
| 60 | <24 |
| 61 | <24 |
| 62 | <24 |
| 63 | <24 |
| 64 | 29 |
| 65 | 31 |
| 66 | 33 |
| 67 | <24 |
| 68 | <24 |
| 69 | <24 |
| 70 | <24 |
| 71 | <24 |
| 72 | <24 |
| 73 | 28 |
| 74 | <24 |
| 75 | <24 |
| 76 | <24 |
| 77 | <24 |
| 78 | <24 |
| 79 | <24 |
| 80 | <24 |
| 81 | 30 |
| 82 | <24 |
| 83 | <24 |
| 84 | <24 |
| 85 | 29 |
| 86 | 41 |
| 87 | 55 |
| 88 | 43 |
| 89 | 50 |
| 90 | 45 |
| 91 | <24 |
| 92 | <24 |
| 93 | <24 |
| 94 | 42 |
| 95 | 49 |
| 96 | 33 |
| 97 | 49 |
| 98 | 48 |
| 99 | 59 |
| 100 | 55 |
| 101 | 61 |
| 102 | 52 |
| 103 | <24 |
| 104 | 33 |
| 105 | 38 |
| 106 | 39 |
| 107 | 53 |
| 108 | <24 |
| 109 | <24 |
| 110 | <24 |
| 111 | <24 |
| 112 | <24 |
| 113 | <24 |
| 114 | <24 |
| 115 | <24 |
| 116 | <24 |
| 117 | 27 |
| 118 | 34 |
| 119 | <24 |
| 120 | <24 |
| 121 | <24 |
| 122 | 43 |
| 123 | <24 |
| 124 | 31 |
| 125 | <24 |
| 126 | <24 |
| 127 | <24 |
| 128 | <24 |
| 129 | <24 |
| 130 | <24 |
| 131 | 33 |
| 132 | 46 |
| 133 | 43 |
| 134 | 53 |
| 135 | <24 |
| 136 | <24 |
| 137 | 32 |
| 138 | <24 |
| 139 | <24 |
| 140 | <24 |
| 141 | <24 |
| 142 | <24 |
| 143 | <24 |
| 144 | <24 |
| 145 | <24 |
| 146 | 26 |
| 147 | <24 |
| 148 | <24 |
| 149 | <24 |
| 150 | <24 |
| 151 | <24 |
| 152 | <24 |
| 153 | <24 |
| 154 | <24 |
| 155 | <24 |
| 156 | <24 |
| 157 | <24 |
| 158 | <24 |
| 159 | 30 |
| 160 | 38 |
| 161 | <24 |
| 162 | 39 |
| 163 | <24 |
| 164 | <24 |
| 165 | <24 |
| 166 | <24 |
| 167 | <24 |
| 168 | <24 |
| 169 | <24 |
| 170 | <24 |
| 171 | <24 |
| 172 | <24 |
| 173 | <24 |
| 174 | <24 |
| 175 | <24 |
| 176 | <24 |
| 177 | <24 |
| 178 | <24 |
| 180 | <24 |
| 181 | <24 |
| 182 | <24 |
| 183 | 42 |
| 185 | 33 |
| 186 | <24 |

TABLE 4-continued

| Number | (Qh %) |
|---|---|
| 187 | <24 |
| 188 | <24 |
| 189 | <24 |
| 190 | <24 |
| 191 | <24 |
| 192 | <24 |
| 193 | 52 |
| 194 | <24 |
| 195 | 24 |
| 196 | 24 |
| 197 | 47 |
| 198 | 76 |
| 199 | 46 |
| 200 | <24 |
| 201 | <24 |
| 202 | 62 |
| 203 | <24 |
| 205 | <24 |
| 207 | <24 |
| 208 | <24 |
| 209 | <24 |
| 210 | <24 |
| 211 | <24 |
| 212 | <24 |
| 213 | <24 |
| 214 | <24 |
| 215 | <24 |
| 216 | 39 |
| 217 | 44 |
| 218 | <24 |
| 219 | <24 |
| 220 | 34 |
| 221 | <24 |
| 222 | <24 |
| 223 | <24 |
| 224 | 31 |
| 225 | 25 |
| 226 | <24 |
| 227 | 30 |
| 228 | <24 |
| 229 | <24 |
| 230 | 83 |
| 231 | 58 |
| 232 | <24 |
| 233 | <24 |
| 234 | 55 |
| 235 | 50 |
| 236 | <24 |
| 237 | <24 |
| 238 | <24 |
| 239 | 87 |
| 240 | 73 |
| 241 | 42.5 |
| 242 | <24 |
| 243 | <24 |
| 244 | <24 |
| 245 | <24 |
| 246 | <24 |
| 247 | <24 |
| 248 | <24 |
| 249 | <24 |
| 250 | 33 |
| 251 | 36 |
| 252 | <24 |
| 253 | <24 |
| 254 | 26 |
| 255 | 25 |
| 256 | 89 |
| 257 | 85 |
| 259 | 44 |
| 260 | 40 |
| 261 | 29 |
| 262 | 25 |
| 263 | <24 |
| 264 | <24 |
| 265 | <24 |
| 266 | <24 |
| 267 | <24 |
| 268 | 40 |
| 269 | <24 |
| 270 | 38 |
| 271 | <24 |
| 272 | <24 |
| 273 | <24 |
| 274 | <24 |
| 275 | 28 |
| 276 | <24 |
| 277 | <24 |
| 278 | <24 |
| 279 | <24 |
| 280 | 30 |
| 281 | 25 |
| 282 | 58 |
| 283 | <24 |
| 284 | <24 |
| 285 | <24 |
| 286 | <24 |
| 287 | <24 |
| 288 | <24 |
| 289 | <24 |
| 290 | <24 |
| 291 | <24 |
| 292 | 47 |
| 293 | 25 |
| 294 | <24 |
| 295 | <24 |
| 296 | <24 |
| 297 | <24 |
| 298 | 34 |
| 299 | 31 |
| 300 | <24 |
| 301 | <24 |
| 302 | <24 |
| 303 | 79 |
| 304 | 48 |
| 305 | 30 |
| 306 | 61 |
| 307 | <24 |
| 308 | 43 |
| 309 | 54 |
| 311 | 63 |
| 312 | <24 |
| 313 | <24 |
| 314 | <24 |
| 315 | <24 |
| 316 | 39 |
| 317 | <24 |
| 318 | <24 |
| 319 | 25 |
| 320 | 26 |
| 321 | 47 |
| 322 | 47 |
| 323 | 45 |
| 324 | <24 |
| 325 | 33 |
| 326 | 59 |
| 327 | 61 |
| 328 | 45 |
| 329 | <24 |
| 330 | 69 |
| 331 | 63 |
| 332 | <24 |
| 336 | 32 |
| 337 | <24 |
| 338 | <24 |

Methods of Therapeutic Use

The compounds disclosed herein effectively activate soluble guanylate cyclase. The activation or potentiation of soluble guanylate cyclase is an attractive means for preventing and treating a variety of diseases or conditions associated with deficient sGC activation. Thus, in one embodiment of the invention, there are provided methods of treating diseases that can be alleviated by sGC activation or potentiation. These include:

Cardiovascular and related diseases including hypertension, atherosclerosis, peripheral artery disease, major adverse cardiac events (MACE), myocardial infarction, restenosis, aortic valve stenosis, stroke, heart failure, coronary vasospasm, cerebral vasospasm, ischemia/reperfusion injury, thromboembolic pulmonary hypertension, pulmonary arterial hypertension, stable and unstable angina and thromboembolic disorders;

Inflammatory diseases including psoriasis, multiple sclerosis, arthritis, asthma, and chronic obstructive pulmonary disease;

Dermal fibrotic disorders including but not limited to systemic sclerosis;

Hepatic fibrotic disorders including but not limited to cirrhosis of any etiology including nonalcoholic steatohepatitis or fibrosis of specific areas of the liver such as periportal fibrosis which may be caused by immunologic injury, hemodynamic effects and/or other causes;

Inflammatory bowel disorders including but not limited to ulcerative colitis and Crohn's disease;

Renal fibrotic disorders including but not limited to glomerulosclerosis, focal glomerulosclerosis, mesangial fibrosis, interstitial fibrosis due to immunologic injury, hemodynamic effects, diabetes (types I and 2), diabetic nephropathy, IgA nephropathy, lupus nephropathy, membranous nephropathy, hypertension, hemolytic uremic syndrome, multiple glomerulonephritides, interstitial nephritis, tubulointerstitial nephritis again of immunologic and non-immunologic causes;

Pulmonary fibrotic disorders, both diffuse and localized, due to immunologic and non-immunologic causes, including but not limited to idiopathic pulmonary fibrosis, pulmonary fibrosis due to exposure to toxins, chemicals, drugs, and cystic fibrosis;

Cardiac fibrotic disorders due to immunologic and non-immunologic causes including ischemic heart disease (coronary artery disease) and transient and/or sustained decreased blood flow in one or more coronary vessels including possibly related to interventions on coronary arteries or veins, associated with cardiac surgery and/or the use of cardiopulmonary bypass procedures and myocarditis due to viral and non-viral causes, as well as immunologically related myocardial injury potentially due to cross-reactivity to other antigens to which the human body is exposed;

Other diseases mediated at least partially by diminished or decreased soluble guanylate cyclase activity, such as renal disease, diabetes, glaucoma, obesity, osteoporosis, muscular dystrophy, urologic disorders including overactive bladder, benign prostatic hyperplasia, erectile dysfunction, and neurological disorders including Alzheimer's disease, dementia, Parkinson's disease and neuropathic pain.

These disorders have been well characterized in man, but also exist with a similar etiology in other mammals, and can be treated by pharmaceutical compositions of the present invention.

Accordingly, a compound of formula I according to any of the embodiments described herein or a pharmaceutically acceptable salt thereof may be used for the preparation of a medicament for treating a disease or disorder mediated by deficient sGC activation, including all of the diseases or disorders mentioned above.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula I (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regimen.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:
1. A compound of the formula I

[Formula I structure shown]

wherein:
X is CHR$^4$;
  R$^1$ is H;
  R$^2$ and R$^3$ together with the carbons they are bonded to form a fused 3-membered ring; and
  R$^4$ is H; or
  R$^1$ is H;
  R$^2$ and R$^4$ form a 2-carbon alkylidene bridge; and
  R$^3$ is H; or
  R$^2$ and R$^3$ are H; and
  R$_1$ and R$_4$ together with the piperidine ring they are bonded to may form an octahydropyrano[3,2-b]pyridine ring; or
  R$^1$ is H;
  R$^2$ is -OMe or -OEt;
  R$^3$ is H; and
  R$^4$ is H; or
X is a bond;
  R$^1$ is H, Me, or —CH$_2$OMe; and
  R$^2$ and R$^3$ together with the carbons they are bonded to form a fused 3-membered ring;
Y is C or N;
W is C or N, provided that Y and W are not both N;
V is —C(R$^{11}$)(R$^{12}$)— or —OCH$_2$—, provided that if V is —OCH$_2$, then Z is —CH$_2$—, Y and W are both C;
Z is —CH$_2$—, —C(R$^{10}$)$_2$CH$_2$— or —C(O)—;
B is

[three ring structures shown: thiazole, pyridine, pyrimidine]

R$^5$ and R$^6$ are independently selected from H, Me, F, Cl and CF$_3$;
R$^7$ is H, Me, Et, -OMe, CN, F, or —CH$_2$OMe or is not present when Y is N;
R$^8$ is H, Me or F or is not present when W is N;
R$^9$ is H or C$_{4-6}$cycloalkyl, optionally substituted with one to two F, or R$^9$ is —(CH$_2$)$_n$ heterocyclyl, wherein the heterocyclyl is selected from tetrahydropyranyl, tetrahydrofuranyl, oxetanyl and [1,4]-dioxanyl or —CH(R$_{10}$) heteroaryl, wherein the heteroaryl is selected from the group consisting of pyrazine, imidazole, pyridyl and isoxazolyl and wherein the heteroaryl is optionally substituted with a methyl group;
each R$^{10}$ is independently H or Me;
R$^{11}$ is H or Me;
R$^{12}$ is H or Me;
m is 0 or 1, provided that if m is 0, Z is —CH$_2$—, V is —C(R$^{11}$)(R$^{12}$)— and R$^{11}$ and R$^{12}$ are both H;
and
n is 0 or 1;
or a salt thereof.

2. The compound according to claim 1, wherein:
X is CHR$^4$;
  R$^1$ is H;
  R$^2$ and R$^3$ together with the carbons they are bonded to form a fused 3-membered ring; and
  R$^4$ is H; or
  R$^1$ is H;
  R$^2$ and R$^4$ form a 2-carbon alkylidene bridge; and
  R$^3$ is H; or
  R$^1$ is H;
  R$^2$ is -OMe or -OEt;
  R$^3$ is H; and
  R$^4$ is H; or
X is a bond;
  R$^1$ is H, Me, or —CH$_2$OMe; and
  R$^2$ and R$^3$ together with the carbons they are bonded to form a fused 3-membered ring;
Y is C or N;
W is C;
V is —C(R$^{11}$)(R$^{12}$)—;
Z is —CH$_2$—, —C(R$^{10}$)$_2$CH$_2$— or —C(O)—;
B is

[three ring structures shown: thiazole, pyridine, pyrimidine]

R$^5$ and R$^6$ are independently selected from H, Me, F and Cl;
R$^7$ is H, Me, Et, -OMe, CN, or F or is not present when Y is N;
R$^8$ is H, Me or F;
R$^9$ is C$_{4-6}$cycloalkyl, optionally substituted with one to two F, or R$^9$ is —(CH$_2$)$_n$ heterocyclyl, wherein the heterocyclyl is selected from tetrahydropyranyl, tetrahydrofuranyl, oxetanyl and [1,4]-dioxanyl;

each $R^{10}$ is independently H or Me;
$R^{11}$ is H or Me;
$R^{12}$ is H or Me;
m is 1; and
n is 0 or 1;
or a salt thereof.
3. The compound according to claim 2, wherein:
Y is C;
Z is —CH$_2$— or —C(R$^{10}$)$_2$CH$_2$—; and
$R^9$ is —(CH$_2$)$_n$ heterocyclyl, wherein the heterocyclyl is selected from tetrahydropyranyl, tetrahydrofuranyl, oxetanyl and [1,4]-dioxanyl;
or a salt thereof.
4. The compound according to claim 2, wherein:
X is CHR$^4$;
$R^1$ is H;
$R^2$ and $R^3$ together with the carbons they are bonded to form a fused 3-membered ring;
$R^4$ is H; and
$R^9$ is —(CH$_2$)$_n$ heterocyclyl, wherein the heterocyclyl is selected from tetrahydropyranyl, tetrahydrofuranyl, oxetanyl and [1,4]-dioxanyl;
or a salt thereof.
5. The compound according to claim 2, wherein:
X is CHR$^4$;
$R^1$ is H;
$R^2$ is -OMe;
$R^3$ is H;
$R^4$ is H; and
$R^9$ is —(CH$_2$)$_n$ heterocyclyl, wherein the heterocyclyl is selected from tetrahydropyranyl, tetrahydrofuranyl, oxetanyl and [1,4]-dioxanyl;
or a salt thereof.
6. The compound according to claim 2, wherein:
X is a bond;
$R^1$ is H, Me, or —CH$_2$OMe;
$R^2$ and $R^3$ together with the carbons they are bonded to form a fused 3-membered ring; and
$R^9$ is —(CH$_2$)$_n$ heterocyclyl, wherein the heterocyclyl is selected from tetrahydropyranyl, tetrahydrofuranyl, oxetanyl and [1,4]-dioxanyl;
or a salt thereof.
7. The compound according to claim 2, wherein:
Z is —CH$_2$—; and
$R^9$ is —(CH$_2$)$_n$ heterocyclyl, wherein the heterocyclyl is selected from tetrahydropyranyl, tetrahydrofuranyl, oxetanyl and [1,4]-dioxanyl;
or a salt thereof.
8. The compound according to claim 2, wherein:
Z is —C(R$^{10}$)$_2$CH$_2$—;
$R^{10}$ is H; and
$R^9$ is —(CH$_2$)$_n$ heterocyclyl, wherein the heterocyclyl is selected from tetrahydropyranyl, tetrahydrofuranyl, oxetanyl and [1,4]-dioxanyl;
or a salt thereof.
9. The compound according to claim 1, wherein
X is CHR$^4$;
Y is C;
W is C;
V is —C(R$^{11}$)(R$^{12}$)—;
Z is —CH$_2$— or —C(R$^{10}$)$_2$CH$_2$;
$R^1$ is H;
$R^2$ is -OMe;
$R^3$ is H;
$R^4$ is H;
B is

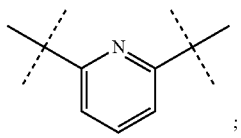

$R^7$ is H, Me, Et, -OMe, CN, F, or —CH$_2$OMe;
$R^8$ is H, Me or F;
$R^9$ is —(CH$_2$)$_n$ heterocyclyl, wherein the heterocyclyl is selected from tetrahydropyranyl, tetrahydrofuranyl, oxetanyl and [1,4]-dioxanyl;
$R^{11}$ is H;
$R^{12}$ is H;
n is 0; and
m is 1;
or a salt thereof.
10. The compound according to claim 1, wherein
X is a bond;
Y is C;
W is C;
V is —C(R$^{11}$)(R$^{12}$)—;
Z is —CH$_2$— or —C(R$^{10}$)$_2$CH$_2$;
$R^1$ is H Me or —CH$_2$OMe;
$R^2$ and $R^3$ together with the carbons they are bonded to form a fused 3-membered ring;
B is

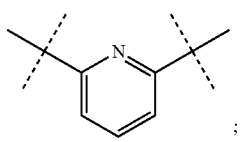

$R^7$ is H, Me, Et, -OMe, CN, F, or —CH$_2$OMe;
$R^8$ is H, Me or F;
$R^9$ is —(CH$_2$)$_n$ heterocyclyl, wherein the heterocyclyl is selected from tetrahydropyranyl, tetrahydrofuranyl, oxetanyl and [1,4]-dioxanyl;
$R^{11}$ is H;
$R^{12}$ is H;
n is 0; and
m is 1;
or a salt thereof.
11. The compound according to claim 1 selected from the group consisting of

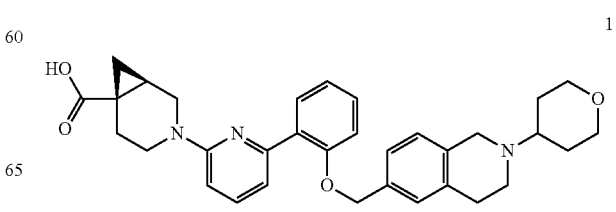

1

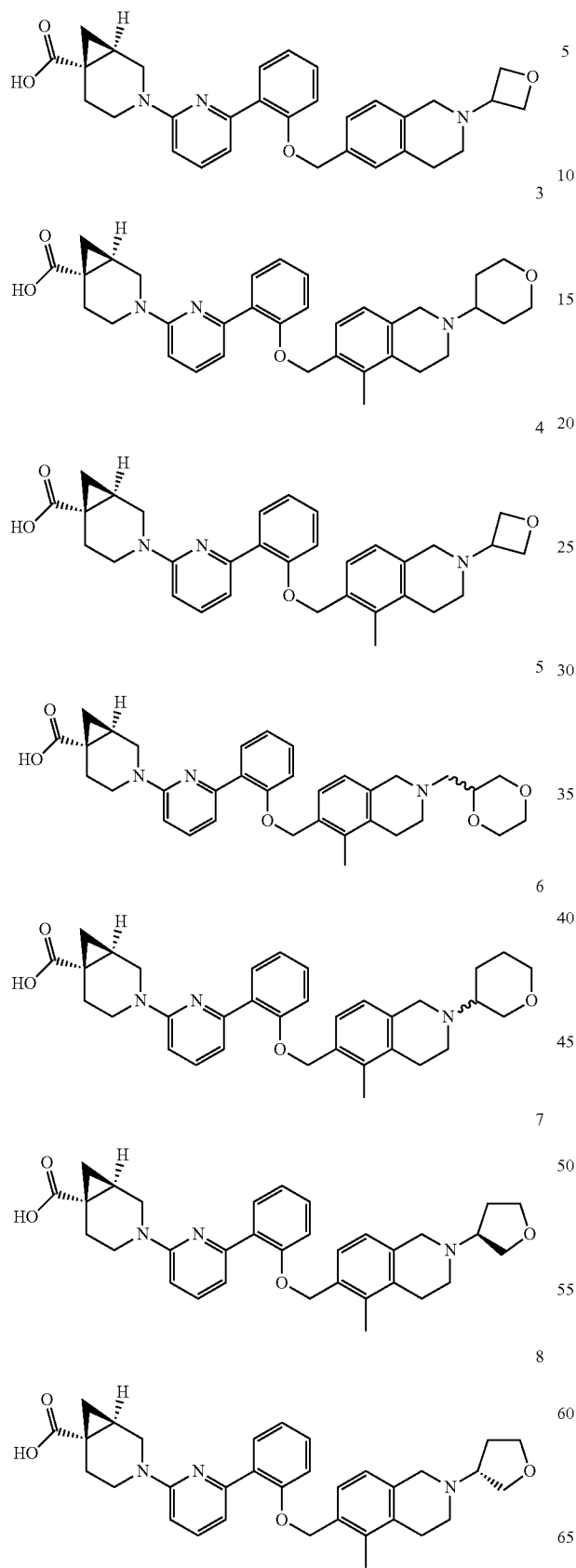
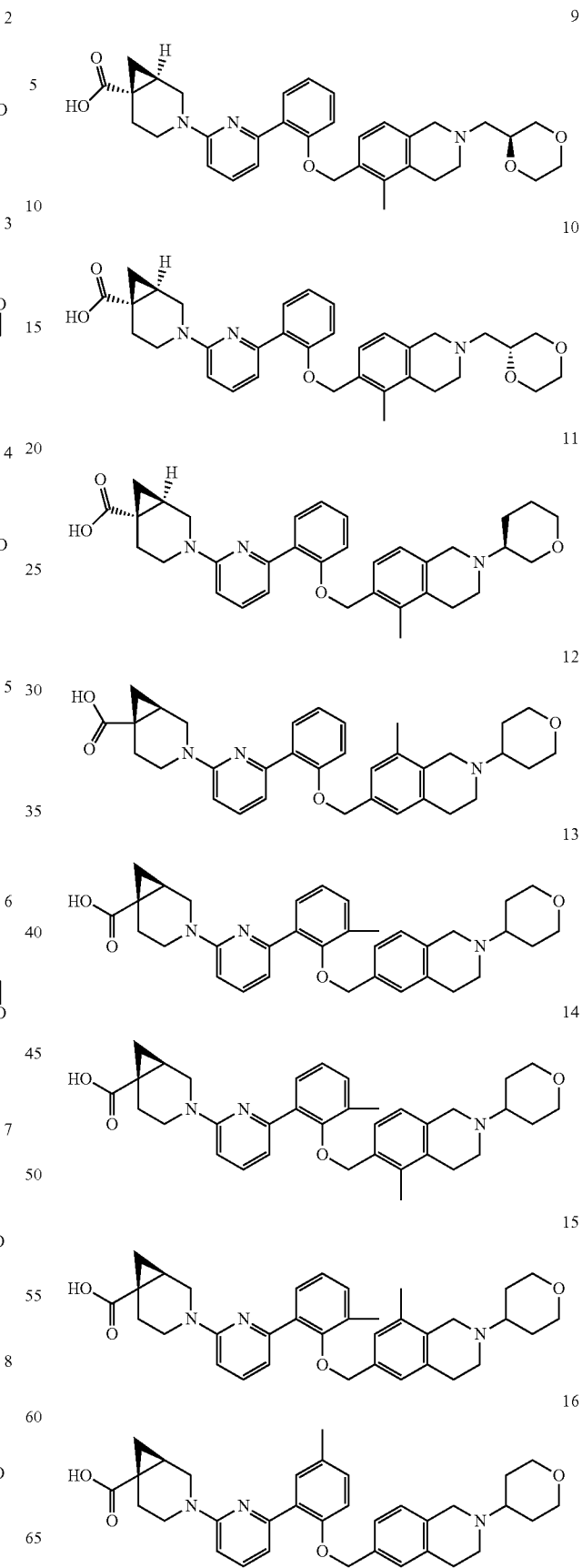

17
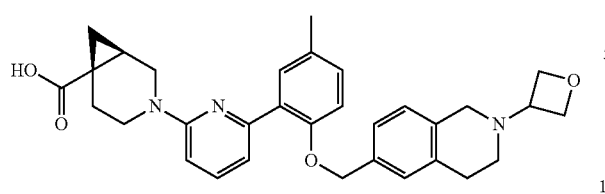
18
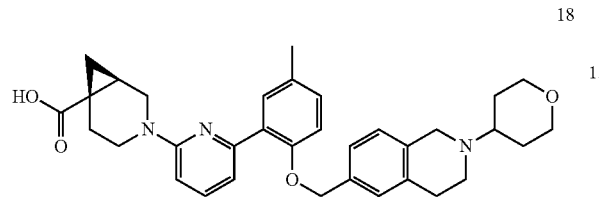
19
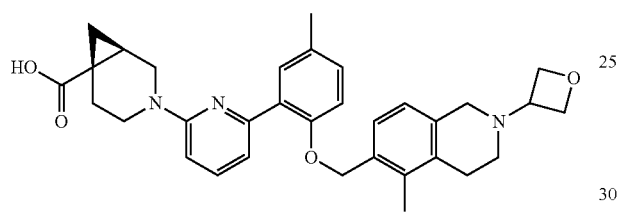
20
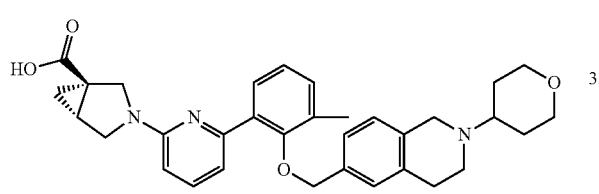
21
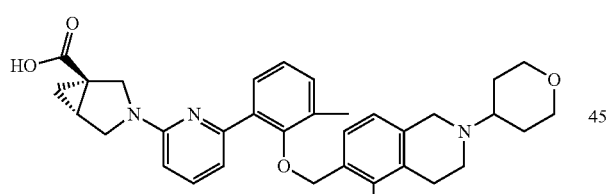
22
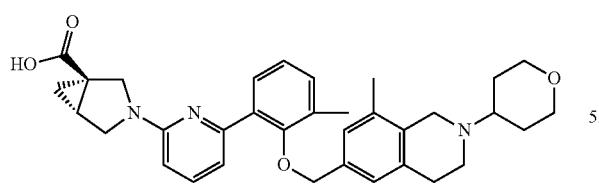
23
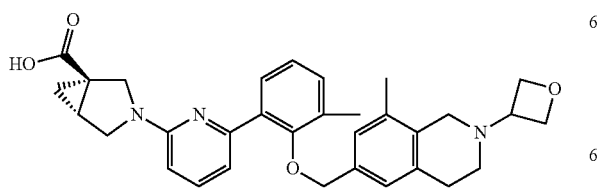
24
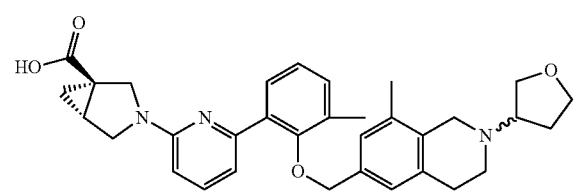
25
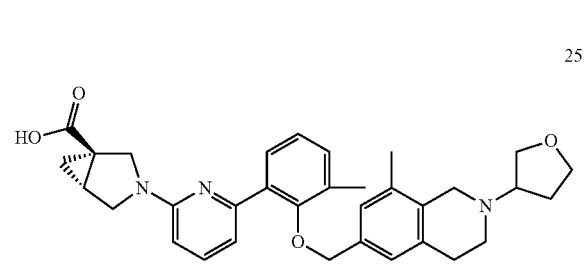
26
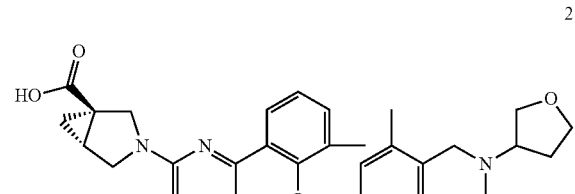
27
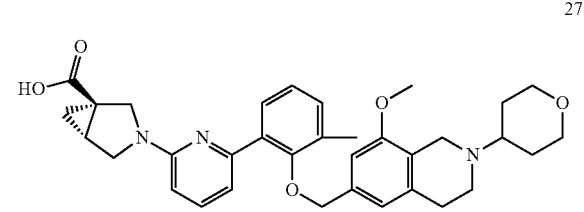
28
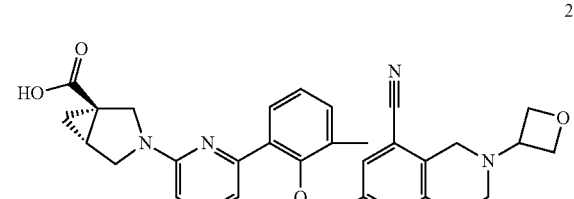
29
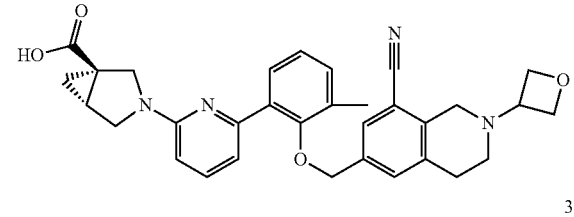
30
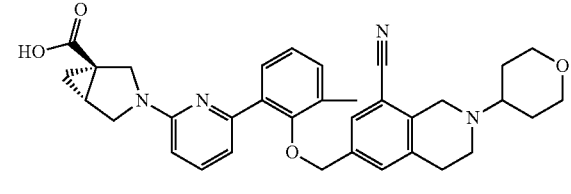

31
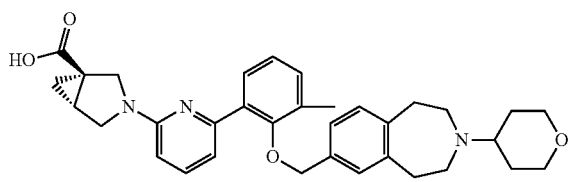
32
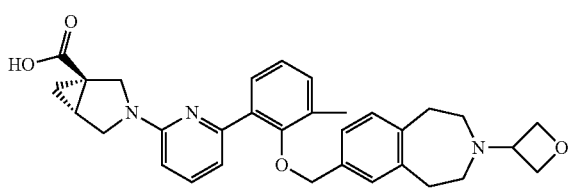
33
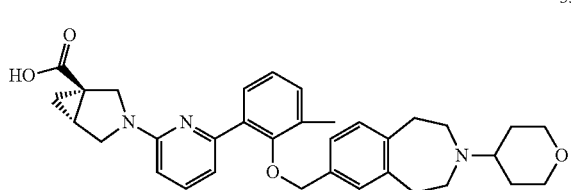
34
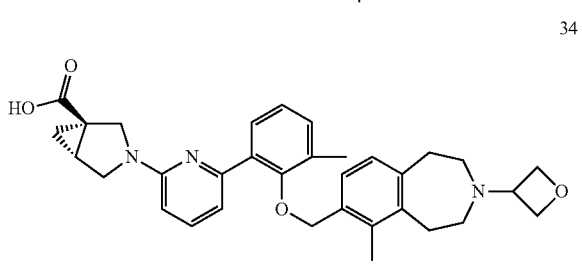
35
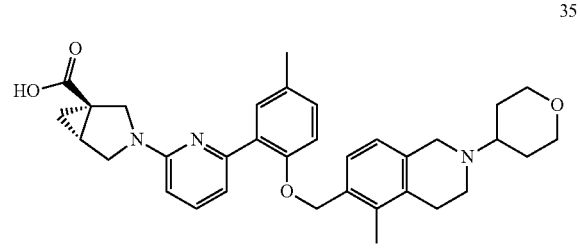
36
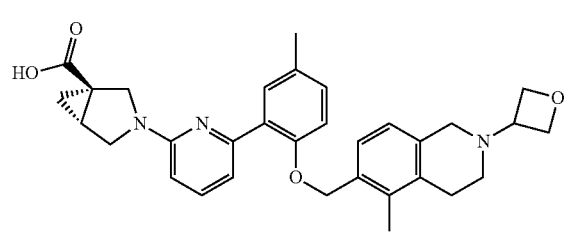
37
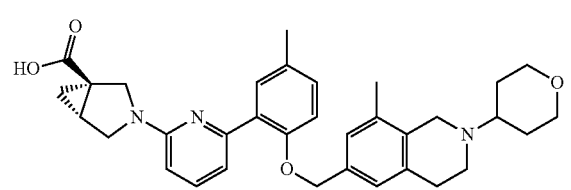
38
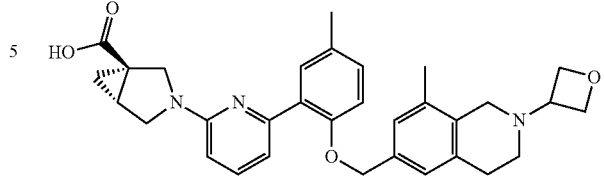
39
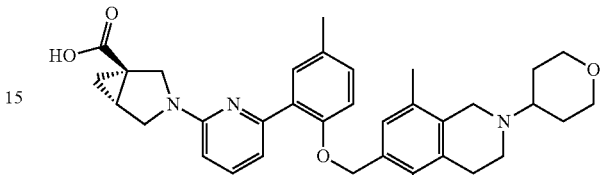
40
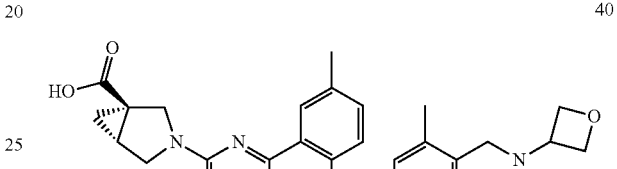
41
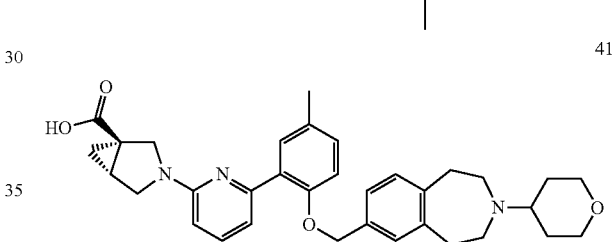
42
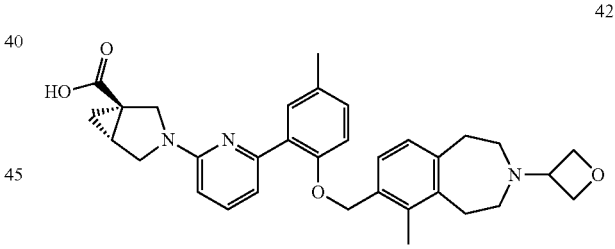
43
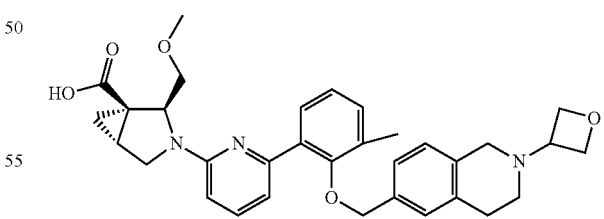
44
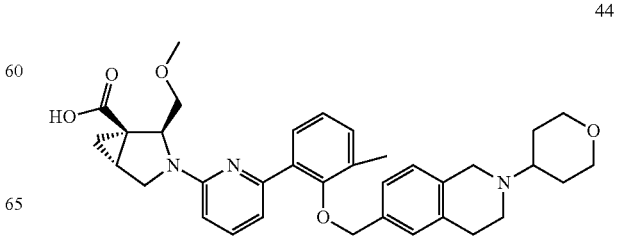

397
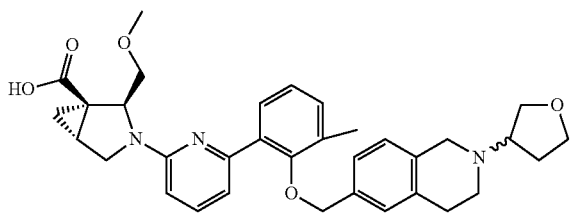
45
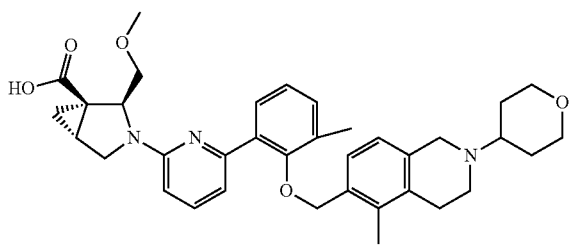 [SMILES: COC[C@H]1N(c2cccc(-c3cccc(C)c3OCc3ccc4c(c3C)CCN(C3CCOCC3)C4)n2)C[C@@H]2C[C@@]21C(=O)O]
46
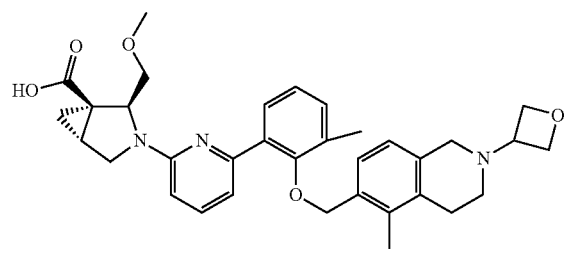
47
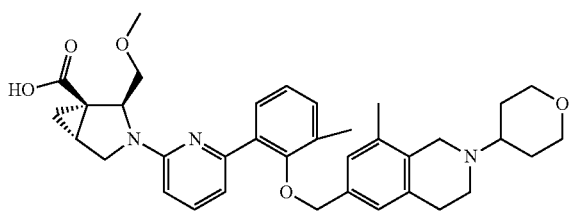
48
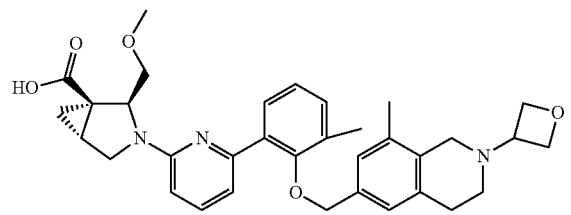
49
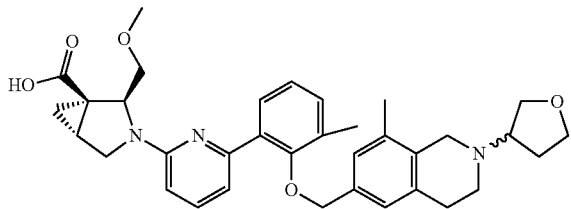
50
398
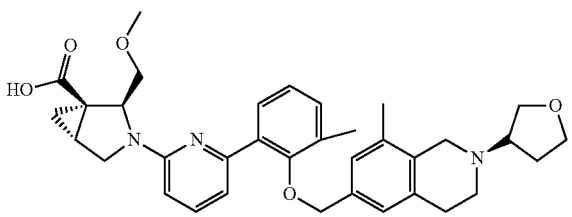
51
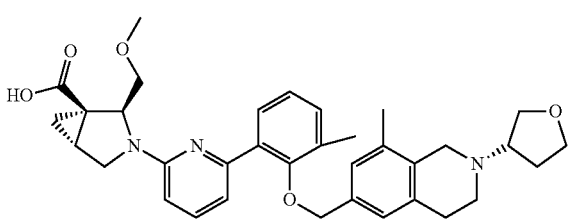
52
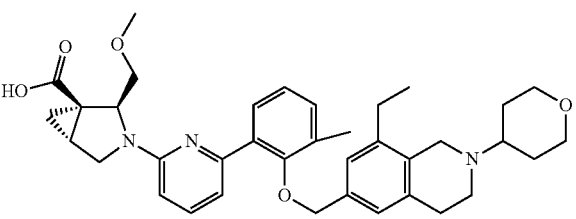
53
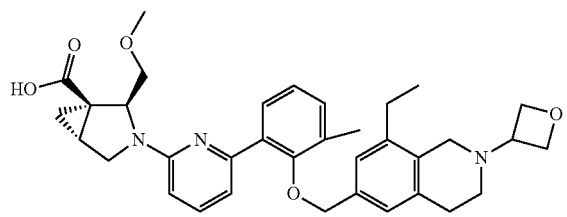
54
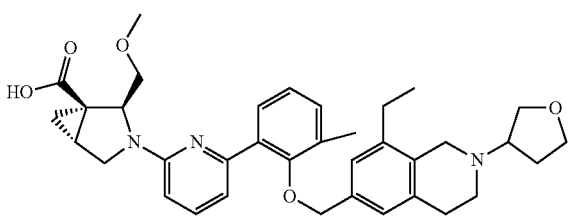
55
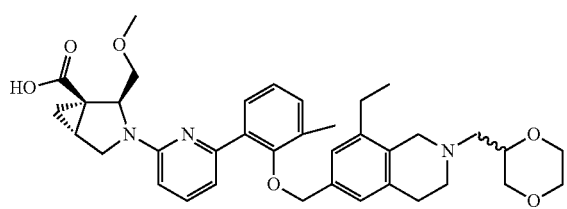
56

399
-continued
| | |
|---|---|
| 57 | 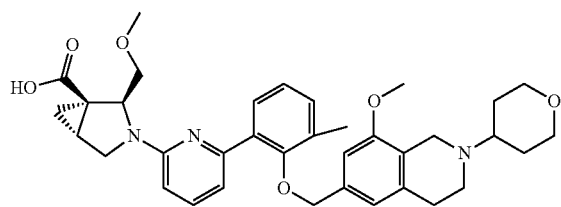 |
| 58 | 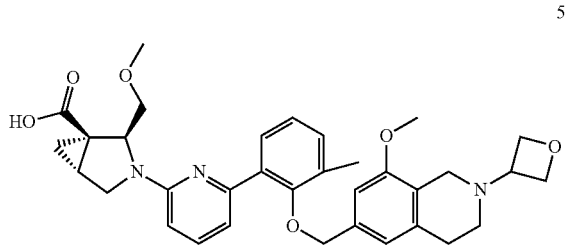 |
| 59 | 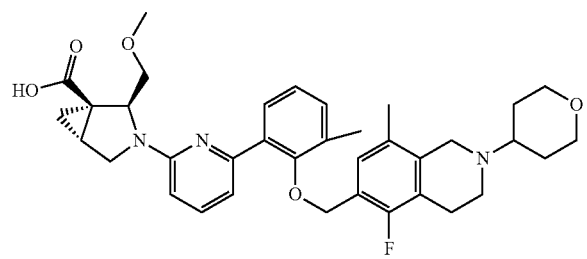 |
| 60 | 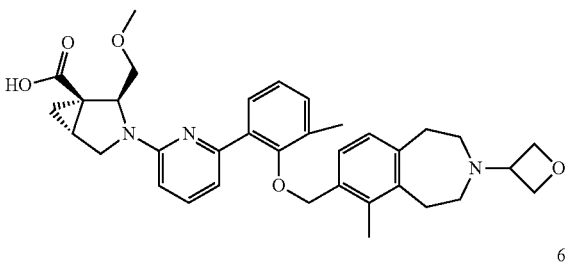 |
| 61 | 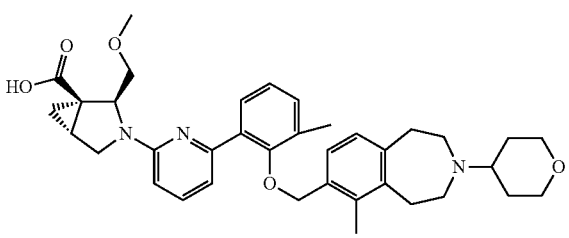 |
| 62 | 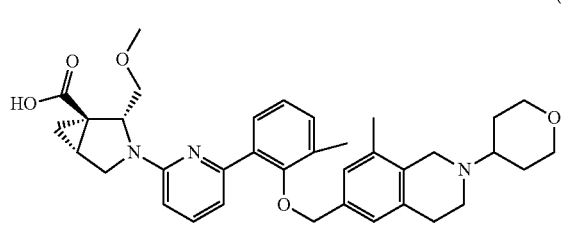 |
400
-continued
| | |
|---|---|
| 63 | 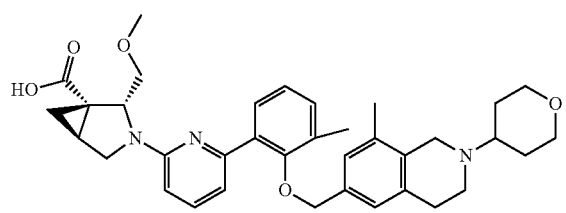 |
| 64 | 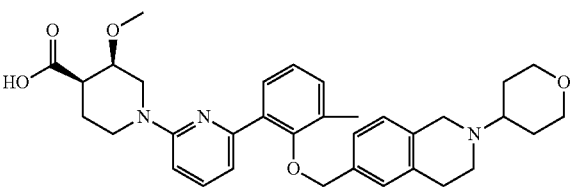 |
| 65 |  |
| 66 | 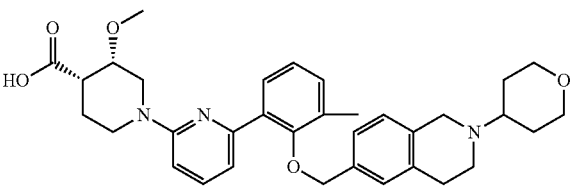 |
| 67 | 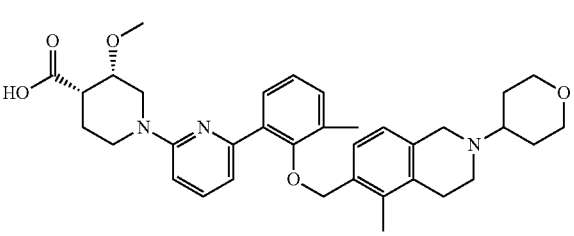 |
| 68 | |
| 69 | 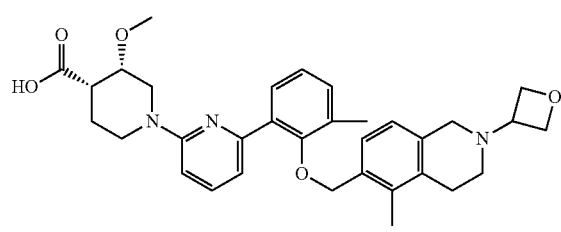 |

70
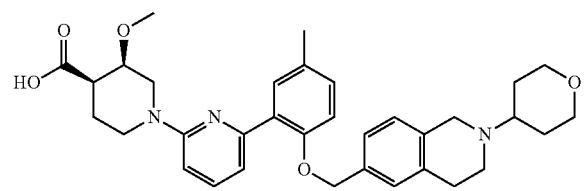
71
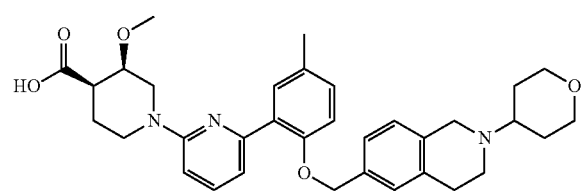
72
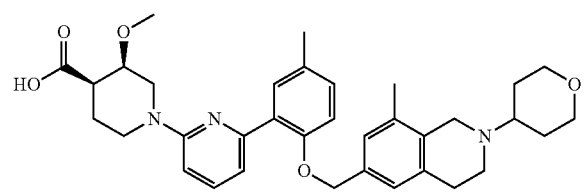
73
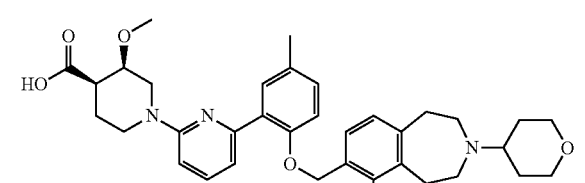
74
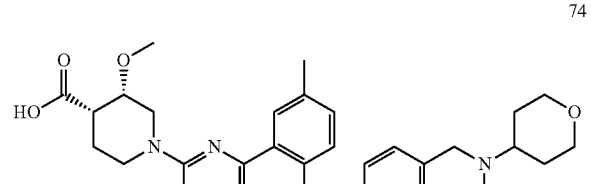
75
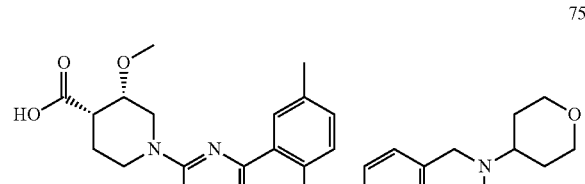
76
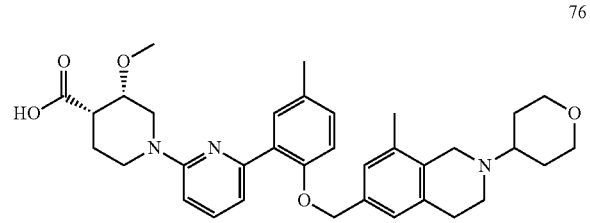
77
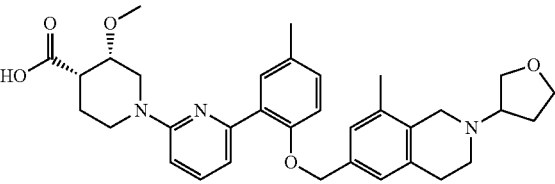
78
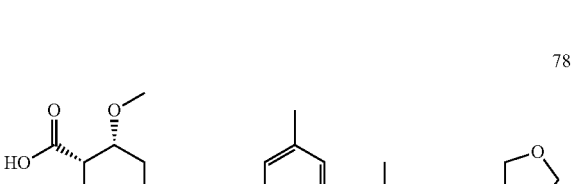
79
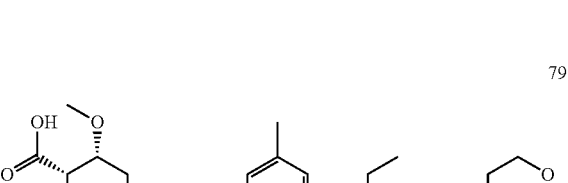
80
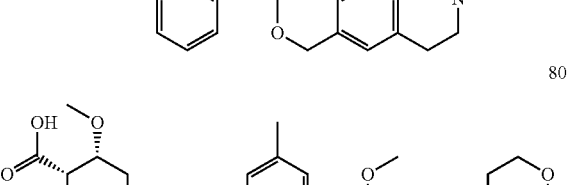
81
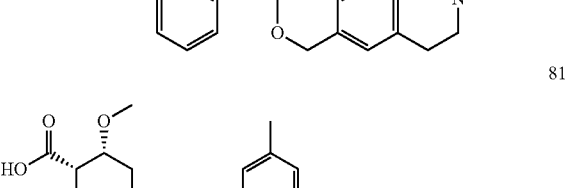
82
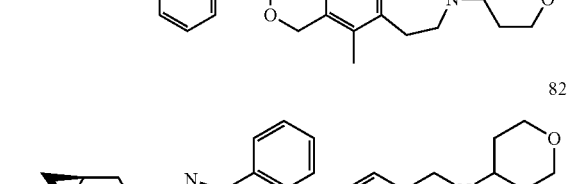
83
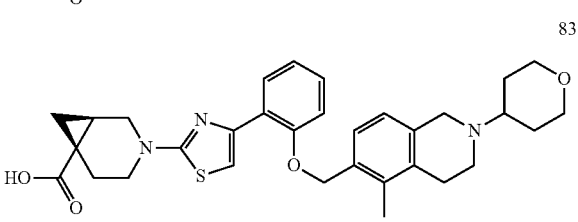

84
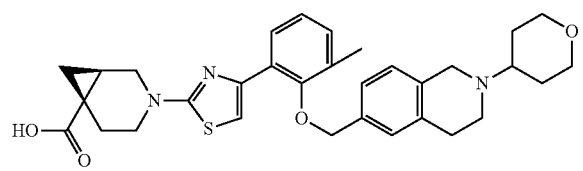
85
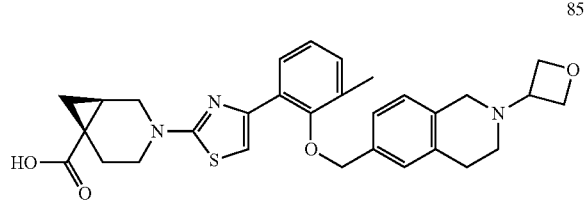
86
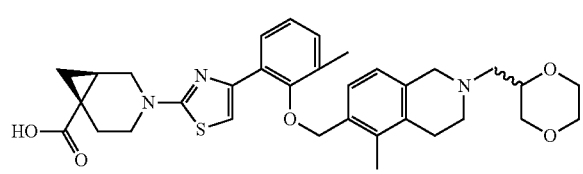
87
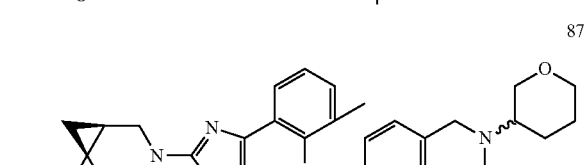
88
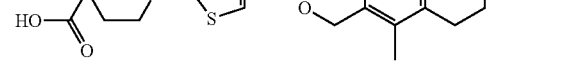
89
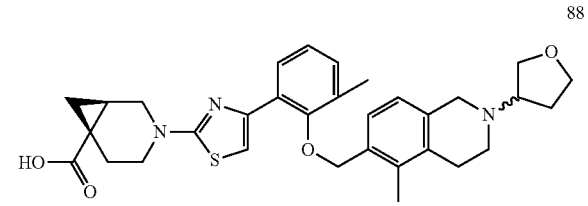
90
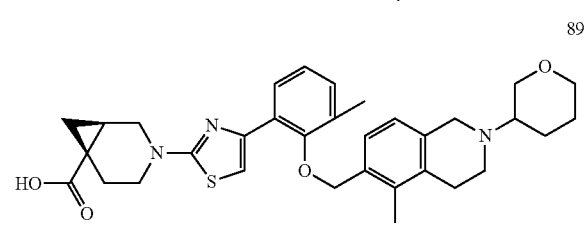
91
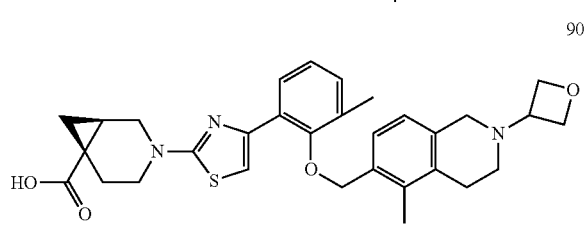
92
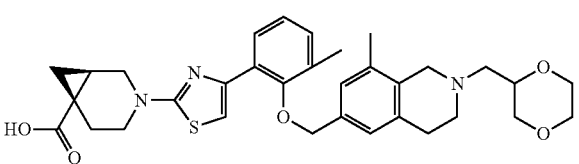
93
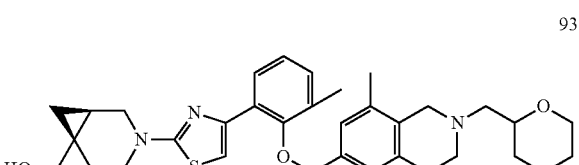
94
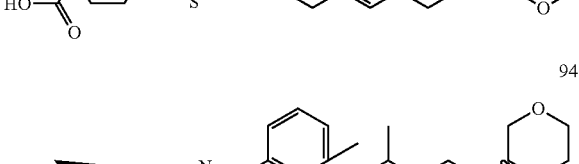
95
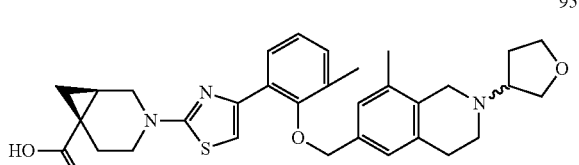
96
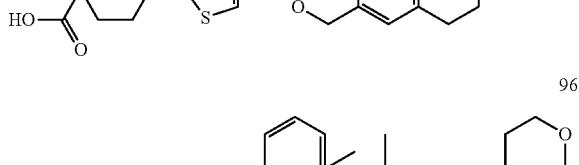
97
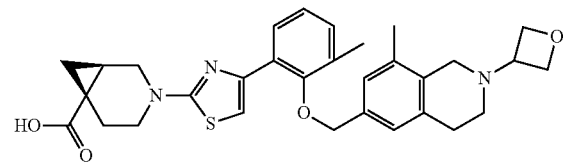
98
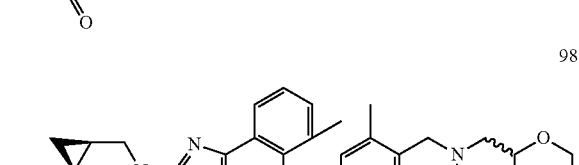
99
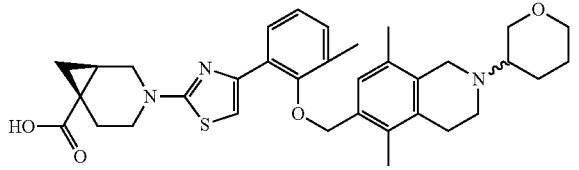

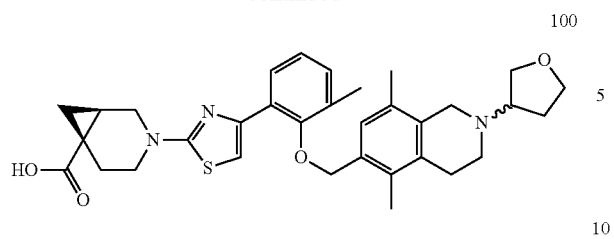
100
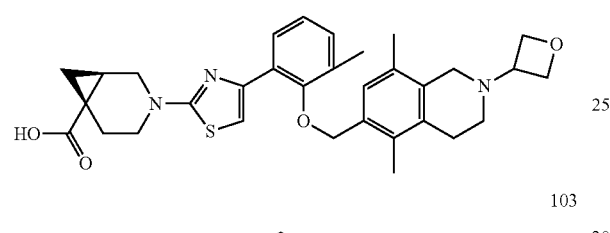
101
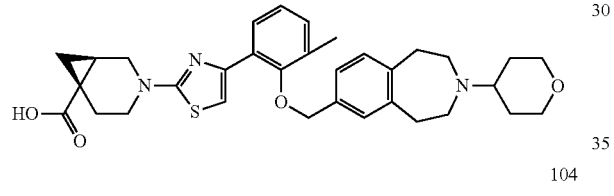
102
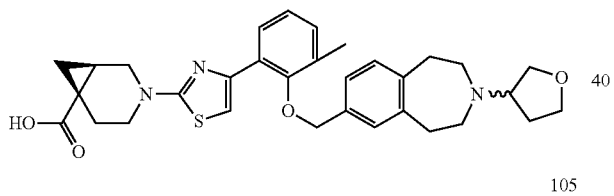
103
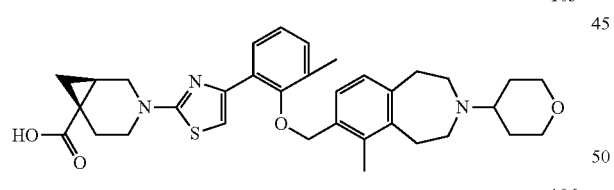
104
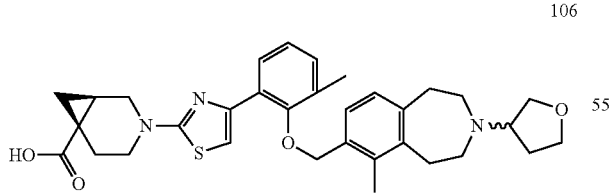
105
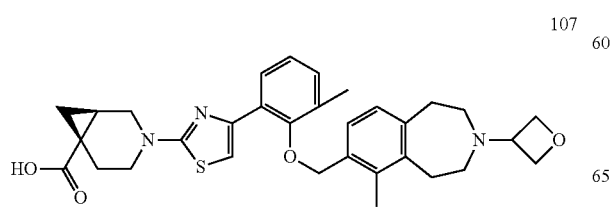
106
107
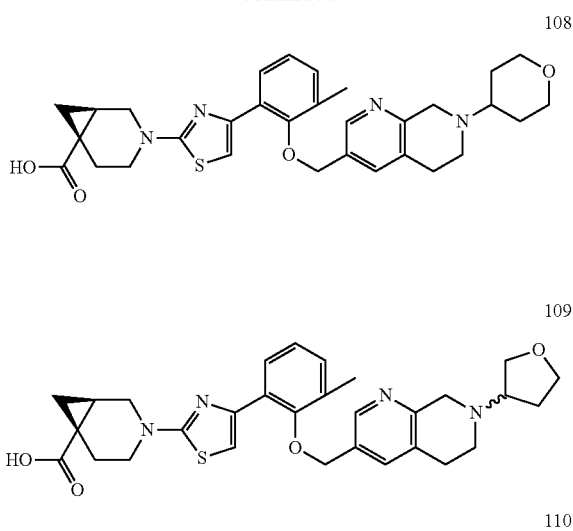
108
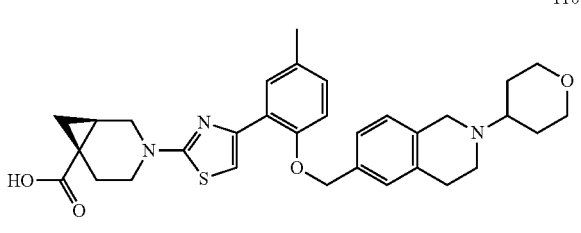
109
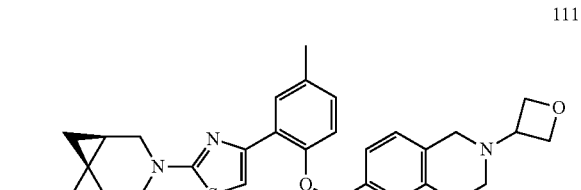
110
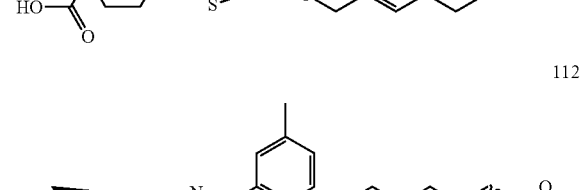
111
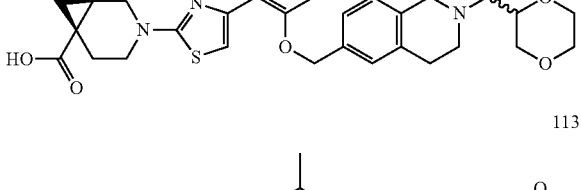
112
113
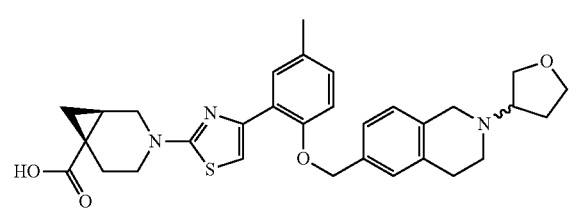
114

407
-continued
115
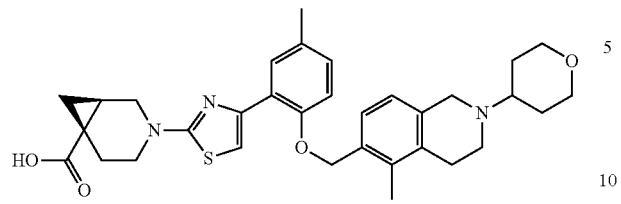
116
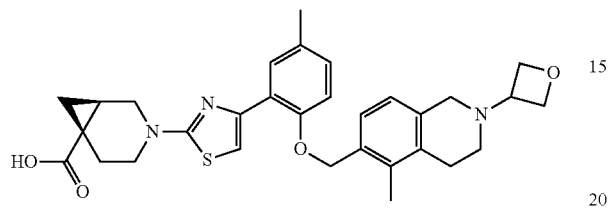
117
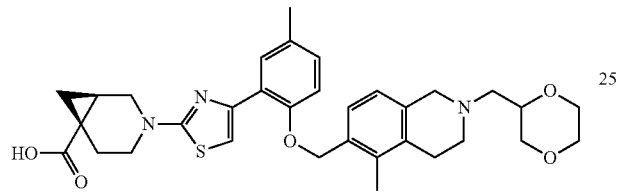
118
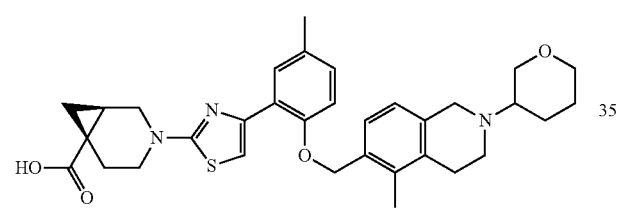
119
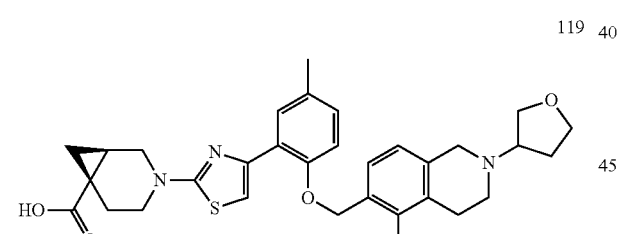
120
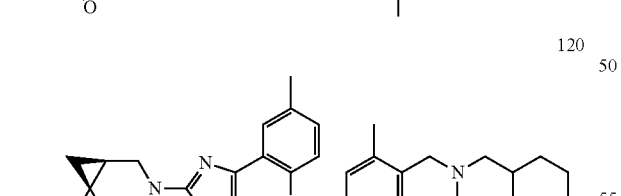
121
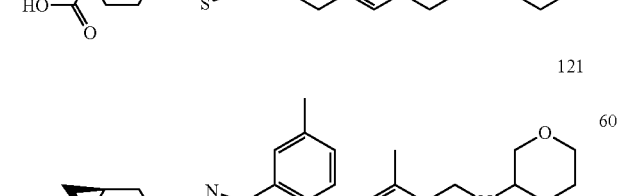
408
-continued
122
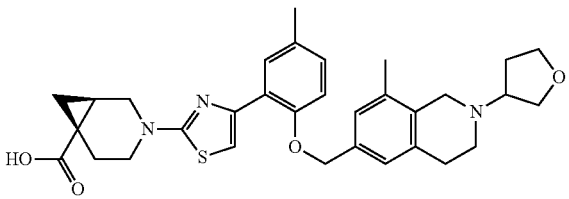
123
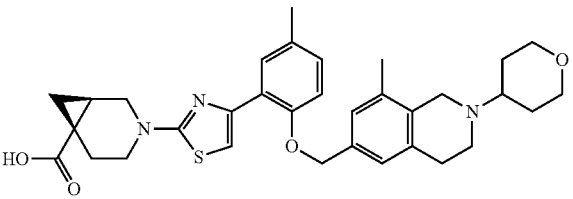
124
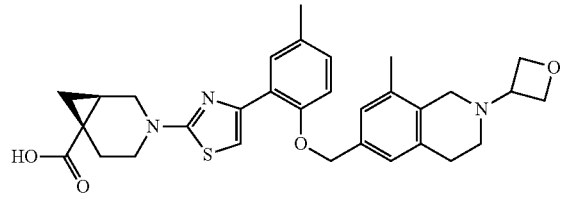
125
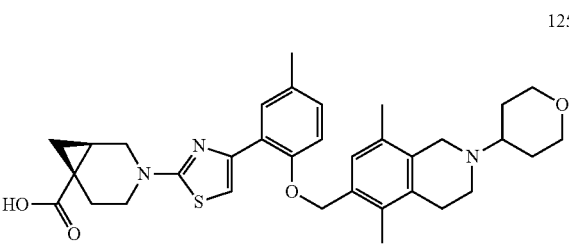
126
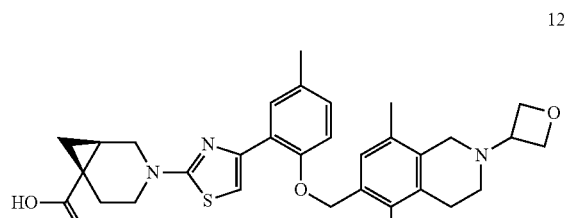
127
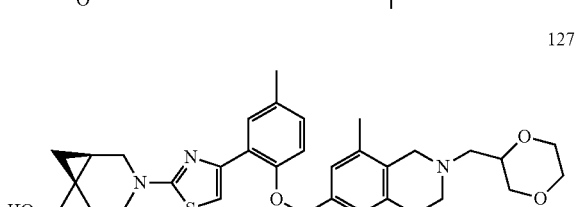
128
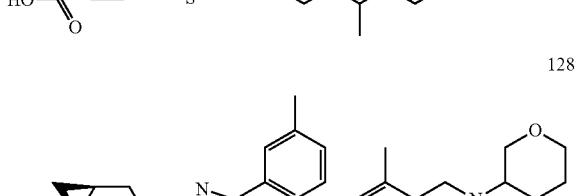

-continued

411
-continued
143
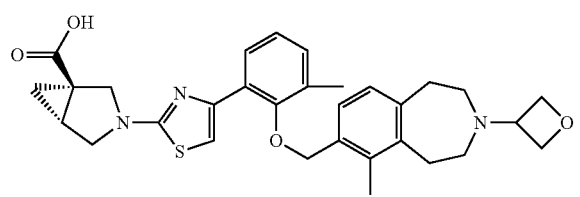
144
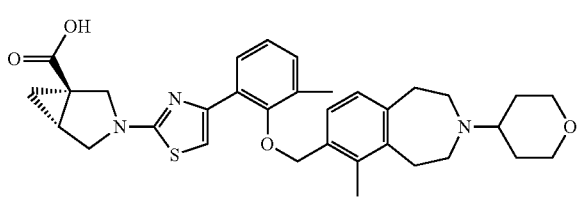
145
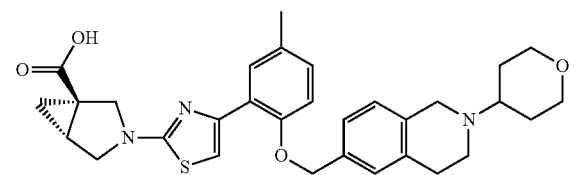
146
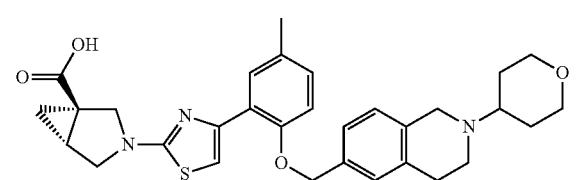
147
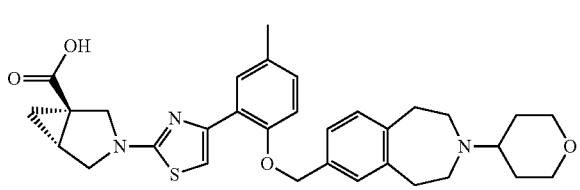
148
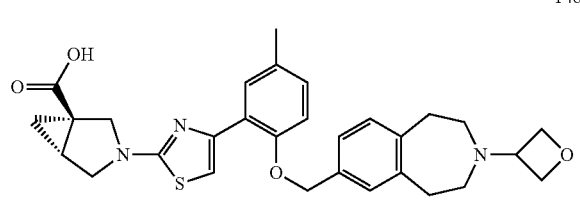
149
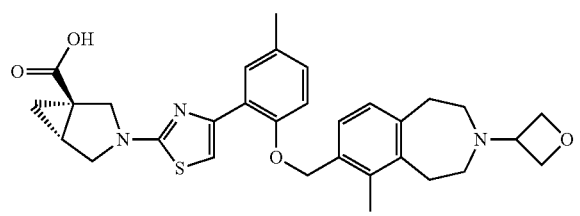
412
-continued
150
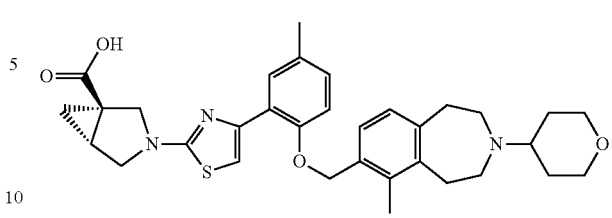
151
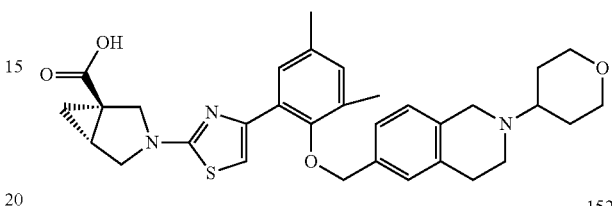
152
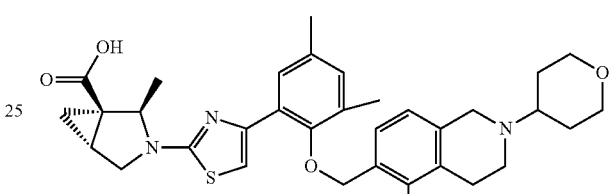
153
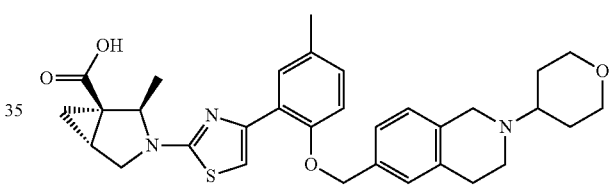
154
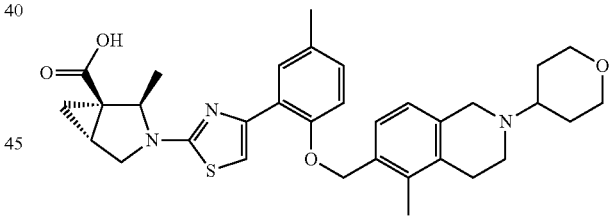
155
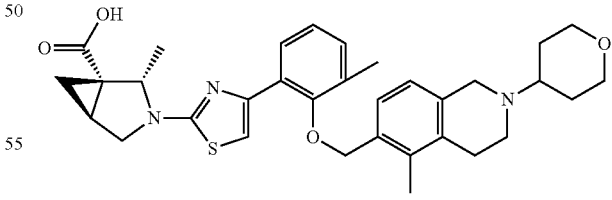
156
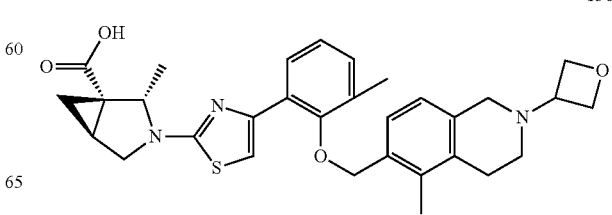

157
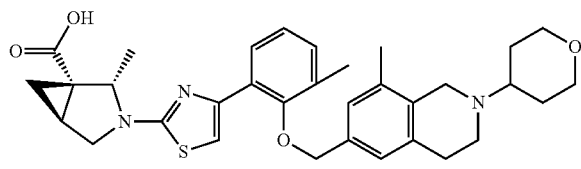
158
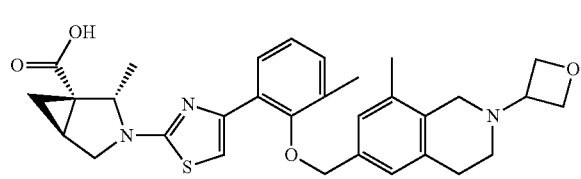
159
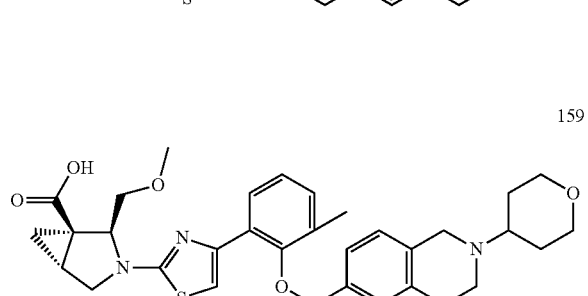
160
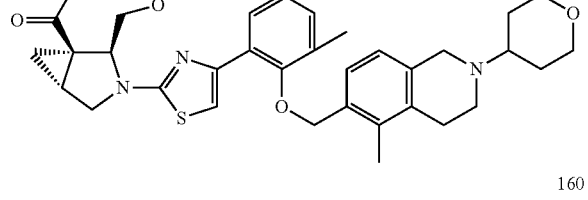
161
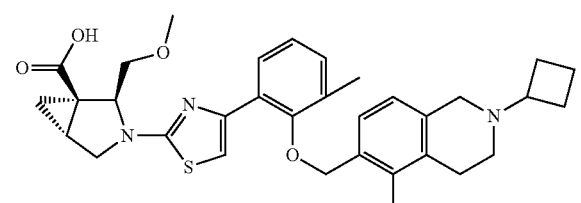
162
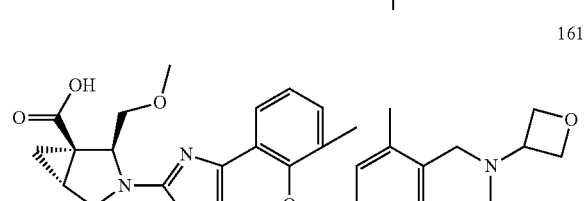
163
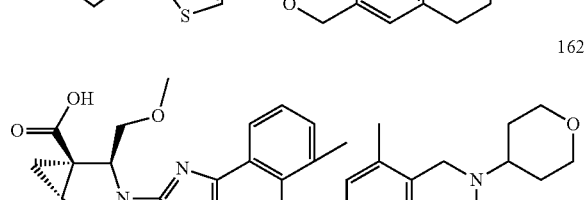
164
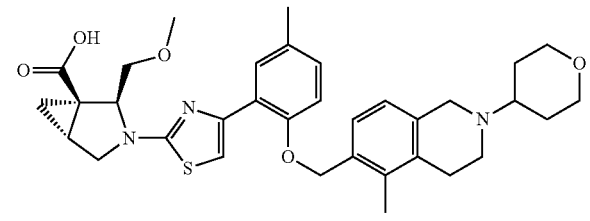
165
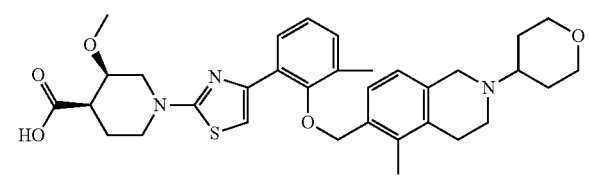
166
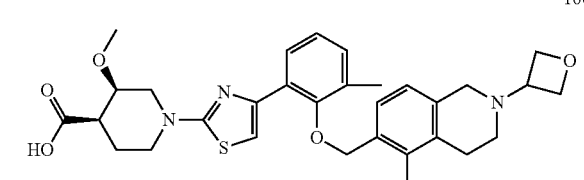
167
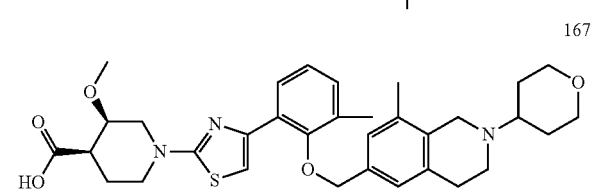
168
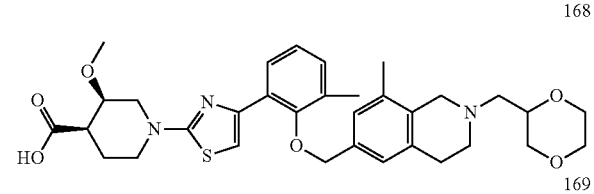
169
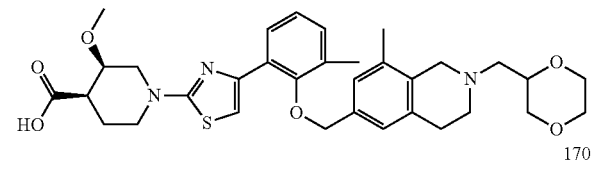
170
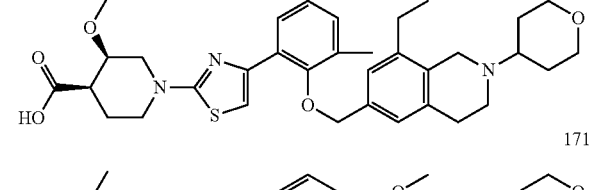
171
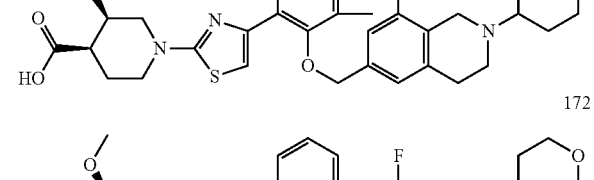
172
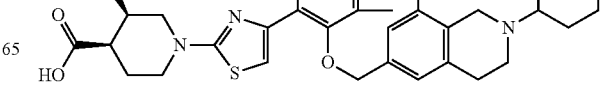

173
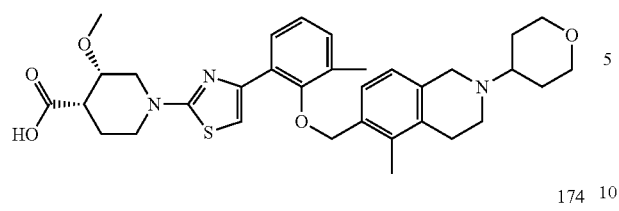
174
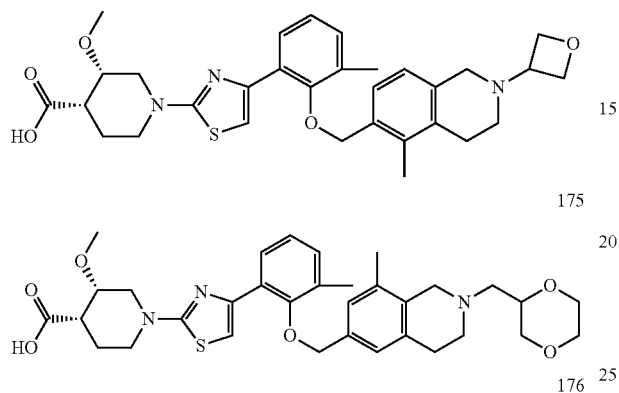
175
176
177
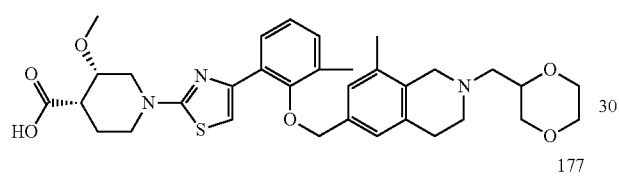
178
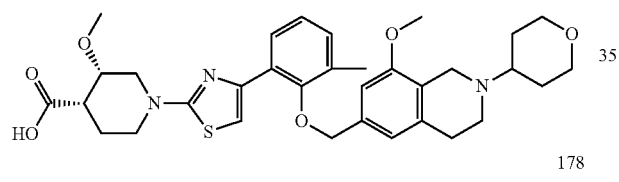
179
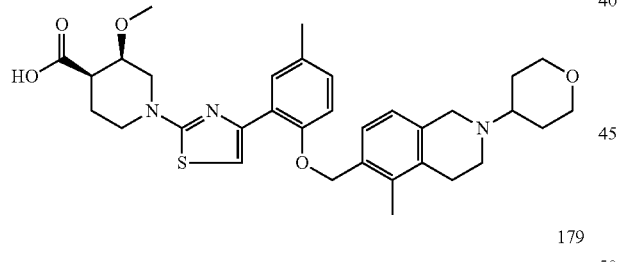
180
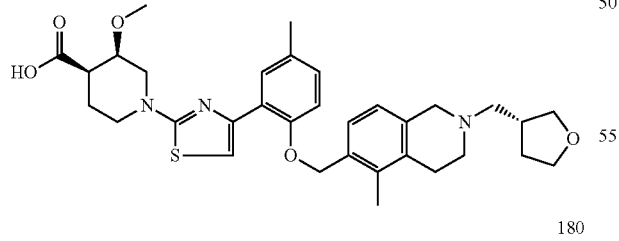
181
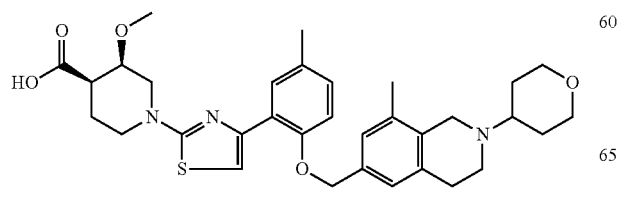
182
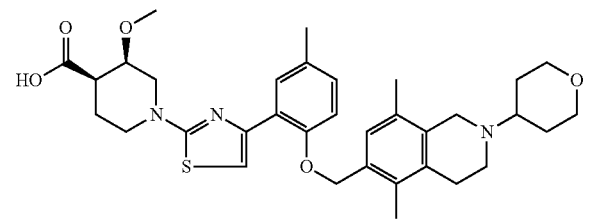
183
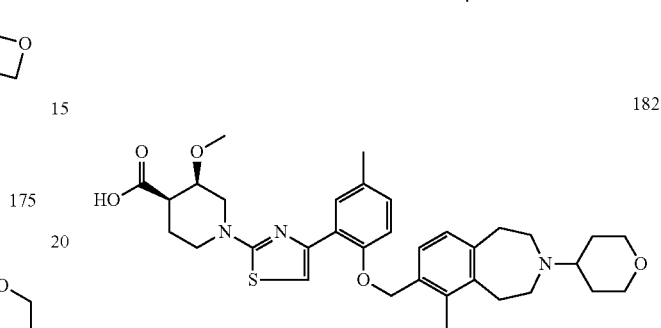
184
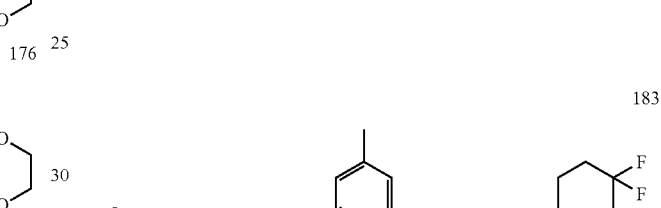
185
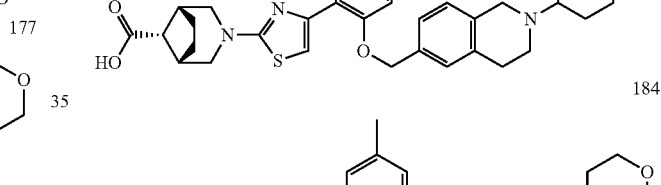
186
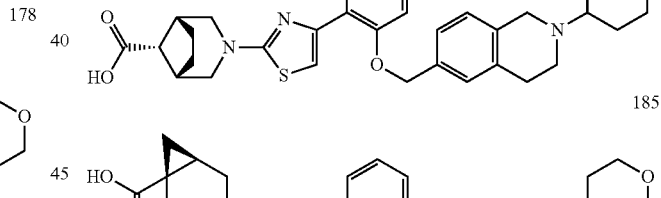
187
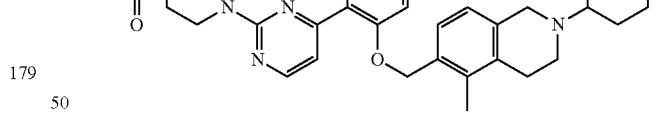
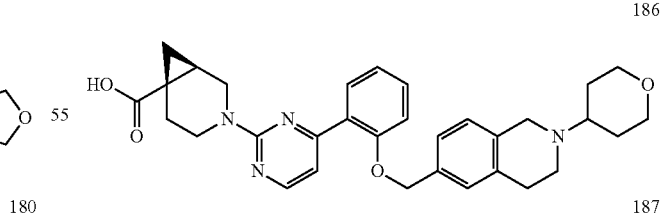

188 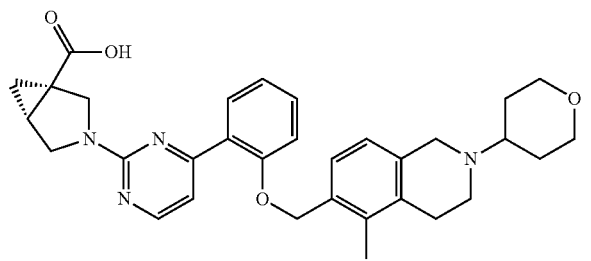
189 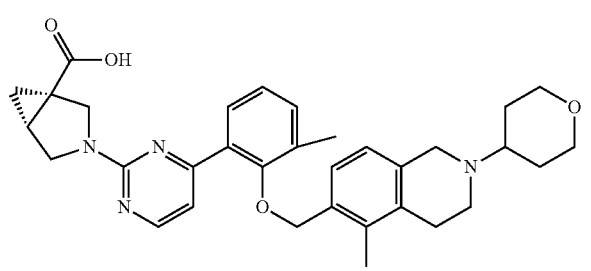
190 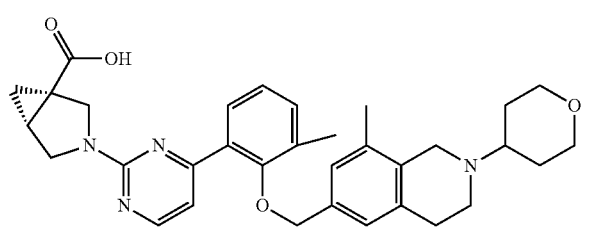
191 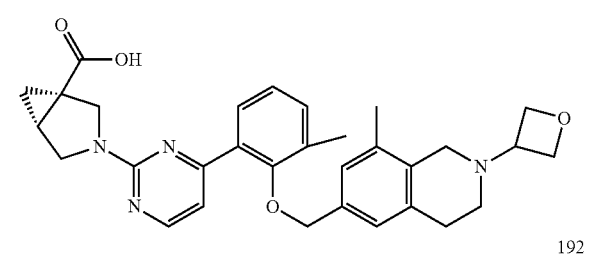
192 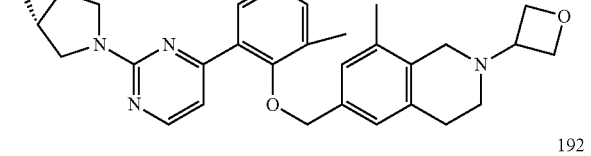
193 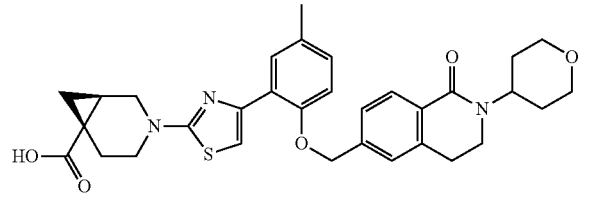
194 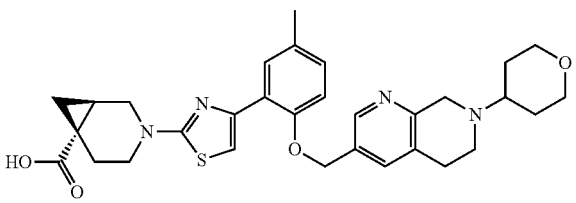
195 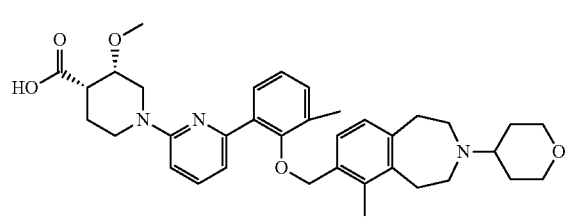
196 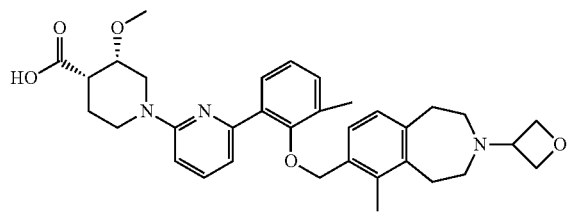
197 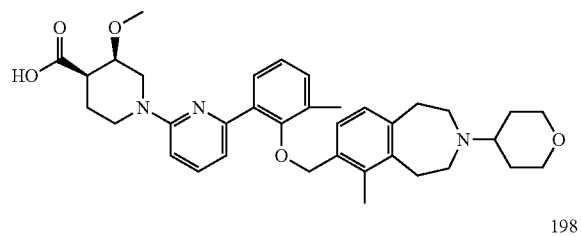
198 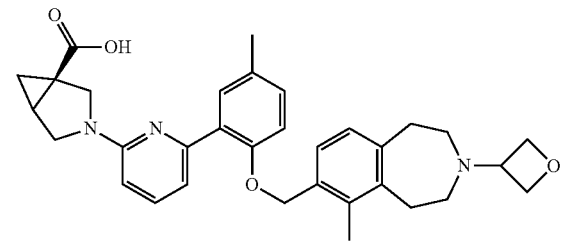
199 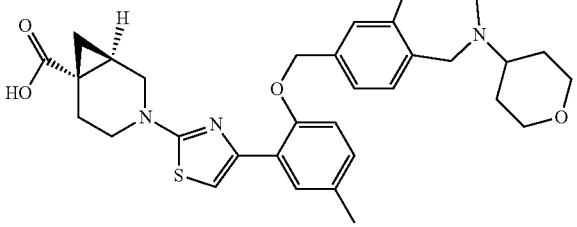

419
-continued
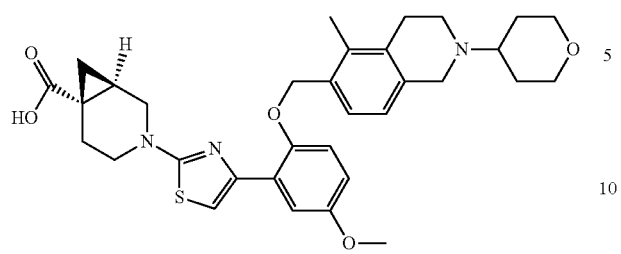
200
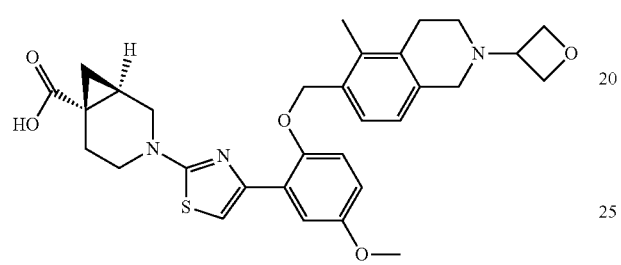
201
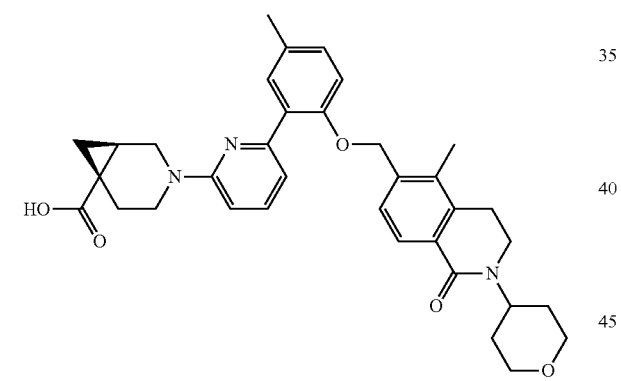
202
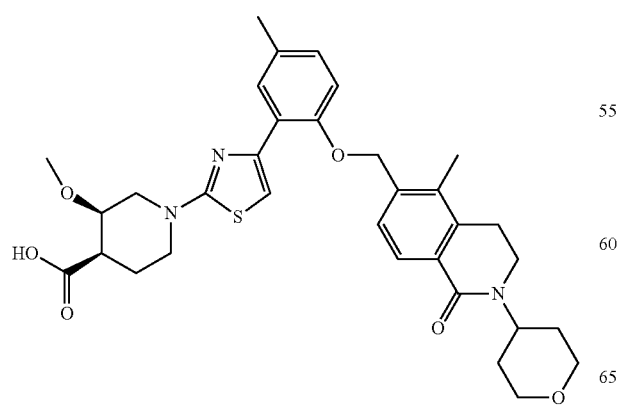
203
420
-continued
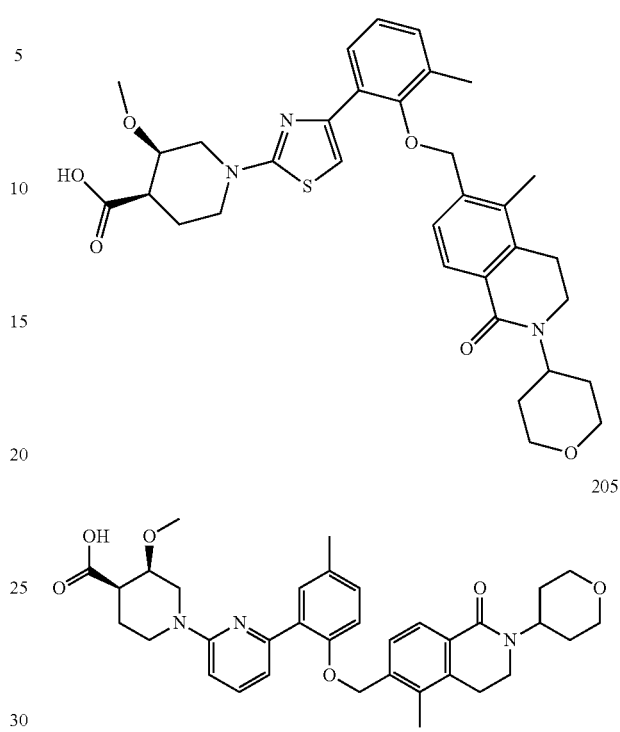
204
205
206
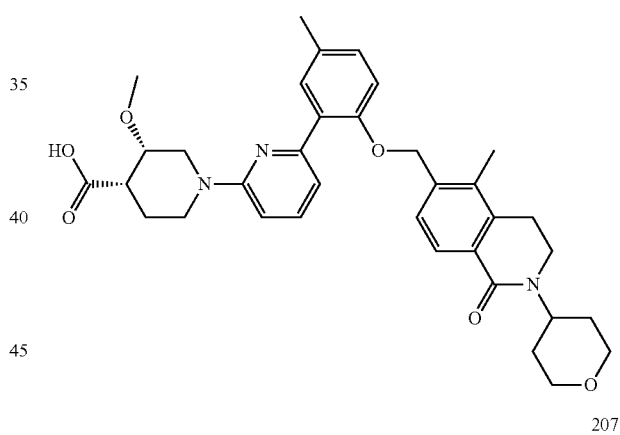
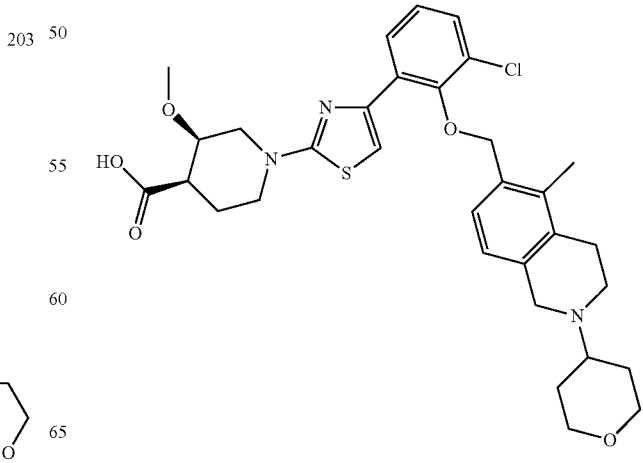
207

421
-continued
208
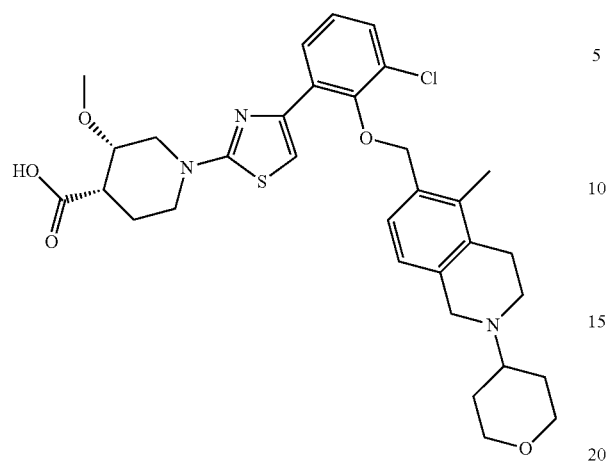
209
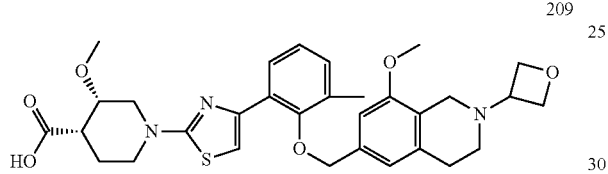
210
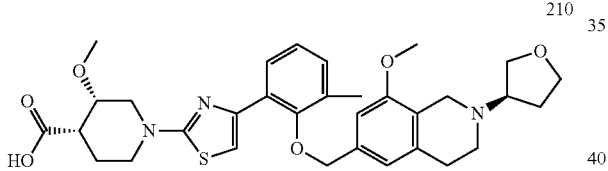
211
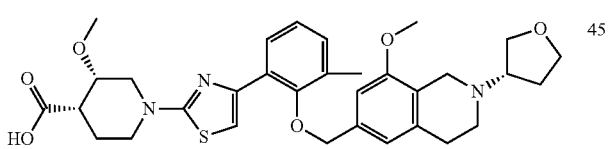
212
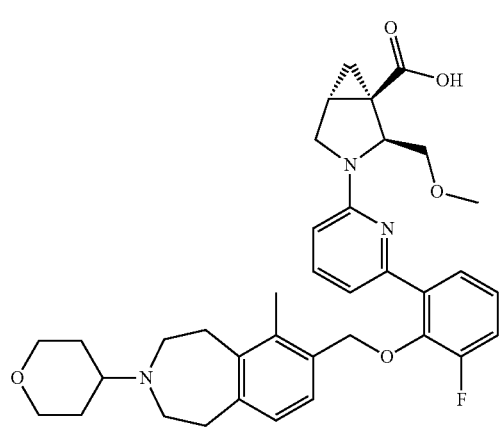
422
-continued
213
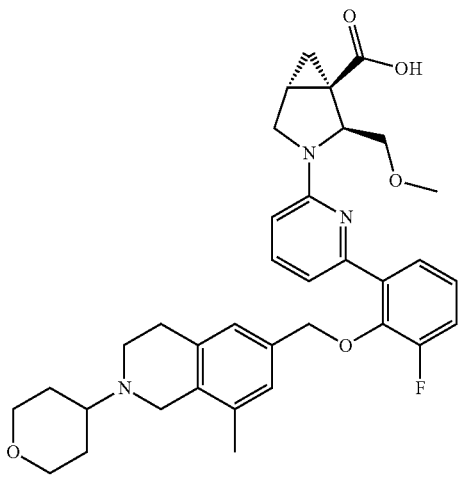
215
216
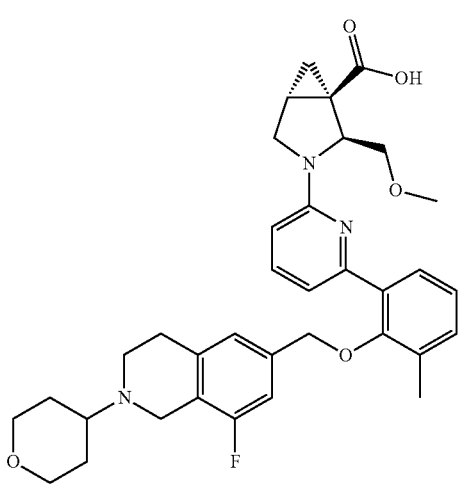

217 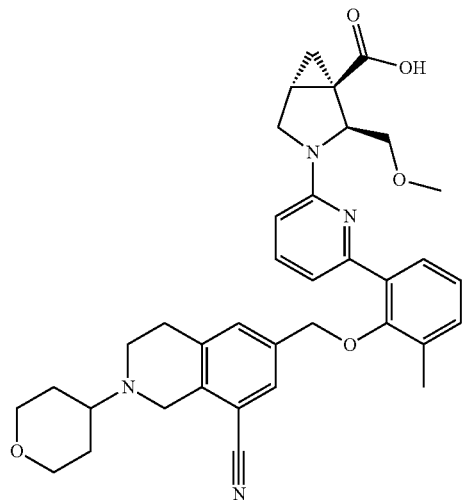
218 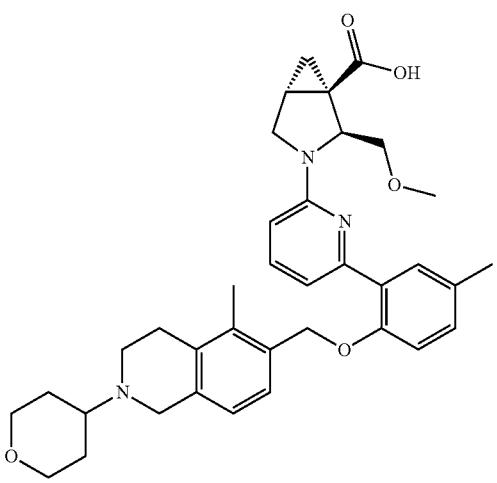
219 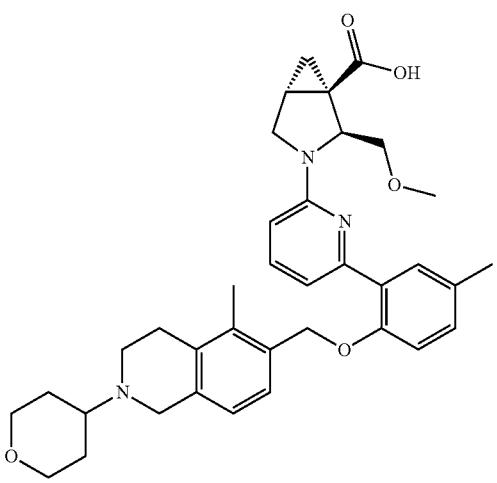
220 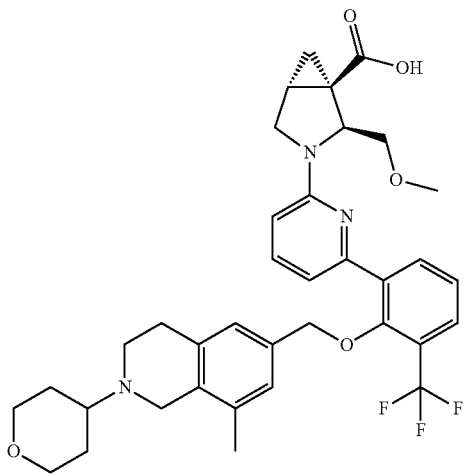
221 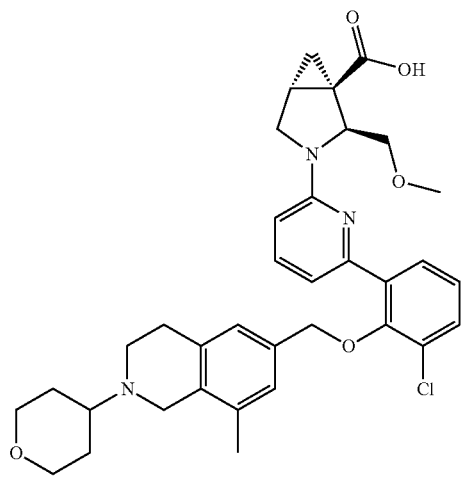
222 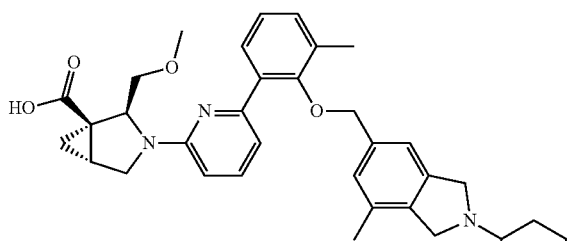
223 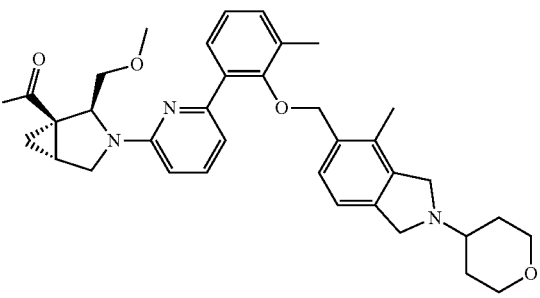

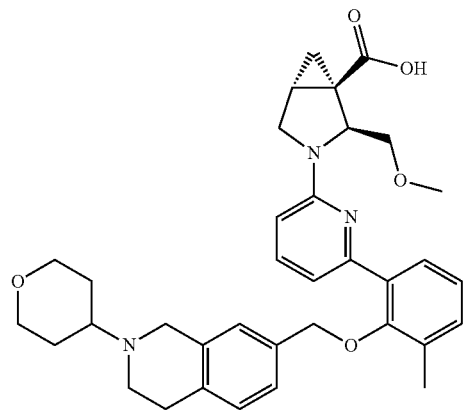
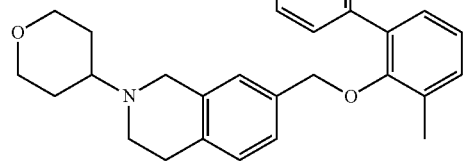
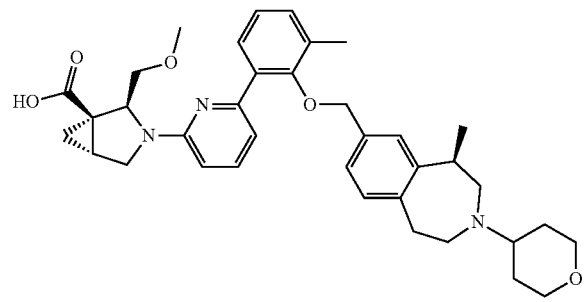
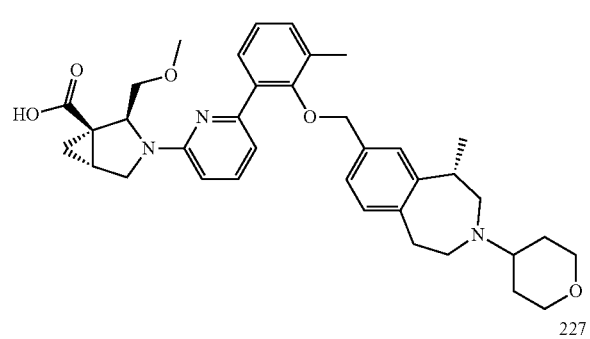
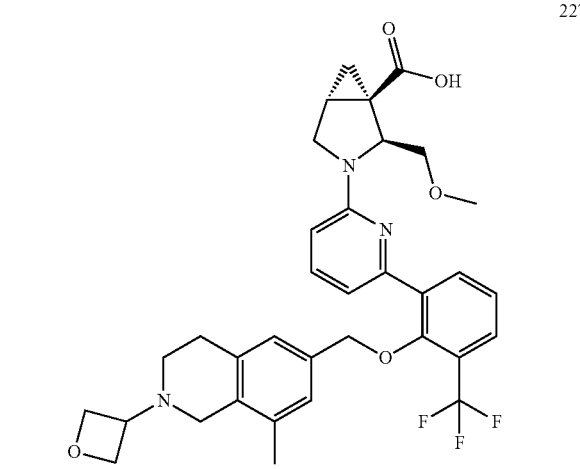
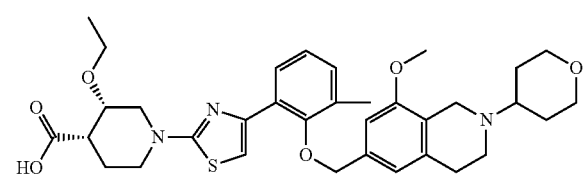

-continued
235
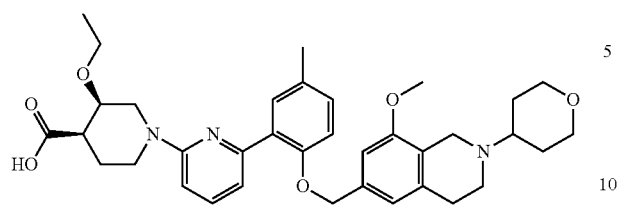
236
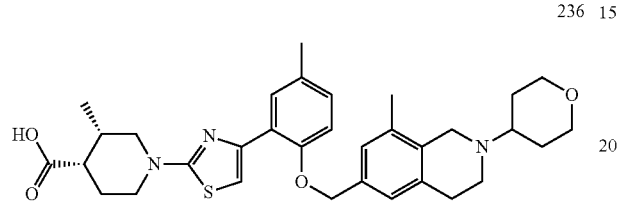
237
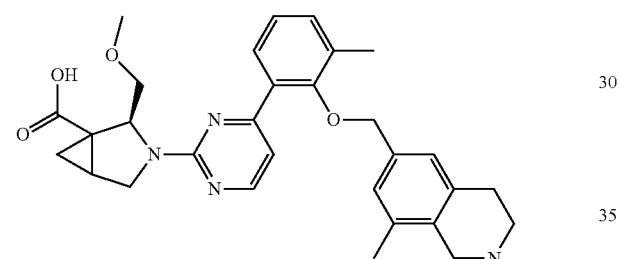
238
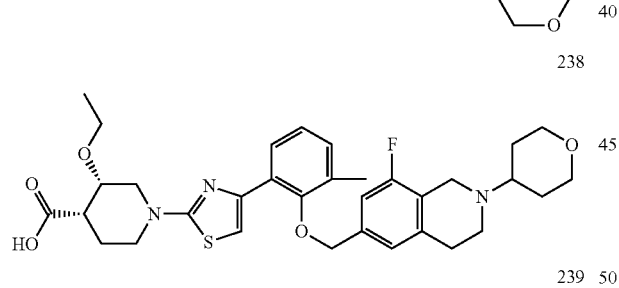
239
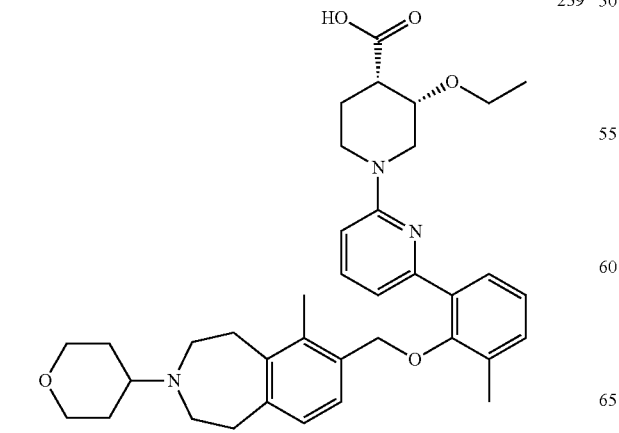
-continued
240
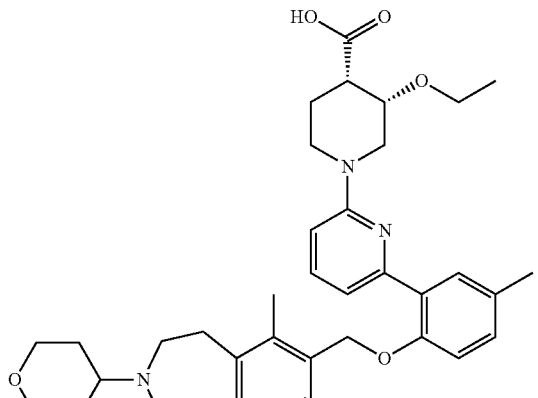
241
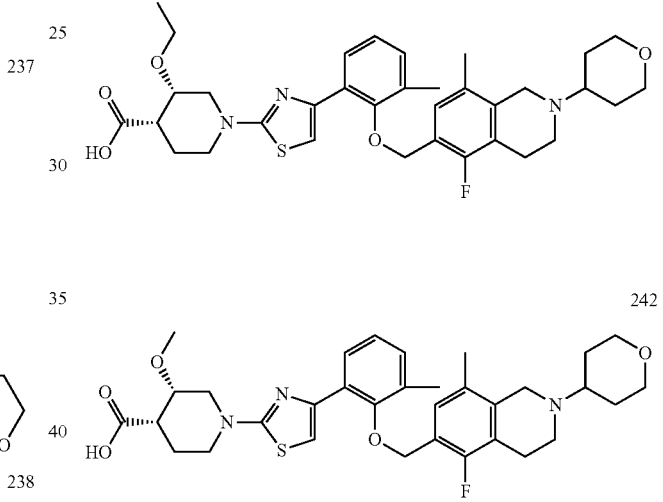
242
243
244
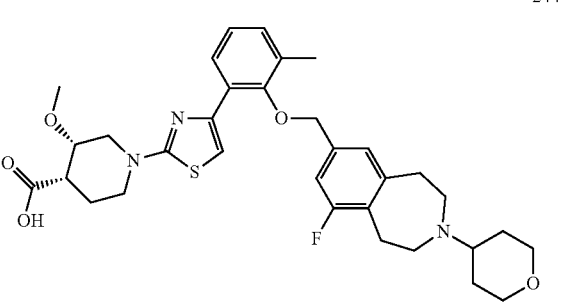

-continued
245
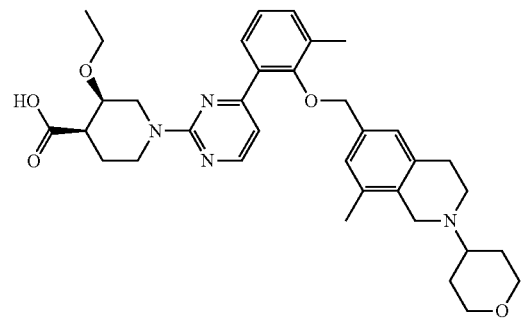
246
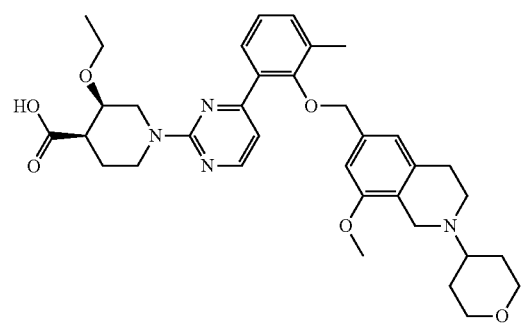
247
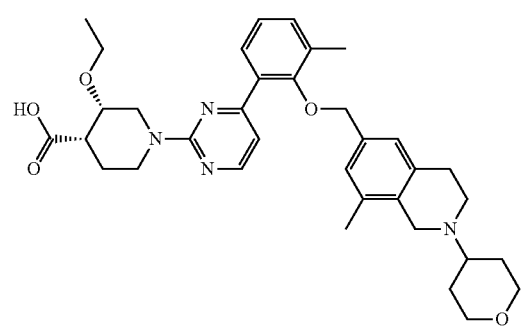
248
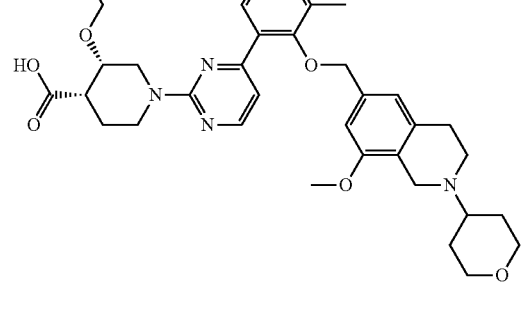
249
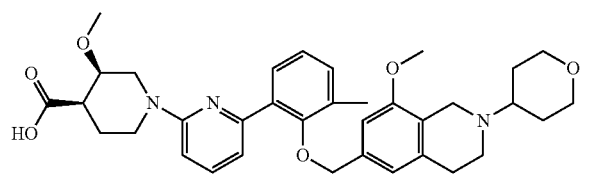
-continued
250
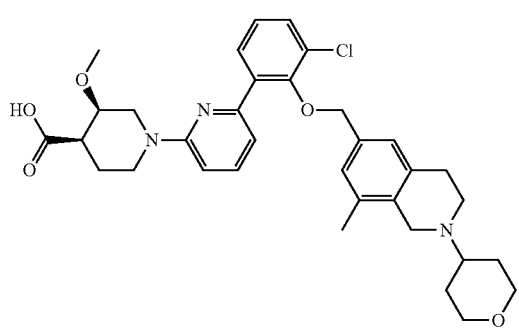
251
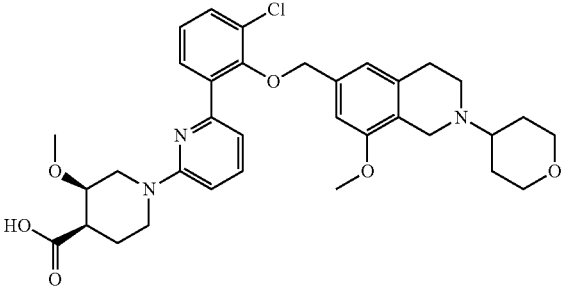
252
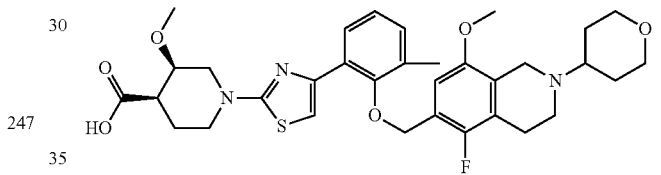
253
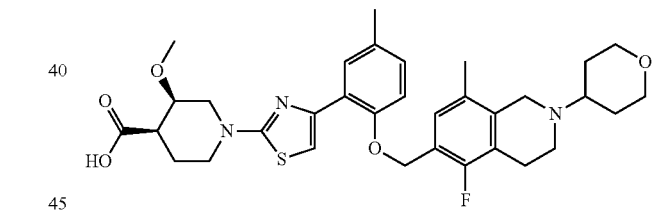
254
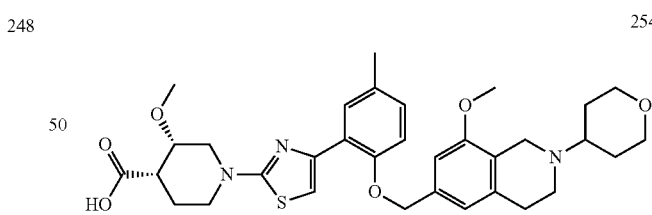
255
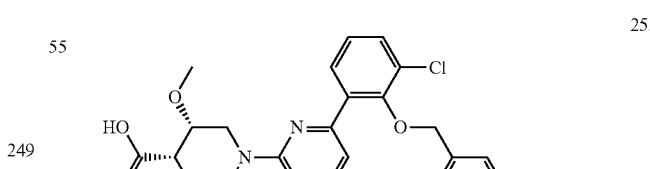

| 256 | 260 |
|---|---|
| 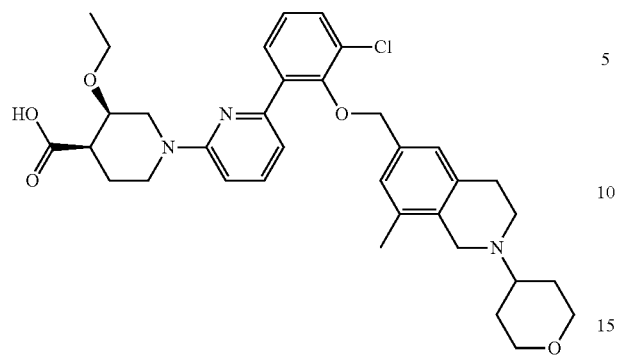 | 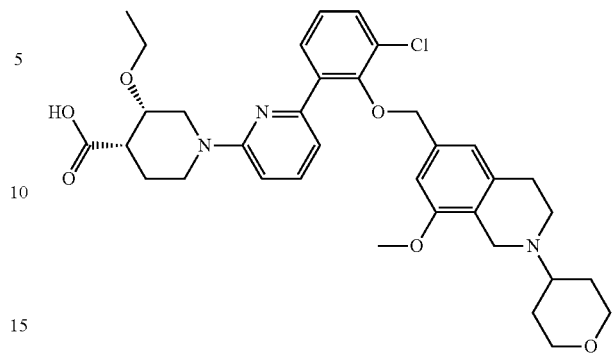 |
| 257 | 261 |
|---|---|
| 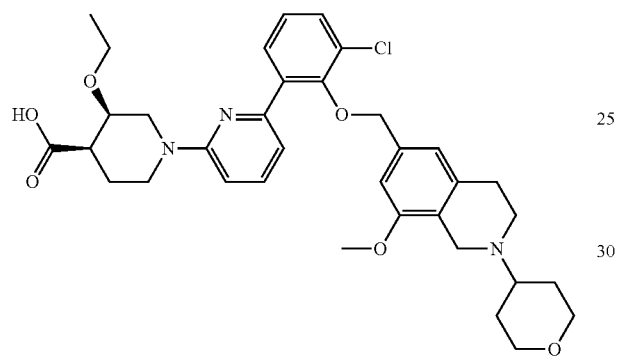 | |
| 258 | 262 |
|---|---|
| 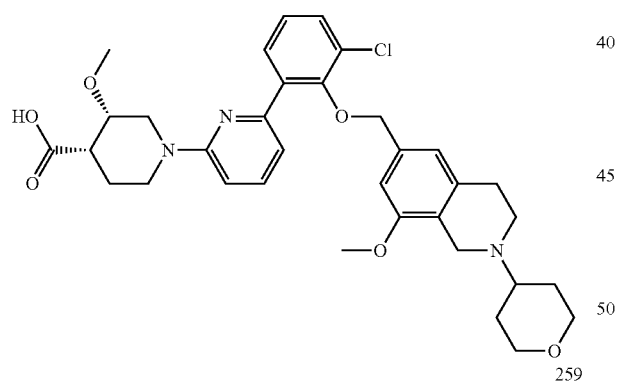 | |
| 259 | 263 |
|---|---|
| 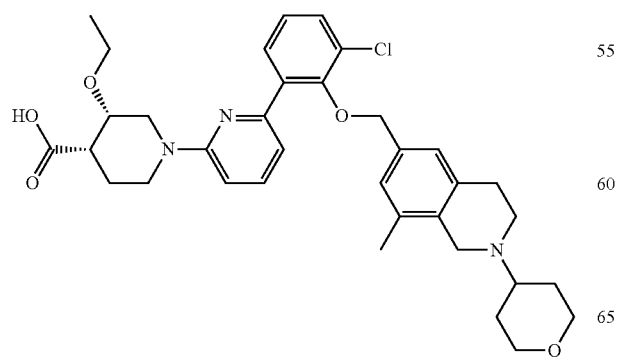 | 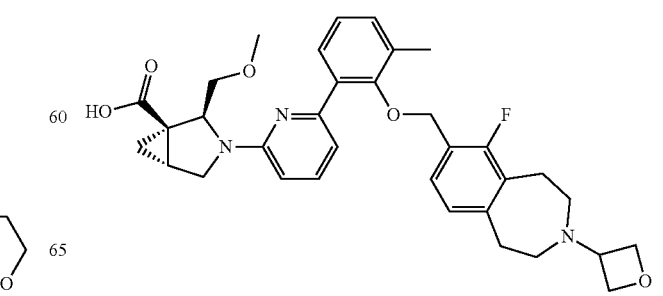 |

433
-continued
264
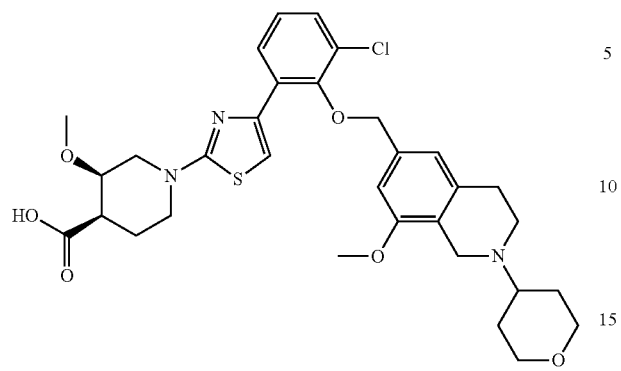
265
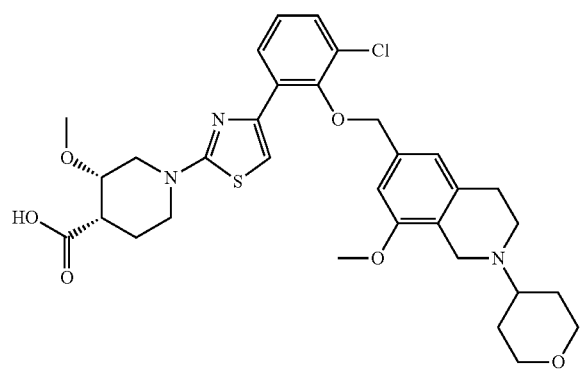
266
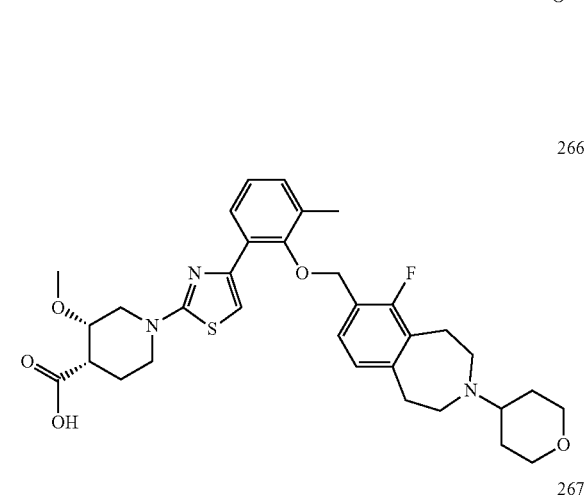
267
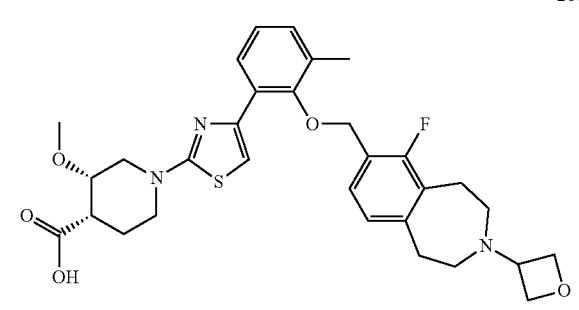
434
-continued
268
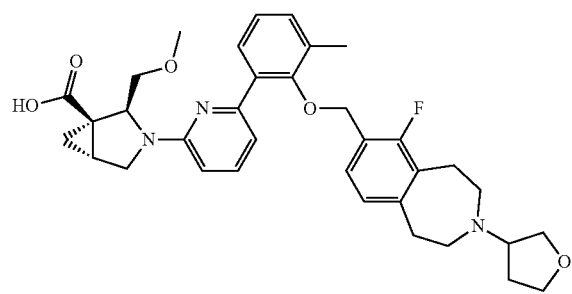
269
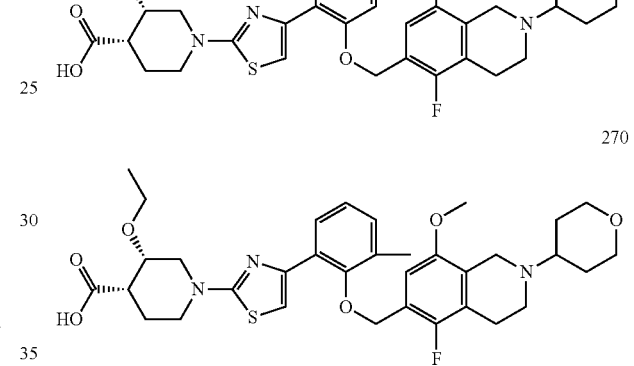
270
271
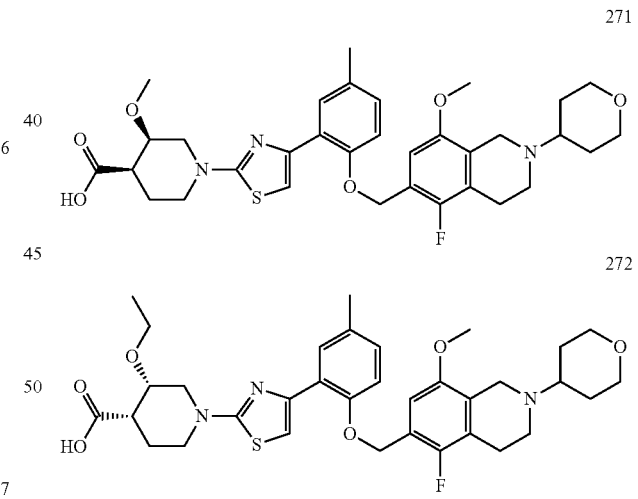
272
273
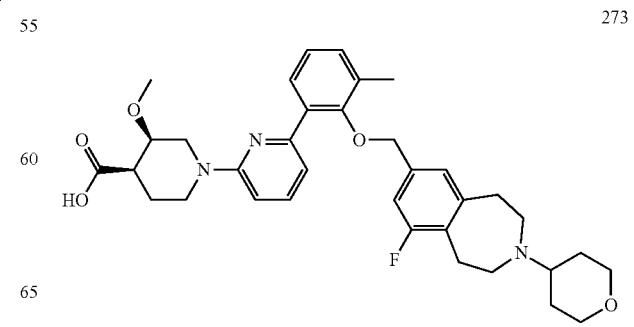

274
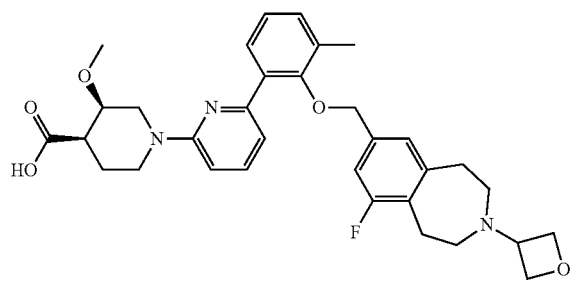
275
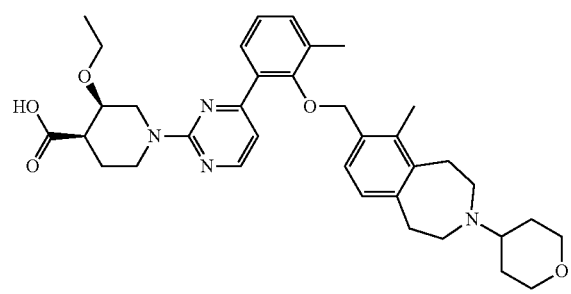
276
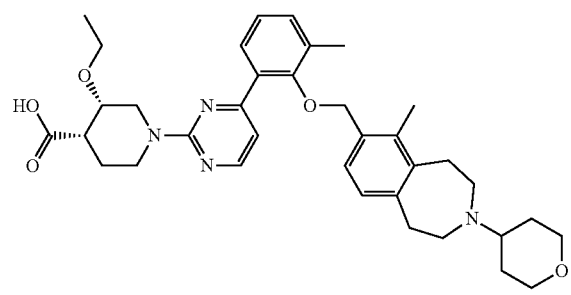
277
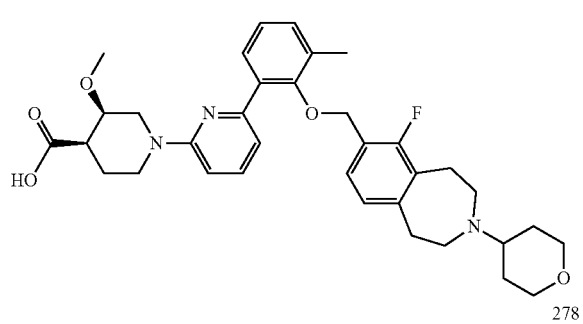
278
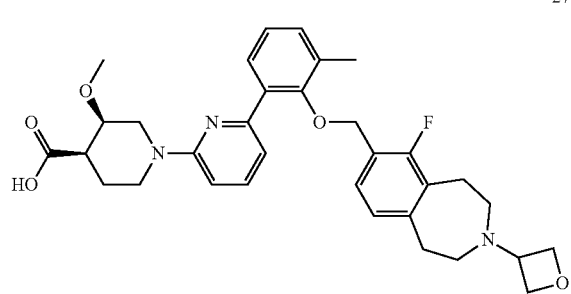
279
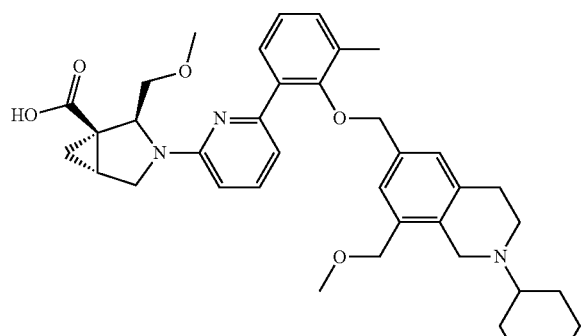
280
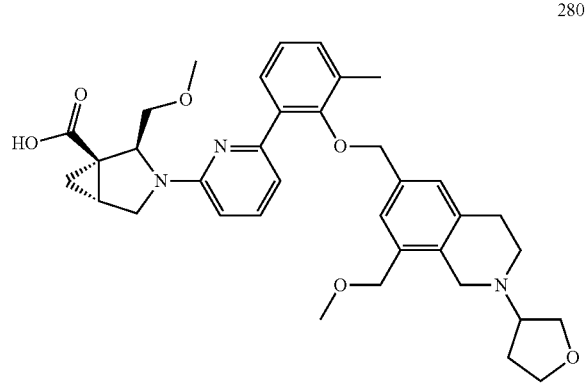
281
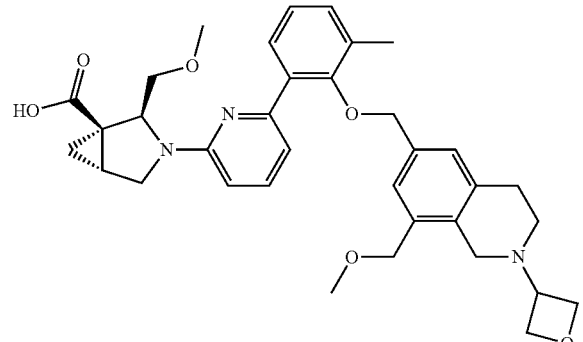
282
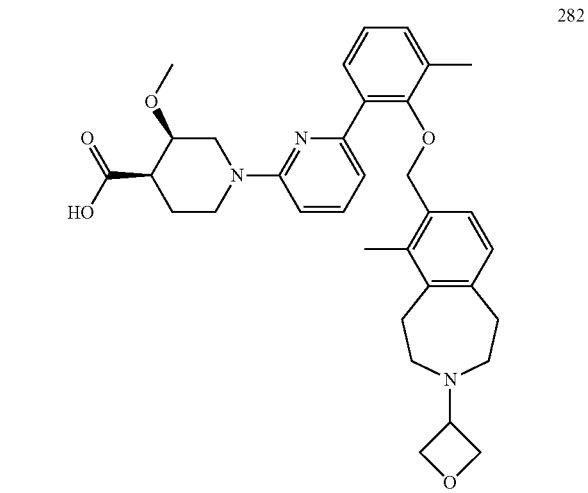

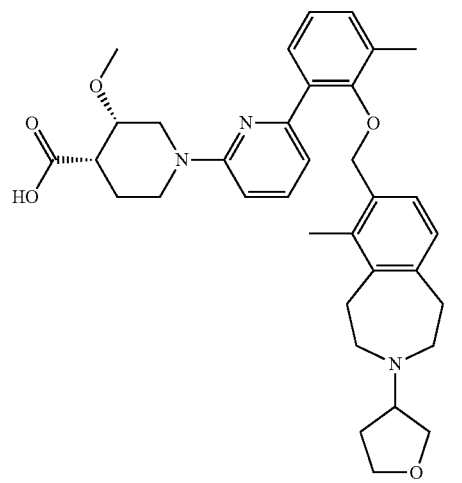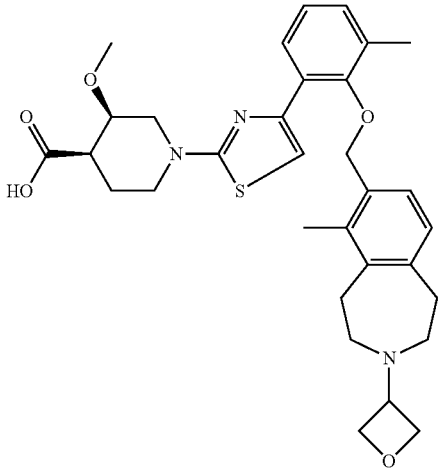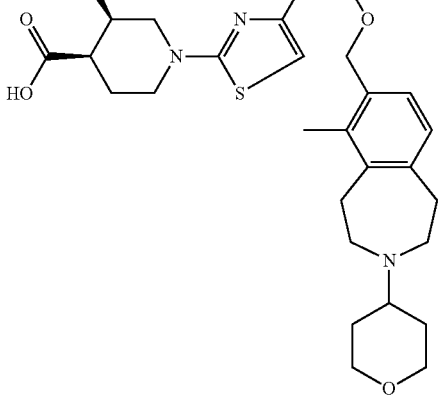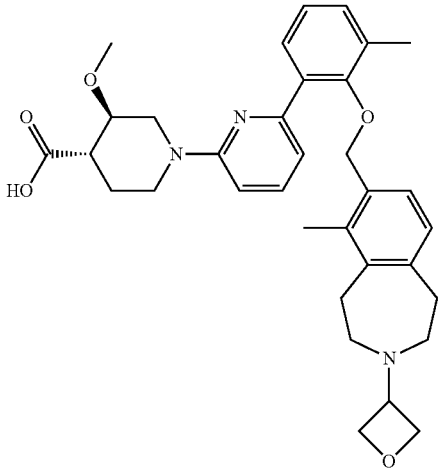

290
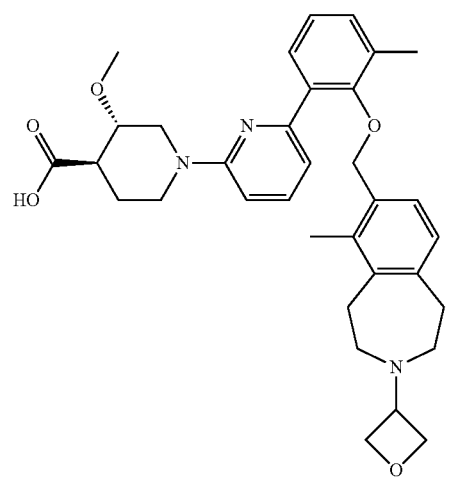
291
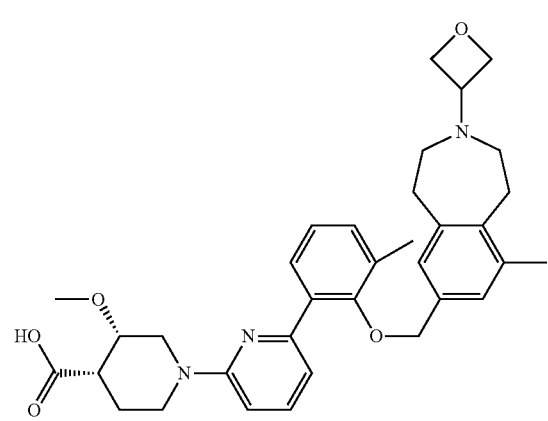
292
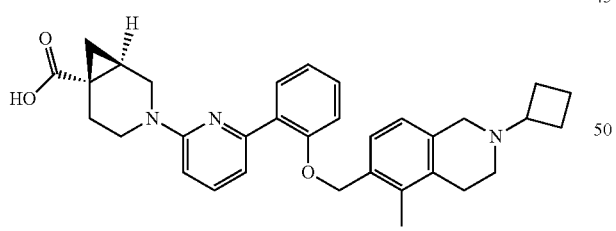
293
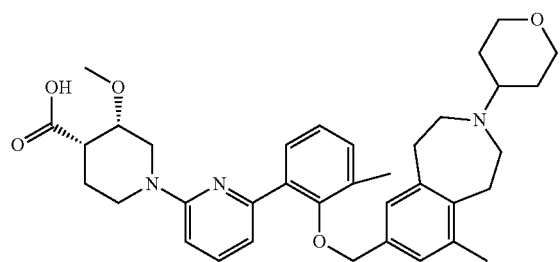
294
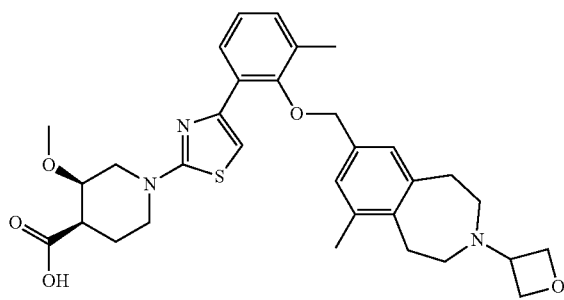
295
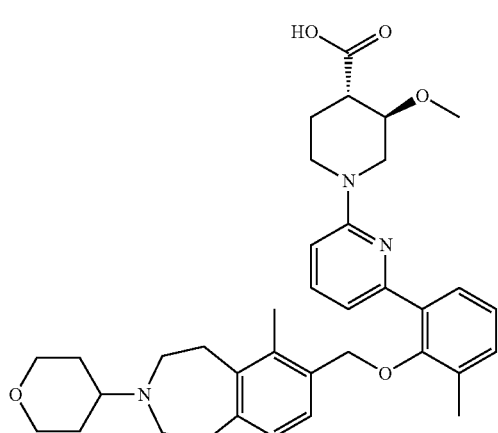
296
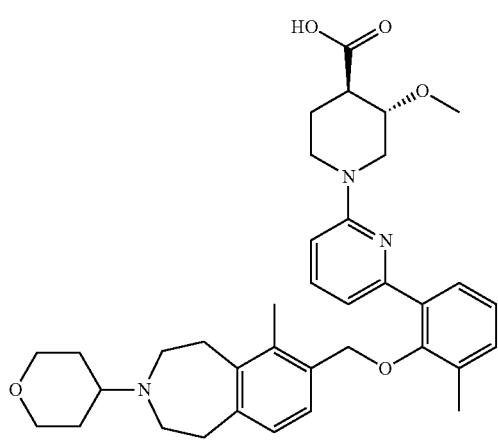
297

-continued
298
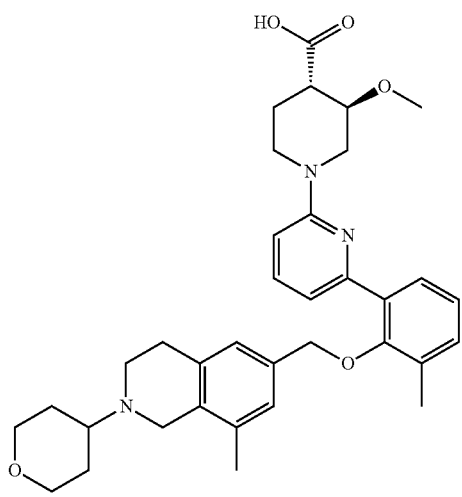
299
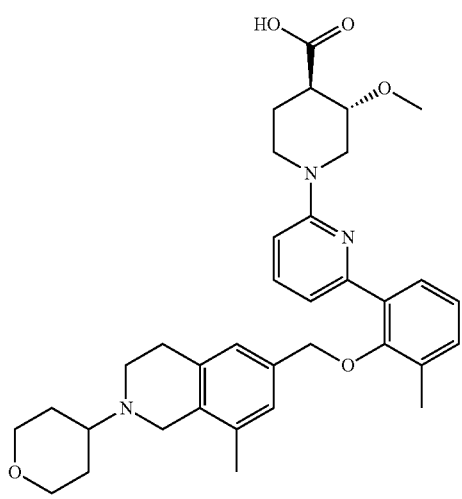
300
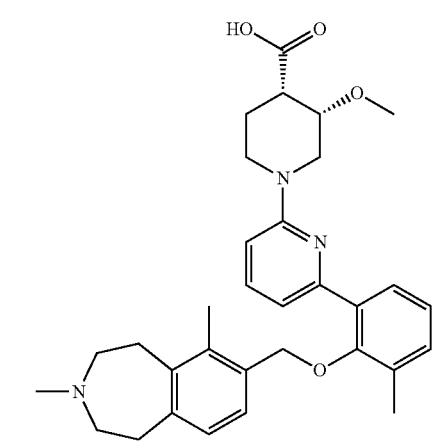
-continued
301
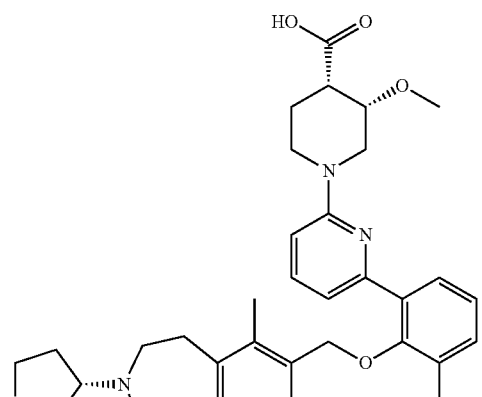
302
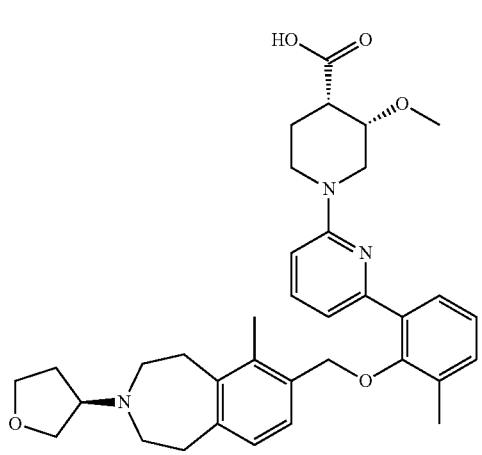
303
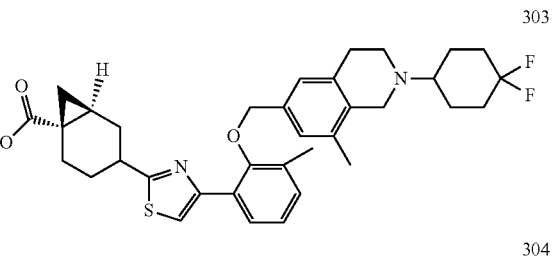
304
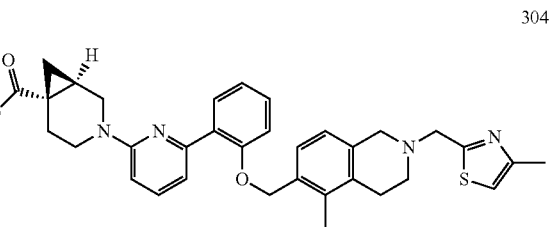
305
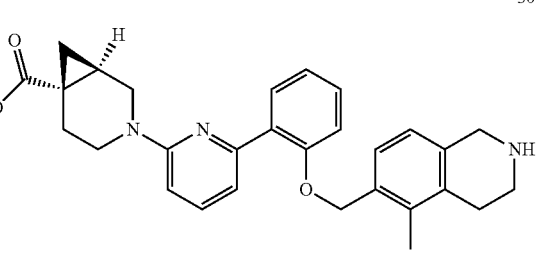

306 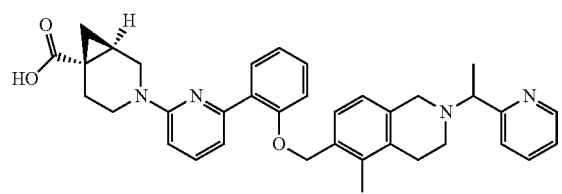
312 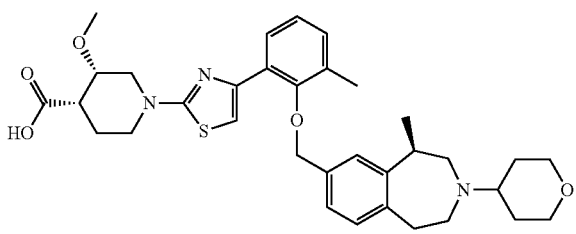
307 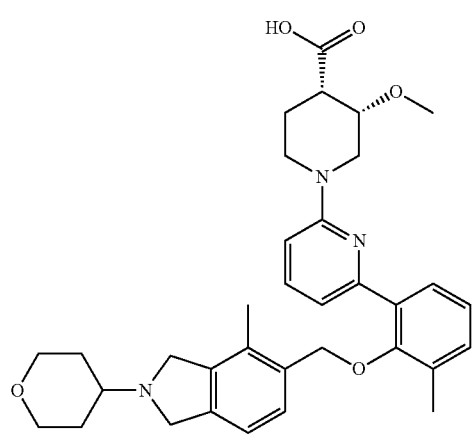
308 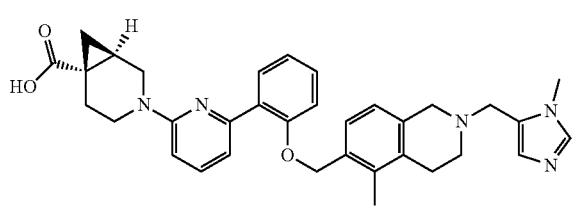
313 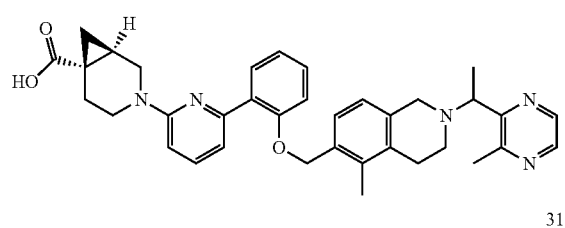
314 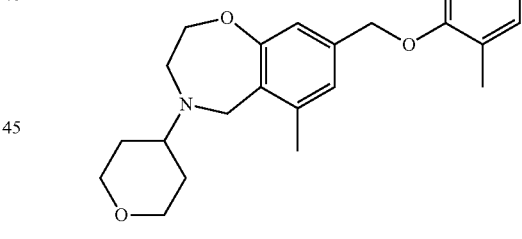
309 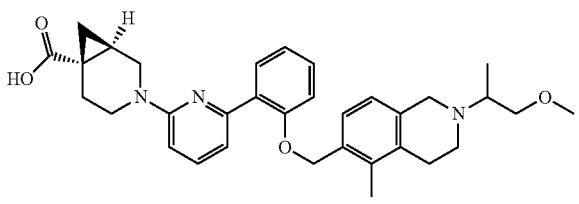
310
311
315 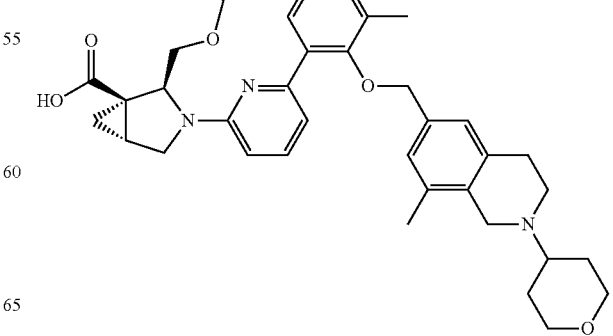

316
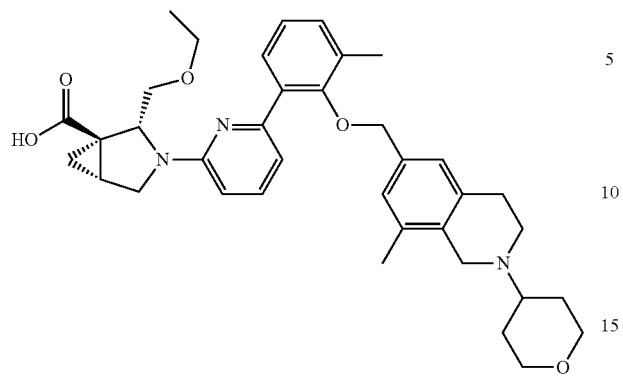
317
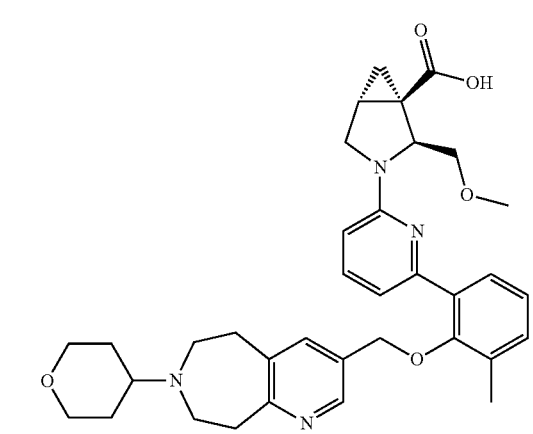
318
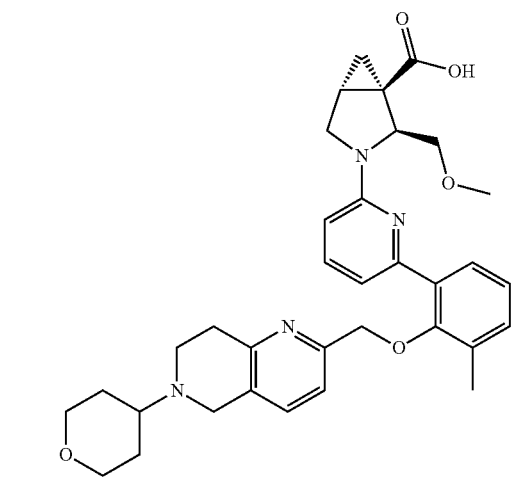
319
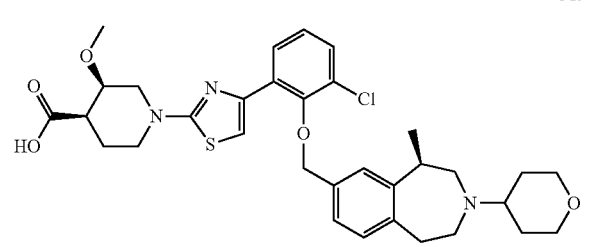
320
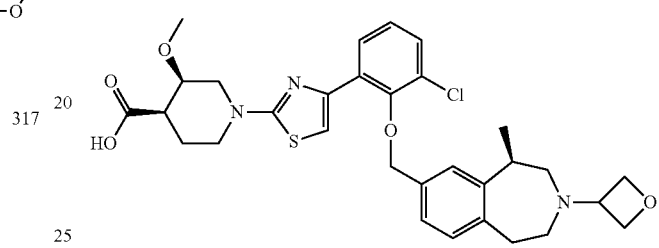
321
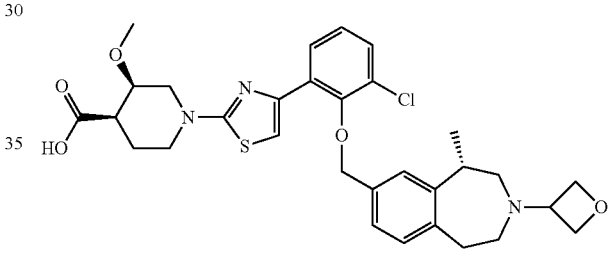
322
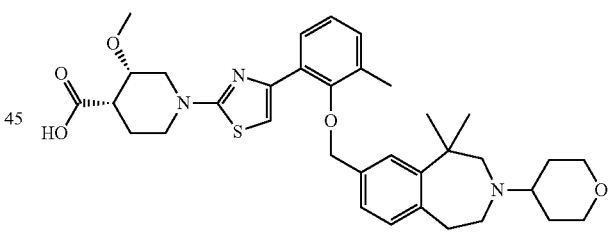
323
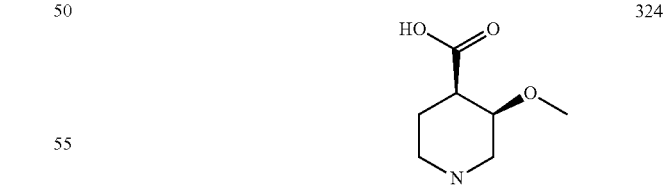
324
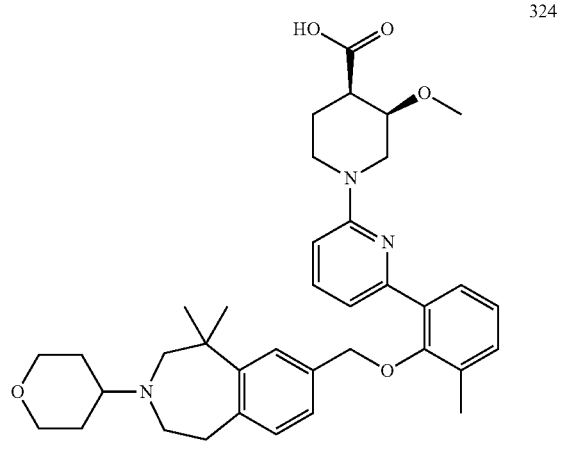

325
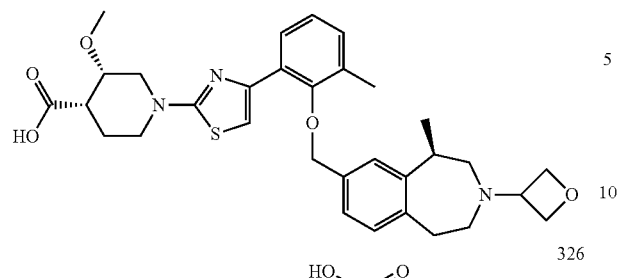
326
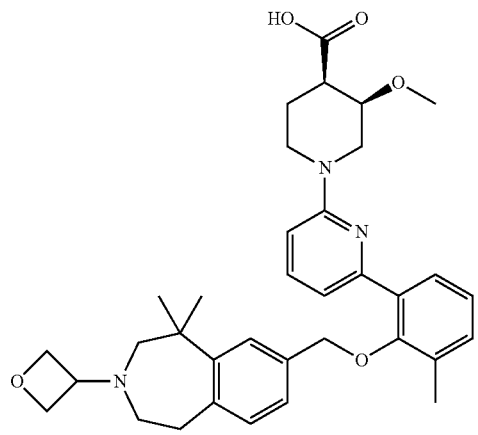
327
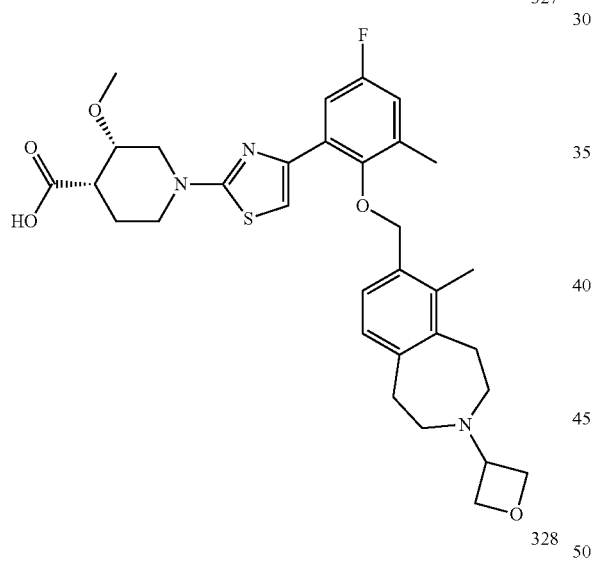
328
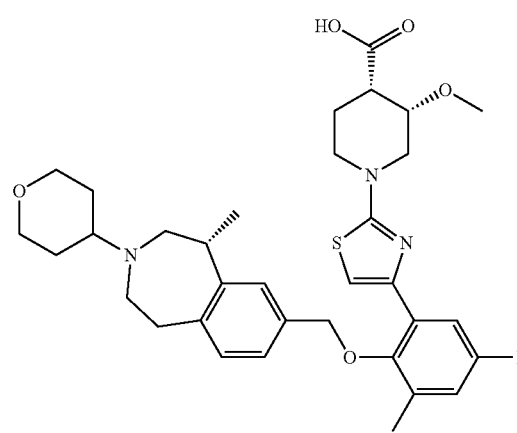
329
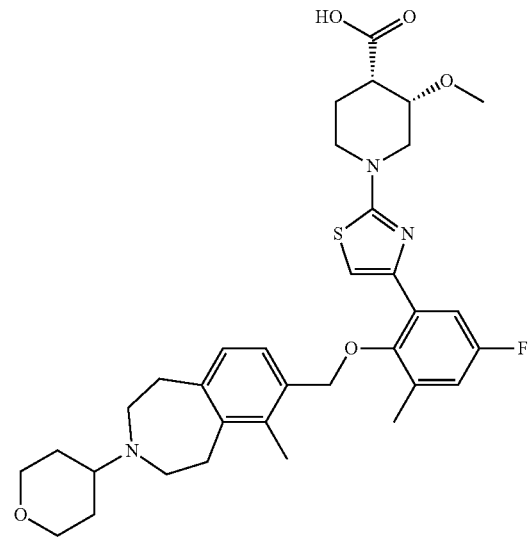
330
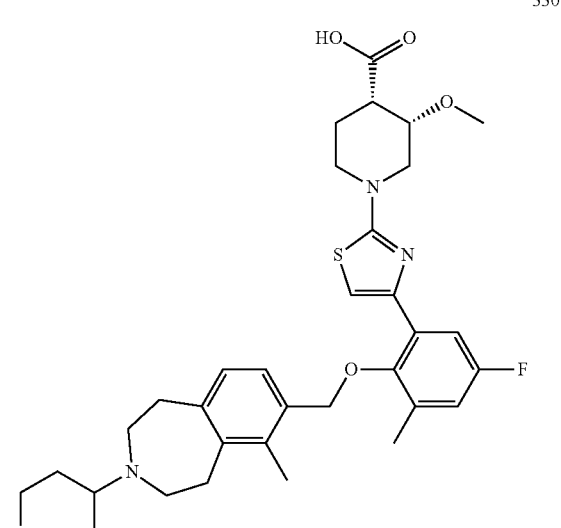
331
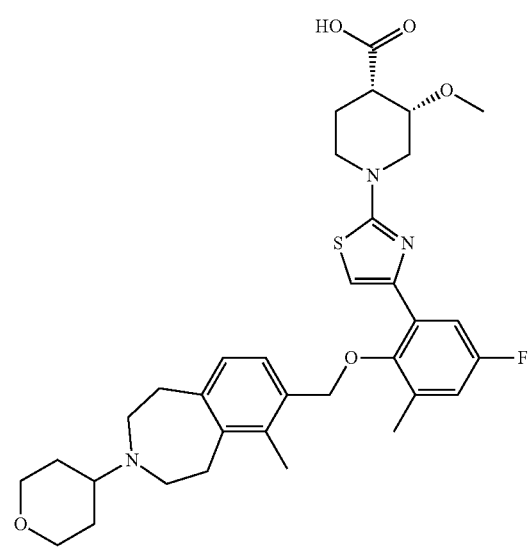

449
-continued
332
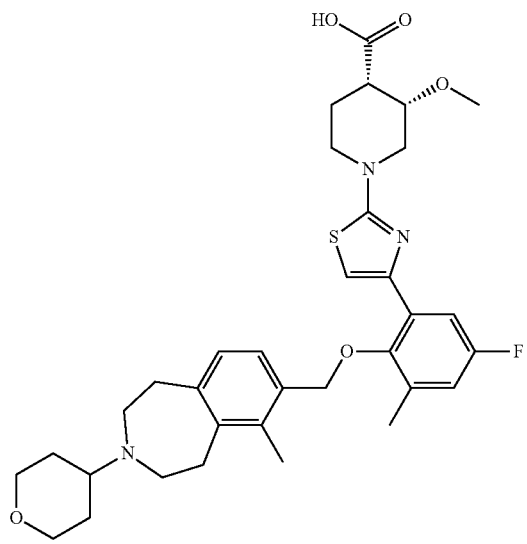
333
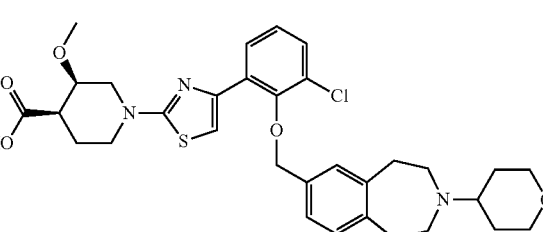
334
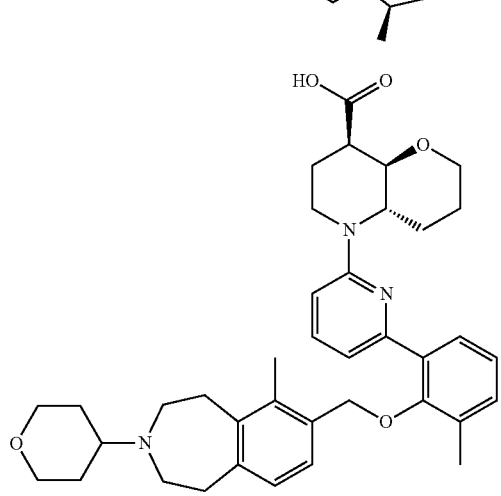
335
450
-continued
336
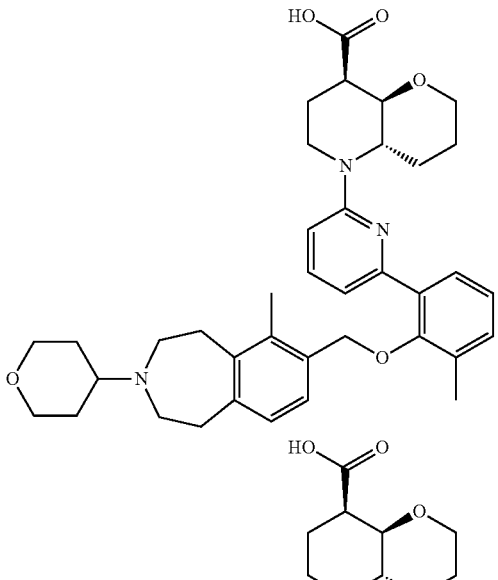
337
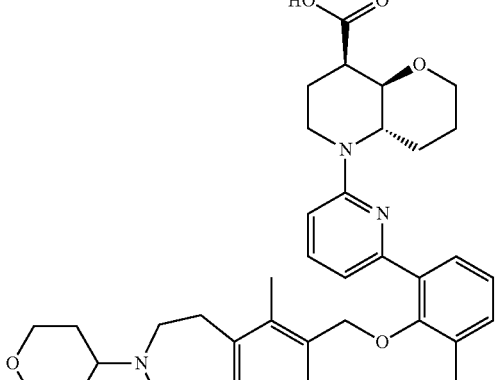
338
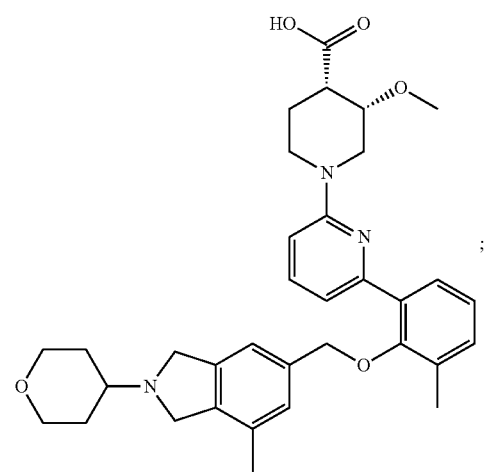
or a pharmaceutically acceptable salt thereof.
12. The compound according to claim 1, wherein the compound is
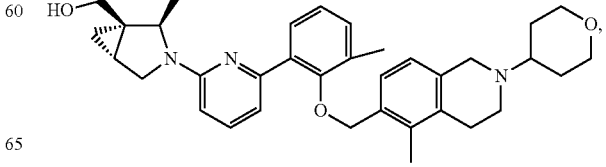
or a pharmaceutically acceptable salt thereof.

13. The compound according to claim 1, wherein the compound is

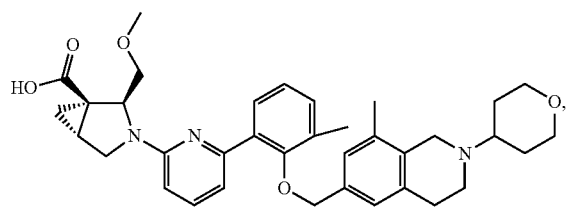 [SMILES: COC[C@H]1N(c2cccc(-c3cccc(C)c3OCc3cc(C)c4c(c3)CCN(C3CCOCC3)C4)n2)C[C@@H]2C[C@@]21C(=O)O]

or a pharmaceutically acceptable salt thereof.

14. The compound according to claim 1, wherein the compound is

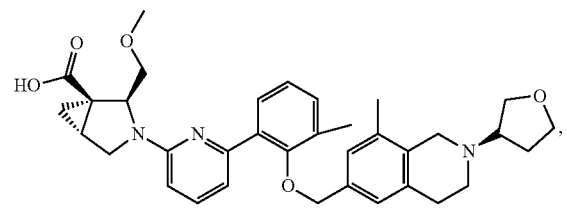

or a pharmaceutically acceptable salt thereof.

15. The compound according to claim 1, wherein the compound is

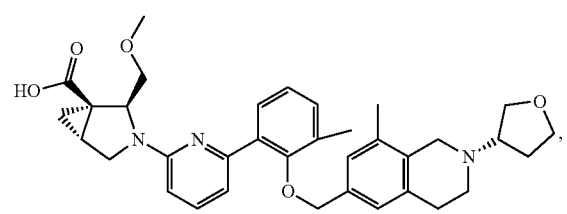

or a pharmaceutically acceptable salt thereof.

16. The compound according to claim 1, wherein the compound is

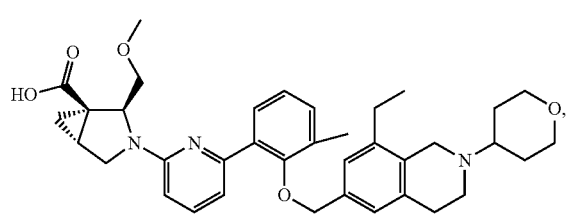 [SMILES: CCc1cc(COc2c(C)cccc2-c2cccc(N3C[C@@H]4C[C@]4(C(=O)O)[C@H]3COC)n2)cc2c1CN(C1CCOCC1)CC2]

or a pharmaceutically acceptable salt thereof.

17. The compound according to claim 1, wherein the compound is

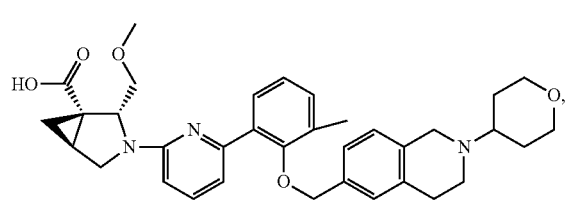 [SMILES: COC[C@@H]1N(c2cccc(-c3cccc(C)c3OCc3ccc4c(c3)CCN(C3CCOCC3)C4)n2)C[C@H]2C[C@]21C(=O)O]

or a pharmaceutically acceptable salt thereof.

18. The compound according to claim 1, wherein the compound is

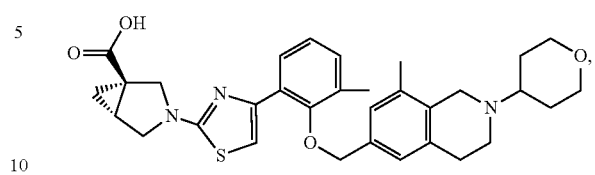

or a pharmaceutically acceptable salt thereof.

19. The compound according to claim 1, wherein the compound is

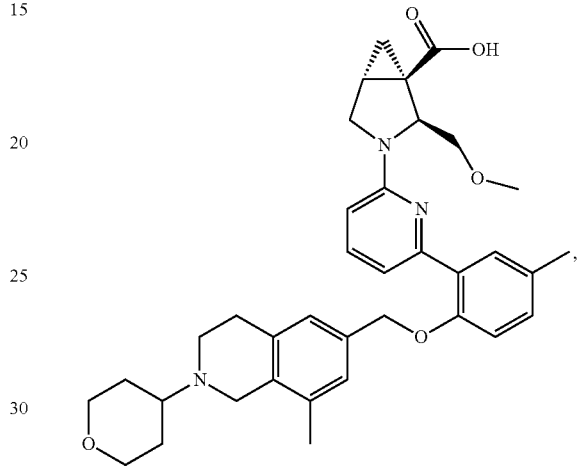

or a pharmaceutically acceptable salt thereof.

20. The compound according to claim 1, wherein the compound is

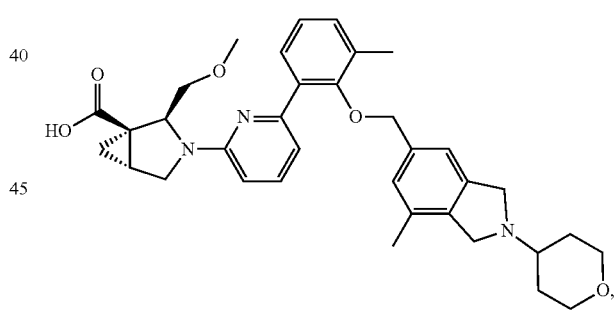

or a pharmaceutically acceptable salt thereof.

21. The compound according to claim 1, wherein the compound is

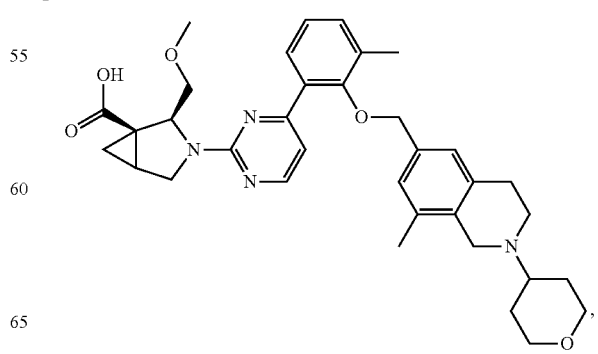

or a pharmaceutically acceptable salt thereof.

22. A pharmaceutical composition comprising a compound according to claim 1 and a pharmaceutically acceptable excipient or carrier.

23. A pharmaceutical composition comprising the compound according to claim 12, or a pharmaceutically acceptable salt thereof, and at least one pharmaceutically acceptable carrier.

24. A pharmaceutical composition comprising the compound according to claim 13, or a pharmaceutically acceptable salt thereof, and at least one pharmaceutically acceptable carrier.

25. A pharmaceutical composition comprising the compound according to claim 14, or a pharmaceutically acceptable salt thereof, and at least one pharmaceutically acceptable carrier.

26. A pharmaceutical composition comprising the compound according to claim 15, or a pharmaceutically acceptable salt thereof, and at least one pharmaceutically acceptable carrier.

27. A pharmaceutical composition comprising the compound according to claim 16, or a pharmaceutically acceptable salt thereof, and at least one pharmaceutically acceptable carrier.

28. A pharmaceutical composition comprising the compound according to claim 17, or a pharmaceutically acceptable salt thereof, and at least one pharmaceutically acceptable carrier.

29. A pharmaceutical composition comprising the compound according to claim 18, or a pharmaceutically acceptable salt thereof, and at least one pharmaceutically acceptable carrier.

30. A pharmaceutical composition comprising the compound according to claim 19, or a pharmaceutically acceptable salt thereof, and at least one pharmaceutically acceptable carrier.

31. A pharmaceutical composition comprising the compound according to claim 20, or a pharmaceutically acceptable salt thereof, and at least one pharmaceutically acceptable carrier.

32. A pharmaceutical composition comprising the compound according to claim 21, or a pharmaceutically acceptable salt thereof, and at least one pharmaceutically acceptable carrier.

33. A method of treating a disease or disorder that can be alleviated by sGC activation or potentiation selected from a cardiovascular disease, inflammatory disease, hepatic fibrotic disorder, skin fibrotic disorder, renal fibrotic disorder, pulmonary fibrotic disorder and cardiac fibrotic disorder, comprising administering a therapeutically effective amount of a compound according to claim 1 to patient in need thereof.

34. A method of treating a disease or disorder that can be alleviated by sGC activation or potentiation wherein the disease is selected from renal disease, diabetes, glaucoma, obesity, osteoporosis, muscular dystrophy, urologic disorders, benign prostatic hyperplasia, erectile dysfunction, and neurological disorders, comprising administering a therapeutically effective amount of a compound according to claim 1 to patient in need thereof.

35. The method according to claim 33 wherein the disease is diabetic nephropathy.

36. The method according to claim 33, wherein the compound of formula (I) is

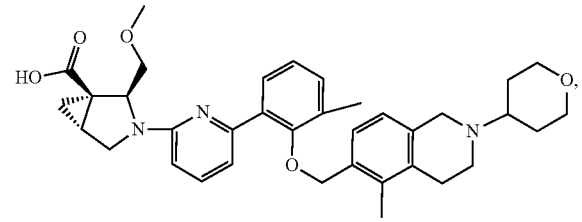 [SMILES: COC[C@H]1N(c2cccc(-c3cccc(C)c3OCc3ccc4c(c3C)CCN(C3CCOCC3)C4)n2)C[C@@H]2C[C@@]21C(=O)O]

or a pharmaceutically acceptable salt thereof.

37. The method according to claim 33, wherein the compound of formula (I) is

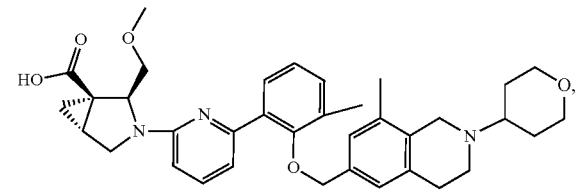 [SMILES: COC[C@H]1N(c2cccc(-c3cccc(C)c3OCc3cc(C)c4c(c3)CCN(C3CCOCC3)C4)n2)C[C@@H]2C[C@@]21C(=O)O]

or a pharmaceutically acceptable salt thereof.

38. The method according to claim 33, wherein the compound of formula (I) is

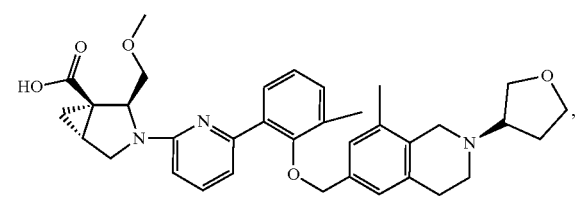

or a pharmaceutically acceptable salt thereof.

39. The method according to claim 33, wherein the compound of formula (I) is

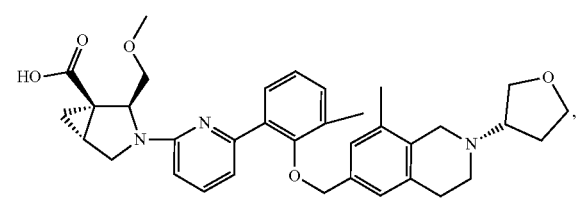

or a pharmaceutically acceptable salt thereof.

40. The method according to claim 33, wherein the compound of formula (I) is

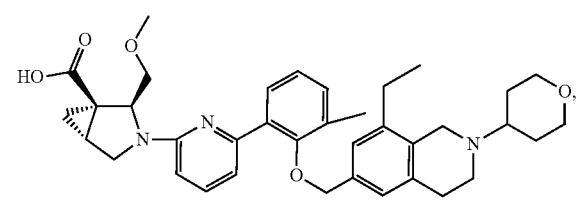 [SMILES: CCc1cc(COc2c(C)cccc2-c2cccc(N3C[C@@H]4C[C@]4(C(=O)O)[C@H]3COC)n2)cc2c1CN(C1CCOCC1)CC2]

or a pharmaceutically acceptable salt thereof.

41. The method according to claim 33, wherein the compound of formula (I) is

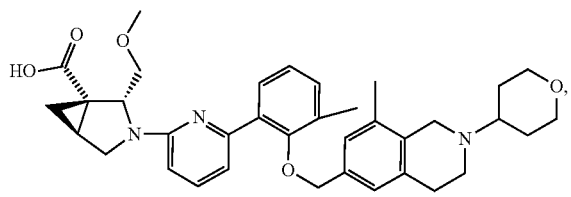 [SMILES: COC[C@@H]1N(c2cccc(-c3cccc(C)c3OCc3cc(C)c4c(c3)CCN(C3CCOCC3)C4)n2)C[C@H]2C[C@]21C(=O)O]

or a pharmaceutically acceptable salt thereof.

42. The method according to claim 33, wherein the compound of formula (I) is

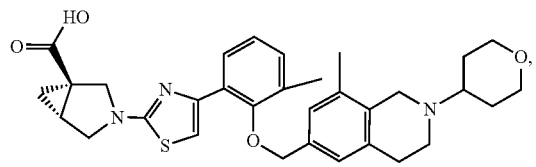 [SMILES: Cc1cc(COc2c(C)cccc2-c2csc(N3C[C@@H]4C[C@]4(C(=O)O)C3)n2)cc2c1CN(C1CCOCC1)CC2]

or a pharmaceutically acceptable salt thereof.

43. The method according to claim 33, wherein the compound of formula (I) is

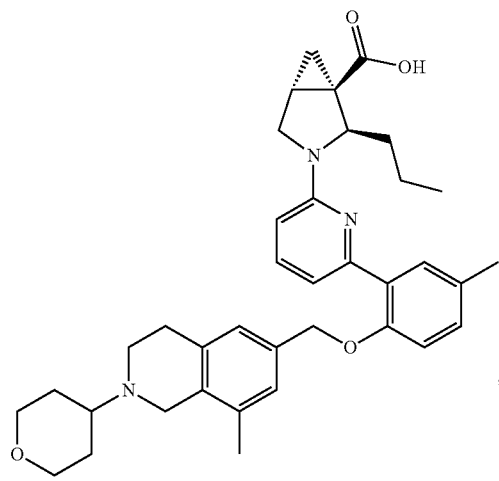

or a pharmaceutically acceptable salt thereof.

44. The method according to claim 33, wherein the compound of formula (I) is

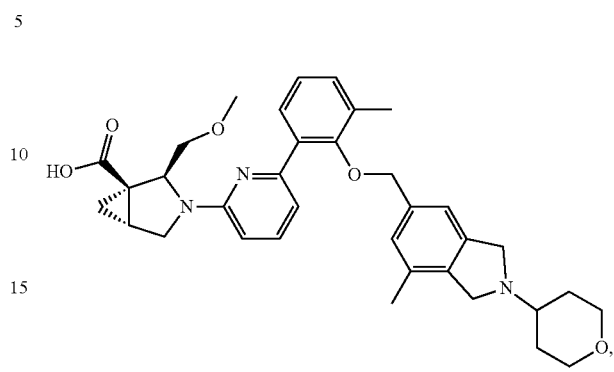

or a pharmaceutically acceptable salt thereof.

45. The method according to claim 33, wherein the compound of formula (I) is

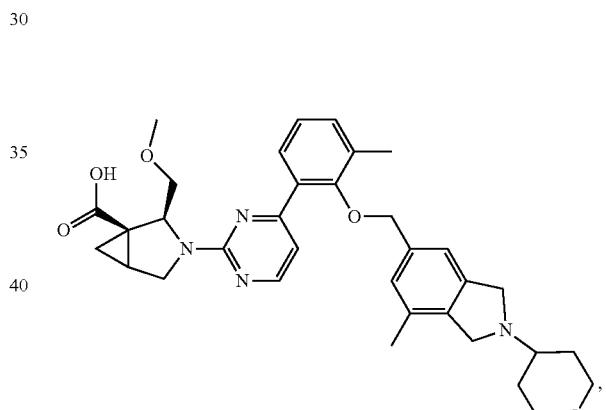

or a pharmaceutically acceptable salt thereof.

* * * * *